US012611427B2

(12) United States Patent
Fardis et al.

(10) Patent No.: US 12,611,427 B2
(45) Date of Patent: Apr. 28, 2026

(54) TREATMENT OF NSCLC PATIENTS REFRACTORY FOR ANTI-PD-1 ANTIBODY

(71) Applicant: Iovance Biotherapeutics, Inc., San Carlos, CA (US)

(72) Inventors: Maria Fardis, San Carlos, CA (US); Arvind Natarajan, Baskin Ridge, NJ (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 1265 days.

(21) Appl. No.: 17/290,710

(22) PCT Filed: Nov. 4, 2019

(86) PCT No.: PCT/US2019/059720
§ 371 (c)(1),
(2) Date: Apr. 30, 2021

(87) PCT Pub. No.: WO2020/096989
PCT Pub. Date: May 14, 2020

(65) Prior Publication Data
US 2022/0088069 A1 Mar. 24, 2022

Related U.S. Application Data

(60) Provisional application No. 62/756,025, filed on Nov. 5, 2018, provisional application No. 62/903,627, filed on Sep. 20, 2019.

(51) Int. Cl.
*A61K 35/13* (2015.01)
*A61K 40/11* (2025.01)
(Continued)

(52) U.S. Cl.
CPC .............. *A61K 35/13* (2013.01); *A61K 40/11* (2025.01); *A61K 40/42* (2025.01); *A61K 45/06* (2013.01);
(Continued)

(58) Field of Classification Search
CPC .......................... A61K 35/13; A61K 39/4611; A61K 39/4644; A61K 45/06; A61K 2239/38;
(Continued)

(56) References Cited

U.S. PATENT DOCUMENTS 4,766,106 A 8/1988 Katre et al.
4,897,355 A 1/1990 Eppstein et al.
(Continued)

FOREIGN PATENT DOCUMENTS

CN 102816734 A 12/2012
CN 106244538 A 12/2016
(Continued)

OTHER PUBLICATIONS

Mathew, Matthen, et al. "Combining chemotherapy with PD-1 blockade in NSCLC." Pharmacology & therapeutics 186 (2018): 130-137 (Year: 2018).*
(Continued)

*Primary Examiner* — Tracy Vivlemore
*Assistant Examiner* — Thomas R. Amick

(57) ABSTRACT
The present invention provides improved and/or shortened processes and methods for preparing TILs in order to prepare therapeutic populations of TILs with increased therapeutic efficacy for the treatment of non-small cell lung carcinoma (NSCLC), wherein the NSCLC is refractory to treatment with an anti-PD-1 antibody.

12 Claims, 130 Drawing Sheets

Specification includes a Sequence Listing.

Process 2A: about 22 days from Steps A - E

1. STEP A
Obtain Patient Tumor Sample

2. STEP B
Fragmentation and First Expansion
3 days to 14 days

3. STEP C
First Expansion to Second Expansion Transition
No Storage and Closed System 4. STEP D
Second Expansion
IL-2, OKT-3, and antigen-presenting feeder cells
Closed System 5. STEP E
Harvest TILS from Step D
Closed System 6. STEP F
Final Formulation and/or Transfer to Infusion Bag
(optionally cryopreserve)

(51) Int. Cl.

| | | |
|---|---|---|
| *A61K 40/42* | (2025.01) | |
| *A61K 45/06* | (2006.01) | |
| *C07K 16/28* | (2006.01) | |
| *C12N 5/0781* | (2010.01) | |
| *C12N 5/0783* | (2010.01) | |

(52) U.S. Cl.
CPC ...... *C07K 16/2809* (2013.01); *C07K 16/2818* (2013.01); *C07K 16/2827* (2013.01); *C12N 5/0635* (2013.01); *C12N 5/0638* (2013.01); *A61K 2239/38* (2023.05); *A61K 2239/48* (2023.05); *A61K 2239/55* (2023.05); *C12N 2501/2302* (2013.01); *C12N 2501/515* (2013.01)

(58) Field of Classification Search
CPC ............ A61K 2239/48; A61K 2239/55; A61K 31/675; A61K 31/7076; A61K 38/2013; A61K 35/17; A61K 31/519; C07K 16/2809; C07K 16/2818; C07K 16/2827; C12N 5/0635; C12N 5/0638; C12N 2501/2302; C12N 2501/515; A61P 35/00
See application file for complete search history.

(56) References Cited

U.S. PATENT DOCUMENTS

| | | | |
|---|---|---|---|
| 4,902,502 | A | 2/1990 | Nitecki et al. |
| 5,019,034 | A | 5/1991 | Weaver et al. |
| 5,089,261 | A | 2/1992 | Nitecki et al. |
| 5,126,132 | A | 6/1992 | Rosenberg |
| 5,128,257 | A | 7/1992 | Baer |
| 5,137,817 | A | 8/1992 | Busta et al. |
| 5,173,158 | A | 12/1992 | Schmukler |
| 5,206,344 | A | 4/1993 | Katre et al. |
| 5,232,856 | A | 8/1993 | Firth |
| 5,273,525 | A | 12/1993 | Hofmann |
| 5,279,833 | A | 1/1994 | Rose |
| 5,304,120 | A | 4/1994 | Crandell et al. |
| 5,318,514 | A | 6/1994 | Hofmann |
| 5,443,983 | A | 8/1995 | Ochoa et al. |
| 5,591,828 | A | 1/1997 | Bosslet et al. |
| 5,593,875 | A | 1/1997 | Wurm et al. |
| 5,648,260 | A | 7/1997 | Winter et al. |
| 5,714,350 | A | 2/1998 | Co et al. |
| 5,739,277 | A | 4/1998 | Presta et al. |
| 5,766,902 | A | 6/1998 | Craig et al. |
| 5,824,778 | A | 10/1998 | Ishikawa et al. |
| 5,834,250 | A | 11/1998 | Wells et al. |
| 5,849,902 | A | 12/1998 | Arrow et al. |
| 5,869,046 | A | 2/1999 | Presta et al. |
| 5,908,635 | A | 6/1999 | Thierry |
| 5,928,893 | A | 7/1999 | Kang et al. |
| 6,010,613 | A | 1/2000 | Walters et al. |
| 6,025,337 | A | 2/2000 | Truong et al. |
| 6,056,938 | A | 5/2000 | Unger et al. |
| 6,078,490 | A | 6/2000 | Walters |
| 6,096,871 | A | 8/2000 | Presta et al. |
| 6,110,490 | A | 8/2000 | Thierry |
| 6,121,022 | A | 9/2000 | Presta et al. |
| 6,194,551 | B1 | 2/2001 | Idusogie et al. |
| 6,210,669 | B1 | 4/2001 | Aruffo et al. |
| 6,242,195 | B1 | 6/2001 | Idusogie et al. |
| 6,277,375 | B1 | 8/2001 | Ward |
| 6,303,121 | B1 | 10/2001 | Kwon |
| 6,312,700 | B1 | 11/2001 | Weinberg |
| 6,350,861 | B1 | 2/2002 | Co et al. |
| 6,352,694 | B1 | 3/2002 | June et al. |
| 6,362,325 | B1 | 3/2002 | Kwon |
| 6,410,517 | B1 | 6/2002 | Truong et al. |
| 6,475,994 | B2 | 11/2002 | Tomalia et al. |
| 6,479,626 | B1 | 11/2002 | Kim et al. |
| 6,489,458 | B2 | 12/2002 | Hackett et al. |
| 6,528,624 | B1 | 3/2003 | Idusogie et al. |
| 6,534,055 | B1 | 3/2003 | June et al. |
| 6,534,261 | B1 | 3/2003 | Cox et al. |
| 6,534,484 | B1 | 3/2003 | Wheeler et al. |
| 6,538,124 | B1 | 3/2003 | Idusogie et al. |
| 6,569,997 | B1 | 5/2003 | Kwon |
| 6,607,882 | B1 | 8/2003 | Cox et al. |
| 6,627,442 | B1 | 9/2003 | Humeau et al. |
| 6,706,289 | B2 | 3/2004 | Lewis et al. |
| 6,737,056 | B1 | 5/2004 | Presta |
| 6,746,838 | B1 | 6/2004 | Choo et al. |
| 6,794,136 | B1 | 9/2004 | Eisenberg et al. |
| 6,821,505 | B2 | 11/2004 | Ward |
| 6,824,978 | B1 | 11/2004 | Cox et al. |
| 6,866,997 | B1 | 3/2005 | Choo et al. |
| 6,867,041 | B2 | 3/2005 | Berenson et al. |
| 6,887,466 | B2 | 5/2005 | June et al. |
| 6,887,673 | B2 | 5/2005 | Kunkel et al. |
| 6,903,185 | B2 | 6/2005 | Kim et al. |
| 6,905,680 | B2 | 6/2005 | June et al. |
| 6,905,681 | B1 | 6/2005 | June et al. |
| 6,905,685 | B2 | 6/2005 | Kwon |
| 6,933,113 | B2 | 8/2005 | Case et al. |
| 6,974,863 | B2 | 12/2005 | Kwon |
| 6,979,539 | B2 | 12/2005 | Cox et al. |
| 6,998,253 | B1 | 2/2006 | Presta et al. |
| 7,013,219 | B2 | 3/2006 | Case et al. |
| 7,030,215 | B2 | 4/2006 | Liu et al. |
| 7,083,784 | B2 | 8/2006 | Dall'Acqua et al. |
| 7,144,575 | B2 | 12/2006 | June et al. |
| 7,175,843 | B2 | 2/2007 | June et al. |
| 7,189,705 | B2 | 3/2007 | Lam et al. |
| 7,214,493 | B2 | 5/2007 | Jure-Kunkel et al. |
| 7,220,719 | B2 | 5/2007 | Case et al. |
| 7,232,566 | B2 | 6/2007 | June et al. |
| 7,241,573 | B2 | 7/2007 | Choo et al. |
| 7,241,574 | B2 | 7/2007 | Choo et al. |
| 7,288,638 | B2 | 10/2007 | Jure-Kunkel et al. |
| 7,479,269 | B2 | 1/2009 | June et al. |
| 7,504,101 | B2 | 3/2009 | Weinberg |
| 7,550,140 | B2 | 6/2009 | Bakker et al. |
| 7,572,631 | B2 | 8/2009 | Berenson et al. |
| 7,585,849 | B2 | 9/2009 | Liu et al. |
| 7,595,376 | B2 | 9/2009 | Kim et al. |
| 7,622,444 | B2 | 11/2009 | Weinberg |
| 7,687,070 | B2 | 3/2010 | Gebeyehu et al. |
| 7,696,175 | B2 | 4/2010 | Epstein et al. |
| 7,943,743 | B2 | 5/2011 | Korman et al. |
| 7,951,365 | B2 | 5/2011 | Winqvist et al. |
| 7,960,515 | B2 | 6/2011 | Min et al. |
| 8,007,785 | B2 | 8/2011 | Winqvist et al. |
| 8,008,449 | B2 | 8/2011 | Korman et al. |
| 8,034,334 | B2 | 10/2011 | Dudley et al. |
| 8,133,983 | B2 | 3/2012 | Bakker et al. |
| 8,168,757 | B2 | 5/2012 | Finnefrock et al. |
| 8,206,702 | B2 | 6/2012 | Winqvist et al. |
| 8,211,424 | B2 | 7/2012 | Winqvist et al. |
| 8,211,425 | B2 | 7/2012 | Winqvist et al. |
| 8,217,149 | B2 | 7/2012 | Irving et al. |
| 8,236,930 | B2 | 8/2012 | Min et al. |
| 8,287,856 | B2 | 10/2012 | Li et al. |
| 8,287,857 | B2 | 10/2012 | Dudley et al. |
| 8,337,850 | B2 | 12/2012 | Ahrens et al. |
| 8,354,509 | B2 | 1/2013 | Carven et al. |
| 8,383,099 | B2 | 2/2013 | Dudley et al. |
| 8,450,460 | B2 | 5/2013 | Hill et al. |
| 8,580,247 | B2 | 11/2013 | Li et al. |
| 8,617,884 | B2 | 12/2013 | Berenson et al. |
| 8,686,119 | B2 | 4/2014 | Rotem-Yehudar et al. |
| 8,697,359 | B1 | 4/2014 | Zhang |
| 8,735,553 | B1 | 5/2014 | Li et al. |
| 8,771,945 | B1 | 7/2014 | Zhang |
| 8,779,108 | B2 | 7/2014 | Queva et al. |
| 8,795,965 | B2 | 8/2014 | Zhang |
| 8,809,050 | B2 | 8/2014 | Vera et al. |
| 8,821,867 | B2 | 9/2014 | Ahrens et al. |
| 8,865,406 | B2 | 10/2014 | Zhang et al. |
| 8,871,445 | B2 | 10/2014 | Cong et al. |
| 8,889,356 | B2 | 11/2014 | Zhang |
| 8,895,308 | B1 | 11/2014 | Zhang et al. |

(56) References Cited

U.S. PATENT DOCUMENTS

| | | | |
|---|---|---|---|
| 8,906,616 B2 | 12/2014 | Zhang et al. |
| 8,907,053 B2 | 12/2014 | Sasikumar et al. |
| 8,921,519 B2 | 12/2014 | Hill et al. |
| 8,932,814 B2 | 1/2015 | Zhang et al. |
| 8,945,839 B2 | 2/2015 | Zhang |
| 8,956,860 B2 | 2/2015 | Vera et al. |
| 8,962,804 B2 | 2/2015 | Williams et al. |
| 8,993,233 B2 | 3/2015 | Zhang et al. |
| 8,999,641 B2 | 4/2015 | Zhang et al. |
| 9,006,399 B2 | 4/2015 | Liu et al. |
| 9,028,824 B2 | 5/2015 | Min et al. |
| 9,044,442 B2 | 6/2015 | Sasikumar et al. |
| 9,074,185 B2 | 7/2015 | Dudley et al. |
| 9,080,171 B2 | 7/2015 | Khvorova et al. |
| 9,096,642 B2 | 8/2015 | Sasikumar et al. |
| 9,163,085 B2 | 10/2015 | Liu et al. |
| 9,340,599 B2 | 5/2016 | Hill et al. |
| 9,359,420 B2 | 6/2016 | Hill et al. |
| 9,468,678 B2 | 10/2016 | Ahrens et al. |
| 9,476,028 B2 | 10/2016 | Karlsson-Parra et al. |
| 9,528,088 B2 | 12/2016 | Berenson et al. |
| 9,687,510 B2 | 6/2017 | Borrello et al. |
| 9,844,569 B2 | 12/2017 | Gros et al. |
| 9,914,783 B1 | 3/2018 | Afar et al. |
| 10,130,659 B2 | 11/2018 | Wardell |
| 10,363,273 B2 | 7/2019 | Wardell |
| 10,517,894 B2 | 12/2019 | Frank |
| 10,537,595 B2 | 1/2020 | Wardell |
| 10,653,723 B1 | 5/2020 | Wardell |
| 10,894,063 B2 | 1/2021 | Wardell et al. |
| 10,905,718 B2 | 2/2021 | Wardell |
| 10,918,666 B2 | 2/2021 | Wardell |
| 10,933,094 B2 | 3/2021 | Wardell |
| 10,946,044 B2 | 3/2021 | Wardell |
| 10,946,045 B2 | 3/2021 | Wardell |
| 10,953,046 B2 | 3/2021 | Wardell |
| 10,953,047 B2 | 3/2021 | Wardell |
| 11,013,770 B1 | 5/2021 | Wardell |
| 11,026,974 B2 | 6/2021 | Frank |
| 11,168,303 B2 | 11/2021 | Wardell |
| 11,168,304 B2 | 11/2021 | Wardell |
| 11,220,670 B2 | 1/2022 | Simpson-Abelson |
| 11,254,913 B1 | 2/2022 | Wardell |
| 11,293,009 B2 | 4/2022 | Simpson-Abelson |
| 11,344,579 B2 | 5/2022 | Wardell et al. |
| 11,351,198 B2 | 6/2022 | Frank |
| 11,357,841 B2 | 6/2022 | Ritthipichai |
| 11,401,507 B2 | 8/2022 | Simpson-Abelson |
| 11,433,097 B2 | 9/2022 | Fardis |
| 11,517,592 B1 | 12/2022 | Wardell |
| 11,529,372 B1 | 12/2022 | Wardell |
| 11,541,077 B2 | 1/2023 | Wardell |
| 11,631,483 B2 | 4/2023 | Brooks |
| 11,713,446 B2 | 8/2023 | Chartier-Courtaud |
| 11,819,517 B2 | 11/2023 | Wardell |
| 2004/0110704 A1 | 6/2004 | Yamane et al. |
| 2005/0095244 A1 | 5/2005 | Jure-Kunkel et al. |
| 2005/0106717 A1 | 5/2005 | Wilson et al. |
| 2009/0028857 A1 | 1/2009 | Li et al. |
| 2010/0136030 A1 | 6/2010 | Salah-Eddine et al. |
| 2010/0203056 A1 | 8/2010 | Irving et al. |
| 2010/0266617 A1 | 10/2010 | Carven et al. |
| 2010/0285013 A1 | 11/2010 | Li et al. |
| 2011/0008369 A1 | 1/2011 | Finnefrock et al. |
| 2011/0027218 A1 | 2/2011 | Hill et al. |
| 2011/0039914 A1 | 2/2011 | Pavco et al. |
| 2011/0052530 A1 | 3/2011 | Dudley et al. |
| 2011/0111494 A1 | 5/2011 | Hill et al. |
| 2011/0136228 A1 | 6/2011 | Vera et al. |
| 2011/0201118 A1 | 8/2011 | Yang et al. |
| 2012/0244133 A1 | 9/2012 | Rosenberg et al. |
| 2013/0022600 A1 | 1/2013 | Li et al. |
| 2013/0034559 A1 | 2/2013 | Queva et al. |
| 2013/0045200 A1 | 2/2013 | Irving et al. |
| 2013/0045201 A1 | 2/2013 | Irving et al. |

| | | | |
|---|---|---|---|
| 2013/0045202 A1 | 2/2013 | Irving et al. |
| 2013/0102075 A1 | 4/2013 | Vera et al. |
| 2013/0108651 A1 | 5/2013 | Carven et al. |
| 2013/0109843 A1 | 5/2013 | Carven et al. |
| 2013/0115617 A1 | 5/2013 | Wilson |
| 2013/0131141 A1 | 5/2013 | Khvorova et al. |
| 2013/0131142 A1 | 5/2013 | Libertine et al. |
| 2013/0315884 A1 | 11/2013 | Galetto et al. |
| 2014/0065135 A1 | 3/2014 | Irving et al. |
| 2014/0227237 A1 | 8/2014 | June et al. |
| 2014/0255368 A1 | 9/2014 | Kim et al. |
| 2014/0294898 A1 | 10/2014 | Miller et al. |
| 2014/0328791 A1 | 11/2014 | Bossard et al. |
| 2014/0341917 A1 | 11/2014 | Nastri et al. |
| 2014/0377284 A1 | 12/2014 | Simons et al. |
| 2014/0377739 A1 | 12/2014 | Welch et al. |
| 2015/0073024 A1 | 3/2015 | Sasikumar et al. |
| 2015/0073042 A1 | 3/2015 | Sasikumar et al. |
| 2015/0087581 A1 | 3/2015 | Sasikumar et al. |
| 2015/0110734 A1 | 4/2015 | Hill et al. |
| 2015/0125491 A1 | 5/2015 | Sasikumar et al. |
| 2015/0126709 A1 | 5/2015 | Hill et al. |
| 2015/0126710 A1 | 5/2015 | Hill et al. |
| 2015/0132288 A1 | 5/2015 | Simons et al. |
| 2015/0175966 A1 | 6/2015 | Vera et al. |
| 2015/0190506 A1 | 7/2015 | Cheung et al. |
| 2015/0203871 A1 | 7/2015 | Juillerat et al. |
| 2015/0320798 A1 | 11/2015 | Borrello et al. |
| 2016/0010058 A1 | 1/2016 | Gros et al. |
| 2016/0120906 A1 | 5/2016 | Galetto et al. |
| 2016/0208216 A1 | 7/2016 | Vera et al. |
| 2016/0215262 A1 | 7/2016 | Powell |
| 2016/0304873 A1 | 10/2016 | Wolfson et al. |
| 2017/0044496 A1 | 2/2017 | Sarnaik et al. |
| 2017/0081635 A1 | 3/2017 | Sarnaik et al. |
| 2017/0107490 A1 | 4/2017 | Maeurer |
| 2017/0114321 A1 | 4/2017 | Berenson et al. |
| 2017/0152478 A1 | 6/2017 | Rosenberg et al. |
| 2017/0258838 A1 | 9/2017 | Borrello et al. |
| 2018/0127715 A1 | 5/2018 | Veerapathran et al. |
| 2018/0148690 A1 | 5/2018 | Gros et al. |
| 2018/0187150 A1 | 7/2018 | De Larichaudy |
| 2018/0207201 A1 | 7/2018 | Wardell et al. |
| 2018/0228841 A1* | 8/2018 | Frank .............. A61K 39/46449 |
| 2018/0280436 A1 | 10/2018 | Wardell et al. |
| 2019/0000070 A1 | 1/2019 | De Larichaudy et al. |
| 2019/0062706 A1 | 2/2019 | Almaasbak et al. |
| 2019/0136186 A1 | 5/2019 | Germeroth et al. |

FOREIGN PATENT DOCUMENTS

| | | |
|---|---|---|
| CN | 106591232 A | 4/2017 |
| CN | 107384867 A | 11/2017 |
| EP | 0154316 A2 | 9/1985 |
| EP | 0401384 A1 | 12/1990 |
| EP | 0404097 A2 | 12/1990 |
| EP | 0672141 B1 | 9/1995 |
| EP | 1176195 A1 | 1/2002 |
| EP | 1539929 B1 | 4/2013 |
| EP | 2925329 A1 | 10/2015 |
| EP | 3188740 A1 | 7/2017 |
| EP | 3365434 A1 | 8/2018 |
| EP | 3368659 A1 | 9/2018 |
| EP | 3487990 A1 | 5/2019 |
| JP | 2021-535128 A | 12/2021 |
| KR | 10-2018-0101584 A | 9/2018 |
| TW | 201839129 A | 11/2018 |
| TW | 202031273 A | 9/2020 |
| WO | WO 1988007089 A1 | 9/1988 |
| WO | WO 1990014074 A1 | 11/1990 |
| WO | WO 1991016024 A1 | 10/1991 |
| WO | WO 1991017424 A1 | 11/1991 |
| WO | WO 1993011161 A1 | 6/1993 |
| WO | WO 1995012673 A1 | 5/1995 |
| WO | WO 1995021925 A1 | 8/1995 |
| WO | WO 1996014339 A1 | 5/1996 |
| WO | WO 1998030679 A1 | 1/1998 |
| WO | WO 1998005787 A1 | 2/1998 |
| WO | WO 1998013526 A1 | 4/1998 |

(56) References Cited

FOREIGN PATENT DOCUMENTS

| | | | |
|---|---|---|---|
| WO | WO 1998023289 A1 | 6/1998 |
| WO | WO 1999051642 A1 | 10/1999 |
| WO | WO 1999054342 A1 | 10/1999 |
| WO | WO 1999058572 A1 | 11/1999 |
| WO | WO 2000009560 A2 | 2/2000 |
| WO | WO 2000032767 A2 | 6/2000 |
| WO | WO 2000042072 A2 | 7/2000 |
| WO | WO 2002044215 A2 | 6/2002 |
| WO | WO 2002060919 A2 | 8/2002 |
| WO | WO 2003035835 A3 | 5/2003 |
| WO | WO 2003074569 A2 | 9/2003 |
| WO | WO 2004016750 A2 | 2/2004 |
| WO | WO 2004029207 A2 | 4/2004 |
| WO | WO 2004031370 A1 | 4/2004 |
| WO | WO 2004035752 A2 | 4/2004 |
| WO | WO 2004063351 A2 | 7/2004 |
| WO | WO 2004074455 A2 | 9/2004 |
| WO | WO 2004099249 A2 | 11/2004 |
| WO | WO 2005040217 A2 | 5/2005 |
| WO | WO 2005070963 A1 | 8/2005 |
| WO | WO 2005077981 A2 | 8/2005 |
| WO | WO 2005092925 A2 | 10/2005 |
| WO | WO 2005123780 A2 | 12/2005 |
| WO | WO 2006019447 A1 | 2/2006 |
| WO | WO 2006047350 A2 | 5/2006 |
| WO | WO 2006085967 A2 | 8/2006 |
| WO | WO 2006121168 A1 | 11/2006 |
| WO | WO 2006121810 A2 | 11/2006 |
| WO | WO 2008025516 A2 | 3/2008 |
| WO | WO 2008156712 A1 | 12/2008 |
| WO | WO 2009007120 A2 | 1/2009 |
| WO | WO 2009040789 A2 | 4/2009 |
| WO | WO 2009045457 A2 | 4/2009 |
| WO | WO 2009102427 A2 | 8/2009 |
| WO | WO 2010003766 A2 | 1/2010 |
| WO | WO 2010010051 A1 | 1/2010 |
| WO | WO 2010033246 A1 | 3/2010 |
| WO | WO 2010033247 A2 | 3/2010 |
| WO | WO 2010042433 A1 | 4/2010 |
| WO | WO 2010078966 A1 | 7/2010 |
| WO | WO 2011072088 A2 | 6/2011 |
| WO | WO 2011119852 A1 | 9/2011 |
| WO | WO 2011119887 A1 | 9/2011 |
| WO | WO 2012027328 A2 | 3/2012 |
| WO | WO 2012032433 A1 | 3/2012 |
| WO | WO 2012065086 A1 | 5/2012 |
| WO | WO 2012177788 A1 | 6/2012 |
| WO | WO 2012129201 A1 | 9/2012 |
| WO | WO 2013028231 A1 | 2/2013 |
| WO | WO 2013038191 A2 | 3/2013 |
| WO | WO 2013057500 A1 | 4/2013 |
| WO | WO 2013059343 A1 | 4/2013 |
| WO | WO 2013088147 A1 | 6/2013 |
| WO | WO 2013173835 A1 | 11/2013 |
| WO | WO 2013188427 A1 | 12/2013 |
| WO | WO 2014148895 A1 | 9/2014 |
| WO | WO 2014210036 A1 | 12/2014 |
| WO | WO 2015009604 A1 | 1/2015 |
| WO | WO 2015119923 A1 | 2/2015 |
| WO | WO 2015033301 A1 | 3/2015 |
| WO | WO 2015036927 A1 | 3/2015 |
| WO | WO 2015157636 A1 | 10/2015 |
| WO | WO 2015188839 A1 | 12/2015 |
| WO | WO 2015189356 A1 | 12/2015 |
| WO | WO 2015189357 A1 | 12/2015 |
| WO | WO 2016053338 A1 | 4/2016 |
| WO | WO 2016096903 A1 | 6/2016 |
| WO | WO 2017001784 A1 | 1/2017 |
| WO | WO 2017008063 A1 | 1/2017 |
| WO | WO 2017048614 A1 | 3/2017 |
| WO | WO 2017070151 A1 | 4/2017 |
| WO | WO 2017123663 A1 | 7/2017 |
| WO | 2017132508 A1 | 8/2017 |
| WO | WO-2017197347 A1 * | 11/2017 | ............ A61K 35/17 |
| WO | WO 2018005712 A1 | 1/2018 |
| WO | 2018081789 A8 | 5/2018 |
| WO | WO 2018081473 A1 | 5/2018 |
| WO | WO 2018094167 A1 | 5/2018 |
| WO | WO 2018102761 A1 | 6/2018 |
| WO | WO 2018129332 A1 | 7/2018 |
| WO | WO 2018129336 A1 | 7/2018 |
| WO | WO 2018170188 A2 | 9/2018 |
| WO | WO 2018182817 A1 | 10/2018 |
| WO | WO 2018209115 A1 | 11/2018 |
| WO | WO 2018226714 A1 | 12/2018 |
| WO | WO 2020096682 A2 | 5/2020 |

OTHER PUBLICATIONS

Besser, Michael J., et al. "Modifying interleukin-2 concentrations during culture improves function of T cells for adoptive immunotherapy." Cytotherapy 11.2 (2009): 206-21 (Year: 2009).*

En-Avi, Ronny, et al. "Establishment of adoptive cell therapy with tumor infiltrating lymphocytes for non-small cell lung cancer patients." Cancer Immunology, Immunotherapy 67.8 (2018): 1221-1230 (Year: 2018).*

AACR Annual Meeting: Phase 2 Study to Assess the Efficacy and Safety of Autologous Tumour Infiltrating Lymphocytes (LN-145) Alone and In Combination with Anti-PD-L1 Inhibitor Durvalumab (MEDI4736) in Patients with Locally Advanced or Metastatic Non-Small Cell Lung Cancer (NSCLC).

Ahmad, Zuhaida Asra et al. "scFv antibody: principles and clinical application." *Clinical & developmental immunology* vol. 2012 (2012): 980250. doi:10.1155/2012/980250.

Akkök, C. A. et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60. doi:10.3109/14653240902980443.

Andersen, Rikke et al. "Long-Lasting Complete Responses in Patients with Metastatic Melanoma after Adoptive Cell Therapy with Tumor-Infiltrating Lymphocytes and an Attenuated IL2 Regimen." Clinical cancer research : an official journal of the American Association for Cancer Research vol. 22,15 (2016): 3734-45. doi:10. 1158/1078-0432.CCR-15-1879.

Anonymous et al: "NCT03645928 Study of Autologous Tumor Infiltrating Lymphocytes in Patients With Solid Tumors", Clinicaltrials. gov, Aug. 22, 2018, Retrieved from the Internet: URL:https:// clinicaltrials.gov/ct2/history/NCT03645928?V _ 1 =View#StudyPageTop.

Augustyns, K et al. "Incorporation of hexose nucleoside analogues into oligonucleotides: synthesis, base-pairing properties and enzymatic stability." *Nucleic acids research* vol. 20,18 (1992): 4711-6. doi:10.1093/nar/20.18.4711.

Axelsson et al., "Cryopreserved peripheral blood mononuclear cells are suitable for the assessment of immunological markers in type 1 diabetic children", Cryobiology, Aug. 2008, 57, 201-208.

Bajgain, P. et al., "Optimizing the production of suspension cells using the G-Rex "M" series", Molecular Therapy—Methods and Clinical Development, vol. 1, Jan. 1, 2014.

Baruch et al., "Adoptive T cell therapy: An overview of obstacles and opportunities : ACT Obstacles and Opportunities", Cancer, vol. 123, No. S11, May 19, 2017, pp. 2154-2162.

Beane, Joal D et al. "Clinical Scale Zinc Finger Nuclease-mediated Gene Editing of PD-1 in Tumor Infiltrating Lymphocytes for the Treatment of Metastatic Melanoma." *Molecular therapy : the journal of the American Society of Gene Therapy* vol. 23,8 (2015): 1380-1390. doi:10.1038/mt.2015.71.

Ben-Avi, Ronny et al. "Establishment of adoptive cell therapy with tumor infiltrating lymphocytes for non-small cell lung cancer patients." Cancer immunology, immunotherapy : CII vol. 67,8 (2018): 1221-1230. doi:10.1007/s00262-018-2174-4.

Bergan, R et al. "Electroporation enhances c-myc antisense oligodeoxynucleotide efficacy." *Nucleic acids research* vol. 21,15 (1993): 3567-73. doi:10.1093/nar/21.15.3567.

Besser, Michal J et al. "Adoptive transfer of tumor-infiltrating lymphocytes in patients with metastatic melanoma: intent-to-treat analysis and efficacy after failure to prior immunotherapies." *Clini-*

(56)  References Cited

OTHER PUBLICATIONS

*cal cancer research : an official journal of the American Association for Cancer Research* vol. 19,17 (2013): 4792-800. doi:10.1158/1078-0432.CCR-13-0380.

Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55. doi:10.1158/1078-0432.CCR-10-0041.

Besser, Michal J et al. "Minimally cultured or selected autologous tumor-infiltrating lymphocytes after a lympho-depleting chemotherapy regimen in metastatic melanoma patients." *Journal of immunotherapy* (Hagerstown, Md. : 1997) vol. 32,4 (2009): 415-23. doi:10.1097/CJI.0b013e31819c8bda.

Bird, R E et al. "Single-chain antigen-binding proteins." *Science* (New York, N.Y.) vol. 242,4877 (1988): 423-6. doi:10.1126/science.3140379.

Brahmer, et al., J. Clin. Oncol. 2014, 32, 5s (supplement, abstract 8021).

Byrne, Michael et al. "Novel hydrophobically modified asymmetric RNAi compounds (sd-rxRNA) demonstrate robust efficacy in the eye." *Journal of ocular pharmacology and therapeutics : the official journal of the Association for Ocular Pharmacology and Therapeutics* vol. 29,10 (2013): 855-64. doi:10.1089/jop.2013.0148.

Cepko, C, and W Pear. "Overview of the retrovirus transduction system." *Current protocols in molecular biology* vol. Chapter 9 (2001): Unit9.9. doi:10.1002/0471142727.mb0909s36.

Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS ONE, vol. 8, No. 4, Apr. 1, 2013, 25 pages.

Chang C.-H. et al., "Metabolic competition in the tumor microenvironment is a driver of cancer progression", Cell., Sep. 10, 2015, vol. 162, No. 6, pp. 1229-1241.

Chang, Chih-Hao, and Erika L Pearce. "Emerging concepts of T cell metabolism as a target of immunotherapy." *Nature immunology* vol. 17,4 (2016): 364-8. doi:10.1038/ni.3415.

Chen, C, and H Okayama. "High-efficiency transformation of mammalian cells by plasmid DNA." *Molecular and cellular biology* vol. 7,8 (1987): 2745-52. doi:10.1128/mcb.7.8.2745-2752.1987.

Cieri, Nicoletta et al. "IL-7 and IL-15 instruct the generation of human memory stem T cells from naive precursors." *Blood* vol. 121,4 (2013): 573-84. doi:10.1182/blood-2012-05-431718.

Cox, David Benjamin Turitz et al. "Therapeutic genome editing: prospects and challenges." *Nature medicine* vol. 21,2 (2015): 121-31. doi:10.1038/nm.3793.

Curti, Brendan D et al. "OX40 is a potent immune-stimulating target in late-stage cancer patients." *Cancer research* vol. 73,24 (2013): 7189-7198. doi:10.1158/0008-5472.CAN-12-4174.

Dang, T. et al. "Pembrolizumab for the treatment of PD-L1 positive advanced or metastatic non-small cell lung cancer." Expert review of anticancer therapy vol. 16,1 (2016): 13-20. doi:10.1586/14737140.2016.1123626.

De Marco, Ario. "Biotechnological applications of recombinant single-domain antibody fragments." *Microbial cell factories* vol. 10 44. Jun. 9, 2011, doi: 10.1186/1475-2859-10-44.

Donia M, et al., Simplified protocol for clinical-grade tumor-infiltrating lymphocyte manufacturing with use of the Wave bioreactor. Cytotherapy. Aug. 2014; 16(8):1117-20. doi:10.1016/j.jcyt.2014.02.004; PubMed PMID: 24831841.

Donia, M et al. "Characterization and comparison of 'standard' and 'young' tumour-infiltrating lymphocytes for adoptive cell therapy at a Danish translational research institution." *Scandinavian journal of immunology* vol. 75,2 (2012): 157-67. doi:10.1111/j.1365-3083.2011.02640.x.

Dudley, Mark E et al. "Adoptive cell therapy for patients with metastatic melanoma: evaluation of intensive myeloablative chemoradiation preparative regimens." *Journal of clinical oncology : official journal of the American Society of Clinical Oncology* vol. 26,32 (2008): 5233-9. doi:10.1200/JCO.2008.16.5449.

Dudley, Mark E et al. "Adoptive cell transfer therapy following non-myeloablative but lymphodepleting chemotherapy for the treatment of patients with refractory metastatic melanoma." *Journal of clinical oncology : official journal of the American Society of Clinical Oncology* vol. 23,10 (2005): 2346-57. doi:10.1200/JCO.2005.00.240.

Dudley, Mark E et al. "Cancer regression and autoimmunity in patients after clonal repopulation with antitumor lymphocytes." *Science* (New York, N. Y.) vol. 298,5594 (2002): 850-4. doi:10.1126/science.1076514.

Dudley, Mark E et al. "CD8+ enriched 'young' tumor infiltrating lymphocytes can mediate regression of metastatic melanoma." *Clinical cancer research : an official journal of the American Association for Cancer Research* vol. 16,24 (2010): 6122-31. doi:10.1158/1078-0432.CCR-10-1297.

Dudley, Mark E et al. "Generation of tumor-infiltrating lymphocyte cultures for use in adoptive transfer therapy for melanoma patients." *Journal of immunotherapy* (Hagerstown, Md. : 1997) vol. 26,4 (2003): 332-42. doi:10.1097/00002371-200307000-00005.

Dull, T et al. "A third-generation lentivirus vector with a conditional packaging system." *Journal of virology* vol. 72,11 (1998): 8463-71. doi:10.1128/JVI.72.11.8463-8471.1998.

Eisenhauer, E A et al. "New response evaluation criteria in solid tumours: revised RECIST guideline (version 1.1)." *European journal of cancer* (Oxford, England : 1990) vol. 45,2 (2009): 228-47. doi:10.1016/j.ejca.2008.10.026.

Eton, O et al. "A phase II study of 'decrescendo' interleukin-2 plus interferon-alpha-2a in patients with progressive metastatic melanoma after chemotherapy." *Cancer* vol. 88,7 (2000): 1703-9.

Fehniger, T A, and M A Caligiuri. "Interleukin 15: biology and relevance to human disease." *Blood* vol. 97,1 (2001): 14-32. doi:10.1182/blood.v97.1.14.

Felgner, P L et al. "Lipofection: a highly efficient, lipid-mediated DNA-transfection procedure." *Proceedings of the National Academy of Sciences of the United States of America* vol. 84,21 (1987): 7413-7. doi:10.1073/pnas.84.21.7413.

Fisher, Timothy S et al. "Targeting of 4-1BB by monoclonal antibody PF-05082566 enhances T-cell function and promotes antitumor activity." *Cancer immunology, immunotherapy : CII* vol. 61,10 (2012): 1721-33. doi:10.1007/s00262-012-1237-1.

Forget et al., "Activation and propagation of tumor infiltrating lymphocytes on clinical-grade designer artificial antigen presenting cells for adoptive immunotherapy of melanoma", Journal of Immunotherapy, vol. 37 No.9, Nov. 1, 2014, pp. 448-460.

Forget, Marie-Andrée et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015, doi:10.1080/2162402X.2015.1057386.

Frank et al., "Remarkably Stable Tumor-Infiltrating Lymphocytes (TIL) for Infusion Phenotype Following Cryopreservation", Nov. 6, 2016, Retrieved from the Internet: http://www.iovance.com/wp-content/uploads/2017/05/LION16701_Frank_POSTER3_final-0005.

Fry, Terry J, and Crystal L Mackall. "Interleukin-7: from bench to clinic." *Blood* vol. 99,11 (2002): 3892-904. doi:10.1182/blood.v99.11.3892.

Fuerst, Mark "Metastatic Melanoma Immunotherapy with Pembrolizumab Induces Durable Responses," *Oncology Times* vol. 36, 13 (2014): 35-36. doi:10.1097/01.COT.0000452086.09862.55.

Garaud, Soizic et al. "A simple and rapid protocol to non-enzymatically dissociate fresh human tissues for the analysis of infiltrating lymphocytes." Journal of visualized experiments : JoVE , 94 52392. Dec. 6, 2014, doi:10.3791/52392.

Gassner, Franz Josef et al. "Fludarabine modulates composition and function of the T cell pool in patients with chronic lymphocytic leukaemia." *Cancer immunology, immunotherapy : CII* vol. 60,1 (2011): 75-85. doi:10.1007/s00262-010-0920-3.

Gattinoni, Luca et al. "A human memory T cell subset with stem cell-like properties." *Nature medicine* vol. 17,10 1290-7. Sep. 18, 2011, doi:10.1038/nm.2446.

Gattinoni, Luca et al. "Adoptive immunotherapy for cancer: building on success." *Nature reviews. Immunology* vol. 6,5 (2006): 383-93. doi:10.1038/nri1842.

(56) References Cited

OTHER PUBLICATIONS

Gattinoni, Luca et al. "Paths to stemness: building the ultimate antitumour T cell." *Nature reviews. Cancer* vol. 12,10 (2012): 671-84. doi:10.1038/nrc3322.

Gattinoni, Luca et al. "Wnt signaling arrests effector T cell differentiation and generates CD8+ memory stem cells." *Nature medicine* vol. 15,7 (2009): 808-13. doi:10.1038/nm.1982.

Gieffers, Christian et al. "APG350 induces superior clustering of TRAIL receptors and shows therapeutic antitumor efficacy independent of cross-linking via Fcγ receptors." *Molecular cancer therapeutics* vol. 12,12 (2013): 2735-47. doi:10.1158/1535-7163. MCT-13-0323.

Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014. 98.

Glassman, A B, and C E Bennett. "Cryopreservation of human lymphocytes: a brief review and evaluation of an automated liquid nitrogen freezer." Transfusion vol. 19,2 (1979): 178-81. doi:10. 1046/j.1537-2995.1979.19279160289.x.

Goff, Stephanie L et al. "Randomized, Prospective Evaluation Comparing Intensity of Lymphodepletion Before Adoptive Transfer of Tumor-Infiltrating Lymphocytes for Patients With Metastatic Melanoma." *Journal of clinical oncology : official journal of the American Society of Clinical Oncology* vol. 34,20 (2016): 2389-97. doi:10.1200/JCO.2016.66.7220.

Goff, Stephanie L et al. "Tumor infiltrating lymphocyte therapy for metastatic melanoma: analysis of tumors resected for TIL." *Journal of immunotherapy* (Hagerstown, Md. : 1997) vol. 33,8 (2010): 840-7. doi:10.1097/CJI.0b013e3181f05b91.

Graham, FL, and A J van der Eb. "A new technique for the assay of infectivity of human adenovirus 5 DNA." *Virology* vol. 52,2 (1973): 456-67. doi:10.1016/0042-6822(73)90341-3.

Griesbeck, Morgane et al. "Sex Differences in Plasmacytoid Dendritic Cell Levels of IRF5 Drive Higher IFN-α Production in Women." *Journal of immunology* (Baltimore, Md. : 1950) vol. 195,11 (2015): 5327-36. doi:10.4049/jimmunol.1501684.

Hackett, Perry B et al. "A transposon and transposase system for human application." *Molecular therapy : the journal of the American Society of Gene Therapy* vol. 18,4 (2010): 674-83. doi:10.1038/mt.2010.2.

Hall et al., "Expansion of tumor-infiltrating lymphocytes (TIL) from human pancreatic tumors", Journal for Immuno Therapy of Cancer, vol. 4, No. 1, pp. 1-12.

Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.

He, Jia et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Henning AL,et al . . . Measurement of T-Cell Telomere Length Using Amplified-Signal FISH Staining and Flow Cytometry. Curr Protoc Cytom. Jan. 5, 2017;79:7.47.1-7.47.10. doi:10.1002/cpcy.11. PubMed PMID 28055115.

Hernandez-Chacon et al., "Costimulation through the CD137/4-1BB Pathway Protects Human Melanoma Tumor-infiltrating Lymphocytes from Activation-induced Cell Death and Enhances Antitumor Effector Function", Journal of ImmunoTherapy, vol. 34, No. 3, Apr. 1, 2011, pp. 236-250.

Hinrichs CS, Rosenberg SA. Exploiting the curative potential of adoptive T-cell therapy for cancer. Immunol Rev. Jan. 2014;257(1):56-71. doi:10.1111/imr.12132. Review. PubMed PMID: 24329789; PubMed Central PMCID: PMC3920180.

Holliger, P et al. ""Diabodies": small bivalent and bispecific antibody fragments." *Proceedings of the National Academy of Sciences of the United States of America* vol. 90,14 (1993): 6444-8. doi:10. 1073/pnas.90.14.6444.

Huang, Jianping et al. "Survival, persistence, and progressive differentiation of adoptively transferred tumor-reactive T cells associated with tumor regression." *Journal of immunotherapy* (Hagerstown, Md. : 1997) vol. 28,3 (2005): 258-67. doi:10.1097/01.cji.0000158855. 92792.7a.

Huston, J S et al. "Protein engineering of antibody binding sites: recovery of specific activity in an anti-digoxin single-chain Fv analogue produced in *Escherichia coli*." *Proceedings of the National Academy of Sciences of the United States of America* vol. 85,16 (1988): 5879-83. doi:10.1073/pnas.85.16.5879.

Ikarashi, H et al., "Solid-phase anti-CD3 antibody activation and cryopreservation of human tumor-infiltrating lymphocytes derived from epithelial ovarian cancer", Japanese Journal of Cancer Research, vol. 83, No. 12, Dec. 1, 1992.

International Search Report and Written Opinion for International Patent Application No. PCT/US2019/059720 dated Apr. 9, 2020, 11 pages.

International Preliminary Report on Patentability for International Patent Application No. PCT/US2019/059720 dated May 11, 2021, 7 pages.

Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20. doi:10.1097/CJI. 0b013e318209c94c.

Iyer, R.K. et al., "Industrializing Autologous Adoptive Immunotherapies: Manufacturing Advances and Challenges", Frontiers in Medicine, vol. 5, May 23, 2018.

Jin et al., "Enhanced clinical-scale manufacturing of TCR transduced T-cells using closed culture system modules", Journal of Transactional Medicine, col. 16. No. 1, Jan. 24, 2018.

Jin, Jianjian et al. "Simplified method of the growth of human tumor infiltrating lymphocytes in gas-permeable flasks to numbers needed for patient treatment." *Journal of immunotherapy* (Hagerstown, Md. : 1997) vol. 35,3 (2012): 283-92. doi:10.1097/CJI. 0b013e31824e801f.

Jones, P T et al. "Replacing the complementarity-determining regions in a human antibody with those from a mouse." *Nature* vol. 321,6069 (1986): 522-5. doi:10.1038/321522a0.

Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi:10.3109/14653249.2011.563291.

Katz, Steven C et al. "Phase I Hepatic Immunotherapy for Metastases Study of Intra-Arterial Chimeric Antigen Receptor-Modified T-cell Therapy for CEA+ Liver Metastases." Clinical cancer research : an official journal of the American Association for Cancer Research vol. 21,14 (2015): 3149-59. doi:10.1158/1078-0432.CCR-14-1421.

Keir, Mary E et al. "PD-1 and its ligands in tolerance and immunity." *Annual review of immunology* vol. 26 (2008): 677-704. doi:10.1146/annurev.immunol.26.021607.090331.

Khvorova, Anastasia, and Jonathan K Watts. "The chemical evolution of oligonucleotide therapies of clinical utility." *Nature biotechnology* vol. 35,3 (2017): 238-248. doi:10.1038/nbt.3765.

Klapper, J.A. et al., "Single-pass, closed-system rapid expansion of lymphocyte cultures for adoptive cell therapy", Journal of Immunological Methods, vol. 345, No. 1-2, Jun. 30, 2009.

Lee et al., "Tumor-Infiltrating Lymphocytes in Melanoma", Curr Oncol Rep. Aug. 2012, 14, 468-474.

Lee, Do Y et al. "4-1BB signaling activates the t cell factor 1 effector/β-catenin pathway with delayed kinetics via ERK signaling and delayed PI3K/AKT activation to promote the proliferation of CD8+ T Cells." *PloS one* vol. 8,7 e69677. Jul. 11, 2013, doi:10. 1371/journal.pone.0069677.

Levine, Bruce L et al. "Gene transfer in humans using a conditionally replicating lentiviral vector." *Proceedings of the National Academy of Sciences of the United States of America* vol. 103,46 (2006): 17372-7. doi:10.1073/pnas.0608138103.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi: 10.4049/jimmunol.0901101. Epub Nov. 30, 2009. PubMed PMID: 19949105.

Ligtenberg, Maarten A et al. "Self-Delivering RNAi Targeting PD-1 Improves Tumor-Specific T Cell Functionality for Adoptive Cell Therapy of Malignant Melanoma." *Molecular therapy : the journal*

(56)        References Cited

OTHER PUBLICATIONS

*of the American Society of Gene Therapy* vol. 26,6 (2018): 1482-1493. doi:10.1016/j.ymthe.2018.04.015.

Malek, Thomas R. "The biology of interleukin-2." *Annual review of immunology* vol. 26 (2008): 453-79. doi:10.1146/annurev.immunol.26.021607.090357.

McDermott, David et al. "Durable benefit and the potential for long-term survival with immunotherapy in advanced melanoma." *Cancer treatment reviews* vol. 40,9 (2014): 1056-64. doi:10.1016/j.ctrv.2014.06.012.

Meng, Qingda et al. "Expansion of Tumor-reactive T Cells From Patients With Pancreatic Cancer." Journal of immunotherapy (Hagerstown, Md. : 1997) vol. 39,2 (2016): 81-9. doi:10.1097/CJI.0000000000000111.

Merhavi-Shoham et al., "Adoptive Cell Therapy for Metastatic Melanoma", Cancer Journal, vol. 23, No. 1, Jan. 1, 2017.

Monnier, Philippe, et al. "In Vivo Applications of Single Chain Fv (Variable Domain) (ScFv) Fragments." *Antibodies,* vol. 2, No. 4, Apr. 2013, pp. 193-208. https://doi.org/10.3390/antib2020193.

Mullinax et al., "Combination of Ipilimumab and Adoptive Cell Therapy with Tumor-Infiltrating Lymphocytes for Patients with Metastatic Melanoma", Frontiers in Oncology, vol. 8, Mar. 2, 2018.

Muranski, Pawel et al. "Increased intensity lymphodepletion and adoptive immunotherapy—how far can we go ?." *Nature clinical practice. Oncology* vol. 3,12 (2006): 668-81. doi:10.1038/ncponc0666.

NCT03374839, ClinicalTrials.gov.

Nelson, Brad H. "IL-2, regulatory T cells, and tolerance." *Journal of immunology* (Baltimore, MD. : 1950) vol. 172,7 (2004): 3983-8. doi:10.4049/jimmunol.172.7.3983.

Nguyen, Linh T et al. "Expansion and characterization of human melanoma tumor-infiltrating lymphocytes (TILs)." PloS one vol. 5,11 e13940. Nov. 10, 2010, doi:10.1371/journal.pone.0013940.

O'Day, S J et al. "Advantages of concurrent biochemotherapy modified by decrescendo interleukin-2, granulocyte colony-stimulating factor, and tamoxifen for patients with metastatic melanoma." *Journal of clinical oncology : official journal of the American Society of Clinical Oncology* vol. 17,9 (1999): 2752-61. doi:10.1200/JCO.1999.17.9.2752.

Page, David B et al. "Immune modulation in cancer with antibodies." *Annual review of medicine* vol. 65 (2014): 185-202. doi:10.1146/annurev-med-092012-112807.

Peng, Weiyi et al. "PD-1 blockade enhances T-cell migration to tumors by elevating IFN-γ inducible chemokines." *Cancer research* vol. 72,20 (2012): 5209-18. doi:10.1158/0008-5472.CAN-12-1187.

Pilon-Thomas, Shari et al. "Efficacy of adoptive cell transfer of tumor-infiltrating lymphocytes after lymphopenia induction for metastatic melanoma." *Journal of immunotherapy* (Hagerstown, Md. : 1997) vol. 35,8 (2012): 615-20. doi:10.1097/CJI.0b013e31826e8f5f.

Presta, L G. "Antibody engineering." *Current Opinion in Structural Biology* (1992) 2:593-6. doi:10.1016/0958-1669(92)90168-i.

Radvanyi, Laszlo G et al. "Specific lymphocyte subsets predict response to adoptive cell therapy using expanded autologous tumor-infiltrating lymphocytes in metastatic melanoma patients." *Clinical cancer research : an official journal of the American Association for Cancer Research* vol. 18,24 (2012): 6758-70. doi:10.1158/1078-0432.CCR-12-1177.

Riddell, S R et al. "Restoration of viral immunity in immunodeficient humans by the adoptive transfer of T cell clones." *Science* (New York, N.Y.) vol. 257,5067 (1992): 238-41. doi:10.1126/science.1352912.

Riechmann, L et al. "Reshaping human antibodies for therapy." *Nature* vol. 332,6162 (1988): 323-7. doi:10.1038/332323a0.

Robbins, Paul F et al. "Cutting edge: persistence of transferred lymphocyte clonotypes correlates with cancer regression in patients receiving cell transfer therapy." *Journal of immunology* (Baltimore, Md. : 1950) vol. 173,12 (2004): 7125-30. doi:10.4049/jimmunol.173.12.7125.

Robert, Caroline et al. "Anti-programmed-death-receptor-1 treatment with pembrolizumab in ipilimumab-refractory advanced melanoma: a randomised dose-comparison cohort of a phase 1 trial." *Lancet* (London, England) vol. 384,9948 (2014): 1109-17. doi:10.1016/S0140-6736(14)60958-2.

Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.

Rose, J K et al. "A new cationic liposome reagent mediating nearly quantitative transfection of animal cells." *Bio Techniques* vol. 10,4 (1991): 520-5.

Rosenberg SA, Dudley ME. Adoptive cell therapy for the treatment of patients with metastatic melanoma. Curr Opin Immunol. Apr. 2009;21(2):233-40.

Rosenberg, "IL-2: The First Effective Immunotherapy for Human Cancer," The Journal of Immunology, col. 192, No. 12, Jun. 6, 2014.

Rosenberg, S A et al. "A new approach to the adoptive immunotherapy of cancer with tumor-infiltrating lymphocytes." Science (New York, N.Y.) vol. 233,4770 (1986): 1318-21. doi:10.1126/science.3489291.

Rosenberg, S A et al. "Treatment of patients with metastatic melanoma with autologous tumor-infiltrating lymphocytes and interleukin 2." Journal of the National Cancer Institute vol. 86,15 (1994): 1159-66. doi:10.1093/jnci/86.15.1159.

Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80. doi:10.1056/NEJM198812223192527.

Rosenberg, Steven A et al. "Durable complete responses in heavily pretreated patients with metastatic melanoma using T-cell transfer immunotherapy." *Clinical cancer research : an official journal of the American Association for Cancer Research* vol. 17,13 (2011): 4550-7. doi:10.1158/1078-0432.CCR-11-0116.

Ruby, et al. "OX40-Enhanced Tumor Rejection and Effector T Cell Differentiation Decreases with Age." J Immunol Feb. 1, 2009; 182 (3): 1481-1489. https://doi.org/10.4049/jimmunol.182.3.1481.

Rufer N, et al., "Telomere length dynamics in human lymphocyte subpopulations measured by flow cytometry", Nat Biotechnol. Aug. 1998;16(8):743-7. PubMed PMID: 9702772.

Sadeghi, Arian et al. "Rapid expansion of T cells: Effects of culture and cryopreservation and importance of short-term cell recovery." *Acta oncologica* (Stockholm, Sweden) vol. 52,5 (2013): 978-86. doi:10.3109/0284186X.2012.737020.

Saint-Jean, M. et al. "Adoptive Cell Therapy with Tumor-Infiltrating Lymphocytes in Advanced Melanoma Patients." Journal of immunology research vol. 2018 3530148. Mar. 19, 2018, doi:10.1155/2018/3530148.

Santegoets, Saskia J A M et al. "IL-21 promotes the expansion of CD27+ CD28+ tumor infiltrating lymphocytes with high cytotoxic potential and low collateral expansion of regulatory T cells." *Journal of translational medicine* vol. 11 37. Feb. 12, 2013, doi:10.1186/1479-5876-11-37.

Schiltz, P M et al. "Characterization of tumor-infiltrating lymphocytes derived from human tumors for use as adoptive immunotherapy of cancer." *Journal of immunotherapy* (Hagerstown, Md. : 1997) vol. 20,5 (1997): 377-86. doi:10.1097/00002371-199709000-00007.

Segal, Neil H et al. "Results from an Integrated Safety Analysis of Urelumab, an Agonist Anti-CD137 Monoclonal Antibody." *Clinical cancer research : an official journal of the American Association for Cancer Research* vol. 23,8 (2017): 1929-1936. doi:10.1158/1078-0432.CCR-16-1272.

Sharei, Armon et al. "A vector-free microfluidic platform for intracellular delivery." *Proceedings of the National Academy of Sciences of the United States of America* vol. 110,6 (2013): 2082-7. doi:10.1073/pnas.1218705110.

Sharei, Armon et al. "Ex vivo cytosolic delivery of functional macromolecules to immune cells." *PloS one* vol. 10,4 e0118803. Apr. 13, 2015, doi:10.1371/journal.pone.0118803.

Shen, Xinglei et al. "Persistence of tumor infiltrating lymphocytes in adoptive immunotherapy correlates with telomere length." *Journal of immunotherapy* (Hagerstown, Md. : 1997) vol. 30,1 (2007): 123-9. doi:10.1097/01.cji.0000211321.07654.b8.

(56)          References Cited

OTHER PUBLICATIONS

Shields, Robert L et al. "Lack of fucose on human IgG1 N-linked oligosaccharide improves binding to human Fcgamma RIII and antibody-dependent cellular toxicity." *The Journal of biological chemistry* vol. 277,30 (2002): 26733-40. doi:10.1074/jbc. M202069200.
Smith, Corey et al. "Ex vivo expansion of human T cells for adoptive immunotherapy using the novel Xeno-free CTS Immune Cell Serum Replacement." *Clinical & translational immunology* vol. 4,1 e31. Jan. 16, 2015, doi:10.1038/cti.2014.31.
Somerville RP, et al . . . Clinical scale rapid expansion of lympho-cytes for adoptive cell transfer therapy in the WAVE® bioreactor. J Transl Med. Apr. 4, 2012;10:69.
Spiess, P J et al. "In vivo antitumor activity of tumor-infiltrating lymphocytes expanded in recombinant interleukin-2." *Journal of the National Cancer Institute* vol. 79,5 (1987): 1067-75.
Spolski, Rosanne, and Warren J Leonard. "Interleukin-21: a double-edged sword with therapeutic potential." *Nature reviews. Drug discovery* vol. 13,5 (2014): 379-95. doi:10.1038/nrd4296.
Steinke, J W, and L Borish. "Th2 cytokines and asthma. Interleukin-4: its role in the pathogenesis of asthma, and targeting it for asthma treatment with interleukin-4 receptor antagonists." *Respiratory research* vol. 2,2 (2001): 66-70. doi:10.1186/rr40.
Swartz, Melody A et al. "Tumor microenvironment complexity: emerging roles in cancer therapy." *Cancer research* vol. 72,10 (2012): 2473-80. doi:10.1158/0008-5472.CAN-12-0122.
Tarentino, A L et al. "The isolation and structure of the core oligosaccharide sequences of IgM." *Biochemistry* vol. 14,25 (1975): 5516-23. doi:10.1021/bi00696a021.
Thomas, Anish, and Marko Jakopovic. "Immunotherapy for non-small-cell lung cancer." *Expert opinion on biological therapy* vol. 14,8 (2014): 1061-4. doi:10.1517/14712598.2014.925874.
Topalian, Suzanne L et al. "Safety, activity, and immune correlates of anti-PD-1 antibody in cancer." *The New England journal of medicine* vol. 366,26 (2012): 2443-54. doi:10.1056/NEJMoa1200690.
Tran, Khoi Q et al. "Minimally cultured tumor-infiltrating lympho-cytes display optimal characteristics for adoptive cell therapy." *Journal of immunotherapy* (Hagerstown, Md. : 1997) vol. 31,8 (2008): 742-51. doi:10.1097/CJI.0b013e31818403d5.
Tsong, T Y. "Electroporation of cell membranes." *Biophysical journal* vol. 60,2 (1991): 297-306. doi:10.1016/S0006-3495(91)82054-9.
Tsoukas, C D et al. "Activation of resting T lymphocytes by anti-CD3 (T3) antibodies in the absence of monocytes." *Journal of immunology* (Baltimore, Md. : 1950) vol. 135,3 (1985): 1719-23.
Umaña, P et al. "Engineered glycoforms of an antineuroblastoma IgG1 with optimized antibody-dependent cellular cytotoxic activ-ity." *Nature biotechnology* vol. 17,2 (1999): 176-80. doi:10.1038/6179.
Van den Bossche, J. et al. "Metabolic Characterization of Polarized M1 and M2 Bone Marrow-derived Macrophages Using Real-time Extracellular Flux Analysis." Journal of visualized experiments : JoVE , 105 53424. Nov. 28, 2015, doi:10.3791/53424.
Wang & Riviere, "Manufacture of tumor- and virus-specific T lymphocytes for adoptive cell therapies", Cancer Gene Therapy, 2015, 22: 85-94.
Wang, Changyu et al. "In vitro characterization of the anti-PD-1 antibody nivolumab, BMS-936558, and in vivo toxicology in non-human primates." *Cancer immunology research* vol. 2,9 (2014): 846-56. doi:10.1158/2326-6066.CIR-14-0040.
Ward, E S et al. "Binding activities of a repertoire of single immunoglobulin variable domains secreted from *Escherichia coli.*" *Nature* vol. 341,6242 (1989): 544-6. doi:10.1038/341544a0.
Wardell et al., "A cryopreserved tumor infiltrating lymphocyte (TIL) product for LN-44", Nov. 8, 2017, retrieved from the Internet: URL:http://www.iovance.com/wp-content/uploads/2017/11/SITC2017_Seth_poster_FINAL_SWDE_PRINT_7Nov2017.pdf.
Weber, Jeffrey S et al. "Safety, efficacy, and biomarkers of nivolumab with vaccine in ipilimumab-refractory or -naive melanoma." *Jour-nal of clinical oncology : official journal of the American Society of Clinical Oncology* vol. 31,34 (2013): 4311-8. doi:10.1200/JCO. 2013.51.4802.
Weinberg, Andrew D et al. "Anti-OX40 (CD134) administration to nonhuman primates: immunostimulatory effects and toxicokinetic study." *Journal of immunotherapy* (Hagerstown, Md. : 1997) vol. 29,6 (2006): 575-85. doi:10.1097/01.cji.0000211319.00031.fc.
Wigler, M et al. "DNA-mediated transfer of the adenine phosphoribosyltransferase locus into mammalian cells." *Proceed-ings of the National Academy of Sciences of the United States of America* vol. 76,3 (1979): 1373-6. doi:10.1073/pnas.76.3.1373.
Wilson Wolf—Superior Cell Culture Devices, G-Rex, Oct. 31, 2016.
Wu, Richard et al. "Adoptive T-cell therapy using autologous tumor-infiltrating lymphocytes for metastatic melanoma: current status and future outlook." Cancer journal (Sudbury, Mass.) vol. 18,2 (2012): 160-75. doi:10.1097/PPO.0b013e31824d4465.
Yamane-Ohnuki, Naoko et al. "Establishment of FUT8 knockout Chinese hamster ovary cells: an ideal host cell line for producing completely defucosylated antibodies with enhanced antibody-dependent cellular cytotoxicity." *Biotechnology and bioengineering* vol. 87,5 (2004): 614-22. doi:10.1002/bit.20151.
Ye, et al., "Engineered Artificial antigen presenting cells facilitate direct and efficient expansion of tumor infiltrating lymphocytes", J. Translat. Med. 2011, 9(131), 13 pages.
Zhou J, et al . . . Telomere length of transferred lymphocytes correlates with in vivo persistence and tumor regression in mela-noma patients receiving cell transfer therapy. J Immunol. Nov. 15, 2005;175(10):7046-52. PubMed PMID: 16272366; PubMed Cen-tral PMCID: PMC135131.
Zhou, Juhua et al. "Persistence of multiple tumor-specific T-cell clones is associated with complete tumor regression in a melanoma patient receiving adoptive cell transfer therapy." *Journal of immunotherapy* (Hagerstown, Md. : 1997) vol. 28,1 (2005): 53-62. doi:10.1097/00002371-200501000-00007.
Zufferey, R et al. "Multiply attenuated lentiviral vector achieves efficient gene delivery in vivo." *Nature biotechnology* vol. 15,9 (1997): 871-5. doi:10.1038/nbt0997-871.
Zuliani, T. et al., "Value of large scale expansion of tumor infil-trating lymphocytes in a compartmentalised gas-permiable bag: interests for adoptive immunotherapy", Journal of Translational Medicine, vol. 9, No. 1, May 16, 2011.
Feldman, SA et al. "Adoptive Cell Therapy-Tumor-Infiltrating Lymphocytes, T-Cell Receptors, and Chimeric Antigen Receptors", Semin. Oncol., vol. 42, No. 4, pp. 626-639, 2015.
Gandhi, L. et al., "Efficacy and safety of entinostat (ENT) and pembrolizumab (PEMBRO) in patients with non-small cell lung cancer (NSCLC) previously treated with anti-PD-(L)1 therapy." Journal of Clinical Oncology, vol. 36, No. 15 (suppl), pp. 9036-9036, 2018.
Gettinger, Set. al. "Impaired HLA Class I Antigen Processing and Presentation as a Mechanism of Acquired Resistance to Immune Checkpoint Inhibitors in Lung Cancer", Cancer Discovery, vol. 7, No. 12, pp. 1420-1435, 2017.
Hellmann, M. et al: "OA05.01 Efficacy/Safety of Entinostat (ENT) and Pembrolizumab (PEMBRO) in NSCLC Patients Previously Treated with Anti-PD-(L)1 Therapy", Journal of Thoracic Oncol-ogy, vol. 13, No. 10, p. S330, Oct. 1, 2018.
Lee, S. et al., "Phase 2 Study to Assess the Efficacy and Safety of Autologous Tumor Infiltrating Lymphocytes (LN-145) Alone and In Combination with Anti-PD-L1 Inhibitor Durvalumab (MEDI4736) in Patients with Locally Advanced or Metastatic Non-small Cell Lung Cancer (NSCLC)", AACR Annual Meeting, pp. Poster CT173, https://www.iovance.com/uploads/AACR2018_NSCLC_TIPposter_FINAL_PRINT_14APR2018.pdf, Apr. 14, 2018 (Apr. 14, 2018), [retrieved on Feb. 8, 2024].
Marusyk, A et al., "Intra-tumour heterogeneity: a looking glass for cancer?" Nature reviews, vol. 12, No. 5, pp. 323-334, Apr. 19, 2012.
Merck & Co, Inc., KEYTRUDA FDA Prescribing Information, Revised May 2017, Reference ID 4098283, Merck Sharp & Dohme Corp., a subsidiary of Merck & Co., Inc., Whitehouse Station, NJ

(56)         References Cited

OTHER PUBLICATIONS

08889, USA. Retrieved from https://www.accessdata.fda.gov/drugsatfda_docs/label/2017/125514s013lbl.pdf; accessed on Oct. 27, 2025.

NCCN.org, "NCCN Clinical Practice Guidelines in Oncology (NCCN Guidelines): Non-Small Cell Lung Cancer," Version 2.2018, Dec. 19, 2017. Retrieved from https://www2.tri-kobe.org/nccn/guideline/archive/lung2018/english/non_small.pdf; accessed on Oct. 27, 2025.

Ratto, G. B. et al., "A Randomized Trial of Adoptive Immunotherapy with Tumor-Infiltrating Lymphocytes and Interleukin-2 versus Standard Therapy in the Postoperative Treatment of Resected Nonsmall Cell Lung Carcinoma," Cancer, vol. 78, No. 2, pp. 244-251, May 1, 1996.

Rosenberg SA, et al. "Durable Complete Responses in Heavily Pretreated Patients with Metastatic Melanoma Using T Cell Transfer Immunotherapy", Clinical Cancer research, vol. 17, No. 13, pp. 4550-4557, Jul. 1, 2011.

Samejima, J. et al. "Prognostic impact of bulky swollen lymph nodes in cN1 non-small cell lung cancer patients", JJCO, vol. 45, No. 11, pp. 1050-1054, 2015.

Schalper, KA et al., "Objective Measurement and Clinical Significance of TILs in Non-Small Cell Lung Cancer," J Natl Cancer Inst, vol. 107, No. 3, pp. 1-9, 2015.

Schoenfeld, AJ et al., "First Phase 2 Results of Autologous Tumor-Infiltrating Lymphocyte (LN-145) Monotherapy in Patients with Advanced, Immune Checkpoint Inhibitor-Treated, Non-Small Cell Lung Cancer (Nsclc)," SITC 2021, Nov. 10-14, 2021, p. 458, Washington DC and Virtual.

Shah, S et al. "Clinical and molecular features of innate and acquired resistance to anti-PD-1/PD-L1 therapy in lung cancer", Oncotarget, vol. 9, No. 4, pp. 4375-4384, 2017.

Wang, Q and Wu, X, "Primary and acquired resistance to PD-1/PD-L1 blockade in cancer treatment", International Immunopharmacology, vol. 46, pp. 210-219, 2017.

Yoneda, Ket. al. "Immune Checkpoint Inhibitors (ICIs) in Non-Small Cell Lung Cancer (NSCLC)", J UOEH, vol. 40, No. 2, pp. 173-189, Jun. 2018.

* cited by examiner

FIG. 1

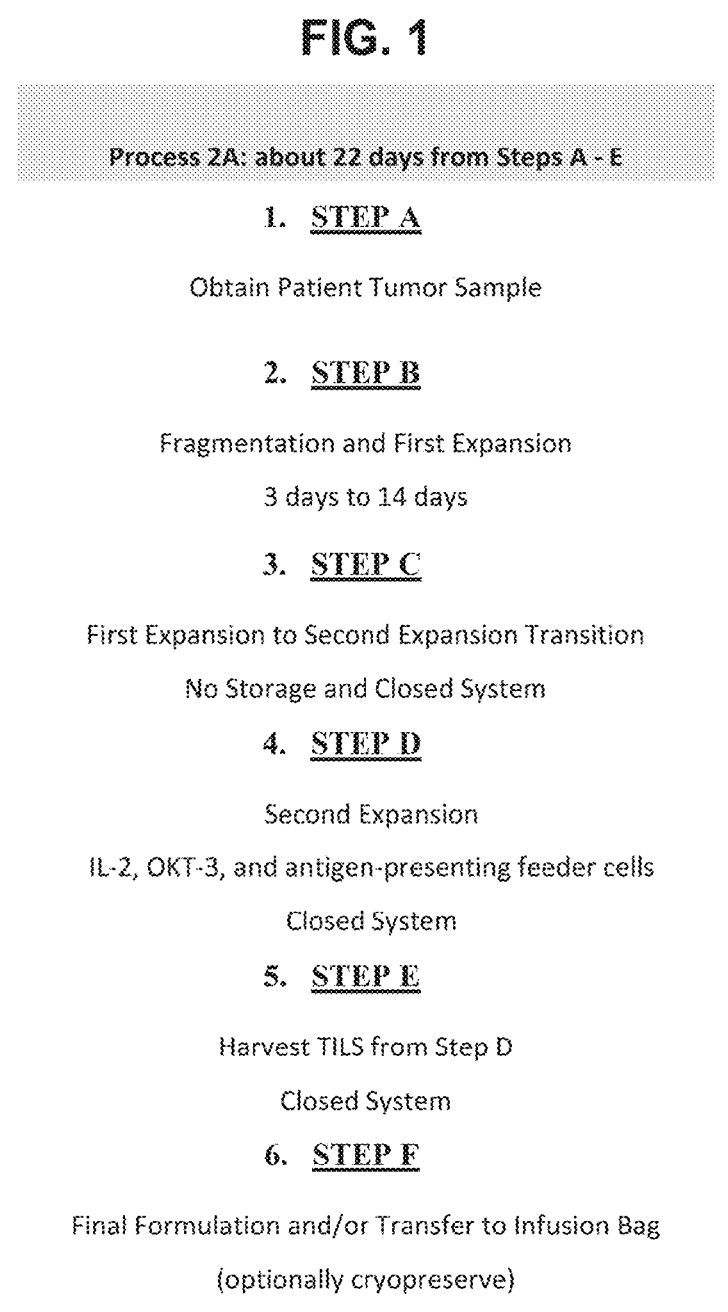

Process 2A: about 22 days from Steps A - E

1. ## STEP A

Obtain Patient Tumor Sample

2. ## STEP B

Fragmentation and First Expansion 3 days to 14 days

3. ## STEP C

First Expansion to Second Expansion Transition

No Storage and Closed System

4. ## STEP D

Second Expansion

IL-2, OKT-3, and antigen-presenting feeder cells

Closed System

5. ## STEP E

Harvest TILS from Step D

Closed System

6. ## STEP F

Final Formulation and/or Transfer to Infusion Bag (optionally cryopreserve)

REP PD Process PFD

REP PD Process
PFD

```
Spent Medium          supernate    Pool supernate              Mycoplasma
removal ≤ 5x     →                  10L Bioprocess      →       PCR
G-Rex 500MCS                        bag(s)                      Sample
                                                                Diluent
        ↓
3L Cell culture Bag (Origen
EV3000 or equivalent)
        ↓
Cell Count & Viability
NC-200
4x 1mL sample
        ↓
Wash Buffer        Volume Reduction LOVO           Formulate
PL-A + 1%     →    2 Cycles, 10:1 concentration  → 1:1 with cold CS10*
HSA                4000 RPM, 75mL/min
                                                        ↓
        IL-2                        Add IL-2
        300 IU/mL          →
```

*Formulate bulk
Product Bag stored
at 2-8°C in between
processing steps

Satellite Vial Prep

```
Cryopreserved         Remove                        Aliquot into CS750
Satellite Vial        QC Release Test Samples   ←   cryobags 90-120mL/
Sample           ←    & Air (Mycoplasma, Endotoxin,  bag
10 x 0.5mL/vial       Sterility, Gram Stain, Cell         ↓
                      Count, viability, flow,
        ↓             INF-g, Retain) (20mL)
                                                    Controlled Rate
Manual Fill                               →         Freeze
0.5 mL / vial                                       Preset-6 Profile
                                                        ↓
                                                    Visually Inspect
                                                        ↓
                                                    Store in vapor
                                                    phase LN
                                                        ↓
REP PD Process                                      Ship*
 PFD
```

FIG. 5

| Process 1C: 43-55 Days for Steps A - E | Process 2A: about 22 days from Steps A - E |
|---|---|
| 1. STEP A<br>Obtain Patient Tumor Sample | 1. STEP A<br>Obtain Patient Tumor Sample |
| 2. STEP B<br>Fragmentation and First Expansion<br>11 days to 21 days | 2. STEP B<br>Fragmentation and First Expansion<br>3 days to 14 days |
| 3. STEP C<br>First Expansion to Second Expansion Transition<br>Optional Storage until Selection | 3. STEP C<br>First Expansion to Second Expansion Transition<br>No Storage and Closed System |
| 4. STEP D<br>Second Expansion<br>IL-2, OKT-3, antigen-presenting feeder cells<br>Optionally repeat one or more times | 4. STEP D<br>Second Expansion<br>IL-2, OKT-3, and antigen-presenting feeder cells<br>Closed System |
| 5. STEP E<br>Harvest TILS from Step D | 5. STEP E<br>Harvest TILS from Step D<br>Closed System |
| 6. STEP F<br>Final Formulation and/or Transfer to Infusion Bag | 6. STEP F<br>Final Formulation and/or Transfer to Infusion Bag<br>(optionally cryopreserve) |

FIG. 6

| Process Step | Process 1C Embodiment | Process 2A Embodiment | Advantages |
|---|---|---|---|
| Pre-REP | • 4 fragments per 10 GREX-10 flasks<br><br>• 11-21 day duration | • 40 fragments per 1 GREX-100M flask<br><br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br><br>• REP requires >40×10⁶ TIL | • Pre-REP TIL directly move to REP on day 11<br><br>• REP requires 25-200×10⁶ TIL | • Shortened pre-REP-to-REP process<br><br>• Reduced number of steps<br><br>• Eliminated phenotyping selection<br>• Amenable to closed system |
| REP | • 6 GREX-100M flasks on REP day 0<br>• 5×10⁶ TIL and 5×10⁸ PBMC feeders per flask on REP day 0<br><br>• Split to 18-36 flasks on REP day 7<br><br>• 14 day duration | • 1 GREX-500M flask on day 11<br>• 25-200×10⁶ TIL and 5x10⁹ PBMC feeders on day 11<br>• Split to ≤ 6 GREX-500M flasks on day 16<br><br>• 11 day duration | • Reduced number of steps<br><br>• Shorter REP duration<br><br>• Closed system transfer of TIL between flasks<br><br>• Closed system media exchanges |
| Harvest | • TIL harvested via centrifugation | • TIL harvested via LOVO automated cell washing system' | • Reduced number of steps<br>• Automated cell washing<br>• Closed system<br>• Reduced loss of product during wash |
| Final Formulation | • Fresh product in Hypothermosol<br><br>• Single infusion bag<br>• Limited shipping stability | • Cyropreserved product in PlasmaLyte-A + 1% HSA and CS10 stored in LN₂<br>• Multiple aliquots<br>• Longer shipping stability | • Shipping flexibility<br><br>• Flexible patient scheduling<br>• More timely release testing |
| Overall Estimated Process Time | • 43-55 days | • 22 days | • Faster turnaround to patient |

Day 0: Tumor / biopsy prep

Day 0: Pre-REP Initiation

Day 5-8: REP initiation

Day 9 to 11: REP Scale Up

Day 12 to16: Harvest

FIG. 8A

| Process 2A: about 22 days from Steps A - E | Process GEN 3: about 14-18 days from Steps A - E |
|---|---|
| STEP A<br>Obtain Patient Tumor Sample<br>(optionally can be frozen before Step B) | STEP A<br>Obtain Patient Tumor Sample<br>(optionally can be frozen before Step B) |
| STEP B<br>First Expansion<br>(physical fragmentation to at least 40 fragments per container grown for about 3 days to 14 days with media comprising IL-2) | STEP B<br>Priming First Expansion<br>(physical fragmentation of up to 60 fragments per container grown for about 1 days to 7 days with media comprising IL-2, OKT-3, and antigen-presenting feeder cells) |
| STEP C<br>First Expansion to Second Expansion Transition<br>(Step B TILs directly move to Step D, optionally on Step B day 11) | STEP C<br>Priming First Expansion to Rapid Second Expansion Transition<br>(Step B TILs directly move to Step D on day 7) |
| STEP D<br>Second Expansion<br>(TILs grown in growth media medium comprising IL-2, OKT-3, and antigen-presenting feeder cells in a closed container) | STEP D<br>Rapid Second Expansion<br>(TILs grown in growth media medium comprising IL-2, OKT-3, and 2X antigen-presenting feeder cells; Days 10-11 scale up and add additional IL-2) |
| STEP E<br>Harvest TILS from Step D<br>(TILs harvested via closed system) | STEP E<br>Harvest TILS from Step D |
| STEP F<br>Final Formulation and/or Transfer to Infusion Bag<br>(optionally cryopreserve) | STEP F<br>Final Formulation and/or Transfer to Infusion Bag<br>(optionally cryopreserve) |

FIG. 8B

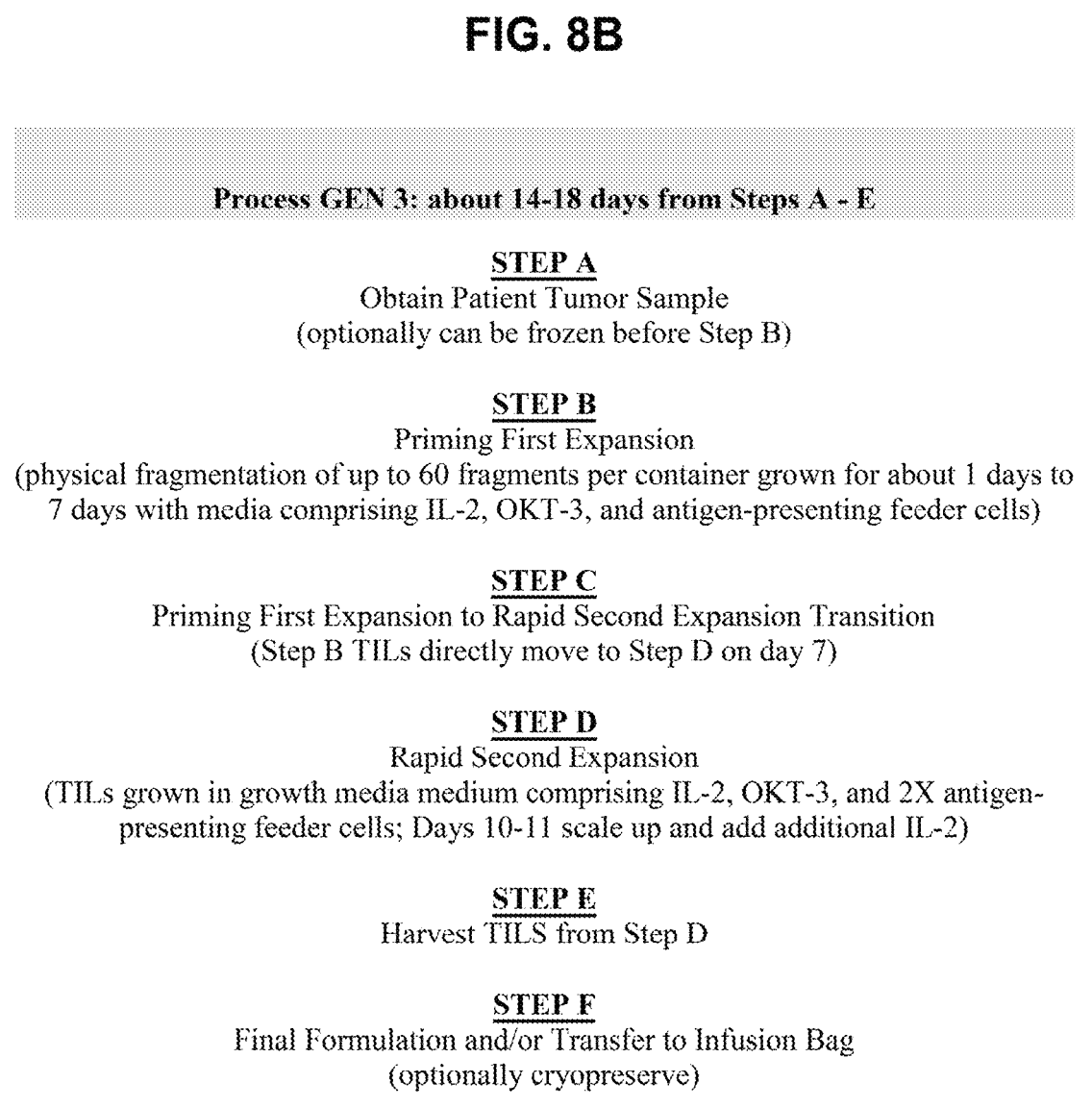

Process GEN 3: about 14-18 days from Steps A - E

STEP A
Obtain Patient Tumor Sample
(optionally can be frozen before Step B)

STEP B
Priming First Expansion
(physical fragmentation of up to 60 fragments per container grown for about 1 days to
7 days with media comprising IL-2, OKT-3, and antigen-presenting feeder cells)

STEP C
Priming First Expansion to Rapid Second Expansion Transition
(Step B TILs directly move to Step D on day 7)

STEP D
Rapid Second Expansion
(TILs grown in growth media medium comprising IL-2, OKT-3, and 2X antigen-
presenting feeder cells; Days 10-11 scale up and add additional IL-2)

STEP E
Harvest TILS from Step D

STEP F
Final Formulation and/or Transfer to Infusion Bag
(optionally cryopreserve)

FIG. 8C

| Embodiment GEN 3.0: about 14-18 days from Steps A - E | Embodiment GEN 3.1 control: about 14-18 days from Steps A - E | Embodiment GEN 3.1 Test/F: about 14-18 days from Steps A - E |
|---|---|---|
| STEP A Obtain Patient Tumor Sample (optionally can be frozen before Step B) | STEP A Obtain Patient Tumor Sample (optionally can be frozen before Step B) | STEP A Obtain Patient Tumor Sample (optionally can be frozen before Step B) |
| STEP B Priming First Expansion (physical fragmentation of up to 60 fragments per container grown for about 1 days to 7/8 days with media comprising IL-2) | STEP B Priming First Expansion (physical fragmentation of up to 60 fragments per container grown for about 1 days to 7/8 days with media comprising IL-2, and OKT-3) | STEP B Priming First Expansion (physical fragmentation of up to 60 fragments per container grown for about 1 days to 7/8 days with media comprising IL-2, OKT-3, and antigen-presenting feeder cells) |
| STEP C Priming First Expansion to Rapid Second Expansion Transition (Step B TILs directly move to Step D on day 7/8) | STEP C Priming First Expansion to Rapid Second Expansion Transition (Step B TILs directly move to Step D on day 7/8) | STEP C Priming First Expansion to Rapid Second Expansion Transition (Step B TILs directly move to Step D on day 7/8) |
| STEP D Rapid Second Expansion (TILs grown in growth media medium comprising IL-2, OKT-3, and antigen-presenting feeder cells; Days 10-11 scale up and add additional IL-2) | STEP D Rapid Second Expansion (TILs grown in growth media medium comprising IL-2, OKT-3, and 2X antigen-presenting feeder cells; Days 10-11 scale up and add additional IL-2) | STEP D Rapid Second Expansion (TILs grown in growth media medium comprising IL-2, OKT-3, and 2X antigen-presenting feeder cells; Days 10-11 scale up and add additional IL-2) |
| STEP E Harvest TILS from Step D | STEP E Harvest TILS from Step D | STEP E Harvest TILS from Step D |
| STEP F Final Formulation and/or Transfer to Infusion Bag (optionally cryopreserve) | STEP F Final Formulation and/or Transfer to Infusion Bag (optionally cryopreserve) | STEP F Final Formulation and/or Transfer to Infusion Bag (optionally cryopreserve) |

FIG. 11

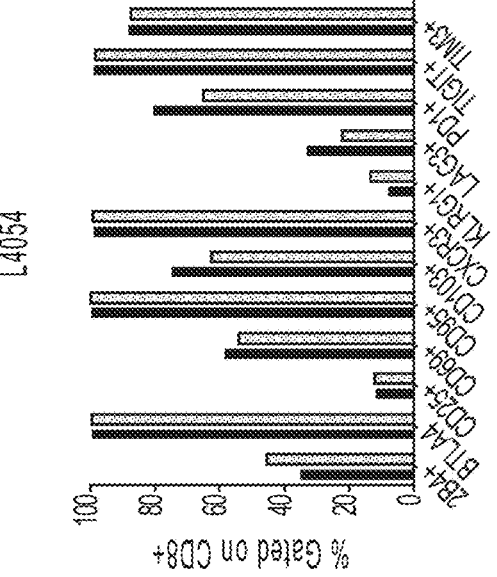
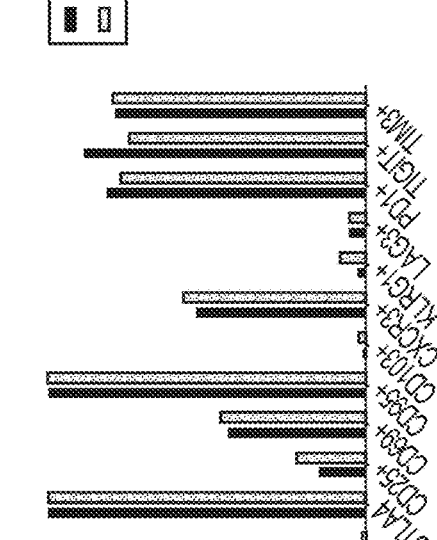
FIG. 12

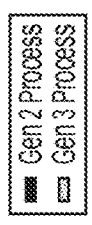
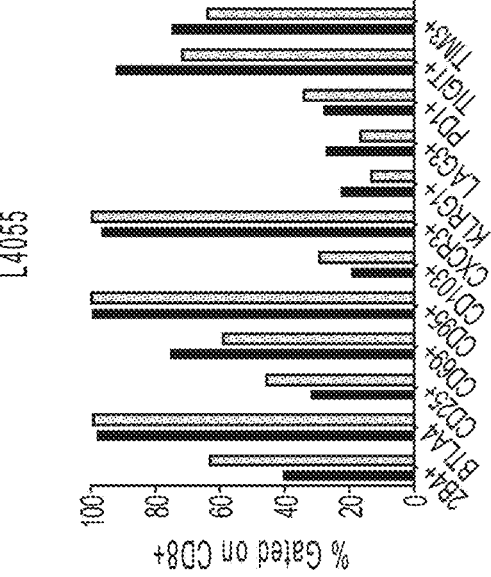
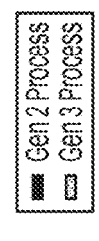
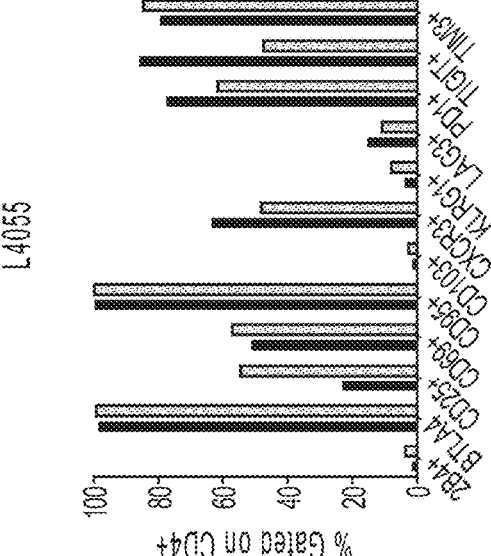
FIG. 13

A

B

C

Frequency of uCDR3

| # uCDR3 (% Overlap) | All uCDR3's | | Top 80% uCDR3's | |
|---|---|---|---|---|
| | Gen 2 | Gen 3 | Gen 2 | Gen 3 |
| Gen 2-L4054 | 8915 | 4355 (48.85%) | 205 | 199 (97.07%) |
| Gen 3-L4054 | - | 18130 | - | 223 |

L54G2

Gen 2

L54G3

Gen 3

- 199 sequences are shared between Gen 3 and Gen 2 final product, corresponding to 97.07% of top 80% of unique CDR3 sequences from Gen 2 shared with Gen 3 final product.

*Cell counts Day 7-Gen 3 REP initiation*

| Volume (mL) | | Count 1 (cells/mL) | Count 2 (cells/mL) | Count 3 (cells/mL) | Average (cells/mL) | Total Cells Average*Volume |
|---|---|---|---|---|---|---|
| 188 | Total | 2.46E+05 | 2.28E+05 | 2.31E+05 | 2.35E+05 | 4.42E+07 |
| | Live | 2.37E+05 | 2.27E+05 | 2.26E+05 | 2.30E+05 | 4.32E+07 |
| | Dead | 9.26E+03 | 7.03E+02 | 4.63E+03 | 4.86E+03 | 9.14E+05 |
| | % Viability | 96.20% | 99.70% | 98.00% | 97.97% | |
| 188 | Total | 8.26E+04 | 8.00E+04 | 7.66E+04 | 7.97E+04 | 1.50E+07 |
| | Live | 7.60E+04 | 7.54E+04 | 6.89E+04 | 7.34E+04 | 1.38E+07 |
| | Dead | 6.61E+03 | 4.63E+03 | 7.73E+03 | 6.32E+03 | 1.19E+06 |
| | % Viability | 92.00% | 94.20% | 89.90% | 92.03% | |
| 200 | Total | 2.44E+04 | 4.20E+04 | 1.05E+04 | 2.56E+04 | 5.13E+06 |
| | Live | 1.74E+04 | 2.80E+04 | 7.03E+03 | 1.75E+04 | 3.50E+06 |
| | Dead | 7.03E+03 | 1.40E+04 | 3.48E+03 | 8.17E+03 | 1.63E+06 |
| | % Viability | 71.20% | 66.70% | 66.90% | 68.27% | |

FIG. 24

[0001] *Cell counts Day 11–Gen 2 REP initiation and Gen 3 Scale Up*

| ID | Volume (mL) | | Count 1 (cells/mL) | Count 3 (cells/mL) | Count 2 (cells/mL) | Average (cells/mL) | Total Cells Average*Volume |
|---|---|---|---|---|---|---|---|
| Gen 3 #L4054 First Round | 1000 | Total | 9.11E+05 | 1.01E+06 | 1.08E+06 | 1.00E+06 | 1.00E+09 |
| | | Live | 8.60E+05 | 9.34E+05 | 1.01E+06 | 9.35E+05 | 9.35E+08 |
| | | Dead | 5.09E+04 | 7.49E+04 | 6.74E+04 | 6.44E+04 | 6.44E+07 |
| | | % Viability | 94.40% | 92.60% | 93.70% | 93.57% | |
| Gen 3 #L4055 Second Round | 1000 | Total | 8.56E+05 | 9.04E+05 | 8.81E+05 | 8.80E+05 | 8.80E+08 |
| | | Live | 8.24E+05 | 8.67E+05 | 8.42E+05 | 8.44E+05 | 8.44E+08 |
| | | Dead | 3.17E+04 | 3.70E+04 | 3.87E+04 | 3.58E+04 | 3.58E+07 |
| | | % Viability | 96.30% | 95.90% | 95.60% | 95.93% | |
| Gen 3 #M1085T | 200 | Total | 2.32E+06 | 2.25E+06 | | 2.29E+06 | 4.57E+08 |
| | | Live | 1.68E+06 | 1.57E+06 | | 1.63E+06 | 3.25E+08 |
| | | Dead | 6.41E+05 | 6.79E+05 | | 6.60E+05 | 1.32E+08 |
| | | % Viability | 72.40% | 69.90% | | 71.15% | |
| Gen 2 #L4054 First Round | 142 | Total | 1.08E+06 | 9.84E+05 | 1.00E+06 | 1.02E+06 | 1.45E+08 |
| | | Live | 1.06E+06 | 9.71E+05 | 9.79E+05 | 1.00E+06 | 1.42E+08 |
| | | Dead | 2.05E+04 | 1.26E+04 | 2.12E+04 | 1.81E+04 | 2.57E+06 |
| | | % Viability | 98.10% | 98.70% | 97.90% | 98.23% | |
| Gen 2 #L4055 Second Round | 96 | Total | 2.93E+05 | 3.05E+05 | 2.64E+05 | 2.87E+05 | 2.76E+07 |
| | | Live | 2.88E+05 | 2.96E+05 | 2.55E+05 | 2.80E+05 | 2.68E+07 |
| | | Dead | 4.72E+03 | 9.14E+03 | 8.26E+03 | 7.37E+03 | 7.08E+05 |
| | | % Viability | 98.40% | 97.00% | 96.90% | 97.43% | |
| Gen 2 #M1085T | 200 | Total | 9.10E+04 | 5.60E+04 | | 7.35E+04 | 1.47E+07 |
| | | Live | 8.05E+04 | 4.21E+04 | | 6.13E+04 | 1.23E+07 |
| | | Dead | 1.04E+04 | 1.39E+04 | | 1.22E+04 | 2.43E+06 |
| | | % Viability | 88.50% | 75.20% | | 81.85% | |

FIG. 25

[0002] *Cell counts Day 16-Gen 2 Scale Up and Gen 3 Harvest*

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4054 First Round -pre LOVO | 1243.1 | Total | 1.40E+07 | 1.46E+07 | | 1.43E+07 | 1.78E+10 |
| | | Live | 1.32E+07 | 1.35E+07 | | 1.34E+07 | 1.66E+10 |
| | | Dead | 8.47E+05 | 1.12E+06 | | 9.84E+05 | 1.22E+09 |
| | | % Viability | 94.00% | 92.40% | | 93.20% | |
| Gen 3 #L4054 First Round -post LOVO | 330 | Total | 6.35E+07 | 6.07E+07 | | 6.21E+07 | 2.05E+10 |
| | | Live | 5.72E+07 | 5.44E+07 | | 5.58E+07 | 1.84E+10 |
| | | Dead | 6.35E+06 | 6.27E+06 | | 6.31E+06 | 2.08E+09 |
| | | % Viability | 90.00% | 89.70% | | 89.85% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4055 Second Round -pre LOVO | 1032.6 | Total | 9.49E+06 | 1.05E+07 | | 1.00E+07 | 1.03E+10 |
| | | Live | 8.90E+06 | 9.79E+06 | | 9.35E+06 | 9.65E+09 |
| | | Dead | 5.85E+05 | 6.75E+05 | | 6.30E+05 | 6.51E+08 |
| | | % Viability | 93.80% | 93.60% | | 93.70% | |
| Gen 3 #L4055 Second Round -post LOVO | 330 | Total | 3.31E+07 | 2.82E+07 | 3.18E+07 | 3.07E+07 | 1.01E+10 |
| | | Live | 2.85E+07 | 2.46E+07 | 2.77E+07 | 2.66E+07 | 8.76E+09 |
| | | Dead | 4.56E+06 | 3.61E+06 | 4.12E+06 | 4.09E+06 | 1.35E+09 |
| | | % Viability | 86.20% | 87.20% | 87.10% | 86.70% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #M1085T pre-LOVO | 5000 | Total | 2.26E+06 | 2.64E+06 | | 2.45E+06 | 1.23E+10 |
| | | Live | 1.97E+06 | 2.31E+06 | | 2.14E+06 | 1.07E+10 |
| | | Dead | 2.85E+05 | 3.30E+05 | | 3.08E+05 | 1.54E+09 |
| | | % Viability | 87.40% | 87.50% | | 87.45% | |
| Gen 3 #M1085T post LOVO pre CS10 addition | 150 | Total | 6.27E+07 | 5.44E+07 | | 5.86E+07 | 8.78E+09 |
| | | Live | 5.50E+07 | 4.74E+07 | | 5.12E+07 | 7.68E+09 |
| | | Dead | 7.70E+06 | 6.96E+06 | | 7.33E+06 | 1.10E+09 |
| | | % Viability | 87.70% | 87.20% | | 87.45% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round | 913 | Total | 3.53E+06 | 4.30E+06 | | 3.92E+06 | 3.57E+09 |
| | | Live | 3.35E+06 | 4.00E+06 | | 3.68E+06 | 3.36E+09 |
| | | Dead | 1.75E+05 | 3.03E+05 | | 2.39E+05 | 2.18E+08 |
| | | % Viability | 95.00% | 93.00% | | 94.00% | |
| Gen 2 #L4055 Second Round | 292 | Total | 1.29E+07 | 1.36E+07 | | 1.33E+07 | 3.87E+09 |
| | | Live | 1.16E+07 | 1.23E+07 | | 1.20E+07 | 3.49E+09 |
| | | Dead | 1.27E+06 | 1.23E+06 | | 1.25E+06 | 3.65E+08 |
| | | % Viability | 90.10% | 90.90% | | 90.50% | |
| Gen 2 #M1085T | 369 | Total | 6.75E+06 | 6.98E+06 | | 6.87E+06 | 2.53E+09 |
| | | Live | 5.22E+06 | 5.58E+06 | | 5.40E+06 | 1.99E+09 |
| | | Dead | 1.54E+06 | 1.40E+06 | | 1.47E+06 | 5.42E+08 |
| | | % Viability | 77.20% | 79.90% | | 78.55% | |

FIG. 26

*[0003] Cell counts Day 22-Gen 2 Harvest*

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round -pre LOVO | 1385.7 | Total | 3.55E+07 | 4.12E+07 | 4.03E+07 | 3.90E+07 | 5.40E+10 |
| | | Live | 3.26E+07 | 3.73E+07 | 3.67E+07 | 3.55E+07 | 4.92E+10 |
| | | Dead | 2.93E+06 | 3.87E+06 | 3.59E+06 | 3.46E+06 | 4.80E+09 |
| | | % Viability | 91.70% | 90.60% | 91.10% | 91.13% | |
| Gen 2 #L4054 First Round -post LOVO | 330 | Total | 1.70E+08 | 1.79E+08 | 1.68E+08 | 1.72E+08 | 5.69E+10 |
| | | Live | 1.49E+08 | 1.58E+08 | 1.48E+08 | 1.52E+08 | 5.01E+10 |
| | | Dead | 2.16E+07 | 2.04E+07 | 2.00E+07 | 2.07E+07 | 6.82E+09 |
| | | % Viability | 87.30% | 88.60% | 88.10% | 87.95% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4055 First Round -pre LOVO | 1968.2 | Total | 3.15E+07 | 2.51E+07 | 2.97E+07 | 2.88E+07 | 5.66E+10 |
| | | Live | 2.89E+07 | 2.25E+07 | 2.72E+07 | 2.62E+07 | 5.16E+10 |
| | | Dead | 2.57E+06 | 2.61E+06 | 2.52E+06 | 2.57E+06 | 5.05E+09 |
| | | % Viability | 91.80% | 89.60% | 91.50% | 90.97% | |
| Gen 2 #L4055 First Round -post LOVO | 330 | Total | 2.33E+08 | 1.89E+08 | 1.53E+08 | 1.92E+08 | 6.33E+10 |
| | | Live | 2.03E+08 | 1.66E+08 | 1.33E+08 | 1.67E+08 | 5.52E+10 |
| | | Dead | 3.00E+07 | 2.24E+07 | 1.94E+07 | 2.39E+07 | 7.90E+09 |
| | | % Viability | 87.10% | 88.10% | 87.30% | 87.50% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #M1085T-pre LOVO | N/A | Total | | | | #DIV/0! | #DIV/0! |
| | | Live | | | | #DIV/0! | #DIV/0! |
| | | Dead | | | | #DIV/0! | #DIV/0! |
| | | % Viability | | | | #DIV/0! | |
| Gen 2 #M1085T - post LOVO pre CS10 addition | 150 | Total | 8.51E+07 | 9.05E+07 | | 8.78E+07 | 1.32E+10 |
| | | Live | 7.33E+07 | 7.79E+07 | | 7.56E+07 | 1.13E+10 |
| | | Dead | 1.18E+07 | 1.26E+07 | | 1.22E+07 | 1.83E+09 |
| | | % Viability | 86.10% | 86.10% | | 86.10% | |

For L4054 Gen 2, post LOVO count was extrapolated to 4 flasks, because was the total number of the study. 1 flask was contaminated, and the extrapolation was done for total = 6.67E+10

| | CD38 | HLA-DR | CCR7-CD45RA+ | CCR7+CD45RA+ | CCR7+CD45RA- | CCR7-CD45RA- |
|---|---|---|---|---|---|---|
| GEN 3-Day 16-Harvest | 42.4 | 95.2 | 4.96 | 0.7 | 1.22 | 93.1 |
| GEN 2-D22-Harvest | 50.4 | 98 | 0.61 | 0.13 | 0.3 | 99 |

CD3/CD8

| | CD38 | HLA-DR | | CCR7-CD45RA+ | CCR7+CD45RA+ | CCR7+CD45RA- | CCR7-CD45RA- |
|---|---|---|---|---|---|---|---|
| CD3 | 77.6 | 83.2 | 90.3 | 20.5 | 0.013 | 0.06 | 79.5 |
| CD8 | 54.3 | 88 | 83.2 | 4.24 | 0.026 | 1.05 | 94.7 |

Figure 29:
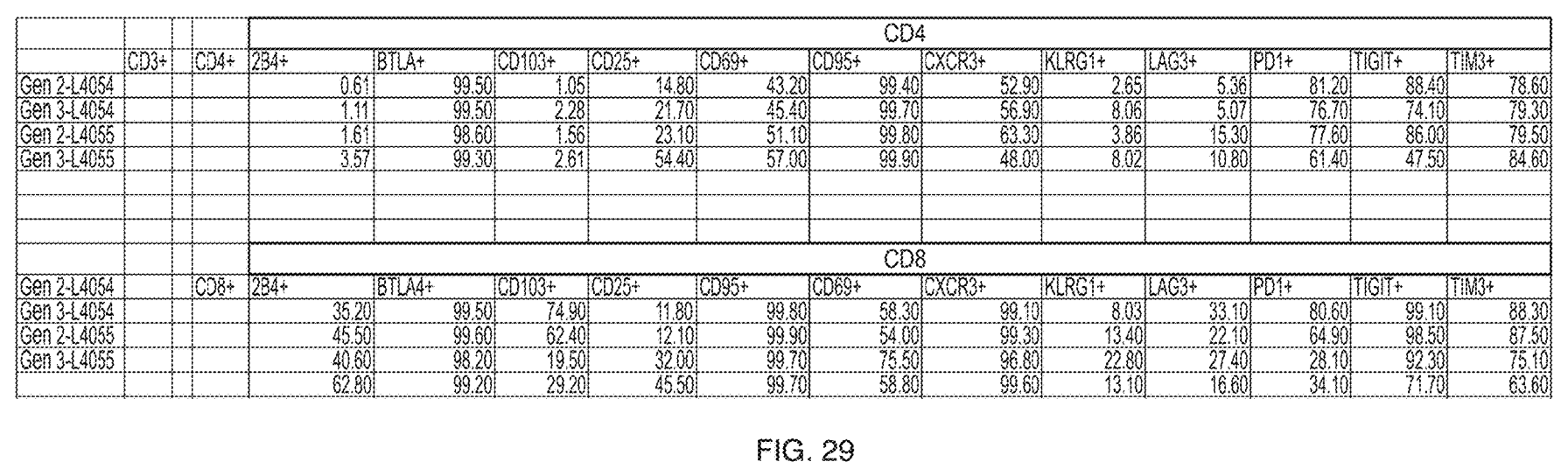

| | CD3+ | CD4+ | 2B4+ | BTLA+ | CD103+ | CD25+ | CD69+ | CD95+ | CXCR3+ | KLRG1+ | LAG3+ | PD1+ | | TIGIT+ | TIM3+ |
|---|---|---|---|---|---|---|---|---|---|---|---|---|---|---|---|
| Gen 2 J-4054 | | | | 0.61 | 99.50 | 1.05 | 14.80 | 43.20 | 99.40 | 52.90 | 2.65 | 5.36 | 81.20 | 88.40 | 78.60 |
| Gen 3 J-4054 | | | | 1.11 | 99.50 | 2.28 | 21.70 | 45.40 | 99.70 | 56.90 | 8.06 | 5.07 | 76.70 | 74.10 | 79.30 |
| Gen 2 J-4055 | | | | 1.61 | 98.60 | 1.56 | 23.10 | 51.10 | 99.80 | 63.30 | 3.86 | 15.30 | 77.60 | 86.00 | 79.50 |
| Gen 3 J-4055 | | | | 3.57 | 99.30 | 2.61 | 54.40 | 57.00 | 99.90 | 48.00 | 8.02 | 10.80 | 61.40 | 47.50 | 84.60 |

CD8

| | CD8+ | 2B4+ | BTLA+ | CD103+ | CD25+ | CD69+ | CD95+ | CXCR3+ | KLRG1+ | LAG3+ | PD1+ | | TIGIT+ | TIM3+ |
|---|---|---|---|---|---|---|---|---|---|---|---|---|---|---|
| Gen 2 J-4054 | | | 35.20 | 99.50 | 74.90 | 11.80 | 99.80 | 98.30 | 99.10 | 8.03 | 33.10 | 80.60 | 99.10 | 88.30 |
| Gen 3 J-4054 | | | 45.50 | 99.60 | 62.40 | 12.10 | 99.90 | 54.00 | 99.30 | 13.40 | 22.10 | 64.90 | 98.50 | 87.50 |
| Gen 2 J-4055 | | | 40.60 | 98.20 | 19.50 | 32.00 | 99.70 | 75.50 | 96.80 | 22.80 | 27.40 | 28.10 | 92.30 | 75.10 |
| Gen 3 J-4055 | | | 62.80 | 99.20 | 29.20 | 45.50 | 99.70 | 58.80 | 99.60 | 13.10 | 16.60 | 34.10 | 71.70 | 63.60 |

| | 1 | 2 | 3 | 4 | 5 | 6 | 7 | 8 | 9 | 10 | 11 | 12 | |
|---|---|---|---|---|---|---|---|---|---|---|---|---|---|
| A Well ID | STD1 | STD1 | STD1 | TIL-Gen 2-stimulated | TIL-Gen 2-stimulated | TIL-Gen 2-stimulated | TIL-Gen 2-Un-stimulated | TIL-Gen 2-Un-stimulated | TIL-Gen 2-Un-stimulated | MC-Stimulated xG2 | MC-Stimulated xG2 | MC-Stimulated xG2 | Well ID |
| A Conc/Dil | 1000 | 1000 | 1000 | 3 | 3 | 3 | 3 | 3 | 3 | 3 | 3 | 3 | Conc/Dil |
| B Well ID | STD2 | STD2 | STD2 | TIL-Gen 2-stimulated | TIL-Gen 2-stimulated | TIL-Gen 2-stimulated | TIL-Gen 2-Un-stimulated | TIL-Gen 2-Un-stimulated | TIL-Gen 2-Un-stimulated | MC-Stimulated xG2 | MC-Stimulated xG2 | MC-Stimulated xG2 | Well ID |
| B Conc/Dil | 500 | 500 | 500 | 9 | 9 | 9 | 9 | 9 | 9 | 9 | 9 | 9 | Conc/Dil |
| C Well ID | STD3 | STD3 | STD3 | TIL-Gen 2-stimulated | TIL-Gen 2-stimulated | TIL-Gen 2-stimulated | TIL-Gen 2-Un-stimulated | TIL-Gen 2-Un-stimulated | TIL-Gen 2-Un-stimulated | MC-Unstimulated xG2 | MC-Unstimulated xG2 | MC-Unstimulated xG2 | Well ID |
| C Conc/Dil | 250 | 250 | 250 | 27 | 27 | 27 | 27 | 27 | 27 | 3 | 3 | 3 | Conc/Dil |
| D Well ID | STD4 | STD4 | STD4 | TIL-Gen 2-stimulated | TIL-Gen 2-stimulated | TIL-Gen 2-stimulated | TIL-Gen 2-Un-stimulated | TIL-Gen 2-Un-stimulated | TIL-Gen 2-Un-stimulated | MC-Unstimulated xG2 | MC-Unstimulated xG2 | MC-Unstimulated xG2 | Well ID |
| D Conc/Dil | 125 | 125 | 125 | 81 | 81 | 81 | 81 | 81 | 81 | 9 | 9 | 9 | Conc/Dil |
| E Well ID | STD5 | STD5 | STD5 | TIL-Gen 3-stimulated | TIL-Gen 3-stimulated | TIL-Gen 3-stimulated | TIL-Gen 3-Un-stimulated | TIL-Gen 3-Un-stimulated | TIL-Gen 3-Un-stimulated | MC-Stimulated xG3 | MC-Stimulated xG3 | MC-Stimulated xG3 | Well ID |
| E Conc/Dil | 62.5 | 62.5 | 62.5 | 3 | 3 | 3 | 3 | 3 | 3 | 3 | 3 | 3 | Conc/Dil |
| F Well ID | STD6 | STD6 | STD6 | TIL-Gen 3-stimulated | TIL-Gen 3-stimulated | TIL-Gen 3-stimulated | TIL-Gen 3-Un-stimulated | TIL-Gen 3-Un-stimulated | TIL-Gen 3-Un-stimulated | MC-Stimulated xG3 | MC-Stimulated xG3 | MC-Stimulated xG3 | Well ID |
| F Conc/Dil | 31.3 | 31.3 | 31.3 | 9 | 9 | 9 | 9 | 9 | 9 | 9 | 9 | 9 | Conc/Dil |
| G Well ID | STD7 | STD7 | STD7 | TIL-Gen 3-stimulated | TIL-Gen 3-stimulated | TIL-Gen 3-stimulated | TIL-Gen 3-Un-stimulated | TIL-Gen 3-Un-stimulated | TIL-Gen 3-Un-stimulated | MC-Unstimulated xG3 | MC-Unstimulated xG3 | MC-Unstimulated xG3 | Well ID |
| G Conc/Dil | 15.6 | 15.6 | 15.6 | 27 | 27 | 27 | 27 | 27 | 27 | 3 | 3 | 3 | Conc/Dil |
| H Well ID | STD8 | STD8 | STD8 | TIL-Gen 3-stimulated | TIL-Gen 3-stimulated | TIL-Gen 3-stimulated | TIL-Gen 3-Un-stimulated | TIL-Gen 3-Un-stimulated | TIL-Gen 3-Un-stimulated | MC-Unstimulated xG3 | MC-Unstimulated xG3 | MC-Unstimulated xG3 | Well ID |
| H Conc/Dil | 0 | 0 | 0 | 81 | 81 | 81 | 81 | 81 | 81 | 9 | 9 | 9 | Conc/Dil |

| Row | | 1 | 2 | 3 | 4 | 5 | 6 | 7 | 8 | 9 | 10 | 11 | 12 | |
|---|---|---|---|---|---|---|---|---|---|---|---|---|---|---|
| A | Well ID | STD1 | STD1 | STD1 | 2A-BEAD+TIL | 2A-BEAD+TIL | 2A-BEAD+TIL | 2A-MC | 2A-MC | 2A-MC | 2A-Uh-stimulated | 2A-Uh-stimulated | 2A-Uh-stimulated | Well ID |
| | Conc/Dil | 1000 | 1000 | 1000 | 3 | 3 | 3 | 3 | 3 | 3 | 3 | 3 | 3 | Conc/Dil |
| B | Well ID | STD2 | STD2 | STD2 | 2A-BEAD+TIL | 2A-BEAD+TIL | 2A-BEAD+TIL | 2A-MC | 2A-MC | 2A-MC | 2A-Uh-stimulated | 2A-Uh-stimulated | 2A-Uh-stimulated | Well ID |
| | Conc/Dil | 500 | 500 | 500 | 9 | 9 | 9 | 9 | 9 | 9 | 9 | 9 | 9 | Conc/Dil |
| C | Well ID | STD3 | STD3 | STD3 | 2A-BEAD+TIL | 2A-BEAD+TIL | 2A-BEAD+TIL | 2A-MC | 2A-MC | 2A-MC | 2A-Uh-stimulated | 2A-Uh-stimulated | 2A-Uh-stimulated | Well ID |
| | Conc/Dil | 250 | 250 | 250 | 27 | 27 | 27 | 27 | 27 | 27 | 27 | 27 | 27 | Conc/Dil |
| D | Well ID | STD4 | STD4 | STD4 | 2A-BEAD+TIL | 2A-BEAD+TIL | 2A-BEAD+TIL | 2A-MC | 2A-MC | 2A-MC | 2A-Uh-stimulated | 2A-Uh-stimulated | 2A-Uh-stimulated | Well ID |
| | Conc/Dil | 125 | 125 | 125 | 81 | 81 | 81 | 81 | 81 | 81 | 81 | 81 | 81 | Conc/Dil |
| E | Well ID | STD5 | STD5 | STD5 | 2A-BEAD+TIL | 2A-BEAD+TIL | 2A-BEAD+TIL | 2B-Uh-stimulated | 2B-Uh-stimulated | 2B-Uh-stimulated | 2B-MC | 2B-MC | 2B-MC | Well ID |
| | Conc/Dil | 62.5 | 62.5 | 62.5 | 3 | 3 | 3 | 3 | 3 | 3 | 3 | 3 | 3 | Conc/Dil |
| F | Well ID | STD6 | STD6 | STD6 | 2A-BEAD+TIL | 2A-BEAD+TIL | 2A-BEAD+TIL | 2B-Uh-stimulated | 2B-Uh-stimulated | 2B-Uh-stimulated | 2B-MC | 2B-MC | 2B-MC | Well ID |
| | Conc/Dil | 31.3 | 31.3 | 31.3 | 9 | 9 | 9 | 9 | 9 | 9 | 9 | 9 | 9 | Conc/Dil |
| G | Well ID | STD7 | STD7 | STD7 | 2A-BEAD+TIL | 2A-BEAD+TIL | 2A-BEAD+TIL | 2B-Uh-stimulated | 2B-Uh-stimulated | 2B-Uh-stimulated | 2B-MC | 2B-MC | 2B-MC | Well ID |
| | Conc/Dil | 15.6 | 15.6 | 15.6 | 27 | 27 | 27 | 27 | 27 | 27 | 27 | 27 | 27 | Conc/Dil |
| H | Well ID | STD8 | STD8 | STD8 | 2A-BEAD+TIL | 2A-BEAD+TIL | 2A-BEAD+TIL | 2B-Uh-stimulated | 2B-Uh-stimulated | 2B-Uh-stimulated | 2B-MC | 2B-MC | 2B-MC | Well ID |
| | Conc/Dil | 0 | 0 | 0 | 81 | 81 | 81 | 81 | 81 | 81 | 81 | 81 | 81 | Conc/Dil |

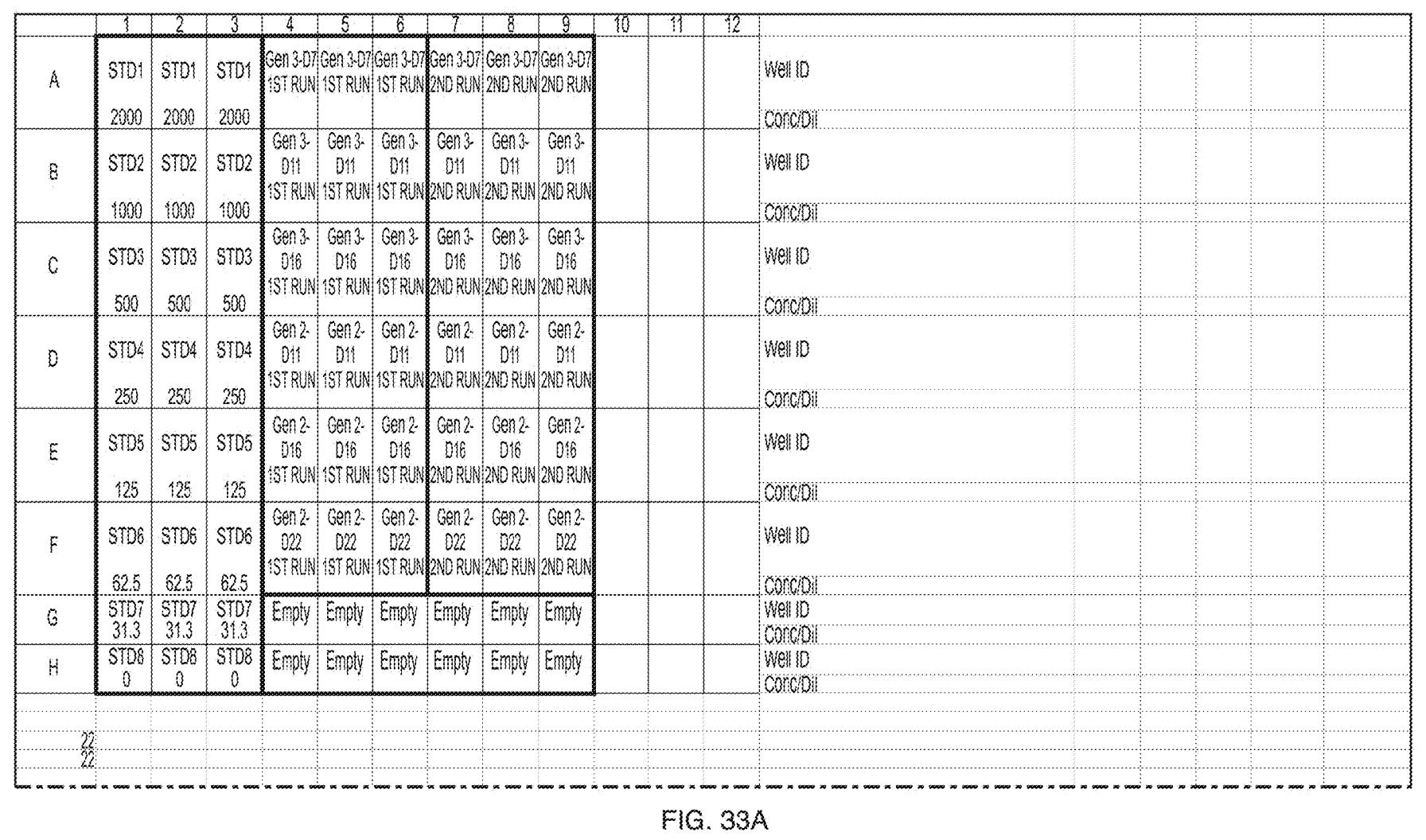

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 / 2000 | STD1 / 2000 | STD1 / 2000 | Gen 3-D7 1ST RUN | Gen 3-D7 1ST RUN | Gen 3-D7 1ST RUN | Gen 3-D7 2ND RUN | Gen 3-D7 2ND RUN | Gen 3-D7 2ND RUN | | | | Well ID / Conc/Dil |
| B | STD2 / 1000 | STD2 / 1000 | STD2 / 1000 | Gen 3-D11 1ST RUN | Gen 3-D11 1ST RUN | Gen 3-D11 1ST RUN | Gen 3-D11 2ND RUN | Gen 3-D11 2ND RUN | Gen 3-D11 2ND RUN | | | | Well ID / Conc/Dil |
| C | STD3 / 500 | STD3 / 500 | STD3 / 500 | Gen 3-D16 1ST RUN | Gen 3-D16 1ST RUN | Gen 3-D16 1ST RUN | Gen 3-D16 2ND RUN | Gen 3-D16 2ND RUN | Gen 3-D16 2ND RUN | | | | Well ID / Conc/Dil |
| D | STD4 / 250 | STD4 / 250 | STD4 / 250 | Gen 2-D11 1ST RUN | Gen 2-D11 1ST RUN | Gen 2-D11 1ST RUN | Gen 2-D11 2ND RUN | Gen 2-D11 2ND RUN | Gen 2-D11 2ND RUN | | | | Well ID / Conc/Dil |
| E | STD5 / 125 | STD5 / 125 | STD5 / 125 | Gen 2-D16 1ST RUN | Gen 2-D16 1ST RUN | Gen 2-D16 1ST RUN | Gen 2-D16 2ND RUN | Gen 2-D16 2ND RUN | Gen 2-D16 2ND RUN | | | | Well ID / Conc/Dil |
| F | STD6 / 62.5 | STD6 / 62.5 | STD6 / 62.5 | Gen 2-D22 1ST RUN | Gen 2-D22 1ST RUN | Gen 2-D22 1ST RUN | Gen 2-D22 2ND RUN | Gen 2-D22 2ND RUN | Gen 2-D22 2ND RUN | | | | Well ID / Conc/Dil |
| G | STD7 / 31.3 | STD7 / 31.3 | STD7 / 31.3 | Empty | Empty | Empty | Empty | Empty | Empty | | | | Well ID / Conc/Dil |
| H | STD8 / 0 | STD8 / 0 | STD8 / 0 | Empty | Empty | Empty | Empty | Empty | Empty | | | | Well ID / Conc/Dil |

FIG. 33A

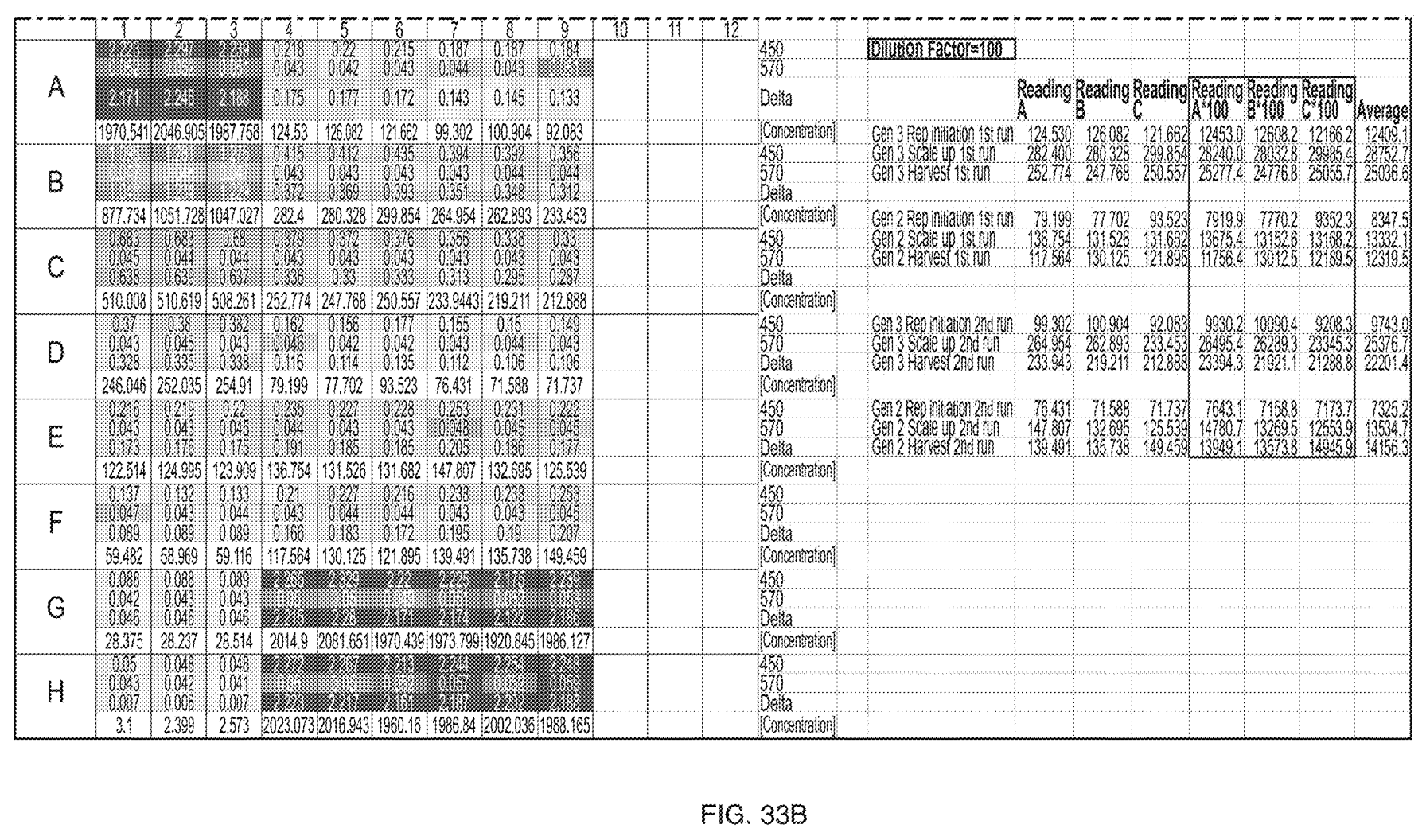

Dilution Factor=100

| | | Reading A | Reading B | Reading C | Reading A*100 | Reading B*100 | Reading C*100 | Average |
|---|---|---|---|---|---|---|---|---|
| Gen 3 Rep initiation 1st run | | 124.530 | 126.082 | 121.662 | 12453.0 | 12608.2 | 12166.2 | 12409.1 |
| Gen 3 Scale up 1st run | | 282.400 | 280.328 | 299.854 | 28240.0 | 28032.8 | 29985.4 | 28752.7 |
| Gen 3 Harvest 1st run | | 252.774 | 247.768 | 250.557 | 25277.4 | 24776.8 | 25055.7 | 25036.6 |
| Gen 2 Rep initiation 1st run | | 79.199 | 77.702 | 93.523 | 7919.9 | 7770.2 | 9352.3 | 8347.5 |
| Gen 2 Scale up 1st run | | 136.754 | 131.526 | 131.662 | 13675.4 | 13152.6 | 13168.2 | 13332.1 |
| Gen 2 Harvest 1st run | | 117.564 | 130.125 | 121.895 | 11756.4 | 13012.5 | 12189.5 | 12319.5 |
| Gen 3 Rep initiation 2nd run | | 99.302 | 100.904 | 92.063 | 9930.2 | 10090.4 | 9206.3 | 9743.0 |
| Gen 3 Scale up 2nd run | | 264.954 | 262.893 | 233.453 | 26495.4 | 26289.3 | 23345.3 | 25376.7 |
| Gen 3 Harvest 2nd run | | 233.943 | 219.211 | 212.888 | 23394.3 | 21921.1 | 21288.8 | 22201.4 |
| Gen 2 Rep initiation 2nd run | | 76.431 | 71.588 | 71.737 | 7643.1 | 7158.8 | 7173.7 | 7325.2 |
| Gen 2 Scale up 2nd run | | 147.807 | 132.695 | 125.539 | 14780.7 | 13269.5 | 12553.9 | 13534.7 |
| Gen 2 Harvest 2nd run | | 139.491 | 135.738 | 149.450 | 13949.1 | 13573.8 | 14945.0 | 14156.3 |

| | | 1 | 2 | 3 | 4 | 5 | 6 | 7 | 8 | 9 | 10 | 11 | 12 |
|---|---|---|---|---|---|---|---|---|---|---|---|---|---|
| A | 450 | | | | 0.218 | 0.22 | 0.215 | 0.187 | 0.187 | 0.184 | | | |
| | 570 | | | | 0.043 | 0.042 | 0.043 | 0.044 | 0.043 | | | | |
| | Delta | | | | 0.175 | 0.177 | 0.172 | 0.143 | 0.145 | 0.133 | | | |
| | [Concentration] | 1970.541 | 2046.905 | 1987.753 | 124.53 | 126.082 | 121.662 | 99.302 | 100.904 | 92.063 | | | |
| B | 450 | | | | 0.415 | 0.412 | 0.436 | 0.394 | 0.392 | 0.356 | | | |
| | 570 | | | | 0.043 | 0.043 | 0.043 | 0.043 | 0.044 | 0.044 | | | |
| | Delta | | | | 0.372 | 0.369 | 0.393 | 0.351 | 0.348 | 0.312 | | | |
| | [Concentration] | 877.734 | 1051.728 | 1047.027 | 282.4 | 280.328 | 299.854 | 264.954 | 262.893 | 233.453 | | | |
| C | 450 | | | | 0.379 | 0.372 | 0.376 | 0.356 | 0.338 | 0.33 | | | |
| | 570 | | | | 0.043 | 0.043 | 0.043 | 0.043 | 0.043 | 0.043 | | | |
| | Delta | | | | 0.336 | 0.33 | 0.333 | 0.313 | 0.295 | 0.207 | | | |
| | [Concentration] | 510.619 | 508.261 | 247.768 | 250.557 | 264.954 | 262.893 | 233.943 | 219.211 | 212.888 | | | |
| D | 450 | | | | 0.162 | 0.156 | 0.177 | 0.155 | 0.15 | 0.149 | | | |
| | 570 | | | | 0.046 | 0.042 | 0.042 | 0.043 | 0.044 | 0.043 | | | |
| | Delta | | | | 0.116 | 0.114 | 0.135 | 0.112 | 0.106 | 0.106 | | | |
| | [Concentration] | 246.046 | 252.035 | 254.91 | 79.199 | 77.702 | 93.523 | 76.431 | 71.588 | 71.737 | | | |
| E | 450 | | | | 0.235 | 0.227 | 0.228 | 0.253 | 0.231 | 0.222 | | | |
| | 570 | | | | 0.044 | 0.043 | 0.043 | 0.048 | 0.045 | 0.045 | | | |
| | Delta | | | | 0.191 | 0.185 | 0.186 | 0.205 | 0.186 | 0.177 | | | |
| | [Concentration] | 122.514 | 123.989 | 136.754 | 131.526 | 131.662 | 147.807 | 132.695 | 125.539 | | | |
| F | 450 | | | | 0.21 | 0.227 | 0.216 | 0.239 | 0.233 | 0.253 | | | |
| | 570 | | | | 0.043 | 0.044 | 0.044 | 0.043 | 0.043 | 0.045 | | | |
| | Delta | | | | 0.166 | 0.183 | 0.172 | 0.196 | 0.19 | 0.207 | | | |
| | [Concentration] | 59.482 | 58.969 | 117.564 | 130.125 | 121.895 | 139.491 | 135.738 | 149.459 | | | |
| G | 450 | 0.089 | 0.088 | 0.089 | | | | | | | | | |
| | 570 | 0.043 | 0.043 | 0.043 | | | | | | | | | |
| | Delta | 0.046 | 0.046 | 0.046 | 2081.651 | 1970.439 | 1973.799 | 1920.845 | 1996.127 | | | | |
| | [Concentration] | | | | 2014.9 | 2081.651 | | | | | | | |
| H | 450 | 0.05 | 0.048 | 0.048 | | | | | | | | | |
| | 570 | 0.043 | 0.042 | 0.041 | | | | | | | | | |
| | Delta | 0.007 | 0.006 | 0.007 | 2023.073 | 2016.943 | 1960.16 | 1986.84 | 2002.036 | 1988.165 | | | |
| | [Concentration] | 3.1 | 2.399 | 2.573 | | | | | | | | | |

FIG. 33B

| Sample number # | Description | Glucose (g/L) | Lactate (g/L) | Ammonia (mmol/L) | Glutamine (mmol/L) | Glutamax (mmol/L) | Glutamax-Glutamine (mmol/L) |
|---|---|---|---|---|---|---|---|
| 1 | Gen 2-Rep initiation First Round #L4054 | 1.78 | 0.14 | 2.16 | 1.56 | 1.71 | 0.16 |
| 2 | Gen 2-Scale Up First Round #L4054 | 1.36 | 0.89 | 1.40 | 1.76 | 1.90 | 0.15 |
| 3 | Gen 2-Harvest First Round #L4054 | 0.83 | 1.68 | 2.46 | 1.69 | 1.85 | 0.17 |
| 4 | Gen 3-REP initiation First Round #L4054 | 1.68 | 0.29 | 1.76 | 2.11 | 2.29 | 0.18 |
| 5 | Gen 3-Scale Up First Round #L4054 | 1.28 | 0.94 | 1.64 | 1.70 | 1.87 | 0.16 |
| 6 | Gen 3-Harvest First Round #L4054 | 1.07 | 1.53 | 2.23 | 1.39 | 1.54 | 0.14 |
| 7 | Gen 2-Rep initiation Second Round #L4055 | 1.91 | 0.08 | 2.29 | 1.60 | 1.74 | 0.14 |
| 8 | Gen 2-Scale up Second Round #L4055 | 1.61 | 0.77 | 1.40 | 1.78 | 1.93 | 0.15 |
| 9 | Gen 2-Harvest Second Round #L4055 | 0.85 | 1.86 | 2.46 | 1.39 | 1.55 | 0.16 |
| 10 | Gen 3-REP initiation Second Round #L4055 | 1.77 | 0.18 | 1.74 | 2.06 | 2.23 | 0.17 |
| 11 | Gen 3-Scale up Second Round #L4055 | 1.60 | 0.72 | 1.54 | 1.68 | 1.84 | 0.15 |
| 12 | Gen 3-Harvest Second Round #L4055 | 1.44 | 1.32 | 2.07 | 1.79 | 1.95 | 0.16 |

Figure 35:
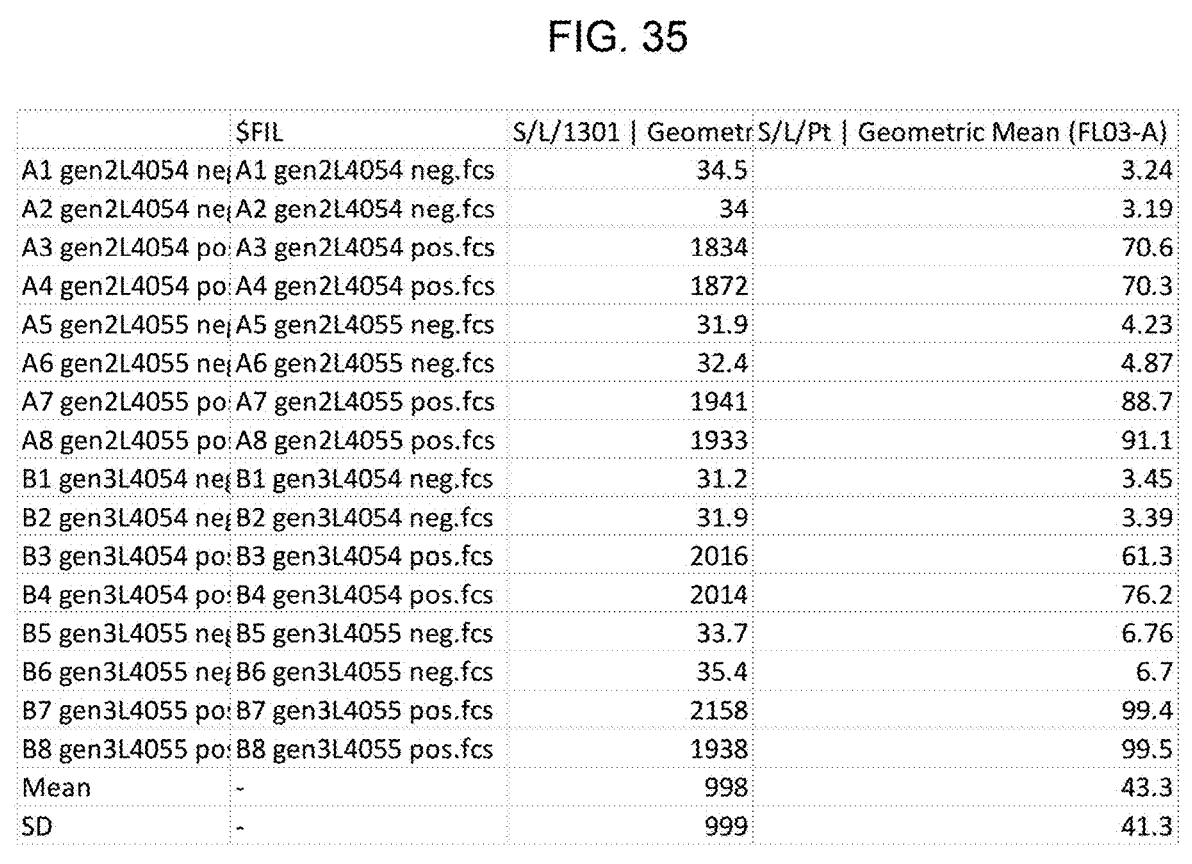

| | $FIL | S/L/1301 \| Geometr | S/L/Pt \| Geometric Mean (FL03-A) |
|---|---|---|---|
| A1 gen2L4054 ne; | A1 gen2L4054 neg.fcs | 34.5 | 3.24 |
| A2 gen2L4054 ne; | A2 gen2L4054 neg.fcs | 34 | 3.19 |
| A3 gen2L4054 po: | A3 gen2L4054 pos.fcs | 1834 | 70.6 |
| A4 gen2L4054 po: | A4 gen2L4054 pos.fcs | 1872 | 70.3 |
| A5 gen2L4055 ne; | A5 gen2L4055 neg.fcs | 31.9 | 4.23 |
| A6 gen2L4055 ne; | A6 gen2L4055 neg.fcs | 32.4 | 4.87 |
| A7 gen2L4055 po: | A7 gen2L4055 pos.fcs | 1941 | 88.7 |
| A8 gen2L4055 po: | A8 gen2L4055 pos.fcs | 1933 | 91.1 |
| B1 gen3L4054 ne; | B1 gen3L4054 neg.fcs | 31.2 | 3.45 |
| B2 gen3L4054 ne; | B2 gen3L4054 neg.fcs | 31.9 | 3.39 |
| B3 gen3L4054 po: | B3 gen3L4054 pos.fcs | 2016 | 61.3 |
| B4 gen3L4054 po: | B4 gen3L4054 pos.fcs | 2014 | 76.2 |
| B5 gen3L4055 ne; | B5 gen3L4055 neg.fcs | 33.7 | 6.76 |
| B6 gen3L4055 ne; | B6 gen3L4055 neg.fcs | 35.4 | 6.7 |
| B7 gen3L4055 po: | B7 gen3L4055 pos.fcs | 2158 | 99.4 |
| B8 gen3L4055 po: | B8 gen3L4055 pos.fcs | 1938 | 99.5 |
| Mean | - | 998 | 43.3 |
| SD | - | 999 | 41.3 |

FIG. 36

| Study | Sample | Sample id | Species | Chain | Reads | CDR3 | Unique CDR3 | D50 |
|---|---|---|---|---|---|---|---|---|
| 20180511_Study1_FCA | Gen2-L4054 | 59990 | TRB | h | 1181732 | 1181732 | 8915 | 0 |
| 20180511_Study1_FCA | Gen3-L4054 | 59991 | TRB | h | 1145697 | 1145697 | 18130 | 0 |
| 20180511_Study1_FCA | Gen2-L4055 | 59987 | TRB | h | 1166465 | 1166465 | 12996 | 0.1 |
| 20180511_Study1_FCA | Gen3-L4055 | 59982 | TRB | h | 1059985 | 1059985 | 27246 | 0.9 |

| STEP | Gen 2 | Gen 2.1 | Gen 3.0 Optimized |
|---|---|---|---|
| Pre REP. day 0 | ≤ 50 fragments/ 1 G-Rex 100MCS - 11 days | ≤ 180 fragments/3 G-Rex, Pre-formulated CM1 warmed media 100MCS - 11 days | *Fresh or Frozen Tumor* Whole tumor with ≤ 30 fragments up to 60 fragments per 1 G-Rex. 100MCS (up to 4 G-Rex), preformulated warmed media - 7 days. Pre REP, Feeders 2.5 E8 cells + OKT-3 (30ng/mL) |
| REP Initiation | Direct to REP- Day 11- <200 E6 TIL 1 G-Rex 500MCS | Direct to REP- Day 11- <200 E6 TIL Pre-formulated CM2 warmed media in one G-Rex 500MCS | Direct to REP - Day 7-all cells TIL- same G-Rex 100MCS (100MCS up to 4 GREX) Standard media or Defined Media (Serum free)  Addition Feeders 5 E8 cells +OKT-3 (30ng/mL) |
| TIL propagation or Scale up | 1 to 5 G-REX 500MCS Split day 16 | 2 to 5 G-REX 500MCS Pre-formulated CM4 warmed media Split day 16 | From G-REX 100MCS transfer TIL suspension to G-REX 500MCS, up to 4 GREX 500 MCS- Standard media or Defined Media (Serum Free) Scale up on day 10 or 11 |
| Harvest | Harvest day 22, LOVO-automated cell washer | Harvest day 22, LOVO-automated cell washer (5 wash cycle) | Harvest day 14 or 16 LOVO- automated cell washer (5 wash cycle) |
| Final formulation | Cryopreserved Product 300IU/ml IL2- CS10 in LN$_2$, multiple aliquots | Cryopreserved Product 300IU/ml IL2- CS10 in LN$_2$, multiple aliquots | Cryopreserved Product 300IU/ml IL-2- CS10 in LN$_2$, multiple aliquots |
| Process time | 22 days | 22 days | 16 days |

FIG. 38

| Process Day | Conditions | Gen 3.1 |
|---|---|---|
| Day 0-<br>pre REP initiation | Media CM1 | 500 mL |
| | IL-2 (6000 IU/mL) | + |
| | OKT-3 (30ng/mL) | + |
| | Feeders (250 E+06) | + |

| Process Day | Conditions | Gen 3.1 |
|---|---|---|
| Day 7-<br>REP initiation | Media CM2 | 500 mL |
| | IL-2 (6000 IU/mL) | + |
| | OKT-3 (30ng/mL) added on Day 7 | + |
| | Feeders Added on Day 7 | 500 E06 |
| | Total Feeders at Day | 750 E+06 |

| Process Day | Conditions | Gen 3.1 |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

| Process Comparison | Key Process Changes | Benefit |
|---|---|---|
| Gen 2 : Gen 2.1 | • Initiate process with two flasks instead of one flask<br>• Divide REP initiation feeder layer between 2 G-Rex500MCS Flasks<br>• Pre-formulate media and warm prior to use | • Potential doubling of final cell count (dose) with increased TIL repertoire.<br>• Process redundancy throughout process |
| Gen 2.1 : Gen 3.1 | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

| Process Comparison | Key Process Changes | Desired Improvement | Criteria for Success | Outcome |
|---|---|---|---|---|
| Gen 2 : Gen 3.0 | • 14-16 days<br><br>• Initiate REP with fragments up to 4 flask.<br><br>• 100MCS scales to 500MCS | • Increased potency<br><br>• Improved phenotype<br><br>• Decreased process time | • Increase potency as measured by INF-g ✓<br><br>• Comparable phenotype ✓<br><br>• Comparable Dose ✓<br><br>• Comparable purity (feeder cell) ✓<br><br>• Maintain clonal diversity ✓ | • Potency increased over Gen2<br><br>• Improved expression of CD28 on CD8 cells<br><br>• Maximum capacity of flask reached by day 16 on Gen 3.1<br><br>• Reduced feeder cell usage<br><br>• Increased diversity |

FIG. 41

| Process | Gen 3 | Gen 3.1 control | Gen 3.1 |
|---------|-------|-----------------|---------|
| L4063 | Standard Media | Standard Media | Standard Media |
| L4064 | Defined Media | Defined Media | Defined Media |

Defined Media:
CTS Optimizer (Serum Free Media) in each day of the process

FIG. 42

| Process | Gen 2 | Gen 3 |
|---------|-------|-------|
| L4054 | Standard Media | Standard Media |
| L4055 | Standard Media | Standard Media |
| M1085T | Standard Media | Standard Media |

Standard Media:
Pre REP: CM1
REP initiation : CM2
Split or Scale up : CM4

FIG. 45
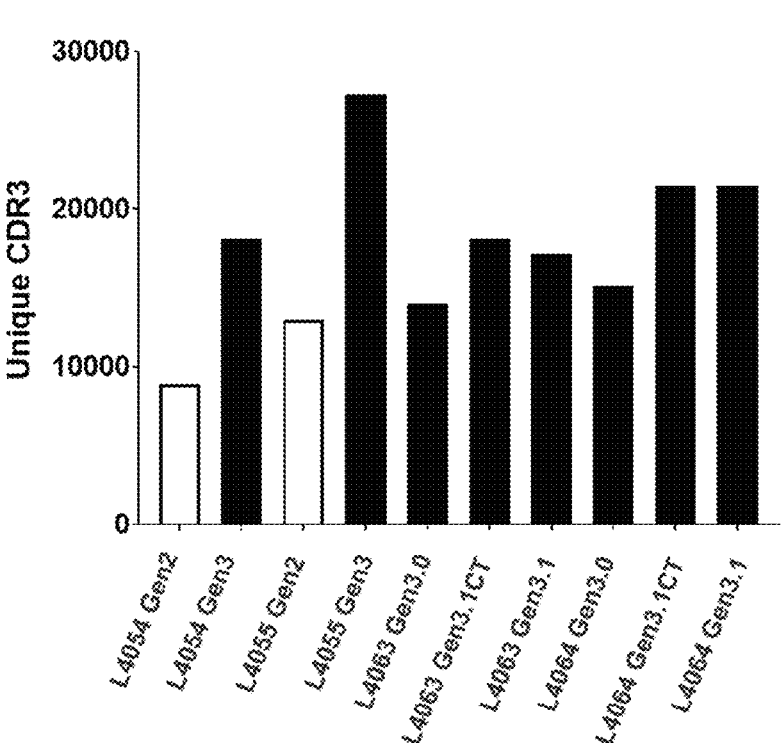
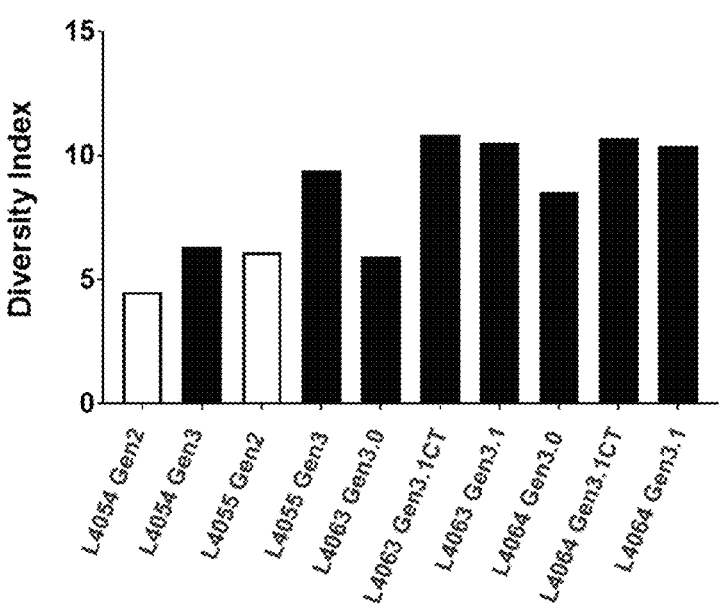

*FIG. 49*

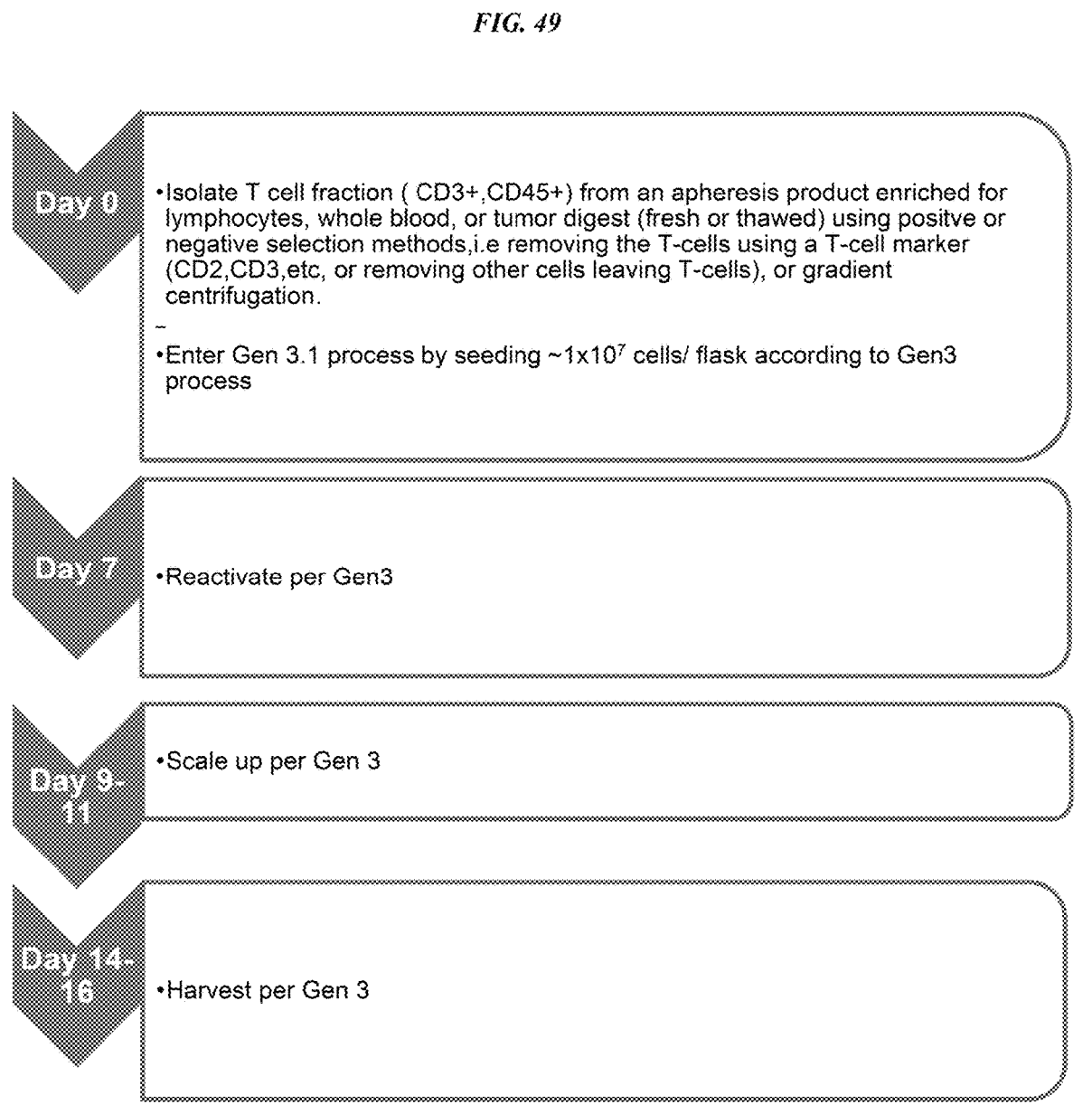

Day 0
- Isolate T cell fraction ( CD3+,CD45+) from an apheresis product enriched for lymphocytes, whole blood, or tumor digest (fresh or thawed) using positve or negative selection methods,i.e removing the T-cells using a T-cell marker (CD2,CD3,etc, or removing other cells leaving T-cells), or gradient centrifugation.
- Enter Gen 3.1 process by seeding ~1x10$^7$ cells/ flask according to Gen3 process

Day 7
- Reactivate per Gen3

Day 9 11
- Scale up per Gen 3

Day 14 16
- Harvest per Gen 3

Structure I-A                    Structure I-B

Figure 52:
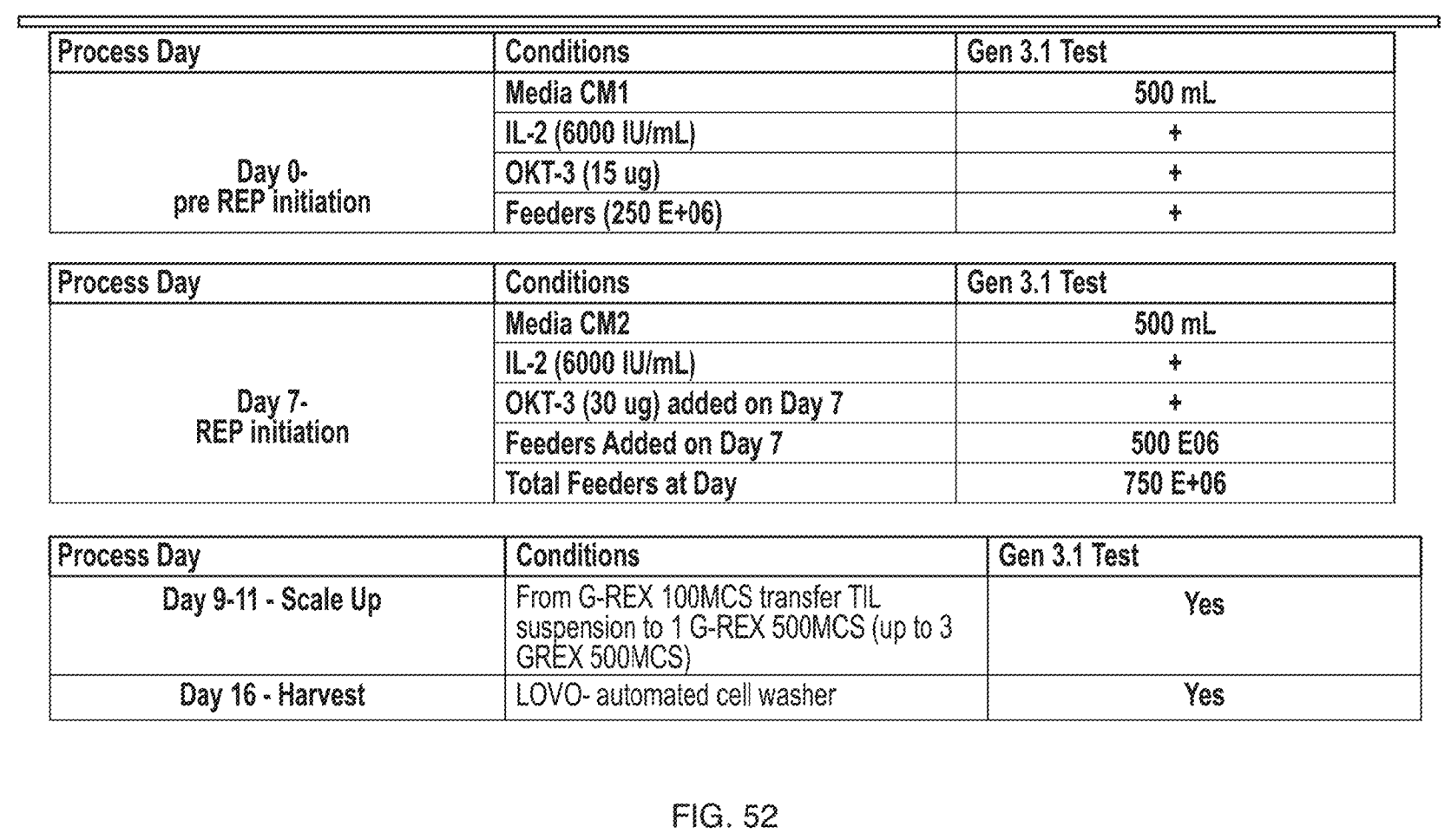

| Process Day | Conditions | Gen 3.1 Test |
|---|---|---|
| Day 0-<br>pre REP initiation | Media CM1 | 500 mL |
| | IL-2 (6000 IU/mL) | + |
| | OKT-3 (15 ug) | + |
| | Feeders (250 E+06) | + |

| Process Day | Conditions | Gen 3.1 Test |
|---|---|---|
| Day 7-<br>REP initiation | Media CM2 | 500 mL |
| | IL-2 (6000 IU/mL) | + |
| | OKT-3 (30 ug) added on Day 7 | + |
| | Feeders Added on Day 7 | 500 E06 |
| | Total Feeders at Day | 750 E+06 |

| Process Day | Conditions | Gen 3.1 Test |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

| Tumor ID | L4063 in Standard Media | | | L4064 in CTS Optimizer Media | | |
|---|---|---|---|---|---|---|
| Process | Gen 3.0 | Gen 3.1 Control | Gen 3.1 Test | Gen 3.0 | Gen 3.1 Control | Gen 3.1 Test |
| Number of fragments | 53 | 53 | 53 | 21 | 21 | 21 |
| Average TVC per fragment | 1.37E+08 | 3.19E+08 | 3.53E+08 | 5.90E+08 | 7.57E+08 | 9.29E+08 |
| % viability at Harvest | 79.53% | 89.43% | 94.80% | 88.80% | 81.90% | 84.90% |
| TVC Harvest | 7.26E+09 | 1.69E+10 | 1.87E+10 * | 1.24E+10 | 1.59E+10 | 1.95E+10 * |

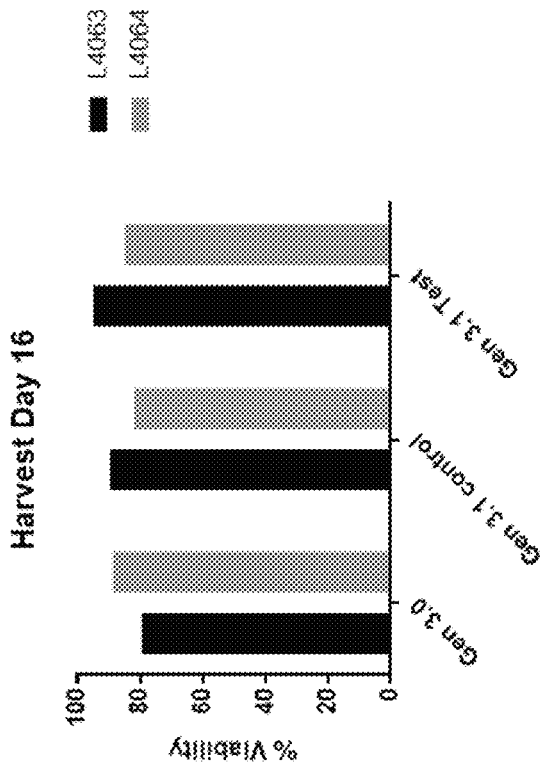
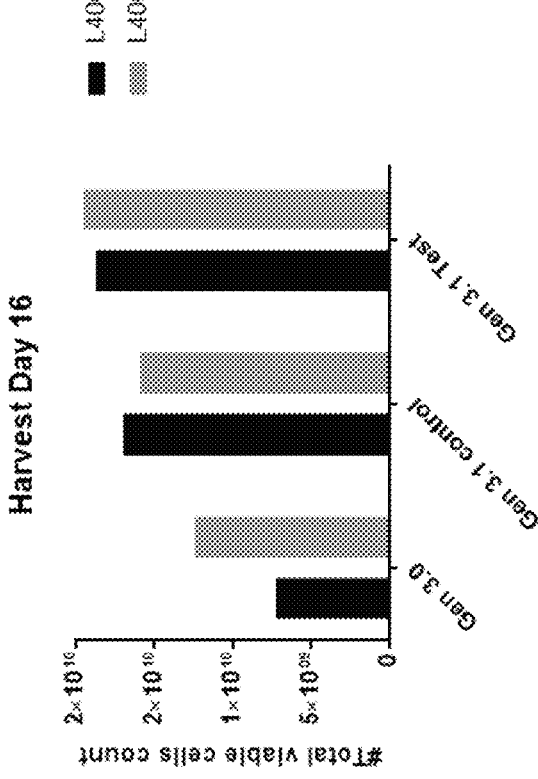
FIG. 54

FIG. 55

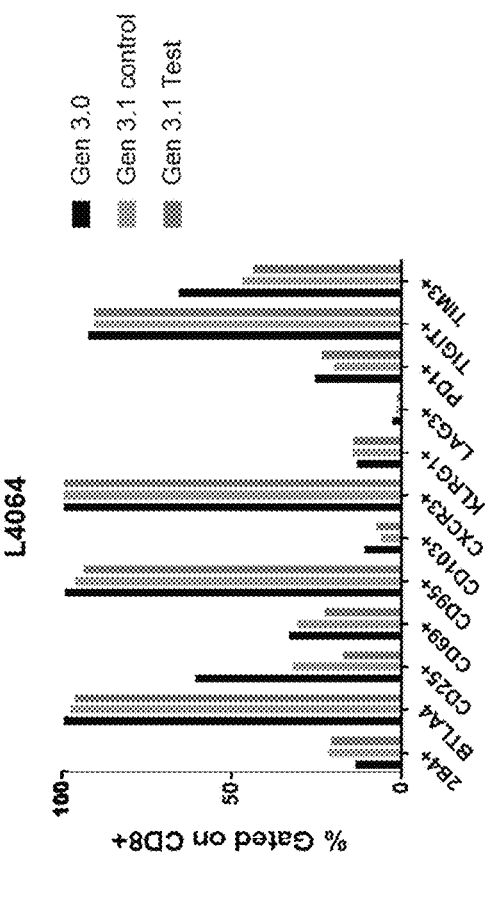
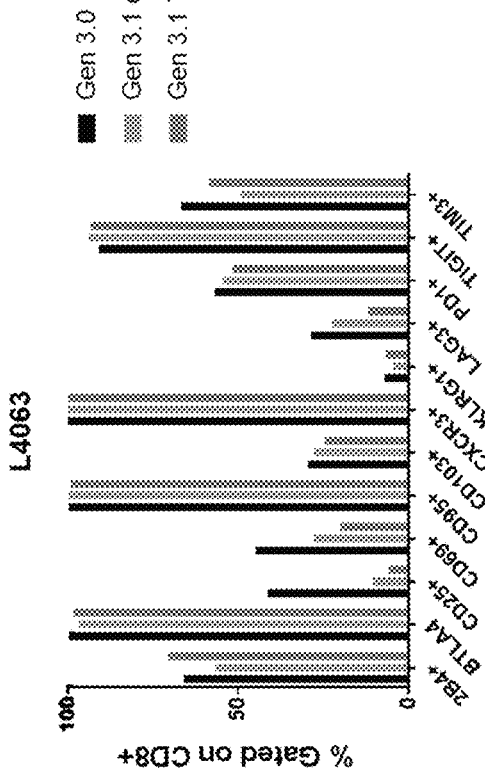
FIG. 58

| Process Day | Conditions | Gen 3.0 | Gen 3.1 Control | Gen 3.1 Test |
|---|---|---|---|---|
| | Media CM1 | 500 mL | 500 mL | 500 mL |
| | IL-2 (6000 IU/mL) | + | + | + |
| Day 0, pre REP initiation | OKT-3 (30ng/mL) | - | + | + |
| | Feeders (250 E+06) | - | - | + |

| | Gen 2 | Gen 3 |
|---|---|---|
| Total Culture Time | 22d | 16-17d |
| Pre-REP | | |
| Fragments/flask | ≤60 fragments in 1 flask | ≤60 fragments/flask in up to 4 flasks |
| Media volume | 1L - Single addition | 1L ~ 2 x 500mL additions |
| Target preREP cell numbers | ≤200e6 TIL | All cells carried through continuous process |
| Screening | No screen | No screen |
| Selection of flasks | No selection | Bac-T sterility, visual inspection for contaminants |
| REP / Scale up | | |
| Feeders | | Reduced by ≥40% |
| Media | Contains HSAB | Defined |
| Scale up | Pooled culture / Volume reduce to 500mL on Day 5 split up to 5 flasks (2500 cm2) | Flasks scaled linearly and treated as subcomponents |
| OKT3 | 150ug | ≤180ug at max scale |
| IL2 | High dose | High dose |
| Number of flasks | 1-5 | 1-4 |
| Harvest-Volume reduction | Closed 10:1 | Closed 10:1 |
| Concentrate/Wash | LOVO 100:1 | LOVO 1000:1 |
| Formulation | 1:1 CS10 (5% DMSO) | 1:1 CS10 (5% DMSO) |
| Shipment | Vapor phase LN | Vapor phase LN |
| Infusion | Thawed IV gravity | Thawed IV gravity |

FIG. 65A

| | | Gen 2 | Gen 3 |
|---|---|---|---|
| Total Culture Time | | 22d | 16 |
| | Fragment Culture | | |
| | Fragments/flask | ≤60 fragments in 1 flask | ≤60 fragments/flask in up to 4 flasks |
| | Media volume | 1L - Single addition | 1L – 2 x 500mL additions |
| | Target preREP cell numbers | ≤200e6 TIL | All cells carried through continuous process |
| | Screening | No screen | No screen |
| | Selection of flasks | No selection | Bac-T sterility, visual inspection for contaminants |
| REP / Scale up | | | |
| | Feeders | | Reduced by ≥40% |
| | Media | Contains HSAB | Defined |
| | Scale up | Pooled culture Volume reduce to 500mL on Day 5 split up to 5 flasks (2500 cm2) | Flasks scaled linearly and treated as subcomponents |
| | OKT3 | 150µg | ≤180µg at max scale |
| | IL2 | High dose | High dose |
| | Number of flasks | 1-5 | 1-4 |
| Harvest-Volume reduction | | Closed 10:1 | Closed 10:1 |
| Concentrate/Wash | | LOVO 100:1 | LOVO 1000:1 |
| Formulation | | 1:1 CS10 (5% DMSO) | 1:1 CS10 (5% DMSO) |
| Shipment | | Vapor phase LN | Vapor phase LN |
| Infusion | | Thawed IV gravity | Thawed IV gravity |

FIG. 65B

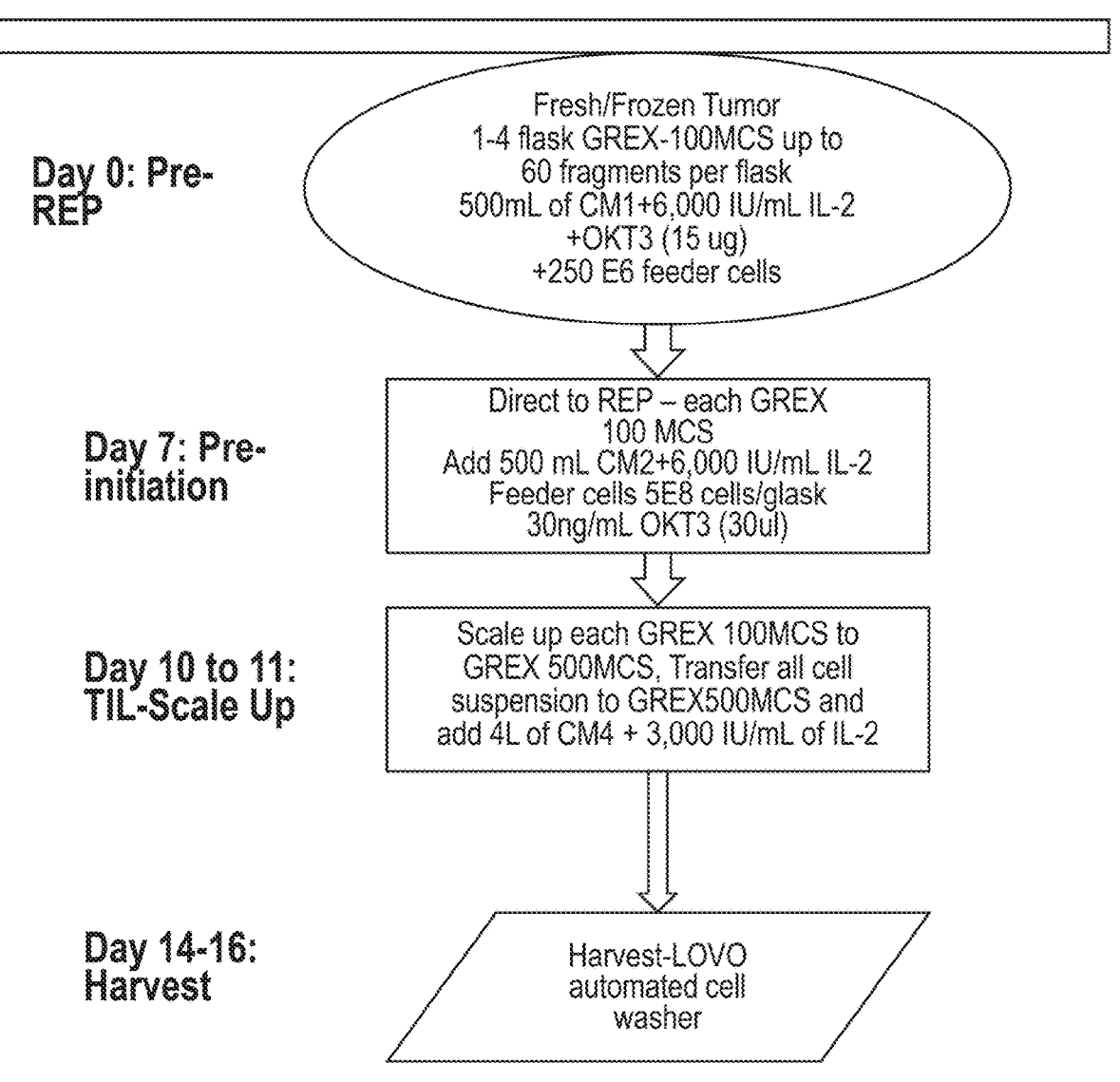

Day 0: Pre-REP

Fresh/Frozen Tumor
1-4 flask GREX-100MCS up to
60 fragments per flask
500mL of CM1+6,000 IU/mL IL-2
+OKT3 (15 ug)
+250 E6 feeder cells

Day 7: Pre-initiation

Direct to REP – each GREX
100 MCS
Add 500 mL CM2+6,000 IU/mL IL-2
Feeder cells 5E8 cells/glask
30ng/mL OKT3 (30ul)

Day 10 to 11: TIL-Scale Up

Scale up each GREX 100MCS to
GREX 500MCS, Transfer all cell
suspension to GREX500MCS and
add 4L of CM4 + 3,000 IU/mL of IL-2

Day 14-16: Harvest

Harvest-LOVO
automated cell
washer

FIG. 67

Data Summary of testing Day 16/17

| Testing Parameter | 1st Eng. Run Day 17 10 March 2019 | 2nd Eng. Run Day 17 11 March 2019 | 3rd Eng. Run Day 17 25 March 2019 | Gen 2 (n=47) Mean | Gen 2 (n=47) Median | Gen 2 (n=47) Stdev |
|---|---|---|---|---|---|---|
| Pre-LOVO TVC | 17.3E+09 | 46.1E+09 | | | | |
| Pre-LOVO % Viability | 90.5% | 94.3% | | | | |
| Post-LOVO TVC | 17.9E+09 | 59.4E+09 | 48.2E+09 | | | |
| Post-LOVO % Viability | 85.3% | 90.7% | 89% | | | |
| TVC Post LOVO % Recovery | 103.5% | 128.9% | | | | |
| %CD45+/CD3+ | 88.0% | 98.3% | | | | |
| IFNγ (pg/mL) | 11,618 | 19,235 | | 10,005 | 9,637 | 5,128 |
| GrzB (pg/mL) | 11,326 | 27,441 | | 19,929 | 16,040 | |
| Sterility | Pending (*) | Pending (*) | | | | |
| Endotoxin (total EU units) | 154.2 EU | 195.9 EU | | | | |
| Mycoplasma | Negative | Negative | | | | |
| Gram Staining | No organisms detected | No organisms detected | | | | |

FIG. 68

*Adds up to entire TIL sample (100% Live, CD14-, except for monocytes)

| Characteristic | Eng run #1 | Eng run #2 |
| --- | --- | --- |
| NK cells (CD3-CD56+) (%) | 10.9 | 1.5 |
| B cells (CD3-CD19+) (%) | 0.2 | 0.2 |
| Monocytes (CD14+) (%) | 0.0 | 0.0 |
| TCRαβ (%) | 87.1 | 96.3 |
| TCRγδ (%) | 1.2 | 1.6 |
| Sum | 99.4 | 99.6 |

*Adds up to 100% TCRab

| Characteristic | Eng run #1 | Eng run #2 |
| --- | --- | --- |
| Naïve: CCR7+CD45RA+ (%) | 0.0 | 0.1 |
| T-EM: CCR7-CD45RA- (%) | 92.2 | 84.4 |
| T-CM: CCR7+CD45RA- (%) | 7.7 | 15.5 |
| T-EFF/TEMRA: CCR7-CD45RA+ (%) | 0.1 | 0.1 |
| Sum | 100.0 | 100.0 |

*Adds up to 100% Live, CD14-

| Characteristic | Eng run #1 | Eng run #2 |
| --- | --- | --- |
| TCRαβ⁺ CD4⁺ (%) | 89.6 | 71.8 |
| TCRαβ⁺ CD8⁺ (%) | 10.0 | 27.8 |
| Sum | 99.6 | 99.6 |

FIG. 69

*Adds up to entire TIL sample (100% Live, CD14-, except for monocytes)

| Characteristic | PD run #1 L4063 | PD run #2 L4064 |
|---|---|---|
| NK cells (CD3-CD56+) (%) | 1.04 | 0.52 |
| B cells (CD3-CD19+) (%) | 0.0076 | 0.013 |
| Monocytes (CD14+) (%) | 0.032 | 0.043 |
| TCRαβ (%) | 95.5 | 96.7 |
| TCRγδ (%) | 2 | 1.86 |
| Sum | 98.6 | 99.14 |

*Adds up to 100% TCRab

| Characteristic | PD run #1 L4063 | PD run #2 L4064 |
|---|---|---|
| Naïve: CCR7+CD45RA+ (%) | 0.35 | 0.07 |
| T-EM: CCR7-CD45RA- (%) | 97.4 | 96.7 |
| T-CM: CCR7+CD45RA- (%) | 1.39 | 2.78 |
| T-EFF/TEMRA: CCR7-CD45RA+ (%) | 0.88 | 0.44 |
| Sum | 100.0 | 100.0 |

| Characteristic | PD run #1 L4063 | PD run #2 L4064 |
|---|---|---|
| TCRαβ⁺ CD4⁺ (%) | 77.5 | 57.4 |
| TCRαβ⁺ CD8⁺ (%) | 16.8 | 36.1 |
| Sum | 94.3 | 93.5 |

FIG. 70

| Characteristic | OV-8025 | | | OV-8026 | | | OV-8028 | | | OV-8022 | | |
|---|---|---|---|---|---|---|---|---|---|---|---|---|
| | FRER* | Gen 2$^γ$ | Gen 3.1 | FRER$^γ$ | Gen 2 | Gen 3.1 | FRER | Gen 2$^γ$ | Gen 3.1 | FRER | Gen 2$^γ$ | Gen 3.1* |
| Purity | | | | | | | | | | | | |
| T cells (CD45+CD3+) (%) | ' | ' | 99.2 | ' | 75.1 | 97.5 | 97 | ' | 97.6 | 53.6 | 16.4 | ' |
| NK cells (CD3-CD56+) (%) | ' | ' | 0.2 | ' | 8.4 | 1.1 | 0.4 | ' | 0.1 | 44.6 | 81.1 | ' |
| B cells (CD3-CD19+) (%) | ' | ' | 0 | ' | 2.1 | 0 | 0 | ' | 0 | 1.3 | 3.3 | ' |
| Monocytes (CD14+) (%) | ' | ' | 0 | ' | 0.2 | 0 | 0 | ' | 0 | 2 | 0.1 | ' |
| Identity T cells | | | | | | | | | | | | |
| TCR αβ (%) | ' | ' | 98.8 | ' | 71.9 | 96.4 | 98.7 | ' | 99.4 | 52.2 | 12.4 | ' |
| TCR γδ (%) | ' | ' | 0.3 | ' | 0.8 | 0.6 | ' | ' | 0.1 | 0.1 | 0 | ' |
| CD3+ CD4+ (%) | ' | ' | 85.7 | ' | 63.1 | 81.5 | 81.8 | ' | 92.3 | 77.3 | 48.6 | ' |
| CD3+ CD8+ (%) | ' | ' | 12 | ' | 23 | 14.4 | 15.5 | ' | 5.2 | 16.6 | 26.1 | ' |
| Memory Phenotype-TCRαβ+ | | | | | | | | | | | | |
| Naïve: CCR7+CD45RA+ (%) | ' | ' | 0 | ' | 0.4 | 0 | 2.1 | ' | 0 | 0 | 0.1 | ' |
| T-EM: CCR7-CD45RA-(%) | ' | ' | 98.5 | ' | 88.7 | 97.5 | 93.6 | ' | 97.1 | 89.1 | 93.8 | ' |
| T-CM: CCR7+CD45RA-(%) | ' | ' | 1 | ' | 7.5 | 0.6 | 1.9 | ' | 2.5 | 0.1 | 0 | ' |
| T-EFF/TEMRA: CCR7-CD45RA+(%) | ' | ' | 0.4 | ' | 3.4 | 1.8 | 2.4 | ' | 0.3 | 10.8 | 6.1 | ' |

FR ER: Frozen tumor, Early REP
*: Condition not test
$^γ$: Sampling issue, low TVC count or non-viable cells on thawing

FIG. 71

| Characteristic | Hierarchy | | Eng run #1 | Eng run #2 |
|---|---|---|---|---|
| NK cells (CD3-CD56+) (%) | S1/S2/All/Live/CD14-/CD3-/NK | Freq. of null (%) | 10.9 | 1.5 |
| B cells (CD3-CD19+) (%) | S1/S2/All/Live/CD14-/CD19 | Freq. of null (%) | 0.2 | 0.2 |
| Monocytes (CD14+) (%) | S1/S2/All/Live/CD14+ | Freq. of Parent (%) | 0.0 | 0.0 |
| TCRαβ (%) | S1/S2/All/Live/CD14-/TCRab | Freq. of null (%) | 87.1 | 96.3 |
| TCRγδ (%) | S1/S2/All/Live/CD14-/TCRgd | Freq. of null (%) | 1.2 | 1.6 |
| TCRαβ+CD4+ (%) | S1/S2/All/Live/CD14-/TCRab/CD4 | Freq. of Parent (%) | 89.6 | 71.8 |
| TCRαβ+CD8+ (%) | S1/S2/All/Live/CD14-/TCRab/CD8 | Freq. of Parent (%) | 10.0 | 27.8 |
| Naïve: CCR7+CD45RA+ (%) | S1/S2/All/Live/CD14-/TCRab/Q2: CCR7+, CD45RA+ | Freq. of Parent (%) | 0.0 | 0.1 |
| T-EM: CCR7-CD45RA- (%) | S1/S2/All/Live/CD14-/TCRab/Q4: CCR7-, CD45RA- | Freq. of Parent (%) | 92.2 | 84.4 |
| T-CM: CCR7+CD45RA- (%) | S1/S2/All/Live/CD14-/TCRab/Q3: CCR7+, CD45RA- | Freq. of Parent (%) | 7.7 | 15.5 |
| T-EFF/TEMRA: CCR7-CD45RA+(%) | S1/S2/All/Live/CD14-/TCRab/Q1: CCR7-, CD45RA+ | Freq. of Parent (%) | 0.1 | 0.1 |
| Naïve: CD62L+CD45RA+ (%) | S1/S2/All/Live/CD14-/TCRab/Q6: CD62L+, CD45RA+ | Freq. of Parent (%) | 0.2 | 0.1 |
| T-EM: CD62L-CD45RA- (%) | S1/S2/All/Live/CD14-/TCRab/Q8: CD62L-, CD45RA- | Freq. of Parent (%) | 47.7 | 49.5 |
| T-CM: CD62L+CD45RA- (%) | S1/S2/All/Live/CD14-/TCRab/Q7: CD62L+, CD45RA- | Freq. of Parent (%) | 52.1 | 50.4 |
| T-EFF/TEMRA: CD62L-CD45RA+(%) | S1/S2/All/Live/CD14-/TCRab/Q5: CD62L-, CD45RA+ | Freq. of Parent (%) | 0.1 | 0.0 |

*Adds up to CD3+CD45+ %

| Characteristic | Eng run #1 | Eng run #2 |
|---|---|---|
| TCRαβ (%) | 87.1 | 96.3 |
| TCRγδ (%) | 1.2 | 1.6 |
| Sum | 88.3 | 97.9 |

FIG. 72

| Characteristic | Hierarchy | CD4+ | | CD8+ | |
|---|---|---|---|---|---|
| | | Eng run #1 | Eng run #2 | Eng run #1 | Eng run #2 |
| CD27+ (%) | S1/S2/All/Live/CD14-/TCRab/CD4 or CD8/CD4+/8+CD27+ \| Freq. of Parent (%) | 0.7 | 2.0 | 2.1 | 12.7 |
| CD28+ (%) | S1/S2/All/Live/CD14-/TCRab/CD4 or CD8/CD4+/8+CD28+ \| Freq. of Parent (%) | 41.2 | 50.1 | 3.6 | 13.9 |
| CD57+ (%) | S1/S2/All/Live/CD14-/TCRab/CD4+/8+CD57+ \| Freq. of Parent (%) | 1.0 | 6.9 | 0.1 | 3.7 |
| 2B4+ (%) | S/S/Live/CD3/CD4 or CD8/btla \| Freq. of Parent (%) | 4.5 | 5.5 | 69.1 | 55.7 |
| BTLA4+ (%) | S/S/Live/CD3/CD4 or CD8/2b4 \| Freq. of Parent (%) | 67.5 | 86.1 | 79.6 | 89.1 |
| CCR4+ (%) | S/S/Live/CD3/CD4 or CD8/CCR4+ \| Freq. of Parent (%) | 94.1 | 93.6 | 84.2 | 96.6 |
| CD25+ (%) | S/S/Live/CD3/CD4 or CD8/CD25 \| Freq. of Parent (%) | 63.1 | 61.0 | 47.5 | 51.8 |
| CD69+ (%) | S/S/Live/CD3/CD4 or CD8/CD69 \| Freq. of Parent (%) | 47.0 | 22.8 | 45.4 | 25.8 |
| CD95+ (%) | S/S/Live/CD3/CD4 or CD8/CD95 \| Freq. of Parent (%) | 99.2 | 98.1 | 99.1 | 97.6 |
| CD103+ (%) | S/S/Live/CD3/CD4 or CD8/CD103 \| Freq. of Parent (%) | 4.2 | 10.7 | 25.0 | 36.9 |
| CXCR3+ (%) | S/S/Live/CD3/CD4 or CD8/CXCR3 \| Freq. of Parent (%) | 58.1 | 76.7 | 89.3 | 88.3 |
| KLRG1+ (%) | S/S/Live/CD3/CD4 or CD8/KLRG1 \| Freq. of Parent (%) | 0.3 | 8.9 | 3.1 | 35.8 |
| LAG3+ (%) | S/S/Live/CD3/CD4 or CD8/Lag3 \| Freq. of Parent (%) | 5.0 | 3.3 | 19.4 | 21.2 |
| PD1+ (%) | S/S/Live/CD3/CD4 or CD8/PD1 \| Freq. of Parent (%) | 29.3 | 22.1 | 11.2 | 7.2 |
| TIGIT+ (%) | S/S/Live/CD3/CD4 or CD8/Tigit \| Freq. of Parent (%) | 68.1 | 53.2 | 74.9 | 65.8 |
| TIM3+ (%) | S/S/Live/CD3/CD4 or CD8/TIM3 \| Freq. of Parent (%) | 93.6 | 81.8 | 91.2 | 84.4 |

FIG. 73

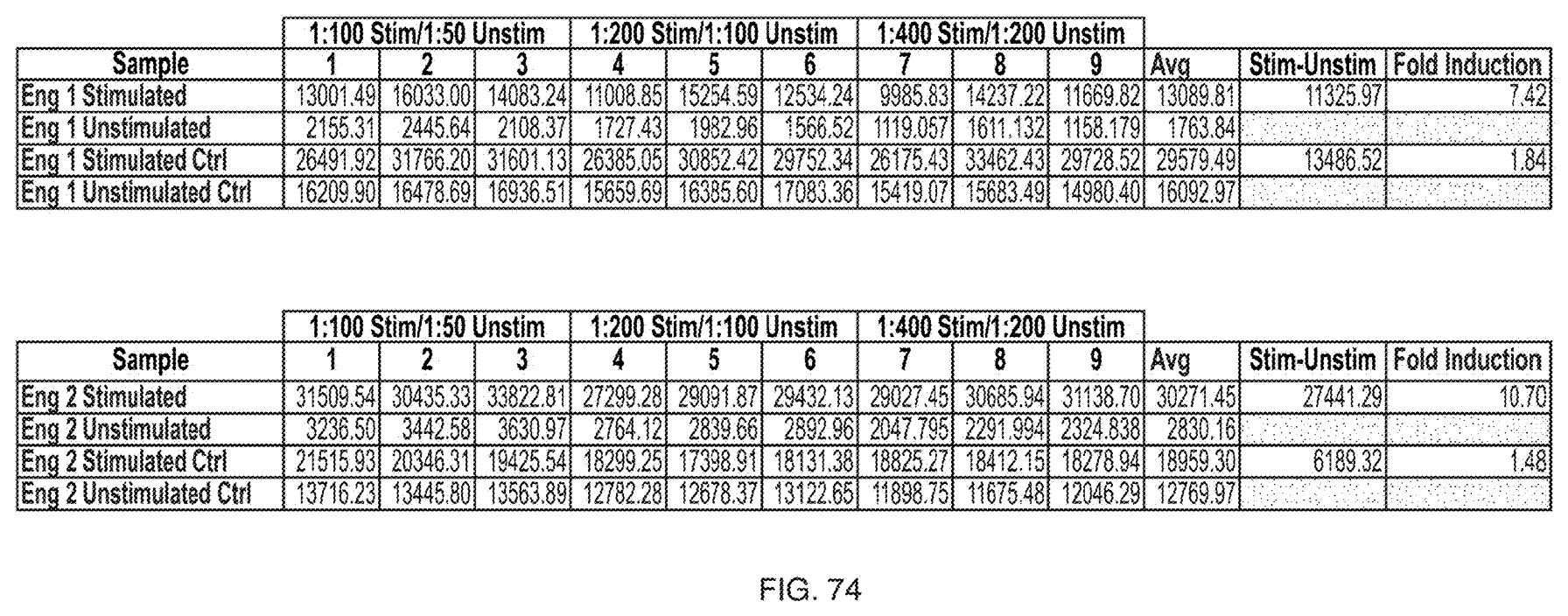

| Sample | 1:100 Stim/1:50 Unstim | | | 1:200 Stim/1:100 Unstim | | | 1:400 Stim/1:200 Unstim | | | Avg | Stim-Unstim | Fold Induction |
| | 1 | 2 | 3 | 4 | 5 | 6 | 7 | 8 | 9 | | | |
|---|---|---|---|---|---|---|---|---|---|---|---|---|
| Eng 1 Stimulated | 13001.49 | 16033.00 | 14083.24 | 11008.85 | 15254.59 | 12534.24 | 9385.83 | 14237.22 | 11669.82 | 13089.81 | 11325.97 | 7.42 |
| Eng 1 Unstimulated | 2155.31 | 2445.64 | 2108.37 | 1727.43 | 1982.96 | 1566.52 | 1119.057 | 1611.132 | 1158.179 | 1763.84 | | |
| Eng 1 Stimulated Ctrl | 26491.92 | 31766.20 | 31601.13 | 26385.05 | 30852.42 | 29752.34 | 26175.43 | 33462.43 | 29728.52 | 29579.49 | 13486.52 | 1.84 |
| Eng 1 Unstimulated Ctrl | 16209.90 | 16478.69 | 16936.51 | 15659.69 | 16385.60 | 17083.36 | 15419.07 | 15683.49 | 14980.40 | 16092.97 | | |

| Sample | 1:100 Stim/1:50 Unstim | | | 1:200 Stim/1:100 Unstim | | | 1:400 Stim/1:200 Unstim | | | Avg | Stim-Unstim | Fold Induction |
| | 1 | 2 | 3 | 4 | 5 | 6 | 7 | 8 | 9 | | | |
|---|---|---|---|---|---|---|---|---|---|---|---|---|
| Eng 2 Stimulated | 31509.54 | 30435.33 | 33822.81 | 27299.28 | 29091.87 | 29432.13 | 28027.45 | 30685.94 | 31138.70 | 30271.45 | 27441.29 | 10.70 |
| Eng 2 Unstimulated | 3236.50 | 3442.58 | 3630.97 | 2764.12 | 2839.66 | 2892.96 | 2047.795 | 2291.994 | 2324.838 | 2830.16 | | |
| Eng 2 Stimulated Ctrl | 21515.93 | 20346.31 | 19425.54 | 18299.25 | 17398.91 | 18131.38 | 18825.27 | 18412.15 | 18278.94 | 18959.30 | 6189.32 | 1.48 |
| Eng 2 Unstimulated Ctrl | 13716.23 | 13445.80 | 13563.89 | 12782.28 | 12678.37 | 13122.65 | 11898.75 | 11675.48 | 12046.29 | 12769.97 | | |

FIG. 74

| STEP | Gen 2 | Gen 2.1 | Gen 3.0 |
|---|---|---|---|
| Pre REP. day 0 | ≤ 50 fragments/ 1 G-Rex 100MCS - 11 days | ≤ 180 fragments/3 G-Rex, Pre-formulated CM1 warmed media 100MCS - 11 days | *Fresh or Frozen Tumor* Whole tumor with ≤ 30 fragments up to 60 fragments per 1 G-Rex. 100MCS (up to 4 G-Rex), preformulated warmed media - 7 days. Pre REP, Feeders 250e6 cells + OKT-3 (15ug) |
| REP Initiation | Direct to REP- Day 11- <200e6 TIL 1 G-Rex 500MCS | Direct to REP- Day 11- <200 e6 TIL Pre-formulated CM2 warmed media in one G-Rex 500MCS | Direct to REP - Day 7-all cells TIL- same G-Rex 100MCS (100MCS up to 4 GREX), Standard media or Defined Media (Serum free). Addition Feeders 500e6 cells +OKT-3 (30ug) |
| TIL propagation or Scale up | 1 to 5 G-REX 500MCS Split day 16 | 2 to 5 G-REX 500MCS Pre-formulated CM4 warmed media Split day 16 | From G-REX 100MCS transfer TIL suspension to G-REX 500MCS, up to 4 GREX 500 MCS- Standard media or Defined Media (Serum Free) Scale up on day 10 or 11 |
| Harvest | Harvest day 22, LOVO-automated cell washer | Harvest day 22, LOVO-automated cell washer (5 wash cycle) | Harvest day 14 or 16 LOVO- automated cell washer (5 wash cycle) |
| Final formulation | Cryopreserved Product 300IU/ml IL2- CS10 in LN₂, multiple aliquots | Cryopreserved Product 300IU/ml IL2- CS10 in LN₂, multiple aliquots | Cryopreserved Product 300IU/ml IL2-CS10 in LN₂, multiple aliquots |
| Process time | 22 days | 22 days | 16 days |

| Process Comparison | Process Changes | Differences |
|---|---|---|
| Gen 2 :<br>Gen 2.1 | • Initiate process with two flasks instead of one flask<br>• Divide REP initiation feeder layer between 2 G-Rex500MCS Flasks<br>• Pre-formulate media and warm prior to use | • Potential doubling of final cell count (dose) with increased TIL repertoire.<br>• Process redundancy throughout process |
| Gen 2.1 :<br>Gen 3.1 | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

FIG. 79

| Process Day | Conditions | Gen 3.0 | Gen 3.1 control | Gen 3.1 Test |
|---|---|---|---|---|
| Day 0 : Tumor Fragment Isolation and Activation | Media (*) | 500 mL | 500 mL | 500 mL |
| | IL-2 | 6000 IU/mL | 6000 IU/mL | 6000 IU/mL |
| | OKT-3 | - | 15 ug | 15 ug |
| | Feeders | - | - | 2.5E+06 |
| Process Day | Conditions | Gen 3.0 | Gen 3.1 control | Gen 3.1 Test |
| Day 7 - 8 : TIL Culture Reactivation | Media (*) | 500 mL | 500 mL | 500 mL |
| | IL-2 | 6000 IU/mL | 6000 IU/mL | 6000 IU/mL |
| | OKT-3 | 30 ug | 30 ug | 30 ug |
| | Feeders | 1 E+09 | 500 E+06 | 500E+06 |
| | Total Feeders added through Day 7 | 1 E+09 | 500 E+06 | 750E+06 |
| Process Day | Conditions | Gen 3.0 | Gen 3.1 control | Gen 3.1 Test |
| Day 10-11 : Culture Scale Up | Conditions | From GREX 100 transfer whole TIL suspension to 1 GREX 500 containing 4L media with IL-2 (3000 IU/mL) | | |
| Process Day | Conditions | Gen 3.0 | Gen 3.1 control | Gen 3.1 Test |
| Day 16 –17: Harvest/Wash/Formulate | | LOVO automated cell washer and cryopreservation with CS10. | | |

(*) Media can be standard media or CTS serum free media.

FIG. 81

| Process Day | L4063 in Standard Media | | | L4064 in Serum Free Media | | |
| --- | --- | --- | --- | --- | --- | --- |
| | Gen 3.0 | Gen 3.1 Control | Gen 3.1 Test | Gen 3.0 | Gen 3.1 Control | Gen 3.1 Test |
| Number of fragments | 53 | 53 | 53 | 21 | 21 | 21 |
| Average TVC at harvest per fragment | 1.37E+08 | 3.19E+08 | 3.53E+08 | 5.90E+08 | 7.57E+08 | 9.29E+08 |
| TVC day 7 (*) | 2.59E+07 | 6.43E+07 | 1.45E+08 | 7.35E+06 | 9.28E+07 | 1.39E+08 |
| TVC day 10/11 (*) | 6.07E+08 | 1.66E+09 | 1.83E+09 | 7.48E+08 | 1.28E+09 | 1.72E+09 |
| TVC harvest day 16/17 | 7.26E+09 | 1.69E+10 | 1.87E+10 | 1.24E+10 | 1.59E+10 | 1.95E+10 |
| Fold Expansion (day 10 or 11 /day 7) | 23.4 | 25.8 | 12.6 | 101.8 | 13.8 | 12.4 |
| Fold Expansion (Harvest day 16 / day 7) | 280.3 | 262.8 | 129.0 | 1687.1 | 171.3 | 140.3 |

(*) Cell counts for Day 7 and Day 10/11 were taken FIO. Based on the design of the process, samples were pulled directly from each flask after swirling its contents without volume reduction. As such, analysis and conclusions of cell count data from these samples is limited by the nature of the sampling methodology.

FIG. 82

| Process Day | L4063 in Standard media | | | | L4064 in CTS Serum Free media | | |
| | Gen 3.0 | Gen 3.1 Control | Gen 3.1 Test | Gen 3.0 | Gen 3.0 | Gen 3.1 Control | Gen 3.1 Test |
|---|---|---|---|---|---|---|---|
| Reactivation | 74.6% | 92.1% | 88.7% | 88.0% | 92.8% | 95.0% |
| Scale up | 92.1% | 95.4% | 94.0% | 90.4% | 94.3% | 95.1% |
| Harvest | 79.5% | 89.4% | 94.8% | 88.8% | 81.9% | 84.9% |

FIG. 83

| Tumor ID | L4063 in Standard media | | | L4064 in CTS Serum Free media | | |
|---|---|---|---|---|---|---|
| Markers | Gen 3.0 | Gen 3.1 Control | Gen 3.1 Test | Gen 3.0 | Gen 3.1 Control | Gen 3.1 Test |
| L/D Aqua | 82.2 | 89.4 | 91.0 | 76.6 | 83.1 | 89.5 |
| NK | 1.3 | 0.4 | 1.0 | 2.5 | 0.2 | 0.5 |
| TCRa/b+ | 88.6 | 97.5 | 95.5 | 93.0 | 97.3 | 96.7 |
| CD4 | 56.4 | 85.8 | 77.5 | 33.8 | 64.8 | 57.4 |
| CD4/CD27 | 3.8 | 2.1 | 3.4 | 6.7 | 0.7 | 2.2 |
| CD4/CD28 | 82.7 | 71.8 | 80.2 | 97.5 | 73.5 | 66.8 |
| CD4/CD56 | 0.4 | 0.5 | 0.7 | 0.5 | 0.5 | 0.3 |
| CD4/CD57 | 6.7 | 17.0 | 20.5 | 16.0 | 7.6 | 8.0 |
| CD8 | 29.6 | 11.2 | 16.8 | 51.9 | 28.9 | 36.1 |
| CD8/CD27 | 15.0 | 25.6 | 30.5 | 14.1 | 3.3 | 6.7 |
| CD8/CD28 | 47.5 | 23.0 | 24.5 | 88.0 | 45.1 | 37.3 |
| CD8/CD56 | 3.3 | 2.3 | 4.2 | 6.6 | 10.3 | 10.0 |
| CD8/CD57 | 0.3 | 1.2 | 1.1 | 1.3 | 2.0 | 2.5 |

FIG. 84

| Tumor ID | L4063 in Standard media | | | L4064 in CTS Serum Free media | | |
|---|---|---|---|---|---|---|
| Markers | Gen 3.0 | Gen 3.1 Control | Gen 3.1 Test | Gen 3.0 | Gen 3.1 Control | Gen 3.1 Test |
| CD3/CD4 | 56.4 | 85.8 | 77.5 | 33.8 | 64.8 | 57.4 |
| TEMRA of CD4 | 0.4 | 0.7 | 0.4 | 1.1 | 0.7 | 0.2 |
| NAIVE of CD4 | 0.3 | 0.2 | 0.2 | 0.5 | 0.1 | 0.0 |
| CM of CD4 | 45.6 | 16.8 | 29.3 | 46.3 | 30.6 | 29.9 |
| EM of CD4 | 53.7 | 82.3 | 70.2 | 52.1 | 68.6 | 69.9 |
| | | | | | | |
| CD3/CD8 | 29.6 | 11.2 | 16.8 | 51.9 | 28.9 | 36.1 |
| TEMRA of CD8 | 3.1 | 0.5 | 0.9 | 6.1 | 8.0 | 5.4 |
| NAIVE of CD8 | 0.7 | 0.1 | 0.4 | 2.2 | 0.7 | 1.0 |
| CM of CD8 | 22.0 | 15.8 | 29.7 | 61.9 | 18.9 | 18.2 |
| EM of CD8 | 74.3 | 83.5 | 69.0 | 29.8 | 72.4 | 75.5 |

FIG. 85

| Tumor ID | L4063 In Standard media | | | | L4064 in CTS Serum Free media | | |
|---|---|---|---|---|---|---|---|
| Markers | Gen 3.0 | Gen 3.1 Control | Gen 3.1 Test | Gen 3.0 | Gen 3.1 Control | Gen 3.1 Test |
| 2B4+ | 2.1 | 0.6 | 1.0 | 2.0 | 1.2 | 1.3 |
| BTLA4 | 99.7 | 95.4 | 96.9 | 99.5 | 98.8 | 98.1 |
| CD25+ | 48.6 | 10.5 | 3.9 | 58.2 | 41.7 | 32.1 |
| CD69+ | 27.1 | 37.7 | 21.5 | 39.4 | 35.6 | 30.5 |
| CD95+ | 99.9 | 99.9 | 99.5 | 99.6 | 99.0 | 97.3 |
| CD103+ | 0.7 | 1.2 | 0.4 | 1.4 | 1.3 | 1.2 |
| KLRG1+ | 1.6 | 3.7 | 3.3 | 11.4 | 8.3 | 10.7 |
| LAG3+ | 5.6 | 8.2 | 3.3 | 1.5 | 1.6 | 1.4 |
| PD1+ | 77.4 | 58.4 | 41.6 | 34.1 | 28.4 | 26.7 |
| TIGIT+ | 68.5 | 40.3 | 30.3 | 45.8 | 52.1 | 52.2 |
| TIM3+ | 58.0 | 42.4 | 59.4 | 61.0 | 58.4 | 56.8 |

FIG. 86

| Tumor ID | L4063 in Standard media | | | L4064 in CTS Serum Free media | | |
|---|---|---|---|---|---|---|
| Markers | Gen 3.0 | Gen 3.1 Control | Gen 3.1 Test | Gen 3.0 | Gen 3.1 Control | Gen 3.1 Test |
| 2B4+ | 65.8 | 56.6 | 70.5 | 13.6 | 21.5 | 20.7 |
| BTLA4 | 99.5 | 96.6 | 98.2 | 99.3 | 97.4 | 96.1 |
| CD25+ | 41.4 | 10.5 | 5.9 | 60.6 | 32.0 | 17.1 |
| CD69+ | 44.9 | 28.0 | 20.0 | 33.2 | 30.6 | 22.7 |
| CD95+ | 99.6 | 99.6 | 98.9 | 98.9 | 96.1 | 93.5 |
| CD103+ | 29.4 | 27.9 | 24.5 | 10.9 | 6.0 | 7.3 |
| CXCR3+ | 99.9 | 99.9 | 99.8 | 99.3 | 99.2 | 99.2 |
| KLRG1+ | 7.1 | 4.6 | 6.7 | 13.2 | 14.5 | 14.1 |
| LAG3+ | 28.6 | 22.5 | 11.9 | 2.8 | 1.6 | 1.4 |
| PD1+ | 56.9 | 54.5 | 51.7 | 25.4 | 20.0 | 23.6 |
| TIGIT+ | 90.8 | 93.7 | 93.3 | 92.1 | 90.4 | 90.5 |
| TIM3+ | 66.7 | 49.1 | 58.6 | 65.6 | 46.8 | 43.6 |

FIG. 87

| TIL Characterization | L4063 in Standard media | | L4064 in CTS Serum Free media | | |
|---|---|---|---|---|---|
| | Gen 3.0 | Gen 3.1 Control | Gen 3.1 Test | Gen 3.0 | Gen 3.1 Control | Gen 3.1 Test |
| IFNγ (pg/mL) | 907 | 428 | 2863 | 1485 | 3130 | 3863 |

*Results are reported as mean of triplicate samples from one representative experiment*

FIG. 88

| Process Day | L4063 in Standard media | | | L4064 in CTS Serum Free media | | |
|---|---|---|---|---|---|---|
| | Gen 3.0 | Gen 3.1 Control | Gen 3.1 Test | Gen 3.0 | Gen 3.1 Control | Gen 3.1 Test |
| Reactivation | 12319.6 | 11928.7 | 11786.7 | 5891.6 | 5671.8 | 389.4[1] |
| Scale Up | 32095.1 | 30368.6 | 26145.0 | * | * | * |
| Harvest | 17309.3 | 13828.4 | 16019.2 | 656.0 | 826.2 | 768.9 |

*Results are reported as mean of triplicate samples from one representative experiment*

*(*) Spent media from day 10/11 on L4064 was not collected during the execution of the runs.*

*(1) The data for Gen 3.1 Test L4064 on reactivation day was significantly below the corresponding values for Gen 3.1 control and Gen 3.0 conditions. Due to the low amount of sample taken, it was not possible to repeat the assay to verify the accuracy of this number.*

FIG. 89

| Glucose (g/L) | | | | | | |
|---|---|---|---|---|---|---|
| | L4063 in Standard media | | | L4064 in CTS Serum Free media | | |
| Process Day | Gen 3.0 | Gen 3.1 Control | Gen 3.1 Test | Gen 3.0 | Gen 3.1 Control | Gen 3.1 Test |
| Reactivation | 1.8 | 1.7 | 1.4 | 4.3 | 4.1 | 3.8 |
| Scale Up | 1.4 | 0.9 | 0.8 | * | * | * |
| Harvest | 1.5 | 0.9 | 1.0 | 2.8 | 2.1 | 2.2 |

(*) Spent media from day 10/11 on L4064 was not collected during the execution of the runs.

FIG. 90

| Lactate (g/L) | L4063 in Standard media | | | L4064 in CTS Serum Free media | | |
|---|---|---|---|---|---|---|
| Process Day | Gen 3.0 | Gen 3.1 Control | Gen 3.1 Test | Gen 3.0 | Gen 3.1 Control | Gen 3.1 Test |
| Reactivation | 0.2 | 0.2 | 0.5 | 0.1 | 0.2 | 0.5 |
| Scale Up | 0.7 | 1.1 | 1.2 | * | * | * |
| Harvest | 1.1 | 1.7 | 1.6 | 1.5 | 2.0 | 1.9 |

(*) Spent media from day 10/11 on L4064 was not collected during the execution of the runs.

FIG. 91

| Glutamine (mmol/L) | | | | | | |
|---|---|---|---|---|---|---|
| | L4063 in Standard media | | L4064 in CTS Serum Free media | | | |
| Process Day | Gen 3.0 | Gen 3.1 Control | Gen 3.1 Test | Gen 3.0 | Gen 3.1 Control | Gen 3.1 Test |
| Reactivation | 2.0 | 2.0 | 2.0 | 1.3 | 1.2 | 1.1 |
| Scale Up | 1.7 | 1.1 | 1.1 | * | * | * |
| Harvest | 1.9 | 1.3 | 1.3 | 0.7 | 0.6 | 0.6 |

(*) Spent media from day 10/11 on L4064 was not collected during the execution of the runs.

FIG. 92

| Glutamax (mmol/L) | | | | | | | |
|---|---|---|---|---|---|---|---|
| | L4063 in Standard media | | | L4064 in CTS Serum Free media | | | |
| Process Day | Gen 3.0 | Gen 3.1 Control | Gen 3.1 Test | Gen 3.0 | Gen 3.1 Control | Gen 3.1 Test |
| Reactivation | 2.2 | 2.2 | 2.2 | 1.4 | 1.3 | 1.2 |
| Scale Up | 1.9 | 1.2 | 1.2 | * | * | * |
| Harvest | 2.1 | 1.5 | 1.5 | 0.8 | 0.7 | 0.7 |

(*) Spent media from day 10/11 on L4064 was not collected during the execution of the runs.

FIG. 93

| Ammonia (mmol/L) | L4063 in Standard media | | | L4064 in CTS Serum Free media | | |
|---|---|---|---|---|---|---|
| | | Gen 3.1 | Gen 3.1 | | Gen 3.1 | Gen 3.1 |
| Process Day | Gen 3.0 | Control | Test | Gen 3.0 | Control | Test |
| Reactivation | 1.9 | 1.9 | 2.0 | 0.7 | 0.8 | 0.9 |
| Scale Up | 1.8 | 2.2 | 2.3 | * | * | * |
| Harvest | 2.1 | 2.5 | 2.5 | 1.0 | 1.0 | 0.9 |

(*) Spent media from day 10 /11 on L4064 was not collected during the execution of the runs.

FIG. 94

| TIL Characterization | L4063 in Standard media | | | L4064 in CTS Serum Free media | | |
|---|---|---|---|---|---|---|
| | Gen 3.0 | Gen 3.1 Control | Gen 3.1 Test | Gen 3.0 | Gen 3.1 Control | Gen 3.1 Test |
| Relative Telomere Length | 7.7 | 6.3 | 6.1 | 6.4 | 6.7 | 6.6 |

FIG. 95

| TIL Characterization | L4063 in Standard media | | | L4064 in CTS Serum Free media | | |
| | Gen 3.0 | Gen 3.1 Control | Gen 3.1 Test | Gen 3.0 | Gen 3.1 Control | Gen 3.1 Test |
| --- | --- | --- | --- | --- | --- | --- |
| uCD3 | 14005.0 | 18149.0 | 171181.0 | 15107.0 | 21460.0 | 21503.0 |
| Shanon Entropy Index | 5.9 | 10.8 | 10.5 | 8.5 | 10.7 | 10.4 |

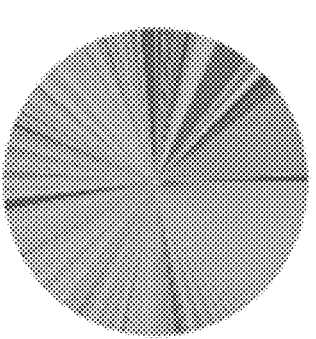
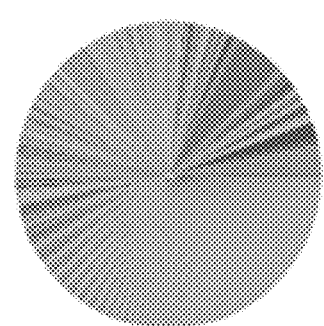
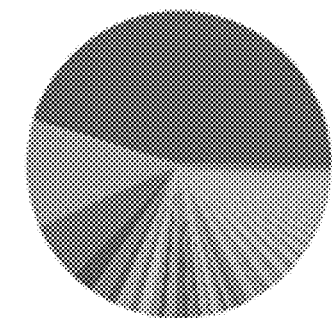
FIG. 96

FIG. 97

| Number of u CDR3 (%overlap) L4063 | All uCDR3's | | | Top 80% uCDR3's | | |
|---|---|---|---|---|---|---|
| | Gen 3.0 | Gen 3.1 Control | Gen 3.1 Test | Gen 3.0 | Gen 3.1 Control | Gen 3.1 Test |
| Gen 3.0 | 14005 | 3240 (23%) | 2959 (21%) | 1104 | 1000 (90 %) | 975 (88%) |
| Gen 3.1 Control | - | 18149 | - | - | 2437 | - |
| Gen 3.1 Test | - | - | 17181 | - | - | 2331 |

*Figure 98*

| Number of u CDR3 (%overlap) L4064 | All uCDR3's | | | Top 80% uCDR3's | | |
|---|---|---|---|---|---|---|
| | Gen 3.0 | Gen 3.1 Control | Gen 3.1 Test | Gen 3.0 | Gen 3.1 Control | Gen 3.1 Test |
| Gen 3.0 | 15107 | 5486 (36%) | 5541 (36%) | 2478 | 2186 (88%) | 2163 (87%) |
| Gen 3.1 Control | - | 21460 | - | - | 3246 | - |
| Gen 3.1 Test | - | - | 21503 | - | - | 3263 |

FIG. 99
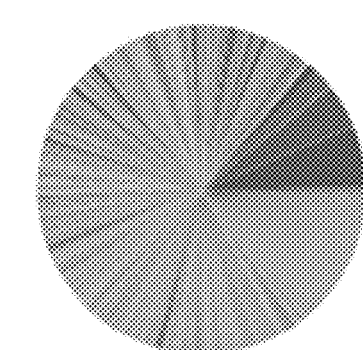
Gen 3.1 Test
Gen 3.1 Control
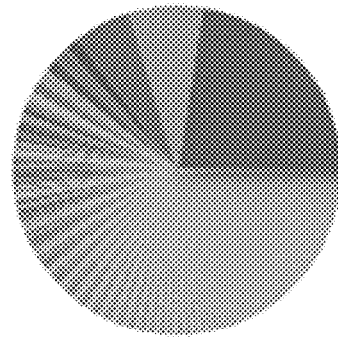
Gen 3.0

FIG. 100

| Step | Process Gen 3-Optimized |
|---|---|
| Day 0 Tumor Isolation and Activation | ≤240 fragments<br>≤60 fragments/flask<br>≤4 flasks<br>≤2L media (500mL/flask)<br>IL-2 (6000IU/mL)<br>2.5x10⁸ feeder cells/flask<br>15ug OKT3/flask |
| Day 7 - 8 Reactivation | Fresh TIL direct to REP<br>Activate entire culture<br>5x10⁸ feeder cells<br>30 ug OKT3/flask<br>G-Rex 100MCS<br>Add 500mL media+ IL-2(6000IU/mL) |
| Day 10 – 11 Scale up or TIL Sub-culture | ≤4 G-REX 500MCS<br>Scale up entire culture transferring 1L from GREX 100MCS into GREX 500MCS and add 4L of media +IL-2 (3000 IU/mL) /flask |
| Day 16 -17 Harvest | Harvest<br>LOVO- automated cell washer<br>Cryopreservation on Plasmalyte 1% HSA: CS10 |

FIG. 101

| Test | Acceptance Criteria | Gen 3.1Test vs Gen 3.0 Process |
|---|---|---|
| Cell Count (TVC) | Gen 3.1 > 30% to Process Gen 3.0 | Met |
| % Viability | ≥70% Viability | Met |
| Immunophenotyping (%CD3+/ %CD45+) | ≤5% difference between Gen 3.1 and Gen 3.0 process | Met |
| IFNγ secretion | Gen 3.1 ≥ to Process Gen 3.0 | Met |

FIG. 102

Cell counts reactivation Day

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3.0 (A) L4063 | 500 | Total | 7.10E+04 | 6.81E+04 | | 6.96E+04 | 3.48E+07 |
| | | Live | 5.27E+04 | 5.09E+04 | | 5.18E+04 | 2.59E+07 |
| | | Dead | 1.83E+04 | 1.72E+04 | | 1.78E+04 | 8.88E+06 |
| | | % Viability | 74.30% | 74.80% | | 74.55% | |
| Gen 3.1 Control L4063 | 500 | Total | 1.41E+05 | 1.38E+05 | | 1.40E+05 | 6.98E+07 |
| | | Live | 1.31E+05 | 1.26E+05 | | 1.29E+05 | 6.43E+07 |
| | | Dead | 9.84E+03 | 1.21E+04 | | 1.10E+04 | 5.49E+06 |
| | | % Viability | 93.00% | 91.20% | | 92.10% | |
| Gen 3.1 Test L4063 | 500 | Total | 3.26E+05 | 3.28E+05 | | 3.27E+05 | 1.64E+08 |
| | | Live | 2.83E+05 | 2.96E+05 | | 2.90E+05 | 1.45E+08 |
| | | Dead | 4.25E+04 | 3.16E+04 | | 3.71E+04 | 1.85E+07 |
| | | % Viability | 87.00% | 90.30% | | 88.65% | |
| Gen 3.0 (A) L4064 | 500 | Total | 1.59E+04 | 1.75E+04 | | 1.67E+04 | 8.35E+06 |
| | | Live | 1.39E+04 | 1.55E+04 | | 1.47E+04 | 7.35E+06 |
| | | Dead | 1.98E+03 | 2.02E+03 | | 2.00E+03 | 1.00E+06 |
| | | % Viability | 87.50% | 88.50% | | 88.00% | |
| Gen 3.1 Control L4064 | 500 | Total | 2.02E+05 | 1.98E+05 | | 2.00E+05 | 1.00E+08 |
| | | Live | 1.88E+05 | 1.83E+05 | | 1.86E+05 | 9.28E+07 |
| | | Dead | 1.38E+04 | 1.51E+04 | | 1.45E+04 | 7.23E+06 |
| | | % Viability | 93.20% | 92.40% | | 92.80% | |
| Gen 3.1 Test L4064 | 500 | Total | 2.70E+05 | 3.15E+05 | | 2.93E+05 | 1.46E+08 |
| | | Live | 2.55E+05 | 3.01E+05 | | 2.78E+05 | 1.39E+08 |
| | | Dead | 1.51E+04 | 1.38E+04 | | 1.45E+04 | 7.23E+06 |
| | | % Viability | 94.40% | 95.60% | | 95.00% | |

FIG. 103

Cell counts Scale Up Day

| ID | Volume (mL) | | Count 1 (cells/mL) | Count 3 (cells/mL) | Count 2 (cells/mL) | Average (cells/mL) | Total Cells Average*Volume |
|---|---|---|---|---|---|---|---|
| Gen 3.0 (A) L4063 | 1000 | Total | 6.57E+05 | 6.61E+05 | | 6.59E+05 | 6.59E+08 |
| | | Live | 6.00E+05 | 6.14E+05 | | 6.07E+05 | 6.07E+08 |
| | | Dead | 5.71E+04 | 4.68E+04 | | 5.20E+04 | 5.20E+07 |
| | | % Viability | 91.30% | 92.90% | | 92.10% | |
| Gen 3.1 Control L4063 | 1000 | Total | 1.66E+06 | 1.82E+06 | | 1.74E+06 | 1.74E+09 |
| | | Live | 1.59E+06 | 1.72E+06 | | 1.66E+06 | 1.66E+09 |
| | | Dead | 7.17E+04 | 9.07E+04 | | 8.12E+04 | 8.12E+07 |
| | | % Viability | 95.70% | 95.00% | | 95.35% | |
| Gen 3.1 Test L4063 | 1000 | Total | 1.88E+06 | 2.00E+06 | | 1.94E+06 | 1.94E+09 |
| | | Live | 1.76E+06 | 1.89E+06 | | 1.83E+06 | 1.83E+09 |
| | | Dead | 1.20E+05 | 1.15E+05 | | 1.18E+05 | 1.18E+08 |
| | | % Viability | 93.60% | 94.30% | | 93.95% | |
| Gen 3.0 (A) L4064 | 1000 | Total | 7.95E+05 | 8.58E+05 | | 8.27E+05 | 8.27E+08 |
| | | Live | 7.17E+05 | 7.78E+05 | | 7.48E+05 | 7.48E+08 |
| | | Dead | 7.85E+04 | 8.05E+04 | | 7.95E+04 | 7.95E+07 |
| | | % Viability | 90.10% | 90.60% | | 90.35% | |
| Gen 3.1 Control L4064 | 1000 | Total | 1.38E+06 | 1.32E+06 | | 1.35E+06 | 1.35E+09 |
| | | Live | 1.31E+06 | 1.24E+06 | | 1.28E+06 | 1.28E+09 |
| | | Dead | 7.20E+04 | 8.13E+04 | | 7.67E+04 | 7.67E+07 |
| | | % Viability | 94.80% | 93.80% | | 94.30% | |
| Gen 3.1 Test L4064 | 1000 | Total | 1.85E+06 | 1.76E+06 | | 1.81E+06 | 1.81E+09 |
| | | Live | 1.76E+06 | 1.67E+06 | | 1.72E+06 | 1.72E+09 |
| | | Dead | 8.62E+04 | 8.95E+04 | | 8.79E+04 | 8.79E+07 |
| | | % Viability | 95.30% | 94.90% | | 95.10% | |

FIG. 104

Cell counts Harvest L4063

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3.0 (A) L4063 pre LOVO | 602.4 | Total | 1.68E+07 | 1.70E+07 | | 1.69E+07 | 1.02E+10 |
| | | Live | 1.52E+07 | 1.54E+07 | | 1.53E+07 | 9.22E+09 |
| | | Dead | 1.60E+06 | 1.65E+06 | | 1.63E+06 | 9.79E+08 |
| | | % Viability | 90.50% | 90.30% | | 90.40% | |
| Gen 3.1 Control L4063 pre LOVO | 497.1 | Total | 3.39E+07 | 3.90E+07 | | 3.65E+07 | 1.81E+10 |
| | | Live | 3.25E+07 | 3.73E+07 | | 3.49E+07 | 1.73E+10 |
| | | Dead | 1.41E+06 | 1.63E+06 | | 1.52E+06 | 7.56E+08 |
| | | % Viability | 95.80% | 95.80% | | 95.80% | |
| Gen 3.1 Test L4063 pre LOVO | 552.3 | Total | 3.71E+07 | 3.62E+07 | | 3.67E+07 | 2.02E+10 |
| | | Live | 3.56E+07 | 3.51E+07 | | 3.54E+07 | 1.95E+10 |
| | | Dead | 1.50E+06 | 1.09E+06 | | 1.30E+06 | 7.15E+08 |
| | | % Viability | 96.00% | 97.00% | | 96.50% | |
| Gen 3.0 (A) L4063 post LOVO | 165 | Total | 5.37E+07 | 5.73E+07 | 5.50E+07 | 5.53E+07 | 9.13E+09 |
| | | Live | 4.32E+07 | 4.52E+07 | 4.36E+07 | 4.40E+07 | 7.26E+09 |
| | | Dead | 1.04E+07 | 1.21E+07 | 1.14E+07 | 1.13E+07 | 1.86E+09 |
| | | % Viability | 80.50% | 78.80% | 79.30% | 79.53% | |
| Gen 3.1 Control L4063 post LOVO | 165 | Total | 1.21E+08 | 1.01E+08 | 1.22E+08 | 1.15E+08 | 1.89E+10 |
| | | Live | 1.10E+08 | 8.85E+07 | 1.09E+08 | 1.03E+08 | 1.69E+10 |
| | | Dead | 1.11E+07 | 1.23E+07 | 1.27E+07 | 1.20E+07 | 1.99E+09 |
| | | % Viability | 90.90% | 87.80% | 89.60% | 89.43% | |
| Gen 3.1 Test L4063 post LOVO | 175 | Total | 1.05E+08 | 1.20E+08 | | 1.13E+08 | 1.97E+10 |
| | | Live | 9.93E+07 | 1.14E+08 | | 1.07E+08 | 1.87E+10 |
| | | Dead | 5.51E+06 | 6.14E+06 | | 5.83E+06 | 1.02E+09 |
| | | % Viability | 94.70% | 94.90% | | 94.80% | |

FIG. 105

Cell counts Harvest L4064

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3.0 (A) L4064 pre LOVO | 641.3 | Total | 1.99E+07 | 1.94E+07 | | 1.97E+07 | 1.26E+10 |
| | | Live | 1.83E+07 | 1.94E+07 | | 1.89E+07 | 1.21E+10 |
| | | Dead | 1.60E+06 | 1.68E+06 | | 1.64E+06 | 1.05E+09 |
| | | % Viability | 92.00% | 92.00% | | 92.00% | |
| Gen 3.1 Control L4064 pre LOVO | 493.4 | Total | 3.98E+07 | 3.87E+07 | | 3.93E+07 | 1.94E+10 |
| | | Live | 3.65E+07 | 3.55E+07 | | 3.60E+07 | 1.78E+10 |
| | | Dead | 3.31E+06 | 3.22E+06 | | 3.27E+06 | 1.61E+09 |
| | | % Viability | 91.70% | 91.70% | | 91.70% | |
| Gen 3.1 Test L4064 pre LOVO | 593.4 | Total | 3.92E+07 | 3.79E+07 | | 3.86E+07 | 2.29E+10 |
| | | Live | 3.67E+07 | 3.54E+07 | | 3.61E+07 | 2.14E+10 |
| | | Dead | 2.55E+06 | 2.50E+06 | | 2.53E+06 | 1.50E+09 |
| | | % Viability | 93.50% | 93.40% | | 93.45% | |
| Gen 3.0 (A) L4064 post LOVO | 165 | Total | 8.58E+07 | 8.34E+07 | | 8.46E+07 | 1.40E+10 |
| | | Live | 7.56E+07 | 7.46E+07 | | 7.51E+07 | 1.24E+10 |
| | | Dead | 1.02E+07 | 8.79E+06 | | 9.50E+06 | 1.57E+09 |
| | | % Viability | 88.10% | 89.50% | | 88.80% | |
| Gen 3.1 Control L4064 post LOVO | 165 | Total | 1.13E+08 | 1.22E+08 | 1.15E+08 | 1.18E+08 | 1.94E+10 |
| | | Live | 9.21E+07 | 1.01E+08 | 9.45E+07 | 9.66E+07 | 1.59E+10 |
| | | Dead | 2.14E+07 | 2.13E+07 | 2.07E+07 | 2.14E+07 | 3.52E+09 |
| | | % Viability | 81.20% | 82.60% | 82.10% | 81.90% | |
| Gen 3.1 Test L4064 post LOVO | 165 | Total | 1.33E+08 | 1.45E+08 | | 1.39E+08 | 2.29E+10 |
| | | Live | 1.14E+08 | 1.22E+08 | | 1.18E+08 | 1.95E+10 |
| | | Dead | 1.94E+07 | 2.26E+07 | | 2.10E+07 | 3.47E+09 |
| | | % Viability | 85.40% | 84.40% | | 84.90% | |

| | S1/S2/AiliLive/CD14-/TCRab/CD4/CD27/ Freq. of Parent (%) | S1/S2/AiliLive/CD14-/TCRab/ CD4/CD28/ Freq. (%) of Parent | S1/S2/AiliLive/CD14-/TCRab/ CD4/CD56/ Freq. (%) of Parent | S1/S2/AiliLive/CD14-/TCRab/ CD4/CD57/ Freq. (%) of Parent | S1/S2/AiliLive/CD14-/TCRab/ CD8/CD27/ Freq. (%) of Parent | S1/S2/AiliLive/CD14-/TCRab/ CD8/CD28/ Freq. (%) of Parent | S1/S2/AiliLive/CD14-/TCRab/ CD8/CD56/ Freq. (%) of Parent | S1/S2/AiliLive/CD14-/TCRab/ CD8/CD57/ Freq. (%) of Parent |
|---|---|---|---|---|---|---|---|---|
| | CD4+/CD27 | CD4+/CD28 | CD4+/CD56 | CD4+/CD57 | CD8+/CD27 | CD8+/CD28 | CD8+/CD56 | CD8+/CD57 |
| L4063-Gen 3.0 | 3.8 | 82.7 | 0.42 | 6.7 | 45 | 47.5 | 3.29 | 0.28 |
| L4063-Gen 3.1 CT | 2.08 | 71.8 | 0.53 | 17 | 25.6 | 23 | 2.33 | 1.18 |
| L4063-Gen 3.1+Feeders | 3.35 | 80.2 | 0.69 | 20.5 | 30.5 | 24.5 | 4.19 | 1.07 |
| L4064-Gen 3.0 | 6.66 | 97.5 | 0.54 | 16 | 14.1 | 88 | 6.62 | 1.29 |
| L4064-Gen 3.1 CT | 0.72 | 73.5 | 0.54 | 7.38 | 3.3 | 45.1 | 10.3 | 1.96 |
| L4063-Gen 3.1+Feeders | 2.24 | 66.8 | 0.34 | 7.98 | 6.69 | 37.3 | 9.98 | 2.54 |

FIG. 106

Table 1

| | S1/S2/All/Live/ Freq. of Parent (%) [LD] | S1/S2/All/Live/CD14+ Freq. of Parent (%) [CD34+] | S1/S2/All/Live/CD14-/CD8-/NK Freq. of null (%) [NK] | S1/S2/All/Live/CD14-/CD19 Freq. of null (%) [CD19] | S1/S2/All/Live/CD14-/TCRab Freq. of null (%) [TCRab+] | S1/S2/All/Live/CD14-/TCRab/CD4 Freq. of null (%) [TCRab+/CD4+] | S1/S2/All/Live/CD14-/TCRab/CD4/CD27 Freq. of null (%) [TCRab+/CD4+/CD27] | S1/S2/All/Live/CD14-/TCRab/CD4/CD28 Freq. of null (%) [TCRab+/CD4+/CD28] | S1/S2/All/Live/CD14-/TCRab/CD4/CD56 Freq. of null (%) [TCRab+/CD4+/CD56] | S1/S2/All/Live/CD14-/TCRab/CD4/CD57 Freq. of null (%) [TCRab+/CD4+/CD57] |
|---|---|---|---|---|---|---|---|---|---|---|
| L4063-Gen 3.0 | 82.2 | 0.58 | 0.13 | 1.3 | 0.063 | 88.6 | 56.4 | 2.34 | 46.6 | 0.24 | 3.78 |
| L4063-Gen 3.1 CT | 83.4 | 0.035 | 0.13 | 0.15 | 0.033 | 97.5 | 85.3 | 1.78 | 61.6 | 0.46 | 14.6 |
| L4063-Gen 3.1+Feeders | 91 | 0.032 | 0.035 | 1.04 | 0.007% | 95.5 | 77.5 | 2.6 | 62.1 | 0.54 | 15.9 |
| L4064-Gen 3.0 | 76.6 | 0.18 | 0.032 | 2.45 | 0.11 | 93 | 33.8 | 2.25 | 32.9 | 0.18 | 5.4 |
| L4064-Gen 3.1 CT | 83.1 | 0.068 | 0.19 | 0.23 | 0.011 | 97.3 | 64.3 | 0.46 | 47.6 | 0.35 | 4.91 |
| L4063-Gen 3.1+Feeders | 89.5 | 0.043 | 0.088 | 0.52 | 0.023 | 96.7 | 57.4 | 1.28 | 38.4 | 0.2 | 4.58 |

Table 2

| | Q1: CCR7-PE-A-, CD45RA-AF700-A+ [TEMRA] | Q2: CCR7-PE-A+, CD45RA-AF700-A+ [NAIVE] | Q3: CCR7-PE-A+, CD45RA-AF700-A- [CM] | Q4: CCR7-PE-A-, CD45RA-AF700-A- [EM] | Q5: CD62L-DV421-A+ CD45RA-AF700-A+ [TEMRA] | Q6: CD62L-DV421-A+ CD45RA-AF700-A+ [NAIVE] | Q7: CD62L-DV421-A+, CD45RA-AF700-A- [CM] | Q8: CD62L-DV421-A-, CD45RA-AF700-A- [EM] |
|---|---|---|---|---|---|---|---|---|
| L4063-gen 3.0 | 0.58 | 0.77 | 0.26 | 87.4 | 0.36 | 0.26 | 45.6 | 53.7 |
| L4063-gen 3.1 CT | 1.22 | 0.8 | 0.22 | 94.4 | 0.66 | 0.22 | 16.8 | 82.3 |
| L4063-gen 3.1+Feeders | 0.88 | 0.35 | 0.17 | 97.4 | 0.36 | 0.17 | 29.3 | 70.2 |
| L4064-gen 3.0 | 1.47 | 1.3 | 0.53 | 83 | 1.09 | 0.53 | 46.3 | 52.1 |
| L4064-gen 3.1 CT | 0.41 | 0.096 | 0.11 | 94.2 | 0.73 | 0.11 | 30.6 | 68.6 |
| L4063-gen 3.1+Feeders | 0.44 | 0.07 | 0.035 | 95.7 | 0.37 | 0.035 | 29.9 | 69.9 |

Table 3

| | CD8 Q1: CCR7-PE-A-, CD45RA-AF700-A+ [TEMRA] | Q2: CCR7-PE-A+, CD45RA-AF700-A+ [NAIVE] | Q3: CCR7-PE-A+, CD45RA-AF700-A- [CM] | Q4: CCR7-PE-A-, CD45RA-AF700-A- [EM] | Q5: CD62L-DV421-A+ CD45RA-AF700-A+ [TEMRA] | Q6: CD62L-DV421-A+ CD45RA-AF700-A+ [NAIVE] | Q7: CD62L-DV421-A+, CD45RA-AF700-A- [CM] | Q8: CD62L-DV421-A-, CD45RA-AF700-A- [EM] | S1/S2/All/Live/CD14-/TCRabd Freq. of Parent (%) |
|---|---|---|---|---|---|---|---|---|---|
| L4063-Gen 3.0 | 1.72 | 1.54 | 18.1 | 79.1 | 3.06 | 0.67 | 32 | 74.3 | 6.47 |
| L4063-Gen 3.1 CT | 1.65 | 0.62 | 3.39 | 94.3 | 0.52 | 0.097 | 15.8 | 83.5 | 1.11 |
| L4063-Gen 3.1+Feeders | 2.65 | 0.73 | 1.66 | 95 | 0.89 | 0.41 | 29.7 | 78.9 | 2 |
| L4064-Gen 3.0 | 6.49 | 4.31 | 10.9 | 70.3 | 6.05 | 3.31 | 61.9 | 39.8 | 2.36 |
| L4064-Gen 3.1 CT | 6.3 | 0.59 | 7.15 | 86 | 8 | 0.72 | 18.9 | 72.4 | 1.68 |
| L4063-Gen 3.1+Feeders | 5.83 | 0.22 | 3.17 | 90.8 | 5.38 | 0.96 | 18.2 | 75.5 | 1.86 |

FIG. 107

| | | S/S/All Live/CD3/ CD4/2B4 Freq. of Parent (%) | S/S/All Live/CD3/ BTLA Freq. of Parent (%) | S/S/All Live/CD3/ CD4/CD25 Freq. of Parent (%) | S/S/All Live/ CD3/CD4/CD69 Freq. of Parent (%) | S/S/All Live/ CD3/CD4/CD95 Freq. of Parent (%) | S/S/All Live/ CD3/CD4/CD103 Freq. of Parent (%) | S/S/All Live/ CD3/CD4/KLRG1+ Freq. of Parent (%) | S/S/All Live/ CD3/CD4/LAG3 Freq. of Parent (%) | S/S/All Live/ CD3/CD4/PD1 Freq. of Parent (%) |
|---|---|---|---|---|---|---|---|---|---|---|
| | | 2B4+ | BTLA | CD25+ | CD69+ | CD4 CD95+ | CD103+ | KLRG1+ | LAG3+ | PD1+ |
| L40b3-Gen 3.0 | G10 10 tcs | 2.1 | 99.7 | 49.6 | 27.1 | 99.9 | 0.69 | 1.61 | 5.57 | 77.4 |
| L40b3-Gen 3.1 CT | G11 11 tcs | 0.62 | 95.4 | 10.5 | 37.7 | 99.9 | 1.15 | 3.7 | 8.24 | 58.4 |
| L40b3-Gen 3.1+Feeders | G12 12 tcs | 0.95 | 96.9 | 3.89 | 21.5 | 99.5 | 0.43 | 3.32 | 3.28 | 41.6 |
| L40b4-Gen 3.0 | H1 13 tcs | 2 | 99.5 | 58.2 | 39.4 | 99.6 | 1.4 | 11.4 | 1.49 | 34.1 |
| L40b4-Gen 3.1 CT | H2 14 tcs | 1.18 | 98.8 | 41.7 | 35.6 | 99 | 1.25 | 8.3 | 1.6 | 28.4 |
| L40b3-Gen 3.1+Feeders | H3 15 tcs | 1.26 | 98.1 | 32.1 | 30.5 | 97.3 | 1.19 | 10.7 | 1.42 | 26.7 |

| S/S/All Live/ CD3/CD4/tigit Freq. of Parent (%) | S/S/All Live/ CD3/CD4/tigit Freq. of Parent (%) |
|---|---|
| CD4+ TIGIT+ | CD4+ TIM3+ |
| 68.5 | 58 |
| 40.3 | 42.4 |
| 30.3 | 59.4 |
| 45.8 | 61 |
| 52.1 | 58.4 |
| 52.2 | 56.6 |

FIG. 108

| S/S/All Live/CD3/CD8/2B4 Freq. of Parent (%) | S/S/All Live/CD3/CD8/BTLA Freq. of Parent (%) | S/S/All Live/CD3/CD8/CD25 Freq. of Parent (%) | S/S/All Live/CD3/CD8/CD69 Freq. of Parent (%) | S/S/All Live/CD3/CD8/CD95 Freq. of Parent (%) | S/S/All Live/CD3/CD8/CD103 Freq. of Parent (%) | S/S/All Live/CD3/CD8/CXCR3 Freq. of Parent (%) | S/S/All Live/CD3/CD8/KLRG1 Freq. of Parent (%) | S/S/All Live/CD3/CD8/LAG3 Freq. of Parent (%) | S/S/All Live/CD3/CD8/PD1 Freq. of Parent (%) |
|---|---|---|---|---|---|---|---|---|---|
| 2B4+ | BTLA | CD25+ | CD69+ | CD95+ | CD103+ | CXCR3 | KLRG1 | LAG3 | PD1 |
| 2.1 | 2.1 | 99.7 | 48.6 | 27.1 | 99.9 | 0.69 | 1.61 | 5.57 | 77.4 |
| 0.62 | 0.62 | 95.4 | 10.5 | 37.7 | 99.9 | 1.15 | 3.7 | 8.24 | 58.4 |
| 0.95 | 0.95 | 96.9 | 3.89 | 21.5 | 99.5 | 0.43 | 3.32 | 3.28 | 41.6 |
| 2 | 2 | 99.5 | 58.2 | 39.4 | 99.6 | 1.4 | 1.14 | 1.49 | 34.1 |
| 1.18 | 1.18 | 98.8 | 41.7 | 35.6 | 99 | 1.25 | 8.3 | 1.6 | 28.4 |
| 1.26 | 1.26 | 98.1 | 32.1 | 30.5 | 97.3 | 1.19 | 10.7 | 1.42 | 26.7 |

| S/S/All Live/CD3/CD8/tigit Freq. of Parent (%) | S/S/All Live/CD3/CD8/tim3 Freq. of Parent (%) |
|---|---|
| CD8 TIGIT | CD8 TIM3 |
| 90.8 | 66.7 |
| 93.7 | 49.1 |
| 93.3 | 58.6 |
| 92.1 | 65.6 |
| 90.4 | 46.8 |
| 90.5 | 43.6 |

FIG. 109

IFN-γ production Data Figure 7-L4063

IFN-γ production Data Figure 7-L4063

TIL- Gen 3.0-A-Gen 3.0
TIL- Gen 3.1-B-Gen 3.1 Control
TIL- Gen 3.1-C-Gen 3.1 Test

|   | 1 | 2 | 3 | 4 | 5 | 6 | 7 | 8 | 9 | 10 | 11 | 12 | |
|---|---|---|---|---|---|---|---|---|---|----|----|----|---|
| A | STD1 2000 | STD1 2000 | STD1 2000 | Gen 3.1 Test-D7 L4063 | Gen 3.1 Test-D7 L4063 | Gen 3.1 Test-D7 L4063 | Gen 3.1 Test-D16 L4063 | Gen 3.1 Test-D16 L4063 | Gen 3.1 Test-D16 L4063 | Empty | Empty | Empty | WellID / ConcDil |
| B | STD2 1000 | STD2 1000 | STD2 1000 | Gen 3.1 Control-D7 L4063 | Gen 3.1 Control-D7 L4063 | Gen 3.1 Control-D7 L4063 | Gen 3.0-D7 L4064 | Gen 3.0-D7 L4064 | Gen 3.0-D7 L4064 | Empty | Empty | Empty | WellID / ConcDil |
| C | STD3 500 | STD3 500 | STD3 500 | Gen 3.0-D7 L4063 | Gen 3.0-D7 L4063 | Gen 3.0-D7 L4063 | Gen 3.1 Control-D7 L4064 | Gen 3.1 Control-D7 L4064 | Gen 3.1 Control-D7 L4064 | Empty | Empty | Empty | WellID / ConcDil |
| D | STD4 250 | STD4 250 | STD4 250 | Gen 3.0-D11 L4063 | Gen 3.0-D11 L4063 | Gen 3.0-D11 L4063 | Gen 3.1 Test-D7 L4064 | Gen 3.1 Test-D7 L4064 | Gen 3.1 Test-D7 L4064 | Empty | Empty | Empty | WellID / ConcDil |
| E | STD5 125 | STD5 125 | STD5 125 | Gen 3.1 Control-D11 L4063 | Gen 3.1 Control-D11 L4063 | Gen 3.1 Control-D11 L4063 | Gen 3.0-D16 L4064 | Gen 3.0-D16 L4064 | Gen 3.0-D16 L4064 | Empty | Empty | Empty | WellID / ConcDil |
| F | STD6 62.5 | STD6 62.5 | STD6 62.5 | Gen 3.1 Test-D11 L4063 | Gen 3.1 Test-D11 L4063 | Gen 3.1 Test-D11 L4063 | Gen 3.1 Control-D16 L4064 | Gen 3.1 Control-D16 L4064 | Gen 3.1 Control-D16 L4064 | Empty | Empty | Empty | WellID / ConcDil |
| G | STD7 31.3 | STD7 31.3 | STD7 31.3 | Gen 3.0-D16 L4063 | Gen 3.0-D16 L4063 | Gen 3.0-D16 L4063 | Gen 3.1 Test-D16 L4063 | Empty | Empty | Empty | Empty | Empty | WellID / ConcDil |
| H | STD8 0 | STD8 0 | STD8 0 | Gen 3.1 Control-D16 L4063 | Gen 3.1 Control-D16 L4063 | Gen 3.1 Control-D16 L4063 | Empty | Empty | Empty | Empty | Empty | Empty | WellID / ConcDil |

D7=Day 7= Rep Initiation
D11= Day 11= Scale up
D16= Day 16= Harvest

| Sample number # | Description Gen 3.1 Optimization | Glucose (g/L) | Lactate (g/L) | Ammonia (mmol/L) | Glutamine (mmol/L) | Glutamax (mmol/L) | Glutamax-Glutamine (mmol/L) |
|---|---|---|---|---|---|---|---|
| 13 | Gen 3.0-Day 16 First Round #L4063 | 1.52 | 1.07 | 2.06 | 1.91 | 2.11 | 0.20 |
| 14 | Gen 3.1 Control-Day 16 First Round #L4063 | 0.90 | 1.74 | 2.50 | 1.34 | 1.49 | 0.15 |
| 15 | Gen 3.1 Test-Day 16 First Round #L4063 | 0.96 | 1.64 | 2.49 | 1.33 | 1.47 | 0.14 |
| 16 | Gen 3.0-Day 11 First Round #L4063 | 1.42 | 0.70 | 1.83 | 1.70 | 1.86 | 0.16 |
| 17 | Gen 3.1 Control-Day 11 First Round #L4063 | 0.90 | 1.08 | 2.24 | 1.07 | 1.19 | 0.11 |
| 18 | Gen 3.1 Test-Day 11 First Round #L4063 | 0.84 | 1.21 | 2.25 | 1.11 | 1.23 | 0.12 |
| 19 | Gen 3.0-Day 7 First Round #L4063 | 1.76 | 0.20 | 1.88 | 2.04 | 2.23 | 0.19 |
| 20 | Gen 3.1 Control-Day 7 First Round #L4063 | 1.73 | 0.22 | 1.86 | 2.00 | 2.19 | 0.19 |
| 21 | Gen 3.1 Test-Day 7 First Round #L4063 | 1.41 | 0.50 | 1.95 | 1.98 | 2.15 | 0.17 |
| 22 | Gen 3.0 Day 16 Second Round #L4064 | 2.76 | 1.52 | 1.00 | 0.68 | 0.77 | 0.09 |
| 23 | Gen 3.1 Control-Day 16 Second Round #L4064 | 2.14 | 1.95 | 0.99 | 0.64 | 0.73 | 0.08 |
| 24 | Gen 3.1 Test-Day 16 Second Round #L4064 | 2.20 | 1.89 | 0.94 | 0.64 | 0.71 | 0.07 |
| 25 | Gen 3.0-Day 7 Second Round #L4064 | 4.26 | 0.08 | 0.71 | 1.29 | 1.43 | 0.14 |
| 26 | Gen 3.1 Control-Day 7 Second Round #L4064 | 4.14 | 0.22 | 0.78 | 1.17 | 1.29 | 0.12 |
| 27 | Gen 3.1 Test-Day 7 Second Round #L4064 | 3.82 | 0.49 | 0.89 | 1.09 | 1.20 | 0.11 |

| Order | Name | Geometric Mean Probe-fitc A | Geometric Mean Probe-fitc A | Average 1301 | Average T | Length relative to 1301 |
|---|---|---|---|---|---|---|
| A1 | Gen 3.0-L4063 | A1 10.1.fcs | 86 | 42.5 | | |
| A2 | | A2 10.2.fcs | 85.4 | 42.3 | 85.7 | 42.4 |
| A3 | | A3 10.3.fcs | 4585 | 207 | | |
| A4 | | A4 10.4.fcs | 4389 | 216 | 4487 | 211.5 | 7.684093 |
| A5 | Gen 3.1 Control-L4063 | A5 11.1.fcs | 82.7 | 33.3 | | |
| A6 | | A6 11.2.fcs | 86 | 32.9 | 84.35 | 33.1 |
| A7 | | A7 11.3.fcs | 4696 | 180 | | |
| A8 | | A8 11.4.fcs | 4641 | 175 | 4668.5 | 177.5 | 6.299968 |
| B1 | Gen 3.1 Test-L4063 | B1 12.1.fcs | 95.1 | 28.8 | | |
| B2 | | B2 12.2.fcs | 84.7 | 26.7 | 89.9 | 27.75 |
| B3 | | B3 12.3.fcs | 4764 | 169 | | |
| B4 | | B4 12.4.fcs | 4800 | 174 | 4782 | 171.5 | 6.12732 |
| B5 | Gen 3.0 -L4064 | B5 13.1.fcs | 101 | 40.3 | | |
| B6 | | B6 13.2.fcs | 89.6 | 34.1 | 95.3 | 37.2 |
| B7 | | B7 13.3.fcs | 4300 | 174 | | |
| B8 | | B8 13.4.fcs | 4367 | 172 | 4333.5 | 173 | 6.408381 |
| C1 | Gen 3.1 Control-L4064 | C1 14.1.fcs | 92.1 | 31.1 | | |
| C2 | | C2 14.2.fcs | 88.6 | 29.6 | 90.35 | 30.35 |
| C3 | | C3 14.3.fcs | 4111 | 169 | | |
| C4 | | C4 14.4.fcs | 4443 | 172 | 4277 | 170.5 | 6.69509 |
| C5 | Gen 3.1 Test-L4064 | C5 15.1.fcs | 89.7 | 25.7 | | |
| C6 | | C6 15.2.fcs | 85.7 | 24.7 | 87.7 | 25.2 |
| C7 | | C7 15.3.fcs | 4342 | 172 | | |
| C8 | | C8 15.4.fcs | 4560 | 166 | 4451 | 169 | 6.591341 |

Shared Frequencies

| Subject | Original Sample | uCDR3 count | Compared Sample | uCDR3 count | shared uCDR3 count | uCDR3 count |
|---|---|---|---|---|---|---|
| L4063 | L63GA | 14005 | L63GB | 18149 | 3240 | 23.13459479 |
| L4063 | L63GA | 14005 | L63GC | 17181 | 2959 | 21.12816851 |
| L4063 | L63GA | 15107 | L64GB | 21460 | 5486 | 36.31429139 |
| L4063 | L63GA | 15107 | L64GC | 21503 | 5541 | 36.67836102 |
| | | | | | | |
| Code: | L63GA = L4063 Gen 3.0 | | | | | |
| | L63GB = L4063 Gen 3.1 control | | | | | |
| | L63GC = L4063 Gen 3.1 Test | | | | | |
| | | | | | | |
| | L64GA = L4064 Gen 3.0 | | | | | |
| | L64GB = L4064 Gen 3.1 control | | | | | |
| | L64GC = L4064 Gen 3.1 Test | | | | | |

Top 80%

| Subject | sample1 | uCDR3 count | sample2 | uCDR3 count | shared uCDR3 count | % shared of col B |
|---|---|---|---|---|---|---|
| L4063 | L63GA | 1104 | L63GB | 2437 | 1000 | 90.57971 |
| L4063 | L63GA | 1104 | L63GC | 2331 | 975 | 88.31522 |
| L4064 | L64GA | 2478 | L64GB | 3246 | 2186 | 88.2163 |
| L4064 | L64GA | 2478 | L64GC | 3263 | 2163 | 87.28814 |
| | | | | | | |
| Code: | L63GA = L4063 Gen 3.0 | | | | | |
| | L63GB = L4063 Gen 3.1 control | | | | | |
| | L63GC = L4063 Gen 3.1 Test | | | | | |
| | | | | | | |
| | L64GA = L4064 Gen 3.0 | | | | | |
| | L64GB = L4064 Gen 3.1 control | | | | | |
| | L64GC = L4064 Gen 3.1 Test | | | | | |

SEQUENCE LISTING

<160> NUMBER OF SEQ ID NOS: 176

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

```
Gly Tyr Ile Asn Pro Ser Arg Gly Tyr Thr Asn Tyr Asn Gln Lys Phe
    50              55              60

Lys Asp Lys Ala Thr Leu Thr Thr Asp Lys Ser Ser Ser Thr Ala Tyr
65              70              75              80

Met Gln Leu Ser Ser Leu Thr Ser Glu Asp Ser Ala Val Tyr Tyr Cys
                85              90              95

Ala Arg Tyr Tyr Asp Asp His Tyr Cys Leu Asp Tyr Trp Gly Gln Gly
            100             105             110

Thr Thr Leu Thr Val Ser Ser Ala Lys Thr Thr Ala Pro Ser Val Tyr
        115             120             125

Pro Leu Ala Pro Val Cys Gly Gly Thr Thr Gly Ser Ser Val Thr Leu
    130             135             140

Gly Cys Leu Val Lys Gly Tyr Phe Pro Glu Pro Val Thr Leu Thr Trp
145             150             155             160

Asn Ser Gly Ser Leu Ser Ser Gly Val His Thr Phe Pro Ala Val Leu
            165             170             175

Gln Ser Asp Leu Tyr Thr Leu Ser Ser Ser Val Thr Val Thr Ser Ser
        180             185             190

Thr Trp Pro Ser Gln Ser Ile Thr Cys Asn Val Ala His Pro Ala Ser
        195             200             205

Ser Thr Lys Val Asp Lys Lys Ile Glu Pro Arg Pro Lys Ser Cys Asp
    210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
        355             360             365

Thr Cys Leu Val Lys Gly Phe Tyr Pro Ser Asp Ile Ala Val Glu Trp
        370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly Lys
    450
```

<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
            165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2 (rhIL-2)

<400> SEQUENCE: 3

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

-continued

Leu Lys Gly Ser Glu Thr Thr Phe Met Cys Glu Tyr Ala Asp Glu Thr
              100                 105                 110

Ala Thr Ile Val Glu Phe Leu Asn Arg Trp Ile Thr Phe Cys Gln Ser
      115                 120                 125

Ile Ile Ser Thr Leu Thr
      130

<210> SEQ ID NO 4
<211> LENGTH: 132
<212> TYPE: PRT
<213> ORGANISM: Artificial Sequence
<220> FEATURE:
<223> OTHER INFORMATION: Aldesleukin

<400> SEQUENCE: 4

Pro Thr Ser Ser Ser Thr Lys Lys Thr Gln Leu Gln Leu Glu His Leu
1                 5                  10                  15

Leu Leu Asp Leu Gln Met Ile Leu Asn Gly Ile Asn Asn Tyr Lys Asn
              20                 25                  30

Pro Lys Leu Thr Arg Met Leu Thr Phe Lys Phe Tyr Met Pro Lys Lys
      35                 40                  45

Ala Thr Glu Leu Lys His Leu Gln Cys Leu Glu Glu Glu Leu Lys Pro
      50                 55                  60

Leu Glu Glu Val Leu Asn Leu Ala Gln Ser Lys Asn Phe His Leu Arg
65                 70                  75                  80

Pro Arg Asp Leu Ile Ser Asn Ile Asn Val Ile Val Leu Glu Leu Lys
              85                 90                  95

Gly Ser Glu Thr Thr Phe Met Cys Glu Tyr Ala Asp Glu Thr Ala Thr
              100                105                 110

Ile Val Glu Phe Leu Asn Arg Trp Ile Thr Phe Ser Gln Ser Ile Ile
      115                120                 125

Ser Thr Leu Thr
      130

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4 (rhIL-4)

<400> SEQUENCE: 5

Met His Lys Cys Asp Ile Thr Leu Gln Glu Ile Ile Lys Thr Leu Asn
1                 5                  10                  15

Ser Leu Thr Glu Gln Lys Thr Leu Cys Thr Glu Leu Thr Val Thr Asp
              20                 25                  30

Ile Phe Ala Ala Ser Lys Asn Thr Thr Glu Lys Glu Thr Phe Cys Arg
      35                 40                  45

Ala Ala Thr Val Leu Arg Gln Phe Tyr Ser His His Glu Lys Asp Thr
      50                 55                  60

Arg Cys Leu Gly Ala Thr Ala Gln Gln Phe His Arg His Lys Gln Leu
65                 70                  75                  80

Ile Arg Phe Leu Lys Arg Leu Asp Arg Asn Leu Trp Gly Leu Ala Gly
              85                 90                  95

Leu Asn Ser Cys Pro Val Lys Glu Ala Asn Gln Ser Thr Leu Glu Asn
              100                105                 110

Phe Leu Glu Arg Leu Lys Thr Ile Met Arg Glu Lys Tyr Ser Lys Cys

```
               115                 120                 125

Ser Ser
    130

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7 (rhIL-7)

<400> SEQUENCE: 6

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15 (rhIL-15)

<400> SEQUENCE: 7

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

<210> SEQ ID NO 8
<211> LENGTH: 132
<212> TYPE: PRT
<213> ORGANISM: Artificial Sequence
<220> FEATURE:
<223> OTHER INFORMATION: recombinant human IL-21 (rhIL-21)

<400> SEQUENCE: 8

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
                20                  25                  30

Ala Pro Glu Asp Val Glu Thr Asn Cys Glu Trp Ser Ala Phe Ser Cys
            35                  40                  45

Phe Gln Lys Ala Gln Leu Lys Ser Ala Asn Thr Gly Asn Asn Glu Arg
        50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
                100                 105                 110

Leu Leu Gln Lys Met Ile His Gln His Leu Ser Ser Arg Thr His Gly
        115                 120                 125

Ser Glu Asp Ser
    130

<210> SEQ ID NO 9
<211> LENGTH: 255
<212> TYPE: PRT
<213> ORGANISM: Artificial Sequence
<220> FEATURE:
<223> OTHER INFORMATION: human 4-1BB, Tumor necrosis factor receptor
      superfamily, member 9 (Homo sapiens)

<400> SEQUENCE: 9

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala

```
                        165             170             175

Pro Ala Arg Glu Pro Gly His Ser Pro Gln Ile Ile Ser Phe Phe Leu
            180             185             190

Ala Leu Thr Ser Thr Ala Leu Leu Phe Leu Leu Phe Phe Leu Thr Leu
        195             200             205

Arg Phe Ser Val Val Lys Arg Gly Arg Lys Lys Leu Leu Tyr Ile Phe
        210             215             220

Lys Gln Pro Phe Met Arg Pro Val Gln Thr Thr Gln Glu Glu Asp Gly
225             230             235             240

Cys Ser Cys Arg Phe Pro Glu Glu Glu Glu Gly Gly Cys Glu Leu
            245             250             255

<210> SEQ ID NO 10
<211> LENGTH: 256
<212> TYPE: PRT
<213> ORGANISM: Artificial Sequence
<220> FEATURE:
<223> OTHER INFORMATION: murine 4-1BB, Tumor necrosis factor receptor
      superfamily, member 9 (Mus musculus)

<400> SEQUENCE: 10

Met Gly Asn Asn Cys Tyr Asn Val Val Val Ile Val Leu Leu Leu Val
1               5               10              15

Gly Cys Glu Lys Val Gly Ala Val Gln Asn Ser Cys Asp Asn Cys Gln
            20              25              30

Pro Gly Thr Phe Cys Arg Lys Tyr Asn Pro Val Cys Lys Ser Cys Pro
        35              40              45

Pro Ser Thr Phe Ser Ser Ile Gly Gly Gln Pro Asn Cys Asn Ile Cys
    50              55              60

Arg Val Cys Ala Gly Tyr Phe Arg Phe Lys Lys Phe Cys Ser Ser Thr
65              70              75              80

His Asn Ala Glu Cys Glu Cys Ile Glu Gly Phe His Cys Leu Gly Pro
            85              90              95

Gln Cys Thr Arg Cys Glu Lys Asp Cys Arg Pro Gly Gln Glu Leu Thr
            100             105             110

Lys Gln Gly Cys Lys Thr Cys Ser Leu Gly Thr Phe Asn Asp Gln Asn
        115             120             125

Gly Thr Gly Val Cys Arg Pro Trp Thr Asn Cys Ser Leu Asp Gly Arg
        130             135             140

Ser Val Leu Lys Thr Gly Thr Thr Glu Lys Asp Val Val Cys Gly Pro
145             150             155             160

Pro Val Val Ser Phe Ser Pro Ser Thr Thr Ile Ser Val Thr Pro Glu
            165             170             175

Gly Gly Pro Gly Gly His Ser Leu Gln Val Leu Thr Leu Phe Leu Ala
            180             185             190

Leu Thr Ser Ala Leu Leu Leu Ala Leu Ile Phe Ile Thr Leu Leu Phe
        195             200             205

Ser Val Leu Lys Trp Ile Arg Lys Lys Phe Pro His Ile Phe Lys Gln
        210             215             220

Pro Phe Lys Lys Thr Thr Gly Ala Ala Gln Glu Glu Asp Ala Cys Ser
225             230             235             240

Cys Arg Cys Pro Gln Glu Glu Glu Gly Gly Gly Gly Tyr Glu Leu
            245             250             255

<210> SEQ ID NO 11
<211> LENGTH: 441
```

```
<212> TYPE: PRT
<213> ORGANISM: Artificial Sequence
<220> FEATURE:
<223> OTHER INFORMATION: heavy chain for utomilumab

<400> SEQUENCE: 11

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
                20                  25                  30

Trp Ile Ser Trp Val Arg Gln Met Pro Gly Lys Gly Leu Glu Trp Met
            35                  40                  45

Gly Lys Ile Tyr Pro Gly Asp Ser Tyr Thr Asn Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
    370                 375                 380
```

```
Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
            435                 440

<210> SEQ ID NO 12
<211> LENGTH: 214
<212> TYPE: PRT
<213> ORGANISM: Artificial Sequence
<220> FEATURE:
<223> OTHER INFORMATION: light chain for utomilumab

<400> SEQUENCE: 12

Ser Tyr Glu Leu Thr Gln Pro Pro Ser Val Ser Val Ser Pro Gly Gln
1                 5                   10                  15

Thr Ala Ser Ile Thr Cys Ser Gly Asp Asn Ile Gly Asp Gln Tyr Ala
                20                  25                  30

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 13
<211> LENGTH: 116
<212> TYPE: PRT
<213> ORGANISM: Artificial Sequence
<220> FEATURE:
<223> OTHER INFORMATION: heavy chain variable region for utomilumab

<400> SEQUENCE: 13

Glu Val Gln Leu Val Gln Ser Gly Ala Glu Val Lys Lys Pro Gly Glu
1                 5                   10                  15

Ser Leu Arg Ile Ser Cys Lys Gly Ser Gly Tyr Ser Phe Ser Thr Tyr
                20                  25                  30
```

```
Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
                100                 105                 110

Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: light chain variable region for utomilumab

<400> SEQUENCE: 14

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
        20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
                100                 105

<210> SEQ ID NO 15
<211> LENGTH: 6
<212> TYPE: PRT
<213> ORGANISM: Artificial Sequence
<220> FEATURE:
<223> OTHER INFORMATION: heavy chain CDR1 for utomilumab

<400> SEQUENCE: 15

Ser Thr Tyr Trp Ile Ser
1               5

<210> SEQ ID NO 16
<211> LENGTH: 17
<212> TYPE: PRT
<213> ORGANISM: Artificial Sequence
<220> FEATURE:
<223> OTHER INFORMATION: heavy chain CDR2 for utomilumab

<400> SEQUENCE: 16

Lys Ile Tyr Pro Gly Asp Ser Tyr Thr Asn Tyr Ser Pro Ser Phe Gln
1               5                   10                  15

Gly
```

```
<210> SEQ ID NO 17
<211> LENGTH: 8
<212> TYPE: PRT
<213> ORGANISM: Artificial Sequence
<220> FEATURE:
<223> OTHER INFORMATION: heavy chain CDR3 for utomilumab

<400> SEQUENCE: 17

Arg Gly Tyr Gly Ile Phe Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: light chain CDR1 for utomilumab

<400> SEQUENCE: 18

Ser Gly Asp Asn Ile Gly Asp Gln Tyr Ala His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: light chain CDR2 for utomilumab

<400> SEQUENCE: 19

Gln Asp Lys Asn Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: light chain CDR3 for utomilumab

<400> SEQUENCE: 20

Ala Thr Tyr Thr Gly Phe Gly Ser Leu Ala Val
1               5                   10

<210> SEQ ID NO 21
<211> LENGTH: 448
<212> TYPE: PRT
<213> ORGANISM: Artificial Sequence
<220> FEATURE:
<223> OTHER INFORMATION: heavy chain for urelumab

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445
```

<210> SEQ ID NO 22
<211> LENGTH: 216
<212> TYPE: PRT
<213> ORGANISM: Artificial Sequence
<220> FEATURE:
<223> OTHER INFORMATION: light chain for urelumab

<400> SEQUENCE: 22

```
Glu Ile Val Leu Thr Gln Ser Pro Ala Thr Leu Ser Leu Ser Pro Gly
1               5                   10                  15
```

-continued

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
    210                 215
```

```
<210> SEQ ID NO 23
<211> LENGTH: 120
<212> TYPE: PRT
<213> ORGANISM: Artificial Sequence
<220> FEATURE:
<223> OTHER INFORMATION: variable heavy chain for urelumab

<400> SEQUENCE: 23

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro
        115                 120
```

```
<210> SEQ ID NO 24
<211> LENGTH: 110
<212> TYPE: PRT
<213> ORGANISM: Artificial Sequence
<220> FEATURE:
```

-continued

<223> OTHER INFORMATION: variable light chain for urelumab

<400> SEQUENCE: 24

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln
            100                 105                 110

<210> SEQ ID NO 25
<211> LENGTH: 5
<212> TYPE: PRT
<213> ORGANISM: Artificial Sequence
<220> FEATURE:
<223> OTHER INFORMATION: heavy chain CDR1 for urelumab

<400> SEQUENCE: 25

Gly Tyr Tyr Trp Ser
1               5

<210> SEQ ID NO 26
<211> LENGTH: 16
<212> TYPE: PRT
<213> ORGANISM: Artificial Sequence
<220> FEATURE:
<223> OTHER INFORMATION: heavy chain CDR2 for urelumab

<400> SEQUENCE: 26

Glu Ile Asn His Gly Gly Tyr Val Thr Tyr Asn Pro Ser Leu Glu Ser
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: heavy chain CDR3 for urelumab

<400> SEQUENCE: 27

Asp Tyr Gly Pro Gly Asn Tyr Asp Trp Tyr Phe Asp Leu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: light chain CDR1 for urelumab

<400> SEQUENCE: 28

Arg Ala Ser Gln Ser Val Ser Ser Tyr Leu Ala
1               5                   10

<210> SEQ ID NO 29

```
<211> LENGTH: 7
<212> TYPE: PRT
<213> ORGANISM: Artificial Sequence
<220> FEATURE:
<223> OTHER INFORMATION: light chain CDR2 for urelumab

<400> SEQUENCE: 29

Asp Ala Ser Asn Arg Ala Thr
1               5

<210> SEQ ID NO 30
<211> LENGTH: 11
<212> TYPE: PRT
<213> ORGANISM: Artificial Sequence
<220> FEATURE:
<223> OTHER INFORMATION: light chain CDR3 for urelumab

<400> SEQUENCE: 30

Gln Gln Arg Ser Asp Trp Pro Pro Ala Leu Thr
1               5                   10

<210> SEQ ID NO 31
<211> LENGTH: 230
<212> TYPE: PRT
<213> ORGANISM: Artificial Sequence
<220> FEATURE:
<223> OTHER INFORMATION: Fc domain

<400> SEQUENCE: 31

Lys Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
    210                 215                 220

Ser Leu Ser Pro Gly Lys
225                 230
```

<210> SEQ ID NO 32
<211> LENGTH: 22
<212> TYPE: PRT
<213> ORGANISM: Artificial Sequence
<220> FEATURE:
<223> OTHER INFORMATION: linker

<400> SEQUENCE: 32

Gly Gly Pro Gly Ser Ser Lys Ser Cys Asp Lys Thr His Thr Cys Pro
1               5                   10                  15

Pro Cys Pro Ala Pro Glu
            20

<210> SEQ ID NO 33
<211> LENGTH: 22
<212> TYPE: PRT
<213> ORGANISM: Artificial Sequence
<220> FEATURE:
<223> OTHER INFORMATION: linker

<400> SEQUENCE: 33

Gly Gly Ser Gly Ser Ser Lys Ser Cys Asp Lys Thr His Thr Cys Pro
1               5                   10                  15

Pro Cys Pro Ala Pro Glu
            20

<210> SEQ ID NO 34
<211> LENGTH: 27
<212> TYPE: PRT
<213> ORGANISM: Artificial Sequence
<220> FEATURE:
<223> OTHER INFORMATION: linker

<400> SEQUENCE: 34

Gly Gly Pro Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 35
<211> LENGTH: 27
<212> TYPE: PRT
<213> ORGANISM: Artificial Sequence
<220> FEATURE:
<223> OTHER INFORMATION: linker

<400> SEQUENCE: 35

Gly Gly Ser Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 36
<211> LENGTH: 29
<212> TYPE: PRT
<213> ORGANISM: Artificial Sequence
<220> FEATURE:
<223> OTHER INFORMATION: linker

<400> SEQUENCE: 36

Gly Gly Pro Gly Ser Ser Ser Ser Ser Ser Ser Ser Lys Ser Cys
1               5                   10                  15

Asp Lys Thr His Thr Cys Pro Pro Cys Pro Ala Pro Glu
            20                  25

-continued

<210> SEQ ID NO 37
<211> LENGTH: 29
<212> TYPE: PRT
<213> ORGANISM: Artificial Sequence
<220> FEATURE:
<223> OTHER INFORMATION: linker

<400> SEQUENCE: 37

Gly Gly Ser Gly Ser Ser Ser Ser Ser Ser Ser Ser Lys Ser Cys
1               5                   10                  15

Asp Lys Thr His Thr Cys Pro Pro Cys Pro Ala Pro Glu
            20                  25

<210> SEQ ID NO 38
<211> LENGTH: 24
<212> TYPE: PRT
<213> ORGANISM: Artificial Sequence
<220> FEATURE:
<223> OTHER INFORMATION: linker

<400> SEQUENCE: 38

Gly Gly Pro Gly Ser Ser Gly Ser Gly Ser Ser Asp Lys Thr His Thr
1               5                   10                  15

Cys Pro Pro Cys Pro Ala Pro Glu
            20

<210> SEQ ID NO 39
<211> LENGTH: 23
<212> TYPE: PRT
<213> ORGANISM: Artificial Sequence
<220> FEATURE:
<223> OTHER INFORMATION: linker

<400> SEQUENCE: 39

Gly Gly Pro Gly Ser Ser Gly Ser Gly Ser Asp Lys Thr His Thr Cys
1               5                   10                  15

Pro Pro Cys Pro Ala Pro Glu
            20

<210> SEQ ID NO 40
<211> LENGTH: 21
<212> TYPE: PRT
<213> ORGANISM: Artificial Sequence
<220> FEATURE:
<223> OTHER INFORMATION: linker

<400> SEQUENCE: 40

Gly Gly Pro Ser Ser Ser Gly Ser Asp Lys Thr His Thr Cys Pro Pro
1               5                   10                  15

Cys Pro Ala Pro Glu
            20

<210> SEQ ID NO 41
<211> LENGTH: 25
<212> TYPE: PRT
<213> ORGANISM: Artificial Sequence
<220> FEATURE:
<223> OTHER INFORMATION: linker

<400> SEQUENCE: 41

Gly Gly Ser Ser Ser Ser Ser Ser Ser Gly Ser Asp Lys Thr His
1               5                   10                  15

Thr Cys Pro Pro Cys Pro Ala Pro Glu

-continued

```
                20              25

<210> SEQ ID NO 42
<211> LENGTH: 246
<212> TYPE: PRT
<213> ORGANISM: Artificial Sequence
<220> FEATURE:
<223> OTHER INFORMATION: Fc domain

<400> SEQUENCE: 42

Met Glu Thr Asp Thr Leu Leu Leu Trp Val Leu Leu Leu Trp Val Pro
1               5                   10                  15

Ala Gly Asn Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 43
<211> LENGTH: 11
<212> TYPE: PRT
<213> ORGANISM: Artificial Sequence
<220> FEATURE:
<223> OTHER INFORMATION: linker

<400> SEQUENCE: 43

Ser Gly Ser Gly Ser Gly Ser Gly Ser Gly Ser
1               5                   10

<210> SEQ ID NO 44
<211> LENGTH: 12
<212> TYPE: PRT
<213> ORGANISM: Artificial Sequence
<220> FEATURE:
```

-continued

<223> OTHER INFORMATION: linker

<400> SEQUENCE: 44

```
Ser Ser Ser Ser Ser Ser Gly Ser Gly Ser Gly Ser
1               5                   10
```

<210> SEQ ID NO 45
<211> LENGTH: 16
<212> TYPE: PRT
<213> ORGANISM: Artificial Sequence
<220> FEATURE:
<223> OTHER INFORMATION: linker

<400> SEQUENCE: 45

```
Ser Ser Ser Ser Ser Ser Gly Ser Gly Ser Gly Ser Gly Ser Gly Ser
1               5                   10                  15
```

<210> SEQ ID NO 46
<211> LENGTH: 254
<212> TYPE: PRT
<213> ORGANISM: Artificial Sequence
<220> FEATURE:
<223> OTHER INFORMATION: 4-1BBL

<400> SEQUENCE: 46

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
        50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 47
<211> LENGTH: 168
<212> TYPE: PRT
<213> ORGANISM: Artificial Sequence
<220> FEATURE:
<223> OTHER INFORMATION: 4-1BBL soluble domain

<400> SEQUENCE: 47

```
Leu Arg Gln Gly Met Phe Ala Gln Leu Val Ala Gln Asn Val Leu Leu
1               5                   10                  15

Ile Asp Gly Pro Leu Ser Trp Tyr Ser Asp Pro Gly Leu Ala Gly Val
                20                  25                  30

Ser Leu Thr Gly Gly Leu Ser Tyr Lys Glu Asp Thr Lys Glu Leu Val
            35                  40                  45

Val Ala Lys Ala Gly Val Tyr Tyr Val Phe Phe Gln Leu Glu Leu Arg
        50                  55                  60

Arg Val Val Ala Gly Glu Gly Ser Gly Ser Val Ser Leu Ala Leu His
65                  70                  75                  80

Leu Gln Pro Leu Arg Ser Ala Ala Gly Ala Ala Ala Leu Ala Leu Thr
                85                  90                  95

Val Asp Leu Pro Pro Ala Ser Ser Glu Ala Arg Asn Ser Ala Phe Gly
            100                 105                 110

Phe Gln Gly Arg Leu Leu His Leu Ser Ala Gly Gln Arg Leu Gly Val
            115                 120                 125

His Leu His Thr Glu Ala Arg Ala Arg His Ala Trp Gln Leu Thr Gln
        130                 135                 140

Gly Ala Thr Val Leu Gly Leu Phe Arg Val Thr Pro Glu Ile Pro Ala
145                 150                 155                 160

Gly Leu Pro Ser Pro Arg Ser Glu
                165
```

<210> SEQ ID NO 48
<211> LENGTH: 118
<212> TYPE: PRT
<213> ORGANISM: Artificial Sequence
<220> FEATURE:
<223> OTHER INFORMATION: variable heavy chain for 4B4-1-1 version 1

<400> SEQUENCE: 48

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
                20                  25                  30

Trp Met His Trp Val Lys Gln Arg Pro Gly Gln Val Leu Glu Trp Ile
            35                  40                  45

Gly Glu Ile Asn Pro Gly Asn Gly His Thr Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
            100                 105                 110

Thr Leu Val Thr Val Ser
            115
```

<210> SEQ ID NO 49
<211> LENGTH: 107

```
<212> TYPE: PRT
<213> ORGANISM: Artificial Sequence
<220> FEATURE:
<223> OTHER INFORMATION: variable light chain for 4B4-1-1 version 1

<400> SEQUENCE: 49

Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys
            100                 105

<210> SEQ ID NO 50
<211> LENGTH: 119
<212> TYPE: PRT
<213> ORGANISM: Artificial Sequence
<220> FEATURE:
<223> OTHER INFORMATION: variable heavy chain for 4B4-1-1 version 2

<400> SEQUENCE: 50

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
            100                 105                 110

Thr Leu Val Thr Val Ser Ala
        115

<210> SEQ ID NO 51
<211> LENGTH: 108
<212> TYPE: PRT
<213> ORGANISM: Artificial Sequence
<220> FEATURE:
<223> OTHER INFORMATION: variable light chain for 4B4-1-1 version 2

<400> SEQUENCE: 51

Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
```

-continued

```
              35                   40                   45

Lys Tyr Ala Ser Gln Ser Ile Ser Gly Ile Pro Ser Arg Phe Ser Gly
        50                   55                   60

Ser Gly Ser Gly Ser Asp Phe Thr Leu Ser Ile Asn Ser Val Glu Pro
65                   70                   75                   80

Glu Asp Val Gly Val Tyr Tyr Cys Gln Asp Gly His Ser Phe Pro Pro
                    85                   90                   95

Thr Phe Gly Gly Gly Thr Lys Leu Glu Ile Lys Arg
            100                  105
```

```
<210> SEQ ID NO 52
<211> LENGTH: 120
<212> TYPE: PRT
<213> ORGANISM: Artificial Sequence
<220> FEATURE:
<223> OTHER INFORMATION: variable heavy chain for H39E3-2

<400> SEQUENCE: 52

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Asp Tyr Trp Met Ser Trp Val Arg Gln Ala Pro Gly Lys Gly Leu
        50                  55                  60

Glu Trp Val Ala Asp Ile Lys Asn Asp Gly Ser Tyr Thr Asn Tyr Ala
65                  70                  75                  80

Pro Ser Leu Thr Asn Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Leu Thr
            115                 120
```

```
<210> SEQ ID NO 53
<211> LENGTH: 109
<212> TYPE: PRT
<213> ORGANISM: Artificial Sequence
<220> FEATURE:
<223> OTHER INFORMATION: variable light chain for H39E3-2

<400> SEQUENCE: 53

Met Glu Ala Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
            35                  40                  45

Leu Leu Ser Ser Gly Asn Gln Lys Asn Tyr Leu Trp Tyr Gln Gln Lys
        50                  55                  60

Pro Gly Gln Pro Pro Lys Leu Leu Ile Tyr Tyr Ala Ser Thr Arg Gln
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala
            100                 105
```

```
<210> SEQ ID NO 54
<211> LENGTH: 277
<212> TYPE: PRT
<213> ORGANISM: Artificial Sequence
<220> FEATURE:
<223> OTHER INFORMATION: human OX40 (Homo sapiens)

<400> SEQUENCE: 54

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 55
<211> LENGTH: 272
<212> TYPE: PRT
<213> ORGANISM: Artificial Sequence
<220> FEATURE:
<223> OTHER INFORMATION: murine OX40 (Mus musculus)

<400> SEQUENCE: 55

Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
                20                  25                  30
```

-continued

```
Pro Ser Gly His Lys Cys Cys Arg Glu Cys Gln Pro Gly His Gly Met
    35              40              45

Val Ser Arg Cys Asp His Thr Arg Asp Thr Leu Cys His Pro Cys Glu
    50              55              60

Thr Gly Phe Tyr Asn Glu Ala Val Asn Tyr Asp Thr Cys Lys Gln Cys
65              70              75              80

Thr Gln Cys Asn His Arg Ser Gly Ser Glu Leu Lys Gln Asn Cys Thr
            85              90              95

Pro Thr Gln Asp Thr Val Cys Arg Cys Arg Pro Gly Thr Gln Pro Arg
            100             105             110

Gln Asp Ser Gly Tyr Lys Leu Gly Val Asp Cys Val Pro Cys Pro Pro
            115             120             125

Gly His Phe Ser Pro Gly Asn Asn Gln Ala Cys Lys Pro Trp Thr Asn
    130             135             140

Cys Thr Leu Ser Gly Lys Gln Thr Arg His Pro Ala Ser Asp Ser Leu
145             150             155             160

Asp Ala Val Cys Glu Asp Arg Ser Leu Leu Ala Thr Leu Leu Trp Glu
            165             170             175

Thr Gln Arg Pro Thr Phe Arg Pro Thr Thr Val Gln Ser Thr Thr Val
            180             185             190

Trp Pro Arg Thr Ser Glu Leu Pro Ser Pro Pro Thr Leu Val Thr Pro
            195             200             205

Glu Gly Pro Ala Phe Ala Val Leu Leu Gly Leu Gly Leu Gly Leu Leu
    210             215             220

Ala Pro Leu Thr Val Leu Leu Ala Leu Tyr Leu Leu Arg Lys Ala Trp
225             230             235             240

Arg Leu Pro Asn Thr Pro Lys Pro Cys Trp Gly Asn Ser Phe Arg Thr
            245             250             255

Pro Ile Gln Glu Glu His Thr Asp Ala His Phe Thr Leu Ala Lys Ile
            260             265             270
```

```
<210> SEQ ID NO 56
<211> LENGTH: 451
<212> TYPE: PRT
<213> ORGANISM: Artificial Sequence
<220> FEATURE:
<223> OTHER INFORMATION: heavy chain for tavolixizumab

<400> SEQUENCE: 56
```

```
Gln Val Gln Leu Gln Glu Ser Gly Pro Gly Leu Val Lys Pro Ser Gln
1               5               10              15

Thr Leu Ser Leu Thr Cys Ala Val Tyr Gly Gly Ser Phe Ser Ser Gly
            20              25              30

Tyr Trp Asn Trp Ile Arg Lys His Pro Gly Lys Gly Leu Glu Tyr Ile
    35              40              45

Gly Tyr Ile Ser Tyr Asn Gly Ile Thr Tyr His Asn Pro Ser Leu Lys
    50              55              60

Ser Arg Ile Thr Ile Asn Arg Asp Thr Ser Lys Asn Gln Tyr Ser Leu
65              70              75              80

Gln Leu Asn Ser Val Thr Pro Glu Asp Thr Ala Val Tyr Tyr Cys Ala
            85              90              95

Arg Tyr Lys Tyr Asp Tyr Asp Gly Gly His Ala Met Asp Tyr Trp Gly
            100             105             110

Gln Gly Thr Leu Val Thr Val Ser Ser Ala Ser Thr Lys Gly Pro Ser
    115             120             125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 57
<211> LENGTH: 214
<212> TYPE: PRT
<213> ORGANISM: Artificial Sequence
<220> FEATURE:
<223> OTHER INFORMATION: light chain for tavolixizumab

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30
```

```
Leu Asn Trp Tyr Gln Gln Lys Pro Gly Lys Ala Pro Lys Leu Leu Ile
        35              40              45

Tyr Tyr Thr Ser Lys Leu His Ser Gly Val Pro Ser Arg Phe Ser Gly
    50              55              60

Ser Gly Ser Gly Thr Asp Tyr Thr Leu Thr Ile Ser Ser Leu Gln Pro
65              70              75              80

Glu Asp Phe Ala Thr Tyr Tyr Cys Gln Gln Gly Ser Ala Leu Pro Trp
            85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
        210

<210> SEQ ID NO 58
<211> LENGTH: 118
<212> TYPE: PRT
<213> ORGANISM: Artificial Sequence
<220> FEATURE:
<223> OTHER INFORMATION: heavy chain variable region for tavolixizumab

<400> SEQUENCE: 58

Gln Val Gln Leu Gln Glu Ser Gly Pro Gly Leu Val Lys Pro Ser Gln
1               5               10              15

Thr Leu Ser Leu Thr Cys Ala Val Tyr Gly Gly Ser Phe Ser Ser Gly
            20              25              30

Tyr Trp Asn Trp Ile Arg Lys His Pro Gly Lys Gly Leu Glu Tyr Ile
        35              40              45

Gly Tyr Ile Ser Tyr Asn Gly Ile Thr Tyr His Asn Pro Ser Leu Lys
    50              55              60

Ser Arg Ile Thr Ile Asn Arg Asp Thr Ser Lys Asn Gln Tyr Ser Leu
65              70              75              80

Gln Leu Asn Ser Val Thr Pro Glu Asp Thr Ala Val Tyr Tyr Cys Ala
            85              90              95

Arg Tyr Lys Tyr Asp Tyr Asp Gly Gly His Ala Met Asp Tyr Trp Gly
            100             105             110

Gln Gly Thr Leu Val Thr
        115

<210> SEQ ID NO 59
<211> LENGTH: 108
<212> TYPE: PRT
<213> ORGANISM: Artificial Sequence
<220> FEATURE:
<223> OTHER INFORMATION: light chain variable region for tavolixizumab
```

-continued

```
<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg
            100                 105

<210> SEQ ID NO 60
<211> LENGTH: 9
<212> TYPE: PRT
<213> ORGANISM: Artificial Sequence
<220> FEATURE:
<223> OTHER INFORMATION: heavy chain CDR1 for tavolixizumab

<400> SEQUENCE: 60

Gly Ser Phe Ser Ser Gly Tyr Trp Asn
1               5

<210> SEQ ID NO 61
<211> LENGTH: 13
<212> TYPE: PRT
<213> ORGANISM: Artificial Sequence
<220> FEATURE:
<223> OTHER INFORMATION: heavy chain CDR2 for tavolixizumab

<400> SEQUENCE: 61

Tyr Ile Gly Tyr Ile Ser Tyr Asn Gly Ile Thr Tyr His
1               5                   10

<210> SEQ ID NO 62
<211> LENGTH: 14
<212> TYPE: PRT
<213> ORGANISM: Artificial Sequence
<220> FEATURE:
<223> OTHER INFORMATION: heavy chain CDR3 for tavolixizumab

<400> SEQUENCE: 62

Arg Tyr Lys Tyr Asp Tyr Asp Gly Gly His Ala Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: light chain CDR1 for tavolixizumab

<400> SEQUENCE: 63

Gln Asp Ile Ser Asn Tyr Leu Asn
1               5

<210> SEQ ID NO 64
<211> LENGTH: 11
<212> TYPE: PRT
```

<213> ORGANISM: Artificial Sequence
<220> FEATURE:
<223> OTHER INFORMATION: light chain CDR2 for tavolixizumab

<400> SEQUENCE: 64

Leu Leu Ile Tyr Tyr Thr Ser Lys Leu His Ser
1               5                   10

<210> SEQ ID NO 65
<211> LENGTH: 8
<212> TYPE: PRT
<213> ORGANISM: Artificial Sequence
<220> FEATURE:
<223> OTHER INFORMATION: light chain CDR3 for tavolixizumab

<400> SEQUENCE: 65

Gln Gln Gly Ser Ala Leu Pro Trp
1               5

<210> SEQ ID NO 66
<211> LENGTH: 444
<212> TYPE: PRT
<213> ORGANISM: Artificial Sequence
<220> FEATURE:
<223> OTHER INFORMATION: heavy chain for 11D4

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

-continued

```
Thr Cys Val Val Val Asp Val Ser His Glu Asp Pro Glu Val Gln Phe
        260             265             270

Asn Trp Tyr Val Asp Gly Val Glu Val His Asn Ala Lys Thr Lys Pro
        275             280             285

Arg Glu Glu Gln Phe Asn Ser Thr Phe Arg Val Val Ser Val Leu Thr
    290             295             300

Val Val His Gln Asp Trp Leu Asn Gly Lys Glu Tyr Lys Cys Lys Val
305             310             315             320

Ser Asn Lys Gly Leu Pro Ala Pro Ile Glu Lys Thr Ile Ser Lys Thr
                325             330             335

Lys Gly Gln Pro Arg Glu Pro Gln Val Tyr Thr Leu Pro Pro Ser Arg
            340             345             350

Glu Glu Met Thr Lys Asn Gln Val Ser Leu Thr Cys Leu Val Lys Gly
        355             360             365

Phe Tyr Pro Ser Asp Ile Ala Val Glu Trp Glu Ser Asn Gly Gln Pro
    370             375             380

Glu Asn Asn Tyr Lys Thr Thr Pro Pro Met Leu Asp Ser Asp Gly Ser
385             390             395             400

Phe Phe Leu Tyr Ser Lys Leu Thr Val Asp Lys Ser Arg Trp Gln Gln
            405             410             415

Gly Asn Val Phe Ser Cys Ser Val Met His Glu Ala Leu His Asn His
            420             425             430

Tyr Thr Gln Lys Ser Leu Ser Leu Ser Pro Gly Lys
        435             440
```

```
<210> SEQ ID NO 67
<211> LENGTH: 214
<212> TYPE: PRT
<213> ORGANISM: Artificial Sequence
<220> FEATURE:
<223> OTHER INFORMATION: light chain for 11D4

<400> SEQUENCE: 67
```

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Ser Ser Trp
                20              25              30

Leu Ala Trp Tyr Gln Gln Lys Pro Glu Lys Ala Pro Lys Ser Leu Ile
            35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Asn Ser Tyr Pro Pro
                85              90              95

Thr Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 68
<211> LENGTH: 118
<212> TYPE: PRT
<213> ORGANISM: Artificial Sequence
<220> FEATURE:
<223> OTHER INFORMATION: heavy chain variable region for 11D4

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
            85                  90                  95

Ala Arg Glu Ser Gly Trp Tyr Leu Phe Asp Tyr Trp Gly Gln Gly Thr
            100                 105                 110

Leu Val Thr Val Ser Ser
        115
```

```
<210> SEQ ID NO 69
<211> LENGTH: 107
<212> TYPE: PRT
<213> ORGANISM: Artificial Sequence
<220> FEATURE:
<223> OTHER INFORMATION: light chain variable region for 11D4

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
            85                  90                  95

Thr Phe Gly Gly Gly Thr Lys Val Glu Ile Lys
            100                 105
```

```
<210> SEQ ID NO 70
<211> LENGTH: 5
<212> TYPE: PRT
```

<213> ORGANISM: Artificial Sequence
<220> FEATURE:
<223> OTHER INFORMATION: heavy chain CDR1 for 11D4

<400> SEQUENCE: 70

Ser Tyr Ser Met Asn
1               5

<210> SEQ ID NO 71
<211> LENGTH: 17
<212> TYPE: PRT
<213> ORGANISM: Artificial Sequence
<220> FEATURE:
<223> OTHER INFORMATION: heavy chain CDR2 for 11D4

<400> SEQUENCE: 71

Tyr Ile Ser Ser Ser Ser Ser Thr Ile Asp Tyr Ala Asp Ser Val Lys
1               5                   10                  15

Gly

<210> SEQ ID NO 72
<211> LENGTH: 9
<212> TYPE: PRT
<213> ORGANISM: Artificial Sequence
<220> FEATURE:
<223> OTHER INFORMATION: heavy chain CDR3 for 11D4

<400> SEQUENCE: 72

Glu Ser Gly Trp Tyr Leu Phe Asp Tyr
1               5

<210> SEQ ID NO 73
<211> LENGTH: 11
<212> TYPE: PRT
<213> ORGANISM: Artificial Sequence
<220> FEATURE:
<223> OTHER INFORMATION: light chain CDR1 for 11D4

<400> SEQUENCE: 73

Arg Ala Ser Gln Gly Ile Ser Ser Trp Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: light chain CDR2 for 11D4

<400> SEQUENCE: 74

Ala Ala Ser Ser Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: light chain CDR3 for 11D4

<400> SEQUENCE: 75

Gln Gln Tyr Asn Ser Tyr Pro Pro Thr
1               5

<210> SEQ ID NO 76
<211> LENGTH: 450

<212> TYPE: PRT
<213> ORGANISM: Artificial Sequence
<220> FEATURE:
<223> OTHER INFORMATION: heavy chain for 18D8

<400> SEQUENCE: 76

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
        290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 77
<211> LENGTH: 213
<212> TYPE: PRT
<213> ORGANISM: Artificial Sequence
<220> FEATURE:
<223> OTHER INFORMATION: light chain for 18D8

<400> SEQUENCE: 77

Glu Ile Val Val Thr Gln Ser Pro Ala Thr Leu Ser Leu Ser Pro Gly
1                   5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 78
<211> LENGTH: 124
<212> TYPE: PRT
<213> ORGANISM: Artificial Sequence
<220> FEATURE:
<223> OTHER INFORMATION: heavy chain variable region for 18D8

<400> SEQUENCE: 78

Glu Val Gln Leu Val Glu Ser Gly Gly Gly Leu Val Gln Pro Gly Arg
1                   5                   10                  15

-continued

```
Ser Leu Arg Leu Ser Cys Ala Ala Ser Gly Phe Thr Phe Asp Asp Tyr
        20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120
```

```
<210> SEQ ID NO 79
<211> LENGTH: 106
<212> TYPE: PRT
<213> ORGANISM: Artificial Sequence
<220> FEATURE:
<223> OTHER INFORMATION: light chain variable region for 18D8

<400> SEQUENCE: 79
```

```
Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
        20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

```
<210> SEQ ID NO 80
<211> LENGTH: 5
<212> TYPE: PRT
<213> ORGANISM: Artificial Sequence
<220> FEATURE:
<223> OTHER INFORMATION: heavy chain CDR1 for 18D8

<400> SEQUENCE: 80
```

```
Asp Tyr Ala Met His
1               5
```

```
<210> SEQ ID NO 81
<211> LENGTH: 17
<212> TYPE: PRT
<213> ORGANISM: Artificial Sequence
<220> FEATURE:
<223> OTHER INFORMATION: heavy chain CDR2 for 18D8

<400> SEQUENCE: 81
```

```
Gly Ile Ser Trp Asn Ser Gly Ser Ile Gly Tyr Ala Asp Ser Val Lys
1               5                   10                  15
```

Gly

<210> SEQ ID NO 82
<211> LENGTH: 15
<212> TYPE: PRT
<213> ORGANISM: Artificial Sequence
<220> FEATURE:
<223> OTHER INFORMATION: heavy chain CDR3 for 18D8

<400> SEQUENCE: 82

Asp Gln Ser Thr Ala Asp Tyr Tyr Phe Tyr Tyr Gly Met Asp Val
1               5               10              15

<210> SEQ ID NO 83
<211> LENGTH: 11
<212> TYPE: PRT
<213> ORGANISM: Artificial Sequence
<220> FEATURE:
<223> OTHER INFORMATION: light chain CDR1 for 18D8

<400> SEQUENCE: 83

Arg Ala Ser Gln Ser Val Ser Ser Tyr Leu Ala
1               5               10

<210> SEQ ID NO 84
<211> LENGTH: 7
<212> TYPE: PRT
<213> ORGANISM: Artificial Sequence
<220> FEATURE:
<223> OTHER INFORMATION: light chain CDR2 for 18D8

<400> SEQUENCE: 84

Asp Ala Ser Asn Arg Ala Thr
1               5

<210> SEQ ID NO 85
<211> LENGTH: 8
<212> TYPE: PRT
<213> ORGANISM: Artificial Sequence
<220> FEATURE:
<223> OTHER INFORMATION: light chain CDR3 for 18D8

<400> SEQUENCE: 85

Gln Gln Arg Ser Asn Trp Pro Thr
1               5

<210> SEQ ID NO 86
<211> LENGTH: 120
<212> TYPE: PRT
<213> ORGANISM: Artificial Sequence
<220> FEATURE:
<223> OTHER INFORMATION: heavy chain variable region for Hu119-122

<400> SEQUENCE: 86

Glu Val Gln Leu Val Glu Ser Gly Gly Gly Leu Val Gln Pro Gly Gly
1               5               10              15

Ser Leu Arg Leu Ser Cys Ala Ala Ser Glu Tyr Glu Phe Pro Ser His
            20              25              30

Asp Met Ser Trp Val Arg Gln Ala Pro Gly Lys Gly Leu Glu Leu Val
        35              40              45

Ala Ala Ile Asn Ser Asp Gly Gly Ser Thr Tyr Tyr Pro Asp Thr Met
    50              55              60

Glu Arg Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
85 90 95

Ala Arg His Tyr Asp Asp Tyr Tyr Ala Trp Phe Ala Tyr Trp Gly Gln
100 105 110

Gly Thr Met Val Thr Val Ser Ser
115 120

<210> SEQ ID NO 87
<211> LENGTH: 111
<212> TYPE: PRT
<213> ORGANISM: Artificial Sequence
<220> FEATURE:
<223> OTHER INFORMATION: light chain variable region for Hu119-122

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110

<210> SEQ ID NO 88
<211> LENGTH: 5
<212> TYPE: PRT
<213> ORGANISM: Artificial Sequence
<220> FEATURE:
<223> OTHER INFORMATION: heavy chain CDR1 for Hu119-122

<400> SEQUENCE: 88

Ser His Asp Met Ser
1               5

<210> SEQ ID NO 89
<211> LENGTH: 17
<212> TYPE: PRT
<213> ORGANISM: Artificial Sequence
<220> FEATURE:
<223> OTHER INFORMATION: heavy chain CDR2 for Hu119-122

<400> SEQUENCE: 89

Ala Ile Asn Ser Asp Gly Gly Ser Thr Tyr Tyr Pro Asp Thr Met Glu
1               5                   10                  15

Arg

<210> SEQ ID NO 90
<211> LENGTH: 11
<212> TYPE: PRT
<213> ORGANISM: Artificial Sequence
<220> FEATURE:
<223> OTHER INFORMATION: heavy chain CDR3 for Hu119-122

<400> SEQUENCE: 90

His Tyr Asp Asp Tyr Tyr Ala Trp Phe Ala Tyr

-continued

```
1               5                    10
```

<210> SEQ ID NO 91
<211> LENGTH: 15
<212> TYPE: PRT
<213> ORGANISM: Artificial Sequence
<220> FEATURE:
<223> OTHER INFORMATION: light chain CDR1 for Hu119-122

<400> SEQUENCE: 91

```
Arg Ala Ser Lys Ser Val Ser Thr Ser Gly Tyr Ser Tyr Met His
1               5                    10                   15
```

<210> SEQ ID NO 92
<211> LENGTH: 7
<212> TYPE: PRT
<213> ORGANISM: Artificial Sequence
<220> FEATURE:
<223> OTHER INFORMATION: light chain CDR2 for Hu119-122

<400> SEQUENCE: 92

```
Leu Ala Ser Asn Leu Glu Ser
1               5
```

<210> SEQ ID NO 93
<211> LENGTH: 9
<212> TYPE: PRT
<213> ORGANISM: Artificial Sequence
<220> FEATURE:
<223> OTHER INFORMATION: light chain CDR3 for Hu119-122

<400> SEQUENCE: 93

```
Gln His Ser Arg Glu Leu Pro Leu Thr
1               5
```

<210> SEQ ID NO 94
<211> LENGTH: 122
<212> TYPE: PRT
<213> ORGANISM: Artificial Sequence
<220> FEATURE:
<223> OTHER INFORMATION: heavy chain variable region for Hu106-222

<400> SEQUENCE: 94

```
Gln Val Gln Leu Val Gln Ser Gly Ser Glu Leu Lys Lys Pro Gly Ala
1               5                    10                   15

Ser Val Lys Val Ser Cys Lys Ala Ser Gly Tyr Thr Phe Thr Asp Tyr
            20                   25                   30

Ser Met His Trp Val Arg Gln Ala Pro Gly Gln Gly Leu Lys Trp Met
        35                   40                   45

Gly Trp Ile Asn Thr Glu Thr Gly Glu Pro Thr Tyr Ala Asp Asp Phe
    50                   55                   60

Lys Gly Arg Phe Val Phe Ser Leu Asp Thr Ser Val Ser Thr Ala Tyr
65                   70                   75                   80

Leu Gln Ile Ser Ser Leu Lys Ala Glu Asp Thr Ala Val Tyr Tyr Cys
                85                   90                   95

Ala Asn Pro Tyr Tyr Asp Tyr Val Ser Tyr Tyr Ala Met Asp Tyr Trp
            100                  105                  110

Gly Gln Gly Thr Thr Val Thr Val Ser Ser
        115                  120
```

<210> SEQ ID NO 95
<211> LENGTH: 107
<212> TYPE: PRT

-continued

```
<213> ORGANISM: Artificial Sequence
<220> FEATURE:
<223> OTHER INFORMATION: light chain variable region for Hu106-222

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105

<210> SEQ ID NO 96
<211> LENGTH: 5
<212> TYPE: PRT
<213> ORGANISM: Artificial Sequence
<220> FEATURE:
<223> OTHER INFORMATION: heavy chain CDR1 for Hu106-222

<400> SEQUENCE: 96

Asp Tyr Ser Met His
1               5

<210> SEQ ID NO 97
<211> LENGTH: 17
<212> TYPE: PRT
<213> ORGANISM: Artificial Sequence
<220> FEATURE:
<223> OTHER INFORMATION: heavy chain CDR2 for Hu106-222

<400> SEQUENCE: 97

Trp Ile Asn Thr Glu Thr Gly Glu Pro Thr Tyr Ala Asp Asp Phe Lys
1               5                   10                  15

Gly

<210> SEQ ID NO 98
<211> LENGTH: 13
<212> TYPE: PRT
<213> ORGANISM: Artificial Sequence
<220> FEATURE:
<223> OTHER INFORMATION: heavy chain CDR3 for Hu106-222

<400> SEQUENCE: 98

Pro Tyr Tyr Asp Tyr Val Ser Tyr Tyr Ala Met Asp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: light chain CDR1 for Hu106-222

<400> SEQUENCE: 99

Lys Ala Ser Gln Asp Val Ser Thr Ala Val Ala
```

1              5              10

<210> SEQ ID NO 100
<211> LENGTH: 7
<212> TYPE: PRT
<213> ORGANISM: Artificial Sequence
<220> FEATURE:
<223> OTHER INFORMATION: light chain CDR2 for Hu106-222

<400> SEQUENCE: 100

Ser Ala Ser Tyr Leu Tyr Thr
1              5

<210> SEQ ID NO 101
<211> LENGTH: 9
<212> TYPE: PRT
<213> ORGANISM: Artificial Sequence
<220> FEATURE:
<223> OTHER INFORMATION: light chain CDR3 for Hu106-222

<400> SEQUENCE: 101

Gln Gln His Tyr Ser Thr Pro Arg Thr
1              5

<210> SEQ ID NO 102
<211> LENGTH: 183
<212> TYPE: PRT
<213> ORGANISM: Artificial Sequence
<220> FEATURE:
<223> OTHER INFORMATION: OX40L

<400> SEQUENCE: 102

Met Glu Arg Val Gln Pro Leu Glu Glu Asn Val Gly Asn Ala Ala Arg
1              5              10             15

Pro Arg Phe Glu Arg Asn Lys Leu Leu Leu Val Ala Ser Val Ile Gln
             20             25             30

Gly Leu Gly Leu Leu Leu Cys Phe Thr Tyr Ile Cys Leu His Phe Ser
          35             40             45

Ala Leu Gln Val Ser His Arg Tyr Pro Arg Ile Gln Ser Ile Lys Val
       50             55             60

Gln Phe Thr Glu Tyr Lys Lys Glu Lys Gly Phe Ile Leu Thr Ser Gln
65                70             75             80

Lys Glu Asp Glu Ile Met Lys Val Gln Asn Asn Ser Val Ile Ile Asn
             85             90             95

Cys Asp Gly Phe Tyr Leu Ile Ser Leu Lys Gly Tyr Phe Ser Gln Glu
             100            105            110

Val Asn Ile Ser Leu His Tyr Gln Lys Asp Glu Glu Pro Leu Phe Gln
       115            120            125

Leu Lys Lys Val Arg Ser Val Asn Ser Leu Met Val Ala Ser Leu Thr
    130            135            140

Tyr Lys Asp Lys Val Tyr Leu Asn Val Thr Thr Asp Asn Thr Ser Leu
145            150            155            160

Asp Asp Phe His Val Asn Gly Gly Glu Leu Ile Leu Ile His Gln Asn
             165            170            175

Pro Gly Glu Phe Cys Val Leu
          180

<210> SEQ ID NO 103
<211> LENGTH: 131
<212> TYPE: PRT
<213> ORGANISM: Artificial Sequence

```
<220> FEATURE:
<223> OTHER INFORMATION: OX40L soluble domain

<400> SEQUENCE: 103

Ser His Arg Tyr Pro Arg Ile Gln Ser Ile Lys Val Gln Phe Thr Glu
1               5                   10                  15

Tyr Lys Lys Glu Lys Gly Phe Ile Leu Thr Ser Gln Lys Glu Asp Glu
            20                  25                  30

Ile Met Lys Val Gln Asn Asn Ser Val Ile Ile Asn Cys Asp Gly Phe
        35                  40                  45

Tyr Leu Ile Ser Leu Lys Gly Tyr Phe Ser Gln Glu Val Asn Ile Ser
    50                  55                  60

Leu His Tyr Gln Lys Asp Glu Glu Pro Leu Phe Gln Leu Lys Lys Val
65                  70                  75                  80

Arg Ser Val Asn Ser Leu Met Val Ala Ser Leu Thr Tyr Lys Asp Lys
                85                  90                  95

Val Tyr Leu Asn Val Thr Thr Asp Asn Thr Ser Leu Asp Asp Phe His
            100                 105                 110

Val Asn Gly Gly Glu Leu Ile Leu Ile His Gln Asn Pro Gly Glu Phe
        115                 120                 125

Cys Val Leu
    130

<210> SEQ ID NO 104
<211> LENGTH: 128
<212> TYPE: PRT
<213> ORGANISM: Artificial Sequence
<220> FEATURE:
<223> OTHER INFORMATION: OX40L soluble domain (alternative)

<400> SEQUENCE: 104

Tyr Pro Arg Ile Gln Ser Ile Lys Val Gln Phe Thr Glu Tyr Lys Lys
1               5                   10                  15

Glu Lys Gly Phe Ile Leu Thr Ser Gln Lys Glu Asp Glu Ile Met Lys
            20                  25                  30

Val Gln Asn Asn Ser Val Ile Ile Asn Cys Asp Gly Phe Tyr Leu Ile
        35                  40                  45

Ser Leu Lys Gly Tyr Phe Ser Gln Glu Val Asn Ile Ser Leu His Tyr
    50                  55                  60

Gln Lys Asp Glu Glu Pro Leu Phe Gln Leu Lys Lys Val Arg Ser Val
65                  70                  75                  80

Asn Ser Leu Met Val Ala Ser Leu Thr Tyr Lys Asp Lys Val Tyr Leu
                85                  90                  95

Asn Val Thr Thr Asp Asn Thr Ser Leu Asp Asp Phe His Val Asn Gly
            100                 105                 110

Gly Glu Leu Ile Leu Ile His Gln Asn Pro Gly Glu Phe Cys Val Leu
        115                 120                 125

<210> SEQ ID NO 105
<211> LENGTH: 120
<212> TYPE: PRT
<213> ORGANISM: Artificial Sequence
<220> FEATURE:
<223> OTHER INFORMATION: variable heavy chain for 008

<400> SEQUENCE: 105

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
        20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser
        115                 120

<210> SEQ ID NO 106
<211> LENGTH: 108
<212> TYPE: PRT
<213> ORGANISM: Artificial Sequence
<220> FEATURE:
<223> OTHER INFORMATION: variable light chain for 008

<400> SEQUENCE: 106

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105

<210> SEQ ID NO 107
<211> LENGTH: 120
<212> TYPE: PRT
<213> ORGANISM: Artificial Sequence
<220> FEATURE:
<223> OTHER INFORMATION: variable heavy chain for 011

<400> SEQUENCE: 107

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Thr Met Asn Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Asp Thr Ala Val Tyr Tyr Cys Ala Arg
                85                  90                  95
```

-continued

Asp Arg Tyr Phe Arg Gln Gln Asn Ala Phe Asp Tyr Trp Gly Gln Gly
            100                 105                 110

Thr Leu Val Thr Val Ser Ser Ala
        115                 120

<210> SEQ ID NO 108
<211> LENGTH: 108
<212> TYPE: PRT
<213> ORGANISM: Artificial Sequence
<220> FEATURE:
<223> OTHER INFORMATION: variable light chain for 011

<400> SEQUENCE: 108

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105

<210> SEQ ID NO 109
<211> LENGTH: 120
<212> TYPE: PRT
<213> ORGANISM: Artificial Sequence
<220> FEATURE:
<223> OTHER INFORMATION: variable heavy chain for 021

<400> SEQUENCE: 109

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ile Thr Leu Pro Asn Ala Leu Asp Tyr Trp Gly
            100                 105                 110

Gln Gly Thr Leu Val Thr Val Ser
        115                 120

<210> SEQ ID NO 110
<211> LENGTH: 108
<212> TYPE: PRT
<213> ORGANISM: Artificial Sequence
<220> FEATURE:
<223> OTHER INFORMATION: variable light chain for 021

-continued

<400> SEQUENCE: 110

Asp Ile Gln Met Thr Gln Ser Pro Val Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Lys Ser Asn Pro Pro Thr Phe Gly Gln Gly Thr Lys
            100                 105

<210> SEQ ID NO 111
<211> LENGTH: 120
<212> TYPE: PRT
<213> ORGANISM: Artificial Sequence
<220> FEATURE:
<223> OTHER INFORMATION: variable heavy chain for 023

<400> SEQUENCE: 111

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Asn Val Met Gly Leu Tyr Trp Phe Asp Tyr Trp Gly Gln
            100                 105                 110

Gly Thr Leu Val Thr Val Ser Ser
        115                 120

<210> SEQ ID NO 112
<211> LENGTH: 108
<212> TYPE: PRT
<213> ORGANISM: Artificial Sequence
<220> FEATURE:
<223> OTHER INFORMATION: variable light chain for 023

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg
            100                 105

<210> SEQ ID NO 113
<211> LENGTH: 119
<212> TYPE: PRT
<213> ORGANISM: Artificial Sequence
<220> FEATURE:
<223> OTHER INFORMATION: heavy chain variable region

<400> SEQUENCE: 113

Glu Val Gln Leu Gln Gln Ser Gly Pro Glu Leu Val Lys Pro Gly Ala
1                   5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115

<210> SEQ ID NO 114
<211> LENGTH: 108
<212> TYPE: PRT
<213> ORGANISM: Artificial Sequence
<220> FEATURE:
<223> OTHER INFORMATION: light chain variable region

<400> SEQUENCE: 114

Asp Ile Gln Met Thr Gln Thr Thr Ser Ser Leu Ser Ala Ser Leu Gly
1                   5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 115
<211> LENGTH: 121
<212> TYPE: PRT

-continued

```
<213> ORGANISM: Artificial Sequence
<220> FEATURE:
<223> OTHER INFORMATION: heavy chain variable region

<400> SEQUENCE: 115

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
                20                  25                  30

Thr Met His Trp Val Lys Gln Ser His Gly Lys Ser Leu Glu Trp Ile
            35                  40                  45

Gly Gly Ile Tyr Pro Asn Asn Gly Gly Ser Thr Tyr Asn Gln Asn Phe
        50                  55                  60

Lys Asp Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 116
<211> LENGTH: 108
<212> TYPE: PRT
<213> ORGANISM: Artificial Sequence
<220> FEATURE:
<223> OTHER INFORMATION: light chain variable region

<400> SEQUENCE: 116

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105

<210> SEQ ID NO 117
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
```

-continued

```
            35                  40                  45
Gly Trp Ile Asn Thr Glu Thr Gly Glu Pro Thr Tyr Ala Asp Asp Phe
    50                  55                  60
Lys Gly Arg Phe Ala Phe Ser Leu Glu Thr Ser Ala Ser Thr Ala Tyr
65                  70                  75                  80
Leu Gln Ile Asn Asn Leu Lys Asn Glu Asp Thr Ala Thr Tyr Phe Cys
                85                  90                  95
Ala Asn Pro Tyr Tyr Asp Tyr Val Ser Tyr Tyr Ala Met Asp Tyr Trp
                100                 105                 110
Gly His Gly Thr Ser Val Thr Val Ser Ser
        115                 120
```

<210> SEQ ID NO 118
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 118

```
Gln Val Gln Leu Val Gln Ser Gly Ser Glu Leu Lys Lys Pro Gly Ala
1                   5                   10                  15
Ser Val Lys Val Ser Cys Lys Ala Ser Gly Tyr Thr Phe Thr Asp Tyr
                20                  25                  30
Ser Met His Trp Val Arg Gln Ala Pro Gly Gln Gly Leu Lys Trp Met
        35                  40                  45
Gly Trp Ile Asn Thr Glu Thr Gly Glu Pro Thr Tyr Ala Asp Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Asn Pro Tyr Tyr Asp Tyr Val Ser Tyr Tyr Ala Met Asp Tyr Trp
                100                 105                 110
Gly Gln Gly Thr Thr Val Thr Val Ser Ser
        115                 120
```

<210> SEQ ID NO 119
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 119

```
Asp Ile Val Met Thr Gln Ser His Lys Phe Met Ser Thr Ser Val Arg
1                   5                   10                  15
Asp Arg Val Ser Ile Thr Cys Lys Ala Ser Gln Asp Val Ser Thr Ala
                20                  25                  30
Val Ala Trp Tyr Gln Gln Lys Pro Gly Gln Ser Pro Lys Leu Leu Ile
        35                  40                  45
Tyr Ser Ala Ser Tyr Leu Tyr Thr Gly Val Pro Asp Arg Phe Thr Gly
    50                  55                  60
Ser Gly Ser Gly Thr Asp Phe Thr Phe Thr Ile Ser Ser Val Gln Ala
65                  70                  75                  80
Glu Asp Leu Ala Val Tyr Tyr Cys Gln Gln His Tyr Ser Thr Pro Arg
```

```
                    85               90              95
Thr Phe Gly Gly Gly Thr Lys Leu Glu Ile Lys
            100               105

<210> SEQ ID NO 120
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 120

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100               105

<210> SEQ ID NO 121
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 121

Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
            20                  25                  30

Asp Met Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Arg His Tyr Asp Asp Tyr Tyr Ala Trp Phe Ala Tyr Trp Gly Gln
            100               105                 110

Gly Thr Leu Val Thr Val Ser Ala
        115               120

<210> SEQ ID NO 122
<211> LENGTH: 120
<212> TYPE: PRT
<213> ORGANISM: Artificial Sequence
<220> FEATURE:
<223> OTHER INFORMATION: heavy chain variable region of humanized
``` antibody

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 123
<211> LENGTH: 111
<212> TYPE: PRT
<213> ORGANISM: Artificial Sequence
<220> FEATURE:
<223> OTHER INFORMATION: light chain variable region of humanized
     antibody

<400> SEQUENCE: 123

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 124
<211> LENGTH: 111
<212> TYPE: PRT
<213> ORGANISM: Artificial Sequence
<220> FEATURE:
<223> OTHER INFORMATION: light chain variable region of humanized
     antibody

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110

<210> SEQ ID NO 125
<211> LENGTH: 138
<212> TYPE: PRT
<213> ORGANISM: Artificial Sequence
<220> FEATURE:
<223> OTHER INFORMATION: heavy chain variable region

<400> SEQUENCE: 125

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
        115                 120                 125

Gly Gln Gly Thr Thr Leu Thr Val Ser Ser
    130                 135

<210> SEQ ID NO 126
<211> LENGTH: 126
<212> TYPE: PRT
<213> ORGANISM: Artificial Sequence
<220> FEATURE:
<223> OTHER INFORMATION: light chain variable region

<400> SEQUENCE: 126

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp

-continued

```
              100              105              110

Asn Leu Leu Thr Phe Gly Ala Gly Thr Lys Leu Glu Leu Lys
         115              120              125

<210> SEQ ID NO 127
<211> LENGTH: 440
<212> TYPE: PRT
<213> ORGANISM: Artificial Sequence
<220> FEATURE:
<223> OTHER INFORMATION: nivolumab heavy chain

<400> SEQUENCE: 127

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
```

-continued 340              345              350
Lys Asn Gln Val Ser Leu Thr Cys Leu Val Lys Gly Phe Tyr Pro Ser
        355              360              365

Asp Ile Ala Val Glu Trp Glu Ser Asn Gly Gln Pro Glu Asn Asn Tyr
    370              375              380

Lys Thr Thr Pro Pro Val Leu Asp Ser Asp Gly Ser Phe Phe Leu Tyr
385              390              395              400

Ser Arg Leu Thr Val Asp Lys Ser Arg Trp Gln Glu Gly Asn Val Phe
        405              410              415

Ser Cys Ser Val Met His Glu Ala Leu His Asn His Tyr Thr Gln Lys
        420              425              430

Ser Leu Ser Leu Ser Leu Gly Lys
        435              440

<210> SEQ ID NO 128
<211> LENGTH: 214
<212> TYPE: PRT
<213> ORGANISM: Artificial Sequence
<220> FEATURE:
<223> OTHER INFORMATION: nivolumab light chain

<400> SEQUENCE: 128

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
        20              25              30

Leu Ala Trp Tyr Gln Gln Lys Pro Gly Gln Ala Pro Arg Leu Leu Ile
        35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Ser Ser Asn Trp Pro Arg
                85              90              95

Thr Phe Gly Gln Gly Thr Lys Val Glu Ile Lys Arg Thr Val Ala Ala
        100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
        180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 129
<211> LENGTH: 113
<212> TYPE: PRT
<213> ORGANISM: Artificial Sequence
<220> FEATURE:
<223> OTHER INFORMATION: nivolumab variable heavy chain

<400> SEQUENCE: 129

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 130
<211> LENGTH: 107
<212> TYPE: PRT
<213> ORGANISM: Artificial Sequence
<220> FEATURE:
<223> OTHER INFORMATION: nivolumab variable light chain

<400> SEQUENCE: 130

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 131
<211> LENGTH: 5
<212> TYPE: PRT
<213> ORGANISM: Artificial Sequence
<220> FEATURE:
<223> OTHER INFORMATION: nivolumab heavy chain CDR1

<400> SEQUENCE: 131

Asn Ser Gly Met His
1               5

<210> SEQ ID NO 132
<211> LENGTH: 17
<212> TYPE: PRT
<213> ORGANISM: Artificial Sequence
<220> FEATURE:
<223> OTHER INFORMATION: nivolumab heavy chain CDR2

<400> SEQUENCE: 132

-continued

```
Val Ile Trp Tyr Asp Gly Ser Lys Arg Tyr Tyr Ala Asp Ser Val Lys
1               5                   10                  15

Gly

<210> SEQ ID NO 133
<211> LENGTH: 4
<212> TYPE: PRT
<213> ORGANISM: Artificial Sequence
<220> FEATURE:
<223> OTHER INFORMATION: nivolumab heavy chain CDR3

<400> SEQUENCE: 133

Asn Asp Asp Tyr
1

<210> SEQ ID NO 134
<211> LENGTH: 11
<212> TYPE: PRT
<213> ORGANISM: Artificial Sequence
<220> FEATURE:
<223> OTHER INFORMATION: nivolumab light chain CDR1

<400> SEQUENCE: 134

Arg Ala Ser Gln Ser Val Ser Ser Tyr Leu Ala
1               5                   10

<210> SEQ ID NO 135
<211> LENGTH: 7
<212> TYPE: PRT
<213> ORGANISM: Artificial Sequence
<220> FEATURE:
<223> OTHER INFORMATION: nivolumab light chain CDR2

<400> SEQUENCE: 135

Asp Ala Ser Asn Arg Ala Thr
1               5

<210> SEQ ID NO 136
<211> LENGTH: 9
<212> TYPE: PRT
<213> ORGANISM: Artificial Sequence
<220> FEATURE:
<223> OTHER INFORMATION: nivolumab light chain CDR3

<400> SEQUENCE: 136

Gln Gln Ser Ser Asn Trp Pro Arg Thr
1               5

<210> SEQ ID NO 137
<211> LENGTH: 447
<212> TYPE: PRT
<213> ORGANISM: Artificial Sequence
<220> FEATURE:
<223> OTHER INFORMATION: pembrolizumab heavy chain

<400> SEQUENCE: 137

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60
```

```
Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445
```

<210> SEQ ID NO 138
<211> LENGTH: 218
<212> TYPE: PRT
<213> ORGANISM: Artificial Sequence
<220> FEATURE:

-continued

<223> OTHER INFORMATION: pembrolizumab light chain

<400> SEQUENCE: 138

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 139
<211> LENGTH: 120
<212> TYPE: PRT
<213> ORGANISM: Artificial Sequence
<220> FEATURE:
<223> OTHER INFORMATION: pembrolizumab variable heavy chain

<400> SEQUENCE: 139

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

```
<210> SEQ ID NO 140
<211> LENGTH: 111
<212> TYPE: PRT
<213> ORGANISM: Artificial Sequence
<220> FEATURE:
<223> OTHER INFORMATION: pembrolizumab variable light chain

<400> SEQUENCE: 140

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 141
<211> LENGTH: 5
<212> TYPE: PRT
<213> ORGANISM: Artificial Sequence
<220> FEATURE:
<223> OTHER INFORMATION: pembrolizumab heavy chain CDR1

<400> SEQUENCE: 141

Asn Tyr Tyr Met Tyr
1               5

<210> SEQ ID NO 142
<211> LENGTH: 16
<212> TYPE: PRT
<213> ORGANISM: Artificial Sequence
<220> FEATURE:
<223> OTHER INFORMATION: pembrolizumab heavy chain CDR2

<400> SEQUENCE: 142

Gly Ile Asn Pro Ser Asn Gly Gly Thr Asn Phe Asn Glu Lys Phe Lys
1               5                   10                  15

<210> SEQ ID NO 143
<211> LENGTH: 11
<212> TYPE: PRT
<213> ORGANISM: Artificial Sequence
<220> FEATURE:
<223> OTHER INFORMATION: pembrolizumab heavy chain CDR3

<400> SEQUENCE: 143

Arg Asp Tyr Arg Phe Asp Met Gly Phe Asp Tyr
1               5                   10

<210> SEQ ID NO 144
<211> LENGTH: 15
<212> TYPE: PRT
<213> ORGANISM: Artificial Sequence
<220> FEATURE:
<223> OTHER INFORMATION: pembrolizumab light chain CDR1
```

-continued

<400> SEQUENCE: 144

Arg Ala Ser Lys Gly Val Ser Thr Ser Gly Tyr Ser Tyr Leu His
1               5                   10                  15

<210> SEQ ID NO 145
<211> LENGTH: 7
<212> TYPE: PRT
<213> ORGANISM: Artificial Sequence
<220> FEATURE:
<223> OTHER INFORMATION: pembrolizumab light chain CDR2

<400> SEQUENCE: 145

Leu Ala Ser Tyr Leu Glu Ser
1               5

<210> SEQ ID NO 146
<211> LENGTH: 9
<212> TYPE: PRT
<213> ORGANISM: Artificial Sequence
<220> FEATURE:
<223> OTHER INFORMATION: pembrolizumab light chain CDR3

<400> SEQUENCE: 146

Gln His Ser Arg Asp Leu Pro Leu Thr
1               5

<210> SEQ ID NO 147
<211> LENGTH: 451
<212> TYPE: PRT
<213> ORGANISM: Artificial Sequence
<220> FEATURE:
<223> OTHER INFORMATION: durvalumab heavy chain

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

-continued

```
Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

```
<210> SEQ ID NO 148
<211> LENGTH: 265
<212> TYPE: PRT
<213> ORGANISM: Artificial Sequence
<220> FEATURE:
<223> OTHER INFORMATION: durvalumab light chain

<400> SEQUENCE: 148
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Glu Ile Val Leu Thr Gln Ser Pro Gly Thr Leu Ser Leu Ser
    50                  55                  60

Pro Gly Glu Arg Ala Thr Leu Ser Cys Arg Ala Ser Gln Arg Val Ser
65                  70                  75                  80

Ser Ser Tyr Leu Ala Trp Tyr Gln Gln Lys Pro Gly Gln Ala Pro Arg
                85                  90                  95

Leu Leu Ile Tyr Asp Ala Ser Ser Arg Ala Thr Gly Ile Pro Asp Arg
            100                 105                 110
```

```
Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
        130                 135                 140

Leu Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
        210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265
```

```
<210> SEQ ID NO 149
<211> LENGTH: 121
<212> TYPE: PRT
<213> ORGANISM: Artificial Sequence
<220> FEATURE:
<223> OTHER INFORMATION: durvalumab variable heavy chain

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120
```

```
<210> SEQ ID NO 150
<211> LENGTH: 108
<212> TYPE: PRT
<213> ORGANISM: Artificial Sequence
<220> FEATURE:
<223> OTHER INFORMATION: durvalumab variable light chain

<400> SEQUENCE: 150

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
```

-continued

```
              20              25              30
Tyr Leu Ala Trp Tyr Gln Gln Lys Pro Gly Gln Ala Pro Arg Leu Leu
      35              40              45
Ile Tyr Asp Ala Ser Ser Arg Ala Thr Gly Ile Pro Asp Arg Phe Ser
      50              55              60
Gly Ser Gly Ser Gly Thr Asp Phe Thr Leu Thr Ile Ser Arg Leu Glu
65              70              75              80
Pro Glu Asp Phe Ala Val Tyr Tyr Cys Gln Gln Tyr Gly Ser Leu Pro
                  85              90              95
Trp Thr Phe Gly Gln Gly Thr Lys Val Glu Ile Lys
              100             105

<210> SEQ ID NO 151
<211> LENGTH: 5
<212> TYPE: PRT
<213> ORGANISM: Artificial Sequence
<220> FEATURE:
<223> OTHER INFORMATION: durvalumab heavy chain CDR1

<400> SEQUENCE: 151

Arg Tyr Trp Met Ser
1               5

<210> SEQ ID NO 152
<211> LENGTH: 17
<212> TYPE: PRT
<213> ORGANISM: Artificial Sequence
<220> FEATURE:
<223> OTHER INFORMATION: durvalumab heavy chain CDR2

<400> SEQUENCE: 152

Asn Ile Lys Gln Asp Gly Ser Glu Lys Tyr Tyr Val Asp Ser Val Lys
1               5               10              15

Gly

<210> SEQ ID NO 153
<211> LENGTH: 12
<212> TYPE: PRT
<213> ORGANISM: Artificial Sequence
<220> FEATURE:
<223> OTHER INFORMATION: durvalumab heavy chain CDR3

<400> SEQUENCE: 153

Glu Gly Gly Trp Phe Gly Glu Leu Ala Phe Asp Tyr
1               5               10

<210> SEQ ID NO 154
<211> LENGTH: 12
<212> TYPE: PRT
<213> ORGANISM: Artificial Sequence
<220> FEATURE:
<223> OTHER INFORMATION: durvalumab light chain CDR1

<400> SEQUENCE: 154

Arg Ala Ser Gln Arg Val Ser Ser Ser Tyr Leu Ala
1               5               10

<210> SEQ ID NO 155
<211> LENGTH: 7
<212> TYPE: PRT
<213> ORGANISM: Artificial Sequence
<220> FEATURE:
<223> OTHER INFORMATION: durvalumab light chain CDR2
```

<400> SEQUENCE: 155

Asp Ala Ser Ser Arg Ala Thr
1                     5

<210> SEQ ID NO 156
<211> LENGTH: 9
<212> TYPE: PRT
<213> ORGANISM: Artificial Sequence
<220> FEATURE:
<223> OTHER INFORMATION: durvalumab light chain CDR3

<400> SEQUENCE: 156

Gln Gln Tyr Gly Ser Leu Pro Trp Thr
1                     5

<210> SEQ ID NO 157
<211> LENGTH: 450
<212> TYPE: PRT
<213> ORGANISM: Artificial Sequence
<220> FEATURE:
<223> OTHER INFORMATION: avelumab heavy chain

<400> SEQUENCE: 157

Glu Val Gln Leu Leu Glu Ser Gly Gly Gly Leu Val Gln Pro Gly Gly
1                     5                     10                    15

Ser Leu Arg Leu Ser Cys Ala Ala Ser Gly Phe Thr Phe Ser Ser Tyr
            20                    25                    30

Ile Met Met Trp Val Arg Gln Ala Pro Gly Lys Gly Leu Glu Trp Val
            35                    40                    45

Ser Ser Ile Tyr Pro Ser Gly Gly Ile Thr Phe Tyr Ala Asp Thr Val
            50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
            85                    90                    95

Ala Arg Ile Lys Leu Gly Thr Val Thr Thr Val Asp Tyr Trp Gly Gln
            100                   105                   110

Gly Thr Leu Val Thr Val Ser Ser Ala Ser Thr Lys Gly Pro Ser Val
            115                   120                   125

Phe Pro Leu Ala Pro Ser Ser Lys Ser Thr Ser Gly Gly Thr Ala Ala
            130                   135                   140

Leu Gly Cys Leu Val Lys Asp Tyr Phe Pro Glu Pro Val Thr Val Ser
145                   150                   155                   160

Trp Asn Ser Gly Ala Leu Thr Ser Gly Val His Thr Phe Pro Ala Val
            165                   170                   175

Leu Gln Ser Ser Gly Leu Tyr Ser Leu Ser Ser Val Val Thr Val Pro
            180                   185                   190

Ser Ser Ser Leu Gly Thr Gln Thr Tyr Ile Cys Asn Val Asn His Lys
            195                   200                   205

Pro Ser Asn Thr Lys Val Asp Lys Lys Val Glu Pro Lys Ser Cys Asp
            210                   215                   220

Lys Thr His Thr Cys Pro Pro Cys Pro Ala Pro Glu Leu Leu Gly Gly
225                   230                   235                   240

Pro Ser Val Phe Leu Phe Pro Pro Lys Pro Lys Asp Thr Leu Met Ile
            245                   250                   255

Ser Arg Thr Pro Glu Val Thr Cys Val Val Val Asp Val Ser His Glu
            260                   265                   270

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450
```

```
<210> SEQ ID NO 158
<211> LENGTH: 216
<212> TYPE: PRT
<213> ORGANISM: Artificial Sequence
<220> FEATURE:
<223> OTHER INFORMATION: avelumab light chain

<400> SEQUENCE: 158
```

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
        20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
                100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175
```

Ala Ala Ser Ser Tyr Leu Ser Leu Thr Pro Glu Gln Trp Lys Ser His
            180                     185                     190

Arg Ser Tyr Ser Cys Gln Val Thr His Glu Gly Ser Thr Val Glu Lys
        195                     200                     205

Thr Val Ala Pro Thr Glu Cys Ser
    210                     215

<210> SEQ ID NO 159
<211> LENGTH: 120
<212> TYPE: PRT
<213> ORGANISM: Artificial Sequence
<220> FEATURE:
<223> OTHER INFORMATION: avelumab variable heavy chain

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 160
<211> LENGTH: 110
<212> TYPE: PRT
<213> ORGANISM: Artificial Sequence
<220> FEATURE:
<223> OTHER INFORMATION: avelumab variable light chain

<400> SEQUENCE: 160

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
            85                  90                  95

Ser Thr Arg Val Phe Gly Thr Gly Thr Lys Val Thr Val Leu
            100                 105                 110

<210> SEQ ID NO 161
<211> LENGTH: 5
<212> TYPE: PRT
<213> ORGANISM: Artificial Sequence -continued

```
<220> FEATURE:
<223> OTHER INFORMATION: avelumab heavy chain CDR1

<400> SEQUENCE: 161

Ser Tyr Ile Met Met
1               5

<210> SEQ ID NO 162
<211> LENGTH: 17
<212> TYPE: PRT
<213> ORGANISM: Artificial Sequence
<220> FEATURE:
<223> OTHER INFORMATION: avelumab heavy chain CDR2

<400> SEQUENCE: 162

Ser Ile Tyr Pro Ser Gly Gly Ile Thr Phe Tyr Ala Asp Thr Val Lys
1               5                   10                  15

Gly

<210> SEQ ID NO 163
<211> LENGTH: 11
<212> TYPE: PRT
<213> ORGANISM: Artificial Sequence
<220> FEATURE:
<223> OTHER INFORMATION: avelumab heavy chain CDR3

<400> SEQUENCE: 163

Ile Lys Leu Gly Thr Val Thr Thr Val Asp Tyr
1               5                   10

<210> SEQ ID NO 164
<211> LENGTH: 14
<212> TYPE: PRT
<213> ORGANISM: Artificial Sequence
<220> FEATURE:
<223> OTHER INFORMATION: avelumab light chain CDR1

<400> SEQUENCE: 164

Thr Gly Thr Ser Ser Asp Val Gly Gly Tyr Asn Tyr Val Ser
1               5                   10

<210> SEQ ID NO 165
<211> LENGTH: 7
<212> TYPE: PRT
<213> ORGANISM: Artificial Sequence
<220> FEATURE:
<223> OTHER INFORMATION: avelumab light chain CDR2

<400> SEQUENCE: 165

Asp Val Ser Asn Arg Pro Ser
1               5

<210> SEQ ID NO 166
<211> LENGTH: 10
<212> TYPE: PRT
<213> ORGANISM: Artificial Sequence
<220> FEATURE:
<223> OTHER INFORMATION: avelumab light chain CDR3

<400> SEQUENCE: 166

Ser Ser Tyr Thr Ser Ser Ser Thr Arg Val
1               5                   10

<210> SEQ ID NO 167
<211> LENGTH: 448
<212> TYPE: PRT
```

<213> ORGANISM: Artificial Sequence
<220> FEATURE:
<223> OTHER INFORMATION: atezolizumab heavy chain

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp

-continued

```
385                390                395                400

Ser Asp Gly Ser Phe Phe Leu Tyr Ser Lys Leu Thr Val Asp Lys Ser
                405                410                415

Arg Trp Gln Gln Gly Asn Val Phe Ser Cys Ser Val Met His Glu Ala
                420                425                430

Leu His Asn His Tyr Thr Gln Lys Ser Leu Ser Leu Ser Pro Gly Lys
                435                440                445

<210> SEQ ID NO 168
<211> LENGTH: 214
<212> TYPE: PRT
<213> ORGANISM: Artificial Sequence
<220> FEATURE:
<223> OTHER INFORMATION: atezolizumab light chain

<400> SEQUENCE: 168

Asp Ile Gln Met Thr Gln Ser Pro Ser Ser Leu Ser Ala Ser Val Gly
1               5                10                 15

Asp Arg Val Thr Ile Thr Cys Arg Ala Ser Gln Asp Val Ser Thr Ala
                20                25                 30

Val Ala Trp Tyr Gln Gln Lys Pro Gly Lys Ala Pro Lys Leu Leu Ile
                35                40                 45

Tyr Ser Ala Ser Phe Leu Tyr Ser Gly Val Pro Ser Arg Phe Ser Gly
            50                55                60

Ser Gly Ser Gly Thr Asp Phe Thr Leu Thr Ile Ser Ser Leu Gln Pro
65                70                 75                 80

Glu Asp Phe Ala Thr Tyr Tyr Cys Gln Gln Tyr Leu Tyr His Pro Ala
                85                90                 95

Thr Phe Gly Gln Gly Thr Lys Val Glu Ile Lys Arg Thr Val Ala Ala
                100               105                110

Pro Ser Val Phe Ile Phe Pro Pro Ser Asp Glu Gln Leu Lys Ser Gly
            115               120                125

Thr Ala Ser Val Val Cys Leu Leu Asn Asn Phe Tyr Pro Arg Glu Ala
            130               135                140

Lys Val Gln Trp Lys Val Asp Asn Ala Leu Gln Ser Gly Asn Ser Gln
145               150                155                160

Glu Ser Val Thr Glu Gln Asp Ser Lys Asp Ser Thr Tyr Ser Leu Ser
                165               170                175

Ser Thr Leu Thr Leu Ser Lys Ala Asp Tyr Glu Lys His Lys Val Tyr
                180               185                190

Ala Cys Glu Val Thr His Gln Gly Leu Ser Ser Pro Val Thr Lys Ser
                195               200                205

Phe Asn Arg Gly Glu Cys
    210

<210> SEQ ID NO 169
<211> LENGTH: 118
<212> TYPE: PRT
<213> ORGANISM: Artificial Sequence
<220> FEATURE:
<223> OTHER INFORMATION: atezolizumab variable heavy chain

<400> SEQUENCE: 169

Glu Val Gln Leu Val Glu Ser Gly Gly Gly Leu Val Gln Pro Gly Gly
1               5                10                 15

Ser Leu Arg Leu Ser Cys Ala Ala Ser Gly Phe Thr Phe Ser Asp Ser
                20                25                 30
```

-continued

```
Trp Ile His Trp Val Arg Gln Ala Pro Gly Lys Gly Leu Glu Trp Val
        35                      40                  45

Ala Trp Ile Ser Pro Tyr Gly Gly Ser Thr Tyr Tyr Ala Asp Ser Val
    50                      55                  60

Lys Gly Arg Phe Thr Ile Ser Ala Asp Thr Ser Lys Asn Thr Ala Tyr
65                      70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ala
        115
```

```
<210> SEQ ID NO 170
<211> LENGTH: 108
<212> TYPE: PRT
<213> ORGANISM: Artificial Sequence
<220> FEATURE:
<223> OTHER INFORMATION: atezolizumab variable light chain

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
                100                 105
```

```
<210> SEQ ID NO 171
<211> LENGTH: 10
<212> TYPE: PRT
<213> ORGANISM: Artificial Sequence
<220> FEATURE:
<223> OTHER INFORMATION: atezolizumab heavy chain CDR1

<400> SEQUENCE: 171

Gly Phe Thr Phe Ser Asp Ser Trp Ile His
1               5                   10
```

```
<210> SEQ ID NO 172
<211> LENGTH: 18
<212> TYPE: PRT
<213> ORGANISM: Artificial Sequence
<220> FEATURE:
<223> OTHER INFORMATION: atezolizumab heavy chain CDR2

<400> SEQUENCE: 172

Ala Trp Ile Ser Pro Tyr Gly Gly Ser Thr Tyr Tyr Ala Asp Ser Val
1               5                   10                  15

Lys Gly
```

```
<210> SEQ ID NO 173
```

-continued

```
<211> LENGTH: 9
<212> TYPE: PRT
<213> ORGANISM: Artificial Sequence
<220> FEATURE:
<223> OTHER INFORMATION: atezolizumab heavy chain CDR3

<400> SEQUENCE: 173

Arg His Trp Pro Gly Gly Phe Asp Tyr
1               5

<210> SEQ ID NO 174
<211> LENGTH: 11
<212> TYPE: PRT
<213> ORGANISM: Artificial Sequence
<220> FEATURE:
<223> OTHER INFORMATION: atezolizumab light chain CDR1

<400> SEQUENCE: 174

Arg Ala Ser Gln Asp Val Ser Thr Ala Val Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: atezolizumab light chain CDR2

<400> SEQUENCE: 175

Ser Ala Ser Phe Leu Tyr Ser
1               5

<210> SEQ ID NO 176
<211> LENGTH: 9
<212> TYPE: PRT
<213> ORGANISM: Artificial Sequence
<220> FEATURE:
<223> OTHER INFORMATION: atezolizumab light chain CDR3

<400> SEQUENCE: 176

Gln Gln Tyr Leu Tyr His Pro Ala Thr
1               5
```

TREATMENT OF NSCLC PATIENTS REFRACTORY FOR ANTI-PD-1 ANTIBODY

CROSS REFERENCE TO RELATED APPLICATIONS

This application claims priority to U.S. Provisional Patent Application No. 62/756,025, filed on Nov. 5, 2018, and U.S. Provisional Patent Application No. 62/903,627, filed on Sep. 20, 2019, which are hereby incorporated by reference in their entirety.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone an REP procedure have produced successful adoptive cell therapy following host immunosuppression in patients with melanoma. Current infusion acceptance parameters rely on readouts of the composition of TILs (e.g., CD28, CD8, or CD4 positivity) and on fold expansion and viability of the REP product.

Current TIL manufacturing and treatment processes are limited by length, cost, sterility concerns, and other factors described herein such that the potential to treat patients which are refractory to anti-PD1 and as such have been severely limited. There is an urgent need to provide TIL manufacturing processes and therapies based on such processes that are appropriate for use in treating patients for whom very few or no viable treatment options remain. The present invention meets this need by providing a shortened manufacturing process for use in generating TILs which can then be employed in the treatment of non-small cell lung carcinoma (NSCLC) patients whom are refractory to anti-PD-1 treatment.

BRIEF SUMMARY OF THE INVENTION

The present invention provides improved and/or shortened methods for expanding TILs and producing therapeutic populations of TILs for use in treatment of non-small cell lung carcinoma (NSCLC) patients whom are refractory to anti-PD-1 treatment.

The present invention provides a method of treating non-small cell lung carcinoma (NSCLC) with a population of tumor infiltrating lymphocytes (TILs) comprising the steps of:

(a) obtaining and/or receiving a first population of TILs from surgical resection, needle biopsy, core biopsy, small biopsy, or other means for obtaining a sample that contains a mixture of tumor and TIL cells from a NSCLC tumor in a patient;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and optionally irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the NSCLC; wherein the NSCLC is refractory to treatment with an anti-PD-1 antibody.

In some embodiments, "obtaining" indicates the TILs employed in the method and/or process can be derived directly from the sample (including from a surgical resection, needle biopsy, core biopsy, small biopsy, or other sample) as part of the method and/or process steps. In some embodiments, "receiving" indicates the TILs employed in the method and/or process can be derived indirectly from the sample (including from a surgical resection, needle biopsy, core biopsy, small biopsy, or other sample) and then employed in the method and/or process, (for example, where step (a) begins will TILs that have already been derived from the sample by a separate process not included in part (a), such TILs could be referred to as "received").

In some embodiments, the first population of TILs comprises a multilesional sampling method.

In some embodiments, the refractory NSCLC has been previously treated with an anti-PD-1 and/or anti-PD-L1 and/or anti-PD-L2 antibody.

In some embodiments, the refractory NSCLC has not been previously treated with an anti-PD-1 and/or anti-PD-L1 antibody.

In some embodiments, the refractory NSCLC has been treated with a chemotherapeutic agent.

In some embodiments, the refractory NSCLC has been previously treated with an anti-PD-1 and/or anti-PD-L1 antibody and has been previously treated a chemotherapeutic agent.

In some embodiments, the refractory NSCLC has not been previously treated with an anti-PD-1 and/or anti-PD-L1 antibody and has been previously treated a chemotherapeutic agent.

In some embodiments, the refractory NSCLC has been treated with a chemotherapeutic agent but is not being currently treated with a chemotherapeutic agent.

In some embodiments, the refractory NSCLC has low expression of PD-L1.

In some embodiments, the refractory NSCLC has been previously treated with an anti-PD-1 and/or anti-PD-L1 antibody and has low expression of PD-L1.

In some embodiments, the refractory NSCLC has not been previously treated with an anti-PD-1 and/or anti-PD-L1 antibody and has low expression of PD-L1.

In some embodiments, the refractory NSCLC has been treated with a chemotherapeutic agent and has low expression of PD-L1.

In some embodiments, the refractory NSCLC has been treated with a chemotherapeutic agent but is not being currently treated with a chemotherapeutic agent and has low expression of PD-L1

In some embodiments, the refractory NSCLC has not been previously treated with an anti-PD-1 and/or anti-PD-L1 antibody and has bulky disease at baseline.

In some embodiments, the refractory NSCLC has been previously treated with an anti-PD-1 and/or anti-PD-L1 antibody and has bulky disease at baseline.

In some embodiments, the refractory NSCLC has been treated with a chemotherapeutic agent and has bulky disease at baseline.

In some embodiments, the refractory NSCLC has been treated with a chemotherapeutic agent but is not being currently treated with a chemotherapeutic agent and has bulky disease at baseline.

In some embodiments, bulky disease is indicated where the maximal tumor diameter is greater than 7 cm measured in either the transverse or coronal plane or swollen lymph nodes with a short-axis diameter of 20 mm or greater.

In some embodiments, the refractory NSCLC is refractory to at least two prior systemic treatment courses, not including neo-adjuvant or adjuvant therapies.

In some embodiments, the refractory NSCLC is refractory to an anti-PD-1 antibody or an anti-PD-L1 selected from the group consisting of nivolumab, pembrolizumab, ipilimumab, JS001, TSR-042, pidilizumab, BGB-A317, SHR-1210, REGN2810, MDX-1106, PDR001, anti-PD-1 from clone: RMP1-14, an anti-PD-1 antibodies disclosed in U.S. Pat. No. 8,008,449, durvalumab, atezolizumab, avelumab, and fragments, derivatives, variants, as well as biosimilars thereof.

In some embodiments, the refractory NSCLC is refractory to pembrolizumab or a biosimilar thereof.

In some embodiments, the refractory NSCLC is refractory to nivolumab or a biosimilar thereof.

In some embodiments, the refractory NSCLC is refractory to ipilimumab or a biosimilar thereof.

In some embodiments, the refractory NSCLC is refractory to ipilimumab or a biosimilar thereof and pembrolizumab or a biosimilar thereof.

In some embodiments, the refractory NSCLC is refractory to ipilimumab or a biosimilar thereof and nivolumab or a biosimilar thereof.

In some embodiments, the refractory NSCLC is refractory to durvalumab or a biosimilar thereof.

In some embodiments, the refractory NSCLC is refractory to atezolizumab or a biosimilar thereof.

In some embodiments, the refractory NSCLC is refractory to avelumab or a biosimilar thereof.

In some embodiments, the initial expansion is performed over a period of 21 days or less.

In some embodiments, the initial expansion is performed over a period of 14 days or less.

In some embodiments, the IL-2 is present at an initial concentration of between 1000 IU/mL and 6000 IU/mL in the first cell culture medium.

In some embodiments, the IL-2 is present at an initial concentration of between 1000 IU/mL and 6000 IU/mL and the OKT-3 antibody is present at an initial concentration of about 30 ng/mL in the second cell culture medium.

In some embodiments, the initial expansion is performed using a gas permeable container.

In some embodiments, the rapid expansion is performed using a gas permeable container.

In some embodiments, the first cell culture medium further comprises a cytokine selected from the group consisting of IL-4, IL-7, IL-15, IL-21, and combinations thereof.

In some embodiments, the second cell culture medium further comprises a cytokine selected from the group consisting of IL-4, IL-7, IL-15, IL-21, and combinations thereof.

In some embodiments, the method further comprises the step of treating the patient with a non-myeloablative lymphodepletion regimen prior to administering the third population of TILs to the patient.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the method further comprises the step of treating the patient with an IL-2 regimen starting on the day after administration of the third population of TILs to the patient.

In some embodiments, the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

In some embodiments, the invention provides a method of treating non-small cell lung carcinoma (NSCLC) with a population of tumor infiltrating lymphocytes (TILs) comprising the steps of:

(a) resecting a tumor from a patient, the tumor comprising a first population of TILs;

(b) fragmenting the tumor into tumor fragments;

(c) contacting the tumor fragments with a first cell culture medium;

(d) performing an initial expansion of the first population of TILs in the first cell culture medium to obtain a second population of TILs, wherein the second population of TILs is at least 5-fold greater in number than the first population of TILs, wherein the first cell culture medium comprises IL-2;

(e) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), and optionally irradiated allogeneic peripheral blood mononuclear cells (PBMCs); and wherein the rapid expansion is performed over a period of 14 days or less;

(f) harvesting the third population of TILs; and (g) administering a therapeutically effective portion of the third population of TILs to a patient with the cancer; wherein the cancer is refractory to treatment with an anti-PD-1 antibody.

In some embodiments, the refractory NSCLC has been previously treated with an anti-PD-1 and/or anti-PD-L1 antibody.

In some embodiments, the refractory NSCLC has not been previously treated with an anti-PD-1 and/or anti-PD-L1 antibody.

In some embodiments, the refractory NSCLC has been treated with a chemotherapeutic agent.

In some embodiments, the refractory NSCLC has been previously treated with an anti-PD-1 and/or anti-PD-L1 antibody and has been previously treated a chemotherapeutic agent.

In some embodiments, the refractory NSCLC has not been previously treated with an anti-PD-1 and/or anti-PD-L1 antibody and has been previously treated a chemotherapeutic agent.

In some embodiments, the refractory NSCLC has been treated with a chemotherapeutic agent but is not being currently treated with a chemotherapeutic agent.

In some embodiments, the refractory NSCLC has low expression of PD-L1.

In some embodiments, the refractory NSCLC has been previously treated with an anti-PD-1 and/or anti-PD-L1 antibody and has low expression of PD-L1.

In some embodiments, the refractory NSCLC has not been previously treated with an anti-PD-1 and/or anti-PD-L1 antibody and has low expression of PD-L1.

In some embodiments, the refractory NSCLC has been treated with a chemotherapeutic agent and has low expression of PD-L1.

In some embodiments, the refractory NSCLC has been treated with a chemotherapeutic agent but is not being currently treated with a chemotherapeutic agent and has low expression of PD-L1

In some embodiments, the refractory NSCLC has not been previously treated with an anti-PD-1 and/or anti-PD-L1 antibody and has bulky disease at baseline.

In some embodiments, the refractory NSCLC has been previously treated with an anti-PD-1 and/or anti-PD-L1 antibody and has bulky disease at baseline.

In some embodiments, the refractory NSCLC has been treated with a chemotherapeutic agent and has bulky disease at baseline.

In some embodiments, the refractory NSCLC has been treated with a chemotherapeutic agent but is not being currently treated with a chemotherapeutic agent and has bulky disease at baseline.

In some embodiments, bulky disease is indicated where the maximal tumor diameter is greater than 7 cm measured in either the transverse or coronal plane or swollen lymph nodes with a short-axis diameter of 20 mm or greater.

In some embodiments, the refractory NSCLC is refractory to at least two prior systemic treatment courses, not including neo-adjuvant or adjuvant therapies.

In some embodiments, the refractory NSCLC is refractory to an anti-PD-1 or an anti-PD-L1 antibody is selected from the group consisting of nivolumab, pembrolizumab, JS001, TSR-042, pidilizumab, (BGB-A317, SHR-1210, REGN2810, MDX-1106, PDR001, anti-PD-1 from clone: RMP1-14, an anti-PD-1 antibodies disclosed in U.S. Pat. No. 8,008,449, durvalumab, atezolizumab, avelumab, and fragments, derivatives, variants, as well as biosimilars thereof.

In some embodiments, the refractory NSCLC is refractory to pembrolizumab or a biosimilar thereof.

In some embodiments, the refractory NSCLC is refractory to nivolumab or a biosimilar thereof.

In some embodiments, the refractory NSCLC is refractory to an anti-CLTA-4 antibody, such as ipilimumab or a biosimilar thereof.

In some embodiments, the refractory NSCLC is refractory to an anti-CLTA-4 antibody, such as ipilimumab or a biosimilar thereof and pembrolizumab or a biosimilar thereof.

In some embodiments, the refractory NSCLC is refractory to an anti-CLTA-4 antibody, such as ipilimumab or a biosimilar thereof and nivolumab or a biosimilar thereof.

In some embodiments, the refractory NSCLC is refractory to durvalumab or a biosimilar thereof.

In some embodiments, the refractory NSCLC is refractory to atezolizumab or a biosimilar thereof.

In some embodiments, the refractory NSCLC is refractory to avelumab or a biosimilar thereof.

In some embodiments, the initial expansion is performed over a period of 21 days or less.

In some embodiments, the initial expansion is performed over a period of 14 days or less.

In some embodiments, the IL-2 is present at an initial concentration of between 1000 IU/mL and 6000 IU/mL in the first cell culture medium.

In some embodiments, the IL-2 is present at an initial concentration of between 1000 IU/mL and 6000 IU/mL and the OKT-3 antibody is present at an initial concentration of about 30 ng/mL in the second cell culture medium.

In some embodiments, the initial expansion is performed using a gas permeable container.

In some embodiments, the rapid expansion is performed using a gas permeable container.

In some embodiments, the first cell culture medium further comprises a cytokine selected from the group consisting of IL-4, IL-7, IL-15, IL-21, and combinations thereof.

In some embodiments, the second cell culture medium further comprises a cytokine selected from the group consisting of IL-4, IL-7, IL-15, IL-21, and combinations thereof.

In some embodiments, the method further comprises the step of treating the patient with a non-myeloablative lymphodepletion regimen prior to administering the third population of TILs to the patient.

In some embodiments, the non-myeloablative lymphodepletion regimen comprises the steps of administration of cyclophosphamide at a dose of 60 mg/m²/day for two days followed by administration of fludarabine at a dose of 25 mg/m²/day for five days.

In some embodiments, the method further comprises the step of treating the patient with an IL-2 regimen starting on the day after administration of the third population of TILs to the patient.

In some embodiments, the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

In some embodiments, the invention provides a method for treating a subject with non-small cell lung carcinoma (NSCLC), wherein the cancer is refractory to treatment with an anti-PD-1 antibody, the method comprising administering expanded tumor infiltrating lymphocytes (TILs) comprising:

(a) obtaining and/or receiving a first population of TILs from a tumor resected from a subject by processing a tumor sample obtained from the subject into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the third population of TILs is a therapeutic population of TILs which comprises an increased sub-population of effector T cells and/or central memory T cells relative to the second population of TILs, wherein the second expansion is performed in a closed container providing a second gas-permeable surface area, and wherein the transition from step (c) to step (d) occurs without opening the system;

(e) harvesting therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject.

In some embodiments, the refractory NSCLC has been previously treated with an anti-PD-1 and/or anti-PD-L1 antibody.

In some embodiments, the refractory NSCLC has not been previously treated with an anti-PD-1 and/or anti-PD-L1 antibody.

In some embodiments, the refractory NSCLC has been treated with a chemotherapeutic agent.

In some embodiments, the refractory NSCLC has been previously treated with an anti-PD-1 and/or anti-PD-L1 antibody and has been previously treated a chemotherapeutic agent.

In some embodiments, the refractory NSCLC has not been previously treated with an anti-PD-1 and/or anti-PD-L1 antibody and has been previously treated a chemotherapeutic agent.

In some embodiments, the refractory NSCLC has been treated with a chemotherapeutic agent but is not being currently treated with a chemotherapeutic agent.

In some embodiments, the refractory NSCLC has low expression of PD-L1.

In some embodiments, the refractory NSCLC has been previously treated with an anti-PD-1 and/or anti-PD-L1 antibody and has low expression of PD-L1.

In some embodiments, the refractory NSCLC has not been previously treated with an anti-PD-1 and/or anti-PD-L1 antibody and has low expression of PD-L1.

In some embodiments, the refractory NSCLC has been treated with a chemotherapeutic agent and has low expression of PD-L1.

In some embodiments, the refractory NSCLC has been treated with a chemotherapeutic agent but is not being currently treated with a chemotherapeutic agent and has low expression of PD-L1.

In some embodiments, the refractory NSCLC has not been previously treated with an anti-PD-1 and/or anti-PD-L1 antibody and has bulky disease at baseline.

In some embodiments, the refractory NSCLC has been previously treated with an anti-PD-1 and/or anti-PD-L1 antibody and has bulky disease at baseline.

In some embodiments, the refractory NSCLC has been treated with a chemotherapeutic agent and has bulky disease at baseline.

In some embodiments, the refractory NSCLC has been treated with a chemotherapeutic agent but is not being currently treated with a chemotherapeutic agent and has bulky disease at baseline.

In some embodiments, bulky disease is indicated where the maximal tumor diameter is greater than 7 cm measured in either the transverse or coronal plane or swollen lymph nodes with a short-axis diameter of 20 mm or greater.

In some embodiments, the refractory NSCLC is refractory to at least two prior systemic treatment courses, not including neo-adjuvant or adjuvant therapies.

In some embodiments, the refractory NSCLC is refractory to an anti-PD-1 or an anti-PD-L1 antibody is selected from the group consisting of nivolumab, pembrolizumab, JS001, TSR-042, pidilizumab, BGB-A317, SHR-1210, REGN2810, MDX-1106, PDR001, anti-PD-1 from clone: RMP1-14, an anti-PD-1 antibodies disclosed in U.S. Pat. No. 8,008,449, durvalumab, atezolizumab, avelumab, and fragments, derivatives, variants, as well as biosimilars thereof.

In some embodiments, the refractory NSCLC is refractory to pembrolizumab or a biosimilar thereof.

In some embodiments, the refractory NSCLC is refractory to nivolumab or a biosimilar thereof.

In some embodiments, the refractory NSCLC is refractory to an anti-CLTA-4 antibody, such as ipilimumab or a biosimilar thereof.

In some embodiments, the refractory NSCLC is refractory to an anti-CLTA-4 antibody, such as ipilimumab or a biosimilar thereof and pembrolizumab or a biosimilar thereof.

In some embodiments, the refractory NSCLC is refractory to an anti-CLTA-4 antibody, such as ipilimumab or a biosimilar thereof and nivolumab or a biosimilar thereof.

In some embodiments, the refractory NSCLC is refractory to durvalumab or a biosimilar thereof.

In some embodiments, the refractory NSCLC is refractory to atezolizumab or a biosimilar thereof.

In some embodiments, the refractory NSCLC is refractory to avelumab or a biosimilar thereof.

In some embodiments, the initial expansion is performed over a period of 21 days or less.

In some embodiments, the initial expansion is performed over a period of 14 days or less.

In some embodiments, the IL-2 is present at an initial concentration of between 1000 IU/mL and 6000 IU/mL in the first cell culture medium.

In some embodiments, the IL-2 is present at an initial concentration of between 1000 IU/mL and 6000 IU/mL and the OKT-3 antibody is present at an initial concentration of about 30 ng/mL in the second cell culture medium.

In some embodiments, the initial expansion is performed using a gas permeable container.

In some embodiments, the rapid expansion is performed using a gas permeable container.

In some embodiments, the first cell culture medium further comprises a cytokine selected from the group consisting of IL-4, IL-7, IL-15, IL-21, and combinations thereof.

In some embodiments, the second cell culture medium further comprises a cytokine selected from the group consisting of IL-4, IL-7, IL-15, IL-21, and combinations thereof.

In some embodiments, the method further comprises the step of treating the patient with a non-myeloablative lymphodepletion regimen prior to administering the third population of TILs to the patient.

In some embodiments, the non-myeloablative lymphodepletion regimen comprises the steps of administration of cyclophosphamide at a dose of 60 mg/m²/day for two days followed by administration of fludarabine at a dose of 25 mg/m²/day for five days.

In some embodiments, the method further comprises the step of treating the patient with an IL-2 regimen starting on the day after administration of the third population of TILs to the patient.

In some embodiments, the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

In some embodiments, the NSCLC is refractory to a combination treatment comprising an anti-PD-1 and chemotherapeutic agent.

In some embodiments, the anti-PD-1 or the anti-PD-L1 antibody is selected from the group consisting of nivolumab, pembrolizumab, JS001, TSR-042, pidilizumab, (BGB-A317, SHR-1210, REGN2810, MDX-1106, PDR001, anti-PD-1 from clone: RMP1-14, an anti-PD-1 antibodies disclosed in U.S. Pat. No. 8,008,449, durvalumab, atezolizumab, avelumab, and fragments, derivatives, variants, as well as biosimilars thereof.

In some embodiments, the antiPD-1 is pembrolizumab.

In some embodiments, the chemotherapeutic agent(s) is a platinum doublet chemotherapeutic agent.

In some embodiments, the platinum doublet therapy comprises:

i) a first chemotherapeutic agent selected from the group consisting of cisplatin and carboplatin, ii) and a second chemotherapeutic agent selected from the group consisting of vinorelbine, gemcitabine and a taxane (including for example, paclitaxel, docetaxel or nab-paclitaxel).

In some embodiments, the chemotherapeutic agent is in combination with pemetrexed.

In some embodiments, the NSCLC is refractory to a combination therapy comprising carboplatin, paclitaxel, pemetrexed, and cisplatin.

In some embodiments, the NSCLC is refractory to a combination therapy comprising carboplatin, paclitaxel, pemetrexed, cisplatin, nivolumab, and ipilimumab.

BRIEF DESCRIPTION OF THE DRAWINGS

FIG. 1: Exemplary Process 2A chart providing an overview of Steps A through F.

FIG. 2A-2C: Process Flow Chart of Process 2A.

FIG. 5: Comparison table of Steps A through F from exemplary embodiments of process 1C and process 2A.

FIG. 6: Detailed comparison of an embodiment of process 1C and an embodiment of process 2A.

FIG. 8A-8C: A) Shows a comparison between the 2A process (approximately 22-day process) and an embodiment of the Gen 3 process for TIL manufacturing (approximately 14-days to 16-days process). B) Exemplary Process Gen3 chart providing an overview of Steps A through F (approximately 14-days to 16-days process). C) Chart providing three exemplary Gen 3 processes with an overview of Steps A through F (approximately 14-days to 16-days process) for each of the three process variations.

Figure 11:
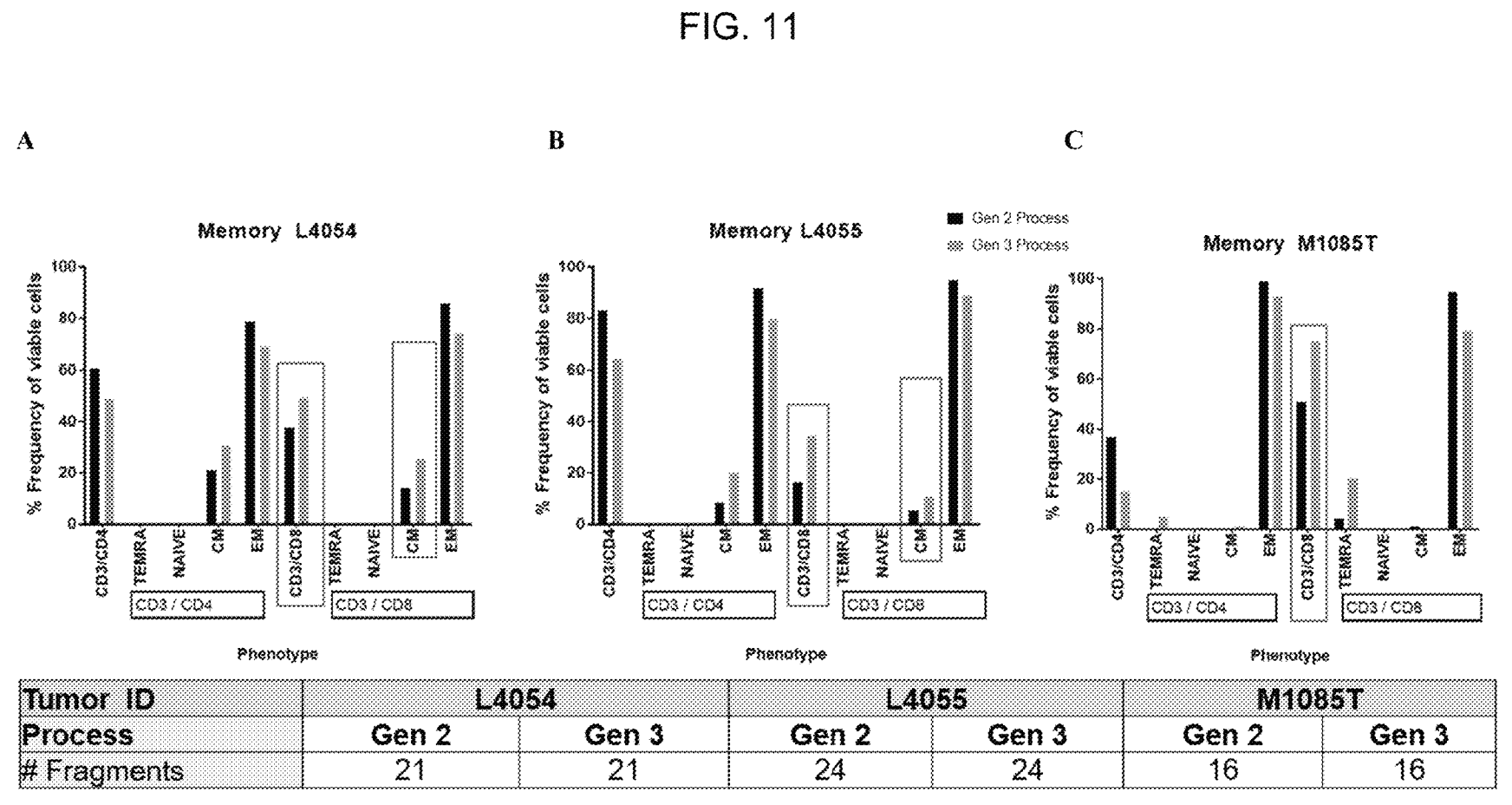

FIG. 11A-11C: A) L4054—Memory markers analysis on TIL product from the Gen 2 and Gen 3 processes. B) L4055—Memory markers analysis on TIL product from the Gen 2 and Gen 3 processes. C) M1085T—Memory markers analysis on TIL product from the Gen 2 and Gen 3 processes.

FIG. 12: L4054 Activation and exhaustion markers (A) Gated on CD4+, (B) Gated on CD8+.

FIG. 13: L4055 Activation and exhaustion markers (A) Gated on CD4+, (B) Gated on CD8+.

FIG. 20: Frequency of unique CDR3 sequences on L4054 IL harvested final cell product (Gen 2 (e.g., day 22) and Gen 3 process (e.g., day 14-16)).

FIG. 23: Raw data for cell counts Day 7-Gen 3 REP initiation presented in Table 45 (see Example 8 below).

FIG. 24: Raw data for cell counts Day 11-Gen 2 REP initiation and Gen 3 Scale Up presented in Table 45 (see Example 8 below).

FIG. 25: Raw data for cell counts Day 16-Gen 2 Scale Up and Gen 3 Harvest (e.g., day 16) presented in Table 46 (see Example 8 below).

FIG. 26: Raw data for cell counts Day 22-Gen 2 Harvest (e.g., day 22) presented in Table 46 (see Example 8 below). For L4054 Gen 2, post LOVO count was extrapolated to 4 flasks, because was the total number of the study. 1 flask was contaminated, and the extrapolation was done for total=6.67E+10.

Figure 27:
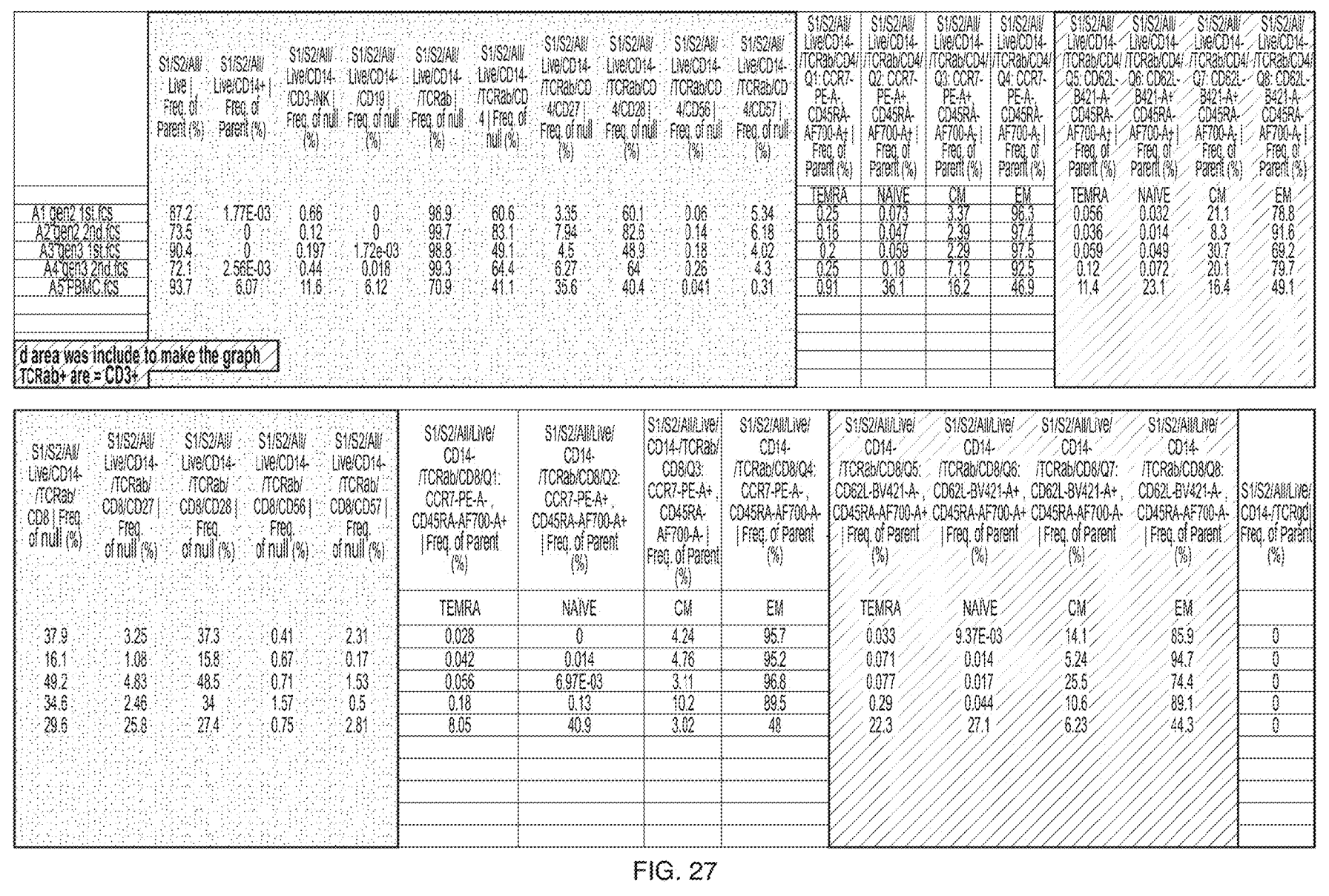

FIG. 27: Raw data for flow cytometry results depicted in FIGS. 10A, 10A, and 10B.

FIG. 28: Raw data for flow cytometry results depicted in FIGS. 10C and 10C.

FIG. 29: Raw data for flow cytometry results depicted in FIGS. 12 and 13.

FIGS. 30A-30B: Raw data for IFNγ production assay results for L4054 samples depicted in FIG. 14.

FIGS. 31A-31B: Raw data for IFNγ production assay results for L4055 samples depicted in FIG. 14.

Figure 32B:
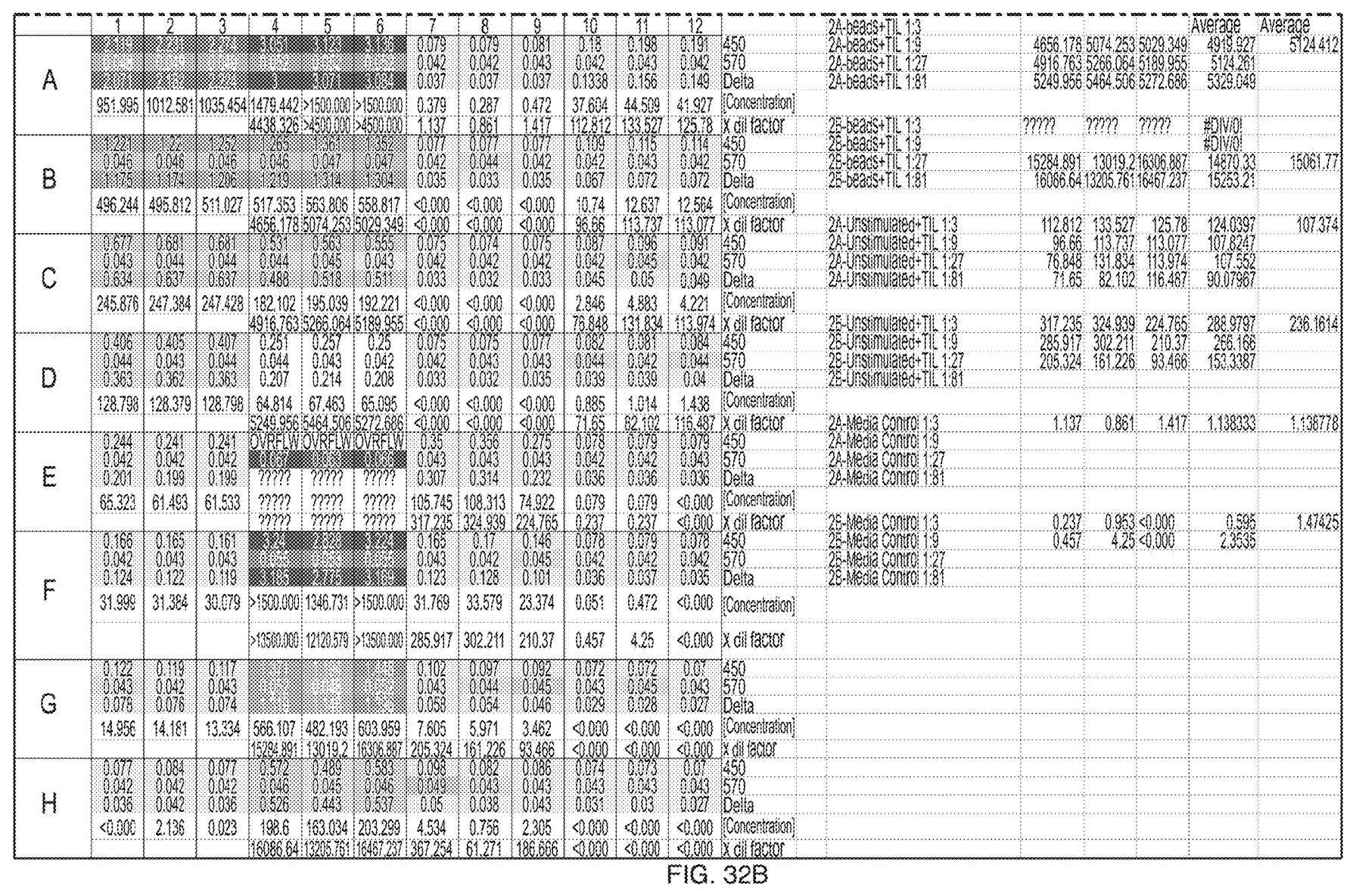

FIGS. 32A-32B: Raw data for IFNγ production assay results for M1085T samples depicted in FIG. 14.

FIGS. 33A-33B: Raw data for IL-2 ELISA assay results depicted in FIG. 15.

FIG. 34: Raw data for the metabolic substrate and metabolic analysis results presented in FIGS. 16 and 17.

FIG. 35: Raw data for the relative telomere length analysis results presented in FIG. 18.

FIG. 36: Raw data for the unique CD3 sequence and clonal diversity analyses results presented in FIGS. 19 and 22.

FIG. 38: Table describing various features of embodiments of the Gen 2, Gen 2.1 and Gen 3.0 process.

FIG. 39: Overview of the media conditions for an embodiment of the Gen 3 process, referred to as Gen 3.1.

FIG. 40: Table describing various features of embodiments of the Gen 2, Gen 2.1 and Gen 3.0 process.

FIG. 41: Table comparing various features of embodiments of the Gen 2 and Gen 3.0 processes.

FIG. 42: Table providing media uses in the various embodiments of the described expansion processes.

FIG. 45: Top: Unique CDR3 sequence analysis for TIL final product: Columns show the number of unique TCR B clonotypes identified from $1\times10^6$ cells collected on Gen 2 (e.g., day 22) and Gen 3 process (e.g., day 14-16). Gen 3 shows higher clonal diversity compared to Gen 2 based on the number of unique peptide CDRs within the sample. Bottom: Diversity Index for TIL final product: Shanon entropy diversity index is a more reliable a common metric for comparison. Gen 3 showed a slightly higher diversity than Gen 2.

Figure 46:
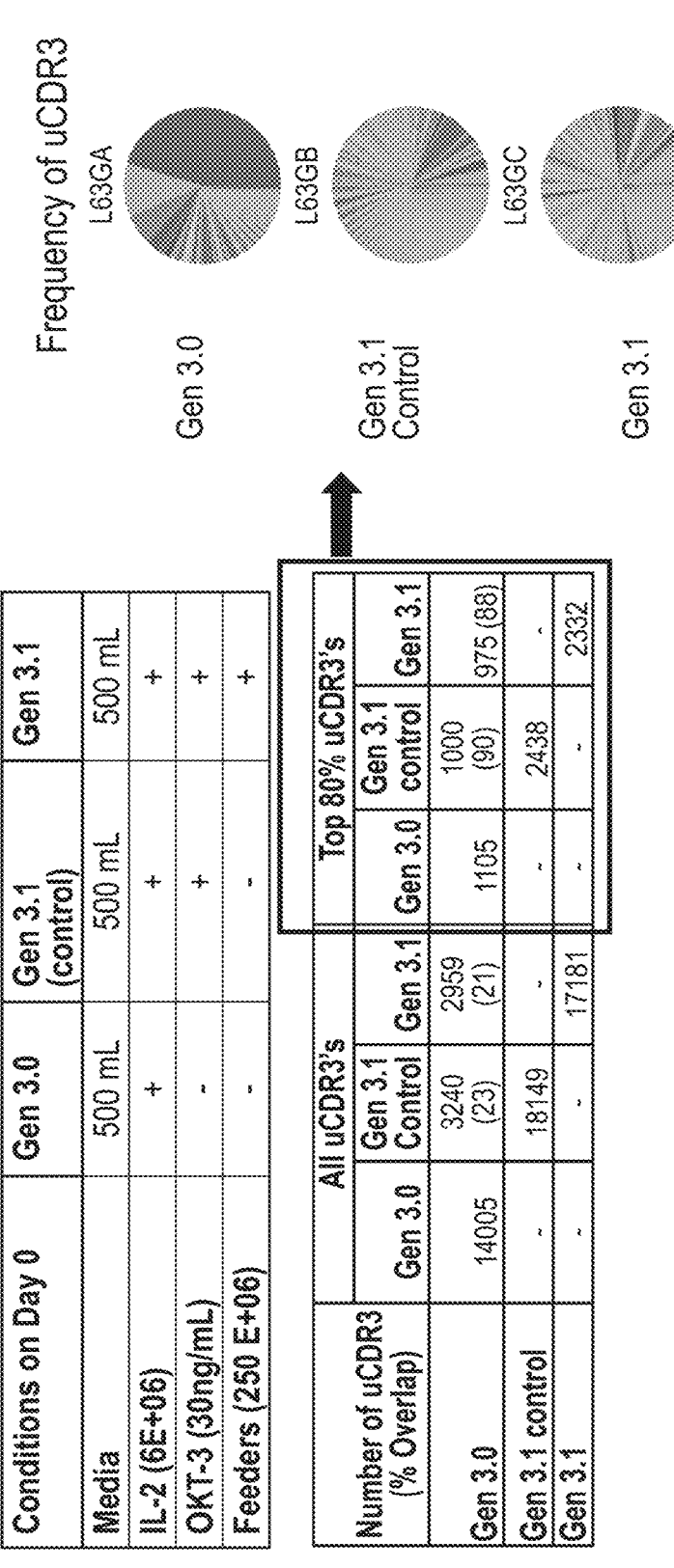

FIG. 46: 199 sequences are shared between Gen 3 and Gen 2 final product, corresponding to 97.07% of top 80% of unique CDR3 sequences from Gen 2 shared with Gen 3 final product.

Figure 47:
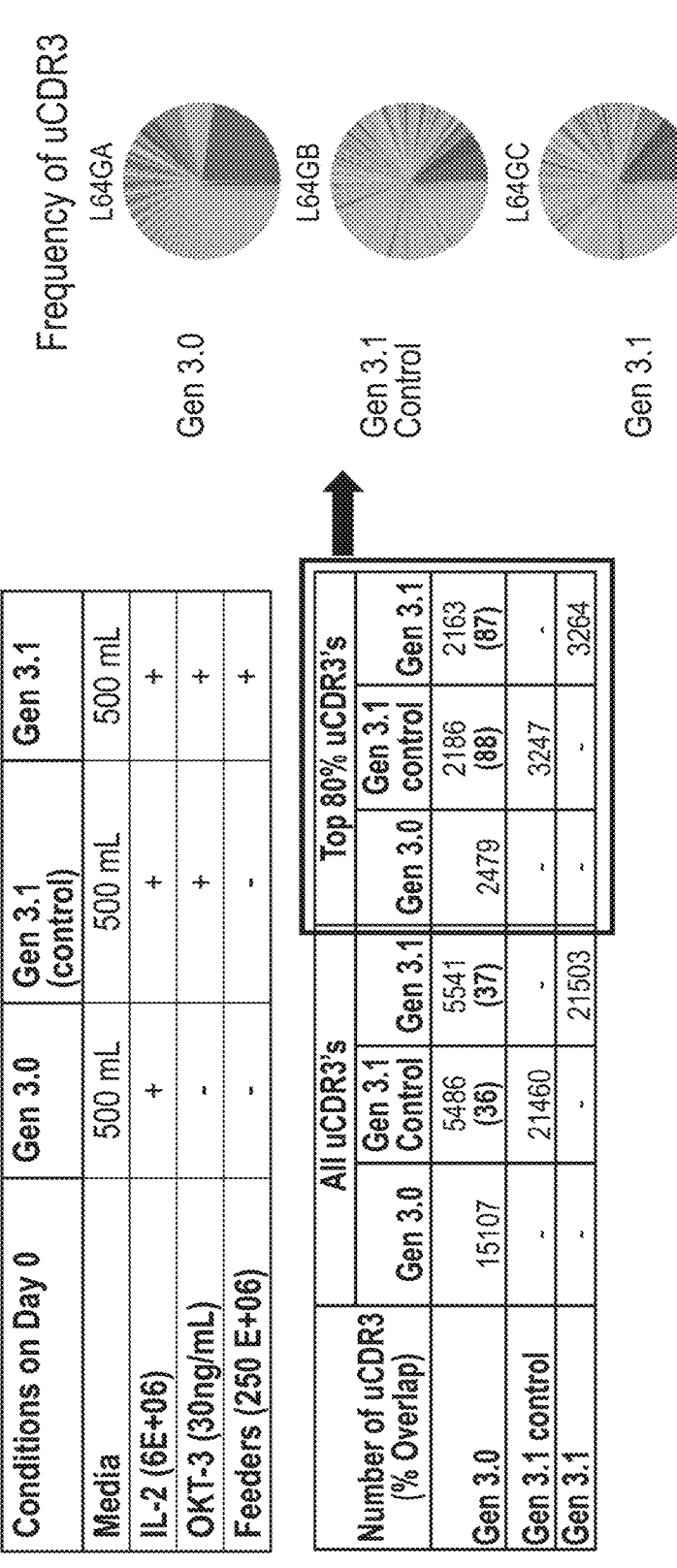

FIG. 47: 1833 sequences are shared between Gen 3 and Gen 2 final product, corresponding to 99.45% of top 80% of unique CDR3 sequences from Gen 2 shared with Gen 3 final product.

Figure 48:
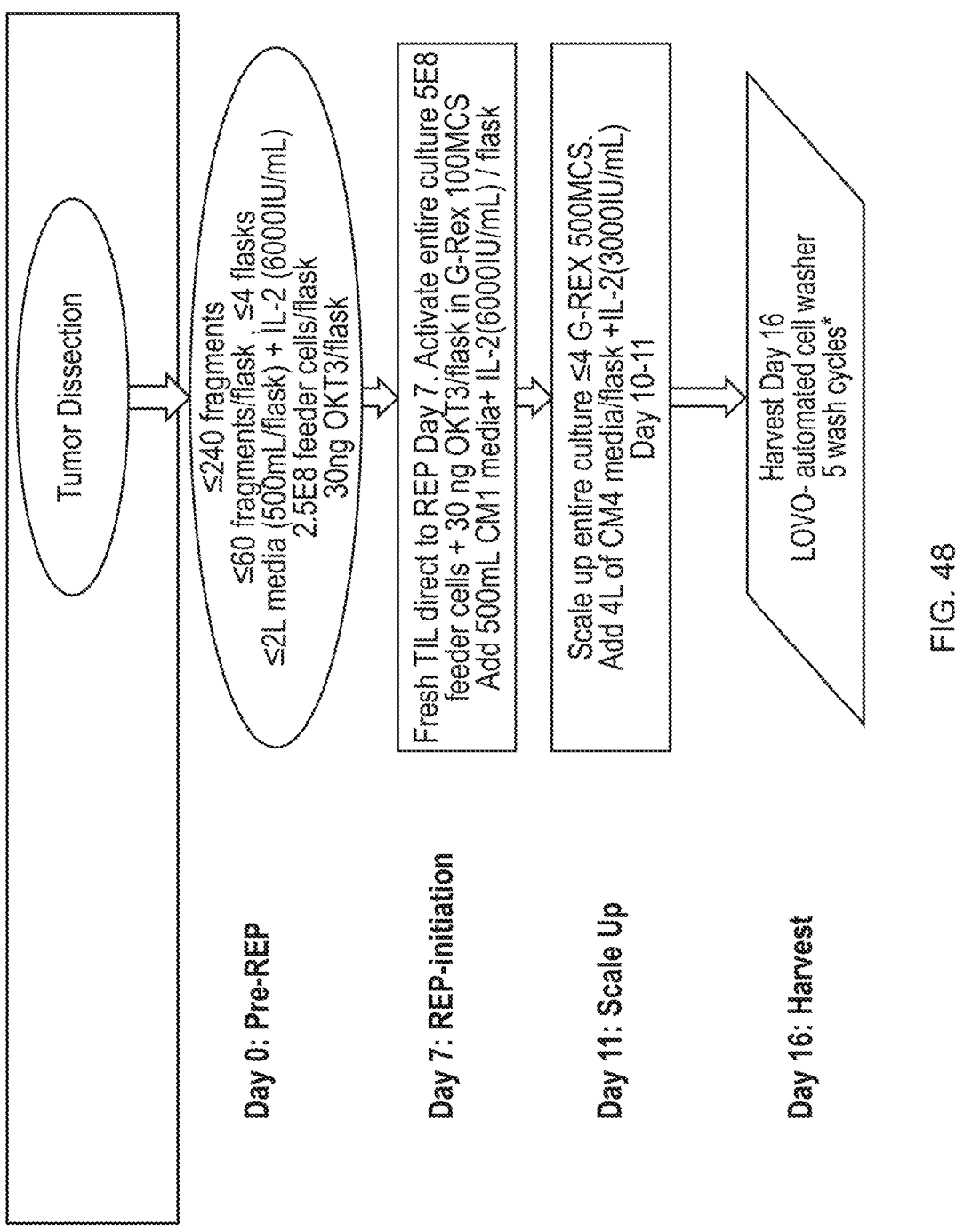

FIG. 48: Schematic of an exemplary embodiment of the Gen 3 process (a 16-day process).

FIG. 49: Schematic of an exemplary embodiment of a method for expanding T cells from hematopoietic malignancies using Gen 3 expansion platform.

Figure 50:
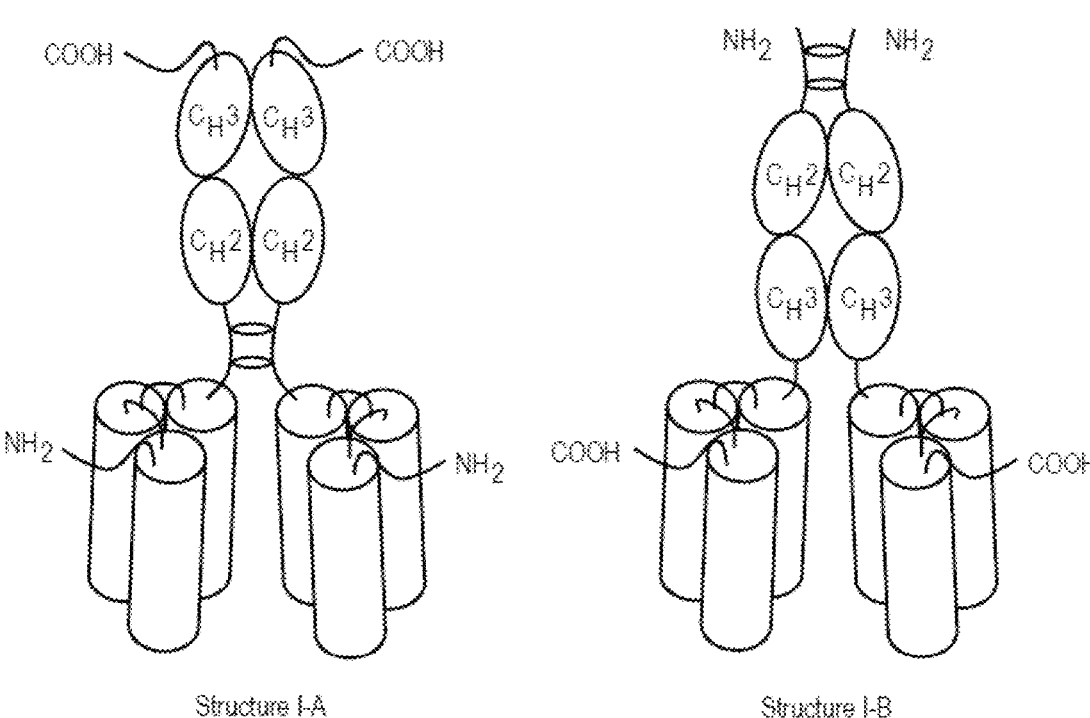

FIG. 50: Provides the structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a VH and a VL chain connected by a linker that may comprise hydrophilic residues and Gly and Ser sequences for flexibility, as well as Glu and Lys for solubility.

Figure 51:
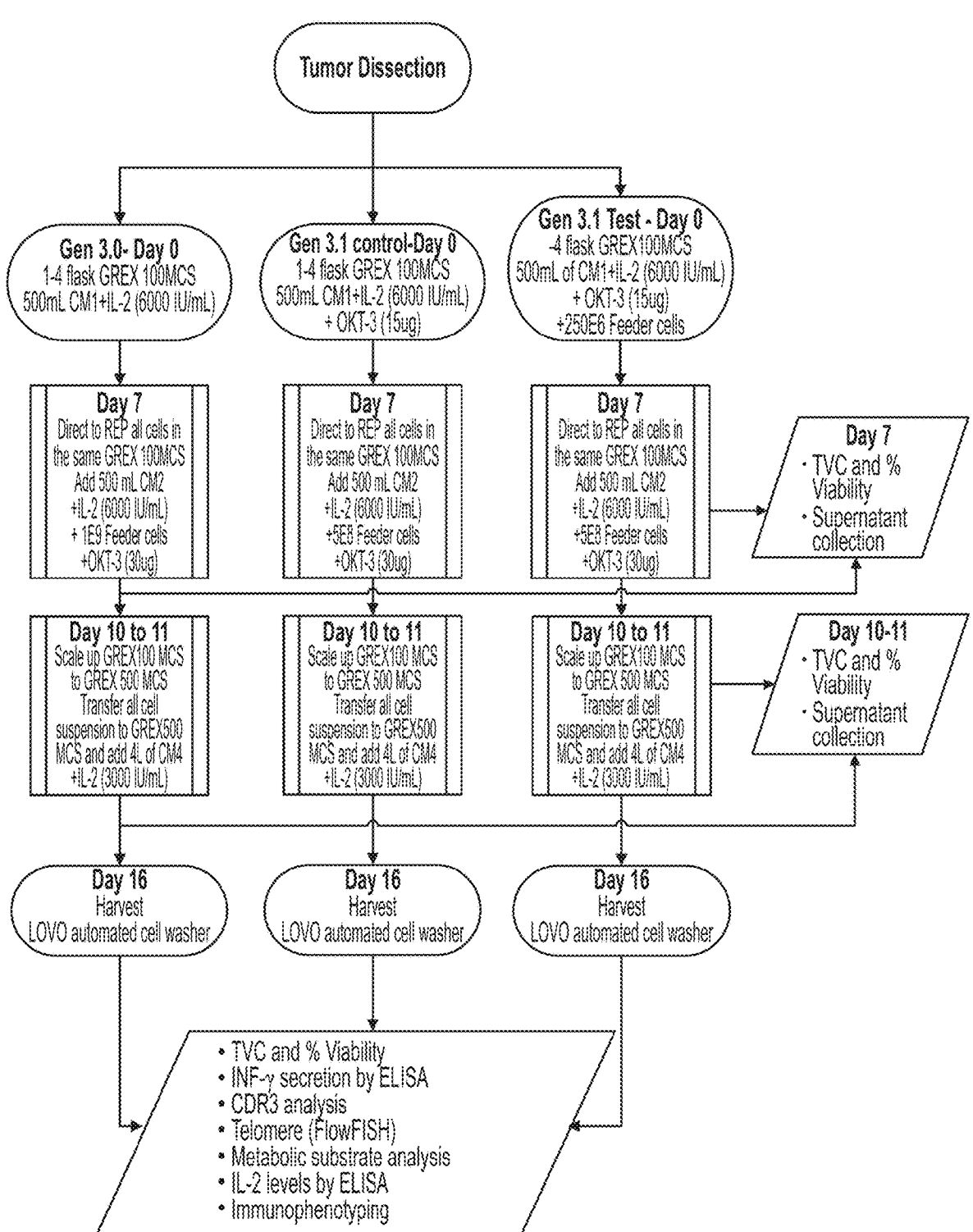

FIG. 51: Schematic of an exemplary embodiment of the Gen 3 process (a 16-day process).

FIG. 52: Provides a process overview for an exemplary embodiment (Gen 3.1 Test) of the Gen 3.1 process (a 16 day process).

FIG. 53: Provides data from TIL proliferation, average total viable cell counts per tumor fragment, percent viability at Harvest Day and total viable cell counts (TVC) at Harvest Day for exemplary embodiments of the Gen 3 process (Gen 3.0, Gen 3.1 Control, Gen 3.1 Test). Gen 3.1 Test (which includes the addition of OKT-3 and feeders on Day 0) reached maximum capacity of the flask at harvest. If a maximum of 4 flasks are initiated on day 0, each TVC harvest should be multiplied by 4.

FIG. 54: Bar graph depicting total viable cell count (TVC) and percent viability for exemplary embodiments of the Gen 3 process (Gen 3.0, Gen 3.1 Control, Gen 3.1 Test), a 16-day process.

Figure 55:
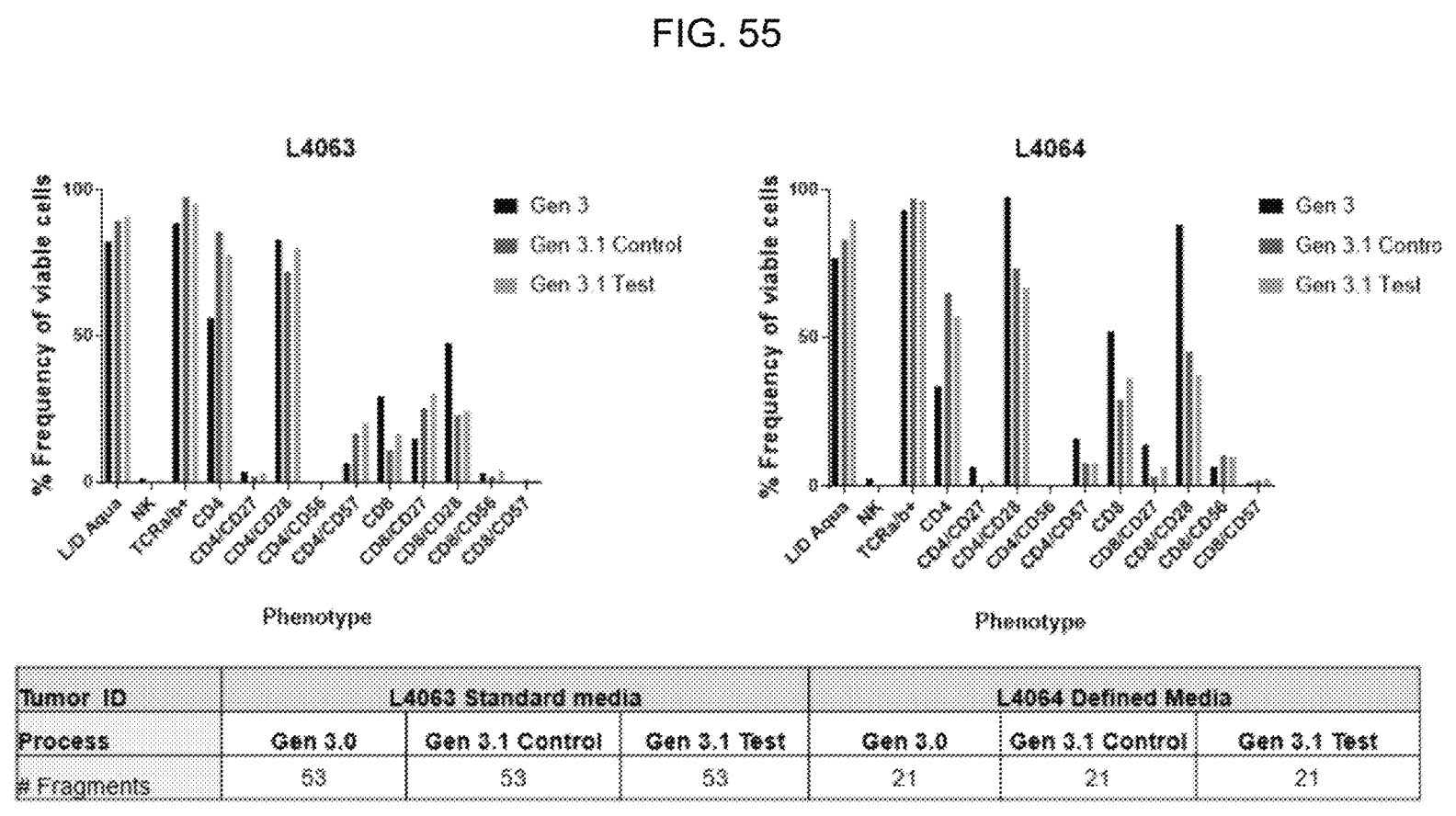

FIG. 55: Provides data showing that exemplary embodiments of the Gen 3 process (Gen 3.0, Gen 3.1 Control and Gen 3.1 Test) yielded cells that showed comparable CD28, CD27 and CD57 expression.

Figure 56:
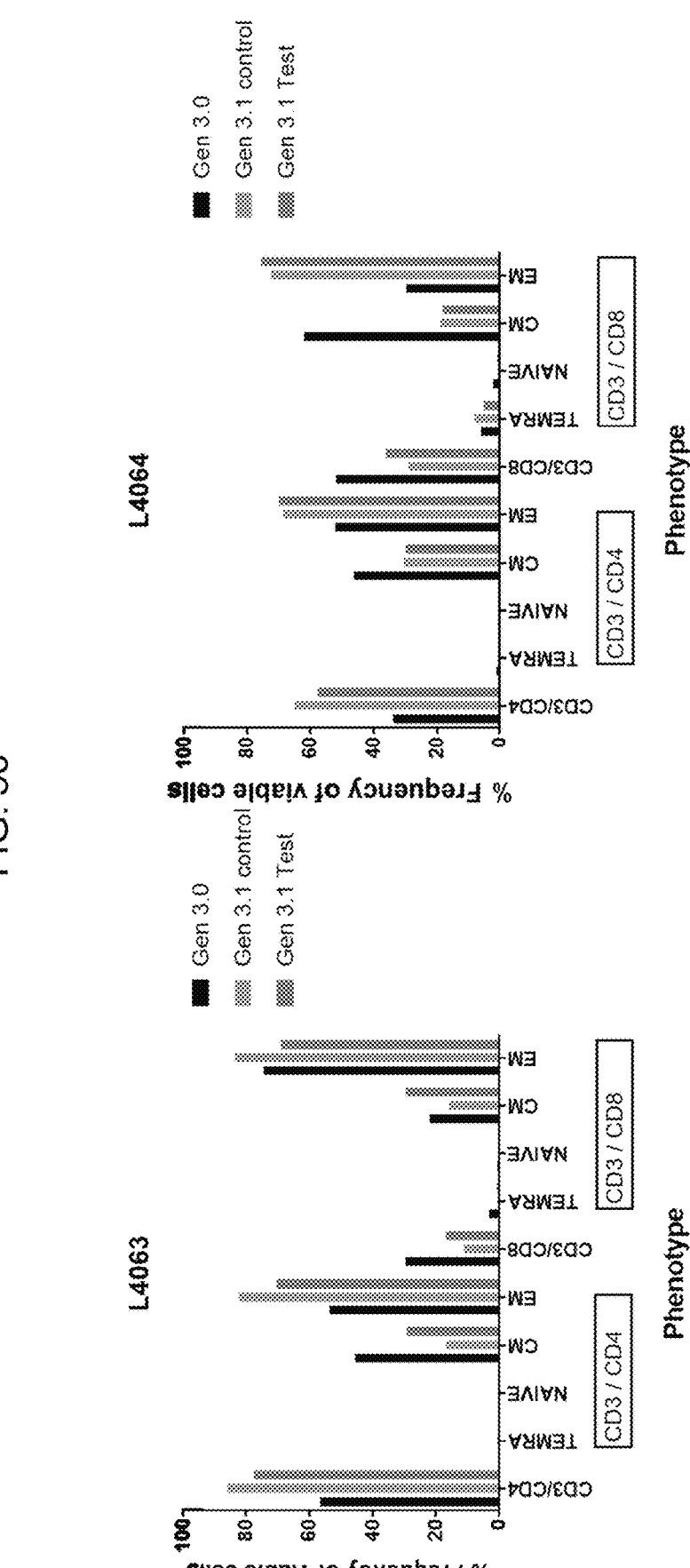

FIG. 56: Provides data showing TIL memory statuses were comparable across cells yielded by exemplary embodiments of the Gen 3 process (Gen 3.0, Gen 3.1 Control, and Gen 3.1 Test). Memory statuses of REP TIL are depicted as follows: CD4+ or CD8+ TIL Memory subsets were divided into different memory subsets. Naïve (CD45RA+CD62L+), CM: Central memory (CD45RA-CD62L+), EM: Effector memory (CD45RA−CD62L−), TEMRA/TEFF: RA+ Effector memory/Effectors (CD45RA+CD62L+). Bar graph presented are percentage positive CD45+/–CD62L+/– when gated on CD4+ or CD8+.

Figure 57:
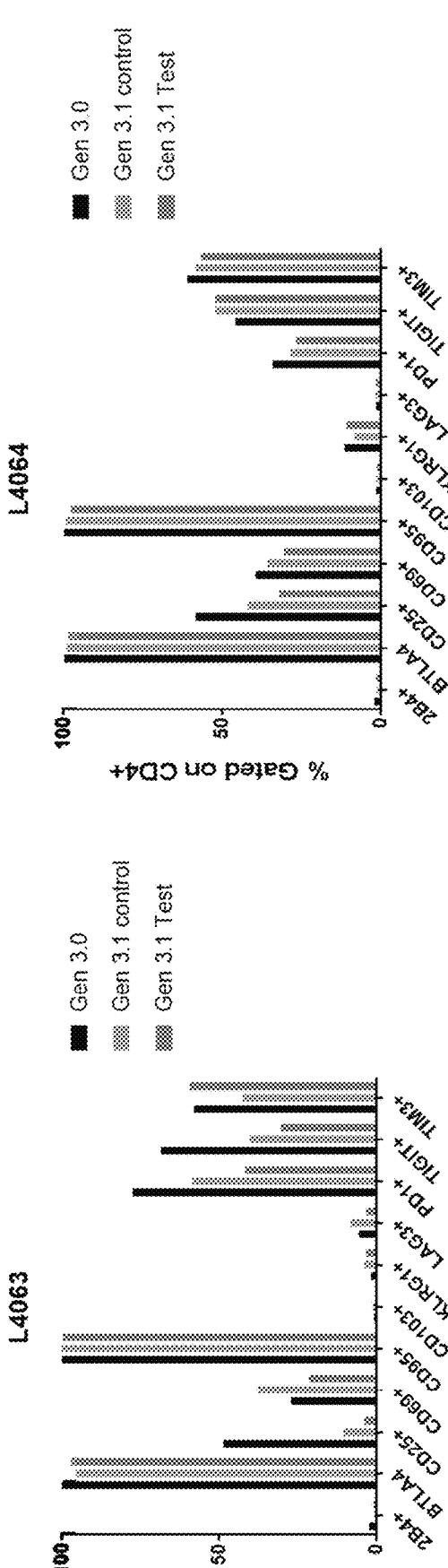

FIG. 57: Provides data showing TIL activation/exhaustion markers were comparable across cells yielded by exemplary embodiments of the Gen 3 process (Gen 3.0, Gen 3.1 Control, and Gen 3.1 Test) when gated on CD4+. Activation and exhaustion of REP TIL were determined by multicolor flow cytometry. Harvested TIL samples were stained with flow cytometry antibodies (CD3-BUV395, PD-1-BV421, 2B4/CD244-PB, CD8-BB515, CD25-BUV563, BTLA-PE, KLRG1-PE-Dazzle 594, TIM-3-BV650, CD194/CCR4-APC, CD4-VioGreen, TIGIT-PerCP-eFluor 710, CD183-BV711, CD69-APC-R700, CD95-BUV737, CD127-PE-Cy7, CD103-BV786, LAG-3-APC-eFluor 780). Bar graph presented are percentage of CD4+ or CD8+ TIL of REP TIL.

FIG. 58: Provides data showing TIL activation/exhaustion markers were comparable across cells yielded by exemplary embodiments of the Gen 3 process (Gen 3.0, Gen 3.0, Gen 3.1 Control and Gen 3.1) when gated on CD8+. Activation and exhaustion of REP TIL were determined by multicolor flow cytometry. TIL Harvested samples were stained with flow cytometry antibodies (CD3-BUV395, PD-1-BV421, 2B4/CD244-PB, CD8-BB515, CD25-BUV563, BTLA-PE, KLRG1-PE-Dazzle 594, TIM-3-BV650, CD194/CCR4-APC, CD4-VioGreen, TIGIT-PerCP-eFluor 710, CD183-BV711, CD69-APC-R700, CD95-BUV737, CD127-PE-Cy7, CD103-BV786, LAG-3-APC-eFluor 780). Bar graph presented are percentage of CD4+ or CD8+ TIL of REP TIL.

Figure 59:
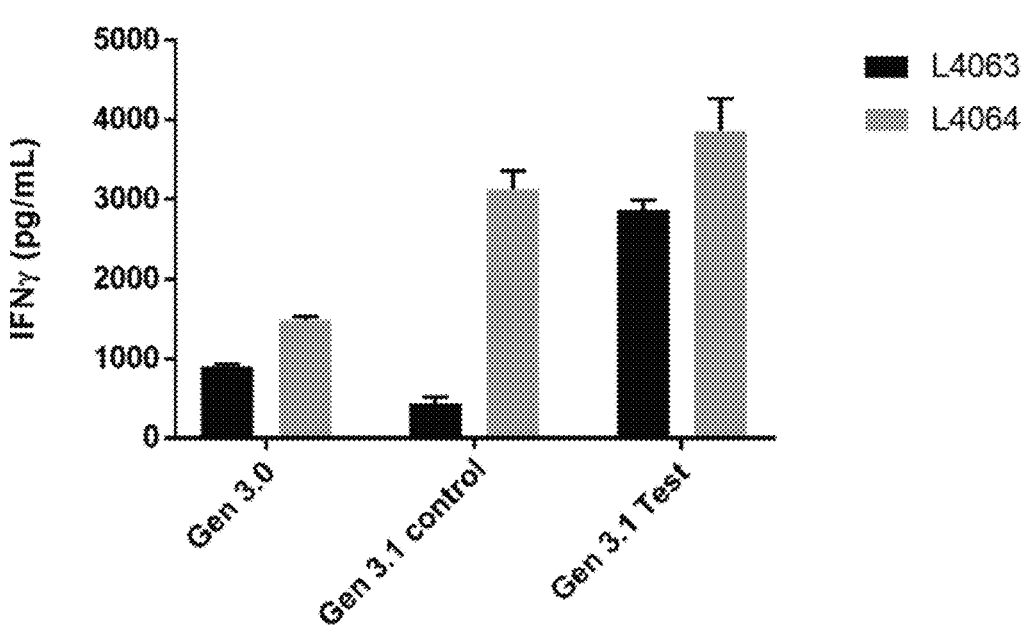

FIG. 59: Provides data showing higher production of IFN-γ exhibited by Gen 3.1 final product. IFNγ analysis ELISA was assessed in the culture frozen supernatant to compare both processes. For each tumor overnight stimulation with coated anti-CD3 plate, using fresh TIL product on each Harvest day. Each bar represents here are IFN-γ levels of stimulated, unstimulated and media control.

Figure 60:
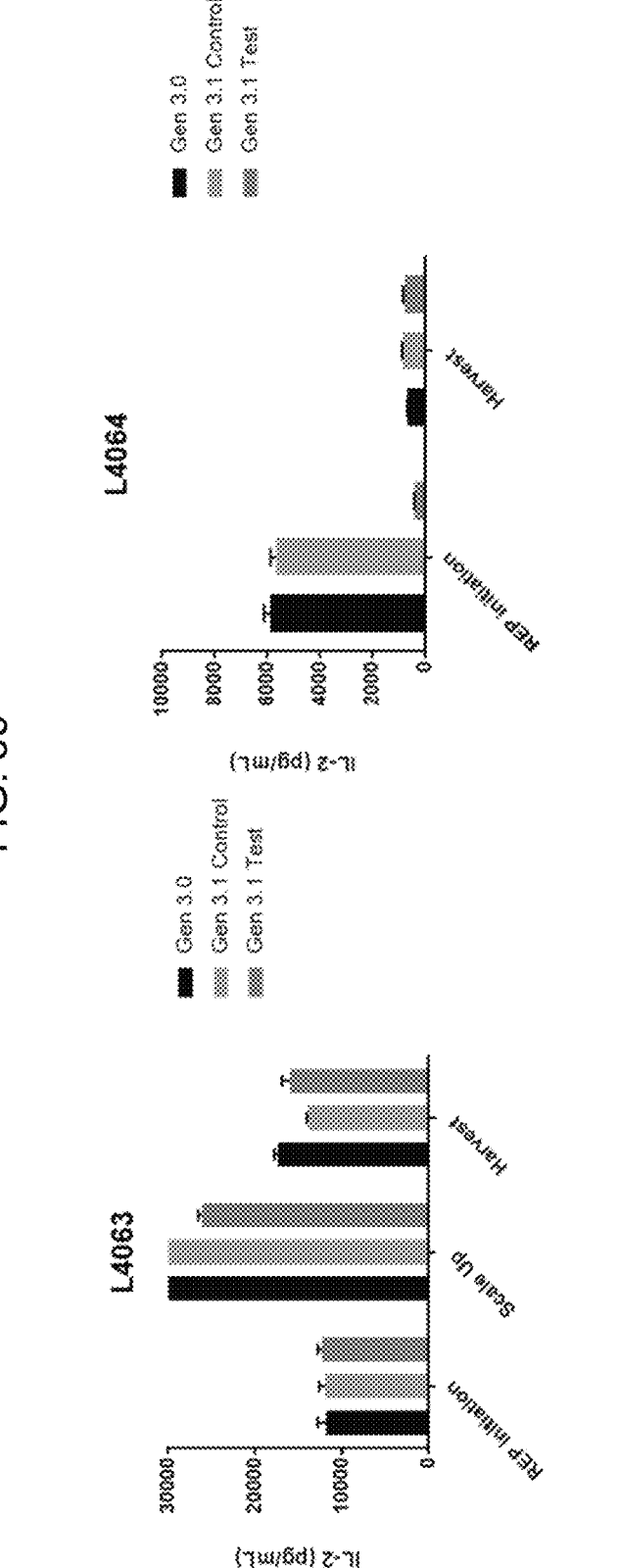
Figure 61:
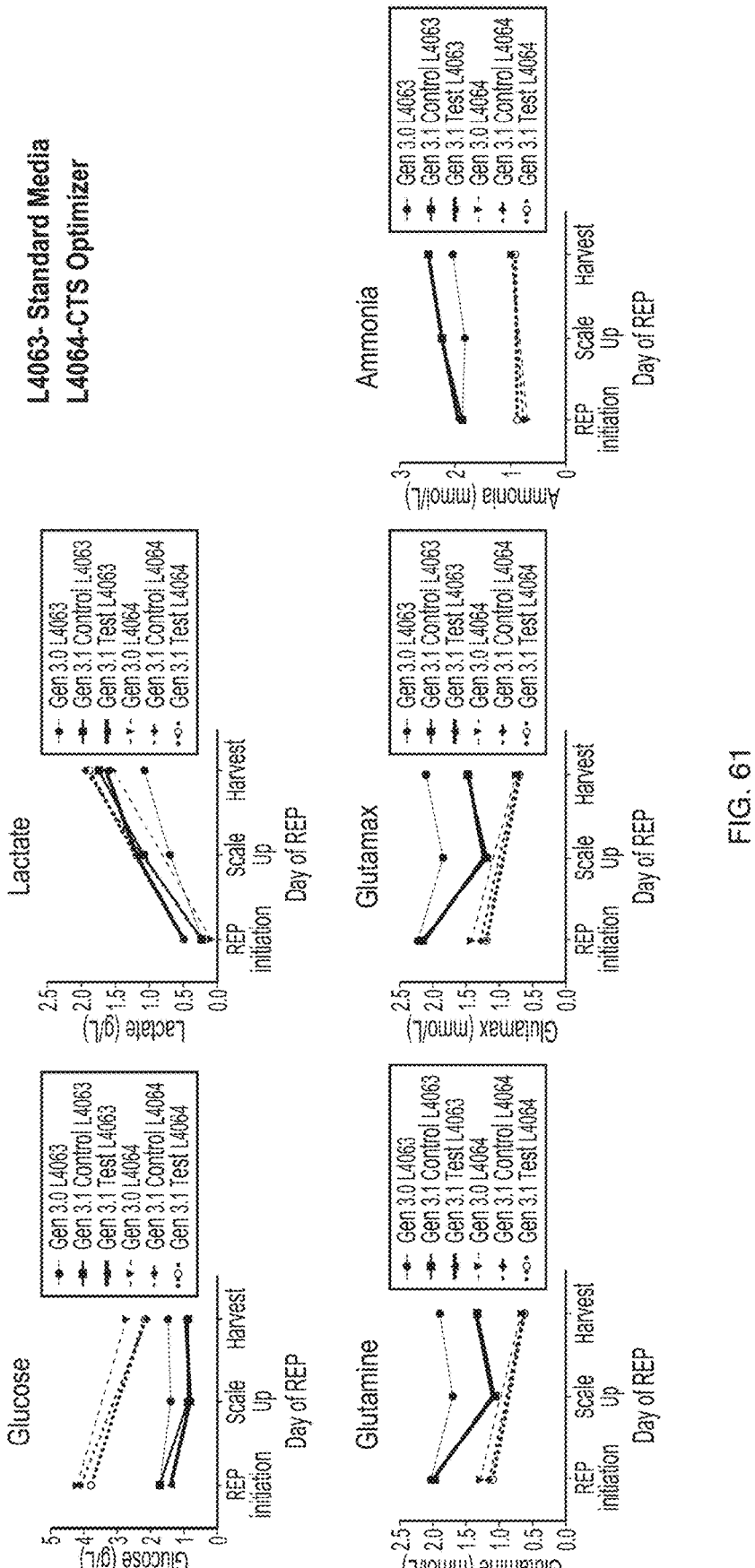

FIG. 60: Provides data showing that IL-2 concentration on supernatant were comparable across exemplary embodiments of the Gen 3 process (Gen 3.0, Gen 3.1 Control, Gen 3.1 Test) using Standard media. Left panel: L4063—Gen 2 Standard Media. Right panel: L4064—CTS Optimizer Media. *ELISA performed with AIM V diluent FIG. 61: Provides data showing that metabolite concentrations were comparable on supernatant supernatants across exemplary embodiments of the Gen 3 process (Gen 3.0, Gen 3.1 Control, Gen 3.1 Test). L4063 TILs were expanded in standard media. L4064 TILs were expanded in CTS Optimizer media.

Figure 62:
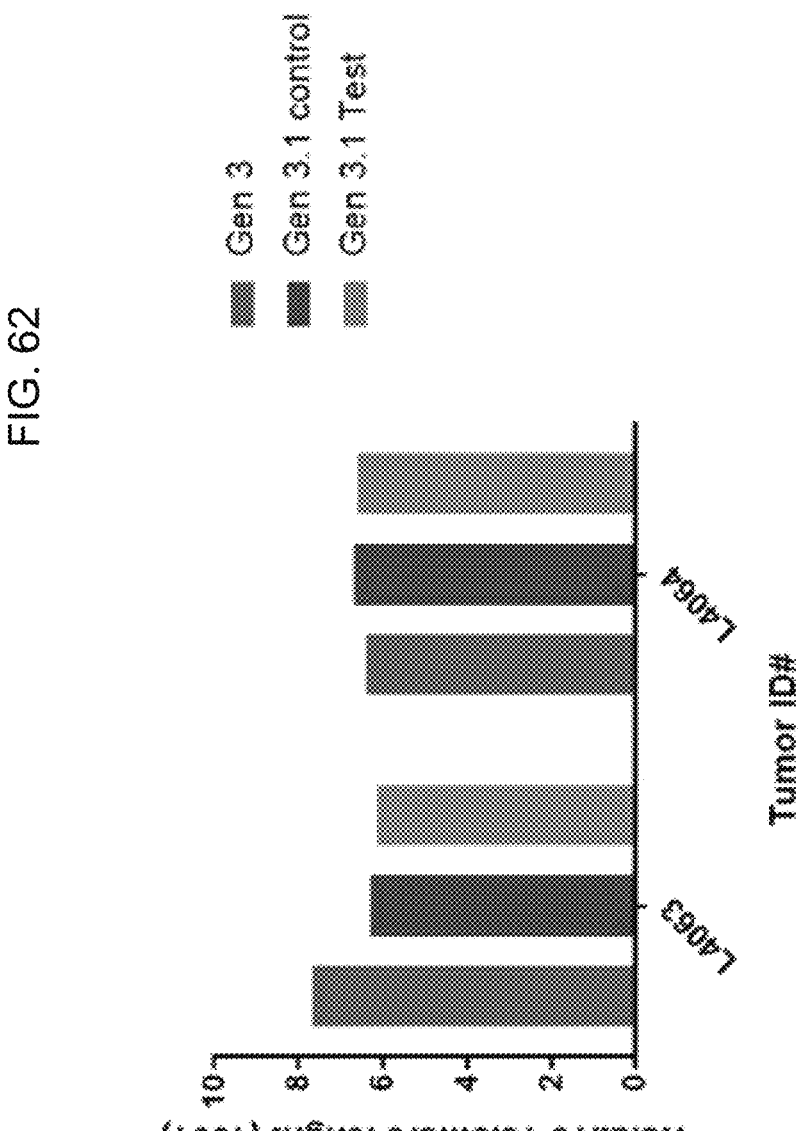

FIG. 62: Telomere length analysis on exemplary embodiments of the Gen 3 process (Gen 3.0, Gen 3.1 Control, Gen 3.1 Test). Telomere length analysis for cells yielded by tumor identification numbers L4063 and L4064: the relative telomere length (RTL) value indicates the average telomere fluorescence per chromosome/genome in cells produced by the Gen 3.0, Gen 3.1 Control and Gen 3.1 Test processes over the telomere fluorescence per chromosome/genome in the control cells line (1301 Leukemia cell line) using DAKO kit.

Figure 63:
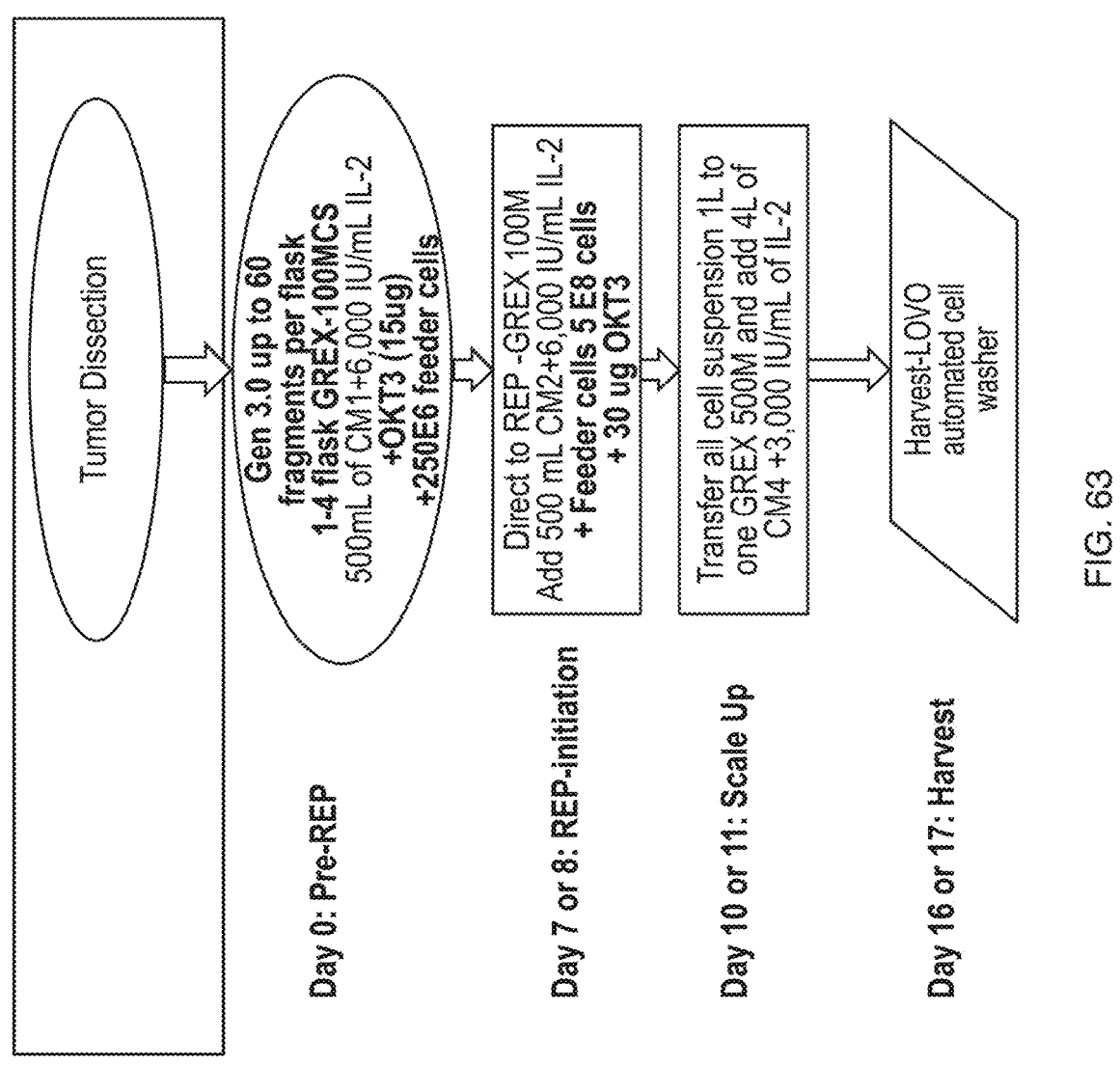

FIG. 63: Schematic of an exemplary embodiment of the Gen 3.1 Test (Gen 3.1 optimized) process (a 16-17 day process).

Figure 64:
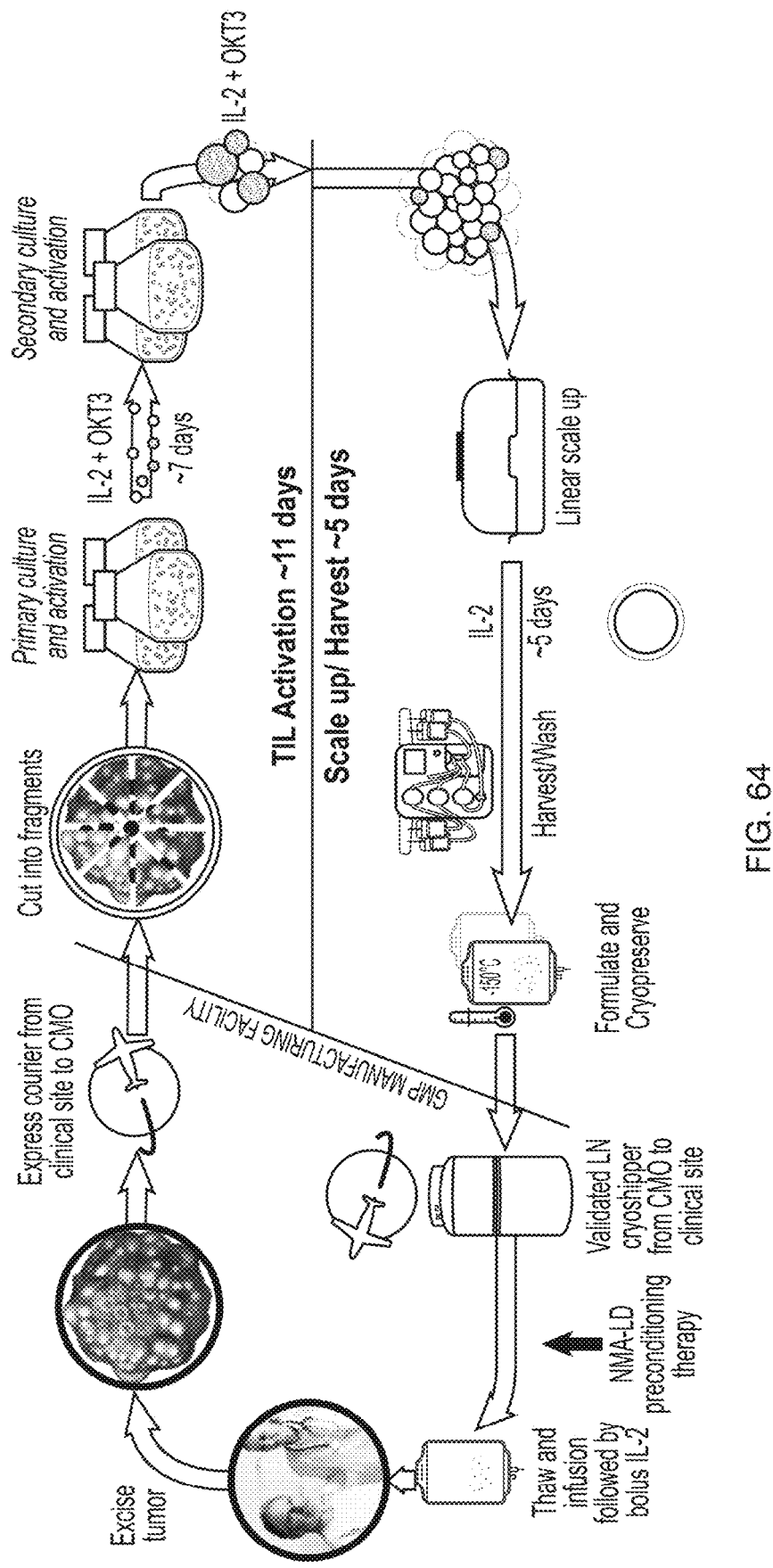

FIG. 64: Schematic of an exemplary embodiment of the Gen 3 process (a 16-day process).

FIG. 65A-65B: Comparison tables for exemplary Gen 2 and exemplary Gen 3 processes with exemplary differences highlighted.

Figure 66:
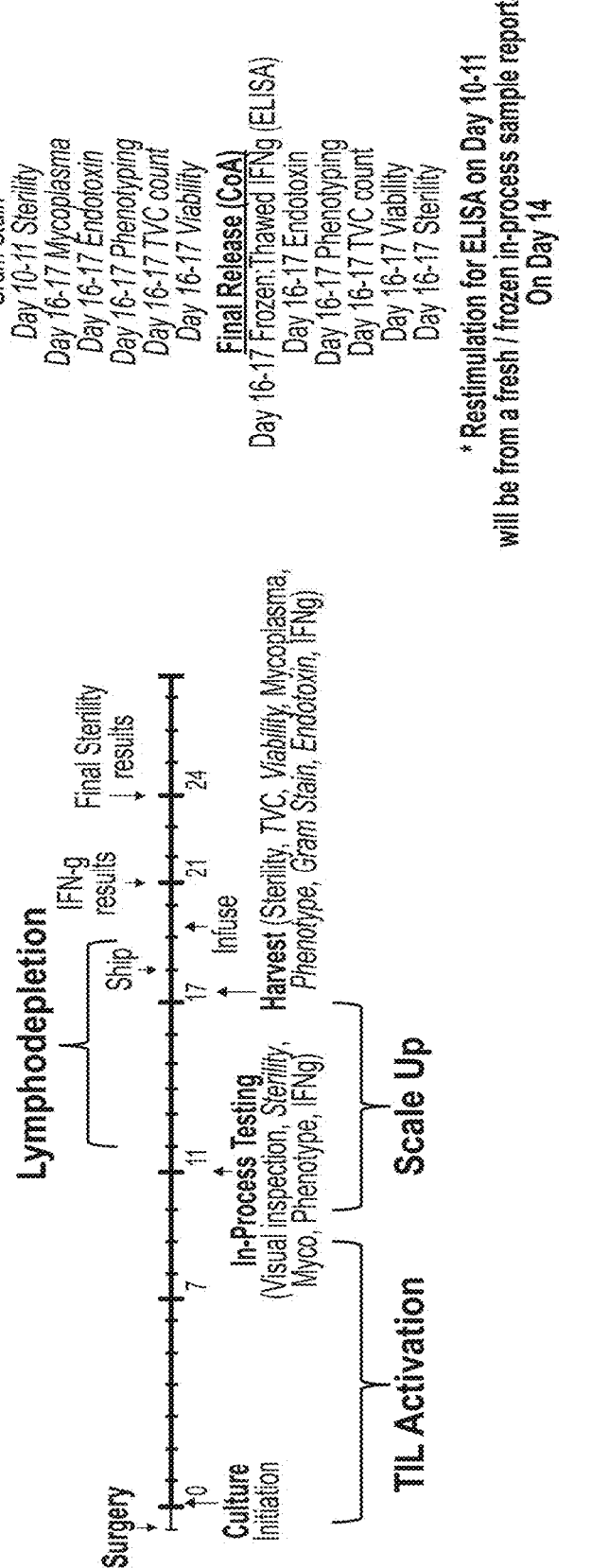

FIG. 66: Schematic of an exemplary embodiment of the Gen 3 process (a 16/17 day process) preparation timeline.

FIG. 67: Schematic of an exemplary embodiment of the Gen 3 process (a 14-16 day process).

FIG. 68: Summary of data from Day 16/17 of three engineering runs of an exemplary Gen 3 process embodiment.

FIG. 69: Data regarding the extended phenotype of TIL: shown are the differentiation characteristics against TIL identity (ID) specifications for cells produced by two engineering runs of an exemplary Gen 3 process embodiment.

FIG. 70: Data regarding the extended phenotype of TIL expanded from lung tumors: shown are the differentiation characteristics against TIL identity (ID) specifications for cells produced by two process development (PD) runs of an exemplary Gen 3 process embodiment using lung tumor tissues.

FIG. 71: Data regarding the extended phenotype (purity, identity and memory) of TIL expanded from ovarian tumors: shown are the purity, identity and memory phenotypic characteristics of cells expanded from ovarian tumors using exemplary Gen 2, Gen 3.1, and FR ER (Frozen tumor, Early REP) process embodiments; * indicates condition not tested; indicates sampling issue, low TVC count or non-viable cells on thawing.

FIG. 72: Shown is the gating strategy for characterization of TIL (gating hierarchy is shown) and data regarding the extended phenotypic characteristics of cells produced by two engineering runs of an exemplary Gen 3 process embodiment.

FIG. 73: Shown is the gating strategy for characterization of TIL (gating hierarchy is shown) and data regarding the extended phenotypic characteristics of the CD4+ subpopulation and the CD8+ subpopulation of cells produced by two engineering runs of an exemplary Gen 3 process embodiment.

FIG. 74: Shown are data regarding Granzyme B ELISA analysis of cells produced by two engineering runs of an exemplary Gen 3 process embodiment.

Figure 75A:
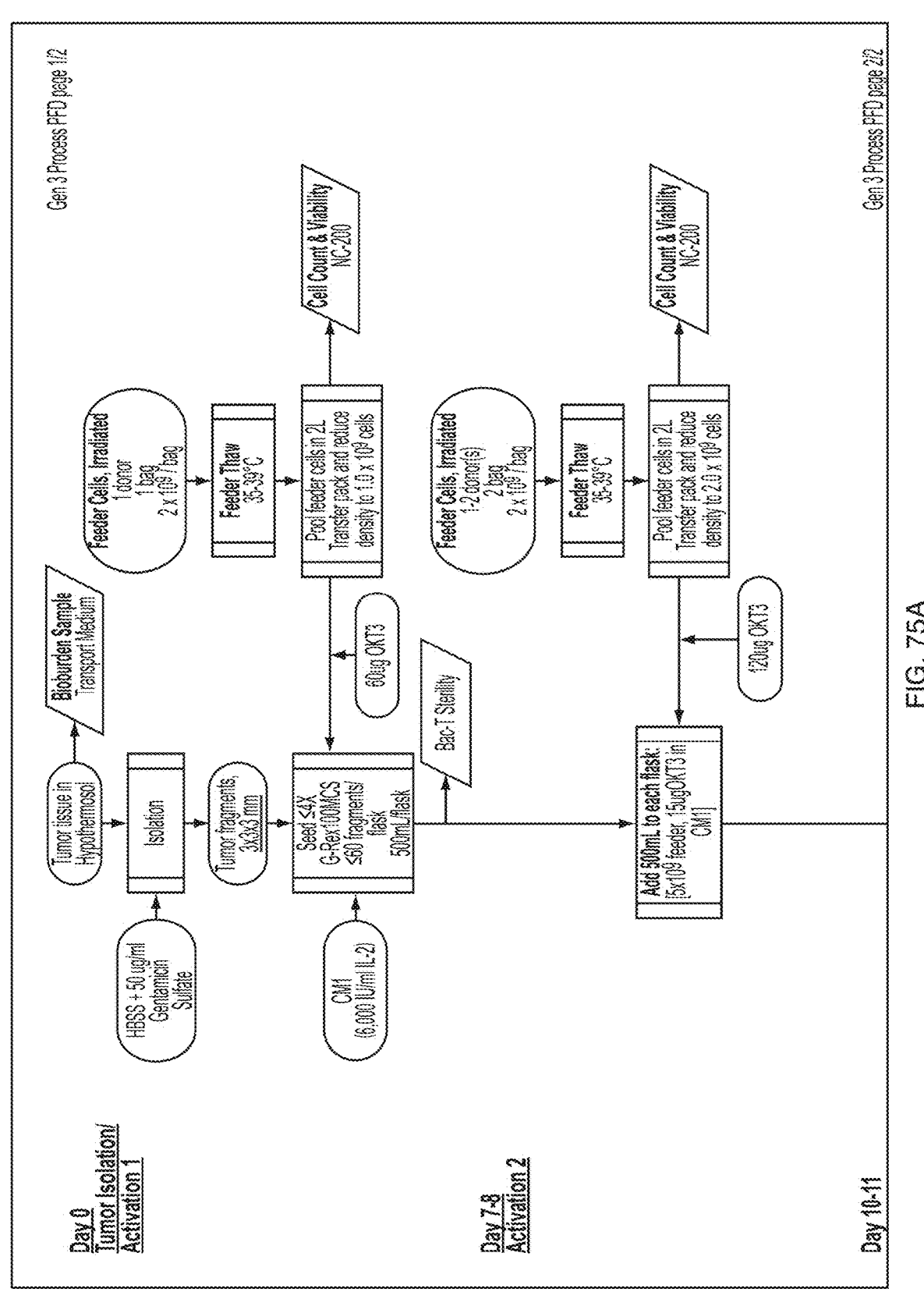
Figure 75B:
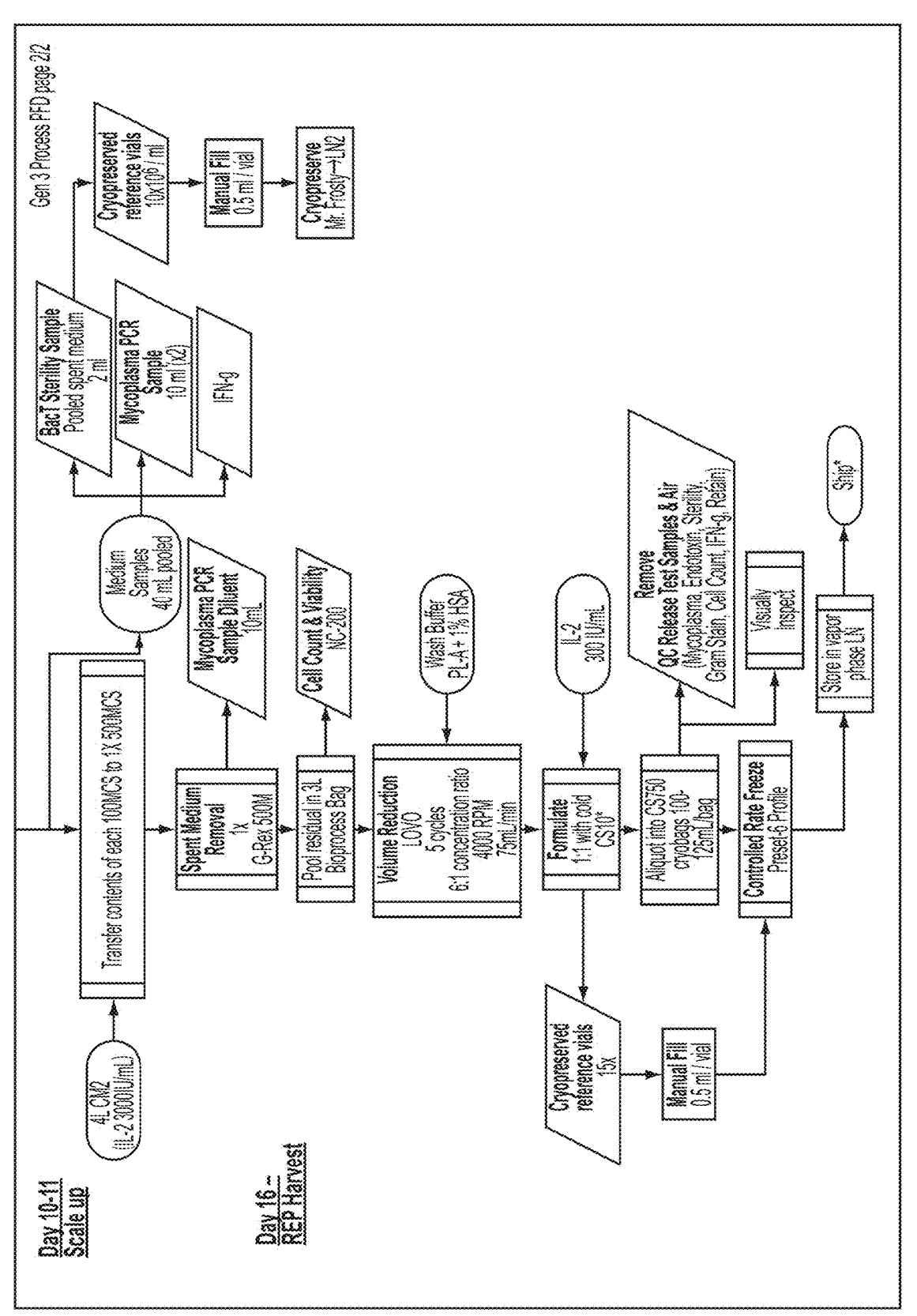

FIG. 75A-75B: Schematic of an exemplary embodiment of the Gen 3 process (a 16 day process).

Figure 76:
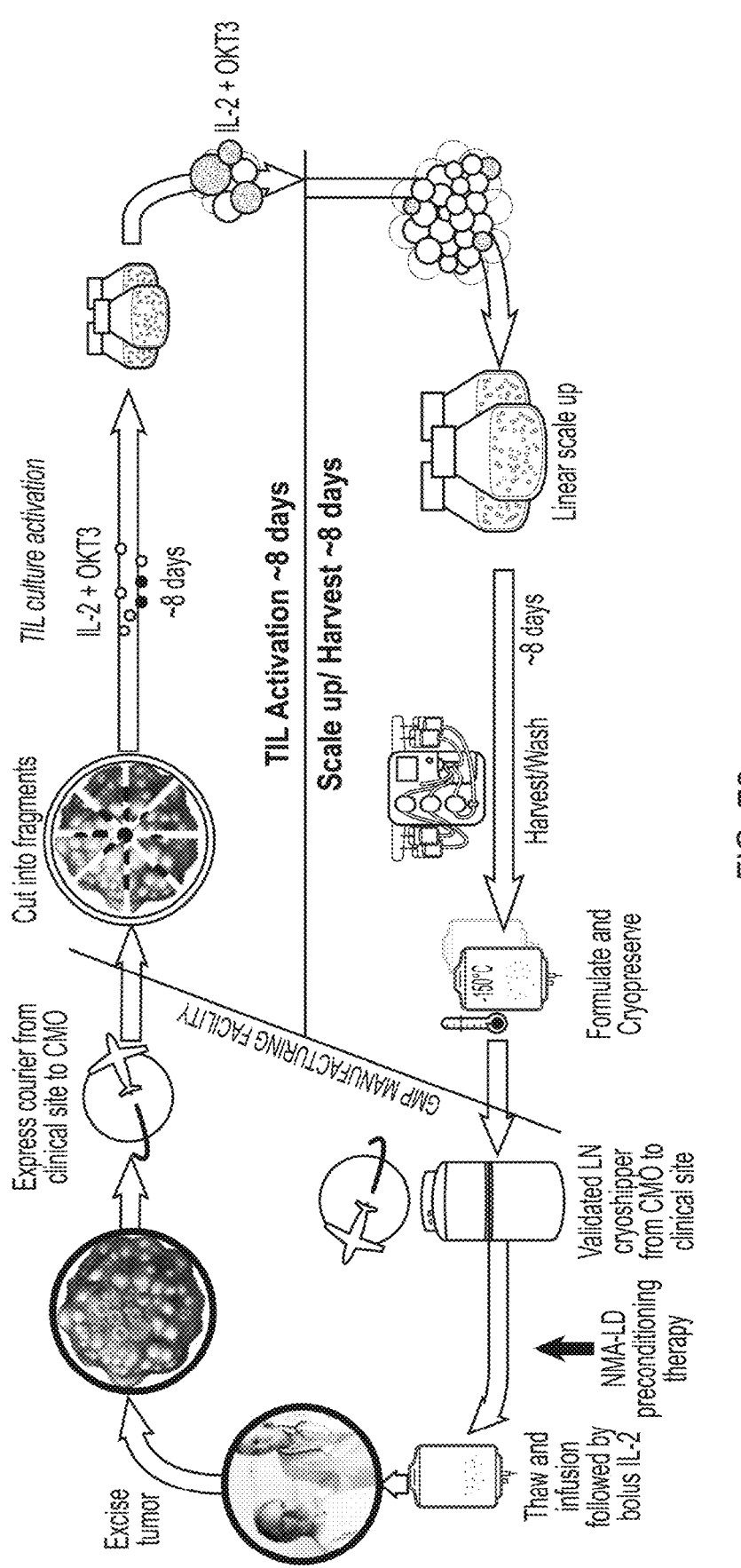

FIG. 76: Schematic of an exemplary embodiment of the Gen 3 process (a 16 day process).

FIG. 77: Comparison of Gen 2, Gen 2.1 and an embodiment of the Gen 3 process (a 16 day process).

FIG. 78: Comparison of Gen 2, Gen 2.1 and an embodiment of the Gen 3 process (a 16 day process).

FIG. 79: Gen 3 embodiment components.

Figure 80:
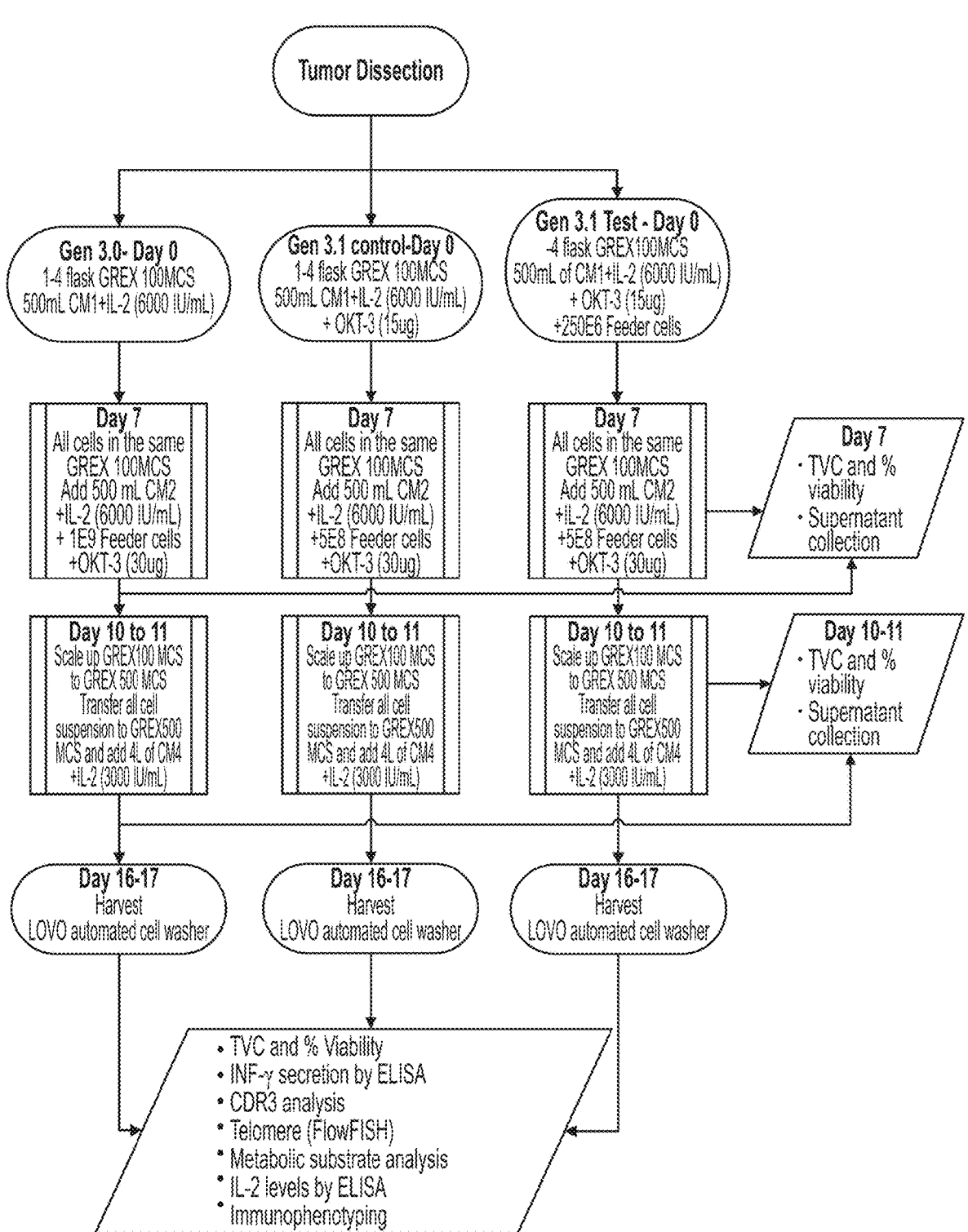

FIG. 80: Gen 3 embodiment flow chart comparison (Gen 3.0, Gen 3.1 control, Gen 3.1 Test).

FIG. 81: Total viable cell count and fold expansion are presented for exemplary Gen 3 embodiments (Gen 3.0, Gen 3.1 Control and Gen 3.1 Test) using standard cell culture media and serum free cell culture media.

FIG. 82: % viability scores upon reactivation, culture scale up and TIL harvest are presented for exemplary Gen 3 embodiments (Gen 3.0, Gen 3.1 Control and Gen 3.1 Test) using standard cell culture media and serum free cell culture media.

FIG. 83: Presented is phenotypic characterization of final TIL product produced by processing L4063 and L4064 tumor samples in exemplary Gen 3 processes (Gen 3.0, Gen 3.1 Control and Gen 3.1 Test) using standard cell culture media and CTS serum free cell culture media.

FIG. 84: Presented is memory marker analysis of TIL product produced by processing L4063 and L4064 tumor samples in exemplary Gen 3 processes (Gen 3.0, Gen 3.1

Control and Gen 3.1 Test) using standard cell culture media and CTS serum free cell culture media.

FIG. 85: Presented are activation and exhaustion markers of TIL produced by processing L4063 and L4064 tumor samples in exemplary Gen 3 processes (Gen 3.0, Gen 3.1 Control and Gen 3.1 Test) using standard cell culture media and CTS serum free cell culture media followed by CD4+ gated cell sorting.

FIG. 86: Presented are activation and exhaustion markers of TIL produced by processing L4063 and L4064 tumor samples in exemplary Gen 3 processes (Gen 3.0, Gen 3.1 Control and Gen 3.1 Test) using standard cell culture media and CTS serum free cell culture media followed by CD8+ gated cell sorting.

FIG. 87: Presented are IFN-γ production (pg/mL) scores for final TIL product produced by processing L4063 and L4064 tumor samples in exemplary Gen 3 processes (Gen 3.0, Gen 3.1 Control and Gen 3.1 Test) using standard cell culture media and CTS serum free cell culture media.

FIG. 88: Presented is IL-2 concentration (pg/mL) analysis of spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 89: Presented is concentration of glucose (g/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 90: Presented is concentration of lactate (g/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 91: Presented is concentration of glutamine (mmol/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 92: Presented is concentration of glutamax (mmol/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 93: Presented is concentration of ammonia (mmol/L) in spent media (collected upon reactivation, culture scale up and TIL harvest) from processing L4063 and L4064tumor samples in exemplary Gen 3 processes (Gen 3.0, Gen 3.1 Control and Gen 3.1 Test) using standard cell culture media and CTS serum free cell culture media. Telomere length analysis on exemplary embodiments of the Gen 3 process (Gen 3.0, Gen 3.1 Control, Gen 3.1 Test). Telomere length analysis for cells yielded by tumor identification numbers L4063 and L4064: the relative telomere length (RTL) value indicates the average telomere fluorescence per chromosome/genome in cells produced by the Gen 3.0, Gen 3.1 Control and Gen 3.1 Test processes over the telomere fluorescence per chromosome/genome in the control cells line (1301 Leukemia cell line) using DAKO kit.

FIG. 94: Telomere length analysis on TIL produced by exemplary embodiments of the Gen 3 process (Gen 3.0, Gen 3.1 Control, Gen 3.1 Test) using standard cell culture media and CTS serum free cell culture media. Telomere length analysis for cells yielded by tumor identification numbers L4063 and L4064: the relative telomere length (RTL) value indicates the average telomere fluorescence per chromosome/genome in cells produced by the Gen 3.0, Gen 3.1 Control and Gen 3.1 Test processes over the telomere fluorescence per chromosome/genome in the control cells line (1301 Leukemia cell line) using DAKO kit.

FIG. 95: TCR Vβ repertoire summary for TIL produced by exemplary embodiments of the Gen 3 process (Gen 3.0, Gen 3.1 Control, Gen 3.1 Test) using standard cell culture media and CTS serum free cell culture media. Described is the clonality of TIL for final TIL product yielded by tumor identification numbers L4063 and L4064 produced by the Gen 3.0, Gen 3.1 Control and Gen 3.1 Test processes as measured by the TCR Vβ repertoire of unique CDR3 sequences.

FIG. 96: Comparison of TIL produced by exemplary embodiments of the Gen 3 process (Gen 3.0, Gen 3.1 Control, Gen 3.1 Test) with respect to frequency of unique CDR3 sequences in TIL harvested product from processing of L4063 tumor samples.

FIG. 97: Comparison of TIL produced by exemplary embodiments of the Gen 3 process (Gen 3.0, Gen 3.1 Control, Gen 3.1 Test) with respect to percentage shared unique CDR3 sequences in TIL harvested cell product from processing of L4063 tumor samples: 975 sequences are shared between Gen 3.0 and Gen 3.1 Test final product, equivalent to 88% of top 80% of unique CDR3 sequences from Gen 3.0 shared with Gen 3.1 Test final product.

FIG. 98: Comparison of TIL produced by exemplary embodiments of the Gen 3 process (Gen 3.0, Gen 3.1 Control, Gen 3.1 Test) with respect to percentage shared unique CDR3 sequences in TIL harvested cell product for from processing of L4064 tumor samples: 2163 sequences are shared between Gen 3.0 and Gen 3.1 Test final product, equivalent to 87% of top 80% of unique CDR3 sequences from Gen 3.0 shared with Gen 3.1 Test final product.

FIG. 99: Comparison of TIL produced by exemplary embodiments of the Gen 3 process (Gen 3.0, Gen 3.1 Control, Gen 3.1 Test) with respect to frequency of unique CDR3 sequences in TIL harvested product from processing of L4064 tumor samples.

FIG. 100: Shown are the components of an exemplary embodiment of the Gen 3 process (Gen 3-Optimized, a 16-17 day process).

FIG. 101: Acceptance criteria table.

FIG. 102: Cell counts reactivation Day.

FIG. 103: Cell counts Scale Up Day.

FIG. 104: Cell counts Harvest L4063.

FIG. 105: Cell counts Harvest L4064.

FIG. 106: Flow data.

FIG. 107: Flow data.

FIG. 108: Flow data.

FIG. 109: Flow data.

Figure 110A:
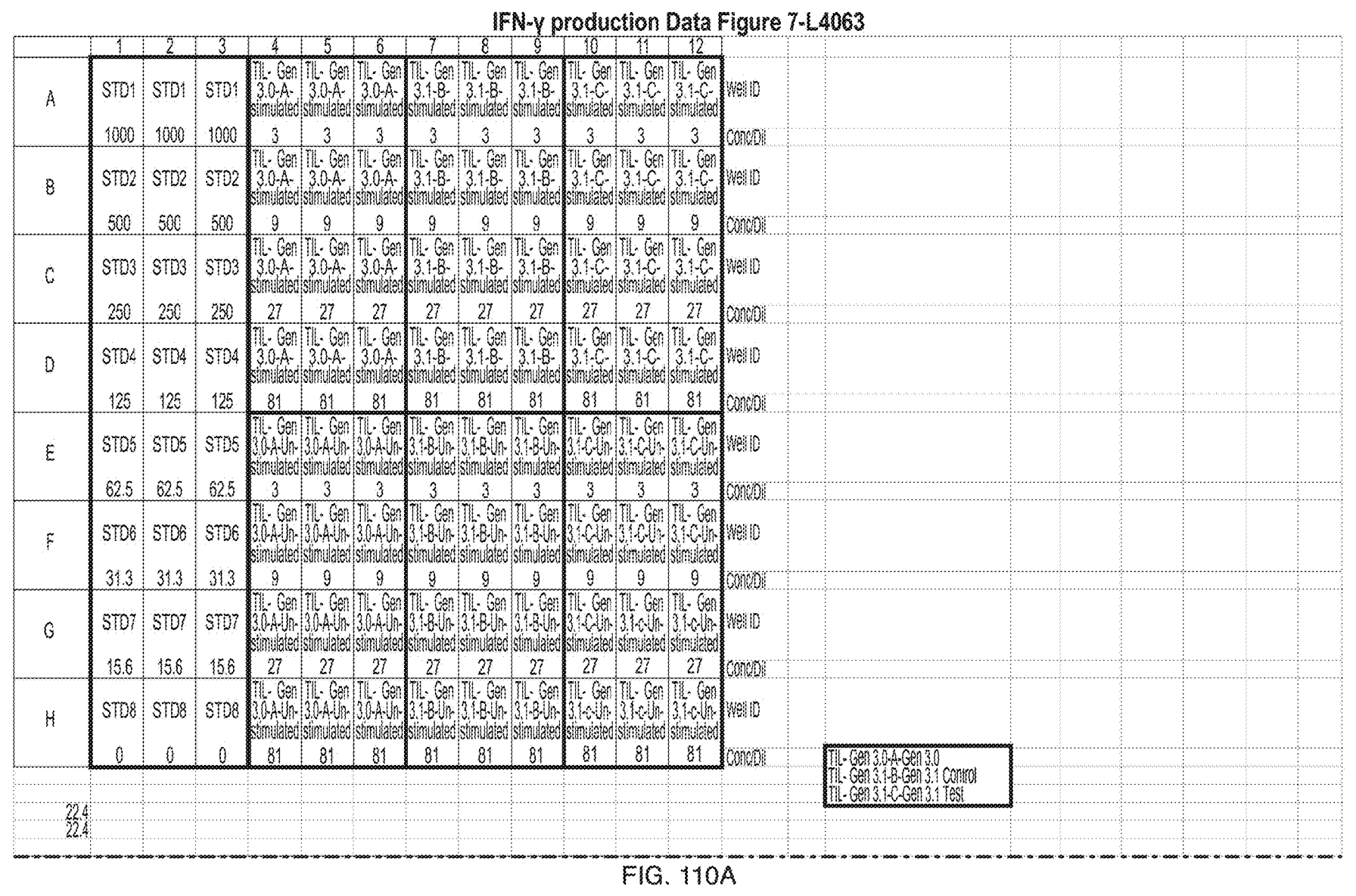
Figure 110B:
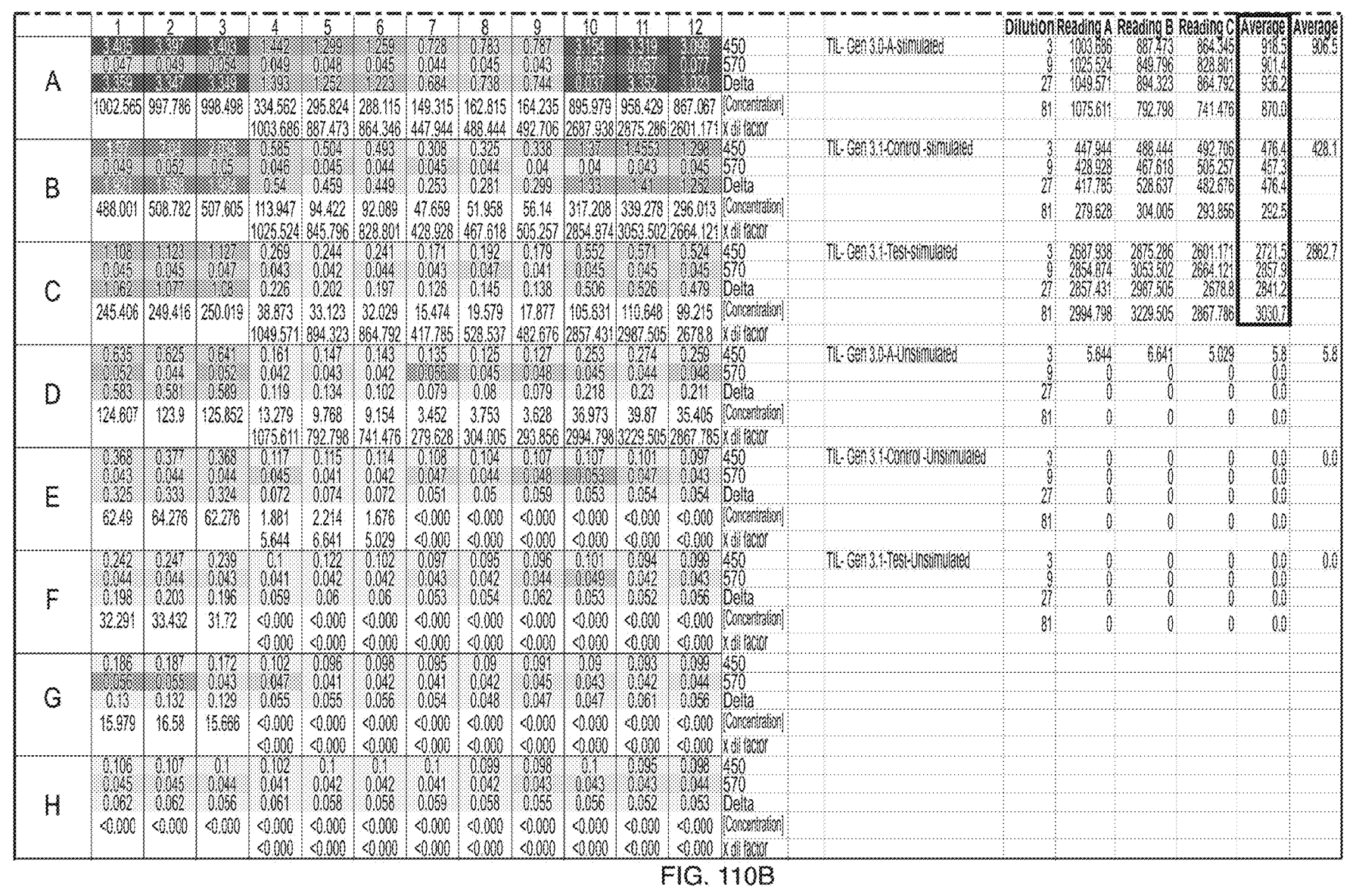

FIGS. 110A-110B: IFN-γ production Data FIG. 7—L4063.

Figure 111A:
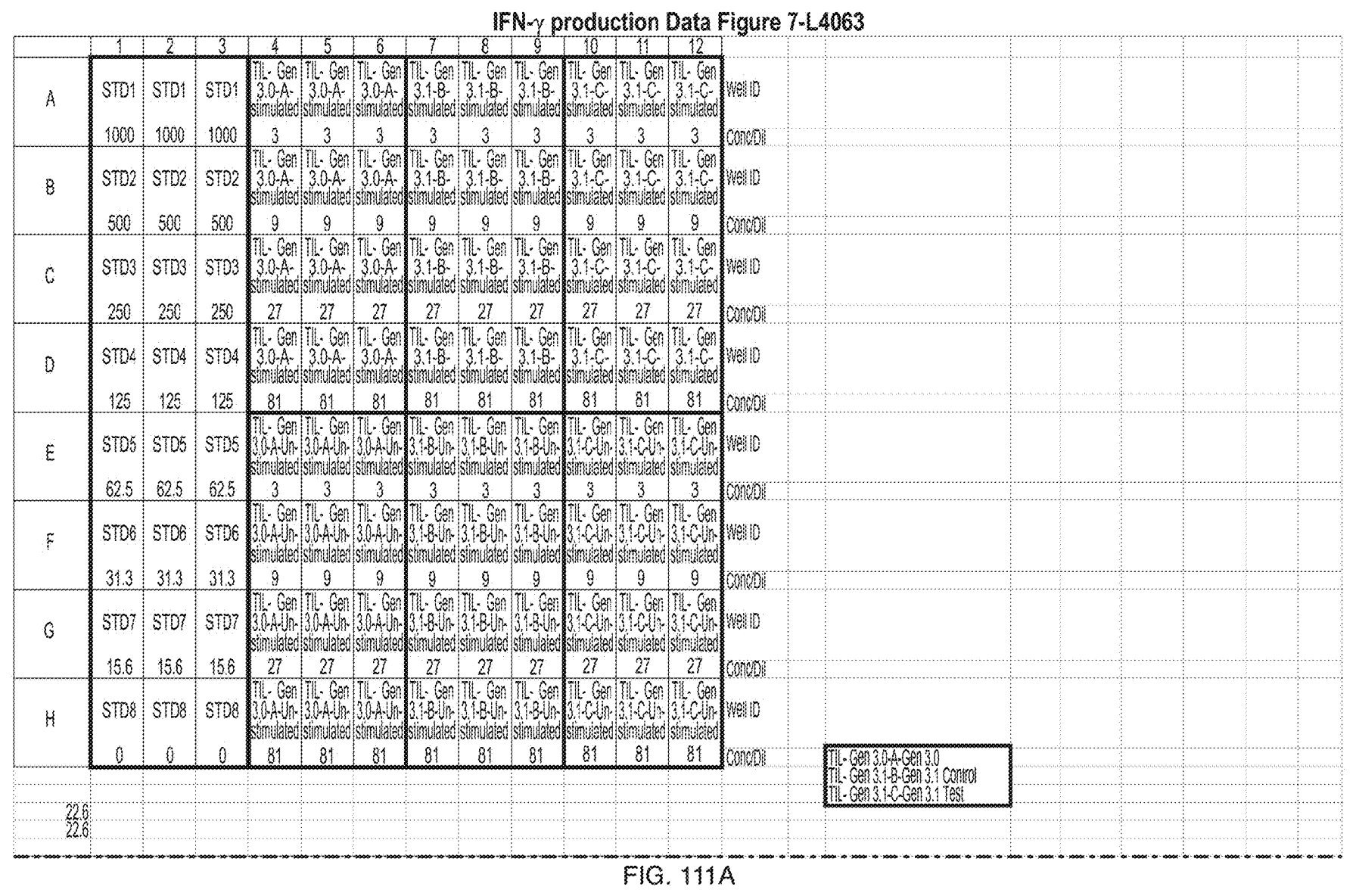
Figure 111B:
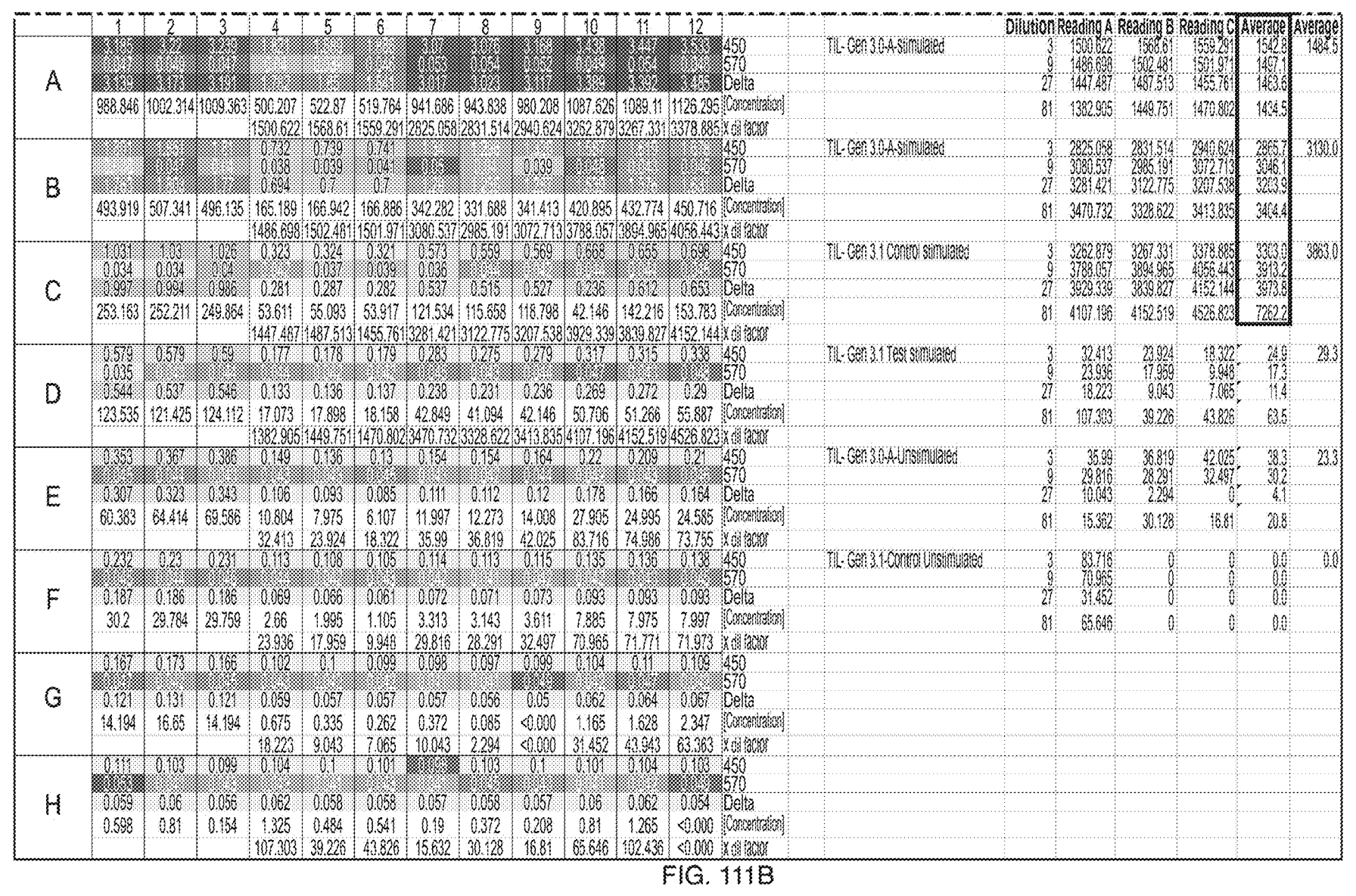

FIGS. 111A-111B: Data IFN-γ production FIG. 7—L4064.

Figure 112B:
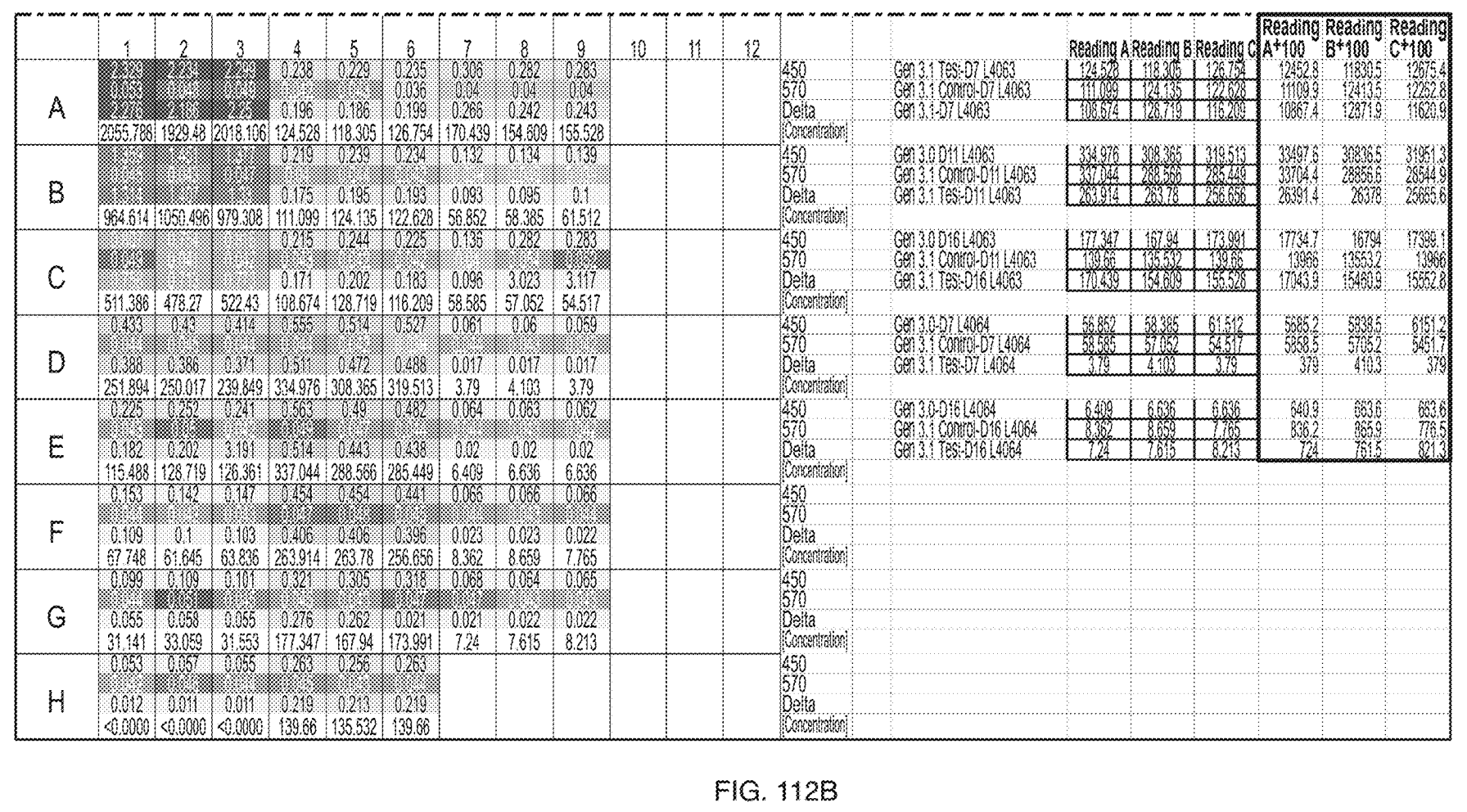

FIGS. 112A-112B: ELISA analysis of IL-2 concentration data.

FIG. 113: Metabolic data summary table.

FIG. 114: Summary data.

FIG. 115: Summary data.

Figure 116:
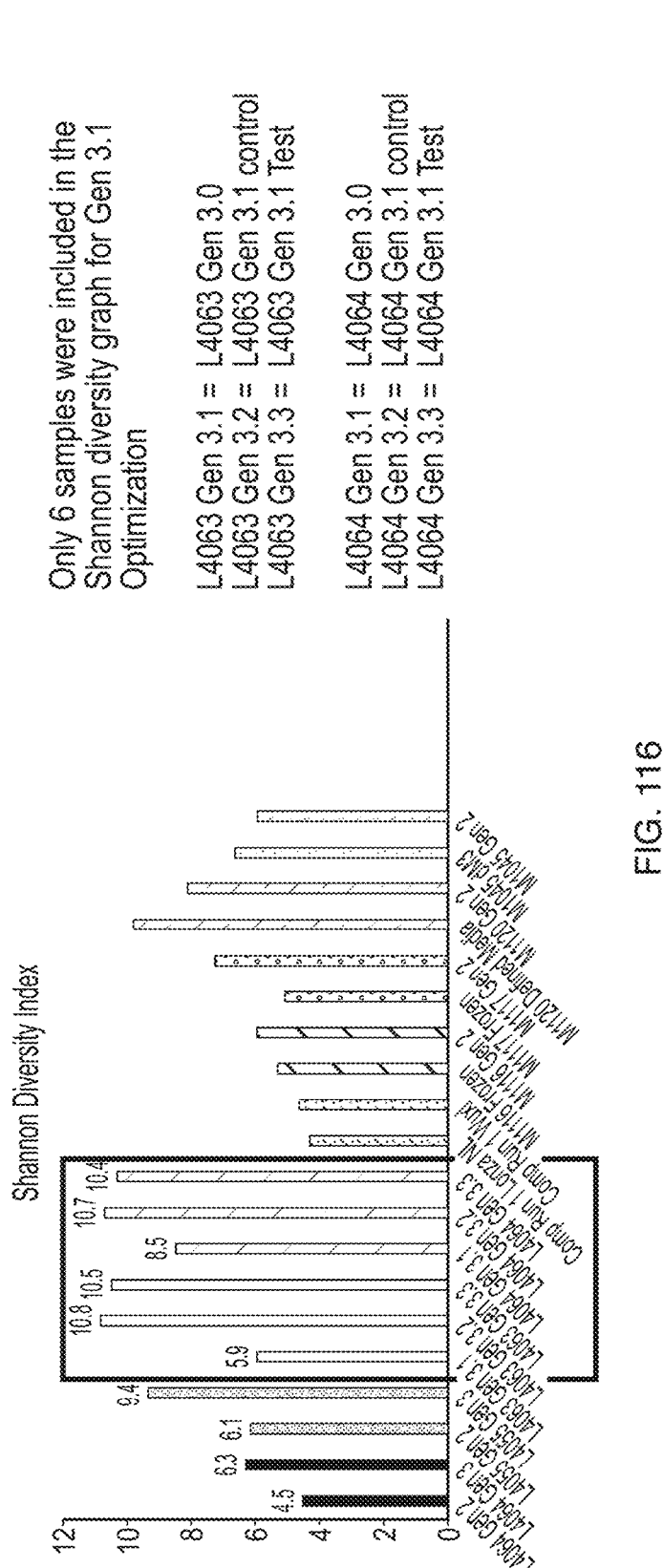

FIG. 116: Shannon diversity index.

BRIEF DESCRIPTION OF THE SEQUENCE LISTING

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is the amino acid sequence of a recombinant human IL-4 protein.

SEQ ID NO:6 is the amino acid sequence of a recombinant human IL-7 protein.

SEQ ID NO:7 is the amino acid sequence of a recombinant human IL-15 protein.

SEQ ID NO:8 is the amino acid sequence of a recombinant human IL-21 protein.

SEQ ID NO:9 is the amino acid sequence of human 4-1BB.

SEQ ID NO:10 is the amino acid sequence of murine 4-1BB.

SEQ ID NO:11 is the heavy chain for the 4-1BB agonist monoclonal antibody utomilumab (PF-05082566).

SEQ ID NO:12 is the light chain for the 4-1BB agonist monoclonal antibody utomilumab (PF-05082566).

SEQ ID NO:13 is the heavy chain variable region (VH) for the 4-1BB agonist monoclonal antibody utomilumab (PF-05082566).

SEQ ID NO:14 is the light chain variable region (VL) for the 4-1BB agonist monoclonal antibody utomilumab (PF-05082566).

SEQ ID NO:15 is the heavy chain CDR1 for the 4-1BB agonist monoclonal antibody utomilumab (PF-05082566).

SEQ ID NO:16 is the heavy chain CDR2 for the 4-1BB agonist monoclonal antibody utomilumab (PF-05082566).

SEQ ID NO:17 is the heavy chain CDR3 for the 4-1BB agonist monoclonal antibody utomilumab (PF-05082566).

SEQ ID NO:18 is the light chain CDR1 for the 4-1BB agonist monoclonal antibody utomilumab (PF-05082566).

SEQ ID NO:19 is the light chain CDR2 for the 4-1BB agonist monoclonal antibody utomilumab (PF-05082566).

SEQ ID NO:20 is the light chain CDR3 for the 4-1BB agonist monoclonal antibody utomilumab (PF-05082566).

SEQ ID NO:21 is the heavy chain for the 4-1BB agonist monoclonal antibody urelumab (BMS-663513).

SEQ ID NO:22 is the light chain for the 4-1BB agonist monoclonal antibody urelumab (BMS-663513).

SEQ ID NO:23 is the heavy chain variable region (VH) for the 4-1BB agonist monoclonal antibody urelumab (BMS-663513).

SEQ ID NO:24 is the light chain variable region (VL) for the 4-1BB agonist monoclonal antibody urelumab (BMS-663513).

SEQ ID NO:25 is the heavy chain CDR1 for the 4-1BB agonist monoclonal antibody urelumab (BMS-663513).

SEQ ID NO:26 is the heavy chain CDR2 for the 4-1BB agonist monoclonal antibody urelumab (BMS-663513).

SEQ ID NO:27 is the heavy chain CDR3 for the 4-1BB agonist monoclonal antibody urelumab (BMS-663513).

SEQ ID NO:28 is the light chain CDR1 for the 4-1BB agonist monoclonal antibody urelumab (BMS-663513).

SEQ ID NO:29 is the light chain CDR2 for the 4-1BB agonist monoclonal antibody urelumab (BMS-663513).

SEQ ID NO:30 is the light chain CDR3 for the 4-1BB agonist monoclonal antibody urelumab (BMS-663513).

SEQ ID NO:31 is an Fc domain for a TNFRSF agonist fusion protein.

SEQ ID NO:32 is a linker for a TNFRSF agonist fusion protein.

SEQ ID NO:33 is a linker for a TNFRSF agonist fusion protein.

SEQ ID NO:34 is a linker for a TNFRSF agonist fusion protein.

SEQ ID NO:35 is a linker for a TNFRSF agonist fusion protein.

SEQ ID NO:36 is a linker for a TNFRSF agonist fusion protein.

SEQ ID NO:37 is a linker for a TNFRSF agonist fusion protein.

SEQ ID NO:38 is a linker for a TNFRSF agonist fusion protein.

SEQ ID NO:39 is a linker for a TNFRSF agonist fusion protein.

SEQ ID NO:40 is a linker for a TNFRSF agonist fusion protein.

SEQ ID NO:41 is a linker for a TNFRSF agonist fusion protein.

SEQ ID NO:42 is an Fc domain for a TNFRSF agonist fusion protein.

SEQ ID NO:43 is a linker for a TNFRSF agonist fusion protein.

SEQ ID NO:44 is a linker for a TNFRSF agonist fusion protein.

SEQ ID NO:45 is a linker for a TNFRSF agonist fusion protein.

SEQ ID NO:46 is a 4-1BB ligand (4-1BBL) amino acid sequence.

SEQ ID NO:47 is a soluble portion of 4-1BBL polypeptide.

SEQ ID NO:48 is a heavy chain variable region (VH) for the 4-1BB agonist antibody 4B4-1-1 version 1.

SEQ ID NO:49 is a light chain variable region (VL) for the 4-1BB agonist antibody 4B4-1-1 version 1.

SEQ ID NO:50 is a heavy chain variable region (VH) for the 4-1BB agonist antibody 4B4-1-1 version 2.

SEQ ID NO:51 is a light chain variable region (VL) for the 4-1BB agonist antibody 4B4-1-1 version 2.

SEQ ID NO:52 is a heavy chain variable region (VH) for the 4-1BB agonist antibody H39E3-2.

SEQ ID NO:53 is a light chain variable region (VL) for the 4-1BB agonist antibody H39E3-2.

SEQ ID NO:54 is the amino acid sequence of human OX40.

SEQ ID NO:55 is the amino acid sequence of murine OX40.

SEQ ID NO:56 is the heavy chain for the OX40 agonist monoclonal antibody tavolixizumab (MEDI-0562).

SEQ ID NO:57 is the light chain for the OX40 agonist monoclonal antibody tavolixizumab (MEDI-0562).

SEQ ID NO:58 is the heavy chain variable region (VH) for the OX40 agonist monoclonal antibody tavolixizumab (MEDI-0562).

SEQ ID NO:59 is the light chain variable region (VL) for the OX40 agonist monoclonal antibody tavolixizumab (MEDI-0562).

SEQ ID NO:60 is the heavy chain CDR1 for the OX40 agonist monoclonal antibody tavolixizumab (MEDI-0562).

SEQ ID NO:61 is the heavy chain CDR2 for the OX40 agonist monoclonal antibody tavolixizumab (MEDI-0562).

SEQ ID NO:62 is the heavy chain CDR3 for the OX40 agonist monoclonal antibody tavolixizumab (MEDI-0562).

SEQ ID NO:63 is the light chain CDR1 for the OX40 agonist monoclonal antibody tavolixizumab (MEDI-0562).

SEQ ID NO:64 is the light chain CDR2 for the OX40 agonist monoclonal antibody tavolixizumab (MEDI-0562).

SEQ ID NO:65 is the light chain CDR3 for the OX40 agonist monoclonal antibody tavolixizumab (MEDI-0562).

SEQ ID NO:66 is the heavy chain for the OX40 agonist monoclonal antibody 11D4.

SEQ ID NO:67 is the light chain for the OX40 agonist monoclonal antibody 11D4.

SEQ ID NO:68 is the heavy chain variable region (VH) for the OX40 agonist monoclonal antibody 11D4.

SEQ ID NO:69 is the light chain variable region (VL) for the OX40 agonist monoclonal antibody 11D4.

SEQ ID NO:70 is the heavy chain CDR1 for the OX40 agonist monoclonal antibody 11D4.

SEQ ID NO:71 is the heavy chain CDR2 for the OX40 agonist monoclonal antibody 11D4.

SEQ ID NO:72 is the heavy chain CDR3 for the OX40 agonist monoclonal antibody 11D4.

SEQ ID NO:73 is the light chain CDR1 for the OX40 agonist monoclonal antibody 11D4.

SEQ ID NO:74 is the light chain CDR2 for the OX40 agonist monoclonal antibody 11D4.

SEQ ID NO:75 is the light chain CDR3 for the OX40 agonist monoclonal antibody 11D4.

SEQ ID NO:76 is the heavy chain for the OX40 agonist monoclonal antibody 18D8.

SEQ ID NO:77 is the light chain for the OX40 agonist monoclonal antibody 18D8.

SEQ ID NO:78 is the heavy chain variable region (VH) for the OX40 agonist monoclonal antibody 18D8.

SEQ ID NO:79 is the light chain variable region (VL) for the OX40 agonist monoclonal antibody 18D8.

SEQ ID NO:80 is the heavy chain CDR1 for the OX40 agonist monoclonal antibody 18D8.

SEQ ID NO:81 is the heavy chain CDR2 for the OX40 agonist monoclonal antibody 18D8.

SEQ ID NO:82 is the heavy chain CDR3 for the OX40 agonist monoclonal antibody 18D8.

SEQ ID NO:83 is the light chain CDR1 for the OX40 agonist monoclonal antibody 18D8.

SEQ ID NO:84 is the light chain CDR2 for the OX40 agonist monoclonal antibody 18D8.

SEQ ID NO:85 is the light chain CDR3 for the OX40 agonist monoclonal antibody 18D8.

SEQ ID NO:86 is the heavy chain variable region (VH) for the OX40 agonist monoclonal antibody Hu119-122.

SEQ ID NO:87 is the light chain variable region (VL) for the OX40 agonist monoclonal antibody Hu119-122.

SEQ ID NO:88 is the heavy chain CDR1 for the OX40 agonist monoclonal antibody Hu119-122.

SEQ ID NO:89 is the heavy chain CDR2 for the OX40 agonist monoclonal antibody Hu119-122.

SEQ ID NO:90 is the heavy chain CDR3 for the OX40 agonist monoclonal antibody Hu119-122.

SEQ ID NO:91 is the light chain CDR1 for the OX40 agonist monoclonal antibody Hu119-122.

SEQ ID NO:92 is the light chain CDR2 for the OX40 agonist monoclonal antibody Hu119-122.

SEQ ID NO:93 is the light chain CDR3 for the OX40 agonist monoclonal antibody Hu119-122.

SEQ ID NO:94 is the heavy chain variable region (VH) for the OX40 agonist monoclonal antibody Hu106-222.

SEQ ID NO:95 is the light chain variable region (VL) for the OX40 agonist monoclonal antibody Hu106-222.

SEQ ID NO:96 is the heavy chain CDR1 for the OX40 agonist monoclonal antibody Hu106-222.

SEQ ID NO:97 is the heavy chain CDR2 for the OX40 agonist monoclonal antibody Hu106-222.

SEQ ID NO:98 is the heavy chain CDR3 for the OX40 agonist monoclonal antibody Hu106-222.

SEQ ID NO:99 is the light chain CDR1 for the OX40 agonist monoclonal antibody Hu106-222.

SEQ ID NO:100 is the light chain CDR2 for the OX40 agonist monoclonal antibody Hu106-222.

SEQ ID NO:101 is the light chain CDR3 for the OX40 agonist monoclonal antibody Hu106-222.

SEQ ID NO:102 is an OX40 ligand (OX40L) amino acid sequence.

SEQ ID NO:103 is a soluble portion of OX40L polypeptide.

SEQ ID NO:104 is an alternative soluble portion of OX40L polypeptide.

SEQ ID NO:105 is the heavy chain variable region (VH) for the OX40 agonist monoclonal antibody 008.

SEQ ID NO:106 is the light chain variable region (VL) for the OX40 agonist monoclonal antibody 008.

SEQ ID NO:107 is the heavy chain variable region (VH) for the OX40 agonist monoclonal antibody 011.

SEQ ID NO:108 is the light chain variable region (VL) for the OX40 agonist monoclonal antibody 011.

SEQ ID NO:109 is the heavy chain variable region (VH) for the OX40 agonist monoclonal antibody 021.

SEQ ID NO:110 is the light chain variable region (VL) for the OX40 agonist monoclonal antibody 021.

SEQ ID NO:111 is the heavy chain variable region (VH) for the OX40 agonist monoclonal antibody 023.

SEQ ID NO:112 is the light chain variable region (VL) for the OX40 agonist monoclonal antibody 023.

SEQ ID NO:113 is the heavy chain variable region (VH) for an OX40 agonist monoclonal antibody.

SEQ ID NO:114 is the light chain variable region (VL) for an OX40 agonist monoclonal antibody.

SEQ ID NO:115 is the heavy chain variable region (VH) for an OX40 agonist monoclonal antibody.

SEQ ID NO:116 is the light chain variable region (VL) for an OX40 agonist monoclonal antibody.

SEQ ID NO:117 is the heavy chain variable region (VH) for a humanized OX40 agonist monoclonal antibody.

SEQ ID NO:118 is the heavy chain variable region (VH) for a humanized OX40 agonist monoclonal antibody.

SEQ ID NO:119 is the light chain variable region (VL) for a humanized OX40 agonist monoclonal antibody.

SEQ ID NO:120 is the light chain variable region (VL) for a humanized OX40 agonist monoclonal antibody.

SEQ ID NO:121 is the heavy chain variable region (VH) for a humanized OX40 agonist monoclonal antibody.

SEQ ID NO:122 is the heavy chain variable region (VH) for a humanized OX40 agonist monoclonal antibody.

SEQ ID NO:123 is the light chain variable region (VL) for a humanized OX40 agonist monoclonal antibody.

SEQ ID NO:124 is the light chain variable region (VL) for a humanized OX40 agonist monoclonal antibody.

SEQ ID NO:125 is the heavy chain variable region (VH) for an OX40 agonist monoclonal antibody.

SEQ ID NO:126 is the light chain variable region (VL) for an OX40 agonist monoclonal antibody.

SEQ ID NO:127-462 are currently not assigned.

SEQ ID NO:463 is the heavy chain amino acid sequence of the PD-1 inhibitor nivolumab.

SEQ ID NO:464 is the light chain amino acid sequence of the PD-1 inhibitor nivolumab.

SEQ ID NO:465 is the heavy chain variable region ($V_H$) amino acid sequence of the PD-1 inhibitor nivolumab.

SEQ ID NO:466 is the light chain variable region ($V_L$) amino acid sequence of the PD-1 inhibitor nivolumab.

SEQ ID NO:467 is the heavy chain CDR1 amino acid sequence of the PD-1 inhibitor nivolumab.

SEQ ID NO:468 is the heavy chain CDR2 amino acid sequence of the PD-1 inhibitor nivolumab.

SEQ ID NO:469 is the heavy chain CDR3 amino acid sequence of the PD-1 inhibitor nivolumab.

SEQ ID NO:470 is the light chain CDR1 amino acid sequence of the PD-1 inhibitor nivolumab.

SEQ ID NO:471 is the light chain CDR2 amino acid sequence of the PD-1 inhibitor nivolumab.

SEQ ID NO:472 is the light chain CDR3 amino acid sequence of the PD-1 inhibitor nivolumab.

SEQ ID NO:473 is the heavy chain amino acid sequence of the PD-1 inhibitor pembrolizumab.

SEQ ID NO:474 is the light chain amino acid sequence of the PD-1 inhibitor pembrolizumab.

SEQ ID NO:475 is the heavy chain variable region ($V_H$) amino acid sequence of the PD-1 inhibitor pembrolizumab.

SEQ ID NO:476 is the light chain variable region ($V_L$) amino acid sequence of the PD-1 inhibitor pembrolizumab.

SEQ ID NO:477 is the heavy chain CDR1 amino acid sequence of the PD-1 inhibitor pembrolizumab.

SEQ ID NO:478 is the heavy chain CDR2 amino acid sequence of the PD-1 inhibitor pembrolizumab.

SEQ ID NO:479 is the heavy chain CDR3 amino acid sequence of the PD-1 inhibitor pembrolizumab.

SEQ ID NO:480 is the light chain CDR1 amino acid sequence of the PD-1 inhibitor pembrolizumab.

SEQ ID NO:481 is the light chain CDR2 amino acid sequence of the PD-1 inhibitor pembrolizumab.

SEQ ID NO:482 is the light chain CDR3 amino acid sequence of the PD-1 inhibitor pembrolizumab.

SEQ ID NO:483 is the heavy chain amino acid sequence of the PD-L1 inhibitor durvalumab.

SEQ ID NO:484 is the light chain amino acid sequence of the PD-L1 inhibitor durvalumab.

SEQ ID NO:485 is the heavy chain variable region ($V_H$) amino acid sequence of the PD-L1 inhibitor durvalumab.

SEQ ID NO:486 is the light chain variable region ($V_L$) amino acid sequence of the PD-L1 inhibitor durvalumab.

SEQ ID NO:487 is the heavy chain CDR1 amino acid sequence of the PD-L1 inhibitor durvalumab.

SEQ ID NO:488 is the heavy chain CDR2 amino acid sequence of the PD-L1 inhibitor durvalumab.

SEQ ID NO:489 is the heavy chain CDR3 amino acid sequence of the PD-L1 inhibitor durvalumab.

SEQ ID NO:490 is the light chain CDR1 amino acid sequence of the PD-L1 inhibitor durvalumab.

SEQ ID NO:491 is the light chain CDR2 amino acid sequence of the PD-L1 inhibitor durvalumab.

SEQ ID NO:492 is the light chain CDR3 amino acid sequence of the PD-L1 inhibitor durvalumab.

SEQ ID NO:493 is the heavy chain amino acid sequence of the PD-L1 inhibitor avelumab.

SEQ ID NO:494 is the light chain amino acid sequence of the PD-L1 inhibitor avelumab.

SEQ ID NO:495 is the heavy chain variable region ($V_H$) amino acid sequence of the PD-L1 inhibitor avelumab.

SEQ ID NO:496 is the light chain variable region ($V_L$) amino acid sequence of the PD-L1 inhibitor avelumab.

SEQ ID NO:497 is the heavy chain CDR1 amino acid sequence of the PD-L1 inhibitor avelumab.

SEQ ID NO:498 is the heavy chain CDR2 amino acid sequence of the PD-L1 inhibitor avelumab.

SEQ ID NO:499 is the heavy chain CDR3 amino acid sequence of the PD-L1 inhibitor avelumab.

SEQ ID NO:500 is the light chain CDR1 amino acid sequence of the PD-L1 inhibitor avelumab.

SEQ ID NO:501 is the light chain CDR2 amino acid sequence of the PD-L1 inhibitor avelumab.

SEQ ID NO:502 is the light chain CDR3 amino acid sequence of the PD-L1 inhibitor avelumab.

SEQ ID NO:503 is the heavy chain amino acid sequence of the PD-L1 inhibitor atezolizumab.

SEQ ID NO:504 is the light chain amino acid sequence of the PD-L1 inhibitor atezolizumab.

SEQ ID NO:505 is the heavy chain variable region ($V_H$) amino acid sequence of the PD-L1 inhibitor atezolizumab.

SEQ ID NO:506 is the light chain variable region ($V_L$) amino acid sequence of the PD-L1 inhibitor atezolizumab.

SEQ ID NO:507 is the heavy chain CDR1 amino acid sequence of the PD-L1 inhibitor atezolizumab.

SEQ ID NO:508 is the heavy chain CDR2 amino acid sequence of the PD-L1 inhibitor atezolizumab.

SEQ ID NO:509 is the heavy chain CDR3 amino acid sequence of the PD-L1 inhibitor atezolizumab.

SEQ ID NO:510 is the light chain CDR1 amino acid sequence of the PD-L1 inhibitor atezolizumab.

SEQ ID NO:511 is the light chain CDR2 amino acid sequence of the PD-L1 inhibitor atezolizumab.

SEQ ID NO:512 is the light chain CDR3 amino acid sequence of the PD-L1 inhibitor atezolizumab.

DETAILED DESCRIPTION OF THE INVENTION

I. Introduction

Adoptive cell therapy utilizing TILs cultured ex vivo by the Rapid Expansion Protocol (REP) has produced successful adoptive cell therapy following host immunosuppression in patients with cancer such as melanoma. Current infusion acceptance parameters rely on readouts of the composition of TILs (e.g., CD28, CD8, or CD4 positivity) and on the numerical folds of expansion and viability of the REP product.

Current REP protocols give little insight into the health of the TIL that will be infused into the patient. T cells undergo a profound metabolic shift during the course of their maturation from naïve to effector T cells (see Chang, et al., *Nat. Immunol.* 2016, 17, 364, hereby expressly incorporated in its entirety, and in particular for the discussion and markers of anaerobic and aerobic metabolism). For example, naïve T cells rely on mitochondrial respiration to produce ATP, while mature, healthy effector T cells such as TIL are highly glycolytic, relying on aerobic glycolysis to provide the bioenergetics substrates they require for proliferation, migration, activation, and anti-tumor efficacy.

Current TIL manufacturing and treatment processes are limited by length, cost, sterility concerns, and other factors described herein such that the potential to treat patients which are refractory to anti-PD1 and as such have been severely limited. There is an urgent need to provide TIL manufacturing processes and therapies based on such processes that are appropriate for use in treating patients for whom very few or no viable treatment options remain. The present invention meets this need by providing a shortened manufacturing process for use in generating TILs which can then be employed in the treatment of non-small cell lung carcinoma (NSCLC) patients whom are refractory to anti-PD-1 treatment.

II. Definitions

Unless defined otherwise, all technical and scientific terms used herein have the same meaning as is commonly understood by one of skill in the art to which this invention belongs. All patents and publications referred to herein are incorporated by reference in their entireties.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are described herein.

By "tumor infiltrating lymphocytes" or "TILs" herein is meant a population of cells originally obtained as white blood cells that have left the bloodstream of a subject and migrated into a tumor. TILs include, but are not limited to, CD8$^+$ cytotoxic T cells (lymphocytes), Th1 and Th17 CD4$^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 (CCR7$^{hi}$) and CD62L (CD62$^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 (CCR7$^{lo}$) and are heterogeneous or low for CD62L expression) (CD62L$^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. When used as an antigen presenting cell (PBMCs are a type of antigen-presenting cell), the peripheral blood mononuclear cells are preferably irradiated allogeneic peripheral blood mononuclear cells.

The terms "peripheral blood lymphocytes" and "PBLs" refer to T cells expanded from peripheral blood. In some embodiments, PBLs are separated from whole blood or apheresis product from a donor. In some embodiments, PBLs are separated from whole blood or apheresis product from a donor by positive or negative selection of a T cell phenotype, such as the T cell phenotype of CD3+CD45+.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELL-GRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

TABLE 1

Amino acid sequences of muromonab.

| Identifier | Sequence (One-Letter Amino Acid Symbols) | | | | | |
|---|---|---|---|---|---|---|
| SEQ ID NO: 1 | QVQLQQSGAE | LARPGASVKM | SCKASGYTFT | RYTMHWVKQR | PGQGLEWIGY | INPSRGYTNY 60 |
| Muromonab heavy | NQKFKDKATL | TTDKSSSTAY | MQLSSLTSED | SAVYYCARYY | DDHYCLDYWG | QGTTLTVSSA 120 |
| chain | KTTAPSVYPL | APVCGGTTGS | SVTLGCLVKG | YFPEPVTLTW | NSGSLSSGVH | TFPAVLQSDL 180 |
| | YTLSSSVTVT | SSTWPSQSIT | CNVAHPASST | KVDKKIEPRP | KSCDKTHTCP | PCPAPELLGG 240 |
| | PSVFLFPPKP | KDTLMISRTP | EVTCVVVDVS | HEDPEVKFNW | YVDGVEVHNA | KTKPREEQYN 300 |
| | STYRVVSVLT | VLHQDWLNGK | EYKCKVSNKA | LPAPIEKTIS | KAKGQPREPQ | VYTLPPSRDE 360 |
| | LTKNQVSLTC | LVKGFYPSDI | AVEWESNGQP | ENNYKTTPPV | LDSDGSFFLY | SKLTVDKSRW 420 |
| | QQGNVFSCSV | MHEALHNHYT | QKSLSLSPGK | | | 450 |
| | | | | | | |
| SEQ ID NO: 2 | QIVLTQSPAI | MSASPGEKVT | MTCSASSSVS | YMNWYQQKSG | TSPKRWIYDT | SKLASGVPAH 60 |
| Muromonab light | FRGSGSGTSY | SLTISGMEAE | DAATYYCQQW | SSNPFTFGSG | TKLEINRADT | APTVSIFPPS 120 |
| chain | SEQLTSGGAS | VVCFLNNFYP | KDINVKWKID | GSERQNGVLN | SWTDQDSKDS | TYSMSSTLTL 180 |
| | TKDEYERHNS | YTCEATHKTS | TSPIVKSFNR | NEC | | 213 |

TABLE 2

Amino acid sequences of interleukins.

| Identifier | Sequence (One-Letter Amino Acid Symbols) | | | | | |
|---|---|---|---|---|---|---|
| SEQ ID NO: 3<br>recombinant<br>human IL-2<br>(rhIL-2) | MAPTSSSTKK<br>EEELKPLEEV<br>RWITFCQSII | TQLQLEHLLL<br>LNLAQSKNFH<br>STLT | DLQMILNGIN<br>LRPRDLISNI | NYKNPKLTRM<br>NVIVLELKGS | LTFKFYMPKK<br>ETTFMCEYAD | ATELKHLQCL<br>ETATIVEFLN | 60<br>120<br>134 |
| SEQ ID NO: 4<br>Aldesleukin | PTSSSTKKTQ<br>ELKPLEEVLN<br>ITFSQSIIST | LQLEHLLLDL<br>LAQSKNFHLR<br>LT | QMILNGINNY<br>PRDLISNINV | KNPKLTRMLT<br>IVLELKGSET | FKFYMPKKAT<br>TFMCEYADET | ELKHLQCLEE<br>ATIVEFLNRW | 60<br>120<br>132 |
| SEQ ID NO: 5<br>recombinant<br>human IL-4<br>(rhIL-4) | MHKCDITLQE<br>EKDTRCLGAT<br>MREKYSKCSS | IIKTLNSLTE<br>AQQFHRHKQL | QKTLCTELTV<br>IRFLKRLDRN | TDIFAASKNT<br>LWGLAGLNSC | TEKETFCRAA<br>PVKEANQSTL | TVLRQFYSHH<br>ENFLERLKTI | 60<br>120<br>130 |
| SEQ ID NO: 6<br>recombinant<br>human IL-7<br>(rhIL-7) | MDCDIEGKDG<br>ARKLRQFLKM<br>KEQKKLNDLC | KQYESVLMVS<br>NSTGDFDLHL<br>FLKRLLQEIK | IDQLLDSMKE<br>LKVSEGTTIL<br>TCWNKILMGT | IGSNCLNNEF<br>LNCTGQVKGR<br>KEH | NFFKRHICDA<br>KPAALGEAQP | NKEGMFLFRA<br>TKSLEENKSL | 60<br>120<br>153 |
| SEQ ID NO: 7<br>recombinant<br>human IL-15<br>(rhIL-15) | MNWVNVISDL<br>HDTVENLIIL | KKIEDLIQSM<br>ANNSLSSNGN | HIDATLYTES<br>VTESGCKECE | DVHPSCKVTA<br>ELEEKNIKEF | MKCFLLELQV<br>LQSFVHIVQM | ISLESGDASI<br>FINTS | 60<br>115 |
| SEQ ID NO: 8<br>recombinant<br>human IL-21<br>(rhIL-21) | MQDRHMIRMR<br>NNERIINVSI<br>HLSSRTHGSE | QLIDIVDQLK<br>KKLKRKPPST<br>DS | NYVNDLVPEF<br>NAGRRQKHRL | LPAPEDVETN<br>TCPSCDSYEK | CEWSAFSCFQ<br>KPPKEFLERF | KAQLKSANTG<br>KSLLQKMIHQ | 60<br>120<br>132 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and $IgG_1$ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human $CD4^+$ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "hematological malignancy", "hematologic malignancy" or terms of correlative meaning refer to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs). TILs obtained from liquid tumors, including liquid tumors circulating in peripheral blood, may also be referred to herein as PBLs. The terms MIL, TIL, and PBL are used interchangeably herein and differ only based on the tissue type from which the cells are derived.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.,* 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 8, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL.

The term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

The term "RNA" defines a molecule comprising at least one ribonucleotide residue. The term "ribonucleotide" defines a nucleotide with a hydroxyl group at the 2' position of a b-D-ribofuranose moiety. The term RNA includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Nucleotides of the RNA molecules described herein may also comprise non-standard nucleotides, such as non-naturally occurring nucleotides or chemically synthesized nucleotides or deoxynucleotides. These altered RNAs can be referred to as analogs or analogs of naturally-occurring RNA.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s).

The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

The terms "antibody" and its plural form "antibodies" refer to whole immunoglobulins and any antigen-binding fragment ("antigen-binding portion") or single chains thereof. An "antibody" further refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions of an antibody may be further subdivided into regions of hypervariability, which are referred to as complementarity determining regions (CDR) or hypervariable regions (HVR), and which can be interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen epitope or epitopes. The constant regions of the antibodies may mediate the binding of the immunoglobulin to host tissues or factors, including various cells of the immune system (e.g., effector cells) and the first component (C1q) of the classical complement system.

The term "antigen" refers to a substance that induces an immune response. In some embodiments, an antigen is a molecule capable of being bound by an antibody or a TCR if presented by major histocompatibility complex (MHC) molecules. The term "antigen", as used herein, also encompasses T cell epitopes. An antigen is additionally capable of being recognized by the immune system. In some embodiments, an antigen is capable of inducing a humoral immune response or a cellular immune response leading to the activation of B lymphocytes and/or T lymphocytes. In some cases, this may require that the antigen contains or is linked to a Th cell epitope. An antigen can also have one or more epitopes (e.g., B- and T-epitopes). In some embodiments, an antigen will preferably react, typically in a highly specific and selective manner, with its corresponding antibody or TCR and not with the multitude of other antibodies or TCRs which may be induced by other antigens.

The terms "monoclonal antibody," "mAb," "monoclonal antibody composition," or their plural forms refer to a preparation of antibody molecules of single molecular composition. A monoclonal antibody composition displays a single binding specificity and affinity for a particular epitope. Monoclonal antibodies specific to certain receptors can be made using knowledge and skill in the art of injecting test subjects with suitable antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

The terms "antigen-binding portion" or "antigen-binding fragment" of an antibody (or simply "antibody portion" or "fragment"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and CH1 domains; (ii) a F(ab')2 fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a domain antibody (dAb) fragment (Ward, et al., *Nature,* 1989, 341, 544-546), which may consist of a $V_H$ or a $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see, e.g., Bird, et al., *Science* 1988, 242, 423-426; and Huston, et al., *Proc. Natl. Acad. Sci. USA* 1988, 85, 5879-5883). Such scFv antibodies are also intended to be encompassed within the terms "antigen-binding portion" or "antigen-binding fragment" of an antibody. These antibody fragments are obtained using conventional techniques known to those with skill in the art, and the fragments are screened for utility in the same manner as are intact antibodies.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). The term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In an embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, including a conjugate of the antibody and another active pharmaceutical ingredient or antibody. The terms "conjugate," "antibody-drug conjugate", "ADC," or "immunoconjugate" refers to an antibody, or a fragment thereof, conjugated to another therapeutic moiety, which can be conjugated to antibodies described herein using methods available in the art.

The terms "humanized antibody," "humanized antibodies," and "humanized" are intended to refer to antibodies in which CDR sequences derived from the germline of another mammalian species, such as a mouse, have been grafted onto human framework sequences. Additional framework region modifications may be made within the human framework sequences. Humanized forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a 15 hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones, et al., *Nature* 1986, 321, 522-525; Riechmann, et al., *Nature* 1988, 332, 323-329; and Presta, *Curr. Op. Struct. Biol.* 1992, 2, 593-596. The antibodies described herein may also be modified to employ any Fc variant which is known to impart an improvement (e.g., reduction) in effector function and/or FcR binding. The Fc variants may include, for example, any one of the amino acid substitutions disclosed in International Patent Application Publication Nos. WO 1988/07089 A1, WO 1996/14339 A1, WO 1998/05787 A1, WO 1998/23289 A1, WO 1999/51642 A1, WO 99/58572 A1, WO 2000/09560 A2, WO 2000/32767 A1, WO 2000/42072 A2, WO 2002/44215 A2, WO 2002/060919 A2, WO 2003/074569 A2, WO 2004/016750 A2, WO 2004/029207 A2, WO 2004/035752 A2, WO 2004/063351 A2, WO 2004/074455 A2, WO 2004/099249 A2, WO 2005/040217 A2, WO 2005/070963 A1, WO 2005/077981 A2, WO 2005/092925 A2, WO 2005/123780 A2, WO 2006/019447 A1, WO 2006/047350 A2, and WO 2006/085967 A2; and U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784; the disclosures of which are incorporated by reference herein.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., European Patent No. EP 404,097, International Patent Publication No. WO 93/11161; and Bolliger, et al., *Proc. Natl. Acad. Sci. USA* 1993, 90, 6444-6448.

The term "glycosylation" refers to a modified derivative of an antibody. An aglycoslated antibody lacks glycosylation. Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Aglycosylation may increase the affinity of the antibody for antigen, as described in U.S. Pat. Nos. 5,714,350 and 6,350,861. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see e.g. U.S. Patent Publication No. 2004/0110704 or Yamane-Ohnuki, et al., *Biotechnol. Bioeng.*, 2004, 87, 614-622). As another example, European Patent No. EP 1,176,195 describes a cell line with a functionally disrupted FUT8 gene, which encodes a fucosyl transferase, such that antibodies expressed in such a cell line exhibit hypofucosylation by reducing or eliminating the alpha 1,6 bond-related enzyme, and also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). International Patent Publication WO 03/035835 describes a variant CHO cell line, Lec 13 cells, with reduced ability to attach fucose to Asn(297)-linked carbohydrates, also resulting in hypofucosylation of antibodies expressed in that host cell (see also Shields, et al., *J. Biol. Chem.* 2002, 277, 26733-26740. International Patent Publication WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana, et al., *Nat. Biotech.* 1999, 17, 176-180). Alternatively, the fucose residues of the antibody may be cleaved off using a fucosidase enzyme. For example, the fucosidase alpha-L-fucosidase removes fucosyl residues from antibodies as described in Tarentino, et al., *Biochem.* 1975, 14, 5516-5523.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono $(C_1-C_{10})$alkoxy- or aryloxy-polyethylene glycol or polyethylene glycol-maleimide. The antibody to be pegylated may be an aglycosylated antibody. Methods for pegylation are known in the art and can be applied to the antibodies of the invention, as described for example in European Patent Nos. EP 0154316 and EP 0401384 and U.S. Pat. No. 5,824,778, the disclosures of each of which are incorporated by reference herein.

The term "biosimilar" means a biological product, including a monoclonal antibody or protein, that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference IL-2 protein is aldesleukin (PROLEUKIN), a protein approved by drug regulatory authorities with reference to aldesleukin is a "biosimilar to" aldesleukin or is a "biosimilar thereof" of aldesleukin. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorized, approved for authorization or subject of an application for authorization under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorized by the EMA. However, in some instances, the biosimilar may be compared to a biological medicinal product which has been authorized outside the European Economic Area (a non-EEA authorized "comparator") in certain studies. Such studies include for example certain clinical and in vivo non-clinical studies. As used herein, the term "biosimilar" also relates to a biological medicinal product which has been or may be compared to a non-EEA authorized comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorized or considered suitable for authorization. In certain circumstances, the biosimilar exhibits different binding characteristics as compared to the reference medicinal product, wherein the different binding characteristics are considered by a Regulatory Authority such as the EMA not to be a barrier for authorization as a similar biological product. The term "biosimilar" is also used synonymously by other national and regional regulatory agencies.

III. TIL Manufacturing Processes—2A

Figures 2A, 2B:
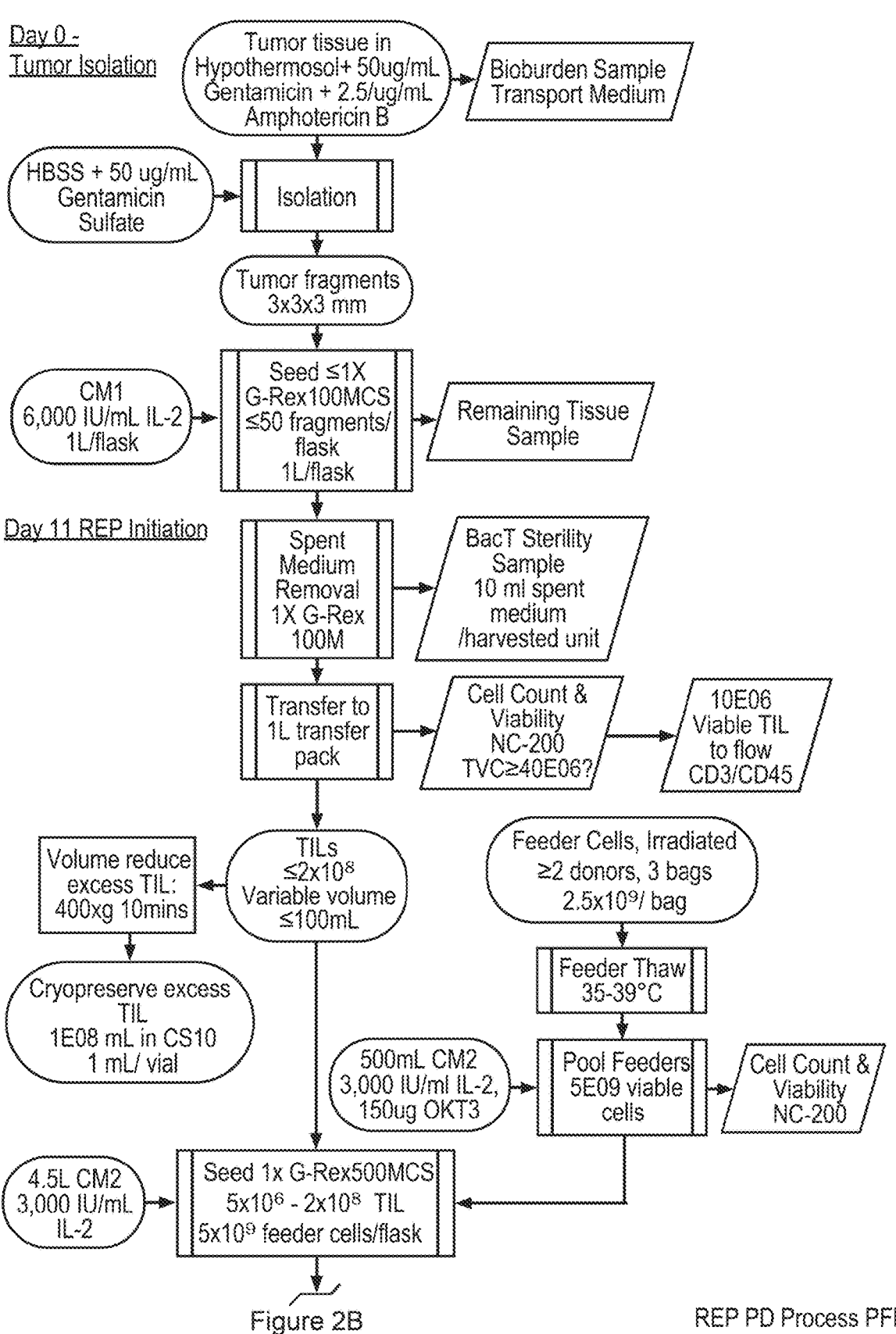
Figure 2B:
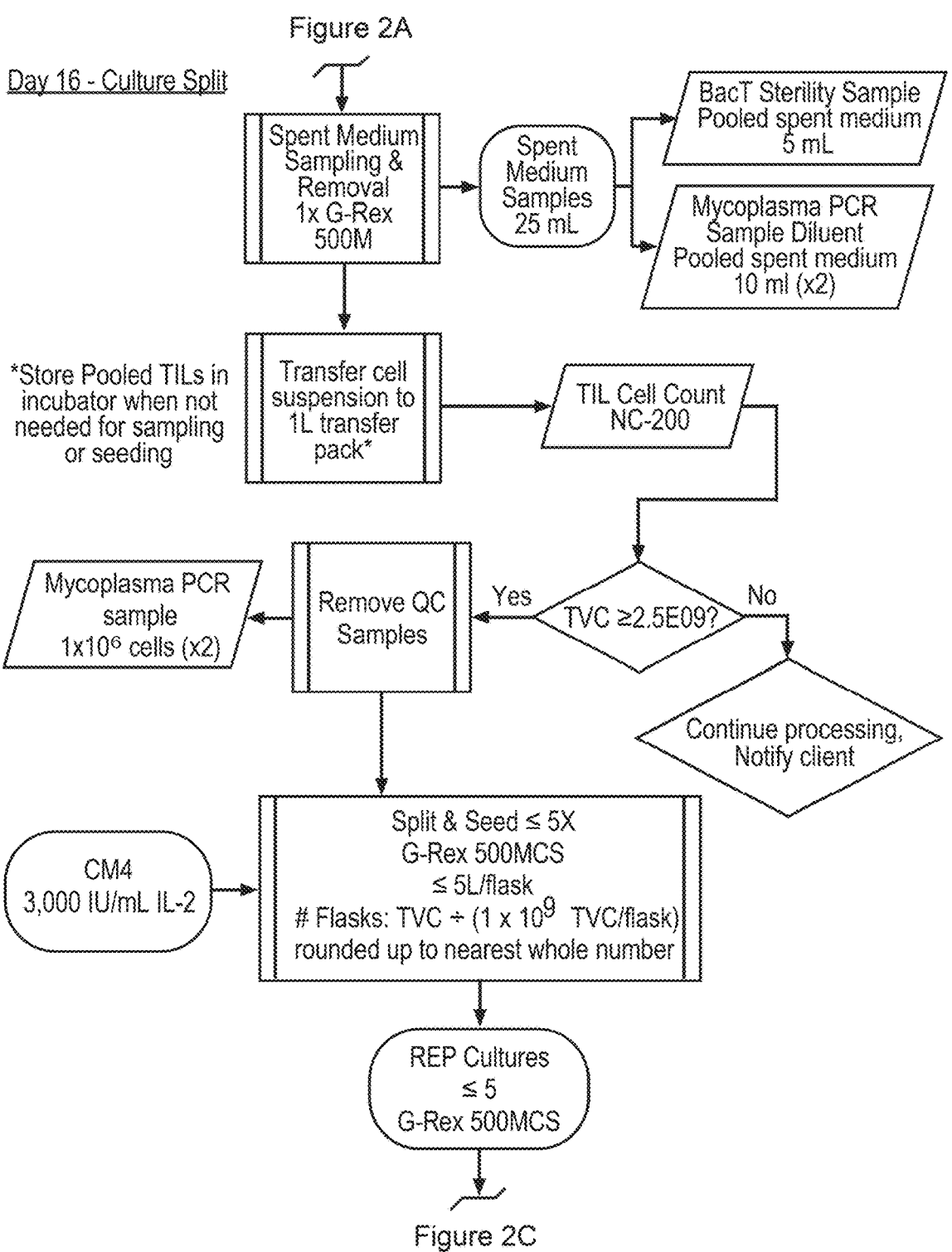

An exemplary TIL process known as process 2A containing some of these features is depicted in FIG. 2, and some of the advantages of this embodiment of the present invention over process 1C are described in Figures F and G. An embodiment of process 2A is shown FIG. 1.

As discussed herein, the present invention can include a step relating to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 1 as Step A) is shortened to 3 to 14 days and the second expansion (including processes referred to as the REP as well as processes shown in FIG. 1 as Step B) is shorted to 7 to 14 days, as discussed in detail below as well as in the examples and figures. In some embodiments, the first expansion (for example, an expansion described as Step B in FIG. 1) is shortened to 11 days and the second expansion (for example, an expansion as described in Step D in FIG. 1) is shortened to 11 days. In some embodiments, the combination of the first expansion and second expansion (for example, expansions described as Step B and Step D in FIG. 1) is shortened to 22 days, as discussed in detail below and in the examples and figures.

The "Step" Designations A, B, C, etc., below are in reference to FIG. 1 and in reference to certain embodiments described herein. The ordering of the Steps below and in FIG. 1 is exemplary and any combination or order of steps, as well as additional steps, repetition of steps, and/or omission of steps is contemplated by the present application and the methods disclosed herein.

A. Step A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy, core biopsy, small biopsy, or other means for obtaining a sample that contains a mixture of tumor and TIL cells. In some embodiments, multilesional sampling is used. In some embodiments, surgical resection, needle biopsy, core biopsy, small biopsy, or other means for obtaining a sample that contains a mixture of tumor and TIL cells includes multilesional sampling (i.e., obtaining samples from one or more tumor cites and/or locations in the patient, as well as one or more tumors in the same location or in close proximity). In general, the tumor sample may be from any solid tumor, including primary tumors, invasive tumors or metastatic tumors. The tumor sample may also be a liquid tumor, such as a tumor obtained from a hematological malignancy. The solid tumor may be of lung tissue. In some embodiments, useful TILs are obtained from non-small cell lung carcinoma (NSCLC).

Once obtained, the tumor sample is generally fragmented using sharp dissection into small pieces of between 1 to about 8 mm³, with from about 2-3 mm³ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/ml 10× working stock.

In some embodiments, the enzyme mixture comprises DNAse. In some embodiments, the working stock for the DNAse is a 10,000 IU/ml 10× working stock.

In some embodiments, the enzyme mixture comprises hyaluronidase. In some embodiments, the working stock for the hyaluronidase is a 10-mg/ml 10× working stock.

In some embodiments, the enzyme mixture comprises 10 mg/ml collagenase, 1000 IU/ml DNAse, and 1 mg/ml hyaluronidase.

In some embodiments, the enzyme mixture comprises 10 mg/ml collagenase, 500 IU/ml DNAse, and 1 mg/ml hyaluronidase.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 1). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumors are 1-4 mm×1-4 mm×1-4 mm. In some embodiments, the tumors are 1 mm×1 mm×1 mm. In some embodiments, the tumors are 2 mm×2 mm×2 mm. In some embodiments, the tumors are 3 mm×3 mm×3 mm. In some embodiments, the tumors are 4 mm×4 mm×4 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 1.

B. Step B: First Expansion

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology*, 75:157-167 (2012); Dudley et al., *Clin Cancer Res*, 16:6122-6131 (2010); Huang et al., *J Immunother*, 28(3):258-267 (2005); Besser et al., *Clin Cancer Res*, 19(17):OF1-OF9 (2013); Besser et al., *J Immunother* 32:415-423 (2009); Robbins, et al., *J Immunol* 2004; 173: 7125-7130; Shen et al., *J Immunother*, 30:123-129 (2007); Zhou, et al., *J Immunother*, 28:53-62 (2005); and Tran, et al., *J Immunother*, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 1. In some embodiments, the TILs obtained by the present method exhibit an increase in the T-cell repertoire diversity as compared to freshly harvested TILs and/or TILs prepared using methods referred to as process 1C, as exemplified in FIG. 5 and/or FIG. 6. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 1, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 1, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10-40× $10^6$ viable tumor digest cells or 5-30 tumor fragments in 10-40 mL of CM with IL-2. Both the G-Rex10 and 24-well plates were incubated in a humidified incubator at 37° C. in 5% CO$_2$ and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of 20-30×$10^6$ IU/mg for a 1 mg vial. In some embodiments the IL-2 stock solution has a specific activity of 20×$10^6$ IU/mg for a 1 mg vial. In some embodiments the IL-2 stock solution has a specific activity of 25×$10^6$ IU/mg for a 1 mg vial. In some embodiments the IL-2 stock solution has a specific activity of 30×$10^6$ IU/mg for a 1 mg vial. In some embodiments, the IL-2 stock solution has a final concentration of 4-8×$10^6$ IU/mg of IL-2. In some embodiments, the IL-2 stock solution has a final concentration of 5-7×$10^6$ IU/mg of IL-2. In some embodiments, the IL-2 stock solution has a final concentration of $6 \times 10^6$ IU/mg of IL-2. In some embodiments, the IL-2 stock solution is prepare as described in Example 5. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

TABLE 3

| Amino acid sequences of muromonab (exemplary OKT-3 antibody) | | | | | | |
|---|---|---|---|---|---|---|
| Identifier | Sequence (One-Letter Amino Acid Symbols) | | | | | |
| SEQ ID NO: 1 | QVQLQQSGAE | LARPGASVKM | SCKASGYTFT | RYTMHWVKQR | PGQGLEWIGY | INPSRGYTNY | 60 |
| Muromonab heavy | NQKFKDKATL | TTDKSSSTAY | MQLSSLTSED | SAVYYCARYY | DDHYCLDYWG | QGTTLTVSSA | 120 |
| chain | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAHPASST | KVDKKIEPRP | KSCDKTHTCP | PCPAPELLGG | 240 |
| | PSVFLFPPKP | KDTLMISRTP | EVTCVVVDVS | HEDPEVKFNW | YVDGVEVHNA | KTKPREEQYN | 300 |
| | STYRVVSVLT | VLHQDWLNGK | EYKCKVSNKA | LPAPIEKTIS | KAKGQPREPQ | VYTLPPSRDE | 360 |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| SEQ ID NO: 2 | QIVLTQSPAI | MSASPGEKVT | MTCSASSSVS | YMNWYQQKSG | TSPKRWIYDT | SKLASGVPAH | 60 |
| Muromonab light | FRGSGSGTSY | SLTISGMEAE | DAATYYCQQW | SSNPFTFGSG | TKLEINRADT | APTVSIFPPS | 120 |
| chain | SEQLTSGGAS | VVCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 | media comprises about 200 IU/mL of IL-15. In some embodiments, the cell culture medium comprises about 180 IU/mL of IL-15. In an embodiment, the cell culture medium In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm² gas-permeable silicon bottom (for example, G-Rex10; Wilson Wolf Manufacturing, New Brighton, MN) (FIG. 1), each flask was loaded with 10-40× 10⁶ viable tumor digest cells or 5-30 tumor fragments in 10-40 mL of CM with IL-2. Both the G-Rex10 and 24-well plates were incubated in a humidified incubator at 37° C. in 5% CO₂ and 5 days after culture initiation, half the media was removed and replaced with fresh CM and IL-2 and after day 5, half the media was changed every 2-3 days. In some embodiments, the CM is the CM1 described in the Examples, see, Example 1. In some embodiments, the first expansion occurs in an initial cell culture medium or a first cell culture medium. In some embodiments, the initial cell culture medium or the first cell culture medium comprises IL-2.

Figure 4:
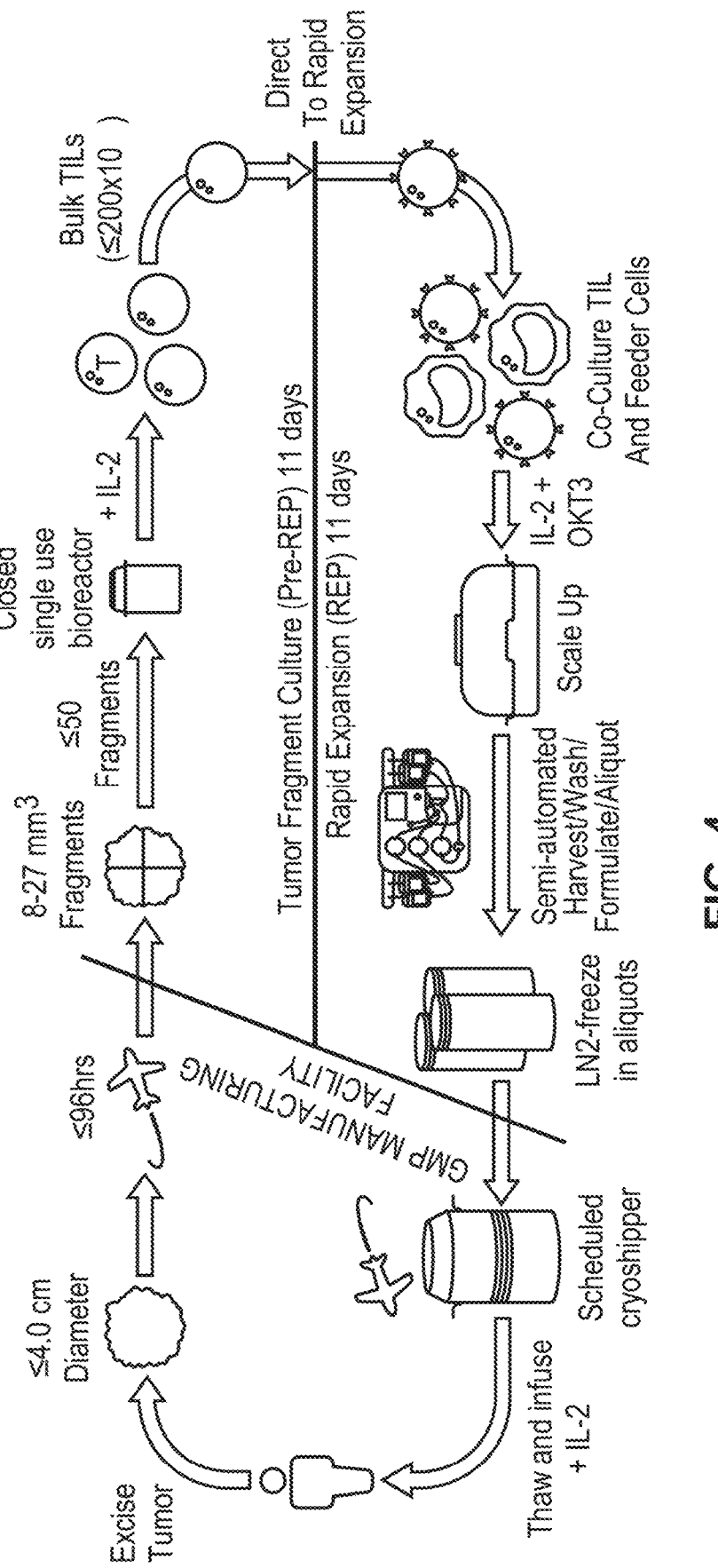
FIG. 4: Shows a diagram of an embodiment of process 2A, a 22-day process for TIL manufacturing.

In some embodiments, the first expansion (including processes such as for example those described in Step B of FIG. 1, which can include those sometimes referred to as the pre-REP) process is shortened to 3-14 days, as discussed in the examples and figures. In some embodiments, the first expansion (including processes such as for example those described in Step B of FIG. 1, which can include those sometimes referred to as the pre-REP) is shortened to 7 to 14 days, as discussed in the Examples and shown in FIGS. 4 and 5, as well as including for example, an expansion as described in Step B of FIG. 1. In some embodiments, the first expansion of Step B is shortened to 10-14 days. In some embodiments, the first expansion is shortened to 11 days, as discussed in, for example, an expansion as described in Step B of FIG. 1.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 1, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 1 and as described herein.

In some embodiments, the first expansion (including processes referred to as the pre-REP; for example, Step B according to FIG. 1) process is shortened to 3 to 14 days, as discussed in the examples and figures. In some embodiments, the first expansion of Step B is shortened to 7 to 14 days. In some embodiments, the first expansion of Step B is shortened to 10 to 14 days. In some embodiments, the first expansion is shortened to 11 days.

In some embodiments, the first expansion, for example, Step B according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

C. Step C: First Expansion to Second Expansion Transition

In some cases, the bulk TIL population obtained from the first expansion, including for example the TIL population obtained from for example, Step B as indicated in FIG. 1, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 1) are stored until phenotyped for selection. In some embodiments, the TILs obtained from the first expansion (for example, from Step B as indicated in FIG. 1) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 1). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

1. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

TABLE 4

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL<br>EEELKPLEEV LNLAQSKNFH LRPRDLISNI NVIVLELKGS ETTFMCEYAD ETATIVEFLN<br>RWITFCQSII STLT | 60<br>120<br>134 |
| SEQ ID NO: 4 Aldesleukin | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI<br>HDTVENLIIL ANNSLSSNGN VTESGCKECE ELEEKNIKEF LQSFVHIVQM FINTS | 60<br>115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

D. Step D: Second Expansion

In some embodiments, the TIL cell population is expanded in number after harvest and initial bulk processing for example, after Step A and Step B, and the transition referred to as Step C, as indicated in FIG. 1). This further expansion is referred to herein as the second expansion, which can include expansion processes generally referred to in the art as a rapid expansion process (REP; as well as processes as indicated in Step D of FIG. 1). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 1) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 1). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 1, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 1 and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks). In some embodiments, the second expansion (including expansions referred to as rapid expansions) is performed in T-175 flasks, and about $1 \times 10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, the second expansion (which can include expansions referred to as REP, as well as those referred to in Step D of FIG. 1) may be performed in 500 mL capacity gas permeable flasks with 100 cm gas-permeable silicon bottoms (G-Rex 100, commercially available from Wilson Wolf Manufacturing Corporation, New Brighton, MN, USA), $5 \times 10^6$ or $10 \times 10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

In some embodiments, the second expansion (including expansions referred to as REP) of TIL can be performed using T-175 flasks and gas-permeable bags as previously described (Tran K Q, Zhou J, Durflinger K H, et al., 2008, *J Immunother,* 31:742-751, and Dudley M E, Wunderlich J R, Shelton T E, et al. 2003, *J Immunother.,* 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1 \times 10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0 \times 10^6$ cells/mL.

In some embodiments, the second expansion (including expansions referred to as REP) are performed in 500 mL capacity flasks with 100 cm² gas-permeable silicon bottoms (G-Rex 100, Wilson Wolf) (FIG. 1), about $5 \times 10^6$ or $10 \times 10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% $CO_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCR$\alpha$/$\beta$).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

1. Feeder Cells and Antigen Presenting Cells

In an embodiment, the second expansion procedures described herein (for example including expansion such as those described in Step D from FIG. 1, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion).

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$ feeder cells to about $100 \times 10^6$ TILs. In another embodiment, the second expansion procedures described herein require a ratio of about $2.5 \times 10^9$ feeder cells to about $50 \times 10^6$ TILs. In yet another embodiment, the second expansion procedures described herein require about $2.5 \times 10^9$ feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the second expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

E. Step E: Harvest TILS

After the second expansion step, cells can be harvested. In some embodiments the TILs are harvested after one, two, three, four or more expansion steps, for example as provided in FIG. 1. In some embodiments the TILs are harvested after two expansion steps, for example as provided in FIG. 1.

TILs can be harvested in any appropriate and sterile manner, including for example by centrifugation. Methods for TIL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 1, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, Step E according to FIG. 1, is performed according to the processes described in Example G. In some embodiments, the closed system is accessed via syringes under sterile conditions in order to maintain the sterility and closed nature of the system. In some embodiments, a closed system as described in Example G is employed.

In some embodiments, TILs are harvested according to the methods described in Example G. In some embodiments, TILs between days 1 and 11 are harvested using the methods as described in Section 8.5 (referred to as the Day 11 TIL harvest in Example G). In some embodiments, TILs between days 12 and 22 are harvested using the methods as described in Section 8.12 (referred to as the Day 22 TIL harvest in Example G).

F. Step F: Final Formulation/Transfer to Infusion Bag

After Steps A through E as provided in an exemplary order in FIG. 1 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

G. Optional Cell Medium Components

1. Anti-CD3 Antibodies

In some embodiments, the culture media used in expansion methods described herein (including those referred to as REP, see for example, FIG. 1) also includes an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-Mc-Neil, Raritan, NJ or Miltenyi Biotech, Auburn, CA).

TABLE 5

| Amino acid sequences of muromonab (exemplary OKT-3 antibody) | | | | | | | |
|---|---|---|---|---|---|---|---|
| Identifier | Sequence (One-Letter Amino Acid Symbols) | | | | | | |
| SEQ ID NO: 1 | QVQLQQSGAE | LARPGASVKM | SCKASGYTFT | RYTMHWVKQR | PGQGLEWIGY | INPSRGYTNY | 60 |
| Muromonab heavy | NQKFKDKATL | TTDKSSSTAY | MQLSSLTSED | SAVYYCARYY | DDHYCLDYWG | QGTTLTVSSA | 120 |
| chain | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAHPASST | KVDKKIEPRP | KSCDKTHTCP | PCPAPELLGG | 240 |
| | PSVFLFPPKP | KDTLMISRTP | EVTCVVVDVS | HEDPEVKFNW | YVDGVEVHNA | KTKPREEQYN | 300 |
| | STYRVVSVLT | VLHQDWLNGK | EYKCKVSNKA | LPAPIEKTIS | KAKGQPREPQ | VYTLPPSRDE | 360 |

TABLE 5-continued

| Amino acid sequences of muromonab (exemplary OKT-3 antibody) | | | | | | |
|---|---|---|---|---|---|---|
| Identifier | Sequence (One-Letter Amino Acid Symbols) | | | | | |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| SEQ ID NO: 2 | QIVLTQSPAI | MSASPGEKVT | MTCSASSSVS | YMNWYQQKSG | TSPKRWIYDT | SKLASGVPAH | 60 |
| Muromonab light | FRGSGSGTSY | SLTISGMEAE | DAATYYCQQW | SSNPFTFGSG | TKLEINRADT | APTVSIFPPS | 120 |
| chain | SEQLTSGGAS | VVCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 |

2. 4-1BB (CD137) Agonists

In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multi specific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 6.

TABLE 6

| Amino acid sequences of 4-1BB antigens. | | | | | | |
|---|---|---|---|---|---|---|
| Identifier | Sequence (One-Letter Amino Acid Symbols) | | | | | |
| SEQ ID NO: 9 | MGNSCYNIVA | TLLLVLNFER | TRSLQDPCSN | CPAGTFCDNN | RNQICSPCPP | NSFSSAGGQR | 60 |
| human 4-1BB, | TCDICRQCKG | VFRTRKECSS | TSNAECDCTP | GFHCLGAGCS | MCEQDCKQGQ | ELTKKGCKDC | 120 |
| Tumor necrosis | CFGTFNDQKR | GICRPWTNCS | LDGKSVLVNG | TKERDVVCGP | SPADLSPGAS | SVTPPAPARE | 180 |
| factor receptor | PGHSPQIISF | FLALTSTALL | FLLFFLTLRF | SVVKRGRKKL | LYIFKQPFMR | PVQTTQEEDG | 240 |
| superfamily, | CSCRFPEEEE | GGCEL | | | | | 255 |
| member 9 (*Homo* | | | | | | |
| *sapiens*) | | | | | | |

TABLE 6-continued

Amino acid sequences of 4-1BB antigens.

| Identifier | Sequence (One-Letter Amino Acid Symbols) | |
|---|---|---|
| SEQ ID NO: 10 | MGNNCYNVVV IVLLLVGCEK VGAVQNSCDN CQPGTFCRKY NPVCKSCPPS TFSSIGGQPN | 60 |
| murine 4-1BB, | CNICRVCAGY FRFKKFCSST HNAECECIEG FHCLGPQCTR CEKDCRPGQE LTKQGCKTCS | 120 |
| Tumor necrosis | LGTFNDQNGT GVCRPWTNCS LDGRSVLKTG TTEKDVVCGP PVVSFSPSTT ISVTPEGGPG | 180 |
| factor receptor | GHSLQVLTLF LALTSALLLA LIFITLLFSV LKWIRKKFPH IFKQPFKKTT GAAQEEDACS | 240 |
| superfamily, | CRCPQEEEGG GGGYEL | 256 |
| member 9 (*Mus musculus*) | | |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5 \times 10^5$ 1/M·s or faster, binds to human or murine 4-1BB with a $k_{assoc}$ of about $7.5 \times 10^5$ 1/M·s or faster, binds to human or murine 4-1BB with a $k_{assoc}$ of about $8 \times 10^5$ 1/M·s or faster, binds to human or murine 4-1BB with a $k_{assoc}$ of about $8.5 \times 10^5$ 1/M·s or faster, binds to human or murine 4-1BB with a $k_{assoc}$ of about $9 \times 10^5$ 1/M·s or faster, binds to human or murine 4-1BB with a $k_{assoc}$ of about $9.5 \times 10^5$ 1/M·s or faster, or binds to human or murine 4-1BB with a $k_{assoc}$ of about $1 \times 10^6$ 1/M·s or faster.

In some embodiments, the compositions, processes and methods described include a 4-1BB agonist that binds to human or murine 4-1BB with a $k_{dissoc}$ of about $2 \times 10^{-5}$ 1/s or slower, binds to human or murine 4-1BB with a $k_{dissoc}$ of about $2.1 \times 10^{-5}$ 1/s or slower, binds to human or murine 4-1BB with a $k_{dissoc}$ of about $2.2 \times 10^{-5}$ 1/s or slower, binds to human or murine 4-1BB with a $k_{dissoc}$ of about $2.3 \times 10^{-5}$ 1/s or slower, binds to human or murine 4-1BB with a $k_{dissoc}$ of about $2.4 \times 10^{-5}$ 1/s or slower, binds to human or murine 4-1BB with a $k_{dissoc}$ of about $2.5 \times 10^{-5}$ 1/s or slower, binds to human or murine 4-1BB with a $k_{dissoc}$ of about $2.6 \times 10^{-5}$ 1/s or slower or binds to human or murine 4-1BB with a $k_{dissoc}$ of about $2.7 \times 10^{-5}$ 1/s or slower, binds to human or murine 4-1BB with a $k_{dissoc}$ of about $2.8 \times 10^{-5}$ 1/s or slower, binds to human or murine 4-1BB with a $k_{dissoc}$ of about $2.9 \times 10^{-5}$ 1/s or slower, or binds to human or murine 4-1BB with a $k_{dissoc}$ of about $3 \times 10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table EE. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 7

Amino acid sequences for 4-1BB agonist antibodies related to utomilumab.

| Identifier | Sequence (One-Letter Amino Acid Symbols) | | | | | | |
|---|---|---|---|---|---|---|---|
| SEQ ID NO: 11 | EVQLVQSGAE | VKKPGESLRI | SCKGSGYSFS | TYWISWVRQM | PGKGLEWMGK | IYPGDSYTNY | 60 |
| heavy chain for | SPSFQGQVTI | SADKSISTAY | LQWSSLKASD | TAMYYCARGY | GIFDYWGQGT | LVTVSSASTK | 120 |
| utomilumab | GPSVFPLAPC | SRSTSESTAA | LGCLVKDYFP | EPVTVSWNSG | ALTSGVHTFP | AVLQSSGLYS | 180 |
| | LSSVVTVPSS | NFGTQTYTCN | VDHKPSNTKV | DKTVERKCCV | ECPPCPAPPV | AGPSVFLFPP | 240 |
| | KPKDTLMISR | TPEVTCVVVD | VSHEDPEVQF | NWYVDGVEVH | NAKTKPREEQ | FNSTFRVVSV | 300 |
| | LTVVHQDWLN | GKEYKCKVSN | KGLPAPIEKT | ISKTKGQPRE | PQVYTLPPSR | EEMTKNQVSL | 360 |
| | TCLVKGFYPS | DIAVEWESNG | QPENNYKTTP | PMLDSDGSFF | LYSKLTVDKS | RWQQGNVFSC | 420 |
| | SVMHEALHNH | YTQKSLSLSP | G | | | | 441 |
| SEQ ID NO: 12 | SYELTQPPSV | SVSPGQTASI | TCSGDNIGDQ | YAHWYQQKPG | QSPVLVIYQD | KNRPSGIPER | 60 |
| light chain for | FSGSNSGNTA | TLTISGTQAM | DEADYYCATY | TGFGSLAVFG | GGTKLTVLGQ | PKAAPSVTLF | 120 |
| utomilumab | PPSSEELQAN | KATLVCLISD | FYPGAVTVAW | KADSSPVKAG | VETTTPSKQS | NNKYAASSYL | 180 |
| | SLTPEQWKSH | RSYSCQVTHE | GSTVEKTVAP | TECS | | | 214 |
| SEQ ID NO: 13 | EVQLVQSGAE | VKKPGESLRI | SCKGSGYSFS | TYWISWVRQM | PGKGLEWMG | KIYPGDSYTN | 60 |
| heavy chain | YSPSFQGQVT | ISADKSISTA | YLQWSSLKAS | DTAMYYCARG | YGIFDYWGQ | GTLVTVSS | 118 |
| variable region | | | | | | | |
| for utomilumab | | | | | | | |
| SEQ ID NO: 14 | SYELTQPPSV | SVSPGQTASI | TCSGDNIGDQ | YAHWYQQKPG | QSPVLVIYQD | KNRPSGIPER | 60 |
| light chain | FSGSNSGNTA | TLTISGTQAM | DEADYYCATY | TGFGSLAVFG | GGTKLTVL | | 108 |
| variable region | | | | | | | |
| for utomilumab | | | | | | | |
| SEQ ID NO: 15 | STYWIS | | | | | | 6 |
| heavy chain CDR1 | | | | | | | |
| for utomilumab | | | | | | | |

TABLE 7-continued

| Amino acid sequences for 4-1BB agonist antibodies related to utomilumab. | | |
|---|---|---|
| Identifier | Sequence (One-Letter Amino Acid Symbols) | |
| SEQ ID NO: 16 heavy chain CDR2 for utomilumab | KIYPGDSYTN YSPSFQG | 17 |
| SEQ ID NO: 17 heavy chain CDR3 for utomilumab | RGYGIFDY | 8 |
| SEQ ID NO: 18 light chain CDR1 for utomilumab | SGDNIGDQYA H | 11 |
| SEQ ID NO: 19 light chain CDR2 for utomilumab | QDKNRPS | 7 |
| SEQ ID NO: 20 light chain CDR3 for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table EE. Urelumab comprises N-glycosylation sites at positions 298 (and 298"); heavy chain intrachain disulfide bridges at positions 22-95 ($V_H$-$V_L$), 148-204 ($C_H$1-$C_L$), 262-322 ($C_H$2) and 368-426 ($C_H$3) (and at positions 22"-95", 148"-204", 262"-322", and 368"-426"); light chain intrachain disulfide bridges at positions 23'-88' ($V_H$-$V_L$) and 136'-196' ($C_H$1-$C_L$) (and at positions 23'''-88''' and 136'''-196'''); interchain heavy chain-heavy chain disulfide bridges at positions 227-227" and 230-230"; and interchain heavy chain-light chain disulfide bridges at 135-216' and 135"-216'''. The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. TABLE 8: Amino acid sequences for 4-1BB agonist antibodies related to urelumab.

| Identifier | Sequence (One-Letter Amino Acid Symbols) | | | | | | |
|---|---|---|---|---|---|---|---|
| SEQ ID NO: 21 heavy chain for urelumab | QVQLQQWGAG | LLKPSETLSL | TCAVGGSFS | GYYWSWIRQS | PEKGLEWIGE | INHGGYVTYN | 60 |
| | PSLESRVTIS | VDTSKNQFSL | KLSSVTAADT | AVYYCARDYG | PGNYDWYFDL | WGRGTLVTVS | 120 |
| | SASTKGPSVF | PLAPCSRSTS | ESTAALGCLV | KDYFPEPVTV | SWNSGALTSG | VHTFPAVLQS | 180 |
| | SGLYSLSSVV | TVPSSSLGTK | TYTCNVDHKP | SNTKVDKRVE | SKYGPPCPPC | PAPEFLGGPS | 240 |
| | VFLFPPKPKD | TLMISRTPEV | TCVVVDVSQE | DPEVQFNWYV | DGVEVHNAKT | KPREEQFNST | 300 |
| | YRVVSVLTVL | HQDWLNGKEY | KCKVSNKGLP | SSIEKTISKA | KGQPREPQVY | TLPPSQEEMT | 360 |
| | KNQVSLTCLV | KGFYPSDIAV | EWESNGQPEN | NYKTTPPVLD | SDGSFFLYSR | LTVDKSRWQE | 420 |
| | GNVFSCSVMH | EALHNHYTQK | SLSLSLGK | | | | 448 |
| SEQ ID NO: 22 light chain for urelumab | EIVLTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | RSNWPPALTF | CGGTKVEIKR | TVAAPSVFIF | 120 |
| | PPSDEQLKSG | TASVVCLLNN | FYPREAKVQW | KVDNALQSGN | SQESVTEQDS | KDSTYSLSST | 180 |
| | LTLSKADYEK | HKVYACEVTH | QGLSSPVTKS | FNRGEC | | | 216 |
| SEQ ID NO: 23 variable heavy chain for urelumab | MKHLWFFLLL | VAAPRWVLSQ | VQLQQWGAGL | LKPSETLSLT | CAVGGSFSG | YYWSWIRQSP | 60 |
| | EKGLEWIGEI | NHGGYVTYNP | SLESRVTISV | DTSKNQFSLK | LSSVTAADTA | VYYCARDYGP | 120 |
| SEQ ID NO: 24 variable light chain for urelumab | MEAPAQLLFL | LLLWLPDTTG | EIVLTQSPAT | LSLSPGERAT | LSCRASQSVS | SYLAWYQQKP | 60 |
| | GQAPRLLIYD | ASNRATGIPA | RFSGSGSGTD | FTLTISSLEP | EDFAVYYCQQ | | 110 |
| SEQ ID NO: 25 heavy chain CDR1 for urelumab | GYYWS | | | | | | 5 |
| SEQ ID NO: 26 heavy chain CDR2 for urelumab | EINHGGYVTY | NPSLES | | | | | 16 |
| SEQ ID NO: 27 heavy chain CDR3 for urelumab | DYGPGNYDWY | FDL | | | | | 13 |
| SEQ ID NO: 28 light chain CDR1 for urelumab | RASQSVSSYL | A | | | | | 11 |
| SEQ ID NO: 29 light chain CDR2 for urelumab | DASNRAT | | | | | | 7 |
| SEQ ID NO: 30 light chain CDR3 for urelumab | QQRSDWPPAL | T | | | | | 11 | embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 (such as 4E9 or BMS-554271), antibodies disclosed in U.S. Pat. No. 7,214, 493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362, 325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303, 121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof (see, FIG. 50). In structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table GG. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 9

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | | | | | | |
|---|---|---|---|---|---|---|---|
| SEQ ID NO: 31 Fc domain | KSCDKTHTCP | PCPAPELLGG | PSVFLFPPKP | KDTLMISRTP | EVTCVVVDVS | HEDPEVKFNW | 60 |
| | YVDGVEVHNA | KTKPREEQYN | STYRVVSVLT | VLHQDWLNGK | EYKCKVSNKA | LPAPIEKTIS | 120 |
| | KAKGQPREPQ | VYTLPPSREE | MTKNQVSLTC | LVKGFYPSDI | AVEWESNGQP | ENNYKTTPPV | 180 |
| | LDSDGSFFLY | SKLTVDKSRW | QQGNVFSCSV | MHEALHNHYT | QKSLSLSPGK | | 230 |
| SEQ ID NO: 32 linker | GGPGSSKSCD | KTHTCPPCPA | PE | | | | 22 |
| SEQ ID NO: 33 linker | GGSGSSKSCD | KTHTCPPCPA | PE | | | | 22 |
| SEQ ID NO: 34 linker | GGPGSSSSSS | SKSCDKTHTC | PPCPAPE | | | | 27 |
| SEQ ID NO: 35 linker | GGSGSSSSSS | SKSCDKTHTC | PPCPAPE | | | | 27 |
| SEQ ID NO: 36 linker | GGPGSSSSSS | SSSKSCDKTH | TCPPCPAPE | | | | 29 |
| SEQ ID NO: 37 linker | GGSGSSSSSS | SSSKSCDKTH | TCPPCPAPE | | | | 29 |
| SEQ ID NO: 38 linker | GGPGSSGSGS | SDKTHTCPPC | PAPE | | | | 24 |
| SEQ ID NO: 39 linker | GGPGSSGSGS | DKTHTCPPCP | APE | | | | 23 |

TABLE 9-continued

Amino acid sequences for TNFRSF fusion proteins, including 4-1BB fusion
proteins, with C-terminal Fc-antibody fragment fusion protein design
(structure I-A).

| Identifier | Sequence (One-Letter Amino Acid Symbols) | |
|---|---|---|
| SEQ ID NO: 40<br>linker | GGPSSSGSDK THTCPPCPAP E | 21 |
| SEQ ID NO: 41<br>linker | GGSSSSSSSS GSDKTHTCPP CPAPE | 25 |

Amino acid sequences for the other polypeptide domains of structure I-B are given in Table HH. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I-B comprises one or more 4-1BB binding domains that is a scFv domain comprising $V_H$ and

TABLE 10

Amino Acid sequences for TNFRSF fusion proteins, including 4-1BB fusion
proteins, with N-terminal Fc-antibody fragment fusion protein
design (structure I-B).

| Identifier | Sequence (One-Letter Amino Acid Symbols) | |
|---|---|---|
| SEQ ID NO: 42<br>Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43<br>linker | SGSGSGSGSG S | 11 |
| SEQ ID NO: 44<br>linker | SSSSSSGSGS GS | 12 |
| SEQ ID NO: 45<br>linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table GG, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL $V_L$ regions that are each at least 95% identical to the sequences shown in SEQ ID NO:13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the $V_H$ and $V_L$ sequences given in Table 11, wherein the $V_H$ and $V_L$ domains are connected by a linker.

TABLE 11: Additional polypeptide domains useful as 4-1BB binding domains in fusion proteins or as scFv 4-1BB agonist antibodies.

TABLE 11

Additional polypeptide domains useful as 4-1BB binding domains in fusion
proteins or as scFv 4-1BB agonist antibodies.

| Identifier | Sequence (One-Letter Amino Acid Symbols) | |
|---|---|---|
| SEQ ID NO: 46<br>4-1BBL | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 47<br>4-1BBL soluble<br>domain | LRQGMFAQLV AQNVLLIDGP LSWYSDPGLA GVSLTGGLSY KEDTKELVVA KAGVYYVFFQ | 60 |
| | LELRRVVAGE GSGSVSLALH LQPLRSAAGA AALALTVDLP PASSEARNSA FGFQGRLLHL | 120 |
| | SAGQRLGVHL HTEARARHAW QLTQGATVLG LFRVTPEIPA GLPSPRSE | 168 |
| SEQ ID NO: 48<br>variable heavy<br>chain for 4B4-1-<br>1 version 1 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVS | 118 |
| SEQ ID NO: 49<br>variable light<br>chain for 4B4-1-<br>1 version 1 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIK | 107 |
| SEQ ID NO: 50<br>variable heavy<br>chain for 4B4-1-<br>1 version 2 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVSA | 119 |
| SEQ ID NO: 51<br>variable light<br>chain for 4B4-1-<br>1 version 2 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIKR | 108 |
| SEQ ID NO: 52<br>variable heavy<br>chain for H39E3-<br>2 | MDWTWRILFL VAAATGAHSE VQLVESGGGL VQPGGSLRLS CAASGFTFSD YWMSWVRQAP | 60 |
| | GKGLEWVADI KNDGSYTNYA PSLTNRFTIS RDNAKNSLYL QMNSLRAEDT AVYYCARELT | 120 |
| SEQ ID NO: 53<br>variable light<br>chain for H39E3-<br>2 | MEAPAQLLFL LLLWLPDTTG DIVMTQSPDS LAVSLGERAT INCKSSQSLL SSGNQKNYL | 60 |
| | WYQQKPGQPP KLLIYYASTR QSGVPDRFSG SGSGTDFTLT ISSLQAEDVA | 110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

3. OX40 (CD134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multi specific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 12.

TABLE 12

| Amino acid sequences of OX40 antigens. | | | | | | |
|---|---|---|---|---|---|---|
| Identifier | Sequence (One-Letter Amino Acid Symbols) | | | | | |
| SEQ ID NO: 54 | MCVGARRLGR | GPCAALLLLG | LGLSTVTGLH | CVGDTYPSND | RCCHECRPGN | GMVSRCSRSQ 60 |
| human OX40 | NTVCRPCGPG | FYNDVVSSKP | CKPCTWCNLR | SGSERKQLCT | ATQDTVCRCR | AGTQPLDSYK 120 |
| (Homo sapiens) | PGVDCAPCPP | GHFSPGDNQA | CKPWTNCTLA | GKHTLQPASN | SSDAICEDRD | PPATQPQETQ 180 |
| | GPPARPITVQ | PTEAWPRTSQ | GPSTRPVEVP | GGRAVAAILG | LGLVLGLLGP | LAILLALYLL 240 |
| | RRDQRLPPDA | HKPPGGGSFR | TPIQEEQADA | HSTLAKI | | 277 |
| SEQ ID NO: 55 | MYVWVQQPTA | LLLLGLTLGV | TARRLNCVKH | TYPSGHKCCR | ECQPGHGMVS | RCDHTRDTLC 60 |
| murine OX40 | HPCETGFYNE | AVNYDTCKQC | TQCNHRSGSE | LKQNCTPTQD | TVCRCRPGTQ | PRQDSGYKLG 120 |
| (Mus musculus) | VDCVPCPPGH | FSPGNNQACK | PWTNCTLSGK | QTRHPASDSL | DAVCEDRSLL | ATLLWETQRP 180 |
| | TFRPTTVQST | TVWPRTSELP | SPPTLVTPEG | PAFAVLLGLG | LGLLAPLTVL | LALYLLRKAW 240 |
| | RLPNTPKPCW | GNSFRTPIQE | EHTDAHFTLA | KI | | 272 |

OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5 \times 10^5$ 1/M·s or faster, binds to human or murine OX40 with a $k_{assoc}$ of about $7.5 \times 10^5$ 1/M·s or faster, binds to human or murine OX40 with a $k_{assoc}$ of about $8 \times 10^5$ 1/M·s or faster, binds to human or murine OX40 with a $k_{assoc}$ of about $8.5 \times 10^5$ 1/M·s or faster, binds to human or murine OX40 with a $k_{assoc}$ of about $9 \times 10^5$ 1/M·s or faster, binds to human or murine OX40 with a $k_{assoc}$ of about $9.5 \times 10^5$ 1/M·s or faster, or binds to human or murine OX40 with a $k_{assoc}$ of about $1 \times 10^6$ 1/M·s or faster.

In some embodiments, the compositions, processes and methods described include a OX40 agonist that binds to human or murine OX40 with a $k_{dissoc}$ of about $2 \times 10^{-5}$ 1/s or slower, binds to human or murine OX40 with a $k_{dissoc}$ of about $2.1 \times 10^{-5}$ 1/s or slower, binds to human or murine OX40 with a $k_{dissoc}$ of about $2.2 \times 10^{-5}$ 1/s or slower, binds to human or murine OX40 with a $k_{dissoc}$ of about $2.3 \times 10^{-5}$ 1/s or slower, binds to human or murine OX40 with a $k_{dissoc}$ of about $2.4 \times 10^{-5}$ 1/s or slower, binds to human or murine OX40 with a $k_{dissoc}$ of about $2.5 \times 10^{-5}$ 1/s or slower, binds to human or murine OX40 with a $k_{dissoc}$ of about $2.6 \times 10^{-5}$ 1/s or slower or binds to human or murine OX40 with a $k_{dissoc}$ of about $2.7 \times 10^{-5}$ 1/s or slower, binds to human or murine OX40 with a $k_{dissoc}$ of about $2.8 \times 10^{-5}$ l/s or slower, binds to human or murine OX40 with a $k_{dissoc}$ of about $2.9 \times 10^{-5}$ l/s or slower, or binds to human or murine OX40 with a $k_{dissoc}$ of about $3 \times 10^{-5}$ l/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table KK. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' ($C_H1$-$C_L$) (and at positions 23'''-88''' and 134'''-194'''); interchain heavy chain-heavy chain disulfide bridges at positions 230-230" and 233-233"; and interchain heavy chain-light chain disulfide bridges at 224-214' and 224"-214'''. Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 13

| Amino acid sequences for OX40 agonist antibodies related to tavolixizumab. | | | | | | |
|---|---|---|---|---|---|---|
| Identifier | Sequence (One-Letter Amino Acid Symbols) | | | | | |
| SEQ ID NO: 56 heavy chain for tavolixizumab | QVQLQESGPG PSLKSRITIN SASTKGPSVF SGLYSLSSVV GPSVFLFPPK NSTYRVVSVL EMTKNQVSLT WQQGNVFSCS | LVKPSQTLSL RDTSKNQYSL PLAPSSKSTS TVPSSSLGTQ PKDTLMISRT TVLHQDWLNG CLVKGFYPSD VMHEALHNHY | TCAVYGGSFS QLNSVTPEDT GGTAALGCLV TYICNVNHKP PEVTCVVVDV KEYKCKVSNK IAVEWESNGQ TQKSLSLSPG | SGYWNWIRKH AVYYCARYKY KDYFPEPVTV SNTKVDKRVE SHEDPEVKFN ALPAPIEKTI PENNYKTTPP K | PGKGLEYIGY DYDGGHAMDY SWNSGALTSG PKSCDKTHTC WYVDGVEVHN SKAKGQPREP VLDSDGSFFL | ISYNGITYHN WGQGTLVTVS VHTFPAVLQS PPCPAPELLG AKTKPREEQY QVYTLPPSRE YSKLTVDKSR | 60 120 180 240 300 360 420 451 |
| SEQ ID NO: 57 light chain for tavolixizumab | DIQMTQSPSS RFSGSGSGTD SDEQLKSGTA LSKADYEKHK | LSASVGDRVT YTLTISSLQP SVVCLLNNFY VYACEVTHQG | ITCRASQDIS EDFATYYCQQ PREAKVQWKV LSSPVTKSFN | NYLNWYQQKP GSALPWTFGQ DNALQSGNSQ RGEC | GKAPKLLIYY GTKVEIKRTV ESVTEQDSKD | TSKLHSGVPS AAPSVFIFPP STYSLSSTLT | 60 120 180 214 |
| SEQ ID NO: 58 heavy chain variable region for tavolixizumab | QVQLQESGPG PSLKSRITIN | LVKPSQTLSL RDTSKNQYSL | TCAVYGGSFS QLNSVTPEDT | SGYWNWIRKH AVYYCARYKY | PGKGLEYIGY DYDGGHAMDY | ISYNGITYHN WGQGTLVT | 60 118 |
| SEQ ID NO: 59 light chain variable region for tavolixizumab | DIQMTQSPSS RFSGSGSGTD | LSASVGDRVT YTLTISSLQP | ITCRASQDIS EDFATYYCQQ | NYLNWYQQKP GSALPWTFGQ | GKAPKLLIYY GTKVEIKR | TSKLHSGVPS | 60 108 |
| SEQ ID NO: 60 heavy chain CDR1 for tavolixizumab | GSFSSGYWN | | | | | | 9 |
| SEQ ID NO: 61 heavy chain CDR2 for tavolixizumab | YIGYISYNGI TYH | | | | | | 13 |
| SEQ ID NO: 62 heavy chain CDR3 for tavolixizumab | RYKYDYDGGH AMDY | | | | | | 14 |
| SEQ ID NO: 63 light chain CDR1 for tavolixizumab | QDISNYLN | | | | | | 8 |
| SEQ ID NO: 64 light chain CDR2 for tavolixizumab | LLIYYTSKLH S | | | | | | 11 |
| SEQ ID NO: 65 light chain CDR3 for tavolixizumab | QQGSALPW | | | | | | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table LL.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region (V$_H$) comprises the sequence shown in SEQ ID NO:68, and the OX40 agonist light chain variable region (V$_L$) comprises the sequence shown in SEQ ID NO:69, and conservative amino acid substitutions thereof. In an embodiment, a OX40 agonist comprises V$_H$ and V$_L$ regions that are each at least 99% identical to the sequences shown in SEQ ID NO:68 and SEQ ID NO:69, respectively. In an embodiment, a OX40 agonist comprises V$_H$ and V$_L$ regions that are each at least 98% identical to the sequences shown in SEQ ID NO:68 and SEQ ID NO:69, respectively. In an embodiment, a OX40 agonist comprises V$_H$ and V$_L$ regions that are each at least 97% identical to the sequences shown in SEQ ID NO:68 and SEQ ID NO:69, respectively. In an embodiment, a OX40 agonist comprises V$_H$ and V$_L$ regions that are each at least 96% identical to the sequences shown in SEQ ID NO:68 and SEQ ID NO:69, respectively. In an embodiment, a OX40 agonist comprises V$_H$ and V$_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 14

| Amino acid sequences for OX40 agonist antibodies related to 11D4. | |
| --- | --- |
| Identifier | Sequence (One-Letter Amino Acid Symbols) |
| SEQ ID NO: 66 heavy chain for 11D4 | EVQLVESGGG LVQPGGSLRL SCAASGFTFS SYSMNWVRQA PGKGLEWVSY ISSSSSTIDY 60<br>ADSVKGRFTI SRDNAKNSLY LQMNSLRDED TAVYYCARES GWYLFDYWGQ GTLVTVSSAS 120<br>TKGPSVFPLA PCSRSTSEST AALGCLVKDY FPEPVTVSWN SGALTSGVHT FPAVLQSSGL 180<br>YSLSSVVTVP SSNFGTQTYT CNVDHKPSNT KVDKTVERKC CVECPPCPAP PVAGPSVFLF 240<br>PPKPKDTLMI SRTPEVTCVV VDVSHEDPEV QFNWYVDGVE VHNAKTKPRE EQFNSTFRVV 300<br>SVLTVVHQDW LNGKEYKCKV SNKGLPAPIE KTISKTKGQP REPQVYTLPP SREEMTKNQV 360<br>SLTCLVKGFY PSDIAVEWES NGQPENNYKT TPPMLDSDGS FFLYSKLTVD KSRWQQGNVF 420<br>SCSVMHEALH NHYTQKSLSL SPGK 444 |
| SEQ ID NO: 67 light chain for 11D4 | DIQMTQSPSS LSASVGDRVT ITCRASQGIS SWLAWYQQKP EKAPKSLIYA ASSLQSGVPS 60<br>RFSGSGSGTD FTLTISSLQP EDFATYYCQQ YNSYPPTFGG GTKVEIKRTV AAPSVFIFPP 120<br>SDEQLKSGTA SVVCLLNNFY PREAKVQWKV DNALQSGNSQ ESVTEQDSKD STYSLSSTLT 180<br>LSKADYEKHK VYACEVTHQG LSSPVTKSFN RGEC 214 |
| SEQ ID NO: 68 heavy chain variable region for 11D4 | EVQLVESGGG LVQPGGSLRL SCAASGFTFS SYSMNWVRQA PGKGLEWVSY ISSSSSTIDY 60<br>ADSVKGRFTI SRDNAKNSLY LQMNSLRDED TAVYYCARES GWYLFDYWGQ GTLVTVSS 118 |
| SEQ ID NO: 69 light chain variable region for 11D4 | DIQMTQSPSS LSASVGDRVT ITCRASQGIS SWLAWYQQKP EKAPKSLIYA ASSLQSGVPS 60<br>RFSGSGSGTD FTLTISSLQP EDFATYYCQQ YNSYPPTFGG GTKVEIK 107 |
| SEQ ID NO: 70 heavy chain CDR1 for 11D4 | SYSMN 5 |
| SEQ ID NO: 71 heavy chain CDR2 for 11D4 | YISSSSSTID YADSVKG 17 |
| SEQ ID NO: 72 heavy chain CDR3 for 11D4 | ESGWYLFDY 9 |

TABLE 14-continued

| Amino acid sequences for OX40 agonist antibodies related to 11D4. | | |
|---|---|---|
| Identifier | Sequence (One-Letter Amino Acid Symbols) | |
| SEQ ID NO: 73 light chain CDR1 for 11D4 | RASQGISSWL A | 11 |
| SEQ ID NO: 74 light chain CDR2 for 11D4 | AASSLQS | 7 |
| SEQ ID NO: 75 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table MM.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 15

| Amino acid sequences for OX40 agonist antibodies related to 18D8. |
|---|

| Identifier | Sequence (One-Letter Amino Acid Symbols) | |
|---|---|---|
| SEQ ID NO: 76<br>heavy chain for<br>18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSSASTKGP SVFPLAPCSR STSESTAALG CLVKDYFPEP VTVSWNSGAL TSGVHTFPAV<br>LQSSGLYSLS SVVTVPSSNF GTQTYTCNVD HKPSNTKVDK TVERKCCVEC PPCPAPPVAG<br>PSVFLFPPKP KDTLMISRTP EVTCVVVDVS HEDPEVQFNW YVDGVEVHNA KTKPREEQFN<br>STFRVVSVLT VVHQDWLNGK EYKCKVSNKG LPAPIEKTIS KTKGQPREPQ VYTLPPSREE<br>MTKNQVSLTC LVKGFYPSDI AVEWESNGQP ENNYKTTPPM LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 77<br>light chain for<br>18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 78<br>heavy chain<br>variable region<br>for 18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSS | 60<br>120<br>124 |
| SEQ ID NO: 79<br>light chain<br>variable region<br>for 18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIK | 60<br>106 |
| SEQ ID NO: 80<br>heavy chain CDR1<br>for 18D8 | DYAMH | 5 |
| SEQ ID NO: 81<br>heavy chain CDR2<br>for 18D8 | GISWNSGSIG YADSVKG | 17 |
| SEQ ID NO: 82<br>heavy chain CDR3<br>for 18D8 | DQSTADYYFY YGMDV | 15 |
| SEQ ID NO: 83<br>light chain CDR1<br>for 18D8 | RASQSVSSYL A | 11 |
| SEQ ID NO: 84<br>light chain CDR2<br>for 18D8 | DASNRAT | 7 |
| SEQ ID NO: 85<br>light chain CDR3<br>for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table NN.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

mithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table OO.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the

TABLE 16

Amino acid sequences for OX40 agonist antibodies related to Hu119-122.

| Identifier | Sequence (One-Letter Amino Acid Symbols) | | | | | | |
|---|---|---|---|---|---|---|---|
| SEQ ID NO: 86 heavy chain variable region for Hu119-122 | EVQLVESGGG PDTMERRFTI | LVQPGGSLRL SRDNAKNSLY | SCAASEYEFP LQMNSLRAED | SHDMSWVRQA TAVYYCARHY | PGKGLELVAA DDYYAWFAYW | INSDGGSTYY GQGTMVTVSS | 60 120 |
| SEQ ID NO: 87 light chain variable region for Hu119-122 | EIVLTQSPAT GVPARFSGSG | LSLSPGERAT SGTDFTLTIS | LSCRASKSVS SLEPEDFAVY | TSGYSYMHWY YCQHSRELPL | QQKPGQAPRL TFGGGTKVEI | LIYLASNLES K | 60 111 |
| SEQ ID NO: 88 heavy chain CDR1 for Hu119-122 | SHDMS | | | | | | 5 |
| SEQ ID NO: 89 heavy chain CDR2 for Hu119-122 | AINSDGGSTY YPDTMER | | | | | | 17 |
| SEQ ID NO: 90 heavy chain CDR3 for Hu119-122 | HYDDYYAWFA Y | | | | | | 11 |
| SEQ ID NO: 91 light chain CDR1 for Hu119-122 | RASKSVSTSG YSYMH | | | | | | 15 |
| SEQ ID NO: 92 light chain CDR2 for Hu119-122 | LASNLES | | | | | | 7 |
| SEQ ID NO: 93 light chain CDR3 for Hu119-122 | QHSRELPLT | | | | | | 9 |

In some embodiments, the OX40 agonist is Hu106-222, which is a humanized antibody available from GlaxoSsequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 17

| | Amino acid sequences for OX40 agonist antibodies related to Hu106-222. | | | | | |
|---|---|---|---|---|---|---|
| Identifier | Sequence (One-Letter Amino Acid Symbols) | | | | | |
| SEQ ID NO: 94 heavy chain variable region for Hu106-222 | QVQLVQSGSE ADDFKGRFVF SS | LKKPGASVKV SLDTSVSTAY | SCKASGYTFT LQISSLKAED | DYSMHWVRQA TAVYYCANPY | PGQGLKWMGW YDYVSYYAMD | INTETGEPTY YWGQGTTVTV | 60 120 122 |
| SEQ ID NO: 95 light chain variable region for Hu106-222 | DIQMTQSPSS RFSGSGSGTD | LSASVGDRVT FTFTISSLQP | ITCKASQDVS EDIATYYCQQ | TAVAWYQQKP HYSTPRTFGQ | GKAPKLLIYS GTKLEIK | ASYLYTGVPS | 60 107 |
| SEQ ID NO: 96 heavy chain CDR1 for Hu106-222 | DYSMH | | | | | | 5 |
| SEQ ID NO: 97 heavy chain CDR2 for Hu106-222 | WINTETGEPT YADDFKG | | | | | | 17 |
| SEQ ID NO: 98 heavy chain CDR3 for Hu106-222 | PYYDYVSYYA MDY | | | | | | 13 |
| SEQ ID NO: 99 light chain CDR1 for Hu106-222 | KASQDVSTAV A | | | | | | 11 |
| SEQ ID NO: 100 light chain CDR2 for Hu106-222 | SASYLYT | | | | | | 7 |
| SEQ ID NO: 101 light chain CDR3 for Hu106-222 | QQHYSTPRT | | | | | | 9 | has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological In some embodiments, the OX40 agonist antibody is MEDI6469 (also referred to as 9B12). MEDI6469 is a murine monoclonal antibody. Weinberg, et al., *J. Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table GG. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table HH. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavo-lixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table OO, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 18, wherein the $V_H$ and $V_L$ domains are connected by a linker.

TABLE 18

| Additional polypeptide domains useful as OX40 binding domains in fusion proteins (e.g., structures I-A and I-B) or as scFv OX40 agonist antibodies. | | |
| --- | --- | --- |
| Identifier | Sequence (One-Letter Amino Acid Symbols) | |
| SEQ ID NO: 102 OX40L | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |

TABLE 18-continued

Additional polypeptide domains useful as OX40 binding domains in fusion
proteins (e.g., structures I-A and I-B) or as scFv OX40 agonist antibodies.

| Identifier | Sequence (One-Letter Amino Acid Symbols) | |
|---|---|---|
| SEQ ID NO: 103<br>OX40L soluble<br>domain | SHRYPRIQSI KVQFTEYKKE KGFILTSQKE DEIMKVQNNS VIINCDGFYL ISLKGYFSQE | 60 |
| | VNISLHYQKD EEPLFQLKKV RSVNSLMVAS LTYKDKVYLN VTTDNTSLDD FHVNGGELIL | 120 |
| | IHQNPGEFCV L | 131 |
| SEQ ID NO: 104<br>OX40L soluble<br>domain<br>(alternative) | YPRIQSIKVQ FTEYKKEKGF ILTSQKEDEI MKVQNNSVII NCDGFYLISL KGYFSQEVNI | 60 |
| | SLHYQKDEEP LFQLKKVRSV NSLMVASLTY KDKVYLNVTT DNTSLDDFHV NGGELILIHQ | 120 |
| | NPGEFCVL | 128 |
| SEQ ID NO: 105<br>variable heavy<br>chain for 008 | EVQLVESGGG LVQPGGSLRL SCAASGFTFS NYTMNWVRQA PGKGLEWVSA ISGSGGSTYY | 60 |
| | ADSVKGRFTI SRDNSKNTLY LQMNSLRAED TAVYYCAKDR YSQVHYALDY WGQGTLVTVS | 120 |
| SEQ ID NO: 106<br>variable light<br>chain for 008 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 107<br>variable heavy<br>chain for 011 | EVQLVESGGG VVQPGRSLRL SCAASGFTFS DYTMNWVRQA PGKGLEWVSS ISGGSTYYAD | 60 |
| | SRKGRFTISR DNSKNTLYLQ MNNLRAEDTA VYYCARDRYF RQQNAFDYWG QGTLVTVSSA | 120 |
| SEQ ID NO: 108<br>variable light<br>chain for 011 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 109<br>variable heavy<br>chain for 021 | EVQLVESGGG LVQPRGSLRL SCAASGFTFS SYAMNWVRQA PGKGLEWVAV ISYDGSNKYY | 60 |
| | ADSVKGRFTI SRDNSKNTLY LQMNSLRAED TAVYYCAKDR YITLPNALDY WGQGTLVTVS | 120 |
| SEQ ID NO: 110<br>variable light<br>chain for 021 | DIQMTQSPVS LPVTPGEPAS ISCRSSQSLL HSNGYNYLDW YLQKPGQSPQ LLIYLGSNRA | 60 |
| | SGVPDRFSGS GSGTDFTLKI SRVEAEDVGV YYCQQYKSNP PTFGQGTK | 108 |
| SEQ ID NO: 111<br>variable heavy<br>chain for 023 | EVQLVESGGG LVHPGGSLRL SCAGSGFTFS SYAMHWVRQA PGKGLEWVSA IGTGGGTYYA | 60 |
| | DSVMGRFTIS RDNSKNTLYL QMNSLRAEDT AVYYCARYDN VMGLYWFDYW GQGTLVTVSS | 120 |
| SEQ ID NO: 112<br>variable light<br>chain for 023 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPAFGG GTKVEIKR | 108 |
| SEQ ID NO: 113<br>heavy chain<br>variable region | EVQLQQSGPE LVKPGASVKM SCKASGYTFT SYVMHWVKQK PGQGLEWIGY INPYNDGTKY | 60 |
| | NEKFKGKATL TSDKSSSTAY MELSSLTSED SAVYYCANYY GSSLSMDYWG QGTSVTVSS | 119 |
| SEQ ID NO: 114<br>light chain<br>variable region | DIQMTQTTSS LSASLGDRVT ISCRASQDIS NYLNWYQQKP DGTVKLLIYY TSRLHSGVPS | 60 |
| | RFSGSGSGTD YSLTISNLEQ EDIATYFCQQ GNTLPWTFGG GTKLEIKR | 108 |
| SEQ ID NO: 115<br>heavy chain<br>variable region | EVQLQQSGPE LVKPGASVKI SCKTSGYTFK DYTMHWVKQS HGKSLEWIGG IYPNNGGSTY | 60 |
| | NQNFKDKATL TVDKSSSTAY MEFRSLTSED SAVYYCARMG YHGPHLDFDV WGAGTTVTVS | 120 |
| | P | 121 |
| SEQ ID NO: 116<br>light chain<br>variable region | DIVMTQSHKF MSTSLGDRVS ITCKASQDVG AAVAWYQQKP GQSPKLLIYW ASTRHTGVPD | 60 |
| | RFTGGGSGTD FTLTISNVQS EDLTDYFCQQ YINYPLTFGG GTKLEIKR | 108 |
| SEQ ID NO: 117<br>heavy chain<br>variable region<br>of humanized<br>antibody | QIQLVQSGPE LKKPGETVKI SCKASGYTFT DYSMHWVKQA PGKGLKWMGW INTETGEPTY | 60 |
| | ADDFKGRFAF SLETSASTAY LQINNLKNED TATYFCANPY YDYVSYYAMD YWGHGTSVTV | 120 |
| | SS | 122 |
| SEQ ID NO: 118<br>heavy chain<br>variable region<br>of humanized<br>antibody | QVQLVQSGSE LKKPGASVKV SCKASGYTFT DYSMHWVRQA PGQGLKWMGW INTETGEPTY | 60 |
| | ADDFKGRFVF SLDTSVSTAY LQISSLKAED TAVYYCANPY YDYVSYYAMD YWGQGTTVTV | 120 |
| | SS | 122 |
| SEQ ID NO: 119<br>light chain<br>variable region<br>of humanized<br>antibody | DIVMTQSHKF MSTSVRDRVS ITCKASQDVS TAVAWYQQKP GQSPKLLIYS ASYLYTGVPD | 60 |
| | RFTGSGSGTD FTFTISSVQA EDLAVYYCQQ HYSTPRTFGG GTKLEIK | 107 |

TABLE 18-continued

Additional polypeptide domains useful as OX40 binding domains in fusion
proteins (e.g., structures I-A and I-B) or as scFv OX40 agonist antibodies.

| Identifier | Sequence (One-Letter Amino Acid Symbols) | |
|---|---|---|
| SEQ ID NO: 120 light chain variable region of humanized antibody | DIVMTQSHKF MSTSVRDRVS ITCKASQDVS TAVAWYQQKP GQSPKLLIYS ASYLYTGVPD RFTGSGSGTD FTFTISSVQA EDLAVYYCQQ HYSTPRTFGG GTKLEIK | 60 107 |
| SEQ ID NO: 121 heavy chain variable region of humanized antibody | EVQLVESGGG LVQPGESLKL SCESNEYEFP SHDMSWVRKT PEKRLELVAA INSDGGSTYY PDTMERRFII SRDNTKKTLY LQMSSLRSED TALYYCARHY DDYYAWFAYW GQGTLVTVSA | 60 120 |
| SEQ ID NO: 122 heavy chain variable region of humanized antibody | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 123 light chain variable region of humanized antibody | DIVLTQSPAS LAVSLGQRAT ISCRASKSVS TSGYSYMHWY QQKPGQPPKL LIYLASNLES GVPARFSGSG SGTDFTLNIH PVEEEDAATY YCQHSRELPL TFGAGTKLEL K | 60 111 |
| SEQ ID NO: 124 light chain variable region of humanized antibody | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 125 heavy chain variable region | MYLGLNYVFI VFLLNGVQSE VKLEESGGGL VQPGGSMKLS CAASGFTFSD AWMDWVRQSP EKGLEWVAEI RSKANNHATY YAESVNGRFT ISRDDSKSSV YLQMNSLRAE DTGIYYCTWG EVFYFDYWGQ GTTLTVSS | 60 120 138 |
| SEQ ID NO: 126 light chain variable region | MRPSIQFLGL LLFWLHGAQC DIQMTQSPSS LSASLGGKVT ITCKSSQDIN KYIAWYQHKP GKGPRLLIHY TSTLQPGIPS RFSGSGSGRD YSFSISNLEP EDIATYYCLQ YDNLLTFGAG TKLELK | 60 120 126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

H. Optional Cell Viability Analyses

Optionally, a cell viability assay can be performed after the first expansion (sometimes referred to as the initial bulk expansion), using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining. The cell viability can also be assayed based on U.S. Ser. No. 15/863,634, incorporated by reference herein in its entirety.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

According to the present disclosure, a method for assaying TILs for viability and/or further use in administration to a subject. In some embodiments, the method for assay tumor infiltrating lymphocytes (TILs) comprises:

(i) obtaining a first population of TILs;

(ii) performing a first expansion by culturing the first population of TILs in a cell culture medium comprising IL-2, and optionally OKT-3, to produce a second population of TILs; and (iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;

(iv) harvesting, washing, and cryopreserving the third population of TILs;

(v) storing the cryopreserved TILs at a cryogenic temperature;

(vi) thawing the third population of TILs to provide a thawed third population of TILs; and (vii) performing an additional second expansion of a portion of the thawed third population of TILs by supplementing the cell culture medium of the third population with IL-2, OKT-3, and APCs for an additional expansion period (sometimes referred to as a reREP period) of at least 3 days, wherein the third expansion is performed to obtain a fourth population of TILs, wherein the number of TILs in the fourth population of TILs is compared to the number of TILs in the third population of TILs to obtain a ratio;

(viii) determining based on the ratio in step (vii) whether the thawed population of TILs is suitable for administration to a patient;

(ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the TILs are assayed for viability after step (vii).

The present disclosure also provides further methods for assaying TILs. In some embodiments, the disclosure provides a method for assaying TILs comprising:

(i) obtaining a portion of a first population of cryopreserved TILs;

(ii) thawing the portion of the first population of cryopreserved TILs;

(iii) performing a first expansion by culturing the portion of the first population of TILs in a cell culture medium comprising IL-2, OKT-3, and antigen presenting cells (APCs) for an additional expansion period (sometimes referred to as a reREP period) of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;

(iv) determining based on the ratio in step (iii) whether the first population of TILs is suitable for use in therapeutic administration to a patient;

(v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

2. Cell Cultures

In an embodiment, a method for expanding TILs, including those discussed above as well as exemplified in FIG. 1, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the first expansion is serum free. In some embodiments, the media in the second expansion is serum free. In some embodiments, the media in the first expansion and the second are both serum free. In an embodiment, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium for a duration of about 7 to 14 days, e.g., about 11 days. In some embodiments pre-REP is about 7 to 14 days, e.g., about 11 days. In some embodiments, REP is about 7 to 14 days, e.g., about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

I. Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

J. Optional Cryopreservation of TILs

As discussed above, and exemplified in Steps A through E as provided in FIG. 1, cryopreservation can occur at numerous points throughout the TIL expansion process. In some embodiments, the expanded population of TILs after the second expansion (as provided for example, according to Step D of FIG. 1) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Examples F and G.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

K. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art.

Sterile connecting devices (STCDs) produce sterile welds between two pieces of compatible tubing. This procedure permits sterile connection of a variety of containers and tube diameters. In some embodiments, the closed systems include luer lock and heat sealed systems as described in for example, Example G. In some embodiments, the closed system is accessed via syringes under sterile conditions in order to maintain the sterility and closed nature of the system. In some embodiments, a closed system as described in Example G is employed. In some embodiments, the TILs are formulated into a final product formulation container according to the method described in Example G, section "Final Formulation and Fill".

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

L. Optional Cryopreservation of TILs

Either the bulk TIL population or the expanded population of TILs can be optionally cryopreserved. In some embodiments, cryopreservation occurs on therapeutic TIL population. In some embodiments, cryopreservation occurs on the TILs harvested after the second expansion. In some embodiments, cryopreservation occurs on the TILs in exemplary Step F of FIG. 1. In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above in Steps A through E, cryopreservation can occur at numerous points throughout the TIL expansion process. In some embodiments, the bulk TIL population after the first expansion according to Step B or the expanded population of TILs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

IV. TIL Manufacturing Processes (Embodiments of GEN3 Processes, Optionally Including Defined Media)

Without being limited to any particular theory, it is believed that the priming first expansion that primes an activation of T cells followed by the rapid second expansion that boosts the activation of T cells as described in the methods of the invention allows the preparation of expanded T cells that retain a "younger" phenotype, and as such the expanded T cells of the invention are expected to exhibit greater cytotoxicity against cancer cells than T cells expanded by other methods. In particular, it is believed that an activation of T cells that is primed by exposure to an anti-CD3 antibody (e.g. OKT-3), IL-2 and optionally antigen-presenting cells (APCs) and then boosted by subsequent exposure to additional anti-CD-3 antibody (e.g. OKT-3), IL-2 and APCs as taught by the methods of the invention limits or avoids the maturation of T cells in culture, yielding a population of T cells with a less mature phenotype, which T cells are less exhausted by expansion in culture and exhibit greater cytotoxicity against cancer cells. In some embodiments, the step of rapid second expansion is split into a plurality of steps to achieve a scaling up of the culture by: (a) performing the rapid second expansion by culturing T cells in a small scale culture in a first container, e.g., a G-REX 100MCS container, for a period of about 3 to 4 days, and then (b) effecting the transfer of the T cells in the small scale culture to a second container larger than the first container, e.g., a G-REX 500MCS container, and culturing the T cells from the small scale culture in a larger scale culture in the second container for a period of about 4 to 7 days. In some embodiments, the step of rapid expansion is split into a plurality of steps to achieve a scaling out of the culture by: (a) performing the rapid second expansion by culturing T cells in a first small scale culture in a first container, e.g., a G-REX 100MCS container, for a period of about 3 to 4 days, and then (b) effecting the transfer and apportioning of the T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the T cells from first small scale culture transferred to such second container is cultured in a second small scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX 100MCS container, for a period of about 3 to 4 days, and then (b) effecting the transfer and apportioning of the T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the T cells from the small scale culture transferred to such second container is cultured in a larger scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX 100MCS container, for a period of about 4 days, and then (b) effecting the transfer and apportioning of the T cells from the small scale culture into and amongst 2, 3 or 4 second containers that are larger in size than the first container, e.g., G-REX 500MCS containers, wherein in each second container the portion of the T cells from the small scale culture transferred to such second container is cultured in a larger scale culture for a period of about 5 days.

In some embodiments, the rapid second expansion is performed after the activation of T cells effected by the priming first expansion begins to decrease, abate, decay or subside.

In some embodiments, the rapid second expansion is performed after the activation of T cells effected by the priming first expansion has decreased by at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the rapid second expansion is performed after the activation of T cells effected by the priming first expansion has decreased by a percentage in the range of at or about 1% to 100%.

In some embodiments, the rapid second expansion is performed after the activation of T cells effected by the priming first expansion has decreased by a percentage in the range of at or about 1% to 10%, 10% to 20%, 20% to 30%, 30% to 40%, 40% to 50%, 50% to 60%, 60% to 70%, 70% to 80%, 80% to 90%, or 90% to 100%.

In some embodiments, the rapid second expansion is performed after the activation of T cells effected by the priming first expansion has decreased by at least at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In some embodiments, the rapid second expansion is performed after the activation of T cells effected by the priming first expansion has decreased by up to at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In some embodiments, the decrease in the activation of T cells effected by the priming first expansion is determined by a reduction in the amount of interferon gamma released by the T cells in response to stimulation with antigen.

In some embodiments, the priming first expansion of T cells is performed during a period of up to at or about 7 days or about 8 days.

In some embodiments, the priming first expansion of T cells is performed during a period of up to at or about 1 day, 2 days, 3 days, 4 days, 5 days, 6 days, 7 days, or 8 days.

In some embodiments, the priming first expansion of T cells is performed during a period of 1 day, 2 days, 3 days, 4 days, 5 days, 6 days, 7 days, or 8 days.

In some embodiments, the rapid second expansion of T cells is performed during a period of up to at or about 11 days.

In some embodiments, the rapid second expansion of T cells is performed during a period of up to at or about 1 day, 2 days, 3 days, 4 days, 5 days, 6 days, 7 days, 8 days, 9 days, 10 days or 11 days.

In some embodiments, the rapid second expansion of T cells is performed during a period of 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 7 days and the rapid second expansion of T cells is performed during a period of from at or about 1 day to at or about 11 days.

In some embodiments, the priming first expansion of T cells is performed during a period of up to at or about 1 day, 2 days, 3 days, 4 days, 5 days, 6 days, 7 days, or 8 days and the rapid second expansion of T cells is performed during a period of up to at or about 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 8 days and the rapid second expansion of T cells is performed during a period of from at or about 1 day to at or about 9 days.

In some embodiments, the priming first expansion of T cells is performed during a period of 8 days and the rapid second expansion of T cells is performed during a period of 9 days.

In some embodiments, the priming first expansion of T cells is performed during a period of from at or about 1 day to at or about 7 days and the rapid second expansion of T cells is performed during a period of from at or about 1 day to at or about 9 days.

In some embodiments, the priming first expansion of T cells is performed during a period of 7 days and the rapid second expansion of T cells is performed during a period of 9 days.

In some embodiments, the T cells are tumor infiltrating lymphocytes (TILs).

In some embodiments, the T cells are marrow infiltrating lymphocytes (MILs).

In some embodiments, the T cells are peripheral blood lymphocytes (PBLs).

In some embodiments, the T cells are obtained from a donor suffering from a cancer.

In some embodiments, the T cells are TILs obtained from a tumor excised from a patient suffering from a cancer.

In some embodiments, the T cells are MILs obtained from bone marrow of a patient suffering from a hematologic malignancy.

In some embodiments, the T cells are PBLs obtained from peripheral blood mononuclear cells (PBMCs) from a donor. In some embodiments, the donor is suffering from a cancer. In some embodiments, the cancer is the cancer is selected from the group consisting of melanoma, ovarian cancer, endometrial cancer, thyroid cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy.

In certain aspects of the present disclosure, immune effector cells, e.g., T cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T cells are isolated from peripheral blood lymphocytes by lysing the red blood cells and depleting the monocytes, for example, by centrifugation through a PERCOLL gradient or by counterflow centrifugal elutriation.

In some embodiments, the T cells are PBLs separated from whole blood or apheresis product enriched for lymphocytes from a donor. In some embodiments, the donor is suffering from a cancer. In some embodiments, the cancer is the cancer is selected from the group consisting of melanoma, ovarian cancer, endometrial cancer, thyroid cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy. In some embodiments, the PBLs are isolated from whole blood or apheresis product enriched for lymphocytes by using positive or negative selection methods, i.e., removing the PBLs using a marker(s), e.g., CD3+CD45+, for T cell phenotype, or removing non-T cell phenotype cells, leaving PBLs. In other embodiments, the PBLs are isolated by gradient centrifugation. Upon isolation of PBLs from donor tissue, the priming first expansion of PBLs can be initiated by seeding a suitable number of isolated PBLs (in some embodiments, approximately $1 \times 10^7$ PBLs) in the priming first expansion culture according to the priming first expansion step of any of the methods described herein.

Figure 30A:
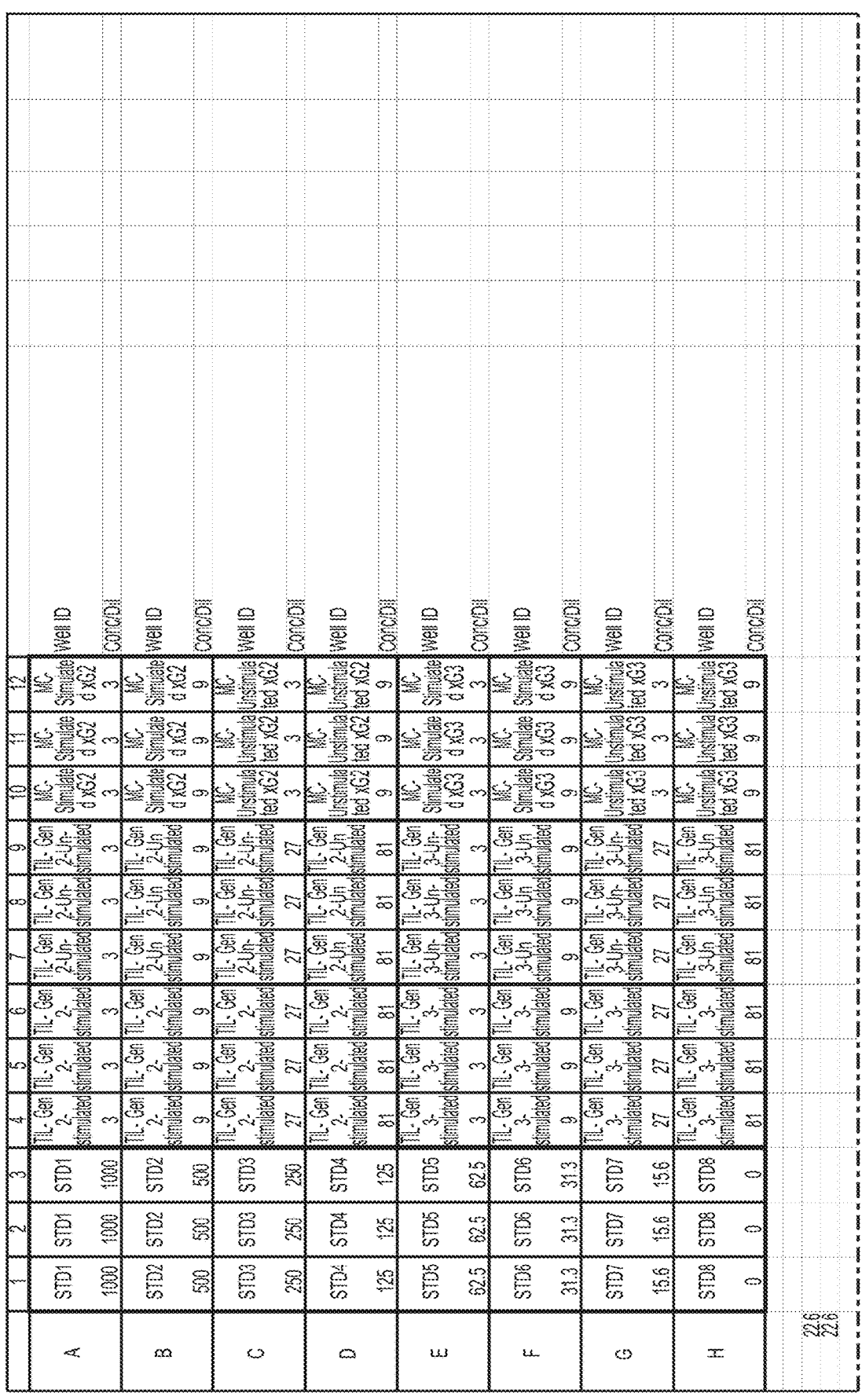
Figure 30B:
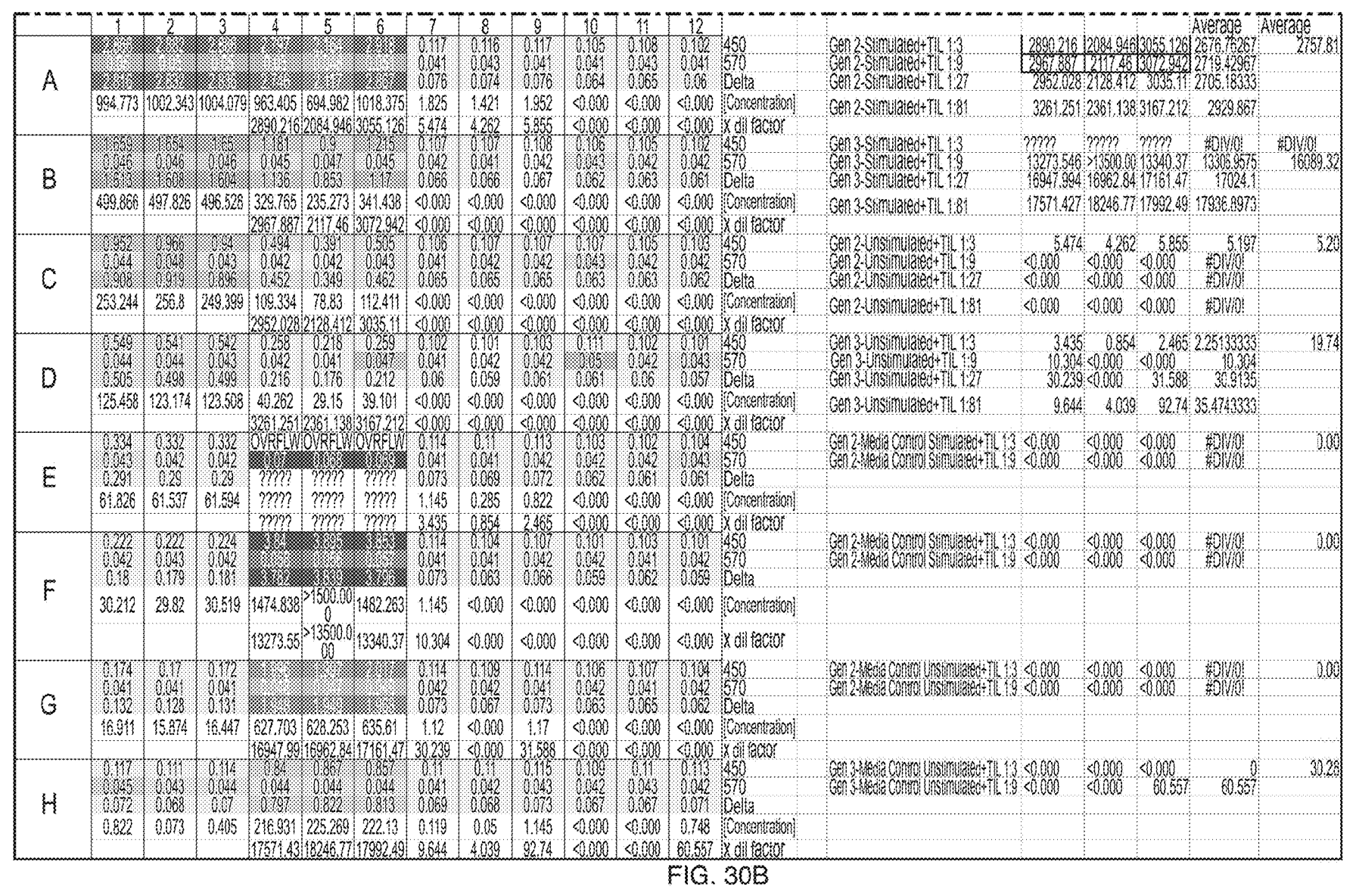
Figure 31B:
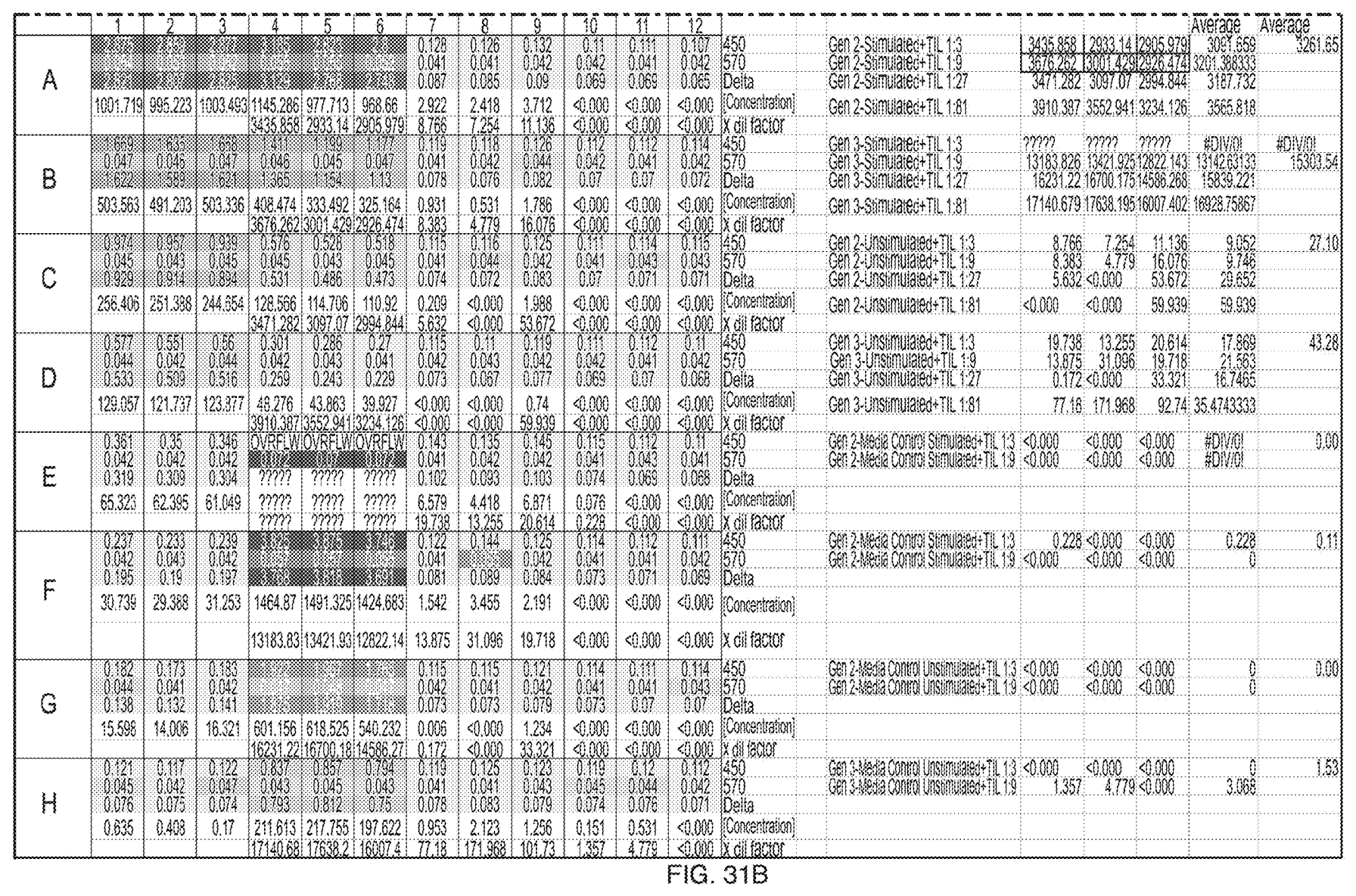
Figure 37:
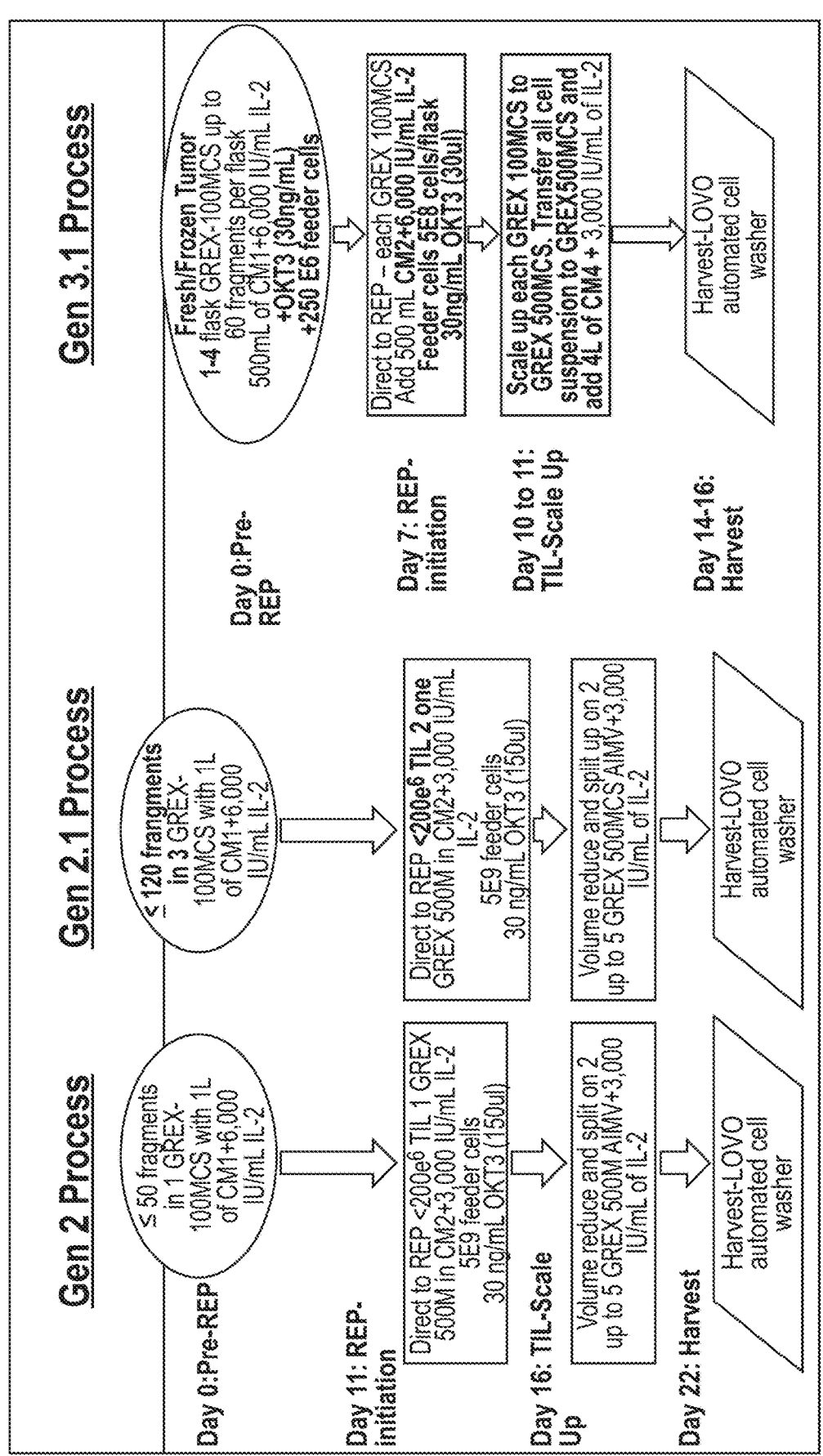
FIG. 37: Shows a comparison between various Gen 2 (2A process) and the Gen 3.1 process embodiment.
Figure 43:
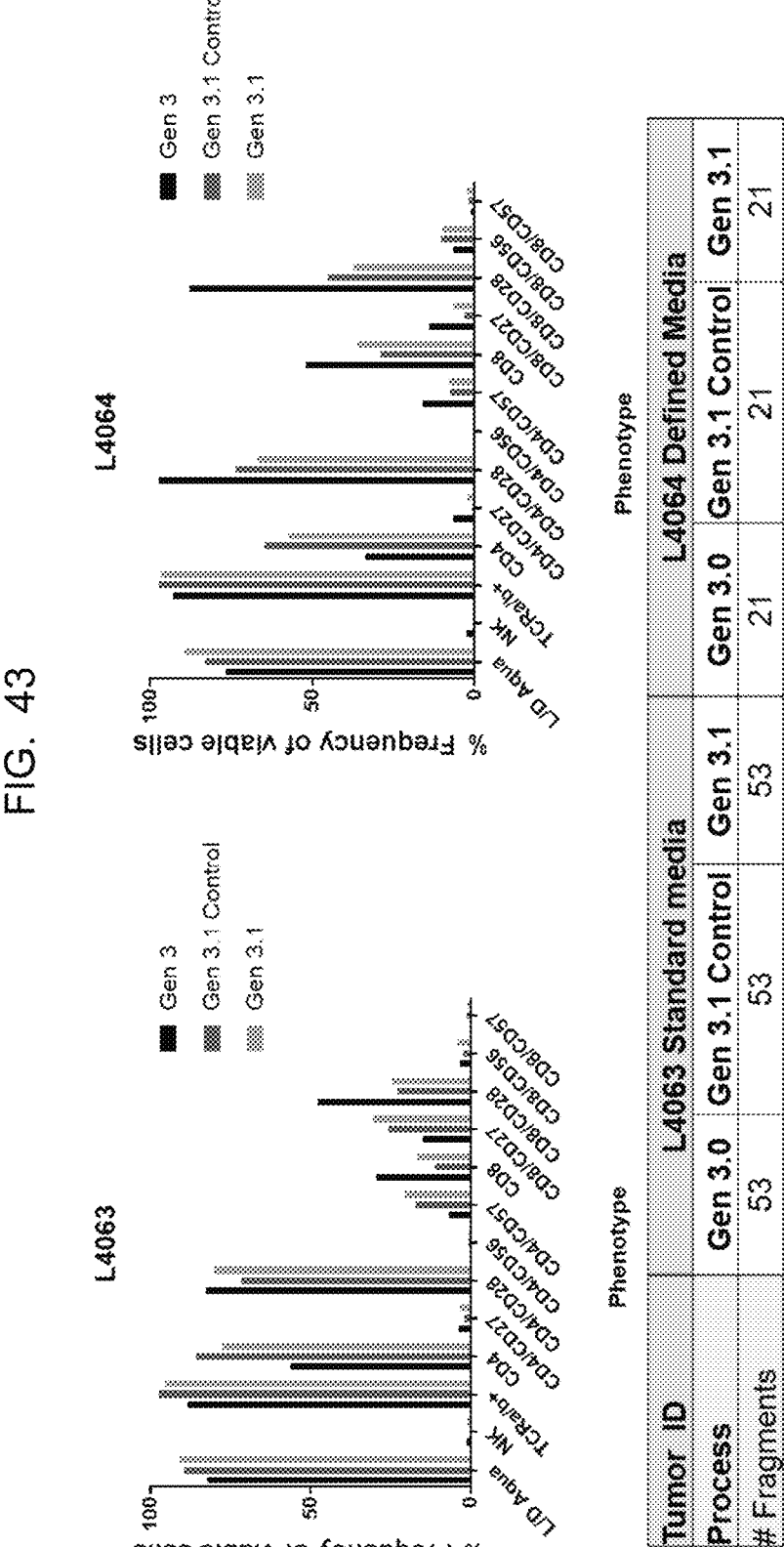
FIG. 43: Phenotype comparison: Gen 3.0 and Gen 3.1 embodiments of the process showed comparable CD28, CD27 and CD57 expression.
Figure 44:
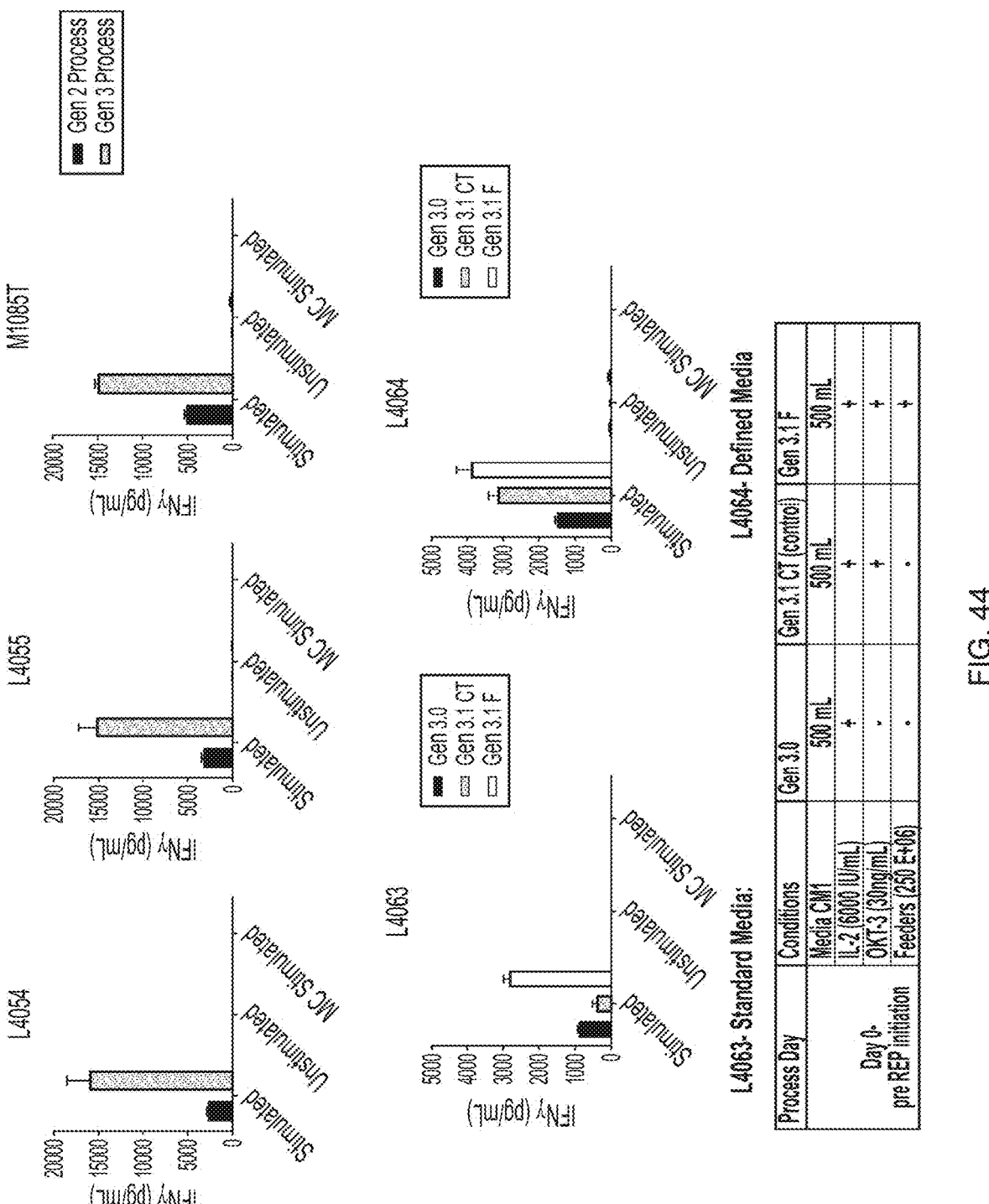
FIG. 44: Higher production of IFNγ on Gen 3 final product. IFNγ analysis (by ELISA) was assessed in the culture frozen supernatant to compared both processes. For each tumor overnight stimulation with coated anti-CD3 plate, using fresh TIL product on each Gen 2 (e.g., day 22) and Gen 3 process (e.g., day 16). Each bar represents here are IFNγ levels of stimulated, unstimulated and media control.

An exemplary TIL process known as process 3 (also referred to herein as GEN3) containing some of these features is depicted in FIG. 8 (in particular, e.g., FIG. 8B and/or FIG. 8C), and some of the advantages of this embodiment of the present invention over process 2A are described in FIGS. 1, 2, 30, and 31 (in particular, e.g., FIG. 8B and/or FIG. 8C). Two embodiments of process 3 are shown in FIGS. 1 and 30 (in particular, e.g., FIG. 8B and/or FIG. 8C). Process 2A or Gen 2 is also described in U.S. Patent Publication No. 2018/0280436, incorporated by reference herein in its entirety. The Gen 3 process is also described in U.S. Ser. No. 62/755,954 filed on Nov. 5, 2018 (116983-5045-PR).

As discussed and generally outlined herein, TILs are taken from a patient sample and manipulated to expand their number prior to transplant into a patient using the TIL expansion process described herein and referred to as Gen 3. In some embodiments, the TILs may be optionally genetically manipulated as discussed below. In some embodiments, the TILs may be cryopreserved prior to or after expansion. Once thawed, they may also be restimulated to increase their metabolism prior to infusion into a patient.

In some embodiments, the priming first expansion (including processes referred herein as the pre-Rapid Expansion (Pre-REP), as well as processes shown in FIG. 8 (in particular, e.g., FIG. 8B and/or FIG. 8C) as Step B) is shortened to 1 to 8 days and the rapid second expansion (including processes referred to herein as Rapid Expansion Protocol (REP) as well as processes shown in FIG. 1 (in particular, e.g., FIG. 8B and/or FIG. 8C) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 8B and/or FIG. 8C) as Step B) is shortened to 1 to 8 days and the rapid second expansion (including processes referred to herein as Rapid Expansion Protocol (REP) as well as processes shown in FIG. 1 (in particular, e.g., FIG. 8B and/or FIG. 8C) as Step D) is shortened to 1 to 8 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 8B and/or FIG. 8C) as Step B) is shortened to 1 to 7 days and the rapid second expansion (including processes referred to herein as Rapid Expansion Protocol (REP) as well as processes shown in FIG. 1 (in particular, e.g., FIG. 8B and/or FIG. 8C) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 1B and/or FIG. 8C) as Step B) is 1 to 7 days and the rapid second expansion (including processes referred to herein as Rapid Expansion Protocol (REP) as well as processes shown in FIG. 1 (in particular, e.g., FIG. 8B and/or FIG. 8C) as Step D) is 1 to 10 days, as discussed in detail below as well as in the examples and figures. In some embodiments, the priming first expansion (for example, an expansion described as Step B in FIG. 1 (in particular, e.g., FIG. 8B and/or FIG. 8C)) is shortened to 8 days and the rapid second expansion (for example, an expansion as described in Step D in FIG. 1 (in particular, e.g., FIG. 8B and/or FIG. 8C)) is 7 to 9 days. In some embodiments, the priming first expansion (for example, an expansion described as Step B in FIG. 1 (in particular, e.g., FIG. 8B and/or FIG. 8C)) is 8 days and the rapid second expansion (for example, an expansion as described in Step D in FIG. 1 (in particular, e.g., FIG. 8B and/or FIG. 8C)) is 8 to 9 days. In some embodiments, the priming first expansion (for example, an expansion described as Step B in FIG. 1 (in particular, e.g., FIG. 8B and/or FIG. 8C)) is shortened to 7 days and the rapid second expansion (for example, an expansion as described in Step D in FIG. 1 (in particular, e.g., FIG. 8B and/or FIG. 8C)) is 7 to 8 days. In some embodiments, the priming first expansion (for example, an expansion described as Step B in FIG. 8 (in particular, e.g., FIG. 8B and/or FIG. 8C)) is shortened to 8 days and the rapid second expansion (for example, an expansion as described in Step D in FIG. 8 (in particular, e.g., FIG. 8B and/or FIG. 8C)) is 8 days. In some embodiments, the priming first expansion (for example, an expansion described as Step B in FIG. 8 (in particular, e.g., FIG. 8B and/or FIG. 8C)) is 8 days and the rapid second expansion (for example, an expansion as described in Step D in FIG. 8 (in particular, e.g., FIG. 8B and/or FIG. 8C)) is 9 days. In some embodiments, the priming first expansion (for example, an expansion described as Step B in FIG. 8 (in particular, e.g., FIG. 8B and/or FIG. 8C)) is 8 days and the rapid second expansion (for example, an expansion as described in Step D in FIG. 8 (in particular, e.g., FIG. 8B and/or FIG. 8C)) is 10 days. In some embodiments, the priming first expansion (for example, an expansion described as Step B in FIG. 8 (in particular, e.g., FIG. 8B and/or FIG. 8C)) is 7 days and the rapid second expansion (for example, an expansion as described in Step D in FIG.

8 (in particular, e.g., FIG. 8B and/or FIG. 8C)) is 7 to 10 days. In some embodiments, the priming first expansion (for example, an expansion described as Step B in FIG. 8 (in particular, e.g., FIG. 8B and/or FIG. 8C)) is 7 days and the rapid second expansion (for example, an expansion as described in Step D in FIG. 8 (in particular, e.g., FIG. 8B and/or FIG. 8C)) is 8 to 10 days. In some embodiments, the priming first expansion (for example, an expansion described as Step B in FIG. 8 (in particular, e.g., FIG. 8B and/or FIG. 8C)) is 7 days and the rapid second expansion (for example, an expansion as described in Step D in FIG. 8 (in particular, e.g., FIG. 8B and/or FIG. 8C)) is 9 to 10 days. In some embodiments, the priming first expansion (for example, an expansion described as Step B in FIG. 8 (in particular, e.g., FIG. 8B and/or FIG. 8C)) is shortened to 7 days and the rapid second expansion (for example, an expansion as described in Step D in FIG. 8 (in particular, e.g., FIG. 8B and/or FIG. 8C)) is 7 to 9 days. In some embodiments, the combination of the priming first expansion and rapid second expansion (for example, expansions described as Step B and Step D in FIG. 1 (in particular, e.g., FIG. 1B and/or FIG. 8C)) is 14-16 days, as discussed in detail below and in the examples and figures. Particularly, it is considered that certain embodiments of the present invention comprise a priming first expansion step in which TILs are activated by exposure to an anti-CD3 antibody, e.g., OKT-3 in the presence of IL-2 or exposure to an antigen in the presence of at least IL-2 and an anti-CD3 antibody e.g. OKT-3. In certain embodiments, the TILs which are activated in the priming first expansion step as described above are a first population of TILs i.e., which are a primary cell population.

The "Step" Designations A, B, C, etc., below are in reference to the non-limiting example in FIG. 8 (in particular, e.g., FIG. 8B and/or FIG. 8C) and in reference to certain non-limiting embodiments described herein. The ordering of the Steps below and in FIG. 8 (in particular, e.g., FIG. 8B and/or FIG. 8C) is exemplary and any combination or order of steps, as well as additional steps, repetition of steps, and/or omission of steps is contemplated by the present application and the methods disclosed herein.

A. Step A: Obtain Patient Tumor Sample

In general, TILs are initially obtained from a patient tumor sample ("primary TILs") or from circulating lymphocytes, such as peripheral blood lymphocytes, including peripheral blood lymphocytes having TIL-like characteristics, and are then expanded into a larger population for further manipulation as described herein, optionally cryopreserved, and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, the cancer is selected from cervical cancer, head and neck cancer (including, for example, head and neck squamous cell carcinoma (HNSCC)), glioblastoma (GBM), gastrointestinal cancer, ovarian cancer, sarcoma, pancreatic cancer, bladder cancer, breast cancer, triple negative breast cancer, and non-small cell lung carcinoma. In some embodiments, useful TILs are obtained from malignant melanoma tumors, as these have been reported to have particularly high levels of TILs.

Once obtained, the tumor sample is generally fragmented using sharp dissection into small pieces of between 1 to about 8 mm$^3$, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/ml 10× working stock.

In some embodiments, the enzyme mixture comprises DNAse. In some embodiments, the working stock for the DNAse is a 10,000 IU/ml 10× working stock.

In some embodiments, the enzyme mixture comprises hyaluronidase. In some embodiments, the working stock for the hyaluronidase is a 10-mg/ml 10× working stock.

In some embodiments, the enzyme mixture comprises 10 mg/ml collagenase, 1000 IU/ml DNAse, and 1 mg/ml hyaluronidase.

In some embodiments, the enzyme mixture comprises 10 mg/ml collagenase, 500 IU/ml DNAse, and 1 mg/ml hyaluronidase.

In general, the cell suspension obtained from the tumor is called a "primary cell population" or a "freshly obtained" or a "freshly isolated" cell population. In certain embodiments, the freshly obtained cell population of TILs is exposed to a cell culture medium comprising antigen presenting cells, IL-12 and OKT-3.

In some embodiments, fragmentation includes physical fragmentation, including, for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 8 (in particular, e.g., FIG. 8B and/or FIG. 8C)). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the step of fragmentation is an in vitro or ex-vivo process. In some embodiments, the tumor is fragmented and 10, 20, 30, 40 or more fragments or pieces are placed in each container for the priming first expansion. In some embodiments, the tumor is fragmented and 30 or 40 fragments or pieces are placed in each container for the priming first expansion. In some embodiments, the tumor is fragmented and 40 fragments or pieces are placed in each container for the priming first expansion. In some embodiments, the multiple fragments comprise about 4 to about 50 fragments, wherein each fragment has a volume of about 27 mm$^3$. In some embodiments, the multiple fragments comprise about 30 to about 60 fragments with a total volume of about 1300 mm$^3$ to about 1500 mm$^3$. In some embodiments, the multiple fragments comprise about 50 fragments with a total volume of about 1350 mm$^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 mm$^3$ and 10 mm$^3$. In some embodiments, the tumor fragment is between about 1 mm$^3$ and 8 mm$^3$. In some embodiments, the tumor fragment is about 1 mm$^3$. In some embodiments, the tumor fragment is about 2 mm$^3$. In some embodiments, the tumor fragment is about 3 mm$^3$. In some embodiments, the tumor fragment is about 4 mm$^3$. In some embodiments, the tumor fragment is about 5 mm$^3$. In some embodiments, the tumor fragment is about 6 mm$^3$. In some embodiments, the tumor fragment is about 7 mm$^3$. In some embodiments, the tumor fragment is about 8 mm$^3$. In some embodiments, the tumor fragment is about 9 mm$^3$. In some embodiments, the tumor fragment is about 10 mm$^3$. In some embodiments, the tumor fragments are 1-4 mm×1-4 mm×1-4 mm. In some embodiments, the tumor fragments are 1 mm×1 mm×1 mm. In some embodiments, the tumor fragments are 2 mm×2 mm×2 mm.

In some embodiments, the tumor fragments are 3 mm×3 mm×3 mm. In some embodiments, the tumor fragments are 4 mm×4 mm×4 mm.

In some embodiments, the tumors are fragmented in order to minimize the amount of hemorrhagic, necrotic, and/or fatty tissues on each piece. In some embodiments, the tumors are fragmented in order to minimize the amount of hemorrhagic tissue on each piece. In some embodiments, the tumors are fragmented in order to minimize the amount of necrotic tissue on each piece. In some embodiments, the tumors are fragmented in order to minimize the amount of fatty tissue on each piece. In certain embodiments, the step of fragmentation of the tumor is an in vitro or ex-vivo method.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the cell suspension prior to the priming first expansion step is called a "primary cell population" or a "freshly obtained" or "freshly isolated" cell population.

In some embodiments, cells can be optionally frozen after sample isolation (e.g., after obtaining the tumor sample and/or after obtaining the cell suspension from the tumor sample) and stored frozen prior to entry into the expansion described in Step B, which is described in further detail below, as well as exemplified in FIG. 8 (in particular, e.g., FIG. 8B).

1. Core/Small Biopsy Derived TILS

In some embodiments, TILs are initially obtained from a patient tumor sample ("primary TILs") obtained by a core biopsy or similar procedure and then expanded into a larger population for further manipulation as described herein, optionally cryopreserved, and optionally evaluated for phenotype and metabolic parameters.

In some embodiments, a patient tumor sample may be obtained using methods known in the art, generally via small biopsy, core biopsy, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. In some embodiments, the sample can be from multiple small tumor samples or biopsies. In some embodiments, the sample can comprise multiple tumor samples from a single tumor from the same patient. In some embodiments, the sample can comprise multiple tumor samples from one, two, three, or four tumors from the same patient. In some embodiments, the sample can comprise multiple tumor samples from multiple tumors from the same patient. The solid tumor may of lung and/or non-small cell lung carcinoma (NSCLC).

In general, the cell suspension obtained from the tumor core or fragment is called a "primary cell population" or a "freshly obtained" or a "freshly isolated" cell population. In certain embodiments, the freshly obtained cell population of TILs is exposed to a cell culture medium comprising antigen presenting cells, IL-2 and OKT-3.

In some embodiments, if the tumor is metastatic and the primary lesion has been efficiently treated/removed in the past, removal of one of the metastatic lesions may be needed. In some embodiments, the least invasive approach is to remove a skin lesion, or a lymph node on the neck or axillary area when available. In some embodiments, a skin lesion is removed or small biopsy thereof is removed. In some embodiments, a lymph node or small biopsy thereof is removed. In some embodiments, a lung or liver metastatic lesion, or an intra-abdominal or thoracic lymph node or small biopsy can thereof can be employed.

In some embodiments, the tumor is a melanoma. In some embodiments, the small biopsy for a melanoma comprises a mole or portion thereof.

In some embodiments, the small biopsy is a punch biopsy. In some embodiments, the punch biopsy is obtained with a circular blade pressed into the skin. In some embodiments, the punch biopsy is obtained with a circular blade pressed into the skin. around a suspicious mole. In some embodiments, the punch biopsy is obtained with a circular blade pressed into the skin, and a round piece of skin is removed. In some embodiments, the small biopsy is a punch biopsy and round portion of the tumor is removed.

In some embodiments, the small biopsy is an excisional biopsy. In some embodiments, the small biopsy is an excisional biopsy and the entire mole or growth is removed. In some embodiments, the small biopsy is an excisional biopsy and the entire mole or growth is removed along with a small border of normal-appearing skin.

In some embodiments, the small biopsy is an incisional biopsy. In some embodiments, the small biopsy is an incisional biopsy and only the most irregular part of a mole or growth is taken. In some embodiments, the small biopsy is an incisional biopsy and the incisional biopsy is used when other techniques can't be completed, such as if a suspicious mole is very large.

In some embodiments, the small biopsy is a lung biopsy. In some embodiments, the small biopsy is obtained by bronchoscopy. Generally, bronchoscopy, the patient is put under anesthesia, and a small tool goes through the nose or mouth, down the throat, and into the bronchial passages, where small tools are used to remove some tissue. In some embodiments, where the tumor or growth cannot be reached via bronchoscopy, a transthoracic needle biopsy can be employed. Generally, for a transthoracic needle biopsy, the patient is also under anesthesia and a needle is inserted through the skin directly into the suspicious spot to remove a small sample of tissue. In some embodiments, a transthoracic needle biopsy may require interventional radiology (for example, the use of x-rays or CT scan to guide the needle). In some embodiments, the small biopsy is obtained by needle biopsy. In some embodiments, the small biopsy is obtained endoscopic ultrasound (for example, an endoscope with a light and is placed through the mouth into the esophagus). In some embodiments, the small biopsy is obtained surgically.

In some embodiments, the small biopsy is a head and neck biopsy. In some embodiments, the small biopsy is an incisional biopsy. In some embodiments, the small biopsy is an incisional biopsy, wherein a small piece of tissue is cut from an abnormal-looking area. In some embodiments, if the abnormal region is easily accessed, the sample may be taken without hospitalization. In some embodiments, if the tumor is deeper inside the mouth or throat, the biopsy may need to be done in an operating room, with general anesthesia. In some embodiments, the small biopsy is an excisional biopsy. In some embodiments, the small biopsy is an excisional biopsy, wherein the whole area is removed. In some embodiments, the small biopsy is a fine needle aspiration (FNA). In some embodiments, the small biopsy is a fine needle aspiration (FNA), wherein a very thin needle attached to a syringe is used to extract (aspirate) cells from a tumor or lump. In some embodiments, the small biopsy is a punch biopsy. In some embodiments, the small biopsy is a punch biopsy, wherein punch forceps are used to remove a piece of the suspicious area.

In some embodiments, the small biopsy is a cervical biopsy. In some embodiments, the small biopsy is obtained via colposcopy. Generally, colposcopy methods employ the use of a lighted magnifying instrument attached to magnifying binoculars (a colposcope) which is then used to biopsy a small section of the surface of the cervix. In some embodiments, the small biopsy is a conization/cone biopsy. In some embodiments, the small biopsy is a conization/cone biopsy, wherein an outpatient surgery may be needed to remove a larger piece of tissue from the cervix. In some embodiments, the cone biopsy, in addition to helping to confirm a diagnosis, a cone biopsy can serve as an initial treatment.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include cancers of the lung. In some embodiments, the cancer is non-small cell lung carcinoma (NSCLC). The tissue structure of solid tumors includes interdependent tissue compartments including the parenchyma (cancer cells) and the supporting stromal cells in which the cancer cells are dispersed and which may provide a supporting microenvironment.

In some embodiments, the sample from the tumor is obtained as a fine needle aspirate (FNA), a core biopsy, a small biopsy (including, for example, a punch biopsy). In some embodiments, sample is placed first into a G-Rex 10. In some embodiments, sample is placed first into a G-Rex 10 when there are 1 or 2 core biopsy and/or small biopsy samples. In some embodiments, sample is placed first into a G-Rex 100 when there are 3, 4, 5, 6, 8, 9, or 10 or more core biopsy and/or small biopsy samples. In some embodiments, sample is placed first into a G-Rex 500 when there are 3, 4, 5, 6, 8, 9, or 10 or more core biopsy and/or small biopsy samples.

The FNA can be obtained from a lung tumor, including, for example, an NSCLC. In some embodiments, the FNA is obtained from a lung tumor, such as a lung tumor from a patient with non-small cell lung cancer (NSCLC). In some cases, the patient with NSCLC has previously undergone a surgical treatment.

TILs described herein can be obtained from an FNA sample. In some cases, the FNA sample is obtained or isolated from the patient using a fine gauge needle ranging from an 18 gauge needle to a 25 gauge needle. The fine gauge needle can be 18 gauge, 19 gauge, 20 gauge, 21 gauge, 22 gauge, 23 gauge, 24 gauge, or 25 gauge. In some embodiments, the FNA sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In some cases, the TILs described herein are obtained from a core biopsy sample. In some cases, the core biopsy sample is obtained or isolated from the patient using a surgical or medical needle ranging from an 11 gauge needle to a 16 gauge needle. The needle can be 11 gauge, 12 gauge, 13 gauge, 14 gauge, 15 gauge, or 16 gauge. In some embodiments, the core biopsy sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In general, the harvested cell suspension is called a "primary cell population" or a "freshly harvested" cell population.

In some embodiments, the TILs are not obtained from tumor digests. In some embodiments, the solid tumor cores are not fragmented.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

2. Methods of Expanding Peripheral Blood Lymphocytes (PBLs) from Peripheral Blood PBL Method 1. In an embodiment of the invention, PBLs are expanded using the processes described herein. In an embodiment of the invention, the method comprises obtaining a PBMC sample from whole blood. In an embodiment, the method comprises enriching T-cells by isolating pure T-cells from PBMCs using negative selection of a non-CD19+ fraction. In an embodiment, the method comprises enriching T-cells by isolating pure T-cells from PBMCs using magnetic bead-based negative selection of a non-CD19+ fraction.

In an embodiment of the invention, PBL Method 1 is performed as follows: On Day 0, a cryopreserved PBMC sample is thawed and PBMCs are counted. T-cells are isolated using a Human Pan T-Cell Isolation Kit and LS columns (Miltenyi Biotec).

PBL Method 2. In an embodiment of the invention, PBLs are expanded using PBL Method 2, which comprises obtaining a PBMC sample from whole blood. The T-cells from the PBMCs are enriched by incubating the PBMCs for at least three hours at 37° C. and then isolating the non-adherent cells.

In an embodiment of the invention, PBL Method 2 is performed as follows: On Day 0, the cryopreserved PMBC sample is thawed and the PBMC cells are seeded at 6 million cells per well in a 6 well plate in CM-2 media and incubated for 3 hours at 37 degrees Celsius. After 3 hours, the non-adherent cells, which are the PBLs, are removed and counted.

PBL Method 3. In an embodiment of the invention, PBLs are expanded using PBL Method 3, which comprises obtaining a PBMC sample from peripheral blood. B-cells are isolated using a CD19+ selection and T-cells are selected using negative selection of the non-CD19+ fraction of the PBMC sample.

In an embodiment of the invention, PBL Method 3 is performed as follows: On Day 0, cryopreserved PBMCs derived from peripheral blood are thawed and counted. CD19+ B-cells are sorted using a CD19 Multisort Kit, Human (Miltenyi Biotec). Of the non-CD19+ cell fraction, T-cells are purified using the Human Pan T-cell Isolation Kit and LS Columns (Miltenyi Biotec).

In an embodiment, PBMCs are isolated from a whole blood sample. In an embodiment, the PBMC sample is used as the starting material to expand the PBLs. In an embodiment, the sample is cryopreserved prior to the expansion process. In another embodiment, a fresh sample is used as the starting material to expand the PBLs. In an embodiment of the invention, T-cells are isolated from PBMCs using methods known in the art. In an embodiment, the T-cells are isolated using a Human Pan T-cell isolation kit and LS columns. In an embodiment of the invention, T-cells are isolated from PBMCs using antibody selection methods known in the art, for example, CD19 negative selection.

In an embodiment of the invention, the PBMC sample is incubated for a period of time at a desired temperature effective to identify the non-adherent cells. In an embodiment of the invention, the incubation time is about 3 hours. In an embodiment of the invention, the temperature is about 37° Celsius. The non-adherent cells are then expanded using the process described above.

In some embodiments, the PBMC sample is from a subject or patient who has been optionally pre-treated with a regimen comprising a kinase inhibitor or an ITK inhibitor. In some embodiments, the tumor sample is from a subject or patient who has been pre-treated with a regimen comprising a kinase inhibitor or an ITK inhibitor. In some embodiments, the PBMC sample is from a subject or patient who has been pre-treated with a regimen comprising a kinase inhibitor or an ITK inhibitor, has undergone treatment for at least 1 month, at least 2 months, at least 3 months, at least 4 months, at least 5 months, at least 6 months, or 1 year or more. In another embodiment, the PBMCs are derived from a patient who is currently on an ITK inhibitor regimen, such as ibrutinib.

In some embodiments, the PBMC sample is from a subject or patient who has been pre-treated with a regimen comprising a kinase inhibitor or an ITK inhibitor and is refractory to treatment with a kinase inhibitor or an ITK inhibitor, such as ibrutinib.

In some embodiments, the PBMC sample is from a subject or patient who has been pre-treated with a regimen comprising a kinase inhibitor or an ITK inhibitor but is no longer undergoing treatment with a kinase inhibitor or an ITK inhibitor. In some embodiments, the PBMC sample is from a subject or patient who has been pre-treated with a regimen comprising a kinase inhibitor or an ITK inhibitor but is no longer undergoing treatment with a kinase inhibitor or an ITK inhibitor and has not undergone treatment for at least 1 month, at least 2 months, at least 3 months, at least 4 months, at least 5 months, at least 6 months, or at least 1 year or more. In another embodiment, the PBMCs are derived from a patient who has prior exposure to an ITK inhibitor, but has not been treated in at least 3 months, at least 6 months, at least 9 months, or at least 1 year.

In an embodiment of the invention, at Day 0, cells are selected for CD19+ and sorted accordingly. In an embodiment of the invention, the selection is made using antibody binding beads. In an embodiment of the invention, pure T-cells are isolated on Day 0 from the PBMCs.

In an embodiment of the invention, for patients that are not pre-treated with ibrutinib or other ITK inhibitor, 10-15 ml of Buffy Coat will yield about $5 \times 10^9$ PBMC, which, in turn, will yield about $5.5 \times 10^7$ PBLs.

In an embodiment of the invention, for patients that are pre-treated with ibrutinib or other ITK inhibitor, the expansion process will yield about $20 \times 10^9$ PBLs. In an embodiment of the invention, $40.3 \times 10^6$ PBMCs will yield about $4.7 \times 10^5$ PBLs.

In any of the foregoing embodiments, PBMCs may be derived from a whole blood sample, by apheresis, from the buffy coat, or from any other method known in the art for obtaining PBMCs.

3. Methods of Expanding Marrow Infiltrating Lymphocytes (MILs) from PBMCs Derived from Bone Marrow MIL Method 3. In an embodiment of the invention, the method comprises obtaining PBMCs from the bone marrow. On Day 0, the PBMCs are selected for CD3+/CD33+/CD20+/CD14+ and sorted, and the non-CD3+/CD33+/CD20+/CD14+ cell fraction is sonicated and a portion of the sonicated cell fraction is added back to the selected cell fraction.

In an embodiment of the invention, MTh Method 3 is performed as follows: On Day 0, a cryopreserved sample of PBMCs is thawed and PBMCs are counted. The cells are stained with CD3, CD33, CD20, and CD14 antibodies and sorted using a S3e cell sorted (Bio-Rad). The cells are sorted into two fractions—an immune cell fraction (or the MIL fraction) (CD3+CD33+CD20+CD14+) and an AML blast cell fraction (non-CD3+CD33+CD20+CD14+).

In an embodiment of the invention, PBMCs are obtained from bone marrow. In an embodiment, the PBMCs are obtained from the bone marrow through apheresis, aspiration, needle biopsy, or other similar means known in the art. In an embodiment, the PBMCs are fresh. In another embodiment, the PBMCs are cryopreserved.

In an embodiment of the invention, MILs are expanded from 10-50 ml of bone marrow aspirate. In an embodiment of the invention, 10 ml of bone marrow aspirate is obtained from the patient. In another embodiment, 20 ml of bone marrow aspirate is obtained from the patient. In another embodiment, 30 ml of bone marrow aspirate is obtained from the patient. In another embodiment, 40 ml of bone marrow aspirate is obtained from the patient. In another embodiment, 50 ml of bone marrow aspirate is obtained from the patient.

In an embodiment of the invention, the number of PBMCs yielded from about 10-50 ml of bone marrow aspirate is about $5 \times 10^7$ to about $10 \times 10^7$ PBMCs. In another embodiment, the number of PMBCs yielded is about $7 \times 10^7$ PBMCs.

In an embodiment of the invention, about $5 \times 10^7$ to about $10 \times 10^7$ PBMCs, yields about $0.5 \times 10^6$ to about $1.5 \times 10^6$ MILs. In an embodiment of the invention, about $1 \times 10^6$ MILs is yielded.

In an embodiment of the invention, $12 \times 10^6$ PBMC derived from bone marrow aspirate yields approximately $1.4 \times 10^5$ MILs.

In any of the foregoing embodiments, PBMCs may be derived from a whole blood sample, from bone marrow, by apheresis, from the buffy coat, or from any other method known in the art for obtaining PBMCs.

B. Step B: Priming First Expansion

In some embodiments, the present methods provide for younger TILs, which may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology*, 75:157-167 (2012); Dudley et al., *Clin Cancer Res*, 16:6122-6131 (2010); Huang et al., *J Immunother*, 28(3):258-267 (2005); Besser et al., *Clin Cancer Res*, 19(17):OF1-OF9 (2013); Besser et al., *J Immunother* 32:415-423 (2009); Robbins, et al., *J Immunol* 2004; 173:7125-7130; Shen et al., *J Immunother*, 30:123-129 (2007); Zhou, et al., *J Immunother*, 28:53-62 (2005); and Tran, et al., *J Immunother*, 31:742-751 (2008), all of which are incorporated herein by reference in their entireties.

After dissection or digestion of tumor fragments and/or tumor fragments, for example such as described in Step A of FIG. 1 (in particular, e.g., FIG. 1B and/or FIG. 8C), the resulting cells are cultured in serum containing IL-2, OKT-3, and feeder cells (e.g., antigen-presenting feeder cells), under conditions that favor the growth of TILs over tumor and other cells. In some embodiments, the IL-2, OKT-3, and feeder cells are added at culture initiation along with the tumor digest and/or tumor fragments (e.g., at Day 0). In some embodiments, the tumor digests and/or tumor fragments are incubated in a container with up to 60 fragments per container and with 6000 IU/mL of IL-2. In some embodiments, this primary cell population is cultured for a period of days, generally from 1 to 8 days, resulting in a bulk TIL population, generally about $1 \times 10^8$ bulk TIL cells. In some embodiments, this primary cell population is cultured for a period of days, generally from 1 to 7 days, resulting in a bulk TIL population, generally about $1 \times 10^8$ bulk TIL cells. In some embodiments, priming first expansion occurs for a period of 1 to 8 days, resulting in a bulk TIL population, generally about $1 \times 10^8$ bulk TIL cells. In some embodiments, priming first expansion occurs for a period of 1 to 7 days, resulting in a bulk TIL population, generally about $1 \times 10^8$ bulk TIL cells. In some embodiments, this priming first expansion occurs for a period of 5 to 8 days, resulting in a bulk TIL population, generally about $1 \times 10^8$ bulk TIL cells. In some embodiments, this priming first expansion occurs for a period of 5 to 7 days, resulting in a bulk TIL population, generally about $1 \times 10^8$ bulk TIL cells. In some embodiments, this priming first expansion occurs for a period of about 6 to 8 days, resulting in a bulk TIL population, generally about $1 \times 10^8$ bulk TIL cells. In some embodiments, this priming first expansion occurs for a period of about 6 to 7 days, resulting in a bulk TIL population, generally about $1 \times 10^8$ bulk TIL cells. In some embodiments, this priming first expansion occurs for a period of about 7 to 8 days, resulting in a bulk TIL population, generally about $1 \times 10^8$ bulk TIL cells. In some embodiments, this priming first expansion occurs for a period of about 7 days, resulting in a bulk TIL population, generally about $1 \times 10^8$ bulk TIL cells. In some embodiments, this priming first expansion occurs for a period of about 8 days, resulting in a bulk TIL population, generally about $1 \times 10^8$ bulk TIL cells.

In a preferred embodiment, expansion of TILs may be performed using a priming first expansion step (for example such as those described in Step B of FIG. 8 (in particular, e.g., FIG. 8B and/or FIG. 8C), which can include processes referred to as pre-REP or priming REP and which contains feeder cells from Day 0 and/or from culture initiation) as described below and herein, followed by a rapid second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein. In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin.

In some embodiments, there are less than or equal to 240 tumor fragments. In some embodiments, there are less than or equal to 240 tumor fragments placed in less than or equal to 4 containers. In some embodiments, the containers are GREX100 MCS flasks. In some embodiments, less than or equal to 60 tumor fragments are placed in 1 container. In some embodiments, each container comprises less than or equal to 500 mL of media per container. In some embodiments, the media comprises IL-2. In some embodiments, the media comprises 6000 IU/mL of IL-2. In some embodiments, the media comprises antigen-presenting feeder cells (also referred to herein as "antigen-presenting cells"). In some embodiments, the media comprises $2.5 \times 10^8$ antigen-presenting feeder cells per container. In some embodiments, the media comprises OKT-3. In some embodiments, the media comprises 30 ng/mL of OKT-3 per container. In some embodiments, the container is a GREX100 MCS flask. In some embodiments, the media comprises 6000 IU/mL of IL-2, 30 ng of OKT-3, and $2.5 \times 10^8$ antigen-presenting feeder cells. In some embodiments, the media comprises 6000 IU/mL of IL-2, 30 ng/mL of OKT-3, and $2.5 \times 10^8$ antigen-presenting feeder cells per container.

After preparation of the tumor fragments, the resulting cells (i.e., fragments which is a primary cell population) are cultured in media containing IL-2, antigen-presenting feeder cells and OKT-3 under conditions that favor the growth of TILs over tumor and other cells and which allow for TIL priming and accelerated growth from initiation of the culture on Day 0. In some embodiments, the tumor digests and/or tumor fragments are incubated in with 6000 IU/mL of IL-2, as well as antigen-presenting feeder cells and OKT-3. This primary cell population is cultured for a period of days, generally from 1 to 8 days, resulting in a bulk TIL population, generally about $1 \times 10^8$ bulk TIL cells. In some embodiments, the growth media during the priming first expansion comprises IL-2 or a variant thereof, as well as antigen-presenting feeder cells and OKT-3. In some embodiments, this primary cell population is cultured for a period of days, generally from 1 to 7 days, resulting in a bulk TIL population, generally about $1 \times 10^8$ bulk TIL cells. In some embodiments, the growth media during the priming first expansion comprises IL-2 or a variant thereof, as well as antigen-presenting feeder cells and OKT-3. In some embodiments, the IL-2 is recombinant human IL-2 (rhIL-2). In some embodiments the IL-2 stock solution has a specific activity of $20$-$30 \times 10^6$ IU/mg for a 1 mg vial. In some embodiments the IL-2 stock solution has a specific activity of $20 \times 10^6$ IU/mg for a 1 mg vial. In some embodiments the IL-2 stock solution has a specific activity of $25 \times 10^6$ IU/mg for a 1 mg vial. In some embodiments the IL-2 stock solution has a specific activity of $30 \times 10^6$ IU/mg for a 1 mg vial. In some embodiments, the IL-2 stock solution has a final concentration of $4$-$8 \times 10^6$ IU/mg of IL-2. In some embodiments, the IL-2 stock solution has a final concentration of $5$-$7 \times 10^6$ IU/mg of IL-2. In some embodiments, the IL-2 stock solution has a final concentration of $6 \times 10^6$ IU/mg of IL-2. In some embodiments, the IL-2 stock solution is prepare as described in Example C. In some embodiments, the priming first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the priming first expansion culture media comprises about 9,000 IU/mL of IL-2 to about 5,000 IU/mL of IL-2. In some embodiments, the priming first expansion culture media comprises about 8,000 IU/mL of IL-2 to about 6,000 IU/mL of IL-2. In some embodiments, the priming first expansion culture media comprises about 7,000 IU/mL of IL-2 to about 6,000 IU/mL of IL-2. In some embodiments, the priming first expansion culture media comprises about 6,000 IU/mL of IL-2. In an embodiment, the cell culture medium further comprises IL-2. In some embodiments, the priming first expansion cell culture medium comprises about 3000 IU/mL of IL-2. In an embodiment, the priming first expansion cell culture medium further comprises IL-2. In a preferred embodiment, the priming first expansion cell culture medium comprises about 3000 IU/mL of IL-2. In an embodiment, the priming first expansion cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the priming first expansion cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, priming first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the priming first expansion culture media comprises about 500 IU/mL of IL-15 to about 100 IU/mL of IL-15. In some embodiments, the priming first expansion culture media comprises about 400 IU/mL of IL-15 to about 100 IU/mL of IL-15. In some embodiments, the priming first expansion culture media comprises about 300 IU/mL of IL-15 to about 100 IU/mL of IL-15. In some embodiments, the priming first expansion culture media comprises about 200 IU/mL of IL-15. In some embodiments, the priming first expansion cell culture medium comprises about 180 IU/mL of IL-15. In an embodiment, the priming first expansion cell culture medium further comprises IL-15. In a preferred embodiment, the priming first expansion cell culture medium comprises about 180 IU/mL of IL-15.

In some embodiments, priming first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the priming first expansion culture media comprises about 20 IU/mL of IL-21 to about 0.5 IU/mL of IL-21. In some embodiments, the priming first expansion culture media comprises about 15 IU/mL of IL-21 to about 0.5 IU/mL of IL-21. In some embodiments, the priming first expansion culture media comprises about 12 IU/mL of IL-21 to about 0.5 IU/mL of IL-21. In some embodiments, the priming first expansion culture media comprises about 10 IU/mL of IL-21 to about 0.5 IU/mL of IL-21. In some embodiments, the priming first expansion culture media comprises about 5 IU/mL of IL-21 to about 1 IU/mL of IL-21. In some embodiments, the priming first expansion culture media comprises about 2 IU/mL of IL-21. In some embodiments, the priming first expansion cell culture medium comprises about 1 IU/mL of IL-21. In some embodiments, the priming first expansion cell culture medium comprises about 0.5 IU/mL of IL-21. In an embodiment, the cell culture medium further comprises IL-21. In a preferred embodiment, the priming first expansion cell culture medium comprises about 1 IU/mL of IL-21.

In an embodiment, the priming first expansion cell culture medium comprises OKT-3 antibody. In some embodiments, the priming first expansion cell culture medium comprises about 30 ng/mL of OKT-3 antibody. In an embodiment, the priming first expansion cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 15 ng/ml and 30 ng/mL of OKT-3 antibody. In an embodiment, the cell culture medium comprises 30 ng/mL of OKT-3 antibody. In some embodiments, the OKT-3 antibody is muromonab.

TABLE 19

| Amino acid sequences of muromonab (exemplary OKT-3 antibody) | | | | | | |
|---|---|---|---|---|---|---|
| Identifier | Sequence (One-Letter Amino Acid Symbols) | | | | | |
| SEQ ID NO: 1 | QVQLQQSGAE | LARPGASVKM | SCKASGYTFT | RYTMHWVKQR | PGQGLEWIGY | INPSRGYTNY | 60 |
| Muromonab heavy | NQKFKDKATL | TTDKSSSTAY | MQLSSLTSED | SAVYYCARYY | DDHYCLDYWG | QGTTLTVSSA | 120 |
| chain | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAHPASST | KVDKKIEPRP | KSCDKTHTCP | PCPAPELLGG | 240 |
| | PSVFLFPPKP | KDTLMISRTP | EVTCVVVDVS | HEDPEVKFNW | YVDGVEVHNA | KTKPREEQYN | 300 |
| | STYRVVSVLT | VLHQDWLNGK | EYKCKVSNKA | LPAPIEKTIS | KAKGQPREPQ | VYTLPPSRDE | 360 |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| | | | | | | |
| SEQ ID NO: 2 | QIVLTQSPAI | MSASPGEKVT | MTCSASSSVS | YMNWYQQKSG | TSPKRWIYDT | SKLASGVPAH | 60 |
| Muromonab light | FRGSGSGTSY | SLTISGMEAE | DAATYYCQQW | SSNPFTFGSG | TKLEINRADT | APTVSIFPPS | 120 |
| chain | SEQLTSGGAS | VVCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 |

In some embodiments, the priming first expansion cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the priming first expansion cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist. In some embodiments, in addition to one or more TNFRSF agonists, the priming first expansion cell culture medium further comprises IL-2 at an initial concentration of about 6000 IU/mL and OKT-3 antibody at an initial concentration of about 30 ng/mL, and wherein the one or more TNFRSF agonists comprises a 4-1BB agonist.

In some embodiments, the priming first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In some embodiments, the CM is the CM1 described in the Examples, see, Example A. In some embodiments, the priming first expansion occurs in an initial cell culture medium or a first cell culture medium. In some embodiments, the priming first expansion culture medium or the initial cell culture medium or the first cell culture medium comprises IL-2, OKT-3 and antigen-presenting feeder cells (also referred to herein as feeder cells).

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell. Expansion SFM, CTS™ AIM-V Medium, CTS™ AIM-V SFM, LymphoONE™ Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^+$, $Sn^{2+}$ and $Zr^{4+}$. In some embodiments, the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific). In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM. In some embodiments, the final concentration of 2-mercaptoethanol in the media is 55 μM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine; L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^+$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM); Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

| | Concentrations of Non-Trace Element Moiety Ingredients | | |
| Ingredient | A preferred embodiment in supplement (mg/L) (About) | Concentration range in 1X medium (mg/L) (About) | A preferred embodiment in 1X medium (mg/L) (About) |
| --- | --- | --- | --- |
| Glycine | 150 | 5-200 | 53 |
| L-Histidine | 940 | 5-250 | 183 |

TABLE A-continued

| | Concentrations of Non-Trace Element Moiety Ingredients | | |
| Ingredient | A preferred embodiment in supplement (mg/L) (About) | Concentration range in 1X medium (mg/L) (About) | A preferred embodiment in 1X medium (mg/L) (About) |
| --- | --- | --- | --- |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-PO$_4$ (Mg Salt) | 330 | 1-200 | 50 |
| Transferrin iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83.000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology*, 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

In some embodiments, the priming first expansion (including processes such as for example those described in Step B of FIG. 1 (in particular, e.g., FIG. 1B and/or FIG. 8C), which can include those sometimes referred to as the pre-REP or priming REP) process is 1 to 8 days, as discussed in the examples and figures. In some embodiments, the priming first expansion (including processes such as for example those described in Step B of FIG. 1 (in particular, e.g., FIG. 1B and/or FIG. 8C), which can include those sometimes referred to as the pre-REP or priming REP) process is 2 to 8 days. In some embodiments, the priming first expansion (including processes such as for example those described in Step B of FIG. 1 (in particular, e.g., FIG. 1B and/or FIG. 8C), which can include those sometimes referred to as the pre-REP or priming REP) process is 3 to 8 days. In some embodiments, the priming first expansion (including processes such as for example those described in Step B of FIG. 1 (in particular, e.g., FIG. 8B and/or FIG. 8C), which can include those sometimes referred to as the pre-REP or priming REP) process is 4 to 8 days, as discussed in the examples and figures. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 1 to 7 days, as discussed in the examples and figures. In some embodiments, the priming first expansion (including processes such as for example those described in Step B of FIG. 1 (in particular, e.g., FIG. 1B and/or FIG. 8C), which can include those sometimes referred to as the pre-REP or priming REP) process is 2 to 8 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 2 to 7 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 3 to 8 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 3 to 7 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 4 to 8 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 4 to 7 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 5 to 8 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 5 to 7 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 6 to 8 days. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 6 to 7 days. In some embodiments, the priming first expansion (including processes such as for example those provided in Step B of FIG. 1 (in particular, e.g., FIG. 8B and/or FIG. 8C), which can include those sometimes referred to as the pre-REP or priming REP) process is 7 to 8 days. In some embodiments, the priming first expansion (including processes such as for example those provided in Step B of FIG. 8 (in particular, e.g., FIG.

8B and/or FIG. 8C), which can include those sometimes referred to as the pre-REP or priming REP) process is 8 days. In some embodiments, the priming first expansion (including processes such as for example those provided in Step B of FIG. 8 (in particular, e.g., FIG. 8B and/or FIG. 8C), which can include those sometimes referred to as the pre-REP or priming REP) process is 7 days.

In some embodiments, the priming first TIL expansion can proceed for 1 days to 8 days from when fragmentation occurs and/or when the first priming expansion step is initiated. In some embodiments, the priming first TIL expansion can proceed for 1 days to 7 days from when fragmentation occurs and/or when the first priming expansion step is initiated. In some embodiments, the priming first TIL expansion can proceed for 2 days to 8 days from when fragmentation occurs and/or when the first priming expansion step is initiated. In some embodiments, the priming first TIL expansion can proceed for 2 days to 7 days from when fragmentation occurs and/or when the first priming expansion step is initiated. In some embodiments, the priming first TIL expansion can proceed for 3 days to 8 days from when fragmentation occurs and/or when the first priming expansion step is initiated. In some embodiments, the priming first TIL expansion can proceed for 3 days to 7 days from when fragmentation occurs and/or when the first priming expansion step is initiated. In some embodiments, the priming first TIL expansion can proceed for 4 days to 8 days from when fragmentation occurs and/or when the first priming expansion step is initiated. In some embodiments, the priming first TIL expansion can proceed for 4 days to 7 days from when fragmentation occurs and/or when the first priming expansion step is initiated. In some embodiments, the priming first TIL expansion can proceed for 5 days to 8 days from when fragmentation occurs and/or when the first priming expansion step is initiated. In some embodiments, the priming first TIL expansion can proceed for 5 days to 7 days from when fragmentation occurs and/or when the first priming expansion step is initiated. In some embodiments, the priming first TIL expansion can proceed for 6 days to 8 days from when fragmentation occurs and/or when the first priming expansion step is initiated. In some embodiments, the priming first TIL expansion can proceed for 6 days to 7 days from when fragmentation occurs and/or when the first priming expansion step is initiated. In some embodiments, the priming first TIL expansion can proceed for 7 to 8 days from when fragmentation occurs and/or when the first priming expansion step is initiated. In some embodiments, the priming first TIL expansion can proceed for 8 days from when fragmentation occurs and/or when the first priming expansion step is initiated. In some embodiments, the priming first TIL expansion can proceed for 7 days from when fragmentation occurs and/or when the first priming expansion step is initiated.

In some embodiments, the priming first expansion of the TILs can proceed for 1 day, 2 days, 3 days, 4 days, 5 days, 6 days, 7 days, or 8 days. In some embodiments, the first TIL expansion can proceed for 1 day to 8 days. In some embodiments, the first TIL expansion can proceed for 1 day to 7 days. In some embodiments, the first TIL expansion can proceed for 2 days to 8 days. In some embodiments, the first TIL expansion can proceed for 2 days to 7 days. In some embodiments, the first TIL expansion can proceed for 3 days to 8 days. In some embodiments, the first TIL expansion can proceed for 3 days to 7 days. In some embodiments, the first TIL expansion can proceed for 4 days to 8 days. In some embodiments, the first TIL expansion can proceed for 4 days to 7 days. In some embodiments, the first TIL expansion can proceed for 5 days to 8 days. In some embodiments, the first TIL expansion can proceed for 5 days to 7 days. In some embodiments, the first TIL expansion can proceed for 6 days to 8 days. In some embodiments, the first TIL expansion can proceed for 6 days to 7 days. In some embodiments, the first TIL expansion can proceed for 7 to 8 days. In some embodiments, the first TIL expansion can proceed for 8 days. In some embodiments, the first TIL expansion can proceed for 7 days.

In some embodiments, a combination of IL-2, IL-7, IL-15, and/or IL-21 are employed as a combination during the priming first expansion. In some embodiments, IL-2, IL-7, IL-15, and/or IL-21 as well as any combinations thereof can be included during the priming first expansion, including, for example during Step B processes according to FIG. 8 (in particular, e.g., FIG. 8B and/or FIG. 8C), as well as described herein. In some embodiments, a combination of IL-2, IL-15, and IL-21 are employed as a combination during the priming first expansion. In some embodiments, IL-2, IL-15, and IL-21 as well as any combinations thereof can be included during Step B processes according to FIG. 8 (in particular, e.g., FIG. 8B and/or FIG. 8C) and as described herein.

In some embodiments, the priming first expansion, for example, Step B according to FIG. 8 (in particular, e.g., FIG. 8B and/or FIG. 8C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-10 or a G-REX-100. In some embodiments, the bioreactor employed is a G-REX-100. In some embodiments, the bioreactor employed is a G-REX-10.

1. Feeder Cells and Antigen Presenting Cells

In an embodiment, the priming first expansion procedures described herein (for example including expansion such as those described in Step B from FIG. 1 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during days 4-8. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during days 4-7. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during days 5-8. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during days 5-7. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during days 6-8. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during days 6-7. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during day 7 or 8. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during day 7. In an embodiment, the priming first expansion procedures described herein (for example including expansion such as those described in Step B from FIG. 8 (in particular, e.g., FIG. 8B and/or FIG. 8C), as well as those referred to as pre-REP or priming REP) does not require feeder cells (also referred to herein as "antigen-presenting cells") at the initiation of the TIL expansion, but rather are added during the priming first expansion at any time during day 8

In an embodiment, the priming first expansion procedures described herein (for example including expansion such as those described in Step B from FIG. 8 (in particular, e.g., FIG. 8B), as well as those referred to as pre-REP or priming REP) require feeder cells (also referred to herein as "anti-gen-presenting cells") at the initiation of the TIL expansion and during the priming first expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, $2.5\times10^8$ feeder cells are used during the priming first expansion. In some embodiments, $2.5\times10^8$ feeder cells per container are used during the priming first expansion. In some embodiments, $2.5\times10^8$ feeder cells per GREX-10 are used during the priming first expansion. In some embodiments, $2.5\times10^8$ feeder cells per GREX-100 are used during the priming first expansion.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 14 is less than the initial viable cell number put into culture on day 0 of the priming first expansion.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 30 ng/ml OKT3 antibody and 3000 IU/ml IL-2. In some embodiments, the PBMCs are cultured in the presence of 30 ng/ml OKT3 antibody and 6000 IU/ml IL-2.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 5-60 ng/mL OKT3 antibody and 1000-6000 IU/mL IL-2. In some embodiments, the PBMCs are cultured in the presence of 10-50 ng/ml OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2. In some embodiments, the PBMCs are cultured in the presence of 30 ng/ml OKT3 antibody and 6000 IU/mL IL-2. In some embodiments, the PBMCs are cultured in the presence of 15 ng/mL OKT3 antibody and 3000 IU/mL IL-2. In some embodiments, the PBMCs are cultured in the presence of 15 ng/mL OKT3 antibody and 6000 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the priming first expansion procedures described herein require a ratio of about $2.5 \times 10^8$ feeder cells to about $100 \times 10^6$ TILs. In another embodiment, the priming first expansion procedures described herein require a ratio of about $2.5 \times 10^8$ feeder cells to about $50 \times 10^6$ TILs. In yet another embodiment, the priming first expansion described herein require about $2.5 \times 10^8$ feeder cells to about $25 \times 10^6$ TILs. In yet another embodiment, the priming first expansion described herein require about $2.5 \times 10^8$ feeder cells. In yet another embodiment, the priming first expansion requires one-fourth, one-third, five-twelfths, or one-half of the number of feeder cells used in the rapid second expansion.

In some embodiments, the media in the priming first expansion comprises IL-2. In some embodiments, the media in the priming first expansion comprises 6000 IU/mL of IL-2. In some embodiments, the media in the priming first expansion comprises antigen-presenting feeder cells. In some embodiments, the media in the priming first expansion comprises $2.5 \times 10^8$ antigen-presenting feeder cells per container. In some embodiments, the media in the priming first expansion comprises OKT-3. In some embodiments, the media comprises 30 ng of OKT-3 per container. In some embodiments, the container is a GREX100 MCS flask. In some embodiments, the media comprises 6000 IU/mL of IL-2, 30 ng/mL of OKT-3, and $2.5 \times 10^8$ antigen-presenting feeder cells. In some embodiments, the media comprises 6000 IU/mL of IL-2, 30 ng/mL of OKT-3, and $2.5 \times 10^8$ antigen-presenting feeder cells per container. In some embodiments, the media comprises 500 mL of culture medium and 15 μg of OKT-3 per $2.5 \times 10^8$ antigen-presenting feeder cells per container. In some embodiments, the media comprises 500 mL of culture medium and 15 μg of OKT-3 per container. In some embodiments, the container is a GREX100 MCS flask. In some embodiments, the media comprises 500 mL of culture medium, 6000 IU/mL of IL-2, 30 ng/mL of OKT-3, and $2.5 \times 10^8$ antigen-presenting feeder cells. In some embodiments, the media comprises 500 mL of culture medium, 6000 IU/mL of IL-2, 15 μg of OKT-3, and $2.5 \times 10^8$ antigen-presenting feeder cells per container. In some embodiments, the media comprises 500 mL of culture medium and 15 μg of OKT-3 per $2.5 \times 10^8$ antigen-presenting feeder cells per container.

In an embodiment, the priming first expansion procedures described herein require an excess of feeder cells over TILs during the second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the priming first expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the priming first expansion of TILs is additionally possible, with combinations of two or more of IL-2, IL-15 and IL-21 as is generally outlined in International Publication No. WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

TABLE 20

| Amino Acid sequences of interleukins. | | | | | | |
|---|---|---|---|---|---|---|
| Identifier | Sequence (One-Letter Amino Acid Symbols) | | | | | |
| SEQ ID NO: 3 recombinant human IL-2 (rhIL-2) | MAPTSSSTKK EEELKPLEEV RWITFCQSII | TQLQLEHLLL LNLAQSKNFH STLT | DLQMILNGIN LRPRDLISNI | NYKNPKLTRM NVIVLELKGS | LTFKFYMPKK ETTFMCEYAD | ATELKHLQCL ETATIVEFLN | 60 120 134 |
| SEQ ID NO: 4 Aldesleukin | PTSSSTKKTQ ELKPLEEVLN ITFSQSIIST | LQLEHLLLDL LAQSKNFHLR LT | QMILNGINNY PRDLISNINV | KNPKLTRMLT IVLELKGSET | FKFYMPKKAT TFMCEYADET | ELKHLQCLEE ATIVEFLNRW | 60 120 132 |
| SEQ ID NO: 5 recombinant human IL-4 (rhIL-4) | MHKCDITLQE EKDTRCLGAT MREKYSKCSS | IIKTLNSLTE AQQFHRHKQL | QKTLCTELTV IRFLKRLDRN | TDIFAASKNT LWGLAGLNSC | TEKETFCRAA PVKEANQSTL | TVLRQFYSHH ENFLERLKTI | 60 120 130 |
| SEQ ID NO: 6 recombinant human IL-7 (rhIL-7) | MDCDIEGKDG ARKLRQFLKM KEQKKLNDLC | KQYESVLMVS NSTGDFDLHL FLKRLLQEIK | IDQLLDSMKE LKVSEGTTIL TCWNKILMGT | IGSNCLNNEF LNCTGQVKGR KEH | NFFKRHICDA KPAALGEAQP | NKEGMFLFRA TKSLEENKSL | 60 120 153 |
| SEQ ID NO: 7 recombinant human IL-15 (rhIL-15) | MNWVNVISDL HDTVENLIIL | KKIEDLIQSM ANNSLSSNGN | HIDATLYTES VTESGCKECE | DVHPSCKVTA ELEEKNIKEF | MKCFLLELQV LQSFVHIVQM | ISLESGDASI FINTS | 60 115 |
| SEQ ID NO: 8 recombinant human IL-21 (rhIL-21) | MQDRHMIRMR NNERIINVSI HLSSRTHGSE | QLIDIVDQLK KKLKRKPPST DS | NYVNDLVPEF NAGRRQKHRL | LPAPEDVETN TCPSCDSYEK | CEWSAFSCFQ KPPKEFLERF | KAQLKSANTG KSLLQKMIHQ | 60 120 132 |

C. Step C: Priming First Expansion to Rapid Second Expansion Transition

In some cases, the bulk TIL population obtained from the priming first expansion (which can include expansions sometimes referred to as pre-REP), including, for example the TIL population obtained from for example, Step B as indicated in FIG. 8 (in particular, e.g., FIG. 8B and/or FIG. 8C), can be subjected to a rapid second expansion (which can include expansions sometimes referred to as Rapid Expansion Protocol (REP)) and then cryopreserved as discussed below. Similarly, in the case where genetically modified TILs will be used in therapy, the expanded TIL population from the priming first expansion or the expanded TIL population from the rapid second expansion can be subjected to genetic modifications for suitable treatments prior to the expansion step or after the priming first expansion and prior to the rapid second expansion.

In some embodiments, the TILs obtained from the priming first expansion (for example, from Step B as indicated in FIG. 1 (in particular, e.g., FIG. 1B and/or FIG. 8C)) are stored until phenotyped for selection. In some embodiments, the TILs obtained from the priming first expansion (for example, from Step B as indicated in FIG. 1 (in particular, e.g., FIG. 1B and/or FIG. 8C)) are not stored and proceed directly to the rapid second expansion. In some embodiments, the TILs obtained from the priming first expansion are not cryopreserved after the priming first expansion and prior to the rapid second expansion. In some embodiments, the transition from the priming first expansion to the second expansion occurs at about 2 days, 3 days, 4, days, 5 days, 6 days, 7 days, or 8 days from when tumor fragmentation occurs and/or when the first priming expansion step is initiated. In some embodiments, the transition from the priming first expansion to the rapid second expansion occurs at about 3 days to 7 days from when fragmentation occurs and/or when the first priming expansion step is initiated. In some embodiments, the transition from the priming first expansion to the rapid second expansion occurs at about 3 days to 8 days from when fragmentation occurs and/or when the first priming expansion step is initiated. In some embodiments, the transition from the priming first expansion to the second expansion occurs at about 4 days to 7 days from when fragmentation occurs and/or when the first priming expansion step is initiated. In some embodiments, the transition from the priming first expansion to the second expansion occurs at about 4 days to 8 days from when fragmentation occurs and/or when the first priming expansion step is initiated. In some embodiments, the transition from the priming first expansion to the second expansion occurs at about 5 days to 7 days from when fragmentation occurs and/or when the first priming expansion step is initiated. In some embodiments, the transition from the priming first expansion to the second expansion occurs at about 5 days to 8 days from when fragmentation occurs and/or when the first priming expansion step is initiated. In some embodiments, the transition from the priming first expansion to the second expansion occurs at about 6 days to 7 days from when fragmentation occurs and/or when the first priming expansion step is initiated. In some embodiments, the transition from the priming first expansion to the second expansion occurs at about 6 days to 8 days from when fragmentation occurs and/or when the first priming expansion step is initiated. In some embodiments, the transition from the priming first expansion to the second expansion occurs at about 7 days to 8 days from when fragmentation occurs and/or when the first priming expansion step is initiated. In some embodiments, the transition from the priming first expansion to the second expansion occurs at about 7 days from when fragmentation occurs and/or when the first priming expansion step is initiated. In some embodiments, the transition from the priming first expansion to the second expansion occurs at about 8 days from when fragmentation occurs and/or when the first priming expansion step is initiated.

In some embodiments, the transition from the priming first expansion to the rapid second expansion occurs at 1 day, 2 days, 3 days, 4 days, 5 days, 6 days, 7 days, or 8 days from when fragmentation occurs and/or when the first priming expansion step is initiated. In some embodiments, the transition from the priming first expansion to the rapid second expansion occurs 1 day to 7 days from when fragmentation occurs and/or when the first priming expansion step is initiated. In some embodiments, the transition from the priming first expansion to the rapid second expansion occurs 1 day to 8 days from when fragmentation occurs and/or when the first priming expansion step is initiated. In some embodiments, the transition from the priming first expansion to the second expansion occurs 2 days to 7 days from when fragmentation occurs and/or when the first priming expansion step is initiated. In some embodiments, the transition from the priming first expansion to the second expansion occurs 2 days to 8 days from when fragmentation occurs and/or when the first priming expansion step is initiated. In some embodiments, the transition from the priming first expansion to the second expansion occurs 3 days to 7 days from when fragmentation occurs and/or when the first priming expansion step is initiated. In some embodiments, the transition from the priming first expansion to the second expansion occurs 3 days to 8 days from when fragmentation occurs and/or when the first priming expansion step is initiated. In some embodiments, the transition from the priming first expansion to the rapid second expansion occurs 4 days to 7 days from when fragmentation occurs and/or when the first priming expansion step is initiated. In some embodiments, the transition from the priming first expansion to the rapid second expansion occurs 4 days to 8 days from when fragmentation occurs and/or when the first priming expansion step is initiated. In some embodiments, the transition from the priming first expansion to the rapid second expansion occurs 5 days to 7 days from when fragmentation occurs and/or when the first priming expansion step is initiated. In some embodiments, the transition from the priming first expansion to the rapid second expansion occurs 5 days to 8 days from when fragmentation occurs and/or when the first priming expansion step is initiated. In some embodiments, the transition from the priming first expansion to the rapid second expansion occurs 6 days to 7 days from when fragmentation occurs and/or when the first priming expansion step is initiated. In some embodiments, the transition from the priming first expansion to the rapid second expansion occurs 6 days to 8 days from when fragmentation occurs and/or when the first priming expansion step is initiated. In some embodiments, the transition from the priming first expansion to the rapid second expansion occurs 7 days to 8 days from when fragmentation occurs and/or when the first priming expansion step is initiated. In some embodiments, the transition from the priming first expansion to the rapid second expansion occurs 7 days from when fragmentation occurs and/or when the first priming expansion step is initiated. In some embodiments, the transition from the priming first expansion to the rapid second expansion occurs 8 days from when fragmentation occurs and/or when the first priming expansion step is initiated In some embodiments, the TILs are not stored after the primary first expansion and prior to the rapid second expansion, and the TILs proceed directly to the rapid second expansion (for example, in some embodiments, there is no storage during the transition from Step B to Step D as shown in FIG. 8 (in particular, e.g., FIG. 8B and/or FIG. 8C)). In some embodiments, the transition occurs in closed system, as described herein. In some embodiments, the TILs from the priming first expansion, the second population of TILs, proceeds directly into the rapid second expansion with no transition period.

In some embodiments, the transition from the priming first expansion to the rapid second expansion, for example, Step C according to FIG. 8 (in particular, e.g., FIG. 8B and/or FIG. 8C), is performed in a closed system bioreactor. In some embodiments, a closed system is employed for the TIL expansion, as described herein. In some embodiments, a single bioreactor is employed. In some embodiments, the single bioreactor employed is for example a GREX-10 or a GREX-100. In some embodiments, the closed system bioreactor is a single bioreactor. In some embodiments, the transition from the priming first expansion to the rapid second expansion involves a scale-up in container size. In some embodiments, the priming first expansion is performed in a smaller container than the rapid second expansion. In some embodiments, the priming first expansion is performed in a GREX-100 and the rapid second expansion is performed in a GREX-500.

D. Step D: Rapid Second Expansion

In some embodiments, the TIL cell population is further expanded in number after harvest and the priming first expansion, after Step A and Step B, and the transition referred to as Step C, as indicated in FIG. 8 (in particular, e.g., FIG. 8B and/or FIG. 8C)). This further expansion is referred to herein as the rapid second expansion, which can include expansion processes generally referred to in the art as a rapid expansion process (Rapid Expansion Protocol or REP; as well as processes as indicated in Step D of FIG. 8 (in particular, e.g., FIG. 8B)). The rapid second expansion is generally accomplished using a culture media comprising a number of components, including feeder cells, a cytokine source, and an anti-CD3 antibody, in a gas-permeable container. In some embodiments, 1 day, 2 days, 3 days, or 4 days after initiation of the rapid second expansion (i.e., at days 8, 9, 10, or 11 of the overall Gen 3 process), the TILs are transferred to a larger volume container.

In some embodiments, the rapid second expansion (which can include expansions sometimes referred to as REP; as well as processes as indicated in Step D of FIG. 1 (in particular, e.g., FIG. 1B and/or FIG. 8C)) of TIL can be performed using any TIL flasks or containers known by those of skill in the art. In some embodiments, the second TIL expansion can proceed for 1 day, 2 days, 3 days, 4, days, 5 days, 6 days, 7 days, 8 days, 9 days or 10 days after initiation of the rapid second expansion. In some embodiments, the second TIL expansion can proceed for about 1 days to about 9 days after initiation of the rapid second expansion. In some embodiments, the second TIL expansion can proceed for about 1 days to about 10 days after initiation of the rapid second expansion. In some embodiments, the second TIL expansion can proceed for about 2 days to about 9 days after initiation of the rapid second expansion. In some embodiments, the second TIL expansion can proceed for about 2 days to about 10 days after initiation of the rapid second expansion. In some embodiments, the second TIL expansion can proceed for about 3 days to about 9 days after initiation of the rapid second expansion. In some embodiments, the second TIL expansion can proceed for about 3 days to about 10 days after initiation of the rapid second expansion. In some embodiments, the second TIL expansion can proceed for about 4 days to about 9 days after initiation of the rapid second expansion. In some embodiments, the second TIL expansion can proceed for about 4 days to about 10 days after initiation of the rapid second expansion. In some embodiments, the second TIL expansion can proceed for about 5 days to about 9 days after initiation of the rapid second expansion. In some embodiments, the second TIL expansion can proceed for about 5 days to about 10 days after initiation of the rapid second expansion. In some embodiments, the second TIL expansion can proceed for about 6 days to about 9 days after initiation of the rapid second expansion. In some embodiments, the second TIL expansion can proceed for about 6 days to about 10 days after initiation of the rapid second expansion. In some embodiments, the second TIL expansion can proceed for about 7 days to about 9 days after initiation of the rapid second expansion. In some embodiments, the second TIL expansion can proceed for about 7 days to about 10 days after initiation of the rapid second expansion. In some embodiments, the second TIL expansion can proceed for about 8 days to about 9 days after initiation of the rapid second expansion. In some embodiments, the second TIL expansion can proceed for about 8 days to about 10 days after initiation of the rapid second expansion. In some embodiments, the second TIL expansion can proceed for about 9 days to about 10 days after initiation of the rapid second expansion. In some embodiments, the second TIL expansion can proceed for about 1 day after initiation of the rapid second expansion. In some embodiments, the second TIL expansion can proceed for about 2 days after initiation of the rapid second expansion. In some embodiments, the second TIL expansion can proceed for about 3 days after initiation of the rapid second expansion. In some embodiments, the second TIL expansion can proceed for about 4 days after initiation of the rapid second expansion. In some embodiments, the second TIL expansion can proceed for about 5 days after initiation of the rapid second expansion. In some embodiments, the second TIL expansion can proceed for about 6 days after initiation of the rapid second expansion. In some embodiments, the second TIL expansion can proceed for about 7 days after initiation of the rapid second expansion. In some embodiments, the second TIL expansion can proceed for about 8 days after initiation of the rapid second expansion. In some embodiments, the second TIL expansion can proceed for about 9 days after initiation of the rapid second expansion. In some embodiments, the second TIL expansion can proceed for about 10 days after initiation of the rapid second expansion.

In an embodiment, the rapid second expansion can be performed in a gas permeable container using the methods of the present disclosure (including, for example, expansions referred to as REP; as well as processes as indicated in Step D of FIG. 8 (in particular, e.g., FIG. 8B and/or FIG. 8C). In some embodiments, the TILs are expanded in the rapid second expansion in the presence of IL-2, OKT-3, and feeder cells (also referred herein as "antigen-presenting cells"). In some embodiments, the TILs are expanded in the rapid second expansion in the presence of IL-2, OKT-3, and feeder cells, wherein the feeder cells are added to a final concentration that is twice, 2.4 times, 2.5 times, 3 times, 3.5 times or 4 times the concentration of feeder cells present in the priming first expansion. For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 µM MART-1: 26-35 (27 L) or gp1 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 15 ng/ml and 30 ng/mL of OKT-3 antibody. In an embodiment, the cell culture medium comprises between 30 ng/ml and 60 ng/mL of OKT-3 antibody. In an embodiment, the cell culture medium comprises about 30 ng/mL OKT-3. In an embodiment, the cell culture medium comprises about 60 ng/mL OKT-3. In some embodiments, the OKT-3 antibody is muromonab.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media in the rapid second expansion comprises $7.5 \times 10^8$ antigen-presenting feeder cells per container. In some embodiments, the media in the rapid second expansion comprises OKT-3.

In some embodiments, the in the rapid second expansion media comprises 500 mL of culture medium and 30 μg of OKT-3 per container. In some embodiments, the container is a GREX100 MCS flask. In some embodiments, the in the rapid second expansion media comprises 6000 IU/mL of IL-2, 60 ng/mL of OKT-3, and 7.5×10$^8$ antigen-presenting feeder cells. In some embodiments, the media comprises 500 mL of culture medium and 6000 IU/mL of IL-2, 30 μg of OKT-3, and 7.5×10$^8$ antigen-presenting feeder cells per container.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media comprises between 5×10$^8$ and 7.5×10$^8$ antigen-presenting feeder cells per container. In some embodiments, the media in the rapid second expansion comprises OKT-3. In some embodiments, the media in the rapid second expansion comprises 500 mL of culture medium and 30 μg of OKT-3 per container. In some embodiments, the container is a GREX100 MCS flask. In some embodiments, the media in the rapid second expansion comprises 6000 IU/mL of IL-2, 60 ng/mL of OKT-3, and between 5×10$^8$ and 7.5×10$^8$ antigen-presenting feeder cells. In some embodiments, the media in the rapid second expansion comprises 500 mL of culture medium and 6000 IU/mL of IL-2, 30 μg of OKT-3, and between 5×10$^8$ and 7.5×10$^8$ antigen-presenting feeder cells per container.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including, for example during a Step D processes according to FIG. 8 (in particular, e.g., FIG. 8B and/or FIG. 8C), as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 8 (in particular, e.g., FIG. 8B and/or FIG. 8C) and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments, the antigen-presenting feeder cells (APCs) are PBMCs. In an embodiment, the ratio of TILs to PBMCs and/or antigen-presenting cells in the rapid expansion and/or the second expansion is about 1 to 10, about 1 to 15, about 1 to 20, about 1 to 25, about 1 to 30, about 1 to 35, about 1 to 40, about 1 to 45, about 1 to 50, about 1 to 75, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the rapid second expansion is performed in flasks with the bulk TILs being mixed with a 100- or 200-fold excess of inactivated feeder cells, wherein the feeder cell concentration is at least 1.1 times (1.1×), 1.2×, 1.3×, 1.4×, 1.5×, 1.6×, 1.7×, 1.8×, 1.8×, 2×, 2.1×2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9× or 4.0× the feeder cell concentration in the priming first expansion, 30 ng/mL OKT3 anti-CD3 antibody and 6000 IU/mL IL-2 in 150 ml media. Media replacement is done (generally ⅔ media replacement via aspiration of ⅔ of spent media and replacement with an equal volume of fresh media) until the cells are transferred to an alternative growth chamber. Alternative growth chambers include G-REX flasks and gas permeable containers as more fully discussed below.

In some embodiments, the rapid second expansion (which can include processes referred to as the REP process) is 7 to 9 days, as discussed in the examples and figures. In some embodiments, the second expansion is 7 days. In some embodiments, the second expansion is 8 days. In some embodiments, the second expansion is 9 days.

In an embodiment, the second expansion (which can include expansions referred to as REP, as well as those referred to in Step D of FIG. 8 (in particular, e.g., FIG. 8B and/or FIG. 8C) may be performed in 500 mL capacity gas permeable flasks with 100 cm gas-permeable silicon bottoms (G-Rex 100, commercially available from Wilson Wolf Manufacturing Corporation, New Brighton, MN, USA), $5 \times 10^6$ or $10 \times 10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 6000 IU per mL of IL-2, and added back to the original GREX-100 flasks. When TIL are expanded serially in GREX-100 flasks, on day 10 or 11 the TILs can be moved to a larger flask, such as a GREX-500. The cells may be harvested on day 14 of culture. The cells may be harvested on day 15 of culture. The cells may be harvested on day 16 of culture. In some embodiments, media replacement is done until the cells are transferred to an alternative growth chamber. In some embodiments, ⅔ of the media is replaced by aspiration of spent media and replacement with an equal volume of fresh media. In some embodiments, alternative growth chambers include GREX flasks and gas permeable containers as more fully discussed below.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpT-mizer™ T-cell Expansion Basal Medium CTS™ OpT-mizer™ T-Cell Expansion SFM, CTS™ AIM-V Medium, CTS™ AIM-V SFM, LymphoONE™T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phe-nylalanine, L-proline, L-hydroxyproline, L-serine, L-threo-nine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^+$, $Sn^{2+}$ and $Zr^{4+}$. In some embodiments, the defined medium further comprises L-glutamine, sodium bicarbonate and/or 2-mer-captoethanol.

In some embodiments, the CTS™OpTmizer™ T-cell Immune Cell Serum Replacement is used with conventional growth media, including but not limited to CTS™ OpT-mizer™ T-cell Expansion Basal Medium, CTS™ OpT-mizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (Ther-moFisher Scientific). Any formulation of CTS™ OpT-mizer™ is useful in the present invention. CTS™ OpT-mizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable a supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments; the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, Br, T, $Mn^{2+}$, P, $Mo^{6+}$, $Ni^{2+}$, $Rb^+$, $Sn^{2+}$ and in some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

| Concentrations of Non-Trace Element Moiety Ingredients | | | |
| --- | --- | --- | --- |
| Ingredient | A preferred embodiment in supplement (mg/L) (About) | Concentration range in 1X medium (mg/L) (About) | A preferred embodiment in 1X medium (mg/L) (About) |
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-PO$_4$ (Mg Salt) | 330 | 1-200 | 50 |
| Transferrin iron saturated) | 55 | 1-50 | 8 |
| insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology*, 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

In an embodiment, the rapid second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the rapid second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as 7.5×10$^8$ antigen-presenting feeder cells (APCs), as discussed in more detail below. In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as $5 \times 10^8$ antigen-presenting feeder cells (APCs), as discussed in more detail below.

In some embodiments, the rapid second expansion, for example, Step D according to FIG. 8 (in particular, e.g., FIG. 8B and/or FIG. 8C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

1. Feeder Cells and Antigen Presenting Cells

In an embodiment, the rapid second expansion procedures described herein (for example including expansion such as those described in Step D from FIG. 8 (in particular, e.g., FIG. 8B and/or FIG. 8C), as well as those referred to as REP) require an excess of feeder cells during REP TIL expansion and/or during the rapid second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 7 or 14 is less than the initial viable cell number put into culture on day 0 of the REP and/or day 0 of the second expansion (i.e., the start day of the second expansion).

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2. In some embodiments, the PBMCs are cultured in the presence of 60 ng/ml OKT3 antibody and 6000 IU/ml IL-2. In some embodiments, the PBMCs are cultured in the presence of 60 ng/ml OKT3 antibody and 3000 IU/ml IL-2. In some embodiments, the PBMCs are cultured in the presence of 30 ng/ml OKT3 antibody and 6000 IU/ml IL-2.

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30-60 ng/ml OKT3 antibody and 1000-6000 IU/ml IL-2. In some embodiments, the PBMCs are cultured in the presence of 30-60 ng/ml OKT3 antibody and 2000-5000 IU/ml IL-2. In some embodiments, the PBMCs are cultured in the presence of 30-60 ng/ml OKT3 antibody and 2000-4000 IU/ml IL-2. In some embodiments, the PBMCs are cultured in the presence of 30-60 ng/ml OKT3 antibody and 2500-3500 IU/ml IL-2. In some embodiments, the PBMCs are cultured in the presence of 30-60 ng/ml OKT3 antibody and 6000 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 10, about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $5 \times 10^8$ feeder cells to about $100 \times 10^6$ TILs. In an embodiment, the second expansion procedures described herein require a ratio of about $7.5 \times 10^8$ feeder cells to about $100 \times 10^6$ TILs. In another embodiment, the second expansion procedures described herein require a ratio of about $5 \times 10^8$ feeder cells to about $50 \times 10^6$ TILs. In another embodiment, the second expansion procedures described herein require a ratio of about $7.5 \times 10^8$ feeder cells to about $50 \times 10^6$ TILs. In yet another embodiment, the second expansion procedures described herein require about $5 \times 10^8$ feeder cells to about $25 \times 10^6$ TILs. In yet another embodiment, the second expansion procedures described herein require about $7.5 \times 10^8$ feeder cells to about $25 \times 10^6$ TILs. In yet another embodiment, the rapid second expansion requires twice the number of feeder cells as the rapid second expansion. In yet another embodiment, when the priming first expansion described herein requires about $2.5 \times 10^8$ feeder cells, the rapid second expansion requires about $5 \times 10^8$ feeder cells. In yet another embodiment, when the priming first expansion described herein requires about $2.5 \times 10^8$ feeder cells, the rapid second expansion requires about $7.5 \times 10^8$ feeder cells. In yet another embodiment, the rapid second expansion requires two times (2.0x), 2.5x, 3.0x, 3.5x or 4.0x the number of feeder cells as the priming first expansion.

In an embodiment, the rapid second expansion procedures described herein require an excess of feeder cells during the rapid second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs. In some embodiments, the PBMCs are added to the rapid second expansion at twice the concentration of PBMCs that were added to the priming first expansion.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the rapid second expansion as a replacement for, or in combination with, PBMCs.

2. Cytokines

The rapid second expansion methods described herein generally use culture media with high doses of a cytokine, in particular IL-2, as is known in the art.

Alternatively, using combinations of cytokines for the rapid second expansion of TILs is additionally possible, with combinations of two or more of IL-2, IL-15 and IL-21 as is generally outlined in WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

E. Step E: Harvest TILS

After the rapid second expansion step, cells can be harvested. In some embodiments the TILs are harvested after one, two, three, four or more expansion steps, for example as provided in FIG. 8 (in particular, e.g., FIG. 8B and/or FIG. 8C). In some embodiments the TILs are harvested after two expansion steps, for example as provided in FIG. 8 (in particular, e.g., FIG. 8B and/or FIG. 8C). In some embodiments the TILs are harvested after two expansion steps, one priming first expansion and one rapid second expansion, for example as provided in FIG. 8 (in particular, e.g., FIG. 8B and/or FIG. 8C).

TILs can be harvested in any appropriate and sterile manner, including, for example by centrifugation. Methods for TIL harvesting are well known in the art and any such known methods can be employed with the present process. In some embodiments, TILS are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing system is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the rapid second expansion, for example, Step D according to FIG. 8 (in particular, e.g., FIG. 8B and/or FIG. 8C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

In some embodiments, Step E according to FIG. 8 (in particular, e.g., FIG. 8B and/or FIG. 8C), is performed according to the processes described herein. In some embodiments, the closed system is accessed via syringes under sterile conditions in order to maintain the sterility and closed nature of the system. In some embodiments, a closed system as described herein is employed.

In some embodiments, TILs are harvested according to the methods described in herein. In some embodiments, TILs between days 14 and 16 are harvested using the methods as described herein. In some embodiments, TILs are harvested at 14 days using the methods as described herein. In some embodiments, TILs are harvested at 15 days using the methods as described herein. In some embodiments, TILs are harvested at 16 days using the methods as described herein.

F. Step F: Final Formulation/Transfer to Infusion Bag

After Steps A through E as provided in an exemplary order in FIG. 8 (in particular, e.g., FIG. 8B) and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using the methods of the present disclosure are administered to a patient as a pharmaceutical composition. In an embodiment, the pharmaceutical composition is a suspension of TILs in a sterile buffer. TILs expanded as disclosed herein may be administered by any suitable route as known in the art. In some embodiments, the TILs are administered as a single intra-arterial or intravenous infusion, which preferably lasts approximately 30 to 60 minutes. Other suitable routes of administration include intraperitoneal, intrathecal, and intralymphatic.

G. PBMC Feeder Cell Ratios

In some embodiments, the culture media used in expansion methods described herein (see for example, FIG. 8 (in particular, e.g., FIG. 8B and/or FIG. 8C)) include an anti-CD3 antibody e.g. OKT-3. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

In an embodiment, the number of PBMC feeder layers is calculated as follows:

A. Volume of a T-cell (10 μm diameter): $V = (4/3) \pi r^3 = 523.6 \ \mu m^3$

B. Column of G-Rex 100 (M) with a 40 μm (4 cells) height: $V = (4/3) \pi r^3 = 4 \times 10^{12} \ \mu m^3$ C. Number cell required to fill column B: $4 \times 10^{12} \ \mu m^3 / 523.6 \ \mu m^3 = 7.6 \times 10^8 \ \mu m^3 \times 0.64 = 4.86 \times 10^8$ D. Number cells that can be optimally activated in 4D space: $4.86 \times 10^8 / 24 = 20.25 \times 10^6$ E. Number of feeders and TIL extrapolated to G-Rex 500: TIL: $100 \times 10^6$ and Feeder: $2.5 \times 10^9$ In this calculation, an approximation of the number of mononuclear cells required to provide an icosahedral geometry for activation of TIL in a cylinder with a 100 cm² base is used. The calculation derives the experimental result of ~$5 \times 10^8$ for threshold activation of T-cells which closely mirrors NCI experimental data.[1] (C) The multiplier (0.64) is the random packing density for equivalent spheres as calculated by Jaeger and Nagel in 1992[2]. (D) The divisor 24 is the number of equivalent spheres that could contact a similar object in 4 dimensional space "the Newton number."[3].

(1)Jin, Jianjian, et. al., Simplified Method of the Growth of Human Tumor Infiltrating Lymphocytes (TIL) in Gas-Permeable Flasks to Numbers Needed for Patient Treatment. J Immunother. 2012 April; 35(3): 283-292.

(2)Jaeger H M, Nagel S R. Physics of the granular state. Science. 1992 Mar. 20; 255(5051):1523-31.

(3)O. R. Musin (2003). "The problem of the twenty-five spheres". Russ. Math. Surv. 58 (4): 794-795.

In an embodiment, the number of antigen-presenting feeder cells exogenously supplied during the priming first expansion is approximately one-half the number of antigen-presenting feeder cells exogenously supplied during the rapid second expansion. In certain embodiments, the method comprises performing the priming first expansion in a cell culture medium which comprises approximately 50% fewer antigen presenting cells as compared to the cell culture medium of the rapid second expansion.

In another embodiment, the number of antigen-presenting feeder cells (APCs) exogenously supplied during the rapid second expansion is greater than the number of APCs exogenously supplied during the priming first expansion.

In another embodiment, the ratio of the number of APCs exogenously supplied during the rapid second expansion to the number of APCs exogenously supplied during the priming first expansion is selected from a range of from at or about 1.1:1 to at or about 20:1.

In another embodiment, the ratio of the number of APCs exogenously supplied during the rapid second expansion to the number of APCs exogenously supplied during the priming first expansion is selected from a range of from at or about 1.1:1 to at or about 10:1.

In another embodiment, the ratio of the number of APCs exogenously supplied during the rapid second expansion to the number of APCs exogenously supplied during the priming first expansion is selected from a range of from at or about 1.1:1 to at or about 9:1.

In another embodiment, the ratio of the number of APCs exogenously supplied during the rapid second expansion to the number of APCs exogenously supplied during the priming first expansion is selected from a range of from at or about 1.1:1 to at or about 8:1.

In another embodiment, the ratio of the number of APCs exogenously supplied during the rapid second expansion to the number of APCs exogenously supplied during the priming first expansion is selected from a range of from at or about 1.1:1 to at or about 7:1.

In another embodiment, the ratio of the number of APCs exogenously supplied during the rapid second expansion to the number of APCs exogenously supplied during the priming first expansion is selected from a range of from at or about 1.1:1 to at or about 6:1.

In another embodiment, the ratio of the number of APCs exogenously supplied during the rapid second expansion to the number of APCs exogenously supplied during the priming first expansion is selected from a range of from at or about 1.1:1 to at or about 5:1.

In another embodiment, the ratio of the number of APCs exogenously supplied during the rapid second expansion to the number of APCs exogenously supplied during the priming first expansion is selected from a range of from at or about 1.1:1 to at or about 4:1.

In another embodiment, the ratio of the number of APCs exogenously supplied during the rapid second expansion to the number of APCs exogenously supplied during the priming first expansion) is selected from a range of from at or about 1.1:1 to at or about 3:1.

In another embodiment, the ratio of the number of APCs exogenously supplied during the rapid second expansion to the number of APCs exogenously supplied during the priming first expansion is selected from a range of from at or about 1.1:1 to at or about 2.9:1.

In another embodiment, the ratio of the number of APCs exogenously supplied during the rapid second expansion to the number of APCs exogenously supplied during the priming first expansion is selected from a range of from at or about 1.1:1 to at or about 2.8:1.

In another embodiment, the ratio of the number of APCs exogenously supplied during the rapid second expansion to the number of APCs exogenously supplied during the priming first expansion is selected from a range of from at or about 1.1:1 to at or about 2.7:1.

In another embodiment, the ratio of the number of APCs exogenously supplied during the rapid second expansion to the number of APCs exogenously supplied during the priming first expansion is selected from a range of from at or about 1.1:1 to at or about 2.6:1.

In another embodiment, the ratio of the number of APCs exogenously supplied during the rapid second expansion to the number of APCs exogenously supplied during the priming first expansion is selected from a range of from at or about 1.1:1 to at or about 2.5:1.

In another embodiment, the ratio of the number of APCs exogenously supplied during the rapid second expansion to the number of APCs exogenously supplied during the priming first expansion is selected from a range of from at or about 1.1:1 to at or about 2.4:1.

In another embodiment, the ratio of the number of APCs exogenously supplied during the rapid second expansion to the number of APCs exogenously supplied during the priming first expansion is selected from a range of from at or about 1.1:1 to at or about 2.3:1.

In another embodiment, the ratio of the number of APCs exogenously supplied during the rapid second expansion to the number of APCs exogenously supplied during the priming first expansion is selected from a range of from at or about 1.1:1 to at or about 2.2:1.

In another embodiment, the ratio of the number of APCs exogenously supplied during the rapid second expansion to the number of APCs exogenously supplied during the priming first expansion is selected from a range of from at or about 1.1:1 to at or about 2.1:1.

In another embodiment, the ratio of the number of APCs exogenously supplied during the rapid second expansion to the number of APCs exogenously supplied during the priming first expansion is selected from a range of from at or about 1.1:1 to at or about 2:1.

In another embodiment, the ratio of the number of APCs exogenously supplied during the rapid second expansion to the number of APCs exogenously supplied during the priming first expansion is selected from a range of from at or about 2:1 to at or about 10:1.

In another embodiment, the ratio of the number of APCs exogenously supplied during the rapid second expansion to the number of APCs exogenously supplied during the priming first expansion is selected from a range of from at or about 2:1 to at or about 5:1.

In another embodiment, the ratio of the number of APCs exogenously supplied during the rapid second expansion to the number of APCs exogenously supplied during the priming first expansion is selected from a range of from at or about 2:1 to at or about 4:1.

In another embodiment, the ratio of the number of APCs exogenously supplied during the rapid second expansion to the number of APCs exogenously supplied during the priming first expansion is selected from a range of from at or about 2:1 to at or about 3:1.

In another embodiment, the ratio of the number of APCs exogenously supplied during the rapid second expansion to the number of APCs exogenously supplied during the priming first expansion is selected from a range of from at or about 2:1 to at or about 2.9:1.

In another embodiment, the ratio of the number of APCs exogenously supplied during the rapid second expansion to the number of APCs exogenously supplied during the priming first expansion is selected from a range of from at or about 2:1 to at or about 2.8:1.

In another embodiment, the ratio of the number of APCs exogenously supplied during the rapid second expansion to the number of APCs exogenously supplied during the priming first expansion is selected from a range of from at or about 2:1 to at or about 2.7:1.

In another embodiment, the ratio of the number of APCs exogenously supplied during the rapid second expansion to the number of APCs exogenously supplied during the priming first expansion is selected from a range of from at or about 2:1 to at or about 2.6:1.

In another embodiment, the ratio of the number of APCs exogenously supplied during the rapid second expansion to the number of APCs exogenously supplied during the priming first expansion is selected from a range of from at or about 2:1 to at or about 2.5:1.

In another embodiment, the ratio of the number of APCs exogenously supplied during the rapid second expansion to the number of APCs exogenously supplied during the priming first expansion is selected from a range of from at or about 2:1 to at or about 2.4:1.

In another embodiment, the ratio of the number of APCs exogenously supplied during the rapid second expansion to the number of APCs exogenously supplied during the priming first expansion is selected from a range of from at or about 2:1 to at or about 2.3:1.

In another embodiment, the ratio of the number of APCs exogenously supplied during the rapid second expansion to the number of APCs exogenously supplied during the priming first expansion is selected from a range of from at or about 2:1 to at or about 2.2:1.

In another embodiment, the ratio of the number of APCs exogenously supplied during the rapid second expansion to the number of APCs exogenously supplied during the priming first expansion is selected from a range of from at or about 2:1 to at or about 2.1:1.

In another embodiment, the ratio of the number of APCs exogenously supplied during the rapid second expansion to the number of APCs exogenously supplied during the priming first expansion is at or about 2:1.

In another embodiment, the ratio of the number of APCs exogenously supplied during the rapid second expansion to the number of APCs exogenously supplied during the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs exogenously supplied during the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and the number of APCs exogenously supplied during the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the number of APCs exogenously supplied during the priming first expansion is selected from the range of at or about $1.5\times10^8$ APCs to at or about $3\times10^8$ APCs, and the number of APCs exogenously supplied during the rapid second expansion is selected from the range of at or about $4\times10^8$ APCs to at or about $7.5\times10^8$ APCs.

In another embodiment, the number of APCs exogenously supplied during the priming first expansion is selected from the range of at or about $2\times10^8$ APCs to at or about $2.5\times10^8$ APCs, and the number of APCs exogenously supplied during the rapid second expansion is selected from the range of at or about $4.5\times10^8$ APCs to at or about $5.5\times10^8$ APCs.

In another embodiment, the number of APCs exogenously supplied during the priming first expansion is at or about $2.5\times10^8$ APCs, and the number of APCs exogenously supplied during the rapid second expansion is at or about $5\times10^8$ APCs.

In an embodiment, the number of APCs (including, for example, PBMCs) added at day 0 of the priming first expansion is approximately one-half of the number of PBMCs added at day 7 of the priming first expansion (e.g., day 7 of the method). In certain embodiments, the method comprises adding antigen presenting cells at day 0 of the priming first expansion to the first population of TILs and adding antigen presenting cells at day 7 to the second population of TILs, wherein the number of antigen presenting cells added at day 0 is approximately 50% of the number of antigen presenting cells added at day 7 of the priming first expansion (e.g., day 7 of the method).

In another embodiment, the number of APCs (including, for example, PBMCs) exogenously supplied at day 7 of the rapid second expansion is greater than the number of PBMCs exogenously supplied at day 0 of the priming first expansion.

In another embodiment, the APCs exogenously supplied in the priming first expansion are seeded in the culture flask at a density selected from a range of at or about $1.0\times10^6$ APCs/cm$^2$ to at or about $4.5\times10^6$ APCs/cm$^2$.

In another embodiment, the APCs exogenously supplied in the priming first expansion are seeded in the culture flask at a density selected from a range of at or about $1.5\times10^6$ APCs/cm$^2$ to at or about $3.5\times10^6$ APCs/cm$^2$.

In another embodiment, the APCs exogenously supplied in the priming first expansion are seeded in the culture flask at a density selected from a range of at or about $2\times10^6$ APCs/cm$^2$ to at or about $3\times10^6$ APCs/cm$^2$.

In another embodiment, the APCs exogenously supplied in the priming first expansion are seeded in the culture flask at a density of at or about $2\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times$ $10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$.

In another embodiment, the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In another embodiment, the APCs exogenously supplied in the rapid second expansion are seeded in the culture flask at a density selected from a range of at or about $3.5\times10^6$ APCs/cm$^2$ to about $6.0\times10^6$ APCs/cm$^2$.

In another embodiment, the APCs exogenously supplied in the rapid second expansion are seeded in the culture flask at a density selected from a range of at or about $4.0\times10^6$ APCs/cm$^2$ to about $5.5\times10^6$ APCs/cm$^2$.

In another embodiment, the APCs exogenously supplied in the rapid second expansion are seeded in the culture flask at a density selected from a range of at or about $4.0\times10^6$ APCs/cm$^2$.

In another embodiment, the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$ and the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density selected from a range of at or about $1.0\times10^6$ APCs/cm$^2$ to at or about $4.5\times10^6$ APCs/cm$^2$, and the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In another embodiment, the APCs exogenously supplied in the priming first expansion are seeded in the culture flask at a density selected from a range of at or about $1.5\times10^6$ APCs/cm$^2$ to at or about $3.5\times10^6$ APCs/cm$^2$, and the APCs exogenously supplied in the rapid second expansion are seeded in the culture flask at a density selected from a range of at or about $3.5\times10^6$ APCs/cm$^2$ to at or about $6\times10^6$ APCs/cm$^2$.

In another embodiment, the APCs exogenously supplied in the priming first expansion are seeded in the culture flask at a density selected from a range of at or about $2\times10^6$ APCs/cm$^2$ to at or about $3\times10^6$ APCs/cm$^2$, and the APCs exogenously supplied in the rapid second expansion are seeded in the culture flask at a density selected from a range of at or about $4\times10^6$ APCs/cm$^2$ to at or about $5.5\times10^6$ APCs/cm$^2$.

In another embodiment, the APCs exogenously supplied in the priming first expansion are seeded in the culture flask at a density at or about $2\times10^6$ APCs/cm$^2$ and the APCs exogenously supplied in the rapid second expansion are seeded in the culture flask at a density of at or about $4\times10^6$ APCs/cm$^2$.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 20:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 10:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 10:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs (including, for example, PBMCs) exogenously supplied at day 0 of the priming first expansion is at or about $1 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3 \times 10^8$, $3.1 \times 10^8$, $3.2 \times 10^8$, $3.3 \times 10^8$, $3.4 \times 10^8$ or $3.5 \times 10^8$ APCs (including, for example, PBMCs), and the number of APCs (including, for example, PBMCs) exogenously supplied at day 7 of the rapid second expansion is at or about $3.5 \times 10^8$, $3.6 \times 10^8$, $3.7 \times 10^8$, $3.8 \times 10^8$, $3.9 \times 10^8$, $4 \times 10^8$, $4.1 \times 10^8$, $4.2 \times 10^8$, $4.3 \times 10^8$, $4.4 \times 10^8$, $4.5 \times 10^8$, $4.6 \times 10^8$, $4.7 \times 10^8$, $4.8 \times 10^8$, $4.9 \times 10^8$, $5 \times 10^8$, $5.1 \times 10^8$, $5.2 \times 10^8$, $5.3 \times 10^8$, $5.4 \times 10^8$, $5.5 \times 10^8$, $5.6 \times 10^8$, $5.7 \times 10^8$, $5.8 \times 10^8$, $5.9 \times 10^8$, $6 \times 10^8$, $6.1 \times 10^8$, $6.2 \times 10^8$, $6.3 \times 10^8$, $6.4 \times 10^8$, $6.5 \times 10^8$, $6.6 \times 10^8$, $6.7 \times 10^8$, $6.8 \times 10^8$, $6.9 \times 10^8$, $7 \times 10^8$, $7.1 \times 10^8$, $7.2 \times 10^8$, $7.3 \times 10^8$, $7.4 \times 10^8$, $7.5 \times 10^8$, $7.6 \times 10^8$, $7.7 \times 10^8$, $7.8 \times 10^8$, $7.9 \times 10^8$, $8 \times 10^8$, $8.1 \times 10^8$, $8.2 \times 10^8$, $8.3 \times 10^8$, $8.4 \times 10^8$, $8.5 \times 10^8$, $8.6 \times 10^8$, $8.7 \times 10^8$, $8.8 \times 10^8$, $8.9 \times 10^8$, $9 \times 10^8$, $9.1 \times 10^8$, $9.2 \times 10^8$, $9.3 \times 10^8$, $9.4 \times 10^8$, $9.5 \times 10^8$, $9.6 \times 10^8$, $9.7 \times 10^8$, $9.8 \times 10^8$, $9.9 \times 10^8$ or $1 \times 10^9$ APCs (including, for example, PBMCs).

In another embodiment, the number of APCs (including, for example, PBMCs) exogenously supplied at day 0 of the priming first expansion is selected from the range of at or about $1 \times 10^8$ APCs (including, for example, PBMCs) to at or about $3.5 \times 10^8$ APCs (including, for example, PBMCs), and the number of APCs (including, for example, PBMCs) exogenously supplied at day 7 of the rapid second expansion is selected from the range of at or about $3.5 \times 10^8$ APCs (including, for example, PBMCs) to at or about $1 \times 10^9$ APCs (including, for example, PBMCs).

In another embodiment, the number of APCs (including, for example, PBMCs) exogenously supplied at day 0 of the priming first expansion is selected from the range of at or about $1.5 \times 10^8$ APCs to at or about $3 \times 10^8$ APCs (including, for example, PBMCs), and the number of APCs (including, for example, PBMCs) exogenously supplied at day 7 of the rapid second expansion is selected from the range of at or about $4 \times 10^8$ APCs (including, for example, PBMCs) to at or about $7.5 \times 10^8$ APCs (including, for example, PBMCs).

In another embodiment, the number of APCs (including, for example, PBMCs) exogenously supplied at day 0 of the priming first expansion is selected from the range of at or about $2 \times 10^8$ APCs (including, for example, PBMCs) to at or about $2.5 \times 10^8$ APCs (including, for example, PBMCs), and the number of APCs (including, for example, PBMCs) exogenously supplied at day 7 of the rapid second expansion is selected from the range of at or about $4.5 \times 10^8$ APCs (including, for example, PBMCs) to at or about $5.5 \times 10^8$ APCs (including, for example, PBMCs).

In another embodiment, the number of APCs (including, for example, PBMCs) exogenously supplied at day 0 of the priming first expansion is at or about $2.5 \times 10^8$ APCs (including, for example, PBMCs) and the number of APCs (including, for example, PBMCs) exogenously supplied at day 7 of the rapid second expansion is at or about $5 \times 10^8$ APCs (including, for example, PBMCs)

In an embodiment, the number of layers of APCs (including, for example, PBMCs) added at day 0 of the priming first expansion is approximately one-half of the number of layers of APCs (including, for example, PBMCs) added at day 7 of the rapid second expansion. In certain embodiments, the method comprises adding antigen presenting cell layers at day 0 of the priming first expansion to the first population of TILs and adding antigen presenting cell layers at day 7 to the second population of TILs, wherein the number of antigen presenting cell layer added at day 0 is approximately 50% of the number of antigen presenting cell layers added at day 7.

In another embodiment, the number of layers of APCs (including, for example, PBMCs) exogenously supplied at day 7 of the rapid second expansion is greater than the number of layers of APCs (including, for example, PBMCs) exogenously supplied at day 0 of the priming first expansion.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about 1.5 cell layers to at or about 2.5 cell layers and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 2 cell layers.

In another embodiment, day 0 of the priming first expansion occurs in the presence of layered APCs (including, for example, PBMCs) with an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers and day 7 of the rapid second expansion occurs in the presence of layered APCs (including, for example, PBMCs) with an average thickness of at or about 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, day 0 of the priming first expansion occurs in the presence of layered APCs (including, for example, PBMCs) with an average thickness of at or about 1 cell layer to at or about 2 cell layers and day 7 of the rapid second expansion occurs in the presence of layered APCs (including, for example, PBMCs) with an average thickness of at or about 3 cell layers to at or about 10 cell layers.

In another embodiment, day 0 of the priming first expansion occurs in the presence of layered APCs (including, for example, PBMCs) with an average thickness of at or about 2 cell layers to at or about 3 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 1, 2 or 3 cell layers and day 7 of the rapid second expansion occurs in the presence of layered APCs (including, for example, PBMCs) with an average thickness of at or about 3, 4, 5, 6, 7, 8, 9 or 10 cell layers.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:10.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.2 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.3 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.4 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.5 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.6 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.7 to at or about 1:3.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.8 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.9 to at or about 1:2.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In some embodiments, the number of APCs in the priming first expansion is selected from the range of about $1.0 \times 10^6$ APCs/cm$^2$ to about $4.5 \times 10^6$ APCs/cm$^2$, and the number of APCs in the rapid second expansion is selected from the range of about $2.5 \times 10^6$ APCs/cm$^2$ to about $7.5 \times 10^6$ APCs/cm$^2$.

In some embodiments, the number of APCs in the priming first expansion is selected from the range of about $1.5 \times 10^6$ APCs/cm$^2$ to about $3.5 \times 10^6$ APCs/cm$^2$, and the number of APCs in the rapid second expansion is selected from the range of about $3.5 \times 10^6$ APCs/cm$^2$ to about $6.0 \times 10^6$ APCs/cm$^2$.

In some embodiments, the number of APCs in the priming first expansion is selected from the range of about $2.0 \times 10^6$ APCs/cm$^2$ to about $3.0 \times 10^6$ APCs/cm$^2$, and the number of APCs in the rapid second expansion is selected from the range of about $4.0 \times 10^6$ APCs/cm$^2$ to about $5.5 \times 10^6$ APCs/cm$^2$.

H. Optional Cell Medium Components

1. Anti-CD3 Antibodies

In some embodiments, the culture media used in expansion methods described herein (see for example, FIG. 8 (in particular, e.g., FIG. 8B)) include an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-Mc-Neil, Raritan, NJ or Miltenyi Biotech, Auburn, CA).

ized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

TABLE 21

Amino acid sequences of muromonab (exemplary OKT-3 antibody)

| Identifier | Sequence (One-Letter Amino Acid Symbols) | | | | | |
|---|---|---|---|---|---|---|
| SEQ ID NO: 1 | QVQLQQSGAE | LARPGASVKM | SCKASGYTFT | RYTMHWVKQR | PGQGLEWIGY | INPSRGYTNY 60 |
| Muromonab heavy | NQKFKDKATL | TTDKSSSTAY | MQLSSLTSED | SAVYYCARYY | DDHYCLDYWG | QGTTLTVSSA 120 |
| chain | KTTAPSVYPL | APVCGGTTGS | SVTLGCLVKG | YFPEPVTLTW | NSGSLSSGVH | TFPAVLQSDL 180 |
| | YTLSSSVTVT | SSTWPSQSIT | CNVAHPASST | KVDKKIEPRP | KSCDKTHTCP | PCPAPELLGG 240 |
| | PSVFLFPPKP | KDTLMISRTP | EVTCVVVDVS | HEDPEVKFNW | YVDGVEVHNA | KTKPREEQYN 300 |
| | STYRVVSVLT | VLHQDWLNGK | EYKCKVSNKA | LPAPIEKTIS | KAKGQPREPQ | VYTLPPSRDE 360 |
| | LTKNQVSLTC | LVKGFYPSDI | AVEWESNGQP | ENNYKTTPPV | LDSDGSFFLY | SKLTVDKSRW 420 |
| | QQGNVFSCSV | MHEALHNHYT | QKSLSLSPGK | | | 450 |
| SEQ ID NO: 2 | QIVLTQSPAI | MSASPGEKVT | MTCSASSSVS | YMNWYQQKSG | TSPKRWIYDT | SKLASGVPAH 60 |
| Muromonab light | FRGSGSGTSY | SLTISGMEAE | DAATYYCQQW | SSNPFTFGSG | TKLEINRADT | APTVSIFPPS 120 |
| chain | SEQLTSGGAS | VVCFLNNFYP | KDINVKWKID | GSERQNGVLN | SWTDQDSKDS | TYSMSSTLTL 180 |
| | TKDEYERHNS | YTCEATHKTS | TSPIVKSFNR | NEC | | 213 |

40

2. 4-1BB (CD137) Agonists

In an embodiment, the cell culture medium of the priming first expansion and/or the rapid second expansion comprises a TNFRSF agonist. In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multi specific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a human- In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 22.

human or murine 4-1BB with a $k_{dissoc}$ of about $2.6 \times 10^{-5}$ l/s or slower or binds to human or murine 4-1BB with a $k_{dissoc}$ of about $2.7 \times 10^{-5}$ l/s or slower, binds to human or murine 4-1BB with a $k_{dissoc}$ of about $2.8 \times 10^{-5}$ l/s or slower, binds to human or murine 4-1BB with a $k_{dissoc}$ of about $2.9 \times 10^{-5}$ l/s or slower, or binds to human or murine 4-1BB with a $k_{dissoc}$ of about $3 \times 10^{-5}$ l/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine

TABLE 22

Amino acid sequences of 4-1BB antigens.

| Identifier | Sequence (One-Letter Amino Acid Symbols) | | | | | |
|---|---|---|---|---|---|---|
| SEQ ID NO: 9 | MGNSCYNIVA | TLLLVLNFER | TRSLQDPCSN | CPAGTFCDNN | RNQICSPCPP | NSFSSAGGQR | 60 |
| human 4-1BB, | TCDICRQCKG | VFRTRKECSS | TSNAECDCTP | GFHCLGAGCS | MCEQDCKQGQ | ELTKKGCKDC | 120 |
| Tumor necrosis | CFGTFNDQKR | GICRPWTNCS | LDGKSVLVNG | TKERDVVCGP | SPADLSPGAS | SVTPPAPARE | 180 |
| factor receptor | PGHSPQIISF | FLALTSTALL | FLLFFLTLRF | SVVKRGRKKL | LYIFKQPFMR | PVQTTQEEDG | 240 |
| superfamily, | CSCRFPEEEE | GGCEL | | | | | 255 |
| member 9 (*Homo sapiens*) | | | | | | | |
| | | | | | | | |
| SEQ ID NO: 10 | MGNNCYNVVV | IVLLLVGCEK | VGAVQNSCDN | CQPGTFCRKY | NPVCKSCPPS | TFSSIGGQPN | 60 |
| murine 4-1BB, | CNICRVCAGY | FRFKKFCSST | HNAECECIEG | FHCLGPQCTR | CEKDCRPGQE | LTKQGCKTCS | 120 |
| Tumor necrosis | LGTFNDQNGT | GVCRPWTNCS | LDGRSVLKTG | TTEKDVVCGP | PVVSFSPSTT | ISVTPEGGPG | 180 |
| factor receptor | GHSLQVLTLF | LALTSALLLA | LIFITLLFSV | LKWIRKKFPH | IFKQPFKKTT | GAAQEEDACS | 240 |
| superfamily, | CRCPQEEEGG | GGGYEL | | | | | 256 |
| member 9 (*Mus musculus*) | | | | | | | |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5 \times 10^5$ l/M·s or faster, binds to human or murine 4-1BB with a $k_{assoc}$ of about $7.5 \times 10^5$ l/M·s or faster, binds to human or murine 4-1BB with a $k_{assoc}$ of about $8 \times 10^5$ l/M·s or faster, binds to human or murine 4-1BB with a $k_{assoc}$ of about $8.5 \times 10^5$ l/M·s or faster, binds to human or murine 4-1BB with a $k_{assoc}$ of about $9 \times 10^5$ l/M·s or faster, binds to human or murine 4-1BB with a $k_{assoc}$ of about $9.5 \times 10^5$ l/M·s or faster, or binds to human or murine 4-1BB with a $k_{assoc}$ of about $1 \times 10^6$ l/M·s or faster.

In some embodiments, the compositions, processes and methods described include a 4-1BB agonist that binds to human or murine 4-1BB with a $k_{dissoc}$ of about $2 \times 10^{-5}$ l/s or slower, binds to human or murine 4-1BB with a $k_{dissoc}$ of about $2.1 \times 10^{-5}$ l/s or slower, binds to human or murine 4-1BB with a $k_{dissoc}$ of about $2.2 \times 10^{-5}$ l/s or slower, binds to human or murine 4-1BB with a $k_{dissoc}$ of about $2.3 \times 10^{-5}$ l/s or slower, binds to human or murine 4-1BB with a $k_{dissoc}$ of about $2.4 \times 10^{-5}$ l/s or slower, binds to human or murine 4-1BB with a $k_{dissoc}$ of about $2.5 \times 10^{-5}$ l/s or slower, binds to 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table 7. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468, 678, and International Patent Application Publication No.

WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 23

Amino acid sequences for 4-1BB agonist antibodies related to utomilumab.

| Identifier | Sequence (One-Letter Amino Acid Symbols) | | | | | | |
|---|---|---|---|---|---|---|---|
| SEQ ID NO: 11 | EVQLVQSGAE | VKKPGESLRI | SCKGSGYSFS | TYWISWVRQM | PGKGLEWMGK | IYPGDSYTNY | 60 |
| heavy chain for | SPSFQGQVTI | SADKSISTAY | LQWSSLKASD | TAMYYCARGY | GIFDYWGQGT | LVTVSSASTK | 120 |
| utomilumab | GPSVFPLAPC | SRSTSESTAA | LGCLVKDYFP | EPVTVSWNSG | ALTSGVHTFP | AVLQSSGLYS | 180 |
| | LSSVVTVPSS | NFGTQTYTCN | VDHKPSNTKV | DKTVERKCCV | ECPPCPAPPV | AGPSVFLFPP | 240 |
| | KPKDTLMISR | TPEVTCVVVD | VSHEDPEVQF | NWYVDGVEVH | NAKTKPREEQ | FNSTFRVVSV | 300 |
| | LTVVHQDWLN | GKEYKCKVSN | KGLPAPIEKT | ISKTKGQPRE | PQVYTLPPSR | EEMTKNQVSL | 360 |
| | TCLVKGFYPS | DIAVEWESNG | QPENNYKTTP | PMLDSDGSFF | LYSKLTVDKS | RWQQGNVFSC | 420 |
| | SVMHEALHNH | YTQKSLSLSP | G | | | | 441 |
| SEQ ID NO: 12 | SYELTQPPSV | SVSPGQTASI | TCSGDNIGDQ | YAHWYQQKPG | QSPVLVIYQD | KNRPSGIPER | 60 |
| light chain for | FSGSNSGNTA | TLTISGTQAM | DEADYYCATY | TGFGSLAVFG | GGTKLTVLGQ | PKAAPSVTLF | 120 |

TABLE 23-continued

Amino acid sequences for 4-1BB agonist antibodies related to utomilumab.

| Identifier | Sequence (One-Letter Amino Acid Symbols) | |
|---|---|---|
| utomilumab | PPSSEELQAN KATLVCLISD FYPGAVTVAW KADSSPVKAG VETTTPSKQS NNKYAASSYL | 180 |
| | SLTPEQWKSH RSYSCQVTHE GSTVEKTVAP TECS | 214 |
| SEQ ID NO: 13 heavy chain variable region for utomilumab | EVQLVQSGAE VKKPGESLRI SCKGSGYSFS TYWISWVRQM PGKGLEWMG KIYPGDSYTN | 60 |
| | YSPSFQGQVT ISADKSISTA YLQWSSLKAS DTAMYYCARG YGIFDYWGQ GTLVTVSS | 118 |
| SEQ ID NO: 14 light chain variable region for utomilumab | SYELTQPPSV SVSPGQTASI TCSGDNIGDQ YAHWYQQKPG QSPVLVIYQD KNRPSGIPER | 60 |
| | FSGSNSGNTA TLTISGTQAM DEADYYCATY TGFGSLAVFG GGTKLTVL | 108 |
| SEQ ID NO: 15 heavy chain CDR1 for utomilumab | STYWIS | 6 |
| SEQ ID NO: 16 heavy chain CDR2 for utomilumab | KIYPGDSYTN YSPSFQG | 17 |
| SEQ ID NO: 17 heavy chain CDR3 for utomilumab | RGYGIFDY | 8 |
| SEQ ID NO: 18 light chain CDR1 for utomilumab | SGDNIGDQYA H | 11 |
| SEQ ID NO: 19 light chain CDR2 for utomilumab | QDKNRPS | 7 |
| SEQ ID NO: 20 light chain CDR3 for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table EE. Urelumab comprises N-glycosylation sites at positions 298 (and 298"); heavy chain intrachain disulfide bridges at positions 22-95 ($V_H$-$V_L$), 148-204 ($C_H$1-$C_L$), 262-322 ($C_H$2) and 368-426 ($C_H$3) (and at positions 22"-95", 148"-204", 262"-322", and 368"-426"); light chain intrachain disulfide bridges at positions 23'-88' ($V_H$-$V_L$) and 136'-196' ($C_H$1-$C_L$) (and at positions 23'-88' and 136'"-196'"); interchain heavy chain-heavy chain disulfide bridges at positions 227-227" and 230-230"; and interchain heavy chain-light chain disulfide bridges at 135-216' and 135"-216'. The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 24

| Amino acid sequences for 4-1BB agonist antibodies related to urelumab. | | | | | | |
|---|---|---|---|---|---|---|
| Identifier | Sequence (One-Letter Amino Acid Symbols) | | | | | |
| SEQ ID NO: 21<br>heavy chain for<br>urelumab | QVQLQQWGAG<br>PSLESRVTIS<br>SASTKGPSVF<br>SGLYSLSSVV<br>VFLFPPKPKD<br>YRVVSVLTVL<br>KNQVSLTCLV<br>GNVFSCSVMH | LLKPSETLSL<br>VDTSKNQFSL<br>PLAPCSRSTS<br>TVPSSSLGTK<br>TLMISRTPEV<br>HQDWLNGKEY<br>KGFYPSDIAV<br>EALHNHYTQK | TCAVYGGSFS<br>KLSSVTAADT<br>ESTAALGCLV<br>TYTCNVDHKP<br>TCVVVDVSQE<br>KCKVSNKGLP<br>EWESNGQPEN<br>SLSLSLGK | GYYWSWIRQS<br>AVYYCARDYG<br>KDYFPEPVTV<br>SNTKVDKRVE<br>DPEVQFNWYV<br>SSIEKTISKA<br>NYKTTPPVLD | PEKGLEWIGE<br>PGNYDWYFDL<br>SWNSGALTSG<br>SKYGPPCPPC<br>DGVEVHNAKT<br>KGQPREPQVY<br>SDGSFFLYSR | INHGGYVTYN 60<br>WGRGTLVTVS 120<br>VHTFPAVLQS 180<br>PAPEFLGGPS 240<br>KPREEQFNST 300<br>TLPPSQEEMT 360<br>LTVDKSRWQE 420<br>448 |
| SEQ ID NO: 22<br>light chain for<br>urelumab | EIVLTQSPAT<br>RFSGSGSGTD<br>PPSDEQLKSG<br>LTLSKADYEK | LSLSPGERAT<br>FTLTISSLEP<br>TASVVCLLNN<br>HKVYACEVTH | LSCRASQSVS<br>EDFAVYYCQQ<br>FYPREAKVQW<br>QGLSSPVTKS | SYLAWYQQKP<br>RSNWPPALTF<br>KVDNALQSGN<br>FNRGEC | GQAPRLLIYD<br>CGGTKVEIKR<br>SQESVTEQDS | ASNRATGIPA 60<br>TVAAPSVFIF 120<br>KDSTYSLSST 180<br>216 |
| SEQ ID NO: 23<br>variable heavy<br>chain for<br>urelumab | MKHLWFFLLL<br>EKGLEWIGEI | VAAPRWVLSQ<br>NHGGYVTYNP | VQLQQWGAGL<br>SLESRVTISV | LKPSETLSLT<br>DTSKNQFSLK | CAVYGGSFSG<br>LSSVTAADTA | YYWSWIRQSP 60<br>VYYCARDYGP 120 |
| SEQ ID NO: 24<br>variable light<br>chain for<br>urelumab | MEAPAQLLFL<br>GQAPRLLIYD | LLLWLPDTTG<br>ASNRATGIPA | EIVLTQSPAT<br>RFSGSGSGTD | LSLSPGERAT<br>FTLTISSLEP | LSCRASQSVS<br>EDFAVYYCQQ | SYLAWYQQKP 60<br>110 |
| SEQ ID NO: 25<br>heavy chain CDR1<br>for urelumab | GYYWS | | | | | 5 |
| SEQ ID NO: 26<br>heavy chain CDR2<br>for urelumab | EINHGGYVTY NPSLES | | | | | 16 |
| SEQ ID NO: 27<br>heavy chain CDR3<br>for urelumab | DYGPGNYDWY FDL | | | | | 13 |

TABLE 24-continued

| Identifier | Sequence (One-Letter Amino Acid Symbols) | |
|---|---|---|
| SEQ ID NO: 28 light chain CDR1 for urelumab | RASQSVSSYL A | 11 |
| SEQ ID NO: 29 light chain CDR2 for urelumab | DASNRAT | 7 |
| SEQ ID NO: 30 light chain CDR3 for urelumab | QQRSDWPPAL T | 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 (such as 4E9 or BMS-554271), antibodies disclosed in U.S. Pat. No. 7,214, 493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362, 325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303, 121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/ 0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof (See, FIG. 50). In structures I-A and I-B, the cylinders refer to individual polypeptide binding domains. Structures I-A and I-B comprise three linearly-linked TNFRSF binding domains derived from e.g., 4-1BBL (4-1BB ligand, CD137 ligand (CD137L), or tumor necrosis factor superfamily member 9 (TNFSF9)) or an antibody that binds 4-1BB, which fold to form a trivalent protein, which is then linked to a second trivalent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 25

Amino acid sequences for TNFRSF agonist fusion proteins,
including 4-1BB agonist fusion proteins, with C-terminal
Fc-antibody fragment fusion protein design (structure I-A).

| Identifier | Sequence (One-Letter Amino Acid Symbols) |
|---|---|
| SEQ ID NO: 31 Fc domain | KSCDKTHTCP PCPAPELLGG PSVFLFPPKP KDTLMISRTP EVTCVVVDVS HEDPEVKFNW 60 YVDGVEVHNA KTKPREEQYN STYRVVSVLT VLHQDWLNGK EYKCKVSNKA LPAPIEKTIS 120 |

TABLE 25-continued

Amino acid sequences for TNFRSF agonist fusion proteins,
including 4-1BB agonist fusion proteins, with C-terminal
Fc-antibody fragment fusion protein design (structure I-A).

| Identifier | Sequence (One-Letter Amino Acid Symbols) | |
| --- | --- | --- |
| | KAKGQPREPQ VYTLPPSREE MTKNQVSLTC LVKGFYPSDI AVEWESNGQP ENNYKTTPPV | 180 |
| | LDSDGSFFLY SKLTVDKSRW QQGNVFSCSV MHEALHNHYT QKSLSLSPGK | 230 |
| SEQ ID NO: 32 linker | GGPGSSKSCD KTHTCPPCPA PE | 22 |
| SEQ ID NO: 33 linker | GGSGSSKSCD KTHTCPPCPA PE | 22 |
| SEQ ID NO: 34 linker | GGPGSSSSSS SKSCDKTHTC PPCPAPE | 27 |
| SEQ ID NO: 35 linker | GGSGSSSSSS SKSCDKTHTC PPCPAPE | 27 |
| SEQ ID NO: 36 linker | GGPGSSSSSS SSSKSCDKTH TCPPCPAPE | 29 |
| SEQ ID NO: 37 linker | GGSGSSSSSS SSSKSCDKTH TCPPCPAPE | 29 |
| SEQ ID NO: 38 linker | GGPGSSGSGS SDKTHTCPPC PAPE | 24 |
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

variable heavy chain and variable light chain of utomilumab, a variable heavy chain and variable light chain of urelumab, a variable heavy chain and variable light chain of utomi-lumab, a variable heavy chain and variable light chain selected from the variable heavy chains and variable light chains described in Table 10, any combination of a variable

TABLE 26

Amino acid sequences for TNFRSF agonist fusion proteins,
including 4-1BB agonist fusion proteins, with N-terminal
Fc-antibody fragment fusion protein design (structure I-B).

| Identifier | Sequence (One-Letter Amino Acid Symbols) | |
| --- | --- | --- |
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to one or more 4-1BB binding domains that is a scFv domain comprising V$_H$ and V$_L$ regions that are each at least 95% identical to the V$_H$ and V$_L$ sequences given in Table 11, wherein the V$_H$ and V$_L$ domains are connected by a linker.

TABLE 27

Additional polypeptide domains useful as 4-1BB binding domains in fusion proteins or as scFv 4-1BB agonist antibodies.

| Identifier | Sequence (One-Letter Amino Acid Symbols) | | | | | | |
|---|---|---|---|---|---|---|---|
| SEQ ID NO: 46 | MEYASDASLD | PEAPWPPAPR | ARACRVLPWA | LVAGLLLLLL | LAAACAVFLA | CPWAVSGARA | 60 |
| 4-1BBL | SPGSAASPRL | REGPELSPDD | PAGLLDLRQG | MFAQLVAQNV | LLIDGPLSWY | SDPGLAGVSL | 120 |
| | TGGLSYKEDT | KELVVAKAGV | YYVFFQLELR | RVVAGEGSGS | VSLALHLQPL | RSAAGAAALA | 180 |
| | LTVDLPPASS | EARNSAFGFQ | GRLLHLSAGQ | RLGVHLHTEA | RARHAWQLTQ | GATVLGLFRV | 240 |
| | TPEIPAGLPS | PRSE | | | | | 254 |
| | | | | | | | |
| SEQ ID NO: 47 | LRQGMFAQLV | AQNVLLIDGP | LSWYSDPGLA | GVSLTGGLSY | KEDTKELVVA | KAGVYYVFFQ | 60 |
| 4-1BBL soluble | LELRRVVAGE | GSGSVSLALH | LQPLRSAAGA | AALALTVDLP | PASSEARNSA | FGFQGRLLHL | 120 |
| domain | SAGQRLGVHL | HTEARARHAW | QLTQGATVLG | LFRVTPEIPA | GLPSPRSE | | 168 |
| | | | | | | | |
| SEQ ID NO: 48 | QVQLQQPGAE | LVKPGASVKL | SCKASGYTFS | SYWMHWVKQR | PGQVLEWIGE | INPGNGHTNY | 60 |
| variable heavy | NEKFKSKATL | TVDKSSSTAY | MQLSSLTSED | SAVYYCARSF | TTARGFAYWG | QGTLVTVS | 118 |
| chain for 4B4-1- | | | | | | | |
| 1 version 1 | | | | | | | |
| | | | | | | | |
| SEQ ID NO: 49 | DIVMTQSPAT | QSVTPGDRVS | LSCRASQTIS | DYLHWYQQKS | HESPRLLIKY | ASQSISGIPS | 60 |
| variable light | RFSGSGSGSD | FTLSINSVEP | EDVGVYYCQD | GHSFPPTFGG | GTKLEIK | | 107 |
| chain for 4B4-1- | | | | | | | |
| 1 version 1 | | | | | | | |
| | | | | | | | |
| SEQ ID NO: 50 | QVQLQQPGAE | LVKPGASVKL | SCKASGYTFS | SYWMHWVKQR | PGQVLEWIGE | INPGNGHTNY | 60 |
| variable heavy | NEKFKSKATL | TVDKSSSTAY | MQLSSLTSED | SAVYYCARSF | TTARGFAYWG | QGTLVTVSA | 119 |
| chain for 4B4-1- | | | | | | | |
| 1 version 2 | | | | | | | |
| | | | | | | | |
| SEQ ID NO: 51 | DIVMTQSPAT | QSVTPGDRVS | LSCRASQTIS | DYLHWYQQKS | HESPRLLIKY | ASQSISGIPS | 60 |
| variable light | RFSGSGSGSD | FTLSINSVEP | EDVGVYYCQD | GHSFPPTFGG | GTKLEIKR | | 108 |
| chain for 4B4-1- | | | | | | | |
| 1 version 2 | | | | | | | |
| | | | | | | | |
| SEQ ID NO: 52 | MDWTWRILFL | VAAATGAHSE | VQLVESGGGL | VQPGGSLRLS | CAASGFTFSD | YWMSWVRQAP | 60 |
| variable heavy | GKGLEWVADI | KNDGSYTNYA | PSLTNRFTIS | RDNAKNSLYL | QMNSLRAEDT | AVYYCARELT | 120 |
| chain for H39E3- | | | | | | | |
| 2 | | | | | | | |
| | | | | | | | |
| SEQ ID NO: 53 | MEAPAQLLFL | LLLWLPDTTG | DIVMTQSPDS | LAVSLGERAT | INCKSSQSLL | SSGNQKNYL | 60 |
| variable light | WYQQKPGQPP | KLLIYYASTR | QSGVPDRFSG | SGSGTDFTLT | ISSLQAEDVA | | 110 |
| chain for H39E3- | | | | | | | |
| 2 | | | | | | | | structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I-B comprises one or more 4-1BB binding domains that is a scFv domain comprising V$_H$ and V$_L$ regions that are each at least 95% identical to the sequences shown in SEQ ID NO:13 and SEQ ID NO:14, respectively, wherein the V$_H$ and V$_L$ domains are connected by a linker. In an embodiment, a 4-1BB agonist fusion protein according to structures I-A or I-B comprises one or more 4-1BB binding domains that is a scFv domain comprising V$_H$ and V$_L$ regions that are each at least 95% identical to the sequences shown in SEQ ID NO:23 and SEQ ID NO:24, respectively, wherein the V$_H$ and V$_L$ domains are connected by a linker. In an embodiment, a 4-1BB agonist fusion protein according to structures I-A or I-B comprises In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

3. OX40 (CD134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multi specific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 12.

TABLE 28

Amino acid sequences of OX40 antigens.

| Identifier | Sequence (One-Letter Amino Acid Symbols) | | | | | |
|---|---|---|---|---|---|---|
| SEQ ID NO: 54 | MCVGARRLGR | GPCAALLLLG | LGLSTVTGLH | CVGDTYPSND | RCCHECRPGN | GMVSRCSRSQ 60 |
| human OX40 | NTVCRPCGPG | FYNDVVSSKP | CKPCTWCNLR | SGSERKQLCT | ATQDTVCRCR | AGTQPLDSYK 120 |
| (*Homo sapiens*) | PGVDCAPCPP | GHFSPGDNQA | CKPWTNCTLA | GKHTLQPASN | SSDAICEDRD | PPATQPQETQ 180 |
| | GPPARPITVQ | PTEAWPRTSQ | GPSTRPVEVP | GGRAVAAILG | LGLVLGLLGP | LAILLALYLL 240 |
| | RRDQRLPPDA | HKPPGGGSFR | TPIQEEQADA | HSTLAKI | | 277 |
| | | | | | | |
| SEQ ID NO: 55 | MYVWVQQPTA | LLLLGLTLGV | TARRLNCVKH | TYPSGHKCCR | ECQPGHGMVS | RCDHTRDTLC 60 |
| murine OX40 | HPCETGFYNE | AVNYDTCKQC | TQCNHRSGSE | LKQNCTPTQD | TVCRCRPGTQ | PRQDSGYKLG 120 |
| (*Mus musculus*) | VDCVPCPPGH | FSPGNNQACK | PWTNCTLSGK | QTRHPASDSL | DAVCEDRSLL | ATLLWETQRP 180 |
| | TFRPTTVQST | TVWPRTSELP | SPPTLVTPEG | PAFAVLLGLG | LGLLAPLTVL | LALYLLRKAW 240 |
| | RLPNTPKPCW | GNSFRTPIQE | EHTDAHFTLA | KI | | 272 | chimeric anti-OX40 antibodies, anti-OX40 adnectins, anti-OX40 domain antibodies, single chain anti-OX40 fragments, heavy chain anti-OX40 fragments, light chain anti- In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5 \times 10^5$ 1/M·s or faster, binds to human or murine OX40 with a $k_{assoc}$ of about $7.5 \times 10^5$ 1/M·s or faster, binds to human or murine OX40 with a $k_{assoc}$ of about $8 \times 10^5$ 1/M·s or faster, binds to human or murine OX40 with a $k_{assoc}$ of about $8.5 \times 10^5$ 1/M·s or faster, binds to human or murine OX40 with a $k_{assoc}$ of about $9 \times 10^5$ 1/M·s or faster, binds to human or murine OX40 with a $k_{assoc}$ of about $9.5 \times 10^5$ 1/M·s or faster, or binds to human or murine OX40 with a $k_{assoc}$ of about $1 \times 10^6$ 1/M·s or faster.

In some embodiments, the compositions, processes and methods described include a OX40 agonist that binds to human or murine OX40 with a $k_{dissoc}$ of about $2 \times 10^{-5}$ 1/s or slower, binds to human or murine OX40 with a $k_{dissoc}$ of about $2.1 \times 10^{-5}$ 1/s or slower, binds to human or murine OX40 with a $k_{dissoc}$ of about $2.2 \times 10^{-5}$ 1/s or slower, binds to human or murine OX40 with a $k_{dissoc}$ of about $2.3 \times 10^{-5}$ 1/s or slower, binds to human or murine OX40 with a $k_{dissoc}$ of about $2.4 \times 10^{-5}$ 1/s or slower, binds to human or murine OX40 with a $k_{dissoc}$ of about $2.5 \times 10^{-5}$ 1/s or slower, binds to human or murine OX40 with a $k_{dissoc}$ of about $2.6 \times 10^{-5}$ 1/s or slower or binds to human or murine OX40 with a $k_{dissoc}$ of about $2.7 \times 10^{-5}$ 1/s or slower, binds to human or murine OX40 with a $k_{dissoc}$ of about $2.8 \times 10^{-5}$ 1/s or slower, binds to human or murine OX40 with a $k_{dissoc}$ of about $2.9 \times 10^{-5}$ 1/s or slower, or binds to human or murine OX40 with a $k_{dissoc}$ of about $3 \times 10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 13. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H$1-$C_L$), 265-325 ($C_H$2) and 371-429 ($C_H$3) (and at positions 22"-95", 148"-204", 265"-325", and 371"-429"); light chain intrachain disulfide bridges at positions 23'-88' ($V_H$-$V_L$) and 134'-194' ($C_H$1-$C_L$) (and at positions 23'''-88''' and 134'''-

194'''); interchain heavy chain-heavy chain disulfide bridges at positions 230-230" and 233-233"; and interchain heavy chain-light chain disulfide bridges at 224-214' and 224"-214'''. Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 29

Amino acid sequences for OX40 agonist antibodies related to tavolixizumab.

| Identifier | Sequence (One-Letter Amino Acid Symbols) | |
|---|---|---|
| SEQ ID NO: 56 heavy chain for tavolixizumab | QVQLQESGPG LVKPSQTLSL TCAVYGGSFS SGYWNWIRKH PGKGLEYIGY ISYNGITYHN | 60 |
| | PSLKSRITIN RDTSKNQYSL QLNSVTPEDT AVYYCARYKY DYDGGHAMDY WGQGTLVTVS | 120 |
| | SASTKGPSVF PLAPSSKSTS GGTAALGCLV KDYFPEPVTV SWNSGALTSG VHTFPAVLQS | 180 |
| | SGLYSLSSVV TVPSSSLGTQ TYICNVNHKP SNTKVDKRVE PKSCDKTHTC PPCPAPELLG | 240 |
| | GPSVFLFPPK PKDTLMISRT PEVTCVVVDV SHEDPEVKFN WYVDGVEVHN AKTKPREEQY | 300 |
| | NSTYRVVSVL TVLHQDWLNG KEYKCKVSNK ALPAPIEKTI SKAKGQPREP QVYTLPPSRE | 360 |
| | EMTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 57 light chain for tavolixizumab | DIQMTQSPSS LSASVGDRVT ITCRASQDIS NYLNWYQQKP GKAPKLLIYY TSKLHSGVPS | 60 |
| | RFSGSGSGTD YTLTISSLQP EDFATYYCQQ GSALPWTFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 58 heavy chain variable region for tavolixizumab | QVQLQESGPG LVKPSQTLSL TCAVYGGSFS SGYWNWIRKH PGKGLEYIGY ISYNGITYHN | 60 |
| | PSLKSRITIN RDTSKNQYSL QLNSVTPEDT AVYYCARYKY DYDGGHAMDY WGQGTLVT | 118 |
| SEQ ID NO: 59 light chain variable region for tavolixizumab | DIQMTQSPSS LSASVGDRVT ITCRASQDIS NYLNWYQQKP GKAPKLLIYY TSKLHSGVPS | 60 |
| | RFSGSGSGTD YTLTISSLQ PEDFATYYCQQ GSALPWTFGQ GTKVEIKR | 108 |
| SEQ ID NO: 60 heavy chain CDR1 for tavolixizumab | GSFSSGYWN | 9 |
| SEQ ID NO: 61 heavy chain CDR2 for tavolixizumab | YIGYISYNGI TYH | 13 |
| SEQ ID NO: 62 heavy chain CDR3 for tavolixizumab | RYKYDYDGGH AMDY | 14 |
| SEQ ID NO: 63 light chain CDR1 for tavolixizumab | QDISNYLN | 8 |

TABLE 29-continued

Amino acid sequences for OX40 agonist antibodies related to tavolixizumab.

| Identifier | Sequence (One-Letter Amino Acid Symbols) | |
|---|---|---|
| SEQ ID NO: 64 light chain CDR2 for tavolixizumab | LLIYYTSKLH S | 11 |
| SEQ ID NO: 65 light chain CDR3 for tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 14.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:68, and the OX40 agonist light chain variable region ($V_L$) comprises the sequence shown in SEQ ID NO:69, and conservative amino acid substitutions thereof. In an embodiment, a OX40 agonist comprises $V_H$ and $V_L$ regions that are each at least 99% identical to the sequences shown in SEQ ID NO:68 and SEQ ID NO:69, respectively. In an embodiment, a OX40 agonist comprises $V_H$ and $V_L$ regions that are each at least 98% identical to the sequences shown in SEQ ID NO:68 and SEQ ID NO:69, respectively. In an embodiment, a OX40 agonist comprises $V_H$ and $V_L$ regions that are each at least 97% identical to the sequences shown in SEQ ID NO:68 and SEQ ID NO:69, respectively. In an embodiment, a OX40 agonist comprises $V_H$ and $V_L$ regions that are each at least 96% identical to the sequences shown in SEQ ID NO:68 and SEQ ID NO:69, respectively. In an embodiment, a OX40 agonist comprises $V_H$ and $V_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 30

| Amino acid sequences for OX40 agonist antibodies related to 11D4. |
| --- |

| Identifier | Sequence (One-Letter Amino Acid Symbols) | |
| --- | --- | --- |
| SEQ ID NO: 66<br>heavy chain for<br>11D4 | EVQLVESGGG LVQPGGSLRL SCAASGFTFS SYSMNWVRQA PKGKGLEWVSY ISSSSSTIDY<br>ADSVKGRFTI SRDNAKNSLY LQMNSLRDED TAVYYCARES GWYLFDYWGQ GTLVTVSSAS<br>TKGPSVFPLA PCSRSTSEST AALGCLVKDY FPEPVTVSWN SGALTSGVHT FPAVLQSSGL<br>YSLSSVVTVP SSNFGTQTYT CNVDHKPSNT KVDKTVERKC CVECPPCPAP PVAGPSVFLF<br>PPKPKDTLMI SRTPEVTCVV VDVSHEDPEV QFNWYVDGVE VHNAKTKPRE EQFNSTFRVV<br>SVLTVVHQDW LNGKEYKCKV SNKGLPAPIE KTISKTKGQP REPQVYTLPP SREEMTKNQV<br>SLTCLVKGFY PSDIAVEWES NGQPENNYKT TPPMLDSDGS FFLYSKLTVD KSRWQQGNVF<br>SCSVMHEALH NHYTQKSLSL SPGK | 60<br>120<br>180<br>240<br>300<br>360<br>420<br>444 |
| SEQ ID NO: 67<br>light chain for<br>11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 68<br>heavy chain<br>variable region<br>for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSS | 60<br>118 |
| SEQ ID NO: 69<br>light chain<br>variable region<br>for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIK | 60<br>107 |
| SEQ ID NO: 70<br>heavy chain CDR1<br>for 11D4 | SYSMN | 5 |
| SEQ ID NO: 71<br>heavy chain CDR2<br>for 11D4 | YISSSSSTID YADSVKG | 17 |
| SEQ ID NO: 72<br>heavy chain CDR3<br>for 11D4 | ESGWYLFDY | 9 |
| SEQ ID NO: 73<br>light chain CDR1<br>for 11D4 | RASQGISSWL A | 11 |
| SEQ ID NO: 74<br>light chain CDR2<br>for 11D4 | AASSLQS | 7 |
| SEQ ID NO: 75<br>light chain CDR3<br>for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 15.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 31

| Amino acid sequences for OX40 agonist antibodies related to 18D8. | | | | | | | |
|---|---|---|---|---|---|---|---|
| Identifier | Sequence (One-Letter Amino Acid Symbols) | | | | | | |
| SEQ ID NO: 76 heavy chain for 18D8 | EVQLVESGGG | LVQPGRSLRL | SCAASGFTFD | DYAMHWVRQA | PGKGLEWVSG | ISWNSGSIGY | 60 |
| | ADSVKGRFTI | SRDNAKNSLY | LQMNSLRAED | TALYYCAKDQ | STADYYFYYG | MDVWGQGTTV | 120 |
| | TVSSASTKGP | SVPPLAPCSR | STSESTAALG | CLVKDYFPEP | VTVSWNSGAL | TSGVHTFPAV | 180 |
| | LQSSGLYSLS | SVVTVPSSNF | GTQTYTCNVD | HKPSNTKVDK | TVERKCCVEC | PPCPAPPVAG | 240 |
| | PSVFLFPPKP | KDTLMISRTP | EVTCVVVDVS | HEDPEVQFNW | YVDGVEVHNA | KTKPREEQFN | 300 |
| | STFRVVSVLT | VVHQDWLNGK | EYKCKVSNKG | LPAPIEKTIS | KTKGQPREPQ | VYTLPPSREE | 360 |
| | MTKNQVSLTC | LVKGFYPSDI | AVEWESNGQP | ENNYKTTPPM | LDSDGSFFLY | SKLTVDKSRW | 420 |
| | QQGNVFSCSV | MHEALHNHYT | QKSLSLSPGK | | | | 450 |
| SEQ ID NO: 77 light chain for 18D8 | EIVVTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | RSNWPTFGQG | TKVEIKRTVA | APSVFIFPPS | 120 |
| | DEQLKSGTAS | VVCLLNNFYP | REAKVQWKVD | NALQSGNSQE | SVTEQDSKDS | TYSLSSTLTL | 180 |
| | SKADYEKHKV | YACEVTHQGL | SSPVTKSFNR | GEC | | | 213 |
| SEQ ID NO: 78 heavy chain variable region for 18D8 | EVQLVESGGG | LVQPGRSLRL | SCAASGFTFD | DYAMHWVRQA | PGKGLEWVSG | ISWNSGSIGY | 60 |
| | ADSVKGRFTI | SRDNAKNSLY | LQMNSLRAED | TALYYCAKDQ | STADYYFYYG | MDVWGQGTTV | 120 |
| | TVSS | | | | | | 124 |
| SEQ ID NO: 79 light chain variable region for 18D8 | EIVVTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | RSNWPTFGQG | TKVEIK | | 106 |
| SEQ ID NO: 80 heavy chain CDR1 for 18D8 | DYAMH | | | | | | 5 |
| SEQ ID NO: 81 heavy chain CDR2 for 18D8 | GISWNSGSIG | YADSVKG | | | | | 17 |
| SEQ ID NO: 82 heavy chain CDR3 for 18D8 | DQSTADYYFY | YGMDV | | | | | 15 |
| SEQ ID NO: 83 light chain CDR1 for 18D8 | RASQSVSSYL | A | | | | | 11 |

TABLE 31-continued

| Amino acid sequences for OX40 agonist antibodies related to 18D8. | | |
|---|---|---|
| Identifier | Sequence (One-Letter Amino Acid Symbols) | |
| SEQ ID NO: 84<br>light chain CDR2<br>for 18D8 | DASNRAT | 7 |
| SEQ ID NO: 85<br>light chain CDR3<br>for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 16.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 32

| Amino acid sequences for OX40 agonist antibodies related to Hu119-122. | | | | | | | |
|---|---|---|---|---|---|---|---|
| Identifier | Sequence (One-Letter Amino Acid Symbols) | | | | | | |
| SEQ ID NO: 86<br>heavy chain<br>variable region<br>for Hu119-122 | EVQLVESGGG<br>PDTMERRFTI | LVQPGGSLRL<br>SRDNAKNSLY | SCAASEYEFP<br>LQMNSLRAED | SHDMSWVRQA<br>TAVYYCARHY | PGKGLELVAA<br>DDYYAWFAYW | INSDGGSTYY<br>GQGTMVTVSS | 60<br>120 |
| SEQ ID NO: 87<br>light chain<br>variable region<br>for Hu119-122 | EIVLTQSPAT<br>GVPARFSGSG | LSLSPGERAT<br>SGTDFTLTIS | LSCRASKSVS<br>SLEPEDFAVY | TSGYSYMHWY<br>YCQHSRELPL | QQKPGQAPRL<br>TFGGGTKVEI | LIYLASNLES<br>K | 60<br>111 |

TABLE 32-continued

| Amino acid sequences for OX40 agonist antibodies related to Hu119-122. | | |
|---|---|---|
| Identifier | Sequence (One-Letter Amino Acid Symbols) | |
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 17.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 33

| Amino acid sequences for OX40 agonist antibodies related to Hu106-222. | | | | | | |
|---|---|---|---|---|---|---|
| Identifier | Sequence (One-Letter Amino Acid Symbols) | | | | | |
| SEQ ID NO: 94<br>heavy chain<br>variable region<br>for Hu106-222 | QVQLVQSGSE<br>ADDFKGRFVF<br>SS | LKKPGASVKV<br>SLDTSVSTAY | SCKASGYTFT<br>LQISSLKAED | DYSMHWVRQA<br>TAVYYCANPY | PGQGLKWMGW<br>YDYVSYYAMD | INTETGEPTY<br>YWGQGTTVTV | 60<br>120<br>122 |
| SEQ ID NO: 95<br>light chain<br>variable region<br>for Hu106-222 | DIQMTQSPSS<br>RFSGSGSGTD | LSASVGDRVT<br>FTFTISSLQP | ITCKASQDVS<br>EDIATYYCQQ | TAVAWYQQKP<br>HYSTPRTFGQ | GKAPKLLIYS<br>GTKLEIK | ASYLYTGVPS | 60<br>107 |
| SEQ ID NO: 96<br>heavy chain CDR1<br>for Hu106-222 | DYSMH | | | | | | 5 |
| SEQ ID NO: 97<br>heavy chain CDR2<br>for Hu106-222 | WINTETGEPT | YADDFKG | | | | | 17 |
| SEQ ID NO: 98<br>heavy chain CDR3<br>for Hu106-222 | PYYDYVSYYA | MDY | | | | | 13 |
| SEQ ID NO: 99<br>light chain CDR1<br>for Hu106-222 | KASQDVSTAV | A | | | | | 11 |
| SEQ ID NO: 100<br>light chain CDR2<br>for Hu106-222 | SASYLYT | | | | | | 7 |
| SEQ ID NO: 101<br>light chain CDR3<br>for Hu106-222 | QQHYSTPRT | | | | | | 9 |

In some embodiments, the OX40 agonist antibody is MEDI6469 (also referred to as 9B12). MEDI6469 is a murine monoclonal antibody. Weinberg, et al., *J. Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 17, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 14, wherein the $V_H$ and $V_L$ domains are connected by a linker.

TABLE 34

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | | | | | |
|---|---|---|---|---|---|---|
| SEQ ID NO: 102 OX40L | MERVQPLEEN SIKVQFTEYK KDEEPLFQLK CVL | VGNAARPRFE KEKGFILTSQ KVRSVNSLMV | RNKLLLVASV KEDEIMKVQN ASLTYKDKVY | IQGLGLLLCF NSVIINCDGF LNVTTDNTSL | TYICLHFSAL YLISLKGYFS DDFHVNGGEL | QVSHRYPRIQ 60 QEVNISLHYQ 120 ILIHQNPGEF 180 183 |
| SEQ ID NO: 103 OX40L soluble domain | SHRYPRIQSI VNISLHYQKD IHQNPGEFCV | KVQFTEYKKE EEPLFQLKKV L | KGFILTSQKE RSVNSLMVAS | DEIMKVQNNS LTYKDKVYLN | VIINCDGFYL VTTDNTSLDD | ISLKGYFSQE 60 FHVNGGELIL 120 131 |
| SEQ ID NO: 104 OX40L soluble domain (alternative) | YPRIQSIKVQ SLHYQKDEEP NPGEFCVL | FTEYKKEKGF LFQLKKVRSV | ILTSQKEDEI NSLMVASLTY | MKVQNNSVII KDKVYLNVTT | NCDGFYLISL DNTSLDDFHV | KGYFSQEVNI 60 NGGELILIHQ 120 128 |
| SEQ ID NO: 105 variable heavy chain for 008 | EVQLVESGGG ADSVKGRFTI | LVQPGGSLRL SRDNSKNTLY | SCAASGFTFS LQMNSLRAED | NYTMNWVRQA TAVYYCAKDR | PGKGLEWVSA YSQVHYALDY | ISGSGGSTYY 60 WGQGTLVTVS 120 |
| SEQ ID NO: 106 variable light chain for 008 | DIVMTQSPDS SGVPDRFSGS | LPVTPGEPAS GSGTDFTLKI | ISCRSSQSLL SRVEAEDVGV | HSNGYNYLDW YYCQQYYNHP | YLQKAGQSPQ TTFGQGTK | LLIYLGSNRA 60 108 |
| SEQ ID NO: 107 variable heavy chain for 011 | EVQLVESGGG SRKGRFTISR | VVQPGRSLRL DNSKNTLYLQ | SCAASGFTFS MNNLRAEDTA | DYTMNWVRQA VYYCARDRYF | PGKGLEWVSS RQQNAFDYWG | ISGGSTYYAD 60 QGTLVTVSSA 120 |
| SEQ ID NO: 108 variable light chain for 011 | DIVMTQSPDS SGVPDRFSGS | LPVTPGEPAS GSGTDFTLKI | ISCRSSQSLL SRVEAEDVGV | HSNGYNYLDW YYCQQYYNHP | YLQKAGQSPQ TTFGQGTK | LLIYLGSNRA 60 108 |

TABLE 34-continued

Additional polypeptide domains useful as OX40 binding domains in
fusion proteins (e.g., structures I-A and I-B) or as scFv OX40
agonist antibodies.

| Identifier | Sequence (One-Letter Amino Acid Symbols) | |
|---|---|---|
| SEQ ID NO: 109<br>variable heavy<br>chain for 021 | EVQLVESGGG LVQPRGSLRL SCAASGFTFS SYAMNWVRQA PGKGLEWVAV ISYDGSNKYY<br>ADSVKGRFTI SRDNSKNTLY LQMNSLRAED TAVYYCAKDR YITLPNALDY WGQGTLVTVS | 60<br>120 |
| SEQ ID NO: 110<br>variable light<br>chain for 021 | DIQMTQSPVS LPVTPGEPAS ISCRSSQSLL HSNGYNYLDW YLQKPGQSPQ LLIYLGSNRA<br>SGVPDRFSGS GSGTDFTLKI SRVEAEDVGV YYCQQYKSNP PTFGQGTK | 60<br>108 |
| SEQ ID NO: 111<br>variable heavy<br>chain for 023 | EVQLVESGGG LVHPGGSLRL SCAGSGFTFS SYAMHWVRQA PGKGLEWVSA IGTGGGTYYA<br>DSVMGRFTIS RDNSKNTLYL QMNSLRAEDT AVYYCARYDN VMGLYWFDYW GQGTLVTVSS | 60<br>120 |
| SEQ ID NO: 112<br>variable light<br>chain for 023 | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPPAFGG GTKVEIKR | 60<br>108 |
| SEQ ID NO: 113<br>heavy chain<br>variable region | EVQLQQSGPE LVKPGASVKM SCKASGYTFT SYVMHWVKQK PGQGLEWIGY INPYNDGTKY<br>NEKFKGKATL TSDKSSSTAY MELSSLTSED SAVYYCANYY GSSLSMDYWG QGTSVTVSS | 60<br>119 |
| SEQ ID NO: 114<br>light chain<br>variable region | DIQMTQTTSS LSASLGDRVT ISCRASQDIS NYLNWYQQKP DGTVKLLIYY TSRLHSGVPS<br>RFSGSGSGTD YSLTISNLEQ EDIATYFCQQ GNTLPWTFGG GTKLEIKR | 60<br>108 |
| SEQ ID NO: 115<br>heavy chain<br>variable region | EVQLQQSGPE LVKPGASVKI SCKTSGYTFK DYTMHWVKQS HGKSLEWIGG IYPNNGGSTY<br>NQNFKDKATL TVDKSSSTAY MEFRSLTSED SAVYYCARMG YHGPHLDFDV WGAGTTVTVS<br>P | 60<br>120<br>121 |
| SEQ ID NO: 116<br>light chain<br>variable region | DIVMTQSHKF MSTSLGDRVS ITCKASQDVG AAVAWYQQKP GQSPKLLIYW ASTRHTGVPD<br>RFTGGGSGTD FTLTISNVQS EDLTDYFCQQ YINYPLTFGG GTKLEIKR | 60<br>108 |
| SEQ ID NO: 117<br>heavy chain<br>variable region<br>of humanized<br>antibody | QIQLVQSGPE LKKPGETVKI SCKASGYTFT DYSMHWVKQA PGKGLKWMGW INTETGEPTY<br>ADDFKGRFAF SLETSASTAY LQINNLKNED TATYFCANPY YDYVSYYAMD YWGHGTSVTV<br>SS | 60<br>120<br>122 |
| SEQ ID NO: 118<br>heavy chain<br>variable region<br>of humanized<br>antibody | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 119<br>light chain<br>variable region<br>of humanized<br>antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |
| SEQ ID NO: 120<br>light chain<br>variable region<br>of humanized<br>antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |
| SEQ ID NO: 121<br>heavy chain<br>variable region<br>of humanized<br>antibody | EVQLVESGGG LVQPGESLKL SCESNEYEFP SHDMSWVRKT PEKRLELVAA INSDGGSTYY<br>PDTMERRFII SRDNTKKTLY LQMSSLRSED TALYYCARHY DDYYAWFAYW GQGTLVTVSA | 60<br>120 |
| SEQ ID NO: 122<br>heavy chain<br>variable region<br>of humanized<br>antibody | EVQLVESGGG LVQPGGSLRL SCAASEYEFP SHDMSWVRQA PGKGLELVAA INSDGGSTYY<br>PDTMERRFTI SRDNAKNSLY LQMNSLRAED TAVYYCARHY DDYYAWFAYW GQGTMVTVSS | 60<br>120 |
| SEQ ID NO: 123<br>light chain<br>variable region<br>of humanized<br>antibody | DIVLTQSPAS LAVSLGQRAT ISCRASKSVS TSGYSYMHWY QQKPGQPPKL LIYLASNLES<br>GVPARFSGSG SGTDFTLNIH PVEEEDAATY YCQHSRELPL TFGAGTKLEL K | 60<br>111 |

TABLE 34-continued

Additional polypeptide domains useful as OX40 binding domains in
fusion proteins (e.g., structures I-A and I-B) or as scFv OX40
agonist antibodies.

| Identifier | Sequence (One-Letter Amino Acid Symbols) |
|---|---|
| SEQ ID NO: 124 light chain variable region of humanized antibody | EIVLTQSPAT LSLSPGERAT LSCRASKSVS TSGYSYMHWY QQKPGQAPRL LIYLASNLES 60<br>GVPARFSGSG SGTDFTLTIS SLEPEDFAVY YCQHSRELPL TFGGGTKVEI K 111 |
| SEQ ID NO: 125 heavy chain variable region | MYLGLNYVFI VFLLNGVQSE VKLEESGGGL VQPGGSMKLS CAASGFTFSD AWMDWVRQSP 60<br>EKGLEWVAEI RSKANNHATY YAESVNGRFT ISRDDSKSSV YLQMNSLRAE DTGIYYCTWG 120<br>EVFYFDYWGQ GTTLTVSS 138 |
| SEQ ID NO: 126 light chain variable region | MRPSIQFLGL LLFWLHGAQC DIQMTQSPSS LSASLGGKVT ITCKSSQDIN KYIAWYQHKP 60<br>GKGPRLLIHY TSTLQPGIPS RFSGSGSGRD YSFSISNLEP EDIATYYCLQ YDNLLTFGAG 120<br>TKLELK 126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

I. Optional Cell Viability Analyses

Optionally, a cell viability assay can be performed after the priming first expansion (sometimes referred to as the initial bulk expansion), using standard assays known in the art. Thus, in certain embodiments, the method comprises performing a cell viability assay subsequent to the priming first expansion. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Bio-sciences). The cells can be counted manually using a disposable c-chip hemocytometer (VWR, Batavia, IL) and viability can be assessed using any method known in the art, including but not limited to trypan blue staining. The cell viability can also be assayed based on U.S. Ser. No. 15/863, 634, incorporated by reference herein in its entirety. Cell viability can also be assayed based on U.S. Patent Publication No. 2018/0280436 or International Patent Publication No. WO/2018/081473, both of which are incorporate herein in their entireties for all purposes.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs, including those discussed above as well as exemplified in FIG. 8, in particular, e.g., FIG. 8B and/or FIG. 8C, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the priming first expansion is serum free. In some embodiments, the media in the second expansion is serum free. In some embodiments, the media in the priming first expansion and the second expansion (also referred to as rapid second expansion) are both serum free. In an embodiment, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell culture medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 8 days, e.g., about 7 days as a priming first expansion, or about 8 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 10 days, e.g., about 7 days, about 8 days, about 9 days or about 10 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5\times10^5$ cells/cm$^2$ to between $10\times10^6$ and $30\times10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., J. Immunotherapy, 2012, 35:283-292.

J. Optional Genetic Engineering of TILs

In some embodiments, the expanded TILs of the present invention are further manipulated before, during, or after an expansion step, including during closed, sterile manufacturing processes, each as provided herein, in order to alter protein expression in a transient manner. In some embodiments, the transiently altered protein expression is due to transient gene editing. In some embodiments, the expanded TILs of the present invention are treated with transcription factors (TFs) and/or other molecules capable of transiently altering protein expression in the TILs. In some embodiments, the TFs and/or other molecules that are capable of transiently altering protein expression provide for altered expression of tumor antigens and/or an alteration in the number of tumor antigen-specific T cells in a population of TILs.

In certain embodiments, the method comprises genetically editing a population of TILs. In certain embodiments, the method comprises genetically editing the first population of TILs, the second population of TILs and/or the third population of TILs.

In some embodiments, the present invention includes genetic editing through nucleotide insertion, such as through ribonucleic acid (RNA) insertion, including insertion of messenger RNA (mRNA) or small (or short) interfering RNA (siRNA), into a population of TILs for promotion of the expression of one or more proteins or inhibition of the expression of one or more proteins, as well as simultaneous combinations of both promotion of one set of proteins with inhibition of another set of proteins.

In some embodiments, the expanded TILs of the present invention undergo transient alteration of protein expression. In some embodiments, the transient alteration of protein expression occurs in the bulk TIL population prior to first expansion, including, for example in the TIL population obtained from for example, Step A as indicated in FIG. 8 (particularly FIG. 8B and/or FIG. 8C). In some embodiments, the transient alteration of protein expression occurs during the first expansion, including, for example in the TIL population expanded in for example, Step B as indicated in FIG. 8 (for example FIG. 8B and/or FIG. 8C). In some embodiments, the transient alteration of protein expression occurs after the first expansion, including, for example in the TIL population in transition between the first and second expansion (e.g. the second population of TILs as described herein), the TIL population obtained from for example, Step B and included in Step C as indicated in FIG. 8. In some embodiments, the transient alteration of protein expression occurs in the bulk TIL population prior to second expansion, including, for example in the TIL population obtained from for example, Step C and prior to its expansion in Step D as indicated in FIG. 8. In some embodiments, the transient alteration of protein expression occurs during the second expansion, including, for example in the TIL population expanded in for example, Step D as indicated in FIG. 8 (e.g. the third population of TILs). In some embodiments, the transient alteration of protein expression occurs after the second expansion, including, for example in the TIL population obtained from the expansion in for example, Step D as indicated in FIG. 8.

In an embodiment, a method of transiently altering protein expression in a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of transiently altering protein expression in population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of transiently altering protein expression in a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534, 484; and 7,687,070, the disclosures of each of which are incorporated by reference herein. In an embodiment, a method of transiently altering protein expression in a population of TILs includes the step of transfection using methods described in U.S. Pat. Nos. 5,766,902; 6,025,337; 6,410, 517; 6,475,994; and 7,189,705; the disclosures of each of which are incorporated by reference herein.

In some embodiments, transient alteration of protein expression results in an increase in Stem Memory T cells (TSCMs). TSCMs are early progenitors of antigen-experienced central memory T cells. TSCMs generally display the long-term survival, self-renewal, and multipotency abilities that define stem cells, and are generally desirable for the generation of effective TIL products. TSCM have shown enhanced anti-tumor activity compared with other T cell subsets in mouse models of adoptive cell transfer (Gattinoni et al. Nat Med 2009, 2011; Gattinoni, Nature Rev. Cancer, 2012; Cieri et al. Blood 2013). In some embodiments, transient alteration of protein expression results in a TIL population with a composition comprising a high proportion of TSCM. In some embodiments, transient alteration of protein expression results in an at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% increase in TSCM percentage. In some embodiments, transient alteration of protein expression results in an at least a 1-fold, 2-fold, 3-fold, 4-fold, 5-fold, or 10-fold increase in TSCMs in the TIL population. In some embodiments, transient alteration of protein expression results in a TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs. In some embodiments, transient alteration of protein expression results in a therapeutic TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs.

In some embodiments, transient alteration of protein expression results in rejuvenation of antigen-experienced T-cells. In some embodiments, rejuvenation includes, for example, increased proliferation, increased T-cell activation, and/or increased antigen recognition.

In some embodiments, transient alteration of protein expression alters the expression in a large fraction of the T-cells in order to preserve the tumor-derived TCR repertoire. In some embodiments, transient alteration of protein expression does not alter the tumor-derived TCR repertoire. In some embodiments, transient alteration of protein expression maintains the tumor-derived TCR repertoire.

In some embodiments, transient alteration of protein results in altered expression of a particular gene. In some embodiments, the transient alteration of protein expression targets a gene including but not limited to PD-1 (also referred to as PDCD1 or CC279), TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1a), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets a gene selected from the group consisting of PD-1, TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1a), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets PD-1. In some embodiments, the transient alteration of protein expression targets TGFBR2. In some embodiments, the transient alteration of protein expression targets CCR4/5. In some embodiments, the transient alteration of protein expression targets CBLB. In some embodiments, the transient alteration of protein expression targets CISH. In some embodiments, the transient alteration of protein expression targets CCRs (chimeric co-stimulatory receptors). In some embodiments, the transient alteration of protein expression targets IL-2. In some embodiments, the transient alteration of protein expression targets IL-12. In some embodiments, the transient alteration of protein expression targets IL-15. In some embodiments, the transient alteration of protein expression targets IL-21. In some embodiments, the transient alteration of protein expression targets NOTCH 1/2 ICD. In some embodiments, the transient alteration of protein expression targets TIM3. In some embodiments, the transient alteration of protein expression targets LAG3. In some embodiments, the transient alteration of protein expression targets TIGIT. In some embodiments, the transient alteration of protein expression targets TGFβ. In some embodiments, the transient alteration of protein expression targets CCR1. In some embodiments, the transient alteration of protein expression targets CCR2. In some embodiments, the transient alteration of protein expression targets CCR4. In some embodiments, the transient alteration of protein expression targets CCR5. In some embodiments, the transient alteration of protein expression targets CXCR1. In some embodiments, the transient alteration of protein expression targets CXCR2. In some embodiments, the transient alteration of protein expression targets CSCR3. In some embodiments, the transient alteration of protein expression targets CCL2 (MCP-1). In some embodiments, the transient alteration of protein expression targets CCL3 (MIP-1α). In some embodiments, the transient alteration of protein expression targets CCL4 (MIP1-β). In some embodiments, the transient alteration of protein expression targets CCL5 (RANTES). In some embodiments, the transient alteration of protein expression targets CXCL1. In some embodiments, the transient alteration of protein expression targets CXCL8. In some embodiments, the transient alteration of protein expression targets CCL22. In some embodiments, the transient alteration of protein expression targets CCL17. In some embodiments, the transient alteration of protein expression targets VHL. In some embodiments, the transient alteration of protein expression targets CD44. In some embodiments, the transient alteration of protein expression targets PIK3CD. In some embodiments, the transient alteration of protein expression targets SOCS1. In some embodiments, the transient alteration of protein expression targets cAMP protein kinase A (PKA).

In some embodiments, the transient alteration of protein expression results in increased and/or overexpression of a chemokine receptor. In some embodiments, the chemokine receptor that is overexpressed by transient protein expression includes a receptor with a ligand that includes but is not limited to CCL2 (MCP-1), CCL3 (MIP-1α), CCL4 (MIP1-β), CCL5 (RANTES), CXCL1, CXCL8, CCL22, and/or CCL17.

In some embodiments, the transient alteration of protein expression results in a decrease and/or reduced expression of PD-1, CTLA-4, TIM-3, LAG-3, TIGIT, TGFβR2, and/or TGFβ (including resulting in, for example, TGFβ pathway blockade). In some embodiments, the transient alteration of protein expression results in a decrease and/or reduced expression of CBLB (CBL-B). In some embodiments, the transient alteration of protein expression results in a decrease and/or reduced expression of CISH.

In some embodiments, the transient alteration of protein expression results in increased and/or overexpression of chemokine receptors in order to, for example, improve TIL trafficking or movement to the tumor site. In some embodiments, the transient alteration of protein expression results in increased and/or overexpression of a CCR (chimeric co-stimulatory receptor). In some embodiments, the transient alteration of protein expression results in increased and/or overexpression of a chemokine receptor selected from the group consisting of CCR1, CCR2, CCR4, CCR5, CXCR1, CXCR2, and/or CSCR3.

In some embodiments, the transient alteration of protein expression results in increased and/or overexpression of an interleukin. In some embodiments, the transient alteration of protein expression results in increased and/or overexpression of an interleukin selected from the group consisting of IL-2, IL-12, IL-15, and/or IL-21.

In some embodiments, the transient alteration of protein expression results in increased and/or overexpression of NOTCH 1/2 ICD. In some embodiments, the transient alteration of protein expression results in increased and/or overexpression of VHL. In some embodiments, the transient alteration of protein expression results in increased and/or overexpression of CD44. In some embodiments, the transient alteration of protein expression results in increased and/or overexpression of PIK3CD. In some embodiments, the transient alteration of protein expression results in increased and/or overexpression of SOCS1, In some embodiments, the transient alteration of protein expression results in decreased and/or reduced expression of cAMP protein kinase A (PKA).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of two molecules selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1 and one molecule selected from the group consisting of LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1, LAG-3, CISH, CBLB, TIM3, and combinations thereof. In some embodiments, the transient alteration of protein expression results in decreased and/or reduced expression of PD-1 and one of LAG3, CISH, CBLB, TIM3, and combinations thereof. In some embodiments, the transient alteration of protein expression results in decreased and/or reduced expression of PD-1 and LAG3. In some embodiments, the transient alteration of protein expression results in decreased and/or reduced expression of PD-1 and CISH. In some embodiments, the transient alteration of protein expression results in decreased and/or reduced expression of PD-1 and CBLB. In some embodiments, the transient alteration of protein expression results in decreased and/or reduced expression of LAG3 and CISH. In some embodiments, the transient alteration of protein expression results in decreased and/or reduced expression of LAG3 and CBLB. In some embodiments, the transient alteration of protein expression results in decreased and/or reduced expression of CISH and CBLB. In some embodiments, the transient alteration of protein expression results in decreased and/or reduced expression of TIM3 and PD-1. In some embodiments, the transient alteration of protein expression results in decreased and/or reduced expression of TIM3 and LAG3. In some embodiments, the transient alteration of protein expression results in decreased and/or reduced expression of TIM3 and CISH. In some embodiments, the transient alteration of protein expression results in decreased and/or reduced expression of TIM3 and CBLB.

In some embodiments, an adhesion molecule selected from the group consisting of CCR2, CCR4, CCR5, CXCR2, CXCR3, CX3CR1, and combinations thereof, is inserted by a gammaretroviral or lentiviral method into the first population of TILs, second population of TILs, or harvested population of TILs (e.g., the expression of the adhesion molecule is increased).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof, and increased and/or enhanced expression of CCR2, CCR4, CCR5, CXCR2, CXCR3, CX3CR1, and combinations thereof. In some embodiments, the transient alteration of protein expression results in decreased and/or reduced expression of a molecule selected from the group consisting of PD-1, LAG3, TIM3, CISH, CBLB, and combinations thereof, and increased and/or enhanced expression of CCR2, CCR4, CCR5, CXCR2, CXCR3, CX3CR1, and combinations thereof.

In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

In some embodiments, there is an increase in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is an increase in expression of at least about 65%, about 70%, about 75%, about 80%, about 85%, about 90%, or about 95%. In some embodiments, there is an increase in expression of at least about 75%, about 80%, about 85%, about 90%, or about 95%. In some embodiments, there is an increase in expression of at least about 80%, about 85%, about 90%, or about 95%. In some embodiments, there is an increase in expression of at least about 85%, about 90%, or about 95%. In some embodiments, there is an increase in expression of at least about 80%. In some embodiments, there is an increase in expression of at least about 85%, In some embodiments, there is an increase in expression of at least about 90%. In some embodiments, there is an increase in expression of at least about 95%. In some embodiments, there is an increase in expression of at least about 99%.

In some embodiments, transient alteration of protein expression is induced by treatment of the TILs with transcription factors (TFs) and/or other molecules capable of transiently altering protein expression in the TILs. In some embodiments, the SQZ vector-free microfluidic platform is employed for intracellular delivery of the transcription factors (TFs) and/or other molecules capable of transiently altering protein expression. Such methods demonstrating the ability to deliver proteins, including transcription factors, to a variety of primary human cells, including T cells (Sharei et al. PNAS 2013, as well as Sharei et al. PLOS ONE 2015 and Greisbeck et al. J. Immunology vol. 195, 2015) have been described; see, for example, International Patent Publications WO 2013/059343A1, WO 2017/008063A1, and WO 2017/123663A1, all of which are incorporated by reference herein in their entireties. Such methods as described in International Patent Publications WO 2013/059343A1, WO 2017/008063A1, and WO 2017/123663A1 can be employed with the present invention in order to expose a population of TILs to transcription factors (TFs) and/or other molecules capable of inducing transient protein expression, wherein said TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population. In some embodiments, the reprogramming results in an increased subpopulation of effector T cells and/or central memory T cells relative to the starting or prior population (i.e., prior to reprogramming) population of TILs, as described herein.

In some embodiments, the transcription factor (TF) includes but is not limited to TCF-1, NOTCH 1/2 ICD, and/or MYB. In some embodiments, the transcription factor (TF) is TCF-1. In some embodiments, the transcription factor (TF) is NOTCH 1/2 ICD. In some embodiments, the transcription factor (TF) is MYB. In some embodiments, the transcription factor (TF) is administered with induced pluripotent stem cell culture (iPSC), such as the commercially available KNOCKOUT Serum Replacement (Gibco/ThermoFisher), to induce additional TIL reprogramming. In some embodiments, the transcription factor (TF) is administered with an iPSC cocktail to induce additional TIL reprogramming. In some embodiments, the transcription factor (TF) is administered without an iPSC cocktail. In some embodiments, reprogramming results in an increase in the percentage of TSCMs. In some embodiments, reprogramming results in an increase in the percentage of TSCMs by about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95% TSCMs.

In some embodiments, a method of transient altering protein expression, as described above, may be combined with a method of genetically modifying a population of TILs includes the step of stable incorporation of genes for production of one or more proteins. In certain embodiments, the method comprises a step of genetically modifying a population of TILs. In certain embodiments, the method comprises genetically modifying the first population of TILs, the second population of TILs and/or the third population of TILs. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tc1-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In some embodiments, transient alteration of protein expression is a reduction in expression induced by self-delivering RNA interference (sdRNA), which is a chemically-synthesized asymmetric siRNA duplex with a high percentage of 2'-OH substitutions (typically fluorine or —OCH₃) which comprises a 20-nucleotide antisense (guide) strand and a 13 to 15 base sense (passenger) strand conjugated to cholesterol at its 3' end using a tetraethylenglycol (TEG) linker. In some embodiments, the method comprises transient alteration of protein expression in a population of TILs, comprising the use of self-delivering RNA interference (sdRNA), which is a chemically-synthesized asymmetric siRNA duplex with a high percentage of 2'-OH substitutions (typically fluorine or —OCH₃) which comprises a 20-nucleotide antisense (guide) strand and a 13 to 15 base sense (passenger) strand conjugated to cholesterol at its 3' end using a tetraethylenglycol (TEG) linker. Methods of using sdRNA have been described in Khvorova and Watts, *Nat. Biotechnol.* 2017, 35, 238-248; Byrne, et al., *J. Ocul. Pharmacol. Ther.* 2013, 29, 855-864; and Ligtenberg, et al., *Mol. Therapy,* 2018, in press, the disclosures of which are incorporated by reference herein. In an embodiment, delivery of sdRNA to a TIL population is accomplished without use of electroporation, SQZ, or other methods, instead using a 1 to 3 day period in which a TIL population is exposed to sdRNA at a concentration of 1 µM/10,000 TILs in medium. In certain embodiments, the method comprises delivery sdRNA to a TILs population comprising exposing the TILs population to sdRNA at a concentration of 1 µM/10,000 TILs in medium for a period of between 1 to 3 days. In an embodiment, delivery of sdRNA to a TIL population is accomplished using a 1 to 3 day period in which a TIL population is exposed to sdRNA at a concentration of 10 µM/10,000 TILs in medium. In an embodiment, delivery of sdRNA to a TIL population is accomplished using a 1 to 3 day period in which a TIL population is exposed to sdRNA at a concentration of 50 µM/10,000 TILs in medium. In an embodiment, delivery of sdRNA to a TIL population is accomplished using a 1 to 3 day period in which a TIL population is exposed to sdRNA at a concentration of between 0.1 µM/10,000 TILs and 50 µM/10,000 TILs in medium. In an embodiment, delivery of sdRNA to a TIL population is accomplished using a 1 to 3 day period in which a TIL population is exposed to sdRNA at a concentration of between 0.1 µM/10,000 TILs and 50 µM/10,000 TILs in medium, wherein the exposure to sdRNA is performed two, three, four, or five times by addition of fresh sdRNA to the media. Other suitable processes are described, for example, in U.S. Patent Application Publication No. US 2011/0039914 A1, US 2013/0131141 A1, and US 2013/0131142 A1, and U.S. Pat. No. 9,080,171, the disclosures of which are incorporated by reference herein.

In some embodiments, sdRNA is inserted into a population of TILs during manufacturing. In some embodiments, the sdRNA encodes RNA that interferes with NOTCH 1/2 ICD, PD-1, CTLA-4 TIM-3, LAG-3, TIGIT, TGFβ, TGFBR2, cAMP protein kinase A (PKA), BAFF BR3, CISH, and/or CBLB. In some embodiments, the reduction in expression is determined based on a percentage of gene silencing, for example, as assessed by flow cytometry and/or qPCR. In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

The self-deliverable RNAi technology based on the chemical modification of siRNAs can be employed with the methods of the present invention to successfully deliver the sdRNAs to the TILs as described herein. The combination of backbone modifications with asymmetric siRNA structure and a hydrophobic ligand (see, for example, Ligtenberg, et al., *Mol. Therapy,* 2018 and US20160304873) allow sdRNAs to penetrate cultured mammalian cells without additional formulations and methods by simple addition to the culture media, capitalizing on the nuclease stability of sdRNAs. This stability allows the support of constant levels of RNAi-mediated reduction of target gene activity simply by maintaining the active concentration of sdRNA in the media. While not being bound by theory, the backbone stabilization of sdRNA provides for extended reduction in gene expression effects which can last for months in non-dividing cells.

In some embodiments, over 95% transfection efficiency of TILs and a reduction in expression of the target by various specific sdRNA occurs. In some embodiments, sdRNAs containing several unmodified ribose residues were replaced with fully modified sequences to increase potency and/or the longevity of RNAi effect. In some embodiments, a reduction in expression effect is maintained for 12 hours, 24 hours, 36 hours, 48 hours, 5 days, 6 days, 7 days, or 8 days or more. In some embodiments, the reduction in expression effect decreases at 10 days or more post sdRNA treatment of the TILs. In some embodiments, more than 70% reduction in expression of the target expression is maintained. In some embodiments, more than 70% reduction in expression of the target expression is maintained TILs. In some embodiments, a reduction in expression in the PD-1/PD-L1 pathway allows for the TILs to exhibit a more potent in vivo effect, which is in some embodiments, due to the avoidance of the suppressive effects of the PD-1/PD-L1 pathway. In some embodiments, a reduction in expression of PD-1 by sdRNA results in an increase TIL proliferation.

Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

sdRNA (self-deliverable RNA) are a new class of covalently modified RNAi compounds that do not require a delivery vehicle to enter cells and have improved pharmacology compared to traditional siRNAs. "Self-deliverable RNA" or "sdRNA" is a hydrophobically modified RNA interfering-antisense hybrid, demonstrated to be highly efficacious in vitro in primary cells and in vivo upon local administration. Robust uptake and/or silencing without toxicity has been demonstrated. sdRNAs are generally asymmetric chemically modified nucleic acid molecules with minimal double stranded regions. sdRNA molecules typically contain single stranded regions and double stranded regions, and can contain a variety of chemical modifications within both the single stranded and double stranded regions of the molecule. Additionally, the sdRNA molecules can be attached to a hydrophobic conjugate such as a conventional and advanced sterol-type molecule, as described herein. sdRNAs and associated methods for making such sdRNAs have also been described extensively in, for example, US20160304873, WO2010033246, WO2017070151, WO2009102427, WO2011119887, WO2010033247A2, WO2009045457, WO2011119852, all of which are incorporated by reference herein in their entireties for all purposes. To optimize sdRNA structure, chemistry, targeting position, sequence preferences, and the like, a proprietary algorithm has been developed and utilized for sdRNA potency prediction (see, for example, US 20160304873). Based on these analyses, functional sdRNA sequences have been generally defined as having over 70% reduction in expression at 1 µM concentration, with a probability over 40%.

In some embodiments, the sdRNA sequences used in the invention exhibit a 70% reduction in expression of the target gene. In some embodiments, the sdRNA sequences used in the invention exhibit a 75% reduction in expression of the target gene.

In some embodiments, the sdRNA sequences used in the invention exhibit an 80% reduction in expression of the target gene. In some embodiments, the sdRNA sequences used in the invention exhibit an 85% reduction in expression of the target gene. In some embodiments, the sdRNA sequences used in the invention exhibit a 90% reduction in expression of the target gene. In some embodiments, the sdRNA sequences used in the invention exhibit a 95% reduction in expression of the target gene. In some embodiments, the sdRNA sequences used in the invention exhibit a 99% reduction in expression of the target gene. In some embodiments, the sdRNA sequences used in the invention exhibit a reduction in expression of the target gene when delivered at a concentration of about 0.25 µM to about 4 µM. In some embodiments, the sdRNA sequences used in the invention exhibit a reduction in expression of the target gene when delivered at a concentration of about 0.25 µM. In some embodiments, the sdRNA sequences used in the invention exhibit a reduction in expression of the target gene when delivered at a concentration of about 0.5 µM. In some embodiments, the sdRNA sequences used in the invention exhibit a reduction in expression of the target gene when delivered at a concentration of about 0.75 µM. In some embodiments, the sdRNA sequences used in the invention exhibit a reduction in expression of the target gene when delivered at a concentration of about 1.0 µM. In some embodiments, the sdRNA sequences used in the invention exhibit a reduction in expression of the target gene when delivered at a concentration of about 1.25 µM. In some embodiments, the sdRNA sequences used in the invention exhibit a reduction in expression of the target gene when delivered at a concentration of about 1.5 µM. In some embodiments, the sdRNA sequences used in the invention exhibit a reduction in expression of the target gene when delivered at a concentration of about 1.75 µM. In some embodiments, the sdRNA sequences used in the invention exhibit a reduction in expression of the target gene when delivered at a concentration of about 2.0 µM. In some embodiments, the sdRNA sequences used in the invention exhibit a reduction in expression of the target gene when delivered at a concentration of about 2.25 µM. In some embodiments, the sdRNA sequences used in the invention exhibit a reduction in expression of the target gene when delivered at a concentration of about 2.5 µM. In some embodiments, the sdRNA sequences used in the invention exhibit a reduction in expression of the target gene when delivered at a concentration of about 2.75 µM. In some embodiments, the sdRNA sequences used in the invention exhibit a reduction in expression of the target gene when delivered at a concentration of about 3.0 µM. In some embodiments, the sdRNA sequences used in the invention exhibit a reduction in expression of the target gene when delivered at a concentration of about 3.25 µM. In some embodiments, the sdRNA sequences used in the invention exhibit a reduction in expression of the target gene when delivered at a concentration of about 3.5 µM. In some embodiments, the sdRNA sequences used in the invention exhibit a reduction in expression of the target gene when delivered at a concentration of about 3.75 µM. In some embodiments, the sdRNA sequences used in the invention exhibit a reduction in expression of the target gene when delivered at a concentration of about 4.0 μM.

In some embodiments, the oligonucleotide agents comprise one or more modification to increase stability and/or effectiveness of the therapeutic agent, and to effect efficient delivery of the oligonucleotide to the cells or tissue to be treated. Such modifications can include a 2'-O-methyl modification, a 2'-O-Fluoro modification, a diphosphorothioate modification, 2' F modified nucleotide, a 2'-O-methyl modified and/or a 2'deoxy nucleotide. In some embodiments, the oligonucleotide is modified to include one or more hydrophobic modifications including, for example, sterol, cholesterol, vitamin D, naphtyl, isobutyl, benzyl, indol, tryptophane, and/or phenyl. In an additional particular embodiment, chemically modified nucleotides are combination of phosphorothioates, 2'-O-methyl, 2'deoxy, hydrophobic modifications and phosphorothioates. In some embodiments, the sugars can be modified and modified sugars can include but are not limited to D-ribose, 2'-O-alkyl (including 2'-O-methyl and 2'-O-ethyl), i.e., 2'-alkoxy, 2'-amino, 2'-S-alkyl, 2'-halo (including 2'-fluoro), T-methoxyethoxy, 2'-allyloxy (—OCH₂CH=CH₂), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., Nucl. Acids. Res. 18:4711 (1992)).

In some embodiments, the double-stranded oligonucleotide of the invention is double-stranded over its entire length, i.e., with no overhanging single-stranded sequence at either end of the molecule, i.e., is blunt-ended. In some embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). In some embodiments, when a single nucleic acid molecule is used a portion of the molecule at either end can remain single-stranded.

In some embodiments, a double-stranded oligonucleotide of the invention contains mismatches and/or loops or bulges, but is double-stranded over at least about 70% of the length of the oligonucleotide. In some embodiments, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In some embodiments, a double-stranded oligonucleotide of the invention is double-stranded over at least about 96%-98% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

In some embodiments, the oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl (CH₂— CH₂—CH₃), glycol (—O—CH₂—CH₂—O—) phosphate (PO₃²⁻), hydrogen phosphonate, or phosphoramidite).

"Blocking groups" can also include "end blocking groups" or "exonuclease blocking groups" which protect the 5' and 3' termini of the oligonucleotide, including modified nucleotides and non-nucleotide exonuclease resistant structures.

In some embodiments, at least a portion of the contiguous polynucleotides within the sdRNA are linked by a substitute linkage, e.g., a phosphorothioate linkage.

In some embodiments, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500 enhancements in cellular uptake. In some embodiments, at least one of the C or U residues includes a hydrophobic modification. In some embodiments, a plurality of Cs and Us contain a hydrophobic modification. In some embodiments, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

In some embodiments, the sdRNA or sd-rxRNAs exhibit enhanced endosomal release of sd-rxRNA molecules through the incorporation of protonatable amines. In some embodiments, protonatable amines are incorporated in the sense strand (in the part of the molecule which is discarded after RISC loading). In some embodiments, the sdRNA compounds of the invention comprise an asymmetric compound comprising a duplex region (required for efficient RISC entry of 10-15 bases long) and single stranded region of 4-12 nucleotides long; with a 13 nucleotide duplex. In some embodiments, a 6 nucleotide single stranded region is employed. In some embodiments, the single stranded region of the sdRNA comprises 2-12 phosphorothioate internucleotide linkages (referred to as phosphorothioate modifications). In some embodiments, 6-8 phosphorothioate internucleotide linkages are employed. In some embodiments, the sdRNA compounds of the invention also include a unique chemical modification pattern, which provides stability and is compatible with RISC entry.

The guide strand, for example, may also be modified by any chemical modification which confirms stability without interfering with RISC entry. In some embodiments, the chemical modification pattern in the guide strand includes the majority of C and U nucleotides being 2' F modified and the 5' end being phosphorylated.

In some embodiments, at least 30% of the nucleotides in the sdRNA or sd-rxRNA are modified. In some embodiments, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sdRNA or sd-rxRNA are modified. In some embodiments, 100% of the nucleotides in the sdRNA or sd-rxRNA are modified.

In some embodiments, the sdRNA molecules have minimal double stranded regions. In some embodiments the region of the molecule that is double stranded ranges from 8-15 nucleotides long. In some embodiments, the region of the molecule that is double stranded is 8, 9, 10, 11, 12, 13, 14 or 15 nucleotides long. In some embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. In some embodiments, the single stranded region can be 4, 5, 6, 7, 8, 9, 10, 11 or 12 nucleotides long. In some embodiments, the single stranded region can also be less than 4 or greater than 12 nucleotides long. In certain embodiments, the single stranded region is 6 or 7 nucleotides long.

In some embodiments, the sdRNA molecules have increased stability. In some instances, a chemically modified sdRNA or sd-rxRNA molecule has a half-life in media that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In some embodiments, the sd-rxRNA has a half-life in media that is longer than 12 hours.

In some embodiments, the sdRNA is optimized for increased potency and/or reduced toxicity. In some embodiments, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. In some embodiments, reduction in 2'F content of a molecule is predicted to reduce toxicity of the molecule. In some embodiments, the number of phosphorothioate modifications in an RNA molecule can influence the uptake of the molecule into a cell, for example the efficiency of passive uptake of the molecule into a cell. In some embodiments, the sdRNA has no 2'F modification and yet are characterized by equal efficacy in cellular uptake and tissue penetration.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contain 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

The self-deliverable RNAi technology provides a method of directly transfecting cells with the RNAi agent, without the need for additional formulations or techniques. The ability to transfect hard-to-transfect cell lines, high in vivo activity, and simplicity of use, are characteristics of the compositions and methods that present significant functional advantages over traditional siRNA-based techniques, and as such, the sdRNA methods are employed in several embodiments related to the methods of reduction in expression of the target gene in the TILs of the present invention. The sdRNAi methods allows direct delivery of chemically synthesized compounds to a wide range of primary cells and tissues, both ex-vivo and in vivo. The sdRNAs described in some embodiments of the invention herein are commercially available from Advirna LLC, Worcester, MA, USA.

The sdRNA are formed as hydrophobically-modified siRNA-antisense oligonucleotide hybrid structures, and are disclosed, for example in Byrne et al., December 2013, J. Ocular Pharmacology and Therapeutics, 29(10): 855-864, incorporated by reference herein in its entirety.

In some embodiments, the sdRNA oligonucleotides can be delivered to the TILs described herein using sterile electroporation. In certain embodiments, the method comprises sterile electroporation of a population of TILs to deliver sdRNA oligonucleotides.

In some embodiments, the oligonucleotides can be delivered to the cells in combination with a transmembrane delivery system. In some embodiments, this transmembrane delivery system comprises lipids, viral vectors, and the like. In some embodiments, the oligonucleotide agent is a self-delivery RNAi agent, that does not require any delivery agents. In certain embodiments, the method comprises use of a transmembrane delivery system to deliver sdRNA oligonucleotides to a population of TILs.

Oligonucleotides and oligonucleotide compositions are contacted with (e.g., brought into contact with, also referred to herein as administered or delivered to) and taken up by TILs described herein, including through passive uptake by TILs. The sdRNA can be added to the TILs as described herein during the first expansion, for example Step B, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sdRNA can be added after thawing from any cryopreservation step in Step F. In an embodiment, one or more sdRNAs targeting genes as described herein, including PD-1, LAG-3, TIM-3, CISH, and CBLB, may be added to cell culture media comprising TILs and other agents at concentrations selected from the group consisting of 100 nM to 20 mM, 200 nM to 10 mM, 500 nm to 1 mM, 1 μM to 100 μM, and 1 μM to 100 μM. In an embodiment, one or more sdRNAs targeting genes as described herein, including PD-1, LAG-3, TIM-3, CISH, and CBLB, may be added to cell culture media comprising TILs and other agents at amounts selected from the group consisting of 0.1 μM sdRNA/10,000 TILs/100 μL media, 0.5 μM sdRNA/10,000 TILs/100 μL media, 0.75 μM sdRNA/10,000 TILs/100 μL media, 1 μM sdRNA/10,000 TILs/100 μL media, 1.25 μM sdRNA/10,000 TILs/100 μL media, 1.5 μM sdRNA/10,000 TILs/100 μL media, 2 μM sdRNA/10,000 TILs/100 μL media, 5 μM sdRNA/10,000 TILs/100 μL media, or 10 μM sdRNA/10,000 TILs/100 μL media. In an embodiment, one or more sdRNAs targeting genes as described herein, including PD-1, LAG-3, TIM-3, CISH, and CBLB, may be added to TIL cultures during the pre-REP or REP stages twice a day, once a day, every two days, every three days, every four days, every five days, every six days, or every seven days.

Oligonucleotide compositions of the invention, including sdRNA, can be contacted with TILs as described herein during the expansion process, for example by dissolving sdRNA at high concentrations in cell culture media and allowing sufficient time for passive uptake to occur. In certain embodiments, the method of the present invention comprises contacting a population of TILs with an oligonucleotide composition as described herein. In certain embodiments, the method comprises dissolving an oligonucleotide e.g. sdRNA in a cell culture media and contacting the cell culture media with a population of TILs. The TILs may be a first population, a second population and/or a third population as described herein.

In some embodiments, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see, e.g., WO 90/14074; WO 91/16024; WO 91/17424; U.S. Pat. No. 4,897,355; Bergan et a 1993. Nucleic Acids Research. 21:3567).

In some embodiments, more than one sdRNA is used to reduce expression of a target gene. In some embodiments, one or more of PD-1, TIM-3, CBLB, LAG3 and/or CISH targeting sdRNAs are used together. In some embodiments, a PD-1 sdRNA is used with one or more of TIM-3, CBLB, LAG3 and/or CISH in order to reduce expression of more than one gene target. In some embodiments, a LAG3 sdRNA is used in combination with a CISH targeting sdRNA to reduce gene expression of both targets. In some embodiments, the sdRNAs targeting one or more of PD-1, TIM-3, CBLB, LAG3 and/or CISH herein are commercially available from Advirna LLC, Worcester, MA, USA.

In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, one sdRNA targets PD-1 and another sdRNA targets a gene selected from the group consisting of LAG3, TIM3, CTLA-4, TIGIT, CISH, TGFβR2, PKA, CBLB, BAFF (BR3), and combinations thereof. In some embodiments, the sdRNA targets a gene selected from PD-1, LAG-3, CISH, CBLB, TIM3, and combinations thereof. In some embodiments, the sdRNA targets a gene selected from PD-1 and one of LAG3, CISH, CBLB, TIM3, and combinations thereof. In some embodiments, one sdRNA targets PD-1 and one sdRNA targets LAG3. In some embodiments, one sdRNA targets PD-1 and one sdRNA targets CISH. In some embodiments, one sdRNA targets PD-1 and one sdRNA targets CBLB. In some embodiments, one sdRNA targets LAG3 and one sdRNA targets CISH. In some embodiments, one sdRNA targets LAG3 and one sdRNA targets CBLB. In some embodiments, one sdRNA targets CISH and one sdRNA targets CBLB. In some embodiments, one sdRNA targets TIM3 and one sdRNA targets PD-1. In some embodiments, one sdRNA targets TIM3 and one sdRNA targets LAG3. In some embodiments, one sdRNA targets TIM3 and one sdRNA targets CISH. In some embodiments, one sdRNA targets TIM3 and one sdRNA targets CBLB.

As discussed above, embodiments of the present invention provide tumor infiltrating lymphocytes (TILs) that have been genetically modified via gene-editing to enhance their therapeutic effect. Embodiments of the present invention embrace genetic editing through nucleotide insertion (RNA or DNA) into a population of TILs for both promotion of the expression of one or more proteins and inhibition of the expression of one or more proteins, as well as combinations thereof. Embodiments of the present invention also provide methods for expanding TILs into a therapeutic population, wherein the methods comprise gene-editing the TILs. There are several gene-editing technologies that may be used to genetically modify a population of TILs, which are suitable for use in accordance with the present invention.

In some embodiments, the method comprises a method of genetically modifying a population of TILs which include the step of stable incorporation of genes for production of one or more proteins. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, Cur. Prot. *Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, the method comprises a method of genetically modifying a population of TILs e.g. a first population, a second population and/or a third population as described herein. In an embodiment, a method of genetically modifying a population of TILs includes the step of stable incorporation of genes for production or inhibition (e.g., silencing) of one ore more proteins. In an embodiment, a method of genetically modifying a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. Other electroporation methods known in the art, such as those described in U.S. Pat. Nos. 5,019,034; 5,128,257; 5,137,817; 5,173,158;

5,232,856; 5,273,525; 5,304,120; 5,318,514; 6,010,613 and 6,078,490, the disclosures of which are incorporated by reference herein, may be used. In an embodiment, the electroporation method is a sterile electroporation method. In an embodiment, the electroporation method is a pulsed electroporation method. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse amplitude. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse width. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to induce pore formation in the TILs, comprising the step of applying a sequence of at least three DC electrical pulses, having field strengths equal to or greater than 100 V/cm, to TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the TILs is maintained. In an embodiment, a method of genetically modifying a population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of genetically modifying a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA*, 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of genetically modifying a population of TILs includes the step of transfection using methods described in U.S. Pat. Nos. 5,766,902; 6,025,337; 6,410,517; 6,475,994; and 7,189,705; the disclosures of each of which are incorporated by reference herein. The TILs may be a first population, a second population and/or a third population of TILs as described herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR/Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine*, 2015, Vol. 21, No. 2.

Non-limiting examples of gene-editing methods that may be used in accordance with TIL expansion methods of the present invention include CRISPR methods, TALE methods, and ZFN methods, which are described in more detail below. According to an embodiment, a method for expanding TILs into a therapeutic population may be carried out in accordance with any embodiment of the methods described herein (e.g., GEN 3 process) or as described in PCT/US2017/058610, PCT/US2018/012605, or PCT/US2018/012633, wherein the method further comprises gene-editing at least a portion of the TILs by one or more of a CRISPR method, a TALE method or a ZFN method, in order to generate TILs that can provide an enhanced therapeutic effect. According to an embodiment, gene-edited TILs can be evaluated for an improved therapeutic effect by comparing them to non-modified TILs in vitro, e.g., by evaluating in vitro effector function, cytokine profiles, etc. compared to unmodified TILs. In certain embodiments, the method comprises gene editing a population of TILs using CRISPR, TALE and/or ZFN methods.

In some embodiments of the present invention, electroporation is used for delivery of a gene editing system, such as CRISPR, TALEN, and ZFN systems. In some embodiments of the present invention, the electroporation system is a flow electroporation system. An example of a suitable flow electroporation system suitable for use with some embodiments of the present invention is the commercially-available MaxCyte STX system. There are several alternative commercially-available electroporation instruments which may be suitable for use with the present invention, such as the AgilePulse system or ECM 830 available from BTX-Harvard Apparatus, Cellaxess Elektra (Cellectricon), Nucleofector (Lonza/Amaxa), GenePulser MXcell (BIORAD), iPorator-96 (Primax) or siPORTer96 (Ambion). In some embodiments of the present invention, the electroporation system forms a closed, sterile system with the remainder of the TIL expansion method. In some embodiments of the present invention, the electroporation system is a pulsed electroporation system as described herein, and forms a closed, sterile system with the remainder of the TIL expansion method.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a CRISPR method (e.g., CRISPR/Cas9 or CRISPR/Cpf1). According to particular embodiments, the use of a CRISPR method during the TIL expansion process causes expression of one or more immune checkpoint genes to be silenced or reduced in at least a portion of the therapeutic population of TILs. Alternatively, the use of a CRISPR method during the TIL expansion process causes expression of one or more immune checkpoint genes to be enhanced in at least a portion of the therapeutic population of TILs.

CRISPR stands for "Clustered Regularly Interspaced Short Palindromic Repeats." A method of using a CRISPR system for gene editing is also referred to herein as a CRISPR method. There are three types of CRISPR systems which incorporate RNAs and Cas proteins, and which may be used in accordance with the present invention: Types I, II, and III. The Type II CRISPR (exemplified by Cas9) is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR/Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. The crRNA and tracrRNA in the native system can be simplified into a single guide RNA (sgRNA) of approximately 100 nucleotides for use in genetic engineering. The CRISPR/Cas system is directly portable to human cells by co-delivery of plasmids expressing the Cas9 endo-nuclease and the necessary crRNA components. Different variants of Cas proteins may be used to reduce targeting limitations (e.g., orthologs of Cas9, such as Cpf1).

Non-limiting examples of genes that may be silenced or inhibited by permanently gene-editing TILs via a CRISPR method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a CRISPR method include CCR2, CCR4, CCR5, CXCR2, CXCR3, CX3CR1, IL-2, IL12, IL-15, and IL-21.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, which are incorporated by reference herein. Resources for carrying out CRISPR methods, such as plasmids for expressing CRISPR/Cas9 and CRISPR/Cpf1, are commercially available from companies such as GenScript.

In an embodiment, genetic modifications of populations of TILs, as described herein, may be performed using the CRISPR/Cpf1 system as described in U.S. Pat. No. 9,790, 490, the disclosure of which is incorporated by reference herein.

A method for expanding TILs into a therapeutic population may be carried out in accordance with any embodiment of the methods described herein (e.g., process 2A) or as described in PCT/US2017/058610, PCT/US2018/012605, or PCT/US2018/012633, wherein the method further comprises gene-editing at least a portion of the TILs by a TALE method. According to particular embodiments, the use of a TALE method during the TIL expansion process causes expression of one or more immune checkpoint genes to be silenced or reduced in at least a portion of the therapeutic population of TILs. Alternatively, the use of a TALE method during the TIL expansion process causes expression of one or more immune checkpoint genes to be enhanced in at least a portion of the therapeutic population of TILs.

TALE stands for "Transcription Activator-Like Effector" proteins, which include TALENs ("Transcription Activator-Like Effector Nucleases"). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35- amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Custom-designed TALE arrays are also commercially available through Cellectis Bioresearch (Paris, France), Transposagen Biopharmaceuticals (Lexington, KY, USA), and Life Technologies (Grand Island, NY, USA). TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of which are incorporated by reference herein.

Non-limiting examples of genes that may be silenced or inhibited by permanently gene-editing TILs via a TALE method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a TALE method include CCR2, CCR4, CCR5, CXCR2, CXCR3, CX3CR1, IL-2, IL12, IL-15, and IL-21.

Examples of systems, methods, and compositions for altering the expression of a target gene sequence by a TALE method, and which may be used in accordance with embodiments of the present invention, are described in U.S. Pat. No. 8,586,526, which is incorporated by reference herein.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a zinc finger or zinc finger nuclease method. According to particular embodiments, the use of a zinc finger method during the TIL expansion process causes expression of one or more immune checkpoint genes to be silenced or reduced in at least a portion of the therapeutic population of TILs. Alternatively, the use of a zinc finger method during the TIL expansion process causes expression of one or more immune checkpoint genes to be enhanced in at least a portion of the therapeutic population of TILs.

An individual zinc finger contains approximately 30 amino acids in a conserved ββα configuration. Several amino acids on the surface of the α-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially; Sangamo Biosciences (Richmond, CA, USA) has developed a propriety platform (CompoZr®) for zinc-finger construction in partnership with Sigma-Aldrich (St. Louis, MO, USA).

Non-limiting examples of genes that may be silenced or inhibited by permanently gene-editing TILs via a zinc finger method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a zinc finger method include CCR2, CCR4, CCR5, CXCR2, CXCR3, CX3CR1, IL-2, IL12, IL-15, and IL-21.

Examples of systems, methods, and compositions for altering the expression of a target gene sequence by a zinc finger method, which may be used in accordance with embodiments of the present invention, are described in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, which are incorporated by reference herein.

Other examples of systems, methods, and compositions for altering the expression of a target gene sequence by a zinc finger method, which may be used in accordance with embodiments of the present invention, are described in Beane, et al., *Mol. Therapy*, 2015, 23 1380-1390, the disclosure of which is incorporated by reference herein.

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). In certain embodiments, the method comprises genetically engineering a population of TILs to include a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). Aptly, the population of TILs may be a first population, a second population and/or a third population as described herein.

K. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art.

Sterile connecting devices (STCDs) produce sterile welds between two pieces of compatible tubing. This procedure permits sterile connection of a variety of containers and tube diameters. In some embodiments, the closed systems include luer lock and heat sealed systems as described in for example, Example G. In some embodiments, the closed system is accessed via syringes under sterile conditions in order to maintain the sterility and closed nature of the system. In some embodiments, a closed system as described in Example G is employed. In some embodiments, the TILs are formulated into a final product formulation container according to the method described in Example G, section "Final Formulation and Fill".

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

L. Optional Cryopreservation of TILs

Either the bulk TIL population (for example the second population of TILs) or the expanded population of TILs (for example the third population of TILs) can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 8 (in particular, e.g., FIG. 8B and/or FIG. 8C). In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above, and exemplified in Steps A through E as provided in FIG. 8 (in particular, e.g., FIG. 8B and/or FIG. 8C), cryopreservation can occur at numerous points throughout the TIL expansion process. In some embodiments, the expanded population of TILs after the second expansion (as provided for example, according to Step D of FIG. 8 (in particular, e.g., FIG. 8B and/or FIG. 8C) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Example D.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

M. Phenotypic Characteristics of Expanded TILs

In some embodiment, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B. In some embodiments, the phenotypic characteristics of the TILs are analyzed during the transition in Step C. In some embodiments, the phenotypic characteristics of the TILs are analyzed during the transition according to Step C and after cryopreservation. In some embodiments, the phenotypic characteristics of the TILs are analyzed after the second expansion according to Step D. In some embodiments, the phenotypic characteristics of the TILs are analyzed after two or more expansions according to Step D.

In some embodiments, the marker is selected from the group consisting of CD8 and CD28. In some embodiments, expression of CD8 is examined. In some embodiments, expression of CD28 is examined. In some embodiments, the expression of CD8 and/or CD28 is higher on TILs produced according the current invention process, as compared to other processes (e.g., the Gen 3 process as provided for example in FIG. 8 (in particular, e.g., FIG. 8B and/or FIG. 8C), as compared to the 2A process as provided for example in FIG. 8 (in particular, e.g., FIG. 8B and/or FIG. 8C). In some embodiments, the expression of CD8 is higher on TILs produced according the current invention process, as compared to other processes (e.g., the Gen 3 process as provided for example in FIG. 8 (in particular, e.g., FIG. 8B), as compared to the 2A process as provided for example in FIG. 8 (in particular, e.g., FIG. 8B and/or FIG. 8C). In some embodiments, the expression of CD28 is higher on TILs produced according the current invention process, as compared to other processes (e.g., the Gen 3 process as provided for example in FIG. 8 (in particular, e.g., FIG. 8B and/or FIG. 8C), as compared to the 2A process as provided for example in FIG. 8 (in particular, e.g., FIG. 8A)). In some embodiments, high CD28 expression is indicative of a younger, more persistent TIL phenotype. In an embodiment, expression of one or more regulatory markers is measured.

In an embodiment, no selection of the first population of TILs, second population of TILs, third population of TILs, or harvested TIL population based on CD8 and/or CD28 expression is performed during any of the steps for the method for expanding tumor infiltrating lymphocytes (TILs) described herein.

In some embodiments, the percentage of central memory cells is higher on TILs produced according the current invention process, as compared to other processes (e.g., the Gen 3 process as provided for example in FIG. 8 (in particular, e.g., FIG. 8B and/or FIG. 8C), as compared to the 2A process as provided for example in FIG. 8 (in particular, e.g., FIG. 8A)). In some embodiments the memory marker for central memory cells is selected from the group consisting of CCR7 and CD62L.

In some embodiments, the CD4+ and/or CD8+ TIL Memory subsets can be divided into different memory subsets. In some embodiments, the CD4+ and/or CD8+ TILs comprise the naïve (CD45RA+CD62L+) TILS. In some embodiments, the CD4+ and/or CD8+ TILs comprise the central memory (CM; CD45RA-CD62L+) TILs. In some embodiments, the CD4+ and/or CD8+ TILs comprise the effector memory (EM; CD45RA−CD62L−) TILs. In some embodiments, the CD4+ and/or CD8+ TILs comprise the, RA+ effector memory/effector (TEMRA/TEFF; CD45RA+CD62L+) TILs.

In some embodiments, the TILs express one more markers selected from the group consisting of granzyme B, perforin, and granulysin. In some embodiments, the TILs express granzyme B. In some embodiments, the TILs express perforin. In some embodiments, the TILs express granulysin.

In an embodiment, restimulated TILs can also be evaluated for cytokine release, using cytokine release assays. In some embodiments, TILs can be evaluated for interferon-γ (IFN-γ) secretion. In some embodiments, the IFN-γ secretion is measured by an ELISA assay. In some embodiments, the IFN-γ secretion is measured by an ELISA assay after the rapid second expansion step, after Step D as provided in for example, FIG. 8 (in particular, e.g., FIG. 8B and/or FIG. 8C). In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D in the Gen 3 process as provided in FIG. 8 (in particular, e.g., FIG. 8B and/or FIG. 8C) TILs as compared to for example Step D in the 2A process as provided in FIG. 8 (in particular, e.g., FIG. 8A) is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TILs ex vivo. In some embodiments, IFN-γ is measured in TILs ex vivo, including TILs produced by the methods of the present invention, including, for example FIG. 8B methods.

Figure 14:
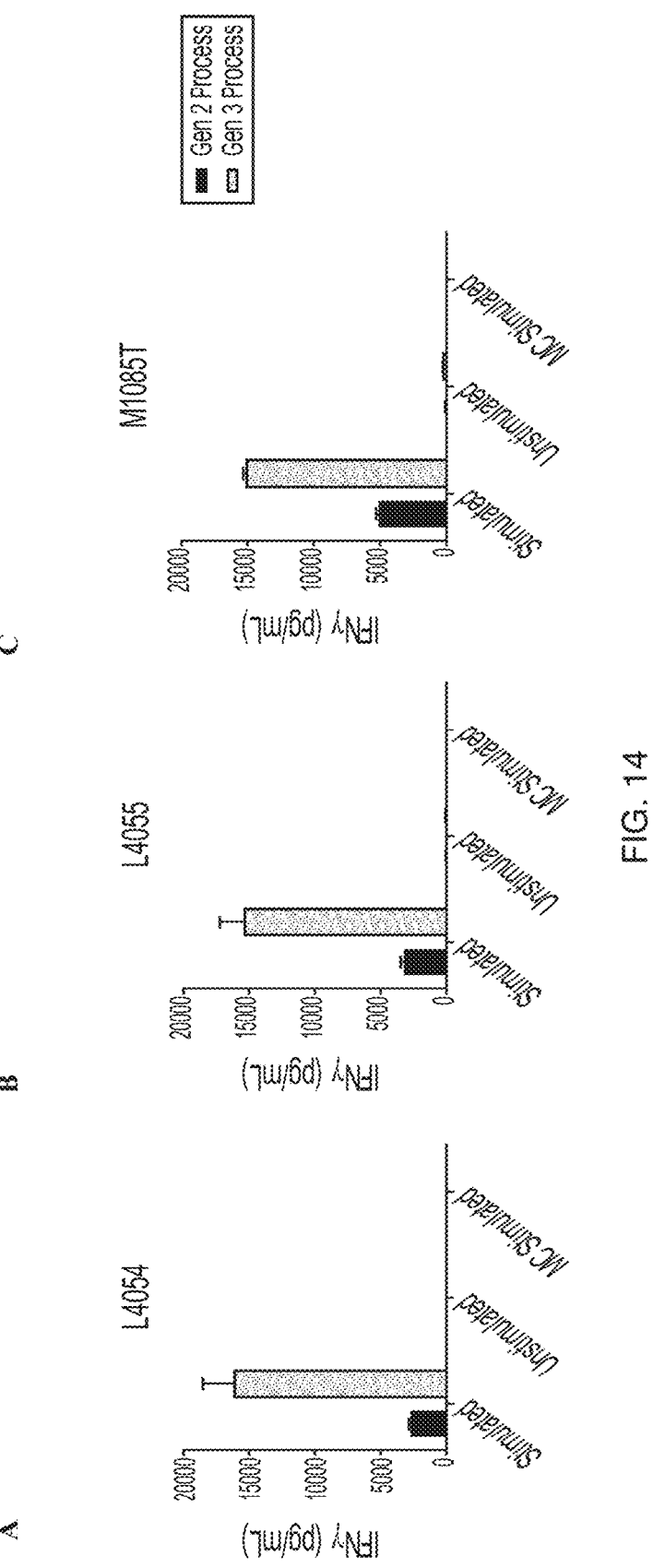
FIG. 14: IFNγ production (pg/mL): (A) L4054, (B) L4055, and (C) M1085T for the Gen 2 and Gen 3 processes: Each bar represented here is mean+SEM for IFNγ levels of stimulated, unstimulated, and media control. Optical density measured at 450 nm.
Figure 15:
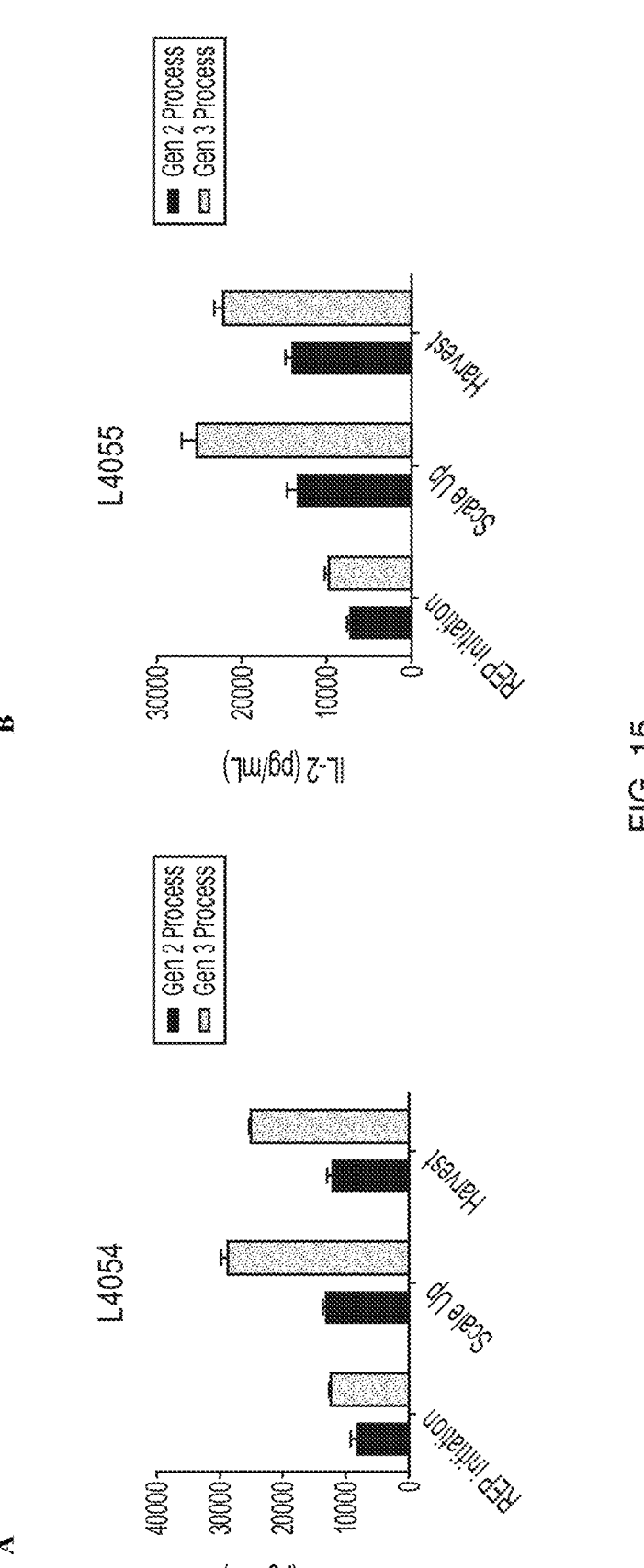
FIG. 15: ELISA analysis of IL-2 concentration in cell culture supernatant: (A) L4054 and (B) L4055. Each bar represented here is mean+SEM for IL-2 levels on spent media. Optical density measured at 450 nm.
Figure 16:
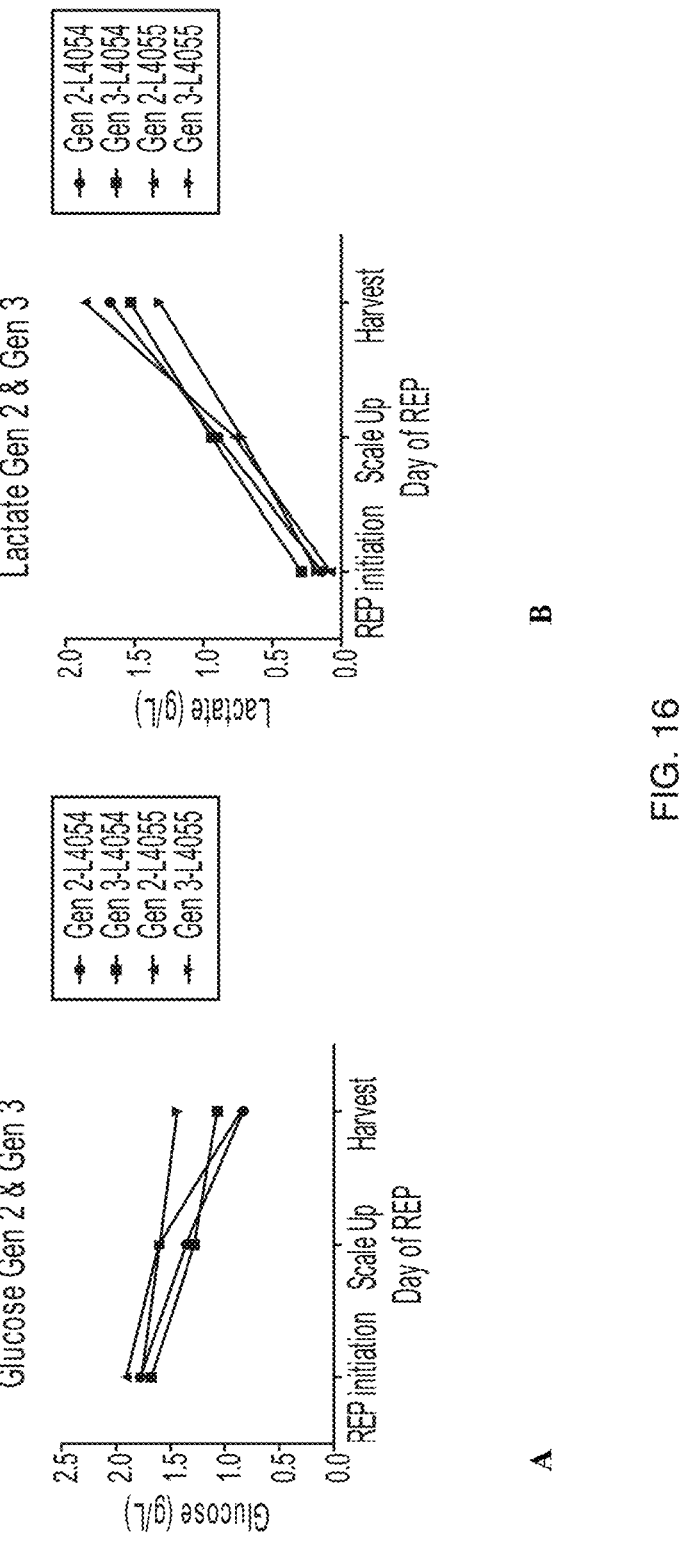
FIG. 16: Quantification of glucose and lactate (g/L) in spent media: (A) Glucose and (B) Lactate: In the two tumor lines, and in both processes, a decrease in glucose was observed throughout the REP expansion. Conversely, as expected, an increase in lactate was observed. Both the decrease in glucose and the increase in lactate were comparable between the Gen 2 and Gen 3 processes.
Figure 17A:
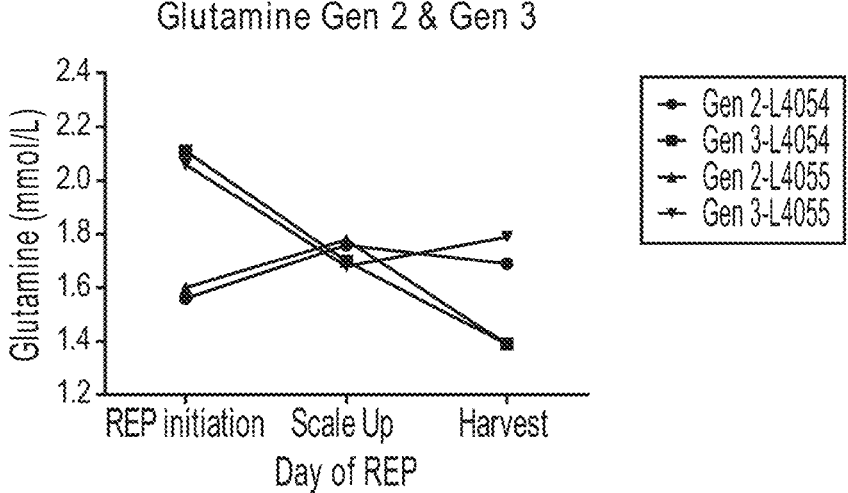
FIG. 17: A) Quantification of L-glutamine in spent media for L4054 and L4055. B) Quantification of Glutamax in spent media for L4054 and L4055. C) Quantification of ammonia in spent media for L4054 and L4055.
Figure 17B:
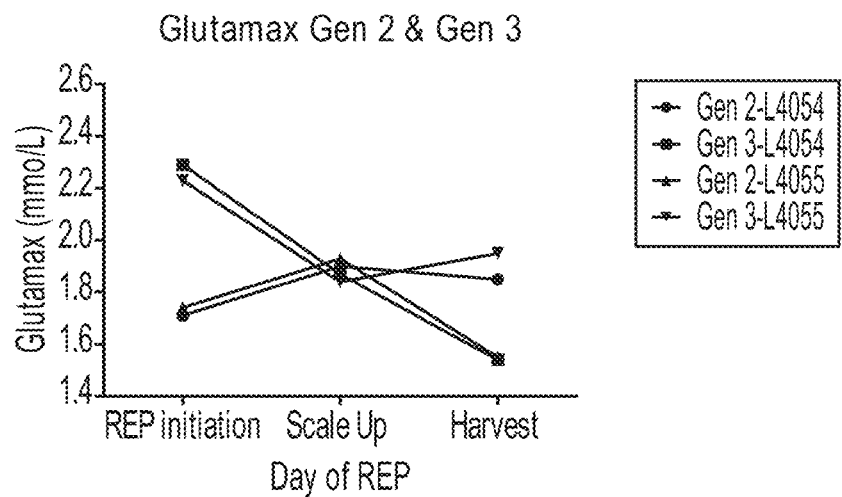
Figure 17C:
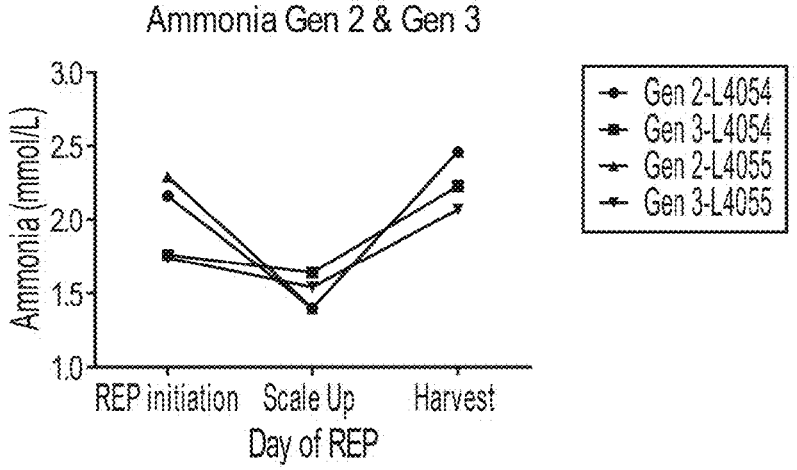
Figure 18:
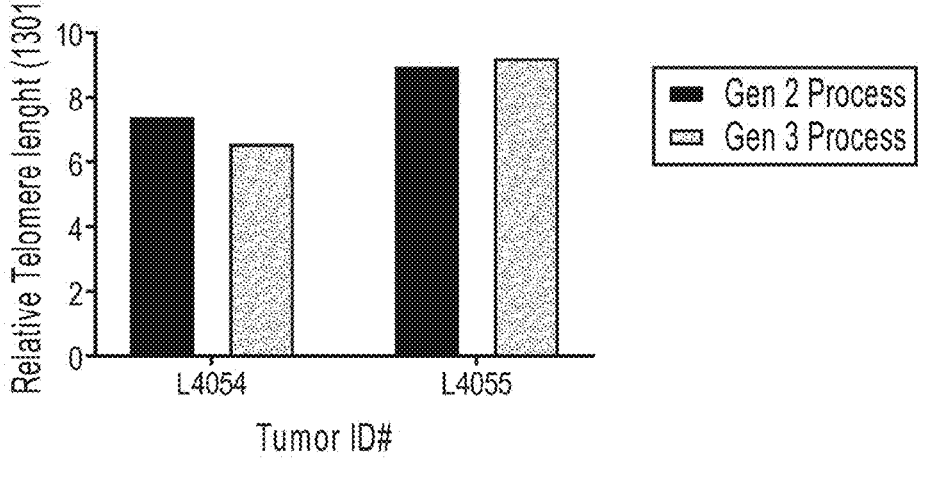
FIG. 18: Telomere length analysis. The relative telomere length (RTL) value indicates that the average telomere fluorescence per chromosome/genome in Gen 2 and Gen 3 process of the telomere fluorescence per chromosome/genome in the control cells line (1301 Leukemia cell line) using DAKO kit.
Figure 19:
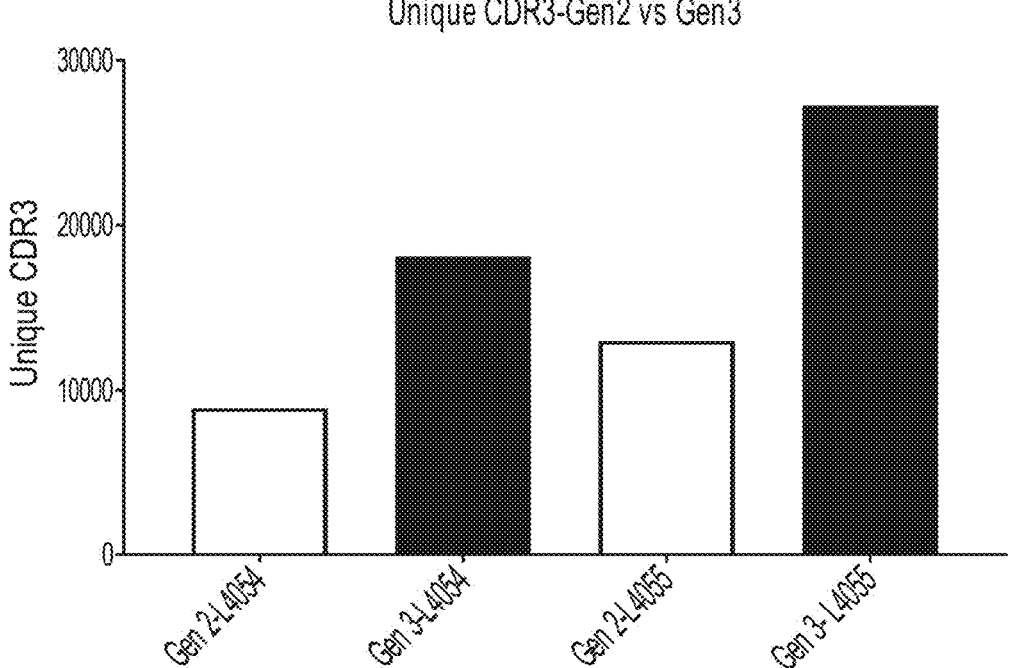
FIG. 19: Unique CDR3 sequence analysis for TIL final product on L4054 and L4055 under Gen 2 and Gen 3 process. Columns show the number of unique TCR B clonotypes identified from 1×10⁶ cells collected on Harvest Day Gen 2 (e.g., day 22) and Gen 3 process (e.g., day 14-16). Gen 3 shows higher clonal diversity compared to Gen 2 based on the number of unique peptide CDRs within the sample.
Figure 21:
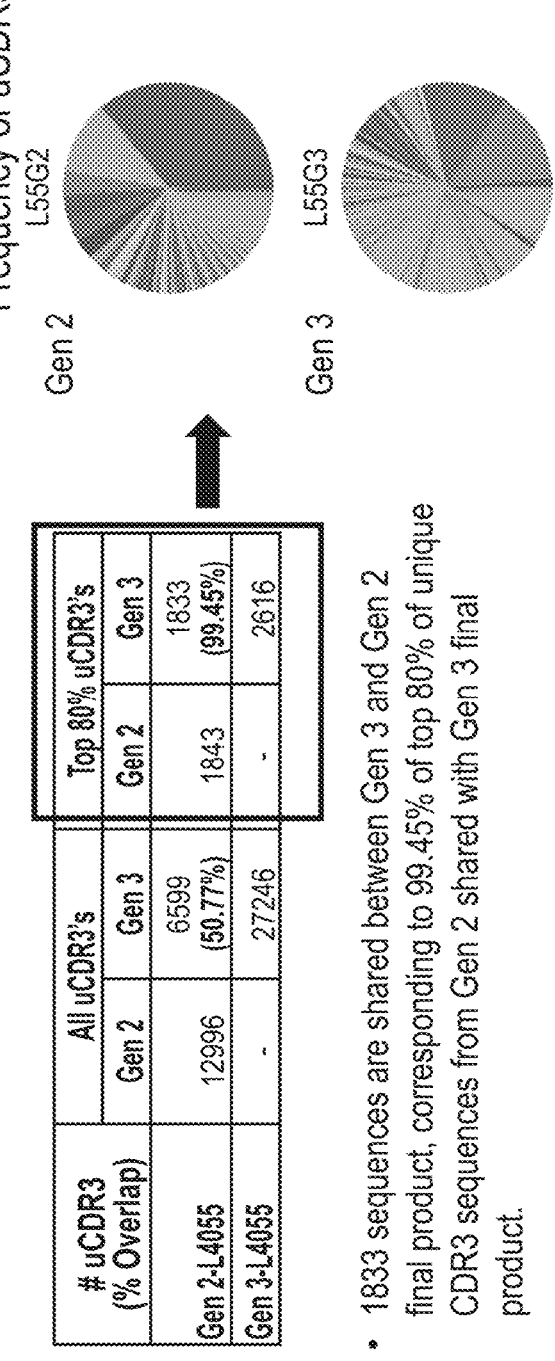
FIG. 21: Frequency of unique CDR3 sequences on L4055 TIL harvested final cell product (Gen 2 (e.g., day 22) and Gen 3 process (e.g., day 14-16)).
Figure 22:
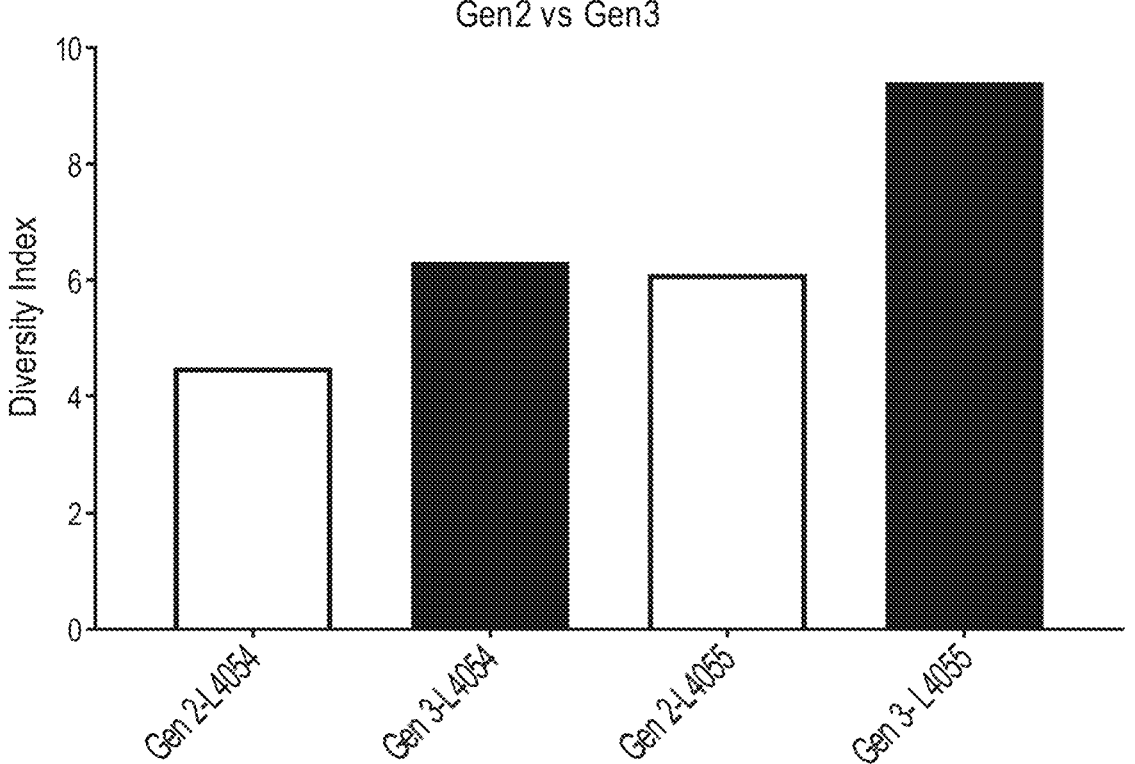
FIG. 22: Diversity Index for TIL final product on L4054 and L4055 under Gen 2 and Gen 3 process. Shanon entropy diversity index is a more reliable and common metric for comparison. Gen 3 L4054 and L4055 showed a slightly higher diversity than Gen 2.

In some embodiments, TILs capable of at least one-fold, two-fold, three-fold, four-fold, or five-fold or more IFN-γ secretion are TILs produced by the expansion methods of the present invention, including, for example FIG. 8B and/or FIG. 8C methods. In some embodiments, TILs capable of at least one-fold more IFN-γ secretion are TILs produced by the expansion methods of the present invention, including, for example FIG. 8B and/or FIG. 8C methods. In some embodiments, TILs capable of at least two-fold more IFN-γ secretion are TILs produced by the expansion methods of the present invention, including, for example FIG. 8B and/or FIG. 8C methods. In some embodiments, TILs capable of at least three-fold more IFN-γ secretion are TILs produced by the expansion methods of the present invention, including, for example FIG. 8B and/or FIG. 8C methods. In some embodiments, TILs capable of at least four-fold more IFN-γ secretion are TILs produced by the expansion methods of the present invention, including, for example FIG. 8B and/or FIG. 8C methods. In some embodiments, TILs capable of at least five-fold more IFN-γ secretion are TILs produced by the expansion methods of the present invention, including, for example FIG. 8B and/or FIG. 8C methods The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including, for example, methods other than those embodied in FIG. 8 (in particular, e.g., FIG. 8B and/or FIG. 8C). In some embodiments, the TILs obtained by the present method exhibit an increase in the T-cell repertoire diversity as compared to freshly harvested TILs and/or TILs prepared using methods referred to as process 2A, as exemplified in FIG. 8 (in particular, e.g., FIG. 8A). In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β). In some embodiments, the process as described herein (e.g., the Gen 3 process) shows higher clonal diversity as compared to other processes, for example the process referred to as the Gen 2 based on the number of unique peptide CDRs within the sample (see, for example FIGS. 12-14).

In some embodiments, the activation and exhaustion of TILs can be determined by examining one or more markers. In some embodiments, the activation and exhaustion can be determined using multicolor flow cytometry. In some embodiments, the activation and exhaustion of markers include but not limited to one or more markers selected from the group consisting of CD3, PD-1, 2B4/CD244, CD8, CD25, BTLA, KLRG, TIM-3, CD194/CCR4, CD4, TIGIT, CD183, CD69, CD95, CD127, CD103, and/or LAG-3). In some embodiments, the activation and exhaustion of markers include but not limited to one or more markers selected from the group consisting of BTLA, CTLA-4, ICOS, Ki67, LAG-3, PD-1, TIGIT, and/or TIM-3. In some embodiments, the activation and exhaustion of markers include but not limited to one or more markers selected from the group consisting of BTLA, CTLA-4, ICOS, Ki67, LAG-3, CD103+/CD69+, CD103+/CD69−, PD-1, TIGIT, and/or TIM-3. In some embodiments, the T-cell markers (including activation and exhaustion markers) can be determined and/or analyzed to examine T-cell activation, inhibition, or function. In some embodiments, the T-cell markers can include but are not limited to one or more markers selected from the group consisting of TIGIT, CD3, FoxP3, Tim-3, PD-1, CD103, CTLA-4, LAG-3, BTLA-4, ICOS, Ki67, CD8, CD25, CD45, CD4, and/or CD59.

In some embodiments, the phenotypic characterization is examined after cryopreservation.

M. Additional Process Embodiments

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days or about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days or about 1 to 10 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 3 to 4 days, or about 2 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 7 days, or about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days, or about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, or about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 7 days, or about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 5 to 7 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 8 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 2 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 4 to 5 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 3 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 7 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 5 days.

In another embodiment, the invention provides the method described in any of the preceding paragraphs as applicable above modified such that in step (b) the primary first expansion is performed by contacting the first population of TILs with a culture medium which further comprises exogenous antigen-presenting cells (APCs), wherein the number of APCs in the culture medium in step (c) is greater than the number of APCs in the culture medium in step (b).

In another embodiment, the invention provides the method described in any of the preceding paragraphs as applicable above modified such that in step (c) the culture medium is supplemented with additional exogenous APCs.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 20:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 7:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 6:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 3:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.6:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.3:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.1:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 5:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 3:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.6:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.4:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.3:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.1:1.

In another embodiment, the invention provides the method described in any of the preceding paragraphs as applicable above modified such that the ratio of number of APCs added in the rapid second expansion to the number of APCs added in step (b) is at or about 2:1.

In another embodiment, the invention provides the method described in any of the preceding paragraphs as applicable above modified such that the ratio of number of APCs added in the rapid second expansion to the number of APCs added in step (b) is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the invention provides the method described in any of the preceding paragraphs as applicable above modified such that the number of APCs added in the primary first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and such that the number of APCs added in the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the invention provides the method described in any of the preceding paragraphs as applicable above modified such that the number of APCs added in the primary first expansion is selected from the range of at or about $1\times10^8$ APCs to at or about $3.5\times10^8$ APCs, and wherein the number of APCs added in the rapid second expansion is selected from the range of at or about $3.5\times10^8$ APCs to at or about $1\times10^9$ APCs.

In another embodiment, the invention provides the method described in any of the preceding paragraphs as applicable above modified such that the number of APCs added in the primary first expansion is selected from the range of at or about $1.5\times10^8$ APCs to at or about $3\times10^8$ APCs, and wherein the number of APCs added in the rapid second expansion is selected from the range of at or about $4\times10^8$ APCs to at or about $7.5\times10^8$ APCs.

In another embodiment, the invention provides the method described in any of the preceding paragraphs as applicable above modified such that the number of APCs added in the primary first expansion is selected from the range of at or about $2\times10^8$ APCs to at or about $2.5\times10^8$ APCs, and wherein the number of APCs added in the rapid second expansion is selected from the range of at or about $4.5\times10^8$ APCs to at or about $5.5\times10^8$ APCs.

In another embodiment, the invention provides the method described in any of the preceding paragraphs as applicable above modified such that at or about $2.5\times10^8$ APCs are added to the primary first expansion and at or about $5\times10^8$ APCs are added to the rapid second expansion.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the multiple tumor fragments are distributed into a plurality of separate containers, in each of which separate containers the first population of TILs is obtained in step (a), the second population of TILs is obtained in step (b), and the third population of TILs is obtained in step (c), and the therapeutic populations of TILs from the plurality of containers in step (c) are combined to yield the harvested TIL population from step (d).

In another embodiment, the invention provides the method described in any of the preceding paragraphs as applicable above modified such that the multiple tumors are evenly distributed into the plurality of separate containers.

In another embodiment, the invention provides the method described in any of the preceding paragraphs as applicable above modified such that the plurality of separate containers comprises at least two separate containers.

In another embodiment, the invention provides the method described in any of the preceding paragraphs as applicable above modified such that the plurality of separate containers comprises from two to twenty separate containers.

In another embodiment, the invention provides the method described in any of the preceding paragraphs as applicable above modified such that the plurality of separate containers comprises from two to fifteen separate containers.

In another embodiment, the invention provides the method described in any of the preceding paragraphs as applicable above modified such that the plurality of separate containers comprises from two to ten separate containers.

In another embodiment, the invention provides the method described in any of the preceding paragraphs as applicable above modified such that the plurality of separate containers comprises from two to five separate containers.

In another embodiment, the invention provides the method described in any of the preceding paragraphs as applicable above modified such that the plurality of separate containers comprises 2, 3, 4, 5, 6, 7, 8, 9, 10, 11, 12, 13, 14, 15, 16, 17, 18, 19, or 20 separate containers.

In another embodiment, the invention provides the method described in any of the preceding paragraphs as applicable above modified such that for each container in which the priming first expansion is performed on a first population of TILs in step (b) the rapid second expansion in step (c) is performed in the same container on the second population of TILs produced from such first population of TILs.

In another embodiment, the invention provides the method described in any of the preceding paragraphs as applicable above modified such that each of the separate containers comprises a first gas-permeable surface area.

In another embodiment, the invention provides the method described in any of the preceding paragraphs as applicable above modified such that the multiple tumor fragments are distributed in a single container.

In another embodiment, the invention provides the method described in any of the preceding paragraphs as applicable above modified such that the single container comprises a first gas-permeable surface area.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in a second container comprising a second gas-permeable surface area.

In another embodiment, the invention provides the method described in any of the preceding paragraphs as applicable above modified such that the second container is larger than the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the second gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the second gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the second gas-permeable surface area at an average thickness of at or about 3, 4, 5, 6, 7, 8, 9 or 10 cell layers.

In another embodiment, the invention provides the method described in any of the preceding paragraphs as applicable modified such that in step (c) the APCs are layered onto the second gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:10.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:9.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.2 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.3 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.4 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.5 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.6 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.7 to at or about 1:3.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.8 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.9 to at or about 1:2.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In another embodiment, the invention provides the method described in any of the preceding paragraphs as applicable above modified such that the ratio of the number of TILs in the second population of TILs to the number of TILs in the first population of TILs is at or about 1.5:1 to at or about 100:1.

In another embodiment, the invention provides the method described in any of the preceding paragraphs as applicable above modified such that the ratio of the number of TILs in the second population of TILs to the number of TILs in the first population of TILs is at or about 50:1.

In another embodiment, the invention provides the method described in any of the preceding paragraphs as applicable above modified such that the ratio of the number of TILs in the second population of TILs to the number of TILs in the first population of TILs is at or about 25:1.

In another embodiment, the invention provides the method described in any of the preceding paragraphs as applicable above modified such that the ratio of the number of TILs in the second population of TILs to the number of TILs in the first population of TILs is at or about 20:1.

In another embodiment, the invention provides the method described in any of the preceding paragraphs as applicable above modified such that the ratio of the number of TILs in the second population of TILs to the number of TILs in the first population of TILs is at or about 10:1.

In another embodiment, the invention provides the method described in any of the preceding paragraphs as applicable above modified such that the second population of TILs is at least at or about 50-fold greater in number than the first population of TILs.

In another embodiment, the invention provides the method described in any of the preceding paragraphs as applicable above modified such that the second population of TILs is at least at or about 1-, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49- or 50-fold greater in number than the first population of TILs.

In another embodiment, the invention provides the method described in any of the preceding paragraphs as applicable above modified such that at or about 2 days or at or about 3 days after the commencement of the second period in step (c), the cell culture medium is supplemented with additional IL-2.

In another embodiment, the invention provides the method described in any of the preceding paragraphs as applicable above modified to further comprise the step of cryopreserving the harvested TIL population in step (d) using a cryopreservation process.

In another embodiment, the invention provides the method described in any of the preceding paragraphs as applicable above modified to comprise performing after step (d) the additional step of (e) transferring the harvested TIL population from step (d) to an infusion bag that optionally contains HypoThermosol.

In another embodiment, the invention provides the method described in any of the preceding paragraphs as applicable above modified to comprise the step of cryopreserving the infusion bag comprising the harvested TIL population in step (e) using a cryopreservation process.

In another embodiment, the invention provides the method described in any of the preceding paragraphs as applicable above modified such that the cryopreservation process is performed using a 1:1 ratio of harvested TIL population to cryopreservation media.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the total number of APCs added to the cell culture in step (b) is $2.5 \times 10^8$.

In another embodiment, the invention provides the method described in any of the preceding paragraphs as applicable above modified such that the total number of APCs added to the cell culture in step (c) is $5 \times 10^8$.

In another embodiment, the invention provides the method described in any of the preceding paragraphs as applicable above modified such that the APCs are PBMCs.

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the antigen-presenting cells are artificial antigen-presenting cells.

In another embodiment, the invention provides the method described in any of the preceding paragraphs as applicable above modified such that the harvesting in step (d) is performed using a membrane-based cell processing system.

In another embodiment, the invention provides the method described in any of the preceding paragraphs as applicable above modified such that the harvesting in step (d) is performed using a LOVO cell processing system.

In another embodiment, the invention provides the method described in any of the preceding paragraphs as applicable above modified such that the multiple fragments comprise at or about 5 to at or about 60 fragments per container in step (b).

In another embodiment, the invention provides the method described in any of the preceding paragraphs as applicable above modified such that the multiple fragments comprise at or about 10 to at or about 60 fragments per container in step (b).

In another embodiment, the invention provides the method described in any of the preceding paragraphs as applicable above modified such that the multiple fragments comprise at or about 15 to at or about 60 fragments per container in step (b).

In another embodiment, the invention provides the method described in any of the preceding paragraphs as applicable above modified such that the multiple fragments comprise at or about 20 to at or about 60 fragments per container in step (b).

In another embodiment, the invention provides the method described in any of the preceding paragraphs as applicable above modified such that the multiple fragments comprise at or about 25 to at or about 60 fragments per container in step (b).

In another embodiment, the invention provides the method described in any of the preceding paragraphs as applicable above modified such that the multiple fragments comprise at or about 30 to at or about 60 fragments per container in step (b).

In another embodiment, the invention provides the method described in any of the preceding paragraphs as applicable above modified such that the multiple fragments comprise at or about 35 to at or about 60 fragments per container in step (b).

In another embodiment, the invention provides the method described in any of the preceding paragraphs as applicable above modified such that the multiple fragments comprise at or about 40 to at or about 60 fragments per container in step (b).

In another embodiment, the invention provides the method described in any of the preceding paragraphs as applicable above modified such that the multiple fragments comprise at or about 45 to at or about 60 fragments per container in step (b).

In another embodiment, the invention provides the method described in any of the preceding paragraphs as applicable above modified such that the multiple fragments comprise at or about 50 to at or about 60 fragments per container in step (b).

In another embodiment, the invention provides the method described in any of the preceding paragraphs as applicable above modified such that the multiple fragments comprise at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 fragment(s) per container in step (b).

In another embodiment, the invention provides the method described in any of the preceding paragraphs as applicable above modified such that each fragment has a volume of at or about 27 mm$^3$.

In another embodiment, the invention provides the method described in any of the preceding paragraphs as applicable above modified such that each fragment has a volume of at or about 20 mm$^3$ to at or about 50 mm$^3$.

In another embodiment, the invention provides the method described in any of the preceding paragraphs as applicable above modified such that each fragment has a volume of at or about 21 mm$^3$ to at or about 30 mm$^3$.

In another embodiment, the invention provides the method described in any of the preceding paragraphs as applicable above modified such that each fragment has a volume of at or about 22 mm$^3$ to at or about 29.5 mm$^3$.

In another embodiment, the invention provides the method described in any of the preceding paragraphs as applicable above modified such that each fragment has a volume of at or about 23 mm$^3$ to at or about 29 mm$^3$.

In another embodiment, the invention provides the method described in any of the preceding paragraphs as applicable above modified such that each fragment has a volume of at or about 24 mm$^3$ to at or about 28.5 mm$^3$.

In another embodiment, the invention provides the method described in any of the preceding paragraphs as applicable above modified such that each fragment has a volume of at or about 25 mm$^3$ to at or about 28 mm$^3$.

In another embodiment, the invention provides the method described in any of the preceding paragraphs as applicable above modified such that each fragment has a volume of at or about 26.5 mm$^3$ to at or about 27.5 mm$^3$.

In another embodiment, the invention provides the method described in any of the preceding paragraphs as applicable above modified such that each fragment has a volume of at or about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mm$^3$.

In another embodiment, the invention provides the method described in any of the preceding paragraphs as applicable above modified such that the multiple fragments comprise at or about 30 to at or about 60 fragments with a total volume of at or about 1300 mm$^3$ to at or about 1500 mm$^3$.

In another embodiment, the invention provides the method described in any of the preceding paragraphs as applicable above modified such that the multiple fragments comprise at or about 50 fragments with a total volume of at or about 1350 mm$^3$.

In another embodiment, the invention provides the method described in any of the preceding paragraphs as applicable above modified such that the multiple fragments comprise at or about 50 fragments with a total mass of at or about 1 gram to at or about 1.5 grams.

In another embodiment, the invention provides the method described in any of the preceding paragraphs as applicable above modified such that the cell culture medium is provided in a container that is a G-container or a Xuri cellbag.

In another embodiment, the invention provides the method described in any of the preceding paragraphs as applicable above modified such that the IL-2 concentration in the cell culture medium is about 10,000 IU/mL to about 5,000 IU/mL.

In another embodiment, the invention provides the method described in any of the preceding paragraphs as applicable above modified such that the IL-2 concentration in the cell culture medium is about 6,000 IU/mL.

In another embodiment, the invention provides the method described in any of the preceding paragraphs as applicable above modified such that the cryopreservation media comprises dimethylsulfoxide (DMSO).

In another embodiment, the invention provides the method described in any of the preceding paragraphs as applicable above modified such that the cryopreservation media comprises 7% to 10% DMSO.

In another embodiment, the invention provides the method described in any of the preceding paragraphs as applicable above modified such that the first period in step (b) is performed within a period of at or about 1 day, 2 days, 3 days, 4 days, 5 days, 6 days, or 7 days.

In another embodiment, the invention provides the method described in any of the preceding paragraphs as applicable above modified such that the second period in step (c) is performed within a period of at or about 1 day, 2 days, 3 days, 4 days, 5 days, 6 days, 7 days, 8 days, 9 days, 10 days or 11 days.

In another embodiment, the invention provides the method described in any of the preceding paragraphs as applicable above modified such that the first period in step (b) and the second period in step (c) are each individually performed within a period of at or about 1 day, 2 days, 3 days, 4 days, 5 days, 6 days, or 7 days.

In another embodiment, the invention provides the method described in any of the preceding paragraphs as applicable above modified such that the first period in step (b) and the second period in step (c) are each individually performed within a period of at or about 5 days, 6 days, or 7 days.

In another embodiment, the invention provides the method described in any of the preceding paragraphs as applicable above modified such that the first period in step (b) and the second period in step (c) are each individually performed within a period of at or about 7 days.

In another embodiment, the invention provides the method described in any of the preceding paragraphs as applicable above modified such that steps (a) through (d) are performed in a total of at or about 14 days to at or about 18 days.

In another embodiment, the invention provides the method described in any of the preceding paragraphs as applicable above modified such that steps (a) through (d) are performed in a total of at or about 15 days to at or about 18 days.

In another embodiment, the invention provides the method described in any of the preceding paragraphs as applicable above modified such that steps (a) through (d) are performed in a total of at or about 16 days to at or about 18 days.

In another embodiment, the invention provides the method described in any of the preceding paragraphs as applicable above modified such that steps (a) through (d) are performed in a total of at or about 17 days to at or about 18 days.

In another embodiment, the invention provides the method described in any of the preceding paragraphs as applicable above modified such that steps (a) through (d) are performed in a total of at or about 14 days to at or about 17 days.

In another embodiment, the invention provides the method described in any of the preceding paragraphs as applicable above modified such that steps (a) through (d) are performed in a total of at or about 15 days to at or about 17 days.

In another embodiment, the invention provides the method described in any of the preceding paragraphs as applicable above modified such that steps (a) through (d) are performed in a total of at or about 16 days to at or about 17 days.

In another embodiment, the invention provides the method described in any of the preceding paragraphs as applicable above modified such that steps (a) through (d) are performed in a total of at or about 14 days to at or about 16 days.

In another embodiment, the invention provides the method described in any of the preceding paragraphs as applicable above modified such that steps (a) through (d) are performed in a total of at or about 15 days to at or about 16 days.

In another embodiment, the invention provides the method described in any of the preceding paragraphs as applicable above modified such that steps (a) through (d) are performed in a total of at or about 14 days.

In another embodiment, the invention provides the method described in any of the preceding paragraphs as applicable above modified such that steps (a) through (d) are performed in a total of at or about 15 days.

In another embodiment, the invention provides the method described in any of the preceding paragraphs as applicable above modified such that steps (a) through (d) are performed in a total of at or about 16 days.

In another embodiment, the invention provides the method described in any of the preceding paragraphs as applicable above modified such that steps (a) through (d) are performed in a total of at or about 17 days.

In another embodiment, the invention provides the method described in any of the preceding paragraphs as applicable above modified such that steps (a) through (d) are performed in a total of at or about 18 days.

In another embodiment, the invention provides the method described in any of the preceding paragraphs as applicable above modified such that steps (a) through (d) are performed in a total of at or about 14 days or less.

In another embodiment, the invention provides the method described in any of the preceding paragraphs as applicable above modified such that steps (a) through (d) are performed in a total of at or about 15 days or less.

In another embodiment, the invention provides the method described in any of the preceding paragraphs as applicable above modified such that steps (a) through (d) are performed in a total of at or about 16 days or less.

In another embodiment, the invention provides the method described in any of the preceding paragraphs as applicable above modified such that steps (a) through (d) are performed in a total of at or about 18 days or less.

In another embodiment, the invention provides the method described in any of the preceding paragraphs as applicable above modified such that the therapeutic population of TILs harvested in step (d) comprises sufficient TILs for a therapeutically effective dosage of the TILs.

In another embodiment, the invention provides the method described in any of the preceding paragraphs as applicable above modified such that the number of TILs sufficient for a therapeutically effective dosage is from at or about $2.3 \times 10^{10}$ to at or about $13.7 \times 10^{10}$.

In another embodiment, the invention provides the method described in any of the preceding paragraphs as applicable above modified such that the third population of TILs in step (c) provides for increased efficacy, increased interferon-gamma production, and/or increased polyclonality.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 16 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 17 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 18 days.

In another embodiment, the invention provides the method described in any of the preceding paragraphs as applicable above modified such that the effector T cells and/or central memory T cells obtained from the third population of TILs step (c) exhibit increased CD8 and CD28 expression relative to effector T cells and/or central memory T cells obtained from the second population of cells step (b).

In another embodiment, the invention provides the method described in any of the preceding paragraphs as applicable above modified such that each container recited in the method is a closed container.

In another embodiment, the invention provides the method described in any of the preceding paragraphs as applicable above modified such that each container recited in the method is a G-container.

In another embodiment, the invention provides the method described in any of the preceding paragraphs as applicable above modified such that each container recited in the method is a GREX-10.

In another embodiment, the invention provides the method described in any of the preceding paragraphs as applicable above modified such that each container recited in the method is a GREX-100.

In another embodiment, the invention provides the method described in any of the preceding paragraphs as applicable above modified such that each container recited in the method is a GREX-500.

In another embodiment, the invention provides the therapeutic population of tumor infiltrating lymphocytes (TILs) made by the method described in any of the preceding paragraphs as applicable above.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs) or OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs).

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed with no added antigen-presenting cells (APCs) and no added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 16 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 17 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 18 days.

In another embodiment, the invention provides for the therapeutic population of TILs described in any of the preceding paragraphs as applicable above that provides for increased interferon-gamma production.

In another embodiment, the invention provides for the therapeutic population of TILs described in any of the preceding paragraphs as applicable above that provides for increased polyclonality.

In another embodiment, the invention provides for the therapeutic population of TILs described in any of the preceding paragraphs as applicable above that provides for increased efficacy.

In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 18 days. In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 18 days. In some embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 18 days. In some embodiments, the TILs are rendered capable of the at least three-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added antigen-presenting cells (APCs). In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added OKT3. In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least two-fold more interferon-gamma production as compared to TILs prepared by a process in which the first expansion of TILs is performed without any added APCs. In some embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least two-fold more interferon-gamma production as compared to TILs prepared by a process in which the first expansion of TILs is performed without any added OKT3. In some embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least three-fold more interferon-gamma production as compared to TILs prepared by a process in which the first expansion of TILs is performed without any added APCs. In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least three-fold more interferon-gamma production as compared to TILs prepared by a process in which the first expansion of TILs is performed without any added OKT3. In some embodiments, the TILs are rendered capable of the at least three-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides a method of expanding T cells comprising: (a) performing a priming first expansion of a first population of T cells obtained from a donor by culturing the first population of T cells to effect growth and to prime an activation of the first population of T cells; (b) after the activation of the first population of T cells primed in step (a) begins to decay, performing a rapid second expansion of the first population of T cells by culturing the first population of T cells to effect growth and to boost the activation of the first population of T cells to obtain a second population of T cells; and (c) harvesting the second population of T cells. In another embodiment, the step of rapid second expansion is split into a plurality of steps to achieve a scaling up of the culture by: (a) performing the rapid second expansion by culturing the first population of T cells in a small scale culture in a first container, e.g., a G-REX 100MCS container, for a period of about 3 to 4 days, and then (b) effecting the transfer of the first population of T cells from the small scale culture to a second container larger than the first container, e.g., a G-REX 500MCS container, and culturing the first population of T cells from the small scale culture in a larger scale culture in the second container for a period of about 4 to 7 days. In another embodiment, the step of rapid expansion is split into a plurality of steps to achieve a scaling out of the culture by: (a) performing the rapid second expansion by culturing the first population of T cells in a first small scale culture in a first container, e.g., a G-REX 100MCS container, for a period of about 3 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the first population of T cells from the small scale culture transferred to such second container is cultured in a larger scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid second expansion is split into a plurality of steps to achieve a scaling up of the culture by: (a) performing the rapid second expansion by culturing the first population of T cells in a small scale culture in a first container, e.g., a G-REX 100MCS container, for a period of about 2 to 4 days, and then (b) effecting the transfer of the first population of T cells from the small scale culture to a second container larger than the first container, e.g., a G-REX 500MCS container, and culturing the first population of T cells from the small scale culture in a larger scale culture in the second container for a period of about 5 to 7 days.

In another embodiment, the invention provides the method described in any of the preceding paragraphs as applicable above modified such that the step of rapid expansion is split into a plurality of steps to achieve a scaling out of the culture by: (a) performing the rapid second expansion by culturing the first population of T cells in a first small scale culture in a first container, e.g., a G-REX 100MCS container, for a period of about 2 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 2 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the first population of T cells from the small scale culture transferred to such second container is cultured in a larger scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 to 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 7 days.

In another embodiment, the invention provides the method described in any of the preceding paragraphs as applicable above modified such that the priming first expansion of step (a) is performed during a period of up to 7 days.

In another embodiment, the invention provides the method described in any of the preceding paragraphs as applicable above modified such that the rapid second expansion of step (b) is performed during a period of up to 8 days.

In another embodiment, the invention provides the method described in any of the preceding paragraphs as applicable above modified such that the rapid second expansion of step (b) is performed during a period of up to 9 days.

In another embodiment, the invention provides the method described in any of the preceding paragraphs as applicable above modified such that the rapid second expansion of step (b) is performed during a period of up to 10 days.

In another embodiment, the invention provides the method described in any of the preceding paragraphs as applicable above modified such that the rapid second expansion of step (b) is performed during a period of up to 11 days.

In another embodiment, the invention provides the method described in any of the preceding paragraphs as applicable above modified such that the priming first expansion in step (a) is performed during a period of 7 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days and the rapid second expansion of step (b) is performed during a period of up to 10 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 10 days.

In another embodiment, the invention provides the method described in any of the preceding paragraphs as applicable above modified such that the priming first expansion in step (a) is performed during a period of 8 days and the rapid second expansion of step (b) is performed during a period of up to 9 days.

In another embodiment, the invention provides the method described in any of the preceding paragraphs as applicable above modified such that the priming first expansion in step (a) is performed during a period of 8 days and the rapid second expansion of step (b) is performed during a period of up to 8 days.

In another embodiment, the invention provides the method described in any of the preceding paragraphs as applicable above modified such that in step (a) the first population of T cells is cultured in a first culture medium comprising OKT-3 and IL-2.

In another embodiment, the invention provides the method described in any of the preceding paragraphs as applicable above modified such that the first culture medium comprises 4-1BB agonist, OKT-3 and IL-2.

In another embodiment, the invention provides the method described in any of the preceding paragraphs as applicable above modified such that the first culture medium comprises OKT-3, IL-2 and antigen-presenting cells (APCs).

In another embodiment, the invention provides the method described in any of the preceding paragraphs as applicable above modified such that the first culture medium comprises 4-1BB agonist, OKT-3, IL-2 and antigen-presenting cells (APCs).

In another embodiment, the invention provides the method described in any of the preceding paragraphs as applicable above modified such that in step (b) the first population of T cells is cultured in a second culture medium comprising OKT-3, IL-2 and antigen-presenting cells (APCs).

In another embodiment, the invention provides the method described in any of the preceding paragraphs as applicable above modified such that the second culture medium comprises 4-1BB agonist, OKT-3, IL-2 and antigen-presenting cells (APCs).

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that the ratio of the number of APCs in the second population of APCs to the number of APCs in the first population of APCs is about 2:1.

In another embodiment, the invention provides the method described in any of the preceding paragraphs as applicable above modified such that the number of APCs in the first population of APCs is about $2.5\times10^8$ and the number of APCs in the second population of APCs is about $5\times10^8$.

In another embodiment, the invention provides the method described in any of the preceding paragraphs as applicable above modified such that in step (a) the first population of APCs is layered onto the first gas-permeable surface at an average thickness of 2 layers of APCs.

In another embodiment, the invention provides the method described in any of the preceding paragraphs as applicable above modified such that in step (b) the second population of APCs is layered onto the first gas-permeable surface at an average thickness selected from the range of 4 to 8 layers of APCs.

In another embodiment, the invention provides the method described in any of the preceding paragraphs as applicable above modified such that the ratio of the average number of layers of APCs layered onto the first gas-permeable surface in step (b) to the average number of layers of APCs layered onto the first gas-permeable surface in step (a) is 2:1.

In another embodiment, the invention provides the method described in any of the preceding paragraphs as applicable above modified such that in step (a) the first population of APCs is seeded on the first gas permeable surface at a density selected from the range of at or about $1.0\times10^6$ APCs/cm$^2$ to at or about $4.5\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.5\times10^6$ APCs/cm$^2$ to at or about $3.5\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$.

In another embodiment, the invention provides the method described in any of the preceding paragraphs as applicable above modified such that in step (a) the first population of APCs is seeded on the first gas permeable surface at a density of at or about $2.0\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $2.5\times10^6$ APCs/cm$^2$ to at or about $7.5\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $3.5\times10^6$ APCs/cm$^2$ to at or about $6.0\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $4.0\times10^6$ APCs/cm$^2$ to at or about $5.5\times10^6$ APCs/cm$^2$.

In another embodiment, the invention provides the method described in any of the preceding paragraphs as applicable above modified such that in step (b) the second population of APCs is seeded on the first gas permeable surface at a density of at or about $4.0\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.0\times10^6$ APCs/cm$^2$ to at or about $4.5\times10^6$ APCs/cm$^2$ and in step (b) the second population of APCs is seeded on the first gas permeable surface at a density selected from the range of at or about $2.5\times10^6$ APCs/cm$^2$ to at or about $7.5\times10^6$ APCs/cm$^2$.

In another embodiment, the invention provides the method described in any of the preceding paragraphs as applicable modified such that in step (a) the first population of APCs is seeded on the first gas permeable surface at a density selected from the range of at or about $1.5\times10^6$ APCs/cm$^2$ to at or about $3.5\times10^6$ APCs/cm$^2$ and in step (b) the second population of APCs is seeded on the first gas permeable surface at a density selected from the range of at or about $3.5\times10^6$ APCs/cm$^2$ to at or about $6.0\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$ and in step (b) the second population of APCs is seeded on the first gas permeable surface at a density selected from the range of at or about $4.0\times10^6$ APCs/cm$^2$ to at or about $5.5\times10^6$ APCs/cm$^2$.

In another embodiment, the invention provides the method described in any of the preceding paragraphs as applicable above modified such that in step (a) the first population of APCs is seeded on the first gas permeable surface at a density of at or about $2.0\times10^6$ APCs/cm$^2$ and in step (b) the second population of APCs is seeded on the first gas permeable surface at a density of at or about $4.0\times10^6$ APCs/cm$^2$.

In another embodiment, the invention provides the method described in any of the preceding paragraphs as applicable above modified such that the APCs are peripheral blood mononuclear cells (PBMCs).

In another embodiment, the invention provides the method described in any of the preceding paragraphs as applicable above modified such that the PBMCs are irradiated and exogenous to the donor of the first population of T cells.

In another embodiment, the invention provides the method described in any of the preceding paragraphs as applicable above modified such that the T cells are tumor infiltrating lymphocytes (TILs).

In another embodiment, the invention provides the method described in any of the preceding paragraphs as applicable above modified such that the T cells are marrow infiltrating lymphocytes (MILs).

In another embodiment, the invention provides the method described in any of the preceding paragraphs as applicable above modified such that the T cells are peripheral blood lymphocytes (PBLs).

In another embodiment, the invention provides the method described in any of the preceding paragraphs as applicable above modified such that the first population of T cells is obtained by separation from the whole blood of the donor.

In another embodiment, the invention provides the method described in any of the preceding paragraphs as applicable above modified such that the first population of T cells is obtained by separation from the apheresis product of the donor.

In another embodiment, the invention provides the method described in any of the preceding paragraphs as applicable above modified such that the first population of T cells is separated from the whole blood or apheresis product of the donor by positive or negative selection of a T cell phenotype.

In another embodiment, the invention provides the method described in any of the preceding paragraphs as applicable above modified such that the T cell phenotype is CD3+ and CD45+.

In another embodiment, the invention provides the method described in any of the preceding paragraphs as applicable above modified such that before performing the priming first expansion of the first population of T cells the T cells are separated from NK cells. In another embodiment, the T cells are separated from NK cells in the first population of T cells by removal of CD3−CD56+ cells from the first population of T cells. In another embodiment, the CD3−CD56+ cells are removed from the first population of T cells by subjecting the first population of T cells to cell sorting using a gating strategy that removes the CD3−CD56+ cell fraction and recovers the negative fraction. In another embodiment, the foregoing method is utilized for the expansion of T cells in a first population of T cells characterized by a high percentage of NK cells. In another embodiment, the foregoing method is utilized for the expansion of T cells in a first population of T cells characterized by a high percentage of CD3−CD56+ cells. In another embodiment, the foregoing method is utilized for the expansion of T cells in tumor tissue characterized by the present of a high number of NK cells. In another embodiment, the foregoing method is utilized for the expansion of T cells in tumor tissue characterized by a high number of CD3−CD56+ cells. In another embodiment, the foregoing method is utilized for the expansion of T cells in tumor tissue obtained from a patient suffering from a tumor characterized by the presence of a high number of NK cells. In another embodiment, the foregoing method is utilized for the expansion of T cells in tumor tissue obtained from a patient suffering from a tumor characterized by the presence of a high number of CD3−CD56+ cells. In another embodiment, the foregoing method is utilized for the expansion of T cells in tumor tissue obtained from a patient suffering from ovarian cancer.

In another embodiment, the invention provides the method described in any of the preceding paragraphs as applicable above modified such that at or about $1\times10^7$ T cells from the first population of T cells are seeded in a container to initiate the primary first expansion culture in such container.

In another embodiment, the invention provides the method described in any of the preceding paragraphs as applicable above modified such that the first population of T cells is distributed into a plurality of containers, and in each container at or about $1\times10^7$ T cells from the first population of T cells are seeded to initiate the primary first expansion culture in such container.

In another embodiment, the invention provides the method described in any of the preceding paragraphs as applicable above modified such that the second population of T cells harvested in step (c) is a therapeutic population of TILs.

V. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^{6}$ to $5\times10^{6}$, $5\times10^{6}$ to $1\times10^{7}$, $1\times10^{7}$ to $5\times10^{7}$, $5\times10^{7}$ to $1\times10^{8}$, $1\times10^{8}$ to $5\times10^{8}$, $5\times10^{8}$ to $1\times10^{9}$, $1\times10^{9}$ to $5\times10^{9}$, $5\times10^{9}$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^{6}$ to $5\times10^{6}$, $5\times10^{6}$ to $1\times10^{7}$, $1\times10^{7}$ to $5\times10^{7}$, $5\times10^{7}$ to $1\times10^{8}$, $1\times10^{8}$ to $5\times10^{8}$, $5\times10^{8}$ to $1\times10^{9}$, $1\times10^{9}$ to $5\times10^{9}$, $5\times10^{9}$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

In another embodiment, the invention provides an infusion bag comprising the therapeutic population of TILs described in any of the preceding paragraphs above.

In another embodiment, the invention provides a tumor infiltrating lymphocyte (TIL) composition comprising the therapeutic population of TILs described in any of the preceding paragraphs above and a pharmaceutically acceptable carrier.

In another embodiment, the invention provides an infusion bag comprising the TIL composition described in any of the preceding paragraphs above.

In another embodiment, the invention provides a cryopreserved preparation of the therapeutic population of TILs described in any of the preceding paragraphs above.

In another embodiment, the invention provides a tumor infiltrating lymphocyte (TIL) composition comprising the therapeutic population of TILs described in any of the preceding paragraphs above and a cryopreservation media.

In another embodiment, the invention provides the TIL composition described in any of the preceding paragraphs above modified such that the cryopreservation media contains DMSO.

In another embodiment, the invention provides the TIL composition described in any of the preceding paragraphs above modified such that the cryopreservation media contains 7-10% DMSO.

In another embodiment, the invention provides a cryopreserved preparation of the TIL composition described in any of the preceding paragraphs above.

VI. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is NSCLC. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, therapeutically effective dosage is about $2.3\times10^{10}$ to about $13.7\times10^{10}$. In some embodiments, therapeutically effective dosage is about $7.8\times10^{10}$ TILs, particularly of the cancer is NSCLC. In some embodiments, therapeutically effective dosage is about $1.2\times10^{10}$ to about $4.3\times10^{10}$ of TILs. In some embodiments, therapeutically effective dosage is about $3\times10^{10}$ to about $12\times10^{10}$ TILs. In some embodiments, therapeutically effective dosage is about $4\times10^{10}$ to about $10\times10^{10}$ TILs. In some embodiments, therapeutically effective dosage is about $5\times10^{10}$ to about $8\times10^{10}$ TILs. In some embodiments, therapeutically effective dosage is about $6\times10^{10}$ to about $8\times10^{10}$ TILs. In some embodiments, therapeutically effective dosage is about $7\times10^{10}$ to about $8\times10^{10}$ TILs.

In some embodiments, the number of the TILs provided in the pharmaceutical compositions of the invention is about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^{6}$ to $5\times10^{6}$, $5\times10^{6}$ to $1\times10^{7}$, $1\times10^{7}$ to $5\times10^{7}$, $5\times10^{7}$ to $1\times10^{8}$, $1\times10^{8}$ to $5\times10^{8}$, $5\times10^{8}$ to $1\times10^{9}$, $1\times10^{9}$ to $5\times10^{9}$, $5\times10^{9}$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25%

13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In some embodiments, an effective dosage of TILs is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{1o}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

VII. Methods of Treating Patients

Methods of treatment begin with the initial TIL collection and culture of TILs. Such methods have been both described in the art by, for example, Jin et al., *J. Immunotherapy*, 2012, 35(3):283-292, incorporated by reference herein in its entirety. Embodiments of methods of treatment are described throughout the sections below, including the Examples.

The expanded TILs produced according the methods described herein, including for example as described in Steps A through F above or according to Steps A through F above (also as shown, for example, in FIG. 1) find particular use in the treatment of patients with cancer (for example, as described in Goff, et al., *J Clinical Oncology*, 2016, 34(20): 2389-239, as well as the supplemental content; incorporated by reference herein in its entirety. In some embodiments, TIL were grown from resected deposits of metastatic melanoma as previously described (see, Dudley, et al., *J Immunother.*, 2003, 26:332-342; incorporated by reference herein in its entirety). Fresh tumor can be dissected under sterile conditions. A representative sample can be collected for formal pathologic analysis. Single fragments of 2 mm$^3$ to 3 mm$^3$ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels >200 pg/mL and twice background. (Goff, et al., *J Immunother.*, 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 1), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 1), are selected for an additional second expansion according to Step D of FIG. 1.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-g was defined as >100 pg/mL and greater than 4 3 baseline levels.

In some embodiments, the TILs produced by the methods provided herein, for example those exemplified in FIG. 1, provide for a surprising improvement in clinical efficacy of the TILs. In some embodiments, the TILs produced by the methods provided herein, for example those exemplified in FIG. 1, exhibit increased clinical efficacy as compared to TILs produced by methods other than those described herein, including for example, methods other than those exemplified in FIG. 1. In some embodiments, the methods other than those described herein include methods referred to as process 1C and/or Generation 1 (Gen 1). In some embodiments, the increased efficacy is measured by DCR, ORR, and/or other clinical responses. In some embodiments, the TILS produced by the methods provided herein, for example those exemplified in FIG. 1, exhibit a similar time to response and safety profile compared to TILs produced by methods other than those described herein, including for example, methods other than those exemplified in FIG. 1, for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 1. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 1. In some embodiments, IFN-γ secretion is increased one-fold as compared to an untreated patient and/or as compared to a patient treated with TILs prepared using other methods than those provide herein including for example, methods other than those embodied in FIG. 1. In some embodiments, IFN-γ secretion is increased two-fold as compared to an untreated patient and/or as compared to a patient treated with TILs prepared using other methods than those provide herein including for example, methods other than those embodied in FIG. 1. In some embodiments, IFN-γ secretion is increased three-fold as compared to an untreated patient and/or as compared to a patient treated with TILs prepared using other methods than those provide herein including for example, methods other than those embodied in FIG. 1. In some embodiments, IFN-γ secretion is increased four-fold as compared to an untreated patient and/or as compared to a patient treated with TILs prepared using other methods than those provide herein including for example, methods other than those embodied in FIG. 1. In some embodiments, IFN-γ secretion is increased five-fold as compared to an untreated patient and/or as compared to a patient treated with TILs prepared using other methods than those provide herein including for example, methods other than those embodied in FIG. 1. In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 1. In some embodiments, IFN-γ is measured in blood of a subject treated with TILs prepared by the methods of the present invention, including those as described for example in FIG. 1. In some embodiments, IFN-γ is measured in TILs serum of a subject treated with TILs prepared by the methods of the present invention, including those as described for example in FIG. 1.

In some embodiments, the TILs prepared by the methods of the present invention, including those as described for example in FIG. 1, exhibit increased polyclonality as compared to TILs produced by other methods, including those not exemplified in FIG. 1, such as for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1. In some embodiments, polyclonality is increased one-fold as compared to an untreated patient and/or as compared to a patient treated with TILs prepared using other methods than those provide herein including for example, methods other than those embodied in FIG. 1. In some embodiments, polyclonality is increased two-fold as compared to an untreated patient and/or as compared to a patient treated with TILs prepared using other methods than those provide herein including for example, methods other than those embodied in FIG. 1. In some embodiments, polyclonality is increased ten-fold as compared to an untreated patient and/or as compared to a patient treated with TILs prepared using other methods than those provide herein including for example, methods other than those embodied in FIG. 1. In some embodiments, polyclonality is increased 100-fold as compared to an untreated patient and/or as compared to a patient treated with TILs prepared using other methods than those provide herein including for example, methods other than those embodied in FIG. 1. In some embodiments, polyclonality is increased 500-fold as compared to an untreated patient and/or as compared to a patient treated with TILs prepared using other methods than those provide herein including for example, methods other than those embodied in FIG. 1. In some embodiments, polyclonality is increased 1000-fold as compared to an untreated patient and/or as compared to a patient treated with TILs prepared using other methods than those provide herein including for example, methods other than those embodied in FIG. 1.

Measures of efficacy can include the disease control rate (DCR) as well as overall response rate (ORR), as known in the art as well as described herein.

1. Methods of Treating NSCLC

The compositions and methods described herein can be used in a method for treating non-small-cell lung cancer (NSCLC), wherein the NSCLC is refractory to treatment with an anti-PD-1 antibody. In some embodiments the anti-PD-1 antibody includes, e.g., but is not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immu2740274ne response, are include. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are included.

In some embodiments, the NSCLC is refractory to the anti-CTLA-4 and/or anti-PD-1 and a chemotherapeutic agent. In some embodiments, the NSCLC is refractory to the anti-CTLA-4 and/or anti-PD-1 and chemotherapy, wherein the chemotherapeutic agent is carboplatin, paclitaxel, pemetrexed, cisplatin. In some embodiments, the anti-CLTA-4 antibody, such as ipilimumab (Yervoy®).

In some embodiments, the NSCLC is refractory to treatment with combined PD-1 (including for example pembrolizumab) and a chemotherapeutic agent. In some embodiments, the chemotherapeutic agent(s) is a platinum doublet chemotherapeutic agent. In some embodiments, the platinum doublet therapy comprises a first chemotherapeutic agent selected from the group consisting of cisplatin and carboplatin and a second chemotherapeutic agent selected from the group consisting of vinorelbine, gemcitabine and a taxane (including for example, paclitaxel, docetaxel or nab-paclitaxel). In some embodiments, the platinum doublet chemotherapeutic agent is in combination with pemetrexed.

In some embodiments, the NSCLC is refractory to a combination treatment or combination therapy comprising an anti-PD-1 and a chemotherapeutic agent. In some embodiments, the anti-PD-1 or the anti-PD-L1 antibody is selected from the group consisting of nivolumab, pembrolizumab, JS001, TSR-042, pidilizumab, (BGB-A317, SHR-1210, REGN2810, MDX-1106, PDR001, anti-PD-1 from clone: RMP1-14, an anti-PD-1 antibodies disclosed in U.S. Pat. No. 8,008,449, durvalumab, atezolizumab, avelumab, and fragments, derivatives, variants, as well as biosimilars thereof. In some embodiments, the anti-PD-1 is pembrolizumab. In some embodiments, the chemotherapeutic agent is a platinum doublet chemotherapeutic agent. In some embodiments, the chemotherapeutic agent is in combination with pemetrexed. In some embodiments, the NSCLC is refractory to a combination therapy comprising carboplatin, paclitaxel, pemetrexed, and cisplatin. In some embodiments, the NSCLC is refractory to a combination therapy comprising carboplatin, paclitaxel, pemetrexed, cisplatin, nivolumab, and ipilimumab.

In some embodiments, the NSCLC is refractory to a combination therapy comprising the anti-PD-1 or the anti-PD-L1 and a platinum doublet therapy, wherein the platinum doublet therapy comprises:

i) a first chemotherapeutic agent selected from the group consisting of cisplatin and carboplatin, ii) and a second chemotherapeutic agent selected from the group consisting of vinorelbine, gemcitabine and a taxane (including for example, paclitaxel, docetaxel or nab-paclitaxel).

In some embodiments, the NSCLC is refractory to a combination therapy comprising the anti-PD-1 or the anti-PD-L1, pemetrexed, and a platinum doublet therapy, wherein the platinum doublet therapy comprises:

i) a first chemotherapeutic agent selected from the group consisting of cisplatin and carboplatin, ii) and a second chemotherapeutic agent selected from the group consisting of vinorelbine, gemcitabine and a taxane (including for example, paclitaxel, docetaxel or nab-paclitaxel).

In some embodiments, the NSCLC has been treated with an anti-PD-1 antibody. In some embodiments, the NSCLC has been treated with an anti-PD-L1 antibody. In some embodiments, the NSCLC subject is treatment naïve. In some embodiments, the NSCLC has not been treated with an anti-PD-1 antibody. In some embodiments, the NSCLC has not been treated with an anti-PD-L1 antibody. In some embodiments, the NSCLC has been previously treated with a chemotherapeutic agent. In some embodiments, the NSCLC has been previously treated with a chemotherapeutic agent but is not longer being treated with the chemotherapeutic agent. In some embodiments, the NSCLC patient is anti-PD-1/PD-L1 naïve. In some embodiments, the NSCLC subject has low expression of PD-L1. In some embodiments, the NSCLC subject has treatment naïve NSCLC or is post-chemotherapeutic treatment but anti-PD-1/PD-L1 naïve. In some embodiments, the NSCLC subject is treatment naïve NSCLC or post-chemotherapeutic treatment but anti-PD-1/PD-L1 naïve and has low expression of PD-L1. In some embodiments, the NSCLC subject has bulky disease at baseline. In some embodiments, the subject has bulky disease at baseline and has low expression of PD-L1. In some embodiments, the NSCLC subject has treatment naïve NSCLC or post chemotherapy (e.g., post chemotherapeutic agent) but anti-PD-1/PD-L1 naïve who have low expression of PD-L1 and/or have bulky disease at baseline. In some embodiments, bulky disease is indicated where the maximal tumor diameter is greater than 7 cm measured in either the transverse or coronal plane. In some embodiments, bulky disease is indicated when there are swollen lymph nodes with a short-axis diameter of 20 mm or greater. In some embodiments, the chemotherapeutic includes a standard of care therapeutic for NSCLC.

In some embodiments, the TILs prepared by the methods of the present invention, including those as described for example in FIG. 1, exhibit increased polyclonality as compared to TILs produced by other methods, including those not exemplified in FIG. 1, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1. In some embodiments, polyclonality is increased one-fold as compared to an untreated patient and/or as compared to a patient treated with TILs prepared using other methods than those provide herein including for example, methods other than those embodied in FIG. 1. In some embodiments, polyclonality is increased two-fold as compared to an untreated patient and/or as compared to a patient treated with TILs prepared using other methods than those provide herein including for example, methods other than those embodied in FIG. 1. In some embodiments, polyclonality is increased ten-fold as compared to an untreated patient and/or as compared to a patient treated with TILs prepared using other methods than those provide herein including for example, methods other than those embodied in FIG. 1. In some embodiments, polyclonality is increased 100-fold as compared to an untreated patient and/or as compared to a patient treated with TILs prepared using other methods than those provide herein including for example, methods other than those embodied in FIG. 1. In some embodiments, polyclonality is increased 500-fold as compared to an untreated patient and/or as compared to a patient treated with TILs prepared using other methods than those provide herein including for example, methods other than those embodied in FIG. 1. In some embodiments, polyclonality is increased 1000-fold as compared to an untreated patient and/or as compared to a patient treated with TILs prepared using other methods than those provide herein including for example, methods other than those embodied in FIG. 1.

a. PD-1 and PD-L1 Inhibitors

Programmed death 1 (PD-1) is a 288-amino acid transmembrane immunocheckpoint receptor protein expressed by T cells, B cells, natural killer (NK) T cells, activated monocytes, and dendritic cells. PD-1, which is also known as CD279, belongs to the CD28 family, and in humans is encoded by the Pdcd1 gene on chromosome 2. PD-1 consists of one immunoglobulin (Ig) superfamily domain, a transmembrane region, and an intracellular domain containing an immunoreceptor tyrosine-based inhibitory motif (ITIM) and an immunoreceptor tyrosine-based switch motif (ITSM). PD-1 and its ligands (PD-L1 and PD-L2) are known to play a key role in immune tolerance, as described in Keir, et al., *Annu. Rev. Immunol.* 2008, 26, 677-704. PD-1 provides inhibitory signals that negatively regulate T cell immune responses. PD-L1 (also known as B7-H1 or CD274) and PD-L2 (also known as B7-DC or CD273) are expressed on tumor cells and stromal cells, which may be encountered by activated T cells expressing PD-1, leading to immunosuppression of the T cells. PD-L1 is a 290 amino acid transmembrane protein encoded by the Cd274 gene on human chromosome 9. Blocking the interaction between PD-1 and its ligands PD-L1 and PD-L2 by use of a PD-1 inhibitor, a PD-L1 inhibitor, and/or a PD-L2 inhibitor can overcome immune resistance, as demonstrated in recent clinical studies, such as that described in Topalian, et al., *N. Eng. J. Med.* 2012, 366, 2443-54. PD-L1 is expressed on many tumor cell lines, while PD-L2 is expressed is expressed mostly on dendritic cells and a few tumor lines. In addition to T cells (which inducibly express PD-1 after activation), PD-1 is also expressed on B cells, natural killer cells, macrophages, activated monocytes, and dendritic cells.

In an embodiment, the PD-1 inhibitor may be any PD-1 inhibitor or PD-1 blocker known in the art. In particular, it is one of the PD-1 inhibitors or blockers described in more detail in the following paragraphs. The terms "inhibitor," "antagonist," and "blocker" are used interchangeably herein in reference to PD-1 inhibitors. For avoidance of doubt, references herein to a PD-1 inhibitor that is an antibody may refer to a compound or antigen-binding fragments, variants, conjugates, or biosimilars thereof. For avoidance of doubt, references herein to a PD-1 inhibitor may also refer to a small molecule compound or a pharmaceutically acceptable salt, ester, solvate, hydrate, cocrystal, or prodrug thereof.

In a preferred embodiment, the PD-1 inhibitor is an antibody (i.e., an anti-PD-1 antibody), a fragment thereof, including Fab fragments, or a single-chain variable fragment (scFv) thereof. In some embodiments the PD-1 inhibitor is a polyclonal antibody. In a preferred embodiment, the PD-1 inhibitor is a monoclonal antibody. In some embodiments, the PD-1 inhibitor competes for binding with PD-1, and/or binds to an epitope on PD-1. In an embodiment, the antibody competes for binding with PD-1, and/or binds to an epitope on PD-1.

In some embodiments, the PD-1 inhibitor is one that binds human PD-1 with a $K_D$ of about 100 pM or lower, binds human PD-1 with a $K_D$ of about 90 pM or lower, binds human PD-1 with a $K_D$ of about 80 pM or lower, binds human PD-1 with a $K_D$ of about 70 pM or lower, binds human PD-1 with a $K_D$ of about 60 pM or lower, binds human PD-1 with a $K_D$ of about 50 pM or lower, binds human PD-1 with a $K_D$ of about 40 pM or lower, binds human PD-1 with a $K_D$ of about 30 pM or lower, binds human PD-1 with a $K_D$ of about 20 pM or lower, binds human PD-1 with a $K_D$ of about 10 pM or lower, or binds human PD-1 with a $K_D$ of about 1 pM or lower.

In some embodiments, the PD-1 inhibitor is one that binds to human PD-1 with a $k_{assoc}$ of about $7.5 \times 10^5$ 1/M·s or faster, binds to human PD-1 with a $k_{assoc}$ of about $7.5 \times 10^5$ 1/M·s or faster, binds to human PD-1 with a $k_{assoc}$ of about $8 \times 10^5$ 1/M·s or faster, binds to human PD-1 with a $k_{assoc}$ of about $8.5 \times 10^5$ 1/M·s or faster, binds to human PD-1 with a $k_{assoc}$ of about $9 \times 10^5$ 1/M·s or faster, binds to human PD-1 with a $k_{assoc}$ of about $9.5 \times 10^5$ 1/M·s or faster, or binds to human PD-1 with a $k_{assoc}$ of about $1 \times 10^6$ 1/M·s or faster.

In some embodiments, the PD-1 inhibitor is one that binds to human PD-1 with a $k_{dissoc}$ of about $2 \times 10^{-5}$ 1/s or slower, binds to human PD-1 with a $k_{dissoc}$ of about $2.1 \times 10^{-5}$ 1/s or slower, binds to human PD-1 with a $k_{dissoc}$ of about $2.2 \times 10^{-5}$ 1/s or slower, binds to human PD-1 with a $k_{dissoc}$ of about $2.3 \times 10^{-5}$ 1/s or slower, binds to human PD-1 with a $k_{dissoc}$ of about $2.4 \times 10^{-5}$ 1/s or slower, binds to human PD-1 with a $k_{dissoc}$ of about $2.5 \times 10^{-5}$ 1/s or slower, binds to human PD-1 with a $k_{dissoc}$ of about $2.6 \times 10^{-5}$ 1/s or slower or binds to human PD-1 with a $k_{dissoc}$ of about $2.7 \times 10^{-5}$ 1/s or slower, binds to human PD-1 with a $k_{dissoc}$ of about $2.8 \times 10^{-5}$ 1/s or slower, binds to human PD-1 with a $k_{dissoc}$ of about $2.9 \times 10^{-5}$ 1/s or slower, or binds to human PD-1 with a $k_{dissoc}$ of about $3 \times 10^{-5}$ 1/s or slower.

In some embodiments, the PD-1 inhibitor is one that blocks or inhibits binding of human PD-L1 or human PD-L2 to human PD-1 with an $IC_{50}$ of about 10 nM or lower, blocks or inhibits binding of human PD-L1 or human PD-L2 to human PD-1 with an $IC_{50}$ of about 9 nM or lower, blocks or inhibits binding of human PD-L1 or human PD-L2 to human PD-1 with an $IC_{50}$ of about 8 nM or lower, blocks or inhibits binding of human PD-L1 or human PD-L2 to human PD-1 with an $IC_{50}$ of about 7 nM or lower, blocks or inhibits binding of human PD-L1 or human PD-L2 to human PD-1 with an $IC_{50}$ of about 6 nM or lower, blocks or inhibits binding of human PD-L1 or human PD-L2 to human PD-1 with an $IC_{50}$ of about 5 nM or lower, blocks or inhibits binding of human PD-L1 or human PD-L2 to human PD-1 with an $IC_{50}$ of about 4 nM or lower, blocks or inhibits binding of human PD-L1 or human PD-L2 to human PD-1 with an $IC_{50}$ of about 3 nM or lower, blocks or inhibits binding of human PD-L1 or human PD-L2 to human PD-1 with an $IC_{50}$ of about 2 nM or lower, or blocks or inhibits binding of human PD-L1 or human PD-L2 to human PD-1 with an $IC_{50}$ of about 1 nM or lower.

In an embodiment, the PD-1 inhibitor is nivolumab (commercially available as OPDIVO from Bristol-Myers Squibb Co.), or biosimilars, antigen-binding fragments, conjugates, or variants thereof. Nivolumab is a fully human IgG4 antibody blocking the PD-1 receptor. In an embodiment, the anti-PD-1 antibody is an immunoglobulin G4 kappa, anti-(human CD274) antibody. Nivolumab is assigned Chemical Abstracts Service (CAS) registry number 946414-94-4 and is also known as 5C4, BMS-936558, MDX-1106, and ONO-4538. The preparation and properties of nivolumab are described in U.S. Pat. No. 8,008,449 and International Patent Publication No. WO 2006/121168, the disclosures of which are incorporated by reference herein. The clinical safety and efficacy of nivolumab in various forms of cancer has been described in Wang, et al., *Cancer Immunol Res.* 2014, 2, 846-56; Page, et al., *Ann. Rev. Med.,* 2014, 65, 185-202; and Weber, et al., *J. Clin. Oncology,* 2013, 31, 4311-4318, the disclosures of which are incorporated by reference herein. The amino acid sequences of nivolumab are set forth in Table 48. Nivolumab has intra-heavy chain disulfide linkages at 22-96, 140-196, 254-314, 360-418, 22"-96", 140"-196", 254"-314", and 360"-418"; intra-light chain disulfide linkages at 23'-88', 134'-194', 23'''-88''', and 134'''-194'''; inter-heavy-light chain disulfide linkages at 127-214', 127"-214'''; inter-heavy-heavy chain disulfide linkages at 219-219" and 222-222"; and N-glycosylation sites (H $CH_2$ 84.4) at 290, 290".

In an embodiment, a PD-1 inhibitor comprises a heavy chain given by SEQ ID NO:463 and a light chain given by SEQ ID NO:464. In an embodiment, a PD-1 inhibitor comprises heavy and light chains having the sequences shown in SEQ ID NO:463 and SEQ ID NO:464, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:463 and SEQ ID NO:464, respectively. In an embodiment, a PD-1 inhibitor comprises heavy and light chains that are each at least 98% identical to the sequences shown in SEQ ID NO:463 and SEQ ID NO:464, respectively. In an embodiment, a PD-1 inhibitor comprises heavy and light chains that are each at least 97% identical to the sequences shown in SEQ ID NO:463 and SEQ ID NO:464, respectively. In an embodiment, a PD-1 inhibitor comprises heavy and light chains that are each at least 96% identical to the sequences shown in SEQ ID NO:463 and SEQ ID NO:464, respectively. In an embodiment, a PD-1 inhibitor comprises heavy and light chains that are each at least 95% identical to the sequences shown in SEQ ID NO:463 and SEQ ID NO:464, respectively.

In an embodiment, the PD-1 inhibitor comprises the heavy and light chain CDRs or variable regions (VRs) of nivolumab. In an embodiment, the PD-1 inhibitor heavy chain variable region ($V_H$) comprises the sequence shown in SEQ ID NO:465, and the PD-1 inhibitor light chain variable region ($V_L$) comprises the sequence shown in SEQ ID NO:466, and conservative amino acid substitutions thereof. In an embodiment, a PD-1 inhibitor comprises $V_H$ and $V_L$ regions that are each at least 99% identical to the sequences shown in SEQ ID NO:465 and SEQ ID NO:466, respectively. In an embodiment, a PD-1 inhibitor comprises $V_H$ and $V_L$ regions that are each at least 98% identical to the sequences shown in SEQ ID NO:465 and SEQ ID NO:466, respectively. In an embodiment, a PD-1 inhibitor comprises $V_H$ and $V_L$ regions that are each at least 97% identical to the sequences shown in SEQ ID NO:465 and SEQ ID NO:466, respectively. In an embodiment, a PD-1 inhibitor comprises $V_H$ and $V_L$ regions that are each at least 96% identical to the sequences shown in SEQ ID NO:465 and SEQ ID NO:466, respectively. In an embodiment, a PD-1 inhibitor comprises $V_H$ and $V_L$ regions that are each at least 95% identical to the sequences shown in SEQ ID NO:465 and SEQ ID NO:466, respectively.

In an embodiment, a PD-1 inhibitor comprises heavy chain CDR1, CDR2 and CDR3 domains having the sequences set forth in SEQ ID NO:467, SEQ ID NO:468, and SEQ ID NO:469, respectively, and conservative amino acid substitutions thereof, and light chain CDR1, CDR2 and CDR3 domains having the sequences set forth in SEQ ID NO:470, SEQ ID NO:471, and SEQ ID NO:472, respectively, and conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to nivolumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is nivolumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is nivolumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab.

TABLE 35

Amino acid sequences for PD-1 inhibitors related to nivolumab.

Identifier Sequence (One-Letter Amino Acid Symbols)

```
SEQ ID NO: 463    QVQLVESGGG VVQPGRSLRL DCKASGITFS NSGMHWVRQA PGKGLEWVAV IWYDGSKRYY   60
nivolumab         ADSVKGRFTI SRDNSKNTLF LQMNSLRAED TAVYYCATND DYWGQGTLVT VSSASTKGPS  120
heavy chain       VFPLAPCSRS TSESTAALGC LVKDYFPEPV TVSWNSGALT SGVHTFPAVL QSSGLYSLSS  180
                  VVTVPSSSLG TKTYTCNVDH KPSNTKVDKR VESKYGPPCP PCPAPEFLGG PSVFLFPPKP  240
                  KDTLMISRTP EVTCVVVDVS QEDPEVQFNW YVDGVEVHNA KTKPREEQFN STYRVVSVLT  300
                  VLHQDWLNGK EYKCKVSNKG LPSSIEKTIS KAKGQPREPQ VYTLPPSQEE MTKNQVSLTC  360
                  LVKGFYPSDI AVEWESNGQP ENNYKTTPPV LDSDGSFFLY SRLTVDKSRW QEGNVFSCSV  420
                  MHEALHNHYT QKSLSLSLGK                                              440

SEQ ID NO: 464    EIVLTQSPAT LSLSPGERAT LSCRASQSVS SYLAWYQQKP GQAPRLLIYD ASNRATGIPA   60
nivolumab         RFSGSGSGTD FTLTISSLEP EDFAVYYCQQ SSNWPRTFGQ GTKVEIKRTV AAPSVFIFPP  120
light chain       SDEQLKSGTA SVVCLLNNFY PREAKVQWKV DNALQSGNSQ ESVTEQDSKD STYSLSSTLT  180
                  LSKADYEKHK VYACEVTHQG LSSPVTKSFN RGEC                              214

SEQ ID NO: 465    QVQLVESGGG VVQPGRSLRL DCKASGITFS NSGMHWVRQA PGKGLEWVAV IWYDGSKRYY   60
nivolumab         ADSVKGRFTI SRDNSKNTLF LQMNSLRAED TAVYYCATND DYWGQGTLVT VSS          113
variable heavy
chain SEQ ID NO: 466    EIVLTQSPAT LSLSPGERAT LSCRASQSVS SYLAWYQQKP GQAPRLLIYD ASNRATGIPA   60
nivolumab         RFSGSGSGTD FTLTISSLEP EDFAVYYCQQ SSNWPRTFGQ GTKVEIK               107
variable light
chain SEQ ID NO: 467    NSGMH                                                               5
nivolumab
heavy chain
CDR1

SEQ ID NO: 468    VIWYDGSKRY YADSVKG                                                  17
nivolumab
heavy chain
CDR2

SEQ ID NO: 469    NDDY                                                                4
nivolumab
heavy chain
CDR3
```

TABLE 35-continued

| Amino acid sequences for PD-1 inhibitors related to nivolumab. | | |
|---|---|---|
| Identifier | Sequence (One-Letter Amino Acid Symbols) | |
| SEQ ID NO: 470 nivolumab light chain CDR1 | RASQSVSSYL A | 11 |
| SEQ ID NO: 471 nivolumab light chain CDR2 | DASNRAT | 7 |
| SEQ ID NO: 472 nivolumab light chain CDR3 | QQSSNWPRT | 9 |

In another embodiment, the PD-1 inhibitor comprises pembrolizumab (commercially available as KEYTRUDA from Merck & Co., Inc., Kenilworth, NJ, USA), or antigen-binding fragments, conjugates, or variants thereof. Pembrolizumab is assigned CAS registry number 1374853-91-4 and is also known as lambrolizumab, MK-3475, and SCH-900475. Pembrolizumab has an immunoglobulin G4, anti-(human protein PDCD1 (programmed cell death 1)) (human-*Mus musculus* monoclonal heavy chain), disulfide with human-*Mus musculus* monoclonal light chain, dimer structure. The structure of pembrolizumab may also be described as immunoglobulin G4, anti-(human programmed cell death 1); humanized mouse monoclonal [228-L-proline(H10-S>P)]γ4 heavy chain (134-218')-disulfide with humanized mouse monoclonal κ light chain dimer (226-226":229-229")-bisdisulfide. The properties, uses, and preparation of pembrolizumab are described in International Patent Publication No. WO 2008/156712 A1, U.S. Pat. No. 8,354,509 and U.S. Patent Application Publication Nos. US 2010/0266617 A1, US 2013/0108651 A1, and US 2013/0109843 A2, the disclosures of which are incorporated herein by reference. The clinical safety and efficacy of pembrolizumab in various forms of cancer is described in Fuerst, *Oncology Times,* 2014, 36, 35-36; Robert, et al., *Lancet,* 2014, 384, 1109-17; and Thomas, et al., *Exp. Opin. Biol. Ther.,* 2014, 14, 1061-1064. The amino acid sequences of pembrolizumab are set forth in Table 49. Pembrolizumab includes the following disulfide bridges: 22-96, 22"-96", 23'-92', 23'"-92", 134-218', 134"-218'", 138'-198', 138'"-198'", 147-203, 147"-203", 226-226", 229-229", 261-321, 261"-321", 367-425, and 367"-425", and the following glycosylation sites (N): Asn-297 and Asn-297". Pembrolizumab is an IgG4/kappa isotype with a stabilizing S228P mutation in the Fc region; insertion of this mutation in the IgG4 hinge region prevents the formation of half molecules typically observed for IgG4 antibodies. Pembrolizumab is heterogeneously glycosylated at Asn297 within the Fc domain of each heavy chain, yielding a molecular weight of approximately 149 kDa for the intact antibody. The dominant glycoform of pembrolizumab is the fucosylated agalacto diantennary glycan form (G0F).

In an embodiment, a PD-1 inhibitor comprises a heavy chain given by SEQ ID NO:473 and a light chain given by SEQ ID NO:474. In an embodiment, a PD-1 inhibitor comprises heavy and light chains having the sequences shown in SEQ ID NO:473 and SEQ ID NO:474, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:473 and SEQ ID NO:474, respectively. In an embodiment, a PD-1 inhibitor comprises heavy and light chains that are each at least 98% identical to the sequences shown in SEQ ID NO:473 and SEQ ID NO:474, respectively. In an embodiment, a PD-1 inhibitor comprises heavy and light chains that are each at least 97% identical to the sequences shown in SEQ ID NO:473 and SEQ ID NO:474, respectively. In an embodiment, a PD-1 inhibitor comprises heavy and light chains that are each at least 96% identical to the sequences shown in SEQ ID NO:473 and SEQ ID NO:474, respectively. In an embodiment, a PD-1 inhibitor comprises heavy and light chains that are each at least 95% identical to the sequences shown in SEQ ID NO:473 and SEQ ID NO:474, respectively.

In an embodiment, the PD-1 inhibitor comprises the heavy and light chain CDRs or variable regions (VRs) of pembrolizumab. In an embodiment, the PD-1 inhibitor heavy chain variable region ($V_H$) comprises the sequence shown in SEQ ID NO:475, and the PD-1 inhibitor light chain variable region ($V_L$) comprises the sequence shown in SEQ ID NO:476, and conservative amino acid substitutions thereof. In an embodiment, a PD-1 inhibitor comprises $V_H$ and $V_L$ regions that are each at least 99% identical to the sequences shown in SEQ ID NO:475 and SEQ ID NO:476, respectively. In an embodiment, a PD-1 inhibitor comprises $V_H$ and $V_L$ regions that are each at least 98% identical to the sequences shown in SEQ ID NO:475 and SEQ ID NO:476, respectively. In an embodiment, a PD-1 inhibitor comprises $V_H$ and $V_L$ regions that are each at least 97% identical to the sequences shown in SEQ ID NO:475 and SEQ ID NO:476, respectively. In an embodiment, a PD-1 inhibitor comprises $V_H$ and $V_L$ regions that are each at least 96% identical to the sequences shown in SEQ ID NO:475 and SEQ ID NO:476, respectively. In an embodiment, a PD-1 inhibitor comprises $V_H$ and $V_L$ regions that are each at least 95% identical to the sequences shown in SEQ ID NO:475 and SEQ ID NO:476, respectively.

In an embodiment, a PD-1 inhibitor comprises the heavy chain CDR1, CDR2 and CDR3 domains having the sequences set forth in SEQ ID NO:477, SEQ ID NO:478, and SEQ ID NO:479, respectively, and conservative amino acid substitutions thereof, and light chain CDR1, CDR2 and CDR3 domains having the sequences set forth in SEQ ID NO:480, SEQ ID NO:481, and SEQ ID NO:482, respectively, and conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to pembrolizumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is pembrolizumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is pembrolizumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab.

TABLE 36

| Amino acid sequences for PD-1 inhibitors related to pembrolizumab. | | | | | | | |
|---|---|---|---|---|---|---|---|
| Identifier | Sequence (One-Letter Amino Acid Symbols) | | | | | | |
| SEQ ID NO: 473<br>pembrolizumab<br>heavy chain | QVQLVQSGVE | VKKPGASVKV | SCKASGYTFT | NYYMYWVRQA | PGQGLEWMGG | INPSNGGTNF | 60 |
| | NEKFKNRVTL | TTDSSTTTAY | MELKSLQFDD | TAVYYCARRD | YRFDMGFDYW | GQGTTVTVSS | 120 |
| | ASTKGPSVFP | LAPCSRSTSE | STAALGCLVK | DYFPEPVTVS | WNSGALTSGV | HTFPAVLQSS | 180 |
| | GLYSLSSVVT | VPSSSLGTKT | YTCNVDHKPS | NTKVDKRVES | KYGPPCPPCP | APEFLGGPSV | 240 |
| | FLFPPKPKDT | LMISRTPEVT | CVVVDVSQED | PEVQFNWYVD | GVEVHNAKTK | PREEQFNSTY | 300 |
| | RVVSVLTVLH | QDWLNGKEYK | CKVSNKGLPS | SIEKTISKAK | GQPREPQVYT | LPPSQEEMTK | 360 |
| | NQVSLTCLVK | GFYPSDIAVE | WESNGQPENN | YKTTPPVLDS | DGSFFLYSRL | TVDKSRWQEG | 420 |
| | NVFSCSVMHE | ALHNHYTQKS | LSLSLGK | | | | 447 |
| SEQ ID NO: 474<br>pembrolizumab<br>light chain | EIVLTQSPAT | LSLSPGERAT | LSCRASKGVS | TSGYSYLHWY | QQKPGQAPRL | LIYLASYLES | 60 |
| | GVPARFSGSG | SGTDFTLTIS | SLEPEDFAVY | YCQHSRDLPL | TFGGGTKVEI | KRTVAAPSVF | 120 |
| | IFPPSDEQLK | SGTASVVCLL | NNFYPREAKV | QWKVDNALQS | GNSQESVTEQ | DSKDSTYSLS | 180 |
| | STLTLSKADY | EKHKVYACEV | THQGLSSPVT | KSFNRGEC | | | 218 |
| SEQ ID NO: 475<br>pembrolizumab<br>variable heavy<br>chain | QVQLVQSGVE | VKKPGASVKV | SCKASGYTFT | NYYMYWVRQA | PGQGLEWMGG | INPSNGGTNF | 60 |
| | NEKFKNRVTL | TTDSSTTTAY | MELKSLQFDD | TAVYYCARRD | YRFDMGFDYW | GQGTTVTVSS | 120 |
| SEQ ID NO: 476<br>pembrolizumab<br>variable light<br>chain | EIVLTQSPAT | LSLSPGERAT | LSCRASKGVS | TSGYSYLHWY | QQKPGQAPRL | LIYLASYLES | 60 |
| | GVPARFSGSG | SGTDFTLTIS | SLEPEDFAVY | YCQHSRDLPL | TFGGGTKVEI | K | 111 |
| SEQ ID NO: 477<br>pembrolizumab<br>heavy chain<br>CDR1 | NYYMY | | | | | | 5 |
| SEQ ID NO: 478<br>pembrolizumab<br>heavy chain<br>CDR2 | GINPSNGGTN | FNEKFK | | | | | 16 |
| SEQ ID NO: 479<br>pembrolizumab<br>heavy chain<br>CDR3 | RDYRFDMGFD | Y | | | | | 11 |
| SEQ ID NO: 480<br>pembrolizumab<br>light chain<br>CDR1 | RASKGVSTSG | YSYLH | | | | | 15 |

TABLE 36-continued

Amino acid sequences for PD-1 inhibitors related to pembrolizumab.

| Identifier | Sequence (One-Letter Amino Acid Symbols) | |
|---|---|---|
| SEQ ID NO: 481 pembrolizumab light chain CDR2 | LASYLES | 7 |
| SEQ ID NO: 482 pembrolizumab light chain CDR3 | QHSRDLPLT | 9 |

In an embodiment, the PD-1 inhibitor is a commercially-available anti-PD-1 monoclonal antibody, such as anti-m-PD-1 clones J43 (Cat #BE0033-2) and RMP1-14 (Cat #BE0146) (Bio X Cell, Inc., West Lebanon, NH, USA). A number of commercially-available anti-PD-1 antibodies are known to one of ordinary skill in the art.

In an embodiment, the PD-1 inhibitor is an antibody disclosed in U.S. Pat. No. 8,354,509 or U.S. Patent Application Publication Nos. 2010/0266617 A1, 2013/0108651 A1, 2013/0109843 A2, the disclosures of which are incorporated by reference herein. In an embodiment, the PD-1 inhibitor is an anti-PD-1 antibody described in U.S. Pat. Nos. 8,287,856, 8,580,247, and 8,168,757 and U.S. Patent Application Publication Nos. 2009/0028857 A1, 2010/0285013 A1, 2013/0022600 A1, and 2011/0008369 A1, the teachings of which are hereby incorporated by reference. In another embodiment, the PD-1 inhibitor is an anti-PD-1 antibody disclosed in U.S. Pat. No. 8,735,553 B1, the disclosure of which is incorporated herein by reference. In an embodiment, the PD-1 inhibitor is pidilizumab, also known as CT-011, which is described in U.S. Pat. No. 8,686,119, the disclosure of which is incorporated by reference herein.

In an embodiment, the PD-1 inhibitor may be a small molecule or a peptide, or a peptide derivative, such as those described in U.S. Pat. Nos. 8,907,053; 9,096,642; and 9,044,442 and U.S. Patent Application Publication No. US 2015/0087581; 1,2,4-oxadiazole compounds and derivatives such as those described in U.S. Patent Application Publication No. 2015/0073024; cyclic peptidomimetic compounds and derivatives such as those described in U.S. Patent Application Publication No. US 2015/0073042; cyclic compounds and derivatives such as those described in U.S. Patent Application Publication No. US 2015/0125491; 1,3,4-oxadiazole and 1,3,4-thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. US 2014/0294898; the disclosures of each of which are hereby incorporated by reference in their entireties.

In an embodiment, the PD-L1 or PD-L2 inhibitor may be any PD-L1 or PD-L2 inhibitor, antagonist, or blocker known in the art. In particular, it is one of the PD-L1 or PD-L2 inhibitors, antagonist, or blockers described in more detail in the following paragraphs. The terms "inhibitor," "antagonist," and "blocker" are used interchangeably herein in reference to PD-L1 and PD-L2 inhibitors. For avoidance of doubt, references herein to a PD-L1 or PD-L2 inhibitor that is an antibody may refer to a compound or antigen-binding fragments, variants, conjugates, or biosimilars thereof. For avoidance of doubt, references herein to a PD-L1 or PD-L2 inhibitor may refer to a compound or a pharmaceutically acceptable salt, ester, solvate, hydrate, cocrystal, or prodrug thereof.

In some embodiments, the compositions, processes and methods described herein include a PD-L1 or PD-L2 inhibitor. In some embodiments, the PD-L1 or PD-L2 inhibitor is a small molecule. In a preferred embodiment, the PD-L1 or PD-L2 inhibitor is an antibody (i.e., an anti-PD-1 antibody), a fragment thereof, including Fab fragments, or a single-chain variable fragment (scFv) thereof. In some embodiments the PD-L1 or PD-L2 inhibitor is a polyclonal antibody. In a preferred embodiment, the PD-L1 or PD-L2 inhibitor is a monoclonal antibody. In some embodiments, the PD-L1 or PD-L2 inhibitor competes for binding with PD-L1 or PD-L2, and/or binds to an epitope on PD-L1 or PD-L2. In an embodiment, the antibody competes for binding with PD-L1 or PD-L2, and/or binds to an epitope on PD-L1 or PD-L2.

In some embodiments, the PD-L1 inhibitors provided herein are selective for PD-L1, in that the compounds bind or interact with PD-L1 at substantially lower concentrations than they bind or interact with other receptors, including the PD-L2 receptor. In certain embodiments, the compounds bind to the PD-L1 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L2 receptor.

In some embodiments, the PD-L2 inhibitors provided herein are selective for PD-L2, in that the compounds bind or interact with PD-L2 at substantially lower concentrations than they bind or interact with other receptors, including the PD-L1 receptor. In certain embodiments, the compounds bind to the PD-L2 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L1 receptor.

Without being bound by any theory, it is believed that tumor cells express PD-L1, and that T cells express PD-1. However, PD-L1 expression by tumor cells is not required for efficacy of PD-1 or PD-L1 inhibitors or blockers. In an embodiment, the tumor cells express PD-L1. In another embodiment, the tumor cells do not express PD-L1. In some embodiments, the methods can include a combination of a PD-1 and a PD-L1 antibody, such as those described herein, in combination with a TIL. The administration of a combination of a PD-1 and a PD-L1 antibody and a TIL may be simultaneous or sequential.

In some embodiments, the PD-L1 and/or PD-L2 inhibitor is one that binds human PD-L1 and/or PD-L2 with a $K_D$ of about 100 pM or lower, binds human PD-L1 and/or PD-L2 with a $K_D$ of about 90 pM or lower, binds human PD-L1 and/or PD-L2 with a $K_D$ of about 80 pM or lower, binds human PD-L1 and/or PD-L2 with a $K_D$ of about 70 pM or lower, binds human PD-L1 and/or PD-L2 with a $K_D$ of about 60 pM or lower, a $K_D$ of about 50 pM or lower, binds human PD-L1 and/or PD-L2 with a $K_D$ of about 40 pM or lower, or binds human PD-L1 and/or PD-L2 with a $K_D$ of about 30 pM or lower, In some embodiments, the PD-L1 and/or PD-L2 inhibitor is one that binds to human PD-L1 and/or PD-L2 with a $k_{assoc}$ of about $7.5 \times 10^5$ 1/M·s or faster, binds to human PD-L1 and/or PD-L2 with a $k_{assoc}$ of about $8 \times 10^5$ 1/M·s or faster, binds to human PD-L1 and/or PD-L2 with a $k_{assoc}$ of about $8.5 \times 10^5$ 1/M·s or faster, binds to human PD-L1 and/or PD-L2 with a $k_{assoc}$ of about $9 \times 10^5$ 1/M·s or faster, binds to human PD-L1 and/or PD-L2 with a $k_{assoc}$ of about $9.5 \times 10^5$ 1/M·s and/or faster, or binds to human PD-L1 and/or PD-L2 with a $k_{assoc}$ of about $1 \times 10^6$ 1/M·s or faster.

In some embodiments, the PD-L1 and/or PD-L2 inhibitor is one that binds to human PD-L1 or PD-L2 with a $k_{dissoc}$ of about $2 \times 10^{-5}$ 1/s or slower, binds to human PD-1 with a $k_{dissoc}$ of about $2.1 \times 10^{-5}$ 1/s or slower, binds to human PD-1 with a $k_{dissoc}$ of about $2.2 \times 10^{-5}$ 1/s or slower, binds to human PD-1 with a $k_{dissoc}$ of about $2.3 \times 10^{-5}$ 1/s or slower, binds to human PD-1 with a $k_{dissoc}$ of about $2.4 \times 10^{-5}$ 1/s or slower, binds to human PD-1 with a $k_{dissoc}$ of about $2.5 \times 10^{-5}$ 1/s or slower, binds to human PD-1 with a $k_{dissoc}$ of about $2.6 \times 10^{-5}$ 1/s or slower, binds to human PD-L1 or PD-L2 with a $k_{dissoc}$ of about $2.7 \times 10^{-5}$ 1/s or slower, or binds to human PD-L1 or PD-L2 with a $k_{dissoc}$ of about $3 \times 10^{-5}$ 1/s or slower.

In some embodiments, the PD-L1 and/or PD-L2 inhibitor is one that blocks or inhibits binding of human PD-L1 or human PD-L2 to human PD-1 with an $IC_{50}$ of about 10 nM or lower; blocks or inhibits binding of human PD-L1 or human PD-L2 to human PD-1 with an $IC_{50}$ of about 9 nM or lower; blocks or inhibits binding of human PD-L1 or human PD-L2 to human PD-1 with an $IC_{50}$ of about 8 nM or lower; blocks or inhibits binding of human PD-L1 or human PD-L2 to human PD-1 with an $IC_{50}$ of about 7 nM or lower; blocks or inhibits binding of human PD-L1 or human PD-L2 to human PD-1 with an $IC_{50}$ of about 6 nM or lower; blocks or inhibits binding of human PD-L1 or human PD-L2 to human PD-1 with an $IC_{50}$ of about 5 nM or lower; blocks or inhibits binding of human PD-L1 or human PD-L2 to human PD-1 with an $IC_{50}$ of about 4 nM or lower; blocks or inhibits binding of human PD-L1 or human PD-L2 to human PD-1 with an $IC_{50}$ of about 3 nM or lower; blocks or inhibits binding of human PD-L1 or human PD-L2 to human PD-1 with an $IC_{50}$ of about 2 nM or lower; or blocks human PD-1, or blocks binding of human PD-L1 or human PD-L2 to human PD-1 with an $IC_{50}$ of about 1 nM or lower.

In an embodiment, the PD-L1 inhibitor is durvalumab, also known as MEDI4736 (which is commercially available from Medimmune, LLC, Gaithersburg, Maryland, a subsidiary of AstraZeneca plc.), or antigen-binding fragments, conjugates, or variants thereof. In an embodiment, the PD-L1 inhibitor is an antibody disclosed in U.S. Pat. No. 8,779,108 or U.S. Patent Application Publication No. 2013/0034559, the disclosures of which are incorporated by reference herein. The clinical efficacy of durvalumab has been described in Page, et al., *Ann. Rev. Med.,* 2014, 65, 185-202; Brahmer, et al., *J. Clin. Oncol.* 2014, 32, 5s (supplement, abstract 8021); and McDermott, et al., *Cancer Treatment Rev.,* 2014, 40, 1056-64. The preparation and properties of durvalumab are described in U.S. Pat. No. 8,779,108, the disclosure of which is incorporated by reference herein. The amino acid sequences of durvalumab are set forth in Table 50. The durvalumab monoclonal antibody includes disulfide linkages at 22-96, 22"-96", 23'-89', 23'''-89''', 135'-195', 135'''-195''', 148-204, 148"-204", 215'-224, 215'''-224", 230-230", 233-233", 265-325, 265"-325", 371-429, and 371"-429"; and N-glycosylation sites at Asn-301 and Asn-301".

In an embodiment, a PD-L1 inhibitor comprises a heavy chain given by SEQ ID NO:483 and a light chain given by SEQ ID NO:484. In an embodiment, a PD-L1 inhibitor comprises heavy and light chains having the sequences shown in SEQ ID NO:483 and SEQ ID NO:484, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:483 and SEQ ID NO:484, respectively. In an embodiment, a PD-L1 inhibitor comprises heavy and light chains that are each at least 98% identical to the sequences shown in SEQ ID NO:483 and SEQ ID NO:484, respectively. In an embodiment, a PD-L1 inhibitor comprises heavy and light chains that are each at least 97% identical to the sequences shown in SEQ ID NO:483 and SEQ ID NO:484, respectively. In an embodiment, a PD-L1 inhibitor comprises heavy and light chains that are each at least 96% identical to the sequences shown in SEQ ID NO:483 and SEQ ID NO:484, respectively. In an embodiment, a PD-L1 inhibitor comprises heavy and light chains that are each at least 95% identical to the sequences shown in SEQ ID NO:483 and SEQ ID NO:484, respectively.

In an embodiment, the PD-L1 inhibitor comprises the heavy and light chain CDRs or variable regions (VRs) of durvalumab. In an embodiment, the PD-L1 inhibitor heavy chain variable region ($V_H$) comprises the sequence shown in SEQ ID NO:485, and the PD-L1 inhibitor light chain variable region ($V_L$) comprises the sequence shown in SEQ ID NO:486, and conservative amino acid substitutions thereof. In an embodiment, a PD-L1 inhibitor comprises $V_H$ and $V_L$ regions that are each at least 99% identical to the sequences shown in SEQ ID NO:485 and SEQ ID NO:486, respectively. In an embodiment, a PD-L1 inhibitor comprises $V_H$ and $V_L$ regions that are each at least 98% identical to the sequences shown in SEQ ID NO:485 and SEQ ID NO:486, respectively. In an embodiment, a PD-L1 inhibitor comprises $V_H$ and $V_L$ regions that are each at least 97% identical to the sequences shown in SEQ ID NO:485 and SEQ ID NO:486, respectively. In an embodiment, a PD-L1 inhibitor comprises $V_H$ and $V_L$ regions that are each at least 96% identical to the sequences shown in SEQ ID NO:485 and SEQ ID NO:486, respectively. In an embodiment, a PD-L1 inhibitor comprises $V_H$ and $V_L$ regions that are each at least 95% identical to the sequences shown in SEQ ID NO:485 and SEQ ID NO:486, respectively.

In an embodiment, a PD-L1 inhibitor comprises heavy chain CDR1, CDR2 and CDR3 domains having the sequences set forth in SEQ ID NO:487, SEQ ID NO:488, and SEQ ID NO:489, respectively, and conservative amino acid substitutions thereof, and light chain CDR1, CDR2 and CDR3 domains having the sequences set forth in SEQ ID NO:490, SEQ ID NO:491, and SEQ ID NO:492, respectively, and conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to durvalumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is durvalumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is durvalumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab.

TABLE 37

| Amino acid sequences for PD-L1 inhibitors related to durvalumab. | | | | | | | |
|---|---|---|---|---|---|---|---|
| Identifier | Sequence (One-Letter Amino Acid Symbols) | | | | | | |
| SEQ ID NO: 483 durvalumab heavy chain | EVQLVESGGG VDSVKGRFTI SASTKGPSVF SGLYSLSSVV GPSVFLFPPK NSTYRVVSVL EMTKNQVSLT WQQGNVFSCS | LVQPGGSLRL SRDNAKNSLY PLAPSSKSTS TVPSSSLGTQ PKDTLMISRT TVLHQDWLNG CLVKGFYPSD VMHEALHNHY | SCAASGFTFS LQMNSLRAED GGTAALGCLV TYICNVNHKP PEVTCVVVDV KEYKCKVSNK IAVEWESNGQ TQKSLSLSPG | RYWMSWVRQA TAVYYCAREG KDYFPEPVTV SNTKVDKRVE SHEDPEVKFN ALPASIEKTI PENNYKTTPP K | PGKGLEWVAN GWFGELAFDY SWNSGALTSG PKSCDKTHTC WYVDGVEVHN SKAKGQPREP VLDSDGSFFL | IKQDGSEKYY WGQGTLVTVS VHTFPAVLQS PPCPAPEFEG AKTKPREEQY QVYTLPPSRE YSKLTVDKSR | 60 120 180 240 300 360 420 451 |
| SEQ ID NO: 484 durvalumab light chain | EVQLVESGGG LSLSPGERAT DFTLTISRLE ASVVCLLNNF KVYACEVTHQ | LVQPGGSLRL LSCRASQRVS PEDFAVYYCQ YPREAKVQWK GLSSPVTKSF | SCAASGFTFS SSYLAWYQQK QYGSLPWTFG VDNALQSGNS NRGEC | RYWMSWVRQA PGQAPRLLIY QGTKVEIKRT QESVTEQDSK | PGKGLEWVAN DASSRATGIP VAAPSVFIFP DSTYSLSSTL | EIVLTQSPGT DRFSGSGSGT PSDEQLKSGT TLSKADYEKH | 60 120 180 240 265 |
| SEQ ID NO: 485 durvalumab variable heavy chain | EVQLVESGGG VDSVKGRFTI S | LVQPGGSLRL SRDNAKNSLY | SCAASGFTFS LQMNSLRAED | RYWMSWVRQA TAVYYCAREG | PGKGLEWVAN GWFGELAFDY | IKQDGSEKYY WGQGTLVTVS | 60 120 121 |
| SEQ ID NO: 486 durvalumab variable light chain | EIVLTQSPGT DRFSGSGSGT | LSLSPGERAT DFTLTISRLE | LSCRASQRVS PEDFAVYYCQ | SSYLAWYQQK QYGSLPWTFG | PGQAPRLLIY QGTKVEIK | DASSRATGIP | 60 120 108 |
| SEQ ID NO: 487 durvalumab heavy chain CDR1 | RYWMS | | | | | | 5 |
| SEQ ID NO: 488 durvalumab heavy chain CDR2 | NIKQDGSEKY YVDSVKG | | | | | | 17 |
| SEQ ID NO: 489 durvalumab heavy chain CDR3 | EGGWFGELAF DY | | | | | | 12 |
| SEQ ID NO: 490 durvalumab light chain CDR1 | RASQRVSSSY LA | | | | | | 12 |

TABLE 37-continued

Amino acid sequences for PD-L1 inhibitors related to durvalumab.

| Identifier | Sequence (One-Letter Amino Acid Symbols) | |
|---|---|---|
| SEQ ID NO: 491 durvalumab light chain CDR2 | DASSRAT | 7 |
| SEQ ID NO: 492 durvalumab light chain CDR3 | QQYGSLPWT | 9 |

In an embodiment, the PD-L1 inhibitor is avelumab, also known as MSB0010718C (commercially available from Merck KGaA/EMD Serono), or antigen-binding fragments, conjugates, or variants thereof. The preparation and properties of avelumab are described in U.S. Patent Application Publication No. US 2014/0341917 A1, the disclosure of which is specifically incorporated by reference herein. The amino acid sequences of avelumab are set forth in Table 51. Avelumab has intra-heavy chain disulfide linkages (C23-C104) at 22-96, 147-203, 264-324, 370-428, 22"-96", 147"-203", 264"-324", and 370"-428"; intra-light chain disulfide linkages (C23-C104) at 22'-90', 138'-197', 22'''-90''', and 138'''-197''; intra-heavy-light chain disulfide linkages (h 5-CL 126) at 223-215' and 223"-215'''; intra-heavy-heavy chain disulfide linkages (h 11, h 14) at 229-229" and 232-232"; N-glycosylation sites (H $CH_2$ N84.4) at 300, 300"; fucosylated complex bi-antennary CHO-type glycans; and H CHS K2 C-terminal lysine clipping at 450 and 450'.

In an embodiment, a PD-L1 inhibitor comprises a heavy chain given by SEQ ID NO:493 and a light chain given by SEQ ID NO:494. In an embodiment, a PD-L1 inhibitor comprises heavy and light chains having the sequences shown in SEQ ID NO:493 and SEQ ID NO:494, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:493 and SEQ ID NO:494, respectively. In an embodiment, a PD-L1 inhibitor comprises heavy and light chains that are each at least 98% identical to the sequences shown in SEQ ID NO:493 and SEQ ID NO:494, respectively. In an embodiment, a PD-L1 inhibitor comprises heavy and light chains that are each at least 97% identical to the sequences shown in SEQ ID NO:493 and SEQ ID NO:494, respectively. In an embodiment, a PD-L1 inhibitor comprises heavy and light chains that are each at least 96% identical to the sequences shown in SEQ ID NO:493 and SEQ ID NO:494, respectively. In an embodiment, a PD-L1 inhibitor comprises heavy and light chains that are each at least 95% identical to the sequences shown in SEQ ID NO:493 and SEQ ID NO:494, respectively.

In an embodiment, the PD-L1 inhibitor comprises the heavy and light chain CDRs or variable regions (VRs) of avelumab. In an embodiment, the PD-L1 inhibitor heavy chain variable region ($V_H$) comprises the sequence shown in SEQ ID NO:495, and the PD-L1 inhibitor light chain variable region ($V_L$) comprises the sequence shown in SEQ ID NO:496, and conservative amino acid substitutions thereof. In an embodiment, a PD-L1 inhibitor comprises $V_H$ and $V_L$ regions that are each at least 99% identical to the sequences shown in SEQ ID NO:495 and SEQ ID NO:496, respectively. In an embodiment, a PD-L1 inhibitor comprises $V_H$ and $V_L$ regions that are each at least 98% identical to the sequences shown in SEQ ID NO:496 and SEQ ID NO:496, respectively. In an embodiment, a PD-L1 inhibitor comprises $V_H$ and $V_L$ regions that are each at least 97% identical to the sequences shown in SEQ ID NO:495 and SEQ ID NO:496, respectively. In an embodiment, a PD-L1 inhibitor comprises $V_H$ and $V_L$ regions that are each at least 96% identical to the sequences shown in SEQ ID NO:495 and SEQ ID NO:496, respectively. In an embodiment, a PD-L1 inhibitor comprises $V_H$ and $V_L$ regions that are each at least 95% identical to the sequences shown in SEQ ID NO:495 and SEQ ID NO:496, respectively.

In an embodiment, a PD-L1 inhibitor comprises heavy chain CDR1, CDR2 and CDR3 domains having the sequences set forth in SEQ ID NO:497, SEQ ID NO:498, and SEQ ID NO:499, respectively, and conservative amino acid substitutions thereof, and light chain CDR1, CDR2 and CDR3 domains having the sequences set forth in SEQ ID NO:500, SEQ ID NO:501, and SEQ ID NO:502, respectively, and conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to avelumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is avelumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is avelumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab.

0045200 A1, 2013/0045201 A1, 2013/0045202 A1, or 2014/0065135 A1, the disclosures of which are specifically incorporated by reference herein. The preparation and properties of atezolizumab are described in U.S. Pat. No. 8,217,149, the disclosure of which is incorporated by reference herein. The amino acid sequences of atezolizumab are set forth in Table 52. Atezolizumab has intra-heavy chain disulfide

TABLE 38

Amino acid sequences for PD-L1 inhibitors related to avelumab.

| Identifier | Sequence (One-Letter Amino Acid Symbols) |
|---|---|
| SEQ ID NO: 493 avelumab heavy chain | EVQLLESGGG LVQPGGSLRL SCAASGFTFS SYIMMWVRQA PGKGLEWVSS IYPSGGITFY 60<br>ADTVKGRFTI SRDNSKNTLY LQMNSLRAED TAVYYCARIK LGTVTTVDYW GQGTLVTVSS 120<br>ASTKGPSVFP LAPSSKSTSG GTAALGCLVK DYFPEPVTVS WNSGALTSGV HTFPAVLQSS 180<br>GLYSLSSVVT VPSSSLGTQT YICNVNHKPS NTKVDKKVEP KSCDKTHTCP PCPAPELLGG 240<br>PSVFLFPPKP KDTLMISRTP EVTCVVVDVS HEDPEVKFNW YVDGVEVHNA KTKPREEQYN 300<br>STYRVVSVLT VLHQDWLNGK EYKCKVSNKA LPAPIEKTIS KAKGQPREPQ VYTLPPSRDE 360<br>LTKNQVSLTC LVKGFYPSDI AVEWESNGQP ENNYKTTPPV LDSDGSFFLY SKLTVDKSRW 420<br>QQGNVFSCSV MHEALHNHYT QKSLSLSPGK 450 |
| SEQ ID NO: 494 avelumab light chain | QSALTQPASV SGSPGQSITI SCTGTSSDVG GYNYVSWYQQ HPGKAPKLMI YDVSNRPSGV 60<br>SNRFSGSKSG NTASLTISGL QAEDEADYYC SSYTSSSTRV FGTGTKVTVL GQPKANPTVT 120<br>LFPPSSEELQ ANKATLVCLI SDFYPGAVTV AWKADGSPVK AGVETTKPSK QSNNKYAASS 180<br>YLSLTPEQWK SHRSYSCQVT HEGSTVEKTV APTECS 216 |
| SEQ ID NO: 495 avelumab variable heavy chain | EVQLLESGGG LVQPGGSLRL SCAASGFTFS SYIMMWVRQA PGKGLEWVSS IYPSGGITFY 60<br>ADTVKGRFTI SRDNSKNTLY LQMNSLRAED TAVYYCARIK LGTVTTVDYW GQGTLVTVSS 120 |
| SEQ ID NO: 496 avelumab variable light chain | QSALTQPASV SGSPGQSITI SCTGTSSDVG GYNYVSWYQQ HPGKAPKLMI YDVSNRPSGV 60<br>SNRFSGSKSG NTASLTISGL QAEDEADYYC SSYTSSSTRV FGTGTKVTVL 110 |
| SEQ ID NO: 497 avelumab heavy chain CDR1 | SYIMM 5 |
| SEQ ID NO: 498 avelumab heavy chain CDR2 | SIYPSGGITF YADTVKG 17 |
| SEQ ID NO: 499 avelumab heavy chain CDR3 | IKLGTVTTVD Y 11 |
| SEQ ID NO: 500 avelumab light chain CDR1 | TGTSSDVGGY NYVS 14 |
| SEQ ID NO: 501 avelumab light chain CDR2 | DVSNRPS 7 |
| SEQ ID NO: 502 avelumab light chain CDR3 | SSYTSSSTRV 10 |

In an embodiment, the PD-L1 inhibitor is atezolizumab, also known as MPDL3280A or RG7446 (commercially available as TECENTRIQ from Genentech, Inc., a subsidiary of Roche Holding AG, Basel, Switzerland), or antigen-binding fragments, conjugates, or variants thereof. In an embodiment, the PD-L1 inhibitor is an antibody disclosed in U.S. Pat. No. 8,217,149, the disclosure of which is specifically incorporated by reference herein. In an embodiment, the PD-L1 inhibitor is an antibody disclosed in U.S. Patent Application Publication Nos. 2010/0203056 A1, 2013/ linkages (C23-C104) at 22-96, 145-201, 262-322, 368-426, 22"-96", 145"-201", 262"-322", and 368"-426"; intra-light chain disulfide linkages (C23-C104) at 23'-88', 134'-194', 23'''-88''', and 134'''-194'''; intra-heavy-light chain disulfide linkages (h 5-CL 126) at 221-214' and 221"-214"; intra-heavy-heavy chain disulfide linkages (h 11, h 14) at 227-227" and 230-230"; and N-glycosylation sites (H CH$_2$ N84.4>A) at 298 and 298'.

In an embodiment, a PD-L1 inhibitor comprises a heavy chain given by SEQ ID NO:503 and a light chain given by SEQ ID NO:504. In an embodiment, a PD-L1 inhibitor comprises heavy and light chains having the sequences shown in SEQ ID NO:503 and SEQ ID NO:504, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:503 and SEQ ID NO:504, respectively. In an embodiment, a PD-L1 inhibitor comprises heavy and light chains that are each at least 98% identical to the sequences shown in SEQ ID NO:503 and SEQ ID NO:504, respectively. In an embodiment, a PD-L1 inhibitor comprises heavy and light chains that are each at least 97% identical to the sequences shown in SEQ ID NO:503 and SEQ ID NO:504, respectively. In an embodiment, a PD-L1 inhibitor comprises heavy and light chains that are each at least 96% identical to the sequences shown in SEQ ID NO:503 and SEQ ID NO:504, respectively. In an embodiment, a PD-L1 inhibitor comprises heavy and light chains that are each at least 95% identical to the sequences shown in SEQ ID NO:503 and SEQ ID NO:504, respectively.

In an embodiment, the PD-L1 inhibitor comprises the heavy and light chain CDRs or variable regions (VRs) of atezolizumab. In an embodiment, the PD-L1 inhibitor heavy chain variable region ($V_H$) comprises the sequence shown in SEQ ID NO:505, and the PD-L1 inhibitor light chain variable region ($V_L$) comprises the sequence shown in SEQ ID NO:506, and conservative amino acid substitutions thereof. In an embodiment, a PD-L1 inhibitor comprises $V_H$ and $V_L$ regions that are each at least 99% identical to the sequences shown in SEQ ID NO:505 and SEQ ID NO:506, respectively. In an embodiment, a PD-L1 inhibitor comprises $V_H$ and $V_L$ regions that are each at least 98% identical to the sequences shown in SEQ ID NO:505 and SEQ ID NO:506, respectively. In an embodiment, a PD-L1 inhibitor comprises $V_H$ and $V_L$ regions that are each at least 97% identical to the sequences shown in SEQ ID NO:505 and SEQ ID NO:506, respectively. In an embodiment, a PD-L1 inhibitor comprises $V_H$ and $V_L$ regions that are each at least 96% identical to the sequences shown in SEQ ID NO:505 and SEQ ID NO:506, respectively. In an embodiment, a PD-L1 inhibitor comprises $V_H$ and $V_L$ regions that are each at least 95% identical to the sequences shown in SEQ ID NO:505 and SEQ ID NO:506, respectively.

In an embodiment, a PD-L1 inhibitor comprises heavy chain CDR1, CDR2 and CDR3 domains having the sequences set forth in SEQ ID NO:507, SEQ ID NO:508, and SEQ ID NO:509, respectively, and conservative amino acid substitutions thereof, and light chain CDR1, CDR2 and CDR3 domains having the sequences set forth in SEQ ID NO:510, SEQ ID NO:511, and SEQ ID NO:512, respectively, and conservative amino acid substitutions thereof. In an embodiment, the antibody competes for binding with, and/or binds to the same epitope on PD-L1 as any of the aforementioned antibodies.

In an embodiment, the anti-PD-L1 antibody is an anti-PD-L1 biosimilar monoclonal antibody approved by drug regulatory authorities with reference to atezolizumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is atezolizumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is atezolizumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab.

TABLE 39

Amino acid sequences for PD-L1 inhibitors related to atezolizumab.

| Identifier | Sequence (One-Letter Amino Acid Symbols) | | | | | |
|---|---|---|---|---|---|---|
| SEQ ID NO: 503 | EVQLVESGGG | LVQPGGSLRL | SCAASGFTFS | DSWIHWVRQA | PGKGLEWVAW | ISPYGGSTYY | 60 |
| atezolizumab | ADSVKGRFTI | SADTSKNTAY | LQMNSLRAED | TAVYYCARRH | WPGGFDYWGQ | GTLVTVSSAS | 120 |
| heavy chain | TKGPSVFPLA | PSSKSTSGGT | AALGCLVKDY | FPEPVTVSWN | SGALTSGVHT | FPAVLQSSGL | 180 |
| | YSLSSVVTVP | SSSLGTQTYI | CNVNHKPSNT | KVDKKVEPKS | CDKTHTCPPC | PAPELLGGPS | 240 |
| | VFLFPPKPKD | TLMISRTPEV | TCVVVDVSHE | DPEVKFNWYV | DGVEVHNAKT | KPREEQYAST | 300 |
| | YRVVSVLTVL | HQDWLNGKEY | KCKVSNKALP | APIEKTISKA | KGQPREPQVY | TLPPSREEMT | 360 |
| | KNQVSLTCLV | KGFYPSDIAV | EWESNGQPEN | NYKTTPPVLD | SDGSFFLYSK | LTVDKSRWQQ | 420 |
| | GNVFSCSVMH | EALHNHYTQK | SLSLSPGK | | | | 448 |
| | | | | | | | |
| SEQ ID NO: 504 | DIQMTQSPSS | LSASVGDRVT | ITCRASQDVS | TAVAWYQQKP | GKAPKLLIYS | ASFLYSGVPS | 60 |
| atezolizumab | RFSGSGSGTD | FTLTISSLQP | EDFATYYCQQ | YLYHPATFGQ | GTKVEIKRTV | AAPSVFIFPP | 120 |
| light chain | SDEQLKSGTA | SVVCLLNNFY | PREAKVQWKV | DNALQSGNSQ | ESVTEQDSKD | STYSLSSTLT | 180 |
| | LSKADYEKHK | VYACEVTHQG | LSSPVTKSFN | RGEC | | | 214 |

TABLE 39-continued

Amino acid sequences for PD-L1 inhibitors related to atezolizumab.

| Identifier | Sequence (One-Letter Amino Acid Symbols) | | | | | | |
|---|---|---|---|---|---|---|---|
| SEQ ID NO: 505 atezolizumab variable heavy chain | EVQLVESGGG ADSVKGRFTI | LVQPGGSLRL SADTSKNTAY | SCAASGFTFS LQMNSLRAED | DSWIHWVRQA TAVYYCARRH | PGKGLEWVAW WPGGFDYWGQ | ISPYGGSTYY GTLVTVSA | 60 118 |
| SEQ ID NO: 506 atezolizumab variable light chain | DIQMTQSPSS RFSGSGSGTD | LSASVGDRVT FTLTISSLQP | ITCRASQDVS EDFATYYCQQ | TAVAWYQQKP YLYHPATFGQ | GKAPKLLIYS GTKVEIKR | ASFLYSGVPS | 60 108 |
| SEQ ID NO: 507 atezolizumab heavy chain CDR1 | GFTFSDSWIH | | | | | | 10 |
| SEQ ID NO: 508 atezolizumab heavy chain CDR2 | AWISPYGGST YYADSVKG | | | | | | 18 |
| SEQ ID NO: 509 atezolizumab heavy chain CDR3 | RHWPGGFDY | | | | | | 9 |
| SEQ ID NO: 510 atezolizumab light chain CDR1 | RASQDVSTAV A | | | | | | 11 |
| SEQ ID NO: 511 atezolizumab light chain CDR2 | SASFLYS | | | | | | 7 |
| SEQ ID NO: 512 atezolizumab light chain CDR3 | QQYLYHPAT | | | | | | 9 |

In an embodiment, PD-L1 inhibitors include those antibodies described in U.S. Patent Application Publication No. US 2014/0341917 A1, the disclosure of which is incorporated by reference herein. In another embodiment, antibodies that compete with any of these antibodies for binding to PD-L1 are also included. In an embodiment, the anti-PD-L1 antibody is MDX-1105, also known as BMS-935559, which is disclosed in U.S. Pat. No. 7,943,743, the disclosures of which are incorporated by reference herein. In an embodiment, the anti-PD-L1 antibody is selected from the anti-PD-L1 antibodies disclosed in U.S. Pat. No. 7,943,743, which are incorporated by reference herein.

In an embodiment, the PD-L1 inhibitor is a commercially-available monoclonal antibody, such as INVIVOMAB anti-m-PD-L1 clone 10F.9G2 (Catalog #BE0101, Bio X Cell, Inc., West Lebanon, NH, USA). In an embodiment, the anti-PD-L1 antibody is a commercially-available monoclonal antibody, such as AFFYMETRIX EBIOSCIENCE (MIH1). A number of commercially-available anti-PD-L1 antibodies are known to one of ordinary skill in the art.

In an embodiment, the PD-L2 inhibitor is a commercially-available monoclonal antibody, such as BIOLEGEND 24F.10C12 Mouse IgG2a, κ isotype (catalog #329602 Biolegend, Inc., San Diego, CA), SIGMA anti-PD-L2 antibody (catalog #SAB3500395, Sigma-Aldrich Co., St. Louis, MO), or other commercially-available anti-PD-L2 antibodies known to one of ordinary skill in the art.

2. Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.,* 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 µg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

3. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total. In some embodiments, IL-2 is administered in 1, 2, 3, 4, 5, or 6 doses. In some embodiments, IL-2 is administered at a maximum dosage of up to 6 doses.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises 18×10$^6$ IU/m$^2$ administered intravenously over 6 hours, followed by 18×10$^6$ IU/m$^2$ administered intravenously over 12 hours, followed by 18×10$^6$ IU/m$^2$ administered intravenously over 24 hrs, followed by 4.5×10$^6$ IU/m$^2$ administered intravenously over 72 hours. This treatment cycle may be repeated every 28 days for a maximum of four cycles. In an embodiment, a decrescendo IL-2 regimen comprises 18,000,000 IU/m$^2$ on day 1, 9,000,000 IU/m$^2$ on day 2, and 4,500,000 IU/m$^2$ on days 3 and 4.

In an embodiment, the IL-2 regimen comprises administration of pegylated IL-2 every 1, 2, 4, 6, 7, 14 or 21 days at a dose of 0.10 mg/day to 50 mg/day.

4. Additional Methods of Treatment

In another embodiment, the invention provides a method for treating a subject with cancer comprising administering to the subject a therapeutically effective dosage of the therapeutic TIL population described in any of the preceding paragraphs above.

In another embodiment, the invention provides a method for treating a subject with cancer comprising administering to the subject a therapeutically effective dosage of the TIL composition described in any of the preceding paragraphs above.

In another embodiment, the invention provides the method for treating a subject with cancer described in any of the preceding paragraphs above modified such that prior to administering the therapeutically effective dosage of the therapeutic TIL population and the TIL composition described in any of the preceding paragraphs above, respectively, a non-myeloablative lymphodepletion regimen has been administered to the subject.

In another embodiment, the invention provides the method for treating a subject with cancer described in any of the preceding paragraphs above modified such that the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In another embodiment, the invention provides the method for treating a subject with cancer described in any of the preceding paragraphs above modified to further comprise the step of treating the subject with a high-dose IL-2 regimen starting on the day after administration of the TIL cells to the subject.

In another embodiment, the invention provides the method for treating a subject with cancer described in any of the preceding paragraphs above modified such that the high-dose IL-2 regimen comprises 600,000 or 720,000 IU/kg administered as a 15-minute bolus intravenous infusion every eight hours until tolerance.

In another embodiment, the invention provides the method for treating a subject with cancer described in any of the preceding paragraphs above modified such that the cancer is a solid tumor.

In another embodiment, the invention provides the method for treating a subject with cancer described in any of the preceding paragraphs above modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the method for treating a subject with cancer described in any of the preceding paragraphs above modified such that the cancer is melanoma, HNSCC, cervical cancers, NSCLC, glioblastoma (including GBM), and gastrointestinal cancer.

In another embodiment, the invention provides the method for treating a subject with cancer described in any of the preceding paragraphs above e modified such that the cancer is melanoma.

In another embodiment, the invention provides the method for treating a subject with cancer described in any of the preceding paragraphs above modified such that the cancer is HNSCC.

In another embodiment, the invention provides the method for treating a subject with cancer described in any of the preceding paragraphs above modified such that the cancer is a cervical cancer.

In another embodiment, the invention provides the method for treating a subject with cancer described in any of the preceding paragraphs above modified such that the cancer is NSCLC.

In another embodiment, the invention provides the method for treating a subject with cancer described in any of the preceding paragraphs above modified such that the cancer is glioblastoma (including GBM).

In another embodiment, the invention provides the method for treating a subject with cancer described in any of the preceding paragraphs above modified such that the cancer is gastrointestinal cancer.

In another embodiment, the invention provides the method for treating a subject with cancer described in any of the preceding paragraphs above modified such that the cancer is a hypermutated cancer.

In another embodiment, the invention provides the method for treating a subject with cancer described in any of the preceding paragraphs above modified such that the cancer is a pediatric hypermutated cancer.

In another embodiment, the invention provides the therapeutic TIL population described in any of the preceding paragraphs above for use in a method for treating a subject with cancer comprising administering to the subject a therapeutically effective dosage of the therapeutic TIL population.

In another embodiment, the invention provides the TIL composition described in any of the preceding paragraphs above for use in a method for treating a subject with cancer comprising administering to the subject a therapeutically effective dosage of the TIL composition.

In another embodiment, the invention provides the therapeutic TIL population described in any of the preceding paragraphs above or the TIL composition described in any of the preceding paragraphs above modified such that prior to administering to the subject the therapeutically effective dosage of the therapeutic TIL population described in any of the preceding paragraphs above or the TIL composition described in any of the preceding paragraphs above, a non-myeloablative lymphodepletion regimen has been administered to the subject.

In another embodiment, the invention provides the therapeutic TIL population or the TIL composition described in any of the preceding paragraphs above modified such that the non-myeloablative lymphodepletion regimen comprises the steps of administration of cyclophosphamide at a dose of 60 mg/m²/day for two days followed by administration of fludarabine at a dose of 25 mg/m²/day for five days.

In another embodiment, the invention provides the therapeutic TIL population or the TIL composition described in any of the preceding paragraphs above modified to further comprise the step of treating patient with a high-dose IL-2 regimen starting on the day after administration of the TIL cells to the patient.

In another embodiment, the invention provides the therapeutic TIL population or the TIL composition described in any of the preceding paragraphs above modified such that the high-dose IL-2 regimen comprises 600,000 or 720,000 IU/kg administered as a 15-minute bolus intravenous infusion every eight hours until tolerance.

In another embodiment, the invention provides the therapeutic TIL population or the TIL composition described in any of the preceding paragraphs above modified such that the cancer is a solid tumor.

In another embodiment, the invention provides the therapeutic TIL population or the TIL composition described in any of the preceding paragraphs above modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the therapeutic TIL population or the TIL composition described in any of the preceding paragraphs above modified such that the cancer is melanoma, HNSCC, cervical cancers, NSCLC, glioblastoma (including GBM), and gastrointestinal cancer.

In another embodiment, the invention provides the therapeutic TIL population or the TIL composition described in any of the preceding paragraphs above modified such that the cancer is melanoma.

In another embodiment, the invention provides the therapeutic TIL population or the TIL composition described in any of the preceding paragraphs above modified such that the cancer is HNSCC.

In another embodiment, the invention provides the therapeutic TIL population or the TIL composition described in any of the preceding paragraphs above modified such that the cancer is a cervical cancer.

In another embodiment, the invention provides the therapeutic TIL population or the TIL composition described in any of the preceding paragraphs above modified such that the cancer is NSCLC.

In another embodiment, the invention provides the therapeutic TIL population or the TIL composition described in any of the preceding paragraphs above modified such that the cancer is glioblastoma (including GBM).

In another embodiment, the invention provides the therapeutic TIL population or the TIL composition described in any of the preceding paragraphs above modified such that the cancer is gastrointestinal cancer.

In another embodiment, the invention provides the therapeutic TIL population or the TIL composition described in any of the preceding paragraphs above modified such that the cancer is a hypermutated cancer.

In another embodiment, the invention provides the therapeutic TIL population or the TIL composition described in any of the preceding paragraphs above modified such that the cancer is a pediatric hypermutated cancer.

In another embodiment, the invention provides the use of the therapeutic TIL population described in any of any of the preceding paragraphs above in a method of treating cancer in a subject comprising administering to the subject a therapeutically effective dosage of the therapeutic TIL population.

In another embodiment, the invention provides the use of the TIL composition described in any of the preceding paragraphs above in a method of treating cancer in a subject comprising administering to the subject a therapeutically effective dosage of the TIL composition.

In another embodiment, the invention provides the use of the therapeutic TIL population described in any of the preceding paragraphs above or the TIL composition described in any of the preceding paragraphs above in a method of treating cancer in a subject comprising administering to the subject a non-myeloablative lymphodepletion regimen and then administering to the subject the therapeutically effective dosage of the therapeutic TIL population described in any of the preceding paragraphs above or the therapeutically effective dosage of the TIL composition described in any of the preceding paragraphs above.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Preparation of Media for Pre-Rep and Rep Processes

This Example describes the procedure for the preparation of tissue culture media for use in protocols involving the culture of tumor infiltrating lymphocytes (TIL) derived from various tumor types including non-small cell lung carcinoma (NSCLC). This media can be used for preparation of any of the TILs described in the present application and Examples.

Preparation of CM1

Removed the following reagents from cold storage and warmed them in a 37° C. water bath: (RPMI1640, Human AB serum, 200 mM L-glutamine). Prepared CM1 medium according to Table 18 below by adding each of the ingredients into the top section of a 0.2 um filter unit appropriate to the volume to be filtered. Store at 4° C.

TABLE 40

| Preparation of CM1 | | | |
| --- | --- | --- | --- |
| Ingredient | Final concentration | Final Volume 500 ml | Final Volume 1L |
| RPMI1640 | NA | 450 ml | 900 ml |
| Human AB serum, heat-inactivated 10% | 50 ml | 100 ml | |
| 200 mM L-glutamine | 2 mM | 5 ml | 10 ml |
| 55 mM BME | 55 μM | 0.5 ml | 1 ml |
| 50 mg/ml gentamicin sulfate | 50 μg/ml | 0.5 ml | 1 ml |

On the day of use, prewarmed required amount of CM1 in 37° C. water bath and add 6000 IU/ml IL-2.

Additional supplementation—as needed according to Table 41.

TABLE 41

| Additional supplementation of CM1 as needed. | | | |
| --- | --- | --- | --- |
| Supplement | Stock concentration | Dilution | Final concentration |
| GlutaMAX ™ | 200 mM | 1:100 | 2 mM |
| Penicillin/ streptomycin | 10,000 U/ml penicillin 10,000 μg/ml streptomycin | 1:100 | 100 U/ml penicillin 100 μg/ml streptomycin |
| Amphotericin B | 250 μg/ml | 1:100 | 2.54 ml |

Preparation of CM2

Removed prepared CM1 from refrigerator or prepare fresh CM1 as per Section 7.3 above. Removed AIM-V® from refrigerator and prepared the amount of CM2 needed by mixing prepared CM1 with an equal volume of AIM-V® in a sterile media bottle. Added 3000 IU/ml IL-2 to CM2 medium on the day of usage. Made sufficient amount of CM2 with 3000 IU/ml IL-2 on the day of usage. Labeled the CM2 media bottle with its name, the initials of the preparer, the date it was filtered/prepared, the two-week expiration date and store at 4° C. until needed for tissue culture.

Preparation of CM3

Prepared CM3 on the day it was required for use. CM3 was the same as AIM-V® medium, supplemented with 3000 IU/ml IL-2 on the day of use. Prepared an amount of CM3 sufficient to experimental needs by adding IL-2 stock solution directly to the bottle or bag of AIM-V. Mixed well by gentle shaking. Label bottle with "3000 IU/ml IL-2" immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days storage at 4° C.

Preparation of CM4

CM4 was the same as CM3, with the additional supplement of 2 mM GlutaMAX™ (final concentration). For every 1L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with "3000 IL/nil IL-2 and GlutaMAX" immediately after adding to the AIM-V. If there was excess CM4, stored it in bottles at 4° C. labeled with the media name, "GlutaMAX", and its expiration date (7 days after preparation). Discarded media supplemented with IL-2 after 7-days storage at 4° C.

Example 2: Use of IL-2, IL-15, and IL-21 Cytokine Cocktail

This example describes the use of IL-2, IL-15, and IL-21 cytokines, which serve as additional T cell growth factors, in combination with the TIL process of Examples A to G.

Using the processes described herein, TILs can be grown from non-small cell lung carcinoma (NSCLC) tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a+ and IFN-γ) and TCR Vβ repertoire. IL-15 and IL-21 are described elsewhere herein and in Gruijl, et al., IL-21 promotes the expansion of CD27+ CD28+ tumor infiltrating lymphocytes with high cytotoxic potential and low collateral expansion of regulatory T cells, Santegoets, S. J., J Transl Med., 2013, 11:37.

The results can show that enhanced TIL expansion (>20%), in both CD4$^+$ and CD8$^+$ cells in the IL-2, IL-15, and IL-21 treated conditions can observed relative to the IL-2 only conditions. There was a skewing towards a predominantly CD8$^+$ population with a skewed TCR Vβ repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 3: Qualifying Individual Lots of Gamma-Irradiated Peripheral Mononuclear Cells This Example describes a novel abbreviated procedure for qualifying individual lots of gamma-irradiated peripheral mononuclear cells (PBMCs, also known as MNC) for use as allogeneic feeder cells in the exemplary methods described herein.

Each irradiated MNC feeder lot was prepared from an individual donor. Each lot or donor was screened individually for its ability to expand TIL in the REP in the presence of purified anti-CD3 (clone OKT3) antibody and interleukin-2 (IL-2). In addition, each lot of feeder cells was tested without the addition of TIL. to verify that the received dose of gamma radiation was sufficient to render them replication incompetent.

BACKGROUND

Gamma-irradiated, growth-arrested MNC feeder cells were required for REP of TIL. Membrane receptors on the feeder MNCs bind to anti-CD3 (clone OKT3) antibody and crosslink to TIL in the REP flask, stimulating the TIL to expand. Feeder lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable feeder cells as this can result in Graft-Versus-Host Disease (GVHD). Feeder cells are therefore growth-arrested by dosing the cells with gamma-irradiation, resulting in double strand DNA breaks and the loss of cell viability of the MNC cells upon reculture.

Evaluation Criteria and Experimental Set-Up

Feeder lots were evaluated on two criteria: 1) their ability to expand TIL in co-culture >100-fold and 2) their replication incompetency.

Feeder lots were tested in mini-REP format utilizing two primary pre-REP TIL lines grown in upright T25 tissue culture flasks. Feeder lots were tested against two distinct TIL lines, as each TIL line is unique in its ability to proliferate in response to activation in a REP. As a control, a lot of irradiated MNC feeder cells which has historically been shown to meet the criteria above was run alongside the test lots.

To ensure that all lots tested in a single experiment receive equivalent testing, sufficient stocks of the same pre-REP TIL lines were available to test all conditions and all feeder lots.

For each lot of feeder cells tested, there was a total of six T25 flasks: Pre-REP TIL line #1 (2 flasks); Pre-REP TIL line #2 (2 flasks); and Feeder control (2 flasks). Flasks containing TIL lines #1 and #2 evaluated the ability of the feeder lot to expand TIL. The feeder control flasks evaluated the replication incompetence of the feeder lot.

EXPERIMENTAL PROTOCOL

Day –2/3, Thaw of TIL Lines

Prepared CM2 medium. Warmed CM2 in 37° C. water bath. Prepared 40 ml of CM2 supplemented with 3000 IU/ml IL-2. Keep warm until use. Placed 20 ml of pre-warmed CM2 without IL-2 into each of two 50 ml conical tubes labeled with names of the TIL lines used. Removed the two designated pre-REP TIL lines from LN2 storage and transferred the vials to the tissue culture room. Thawed vials by placing them inside a sealed zipper storage bag in a 37° C. water bath until a small amount of ice remains.

Using a sterile transfer pipet, immediately transferred the contents of vial into the 20 ml of CM2 in the prepared, labeled 50 ml conical tube. QS to 40 ml using CM2 without IL-2 to wash cells. Centrifuged at 400×CF for 5 minutes. Aspirated the supernatant and resuspend in 5 ml warm CM2 supplemented with 3000 IU/ml IL-2.

Removed small aliquot (20 μl) in duplicate for cell counting using an automated cell counter. Record the counts. While counting, placed the 50 ml conical tube with TIL cells into a humidified 37° C., 5% $CO_2$ incubator, with the cap loosened to allow for gas exchange. Determined cell concentration and diluted TIL to $1 \times 10^6$ cells/ml in CM2 supplemented with IL-2 at 3000 IU/ml.

Cultured in 2 ml/well of a 24-well tissue culture plate in as many wells as needed in a humidified 37° C. incubator until Day 0 of the mini-REP. Cultured the different TIL lines in separate 24-well tissue culture plates to avoid confusion and potential cross-contamination.

Day 0, Initiate Mini-REP

Prepared enough CM2 medium for the number of feeder lots to be tested. (e.g., for testing 4 feeder lots at one time, prepared 800 ml of CM2 medium). Aliquoted a portion of the CM2 prepared above and supplemented it with 3000 IU/ml IL-2 for the culturing of the cells. (e.g., for testing 4 feeder lots at one time, prepare 500 ml of CM2 medium with 3000 IU/ml IL-2).

Working with each TIL line separately to prevent cross-contamination, removed the 24-well plate with TIL culture from the incubator and transferred to the BSC.

Using a sterile transfer pipet or 100-1000 μl Pipettor and tip, removed about 1 ml of medium from each well of TIL to be used and place in an unused well of the 24-well tissue culture plate.

Using a fresh sterile transfer pipet or 100-1000 μl Pipettor and tip, mixed remaining medium with TIL in wells to resuspend the cells and then transferred the cell suspension to a 50 ml conical tube labeled with the TIL name and recorded the volume.

Washed the wells with the reserved media and transferred that volume to the same 50 ml conical tube. Spun the cells at 400×CF to collect the cell pellet. Aspirated off the media supernatant and resuspend the cell pellet in 2-5 ml of CM2 medium containing 3000 IU/ml IL-2, volume to be used based on the number of wells harvested and the size of the pellet—volume should be sufficient to ensure a concentration of $>1.3 \times 10^6$ cells/ml.

Using a serological pipet, mixed the cell suspension thoroughly and recorded the volume. Removed 200 μl for a cell count using an automated cell counter. While counting, placed the 50 ml conical tube with TIL cells into a humidified, 5% $CO_2$, 37° C. incubator, with the cap loosened to allow gas exchange. Recorded the counts.

Removed the 50 ml conical tube containing the TIL cells from the incubator and resuspend them cells at a concentration of $1.3 \times 10^6$ cells/ml in warm CM2 supplemented with 3000 IU/ml IL-2. Returned the 50 ml conical tube to the incubator with a loosened cap.

Repeated steps above for the second TIL line.

Just prior to plating the TIL into the T25 flasks for the experiment, TIL were diluted 1:10 for a final concentration of $1.3\times10^5$ cells/ml as per below.

Prepare MACS GMP CD3 Pure (OKT3) Working Solution

Took out stock solution of OKT3 (1 mg/ml) from 4° C. refrigerator and placed in BSC. A final concentration of 30 ng/ml OKT3 was used in the media of the mini-REP.

600 ng of OKT3 were needed for 20 ml in each T25 flask of the experiment; this was the equivalent of 60 μl of a 10 ng/ml solution for each 20 ml, or 360 μl for all 6 flasks tested for each feeder lot.

For each feeder lot tested, made 400 μl of a 1:100 dilution of 1 mg/ml OKT3 for a working concentration of 10 ng/ml (e.g., for testing 4 feeder lots at one time, make 1600 μl of a 1:100 dilution of 1 mg/ml OKT3: 16 μl of 1 mg/ml OKT3+1.584 ml of CM2 medium with 3000 IU/ml IL-2.)

Prepare T25 Flasks

Labeled each flask and filled flask with the CM2 medium prior to preparing the feeder cells. Placed flasks into 37° C. humidified 5% $CO_2$ incubator to keep media warm while waiting to add the remaining components. Once feeder cells were prepared, the components will be added to the CM2 in each flask.

TABLE 42

| | Solutions | |
|---|---|---|
| Component | Volume in co-culture flasks | Volume in control (feeder only) flasks |
| CM2 + 3000 IU/ml IL-2 | 18 ml | 19 ml |
| MNC: $1.3 \times 10^7$/ml in CM2 + 3000 IU IL-2 (final concentration $1.3 \times 10^7$/flask) | 1 ml | 1 ml |
| OKT3: 10 μl/ml in CM2 + 3000 IU IL-2 | 60 μl | 60 μl |
| TIL: $1.3 \times 10^5$/ml in CM2 with 3000 IU of IL-2 (final concentration $1.3 \times 10^5$/flask) | 1 ml | 0 |

Prepare Feeder Cells

A minimum of $78\times10^6$ feeder cells were needed per lot tested for this protocol. Each 1 ml vial frozen by SDBB had $100\times10^6$ viable cells upon freezing. Assuming a 50% recovery upon thaw from LN2 storage, it was recommended to thaw at least two 1 ml vials of feeder cells per lot giving an estimated $100\times10^6$ viable cells for each REP. Alternately, if supplied in 1.8 ml vials, only one vial provided enough feeder cells.

Before thawing feeder cells, pre-warmed approximately 50 ml of CM2 without IL-2 for each feeder lot to be tested. Removed the designated feeder lot vials from LN2 storage, placed in zipper storage bag, and place on ice. Thawed vials inside closed zipper storage bag by immersing in a 37° C. water bath. Removed vials from zipper bag, spray or wipe with 70% EtOH and transferred vials to BSC.

Using a transfer pipet immediately transferred the contents of feeder vials into 30 ml of warm CM2 in a 50 ml conical tube. Washed vial with a small volume of CM2 to remove any residual cells in the vial. Centrifuged at 400×CF for 5 minutes. Aspirated the supernatant and resuspended in 4 ml warm CM2 plus 3000 IU/ml IL-2. Removed 200 μl for cell counting using the Automated Cell Counter. Recorded the counts.

Resuspended cells at $1.3\times10^7$ cells/ml in warm CM2 plus 3000 IU/ml IL-2. Diluted TIL cells from $1.3\times10^6$ cells/ml to $1.3\times10^5$ cells/ml.

Setup Co-Culture

Diluted TIL cells from $1.3\times10^6$ cells/ml to $1.3\times10^5$ cells/ml. Added 4.5 ml of CM2 medium to a 15 ml conical tube. Removed TIL cells from incubator and resuspended well using a 10 ml serological pipet. Removed 0.5 ml of cells from the $1.3\times10^6$ cells/ml TIL suspension and added to the 4.5 ml of medium in the 15 ml conical tube. Returned TIL stock vial to incubator. Mixed well. Repeated for the second TIL line.

Transferred flasks with pre-warmed media for a single feeder lot from the incubator to the BSC. Mixed feeder cells by pipetting up and down several times with a 1 ml pipet tip and transferred 1 ml ($1.3\times10^7$ cells) to each flask for that feeder lot. Added 60 μl of OKT3 working stock (10 μg/ml) to each flask. Returned the two control flasks to the incubator.

Transferred 1 ml ($1.3\times10^5$) of each TIL lot to the correspondingly labeled T25 flask. Returned flasks to the incubator and incubate upright. Did not disturb until Day 5.

Repeated for all feeder lots tested.

Day 5, Media Change

Prepared CM2 with 3000 IU/ml IL-2. 10 ml is needed for each flask. With a 10 ml pipette, transferred 10 ml warm CM2 with 3000 IU/ml IL-2 to each flask. Returned flasks to the incubator and incubated upright until Day 7. Repeated for all feeder lots tested.

Day 7, Harvest

Removed flasks from the incubator and transfer to the BSC, care as taken not to disturb the cell layer on the bottom of the flask. Without disturbing the cells growing on the bottom of the flasks, removed 10 ml of medium from each test flask and 15 ml of medium from each of the control flasks.

Using a 10 ml serological pipet, resuspended the cells in the remaining medium and mix well to break up any clumps of cells. After thoroughly mixing cell suspension by pipetting, removed 200 μl for cell counting. Counted the TIL using the appropriate standard operating procedure in conjunction with the automatic cell counter equipment. Recorded counts in Day 7.

Repeated for all feeder lots tested.

Feeder control flasks were evaluated for replication incompetence and flasks containing TIL were evaluated for fold expansion from Day 0 according to Table TT below.

Day 7, Continuation of Feeder Control Flasks to Day 14

After completing the Day 7 counts of the feeder control flasks, added 15 ml of fresh CM2 medium containing 3000 IU/ml IL-2 to each of the control flasks. Returned the control flasks to the incubator and incubated in an upright position until Day 14.

Day 14, Extended Non-Proliferation of Feeder Control Flasks

Removed flasks from the incubator and transfer to the BSC, care was taken not to disturb the cell layer on the bottom of the flask. Without disturbing the cells growing on the bottom of the flasks, removed approximately 17 ml of medium from each control flasks. Using a 5 ml serological pipet, resuspended the cells in the remaining medium and mixed well to break up any clumps of cells. Recorded the volumes for each flask.

After thoroughly mixing cell suspension by pipetting, removed 200 μl for cell counting. Counted the TIL using the appropriate standard operating procedure in conjunction with the automatic cell counter equipment. Recorded counts.

Repeated for all feeder lots tested.

Results and Acceptance Criteria

Results

The dose of gamma irradiation was sufficient to render the feeder cells replication incompetent. All lots were expected to meet the evaluation criteria and also demonstrated a reduction in the total viable number of feeder cells remaining on Day 7 of the REP culture compared to Day 0.

All feeder lots were expected to meet the evaluation criteria of 100-fold expansion of TIL growth by Day 7 of the REP culture.

Day 14 counts of Feeder Control flasks were expected to continue the non-proliferative trend seen on Day 7.

Acceptance Criteria

The following acceptance criteria were met for each replicate TIL line tested for each lot of feeder cells Acceptance was two-fold, as follows (outlined in Table 27 below).

TABLE 43

Acceptance Criteria

| Test | Acceptance criteria |
|---|---|
| Irradiation of MNC/ Replication Incompetence | No growth observed at 7 and 14 days |
| TIL expansion | At least a 100-fold expansion of each TIL (minimum of $1.3 \times 10^7$ viable cells) |

Evaluated whether the dose of radiation was sufficient to render the MNC feeder cells replication incompetent when cultured in the presence of 30 ng/ml OKT3 antibody and 3000 IU/ml IL-2. Replication incompetence was evaluated by total viable cell count (TVC) as determined by automated cell counting on Day 7 and Day 14 of the REP.

Acceptance criteria was "No Growth," meaning the total viable cell number has not increased on Day 7 and Day 14 from the initial viable cell number put into culture on Day 0 of the REP.

Evaluated the ability of the feeder cells to support TIL expansion. TIL growth was measured in terms of fold expansion of viable cells from the onset of culture on Day 0 of the REP to Day 7 of the REP. On Day 7, TIL cultures achieved a minimum of 100-fold expansion, (i.e., greater than 100 times the number of total viable TIL cells put into culture on REP Day 0), as evaluated by automated cell counting.

Contingency Testing of MNC Feeder Lots that do not Meet Acceptance Criteria

In the event that an MNC feeder lot did not meet the either of the acceptance criteria outlined above, the following steps will be taken to retest the lot to rule out simple experimenter error as its cause.

If there are two or more remaining satellite testing vials of the lot, then the lot was retested. If there were one or no remaining satellite testing vials of the lot, then the lot was failed according to the acceptance criteria listed above.

In order to be qualified, the lot in question and the control lot had to achieve the acceptance criteria above. Upon meeting these criteria, the lot was then released for use.

Example 4: Qualifying Individual Lots of Gamma-Irradiated Peripheral Blood Mononuclear Cells This Example describes a novel abbreviated procedure for qualifying individual lots of gamma-irradiated peripheral blood mononuclear cells (PBMC) for use as allogeneic feeder cells in the exemplary methods described herein. This example provides a protocol for the evaluation of irradiated PBMC cell lots for use in the production of clinical lots of TIL. Each irradiated PBMC lot was prepared from an individual donor. Over the course of more than 100 qualification protocols, it was been shown that, in all cases, irradiated PBMC lots from SDBB (San Diego Blood Bank) expand TIL >100-fold on Day 7 of a REP. This modified qualification protocol was intended to apply to irradiated donor PBMC lots from SDBB which were then further tested to verify that the received dose of gamma radiation was sufficient to render them replication incompetent. Once demonstrated that they maintained replication incompetence over the course of 14 days, donor PBMC lots were considered "qualified" for usage to produce clinical lots of TIL.

BACKGROUND

Gamma-irradiated, growth-arrested PBMC were required for current standard REP of TIL. Membrane receptors on the PBMCs bind to anti-CD3 (clone OKT3) antibody and cross-link to TIL in culture, stimulating the TIL to expand. PBMC lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable PBMCs as this could result in Graft-Versus-Host Disease (GVHD). Donor PBMCs are therefore growth-arrested by dosing the cells with gamma-irradiation, resulting in double strand DNA breaks and the loss of cell viability of the PBMCs upon reculture.

Evaluation Criteria 7.2.1 Evaluation criterion for irradiated PBMC lots was their replication incompetency.

Experimental Set-Up

Feeder lots were tested in mini-REP format as if they were to be co-cultured with TIL, using upright T25 tissue culture flasks. Control lot: One lot of irradiated PBMCs, which had historically been shown to meet the criterion of 7.2.1, was run alongside the experimental lots as a control. For each lot of irradiated donor PBMC tested, duplicate flasks were run.

Experimental Protocol

Day 0

Prepared ~90 ml of CM2 medium for each lot of donor PBMC to be tested. Kept CM2 warm in 37° C. water bath. Thawed an aliquot of $6\times10^6$ IU/ml IL-2. Returned the CM2 medium to the BSC, wiping with 70% EtOH prior to placing in hood. For each lot of PBMC tested, removed about 60 ml of CM2 to a separate sterile bottle. Added IL-2 from the thawed $6\times10^6$ IU/ml stock solution to this medium for a final concentration of 3000 IU/ml. Labeled this bottle as "CM2/ IL2" (or similar) to distinguish it from the unsupplemented CM2.

Prepare OKT3

Took out the stock solution of anti-CD3 (OKT3) from the 4° C. refrigerator and placed in the BSC. A final concentration of 30 ng/ml OKT3 was used in the media of the mini-REP. Prepared a 10 µg/ml working solution of anti-CD3 (OKT3) from the 1 mg/ml stock solution. Placed in refrigerator until needed.

For each PBMC lot tested, prepare 150 µl of a 1:100 dilution of the anti-CD3 (OKT3) stock. For example, for testing 4 PBMC lots at one time, prepare 600 µl of 10 µg/ml anti-CD3 (OKT3) by adding 6 µl of the 1 mg/ml stock solution to 594 µl of CM2 supplemented with 3000 IU/ml IL-2.

Prepare Flasks

Added 19 ml per flask of CM2/IL-2 to the labeled T25 flasks and placed flasks into 37° C., humidified, 5% CO$_2$ incubator while preparing cells.

Prepare Irradiate PBMC

Retrieved vials of PBMC lots to be tested from LN2 storage. These were placed at −80° C. or kept on dry ice prior to thawing. Placed 30 ml of CM2 (without IL-2 supplement) into 50 ml conical tubes for each lot to be thawed. Labeled each tube with the different lot numbers of the PBMC to be thawed. Capped tubes tightly and place in 37° C. water bath prior to use. As needed, returned 50 ml conical tubes to the BSC, wiping with 70% EtOH prior to placing in the hood.

Removed a vial PBMC from cold storage and place in a floating tube rack in a 37° C. water bath to thaw. Allowed thaw to proceed until a small amount of ice remains in the vial. Using a sterile transfer pipet, immediately transferred the contents of the vial into the 30 ml of CM2 in the 50 ml conical tube. Removed about 1 ml of medium from the tube to rinse the vial; returned rinse to the 50 ml conical tube. Capped tightly and swirl gently to wash cells.

Centrifuged at 400×g for 5 min at room temperature. Aspirated the supernatant and resuspend the cell pellet in 1 ml of warm CM2/IL-2 using a 1000 µl pipet tip. Alternately, prior to adding medium, resuspended cell pellet by dragging capped tube along an empty tube rack. After resuspending the cell pellet, brought volume to 4 ml using CM2/IL-2 medium. Recorded volume.

Removed a small aliquot (e.g., 100 µl) for cell counting using an automated cell counter. Performed counts in duplicate according to the particular automated cell counter SOP. It most likely was necessary to perform a dilution of the PBMC prior to performing the cell counts. A recommended starting dilution was 1:10, but this varied depending on the type of cell counter used. Recorded the counts.

Adjusted concentration of PBMC to $1.3 \times 10^7$ cells/ml using CM2/IL-2 medium. Mixed well by gentle swirling or by gently aspirating up-and-down using a serological pipet.

Set Up Culture Flasks

Returned two labeled T25 flasks to the BSC from the tissue culture incubator. Returned the 10 µg/ml vial of anti-CD3/OKT3 to the BSC. Added 1 ml of the $1.3 \times 10^7$ PBMC cell suspension to each flask. Added 60 µl of the 10 µg/ml anti-CD3/OKT3 to each flask. Returned capped flasks to the tissue culture incubators for 14 days of growth without disturbance. Placed anti-CD3/OKT3 vial back into the refrigerator until needed for the next lot. Repeated for each lot of PBMC to be evaluated.

Day 14, Measurement of Non-Proliferation of PBMC

Returned the duplicate T25 flasks to the BSC. For each flask, using a fresh 10 ml serological pipet, removed ~17 ml from each of the flasks, then carefully pulled up the remaining media to measure the volume remaining in the flasks. Recorded volume.

Mixed sample well by pipetting up and down using the same serological pipet.

Removed a 200 µl sample from each flask for counting. Counted cells using an automated cell counter. Repeated steps 7.4.26-7.4.31 for each lot of PBMC being evaluated.

Results and Acceptance Criterion

Results

The dose of gamma irradiation was expected to be sufficient to render the feeder cells replication incompetent. All lots were expected to meet the evaluation criterion, demonstrating a reduction in the total viable number of feeder cells remaining on Day 14 of the REP culture compared to Day 0.

Acceptance Criterion

The following acceptance criterion were met for each irradiated donor PBMC lot tested: "No growth"—meant that the total number of viable cells on Day 14 was less than the initial viable cell number put into culture on Day 0 of the REP.

Contingency Testing of PBMC Lots which do not Meet Acceptance Criterion.

In the event than an irradiated donor PBMC lot did not meet the acceptance criterion above, the following steps were taken to retest the lot to rule out simple experimenter error as the cause of its failure. If there were two or more remaining satellite vials of the lot, then the lot was retested. If there are one or no remaining satellite vials of the lot, then the lot was failed according to the acceptance criterion above.

To be qualified, a PBMC lot going through contingency testing had both the control lot and both replicates of the lot in question achieve the acceptance criterion. Upon meeting this criterion, the lot was then released for use.

Example 5: Preparation of IL-2 Stock Solution (Cellgenix)

This Example describes the process of dissolving purified, lyophilized recombinant human interleukin-2 into stock samples suitable for use in further tissue culture protocols, including all of those described in the present application and Examples, including those that involve using rhIL-2.

Procedure

Prepared 0.2% Acetic Acid solution (HAc). Transferred 29 mL sterile water to a 50 mL conical tube. Added 1 mL 1N acetic acid to the 50 mL conical tube. Mixed well by inverting tube 2-3 times. Sterilized the HAc solution by filtration using a Steriflip filter Prepare 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution ($6 \times 10^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left( \frac{\text{Vial Mass (mg)} \times \text{Biological Activity} \left( \frac{IU}{mg} \right)}{6 \times 10^6 \frac{IU}{mL}} \right) - HAc \text{ vol (mL)} =$$

$$1\% \ HSA \text{ vol (mL)}$$

For example, according to CellGenix's rhIL-2 lot 10200121 COA, the specific activity for the 1 mg vial is $25 \times 10^6$ IU/mg. It recommends reconstituting the rhIL-2 in 2 mL 0.2% HAc.

$$\left( \frac{1 \text{ mg} \times 25 \times 10^6 \frac{IU}{mg}}{6 \times 10^6 \frac{IU}{mL}} \right) - 2 \text{ mL} = 2.167 \text{ mL } HSA$$

Wiped rubber stopper of IL-2 vial with alcohol wipe. Using a 16G needle attached to a 3 mL syringe, injected recommended volume of 0.2% HAc into vial. Took care to not dislodge the stopper as the needle is withdrawn. Inverted vial 3 times and swirled until all powder is dissolved. Carefully removed the stopper and set aside on an alcohol wipe. Added the calculated volume of 1% HSA to the vial.

Storage of rhIL-2 solution. For short-term storage (<72 hrs), stored vial at 4° C. For long-term storage (>72 hrs), aliquoted vial into smaller volumes and stored in cryovials at −20° C. until ready to use. Avoided freeze/thaw cycles. Expired 6 months after date of preparation. Rh-IL-2 labels included vendor and catalog number, lot number, expiration date, operator initials, concentration and volume of aliquot.

Example 6: Cryopreservation Process

This example describes the cryopreservation process method for TILs prepared with the abbreviated, closed procedure described in Example G using the CryoMed Controlled Rate Freezer, Model 7454 (Thermo Scientific).

The equipment used was as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provides for a 0.5° C. rate from nucleation to −20° C. and 1° C. per minute cooling rate to −80° C. end temperature. The program parameters are as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

Example 7: NSCLC Treatment with Anti-PD-1 Antibodies

Patient Population:
Treatment naïve NSCLC or post chemotherapy but anti-PD-1/PD-L1 naïve Treatment schedules:
Tumor fragment, treat with up to 4 doses of anti-PD-1/PD-L1, treat the primary refractory patients with TIL product which is cryo-preserved and ready for use upon immediate progression. Primary refractory patients may have progressed after 2 doses.
Relapse patients can also be treated upon progression (the timing may vary from months to years later).
Full strength IL-2 up to 6 doses.
Patient populations to further consider with the same manufacturing permutations noted earlier:
Treatment naïve NSCLC or post chemotherapy but anti-PD-1/PD-L1 naïve
Treatment naïve NSCLC or post chemotherapy but anti-PD-1/PD-L1 naïve who have low expression of PD-L1
Treatment naïve NSCLC or post chemotherapy but anti-PD-1/PD-L1 naïve who have low expression of PD-L1 and/or have bulky disease at baseline (for example, bulky disease is indicated where the maximal tumor diameter is greater than 7 cm measured in either the transverse or coronal plane or swollen lymph nodes with a short-axis diameter of 20 mm or greater on CT were defined as bulky; see for example, Samejima, J., *Japanese Journal of Clinical Oncology*, 45(11): 1050-10541 2015, incorporated herein by reference)

Example 8: Gen 3 Exemplary Process

The example provides a comparison between the Gen 2 and Gen 3 processes. This example describes the development of a robust TIL expansion platform. The modifications to the Gen 2 process reduce risk and streamline the manufacturing process by reducing the number of operator interventions, reduce the overall time of manufacturing, optimize the use of reagents, and facilitate a flexible semi-closed and semi-automated cell production process amenable to high-throughput manufacturing on a commercial scale.

Process Gen 2 and Gen 3 TILs are composed of autologous TIL derived from an individual patient through surgical resection of a tumor and then expanded ex vivo. The Priming First Expansion step of the Gen 3 process was a cell culture in the presence of interleukin-2 (IL-2) and the monoclonal antibody OKT3, which targets the T-cell co-receptor CD3 on a scaffold of irradiated peripheral blood mononuclear cells (PBMCs).

The manufacture of Gen 2 TIL products consisted of two phases: 1) pre-Rapid Expansion (Pre-REP) and 2) Rapid Expansion Protocol (REP). During the Pre-REP resected tumors were cut up into ≤50 fragments 2-3 mm in each dimension which were cultured with serum-containing culture medium (RPMI 1640 media containing 10% HuSAB supplemented) and 6,000 IU/mL of Interleukin-2 (IL-2) for a period of 11 days. On day 11 TIL were harvested and introduced into the large-scale secondary REP expansion. The REP consists of activation of ≤200×10⁶ of the viable cells from pre-REP in a co-culture of 5×10⁹ irradiated allogeneic PBMCs feeder cells loaded with 150 ug of monoclonal anti-CD3 antibody (OKT3) in a 5L volume of CM2 supplemented with 3000 IU/mL of rhIL-2 for 5 days. On day 16 the culture is volume reduced 90% and the cell fraction is split into multiple G-REX-500 flasks at ≥1×10⁹ viable lymphocytes/flask and QS to 5L with CM4. TIL are incubated an additional 6 days. The REP is harvested on day 22, washed, formulated, and cryo-preserved prior to shipping at −150° C. to the clinical site for infusion.

The manufacture of Gen 3 TIL products consisted of three phases: 1) Priming First Expansion Protocol 2) Rapid Second Expansion Protocol (also referred to as rapid expansion phase or REP) and 3) Subculture Split. To effect the Priming First Expansion TIL propagation, resected tumor was cut up into ≤120 fragments 2-3 mm in each dimension. On day 0 of the Priming First Expansion, a feeder layer of approximately 2.5×10⁸ allogeneic irradiated PBMCs feeder cells loaded with OKT-3 was established on a surface area of approximately 100 cm² in each of 3 100 MCS vessels. The tumor fragments were distributed among and cultured in the 3 100 MCS vessels each with 500 mL serum-containing CM1 culture medium and 6,000 IU/mL of Interleukin-2 (IL-2) and 15 ug OKT-3 for a period of 7 days. On day 7, REP was initiated by incorporating an additional feeder cell layer of approximately 5×10⁸ allogeneic irradiated PBMCs feeder cells loaded with OKT-3 into the tumor fragmented culture phase in each of the 3 100 MCS vessels and culturing with 500 mL CM2 culture medium and 6,000 IU/mL IL-2 and 30 ug OKT-3. The REP initiation was enhanced by activating the entire Priming First Expansion culture in the same vessel using closed system fluid transfer of OKT3 loaded feeder cells into the 100MCS vessel. For Gen 3, the TIL scale up or split involved process steps where the whole cell culture was scaled to a larger vessel through closed system fluid transfer and was transferred (from 100 M flask to a 500 M flask) and additional 4L of CM4 media was added. The REP cells were harvested on day 16, washed, formulated, and cryo-preserved prior to shipping at −150° C. to the clinical site for infusion.

Overall, the Gen 3 process is a shorter, more scalable, and easily modifiable expansion platform that will accommodate to fit robust manufacturing and process comparability.

TABLE 44

Comparison of Exemplary Gen 2 and
Exemplary Gen 3 manufacturing process.

| Step | Process (Gen 2) | Process (Gen 3) |
|---|---|---|
| Pre REP-day 0 | Up to 50 fragments/ 1-G-Rex 100 MCS-11 days In 1 L of CM1 media + IL-2 (6000 IU/mL) | Whole tumor up to 120 fragments divided evenly among up to 3 flasks. 1 flask: 1-60 fragments 2 flasks: 61-89 fragments 3 flasks 90-120 fragments 7 days in 500 mL of CM1 media + IL-2 (6000 IU/mL) $2.5 \times 10^8$ feeder cells/flask 15 ug OKT-3/flask |
| REP Initiation | Direct to REP-Day 11- $<200e^6$ TIL (1)G-Rex 500 MCS in 5 L CM2 media IL-2 (3000 IU/mL) $5 \times 10^9$ feeder cells 150 ug OKT-3 | Direct to REP-Day 7- all cells TIL-same G-Rex 100 MCS Add 500 CM2 media IL-2 (6000 IU/mL) $5 \times 10^8$ feeder cells/flask 30 ug OKT-3/flask |
| TIL propagation or Scale up | Volume reduce and split cell fraction in up to 5 G-REX 500 MCS 4.5 L CM4 media + IL-2 (3000 IU/mL) $\geq 1 \times 10^9$ TVC/flask Split day 16 | Each G-REX 100 MCS (1 L) transfers to 1 G-REX 500 MCS Add 4 L CM4 media + IL-2 (3000 IU/mL) Scale up on day 9 to 11 |
| Harvest | Harvest day 22, LOVO-automated cell washer | Harvest day 16 LOVO-automated cell washer |
| Final formulation | Cryopreserved Product 300 IU/ml IL2-CS10 in LN₂, multiple aliquots | Cryopreserved product 300 IU/ml IL-2-CS10 in LN₂, multiple aliquots |
| Process time | 22 days | 16 days |

On day 0, for both processes, the tumor was washed 3 times and the fragments were randomized and divided into two pools; one pool per process. For the Gen 2 Process, the fragments were transferred to one GREX 100MCS flask with 1 L of CM1 media containing 6,000IU/mL rhIL-2. For the Gen 3 Process, fragments were transferred to one GREX100MCS flask with 500 mL of CM1 containing 6,000IU/mL rhIL-2, 15 ug OKT-3 and $2.5 \times 10^8$ feeder cells.

Seeding of TIL for Rep initiation day occurred on different days according to each process. For the Gen 2 Process, in which the G-REX 100MCS flask was 90% volume reduced, collected cell suspension was transferred to a new G-REX 500MCS to start REP initiation on day 11 in CM2 media containing IL-2 (3000 IU/mL), plus 5e9 feeder cells and OKT-3 (30 ng/mL). Cells were expanded and split on day 16 into multiple GREX 500 MCS flasks with CM4 media with IL-2 (3000 IU/mL) per protocol. The culture was then harvested and cryopreserved on day 22 per protocol. For the Gen 3 process, the REP initiation occurred on day 7, in which the same G-REX 100MCS used for REP initiation. Briefly, 500 mL of CM2 media containing IL-2 (6000 IU/mL) and $5 \times 10^8$ feeder cells with 30 ug OKT-3 was added to each flask. On day 9-11 the culture was scaled up. The entire volume of the G-Rex100M (1L) was transferred to a G-REX 500MCS and 4L of CM4 containing IL-2 (3000 IU/mL) was added. Flasks were incubated 5 days. Cultures were harvested and cryopreserved on Day 16.

Three different tumors were included in the comparison, two lung tumors (L4054 and L4055) and one melanoma tumor (M1085T).

CM1 (culture media 1), CM2 (culture media 2), and CM4 (culture media 4) media were prepared in advance and held at 4° C. for L4054 and L4055. CM1 and CM2 media were prepared without filtration to compare cell growth with and without filtration of media.

Media was warmed at 37° C. up to 24 hours in advance for L4055 tumor on REP initiation and scale-up.

Results Summary

Gen 3 fell within 30% of Gen 2 for total viable cells achieved. Gen 3 final product exhibited higher production of INF-γ after restimulation. Gen 3 final product exhibited increased clonal diversity as measured by total unique CDR3 sequences present. Gen 3 final product exhibited longer mean telomere length.

Results Achieved

Cell Count and % Viability:

Pre REP and REP expansion on Gen 2 and Gen 3 processes followed details described above.

Table 45: Pre-REP cell counts. For each tumor, the two pools contained equal number of fragments. Due to the small size of tumors, the maximum number of fragments per flask was not achieved. Total pre-REP cells (TVC) were harvested and counted at day 11 for the Gen 2 process and at day 7 for the Gen 3 process. To compare the two pre-REP arms, the cell count was divided over the number of fragments provided in the culture in order to calculate an average of viable cells per fragment. As indicated in the table below, the Gen 2 process consistently grew more cells per fragment compared to the Gen 3 Process. An extrapolated calculation of the number of TVC expected for Gen 3 process at day 11, which was calculated dividing the pre-REP TVC by 7 and then multiply by 11.

TABLE 45

| | pre-REP cell counts | | | | | |
|---|---|---|---|---|---|---|
| Tumor ID | L4054 | | L4055* | | M1085T | |
| Process | Gen 2 | Gen 3 | Gen 2 | Gen 3 | Gen 2 | Gen 3 |
| pre-REP TVC | 1.42E+08 | 4.32E+07 | 2.68E+07 | 1.38E+07 | 1.23E+07 | 3.50E+06 |
| Number of fragments | 21 | 21 | 24 | 24 | 16 | 16 |

TABLE 45-continued

| | pre-REP cell counts | | | | | |
|---|---|---|---|---|---|---|
| Tumor ID | L4054 | | L4055* | | M1085T | |
| Process | Gen 2 | Gen 3 | Gen 2 | Gen 3 | Gen 2 | Gen 3 |
| Average TVC per fragment at pre-REP | 6.65E+06 | 2.06E+06 | 1.12E+06 | 5.75E+05 | 7.66E+05 | 2.18E+05 |
| Gen 3 extrapolated value at pre REP day 11 | N/A | 6.79E+07 | N/A | 2.17E+07 | N/A | 5.49E+06 |

*L4055, unfiltered media.

Table 46: Total viable cell count and fold expansion on TIL final product: For the Gen 2 and Gen 3 processes, TVC was counted per process condition and percent viable cells was generated for each day of the process. On harvest, day 22 (Gen 2) and day 16 (Gen 3) cells were collected and the TVC count was established. The TVC was then divided by the number of fragments provided on day 0, to calculate an average of viable cells per fragment. Fold expansion was calculated by dividing harvest TVC by over the REP initia-tion TVC. As exhibited in the table, comparing Gen 2 and the Gen 3, fold expansions were similar for L4054; in the case of L4055, the fold expansion was higher for the Gen 2 process. Specifically, in this case, the media was warmed up 24 in advance of REP initiation day. A higher fold expansion was also observed in Gen 3 for M1085T. An extrapolated calculation of the number of TVC expected for Gen 3 process at day 22, which was calculated dividing the REP TVC by 16 and then multiply by 22.

TABLE 46

| | Total viable cell count and fold expansion on TIL final product | | | | | |
|---|---|---|---|---|---|---|
| Tumor ID | L4054 | | L4055 | | M1085T | |
| Process | Gen 2 | Gen 3 | Gen 2 | Gen 3 | Gen 2 | Gen 3 |
| #Fragments | 21 | 21 | 24 | 24 | 16 | 16 |
| TVC/fragment (at Harvest) | 3.18E+09 | 8.77E+08 | 2.30E+09 | 3.65E+08 | 7.09E+08 | 4.80E+08 |
| REP initiation | 1.42E+08 | 4.32E+07 | 2.68E+07 | 1.38E+07 | 1.23E+07 | 3.50E+06 |
| Scale up | 3.36E+09 | 9.35E+08 | 3.49E+09 | 8.44E+08 | 1.99E+09 | 3.25E+08 |
| Harvest | 6.67E+10 | 1.84E+10 | 5.52E+10 | 8.76E+09 | 1.13E+10 | 7.68E+09 |
| Fold Expansion Harvest/REP initiation | 468.4 | 425.9 | 2056.8 | 634.6 | 925.0 | 2197.2 |
| Gen 3 extrapolated value at REP harvest day 22 | N/A | 2.53E+10 | N/A | 1.20E+10 | N/A | 1.06E+10 |

*L4055, unfiltered media.

Table 47: % Viability of TIL final product: Upon harvest, the final TIL REP products were compared against release criteria for % viability. All of the conditions for the Gen 2 and Gen 3 processes surpassed the 70% viability criterion and were comparable across processes and tumors.

TABLE 47

| | % Viability of REP | | | | | |
|---|---|---|---|---|---|---|
| Tumor ID | L4054 | | L4055 | | M1085T | |
| Process | Gen 2 | Gen 3 | Gen 2 | Gen 3 | Gen 2 | Gen3 |
| REP initiation | 98.23% | 97.97% | 97.43% | 92.03% | 81.85% | 68.27% |
| Scale up | 94.00% | 93.57% | 90.50% | 95.93% | 78.55% | 71.15% |
| Harvest | 87.95% | 89.85% | 87.50% | 86.70% | 86.10% | 87.45% |

Table 48: Estimate cell count per additional flask for Gen 3 process. Due to the number of fragments per flask below the maximum required number, an estimated cell count at harvest day was calculated for each tumor. The estimation was based on the expectation that clinical tumors were large enough to seed 2 or 3 flasks on day 0.

TABLE 49

| Extrapolated estimate cell count calculation to full scale 2 and 3 flask on Gen 3 Process | | | | | | |
|---|---|---|---|---|---|---|
| Tumor ID | L4054 | | L4055 | | M1085T | |
| Gen 3 Process | 2 flasks | 3 Flasks | 2 flasks | 3 Flasks | 2 flasks | 3 Flasks |
| Estimate Harvest | 3.68E+10 | 5.52E+10 | 1.75E+10 | 2.63E+10 | 1.54E+10 | 2.30E+10 |

Immunophenotyping:

Phenotypic Markers Comparison on TIL Final Product:

Three tumors L4054, L4055, and M1085T underwent TIL expansion in both the Gen 2 and Gen 3 processes. Upon harvest, the REP TIL final products were subjected to flow cytometry analysis to test purity, differentiation, and memory markers. For all the conditions the percentage of TCR a/b+ cells was over 90%.

Figure 3:
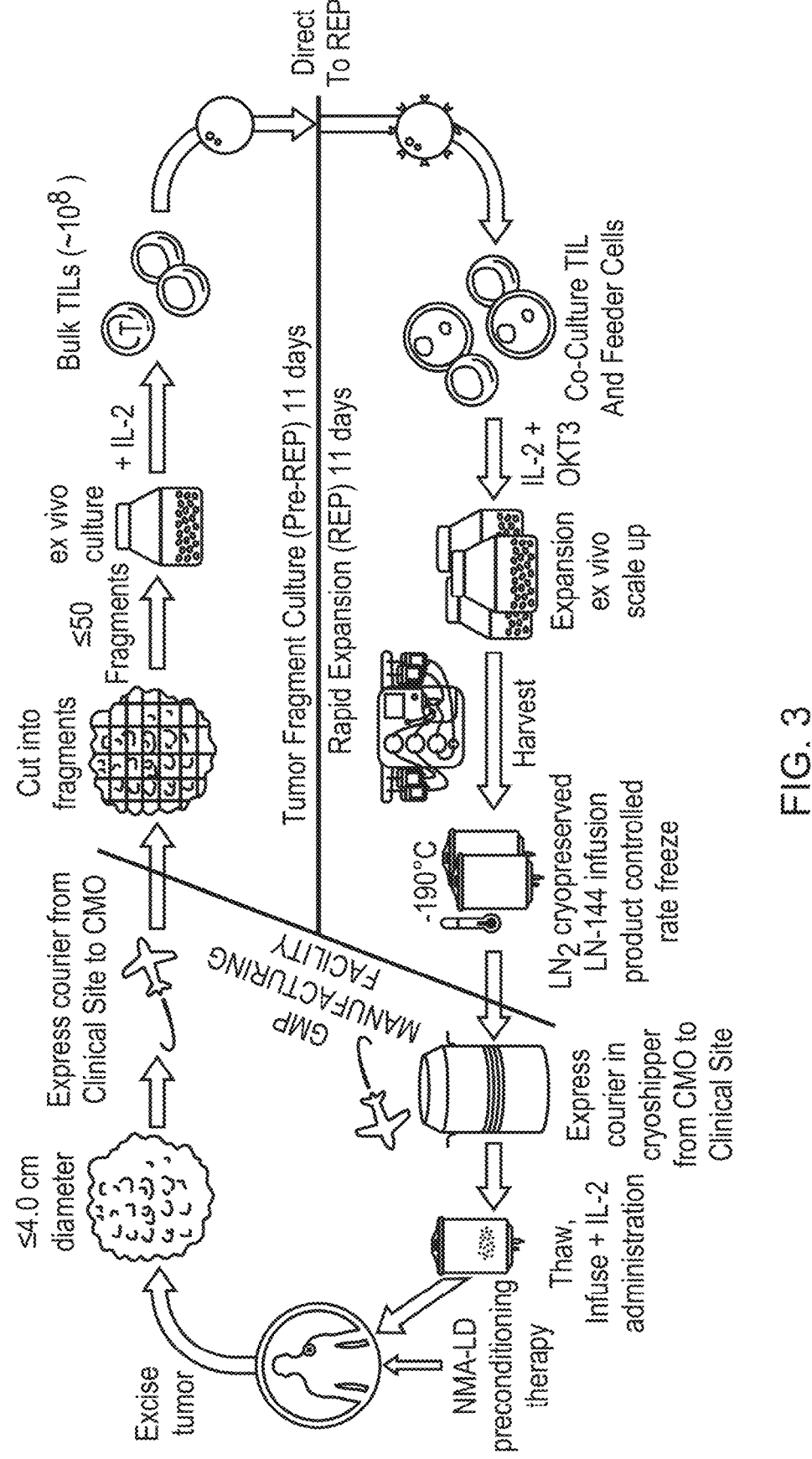
FIG. 3: Shows a diagram of an embodiment of a cryopreserved TIL exemplary manufacturing process (~22 days).

TIL harvested from the Gen 3 process showed a higher expression of CD8 and CD28 compared to TIL harvested from the Gen 2 process. The Gen 2 process showed a higher percentage of CD4+. See, FIG. 3 (A, B, C).

Memory Markers Comparison on TIL Final Product:

TIL harvested from the Gen 3 process showed a higher expression on central memory compartments compared to TIL from the Gen 2 process. See, FIG. 4 (A, B, C).

Activation and Exhaustion Markers Comparison on TIL Final Product:

Activation and exhaustion marker were analyzed in TIL from two, tumors L4054 and L4055 to compare the final TIL product by from the Gen 2 and Gen 3 TIL expansion processes. Activation and exhaustion markers were comparable between the Gen 2 and Gen 3 processes. See, FIG. 5 (A, B); FIG. 6 (A, B).

Interferon Gamma Secretion Upon Restimulation:

On harvest day, day 22 for Gen 2 and day 16 for Gen 3, TIL underwent an overnight restimulation with coated anti-CD3 plates for L4054 and L4055. The restimulation on M1085T was performed using anti-CD3, CD28, and CD137 beads. Supernatant was collected after 24 hours of the restimulation in all conditions and the supernatant was frozen. IFNγ analysis by ELISA was assessed on the supernatant from both processes at the same time using the same ELISA plate. Higher production of IFNγ from the Gen 3 process was observed in the three tumors analyzed. See, FIG. 7 (A, B, C).

Measurement of IL-2 Levels in Culture Media:

To compare the IL-2 consumption between Gen 2 and Gen 3 process, cell supernatant was collected on REP initiation, scale up, and harvest day, on tumor L4054 and L4055. The quantity of IL-2 in cell culture supernatant was measured by Quantitate ELISA Kit from R&D. The general trend indicates that the IL-2 concentration remains higher in the Gen 3 process when compared to the Gen 2 process. This is likely due to the higher concentration of IL-2 on REP initiation (6000 IU/mL) for Gen 3 coupled with the carry-over of the media throughout the process. See, FIG. 8 (A, B).

Metabolic Substrate and Metabolite Analysis

Figure 9:
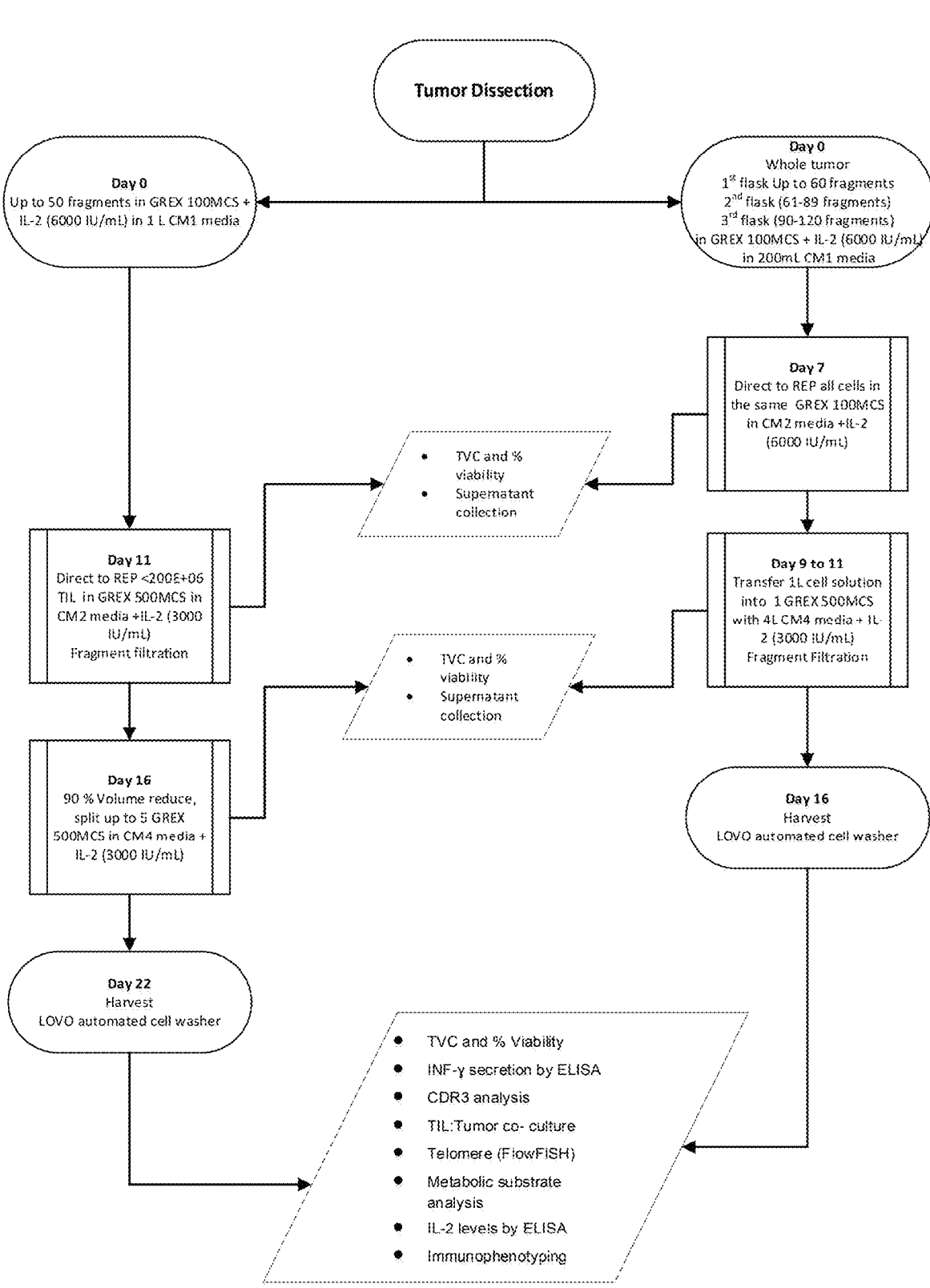
FIG. 9: Provides an experimental flow chart for comparability between GEN 2 (process 2A) versus GEN 3.

The levels of metabolic substrates such as D-glucose and L-glutamine were measured as surrogates of overall media consumption. Their reciprocal metabolites, such lactic acid and ammonia, were measured. Glucose is a simple sugar in media that is utilized by mitochondria to produce energy in the form of ATP. When glucose is oxidized, lactic acid is produced (lactate is an ester of lactic acid). Lactate is strongly produced during the cells exponential growth phase. High levels of lactate have a negative impact on cell culture processes. See, FIG. 9 (A, B).

Spent media for L4054 and L4055 was collected at REP initiation, scale up, and harvest days for both process Gen 2 and Gen 3. The spent media collection was for Gen 2 on Day 11, day 16 and day 22; for Gen 3 was on day 7, day 11 and day 16. Supernatant was analyzed on a CEDEX Bio-analyzer for concentrations of glucose, lactic acid, glutamine, glutamax, and ammonia.

Figure 10:
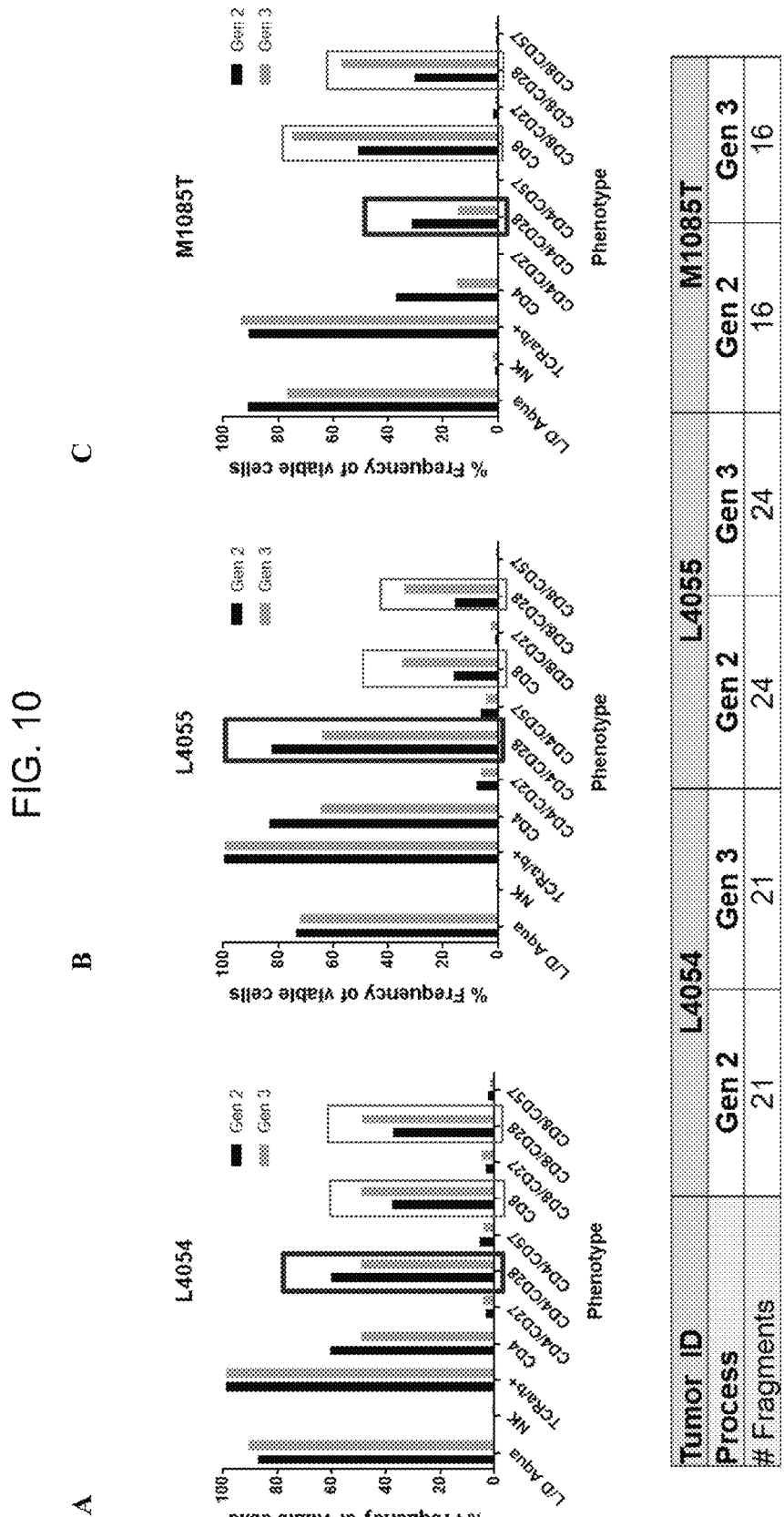
FIG. 10A-10C: A) L4054—Phenotypic characterization on TIL product on Gen 2 and Gen 3 process. B) L4055—Phenotypic characterization on TIL product on Gen 2 and Gen 3 process. C) M1085T—Phenotypic characterization on TIL product on Gen 2 and Gen 3 process.

L-glutamine is an unstable essential amino acid required in cell culture media formulations. Glutamine contains an amine, and this amide structural group can transport and deliver nitrogen to cells. When L-glutamine oxidizes, a toxic ammonia by-product is produced by the cell. To counteract the degradation of L-glutamine the media for the Gen 2 and Gen 3 processes was supplemented with Glutamax, which is more stable in aqueous solutions and does not spontaneously degrade. In the two tumor lines, the Gen 3 arm showed a decrease in L-glutamine and Glutamax during the process and an increase in ammonia throughout the REP. In the Gen 2 arm a constant concentration of L-glutamine and Glutamax, and a slight increase in the ammonia production was observed. The Gen 2 and Gen 3 processes were comparable at harvest day for ammonia and showed a slight difference in L-glutamine degradation. See, FIG. 10 (A, B, C).

Telomere Repeats by Flow—Fish:

Flow-FISH technology was used to measure the average length of the telomere repeat on L4054 and L4055 under Gen 2 and Gen 3 process. The determination of a relative telomere length (RTL) was calculated using Telomere PNA kit/FITC for flow cytometry analysis from DAKO. Gen 3 showed comparable telomere length to Gen 2.

CD3 Analysis

To determine the clonal diversity of the cell products generated in each process, TIL final product harvested for L4054 and L4055, were sampled and assayed for clonal diversity analysis through sequencing of the CDR3 portion of the T-cell receptors.

Table 50: Comparison of Gen 2 and Gen3 of percentage shared unique CDR3 sequences on L4054 on TIL harvested cell product. 199 sequences are shared between Gen 3 and Gen 2 final product, corresponding to 97.07% of top 80% of unique CDR3 sequences from Gen 2 shared with Gen 3 final product.

TABLE 50

| Comparison of shared uCDR3 sequences between Gen 2 and Gen 3 processes on L4054. | | | | |
|---|---|---|---|---|
| # uCDR3 | All uCDR3's | | Top 80% uCDR3's | |
| (% Overlap) | Gen 2 | Gen 3 | Gen 2 | Gen 3 |
| Gen 2-14054 | 8915 | 4355 (48.85%) | 205 | 199 (97.07%) |
| Gen 3-14054 | — | 18130 | — | 223 |

Table 51: Comparison of Gen 2 and Gen3 of percentage shared unique CDR3 sequences on L4055 on TIL harvested cell product. 1833 sequences are shared between Gen 3 and Gen 2 final product, corresponding to 99.45% of top 80% of unique CDR3 sequences from Gen 2 shared with Gen 3 final product.

TABLE 51

| Comparison of shared uCDR3 sequences between Gen 2 and Gen 3 processes on L4055. | | | | |
|---|---|---|---|---|
| # uCDR3 | All uCDR3's | | Top 80% uCDR3's | |
| (% Overlap) | Gen 2 | Gen 3 | Gen 2 | Gen 3 |
| Gen 2-14055 | 12996 | 6599 (50.77%) | 1843 | 1833 (99.45%) |
| Gen 3-14055 | — | 27246 | — | 2616 |

CM1 and CM2 media was prepared in advanced without filtration and held at 4 degree C. until use for tumor L4055 to use on Gen 2 and Gen 3 process.

Media was warmed up at 37 degree C. for 24 hours in advance for tumor L4055 on REP initiation day for Gen 2 and Gen 3 process.

LDH was not measured in the supernatants collected on the processes.

M1085T TIL cell count was executed with K2 cellometer cell counter.

On tumor M1085T, samples were not available such as supernatant for metabolic analysis, TIL product for activation and exhaustion markers analysis, telomere length and CD3-TCR vb Analysis.

CONCLUSIONS

This example compares 3 independent donor tumors tissue in terms of functional quality attributes, plus extended phenotypic characterization and media consumption among Gen 2 and Gen 3 processes.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

An extrapolated cell number was calculated for Gen 3 process assuming the pre-REP harvest occurred at day 11 instead day 7 and REP Harvest at Day 22 instead day 16. In both cases shows closer number on TVC compared to Gen 2 process, indicating that the early activation could allow an overall better performance on TIL growth. Table 4 and 5 bottom row.

In the case of extrapolated value for extra flasks (2 or 3) on Gen 3 process assuming a bigger size of tumor processed, and reaching the maximum number of fragments required per process as described. It was observed that a similar dose can be reachable on TVC at Day 16 Harvest for Gen 3 process compared to Gen 2 process at Day 22. This observation is important and indicates an early activation of the culture can allow better performance of TIL in less processing time.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

In terms of phenotypic characterization, a higher CD8+ and CD28+ expression was observed on three tumors on Gen 3 process compared to Gen 2 process. This data indicates the Gen 3 process has improved attributes of final TIL product compared to Gen 2.

Gen 3 process showed slightly higher central memory compartments compared to Gen 2 process.

Gen 2 and Gen 3 process showed comparable activation and exhaustion markers, despite the shorter duration of the Gen 3 process.

IFN gamma (IFN$\gamma$) production was 3 times higher on Gen 3 final product compared to Gen 2 in the three tumors analyzed. This data indicates the Gen 3 process generated a highly functional and more potent TIL product as compared to the Gen 2 process, possibly due to the higher expression of CD8 and CD28 expression on Gen 3. Phenotypic characterization suggested positive trends in Gen 3 toward CD8+, CD28+ expression on three tumors compared to Gen 2 process.

Telomere length on TIL final product between Gen 2 and Gen 3 were comparable.

Glucose and Lactate levels were comparable between Gen 2 and Gen 3 final product, suggesting the levels of nutrients on the media of Gen 3 process were not affected due to the non-execution of volume reduction removal in each day of the process and less volume media overall in the process, compared to Gen 2.

Overall Gen 3 process showed a reduction almost two times of the processing time compared to Gen 2 process, which would yield a substantial reduction on the cost of goods (COGs) for TIL product expanded by the Gen 3 process.

IL-2 consumption indicates a general trend of IL-2 consumption on Gen 2 process, and in Gen 3 process IL-2 was higher due to the non-removal of the old media.

The Gen 3 process showed a higher clonal diversity measured by CDR3 TCRab sequence analysis.

The addition of feeders and OKT-3 on day 0 of the pre-REP allowed an early activation of TIL and overall a better growth TIL performance using the Gen 3 process.

Table 52 describes various embodiments and outcomes for the Gen 3 process as compared to the current Gen 2 process:

TABLE 52

| Exemplary Gen 3 process. | | |
|---|---|---|
| Step | Process Gen 2 | Process Gen 3-Optimized |
| Pre REP-day 0 | ≤50 fragments<br>1X G-Rex 100 MCS<br>1 L media<br>IL-2 (6000 IU/mL)<br>11 days | ≤240 fragments<br>≤60 fragments/flask<br>≤4 flasks<br>≤2 L media (500 mL/flask)<br>IL-2 (6000 IU/mL)<br>$2.5 \times 10^8$ feeder cells/flask<br>15 ug OKT3/flask |
| REP Initiation | Fresh TIL direct to REP<br>Day 11<br>≤200e$^6$ TIL<br>$5 \times 10^9$ feeder cells<br>G-Rex 500 MCS<br>5 L CM2 media + IL-2<br>(3000 IU/mL)<br>150 ug OKT3 | Fresh TIL direct to REP<br>Day 7<br>Activate entire culture<br>$5 \times 10^8$ feeder cells<br>30 ug OKT3/flask<br>G-Rex 100 MCS<br>500 mL media + IL-2<br>(6000 IU/mL) |

TABLE 52-continued

Exemplary Gen 3 process.

| Step | Process Gen 2 | Process Gen 3-Optimized |
|------|---------------|-------------------------|
| TIL Sub-culture or Scale up | ≤5 G-REX 500 MCS ≤1 × 10 viable cells/flask 5 L/flask Day 16 | ≤4 G-REX 500 MCS Scale up entire culture 4 L/flask Day 10-11 |
| Harvest | Harvest Day 22, LOVO-automated cell washer 2 wash cycles | Harvest Day 16 LOVO-automated cell washer 5 wash cycles |
| Final formulation | Cryopreserved Product 300 IU/ml IL2-CS10 in LN₂, multiple aliquots | Cryopreserved product 300 IU/ml IL-2-CS10 in LN₂, multiple aliquots |
| Process time | 22 days | 16 days |

Example 9: An Exemplary Embodiment of Selecting and Expanding PBLS from PBMCS in CLL Patients PBMCs are collected from patients and either frozen for later use, or used fresh. Enough volume of peripheral blood is collected to yield at least about 400,000,000 ($400\times10^6$) PBMCs for starting material in the method of the present invention. On Day 0 of the method, IL-2 at $6\times10^6$ IU/mL is either prepared fresh or thawed, and stored at 4° C. or on ice until ready to use. 200 mL of CM2 medium is prepared by combining 100 mL of CM1 medium (containing Gluta-MAX®), then diluting it with 100 mL (1:1) with AIM-V to make CM2. The CM2 is protected from light, and sealed tightly when not in use.

All of the following steps are performed under sterile cell culture conditions. An aliquot of CM2 is warmed in a 50 mL conical tube in a 37° C. water bath for use in thawing and/or washing a frozen PBMC sample. If a frozen PBMC sample is used, the sample is removed from freezer storage and kept on dry ice until ready to thaw. When ready to thaw the PBMC cryovial, 5 mL of CM2 medium is placed in a sterile 50 mL conical tube. The PBMC sample cryovial is placed in a 37° C. water bath until only a few ice crystals remain. Warmed CM2 medium is added, dropwise, to the sample vial in a 1:1 volume ratio of sample:medium (about 1 mL). The entire contents is removed from the cryovial and transferred to the remaining CM2 medium in the 50 mL conical tube. An additional 1-2 mL of CM2 medium is used to rinse the cryovial and the entire contents of the cryovial is removed and transferred to the 50 mL conical tube. The volume in the conical tube is then adjusted with additional CM2 medium to 15 mL, and swirled gently to rinse the cells. The conical tube is then centrifuged at 400 g for 5 minutes at room temperature in order to collect the cell pellet.

The supernatant is removed from the pellet, the conical tube is capped, and then the cell pellet is disrupted by, for example, scraping the tube along a rough surface. About 1 mL of CM2 medium is added to the cell pellet, and the pellet and medium are aspirated up and down 5-10 times with a pipette to break up the cell pellet. An additional 3-5 mL of CM2 medium is added to the tube and mixed via pipette to suspend the cells. At this point, the volume of the cell suspension is recorded. Remove 100 uL of the cell suspension from the tube for cell counting with an automatic cell counter, for example, a Nexcelom Cellometer K2. Determine the number of live cells in the sample and record.

Reserve a minimum of $5\times10^6$ cells for phenotyping and other characterization experiments. Spin the reserved cells at 400 g for 5 minutes at room temperature to collect the cell pellet. Resuspend the cell pellet in freezing medium (sterile, heat-inactivated FBS containing 20% DMSO). Freeze one or two aliquots of the reserved cells in freezing medium, and slow-freeze the aliquots in a cell freezer (Mr. Frosty) in a −80° C. freezer. Transfer to liquid nitrogen storage after a minimum of 24 hours at −80° C.

For the following steps, use pre-cooled solutions, work quickly, and keep the cells cold. The next step is to purify the T-cell fraction of the PBMC sample. This is completed using a Pan T-cell Isolation Kit (Miltenyi, catalog #130-096-535). Prepare the cells for purification by washing the cells with a sterile-filtered wash buffer containing PBS, 0.5% BSA, and 2 mM EDTA at pH 7.2. The PBMC sample is centrifuged at 400 g for 5 minutes to collect the cell pellet. The supernatant is aspirated off and the cell pellet is resuspended in 40 uL of wash buffer for every $10^7$ cells. Add 10 uL of Pan T Cell Biotin-Antibody Cocktail for every $10^7$ cells. Mix well and incubate for 5 minutes in refrigerator or on ice. Add 30 uL of wash buffer for every $10^7$ cells. Add 20 uL of Pan T-cell MicroBead Cocktail for every $10^7$ cells. Mix well and incubate for 10 minutes in refrigerator or on ice. Prepare an LS column and magnetically separate cells from the microbeads. The LS column is placed in the QuadroMACS magnetic field. The LS column is washed with 3 mL of cold wash buffer, and the wash is collected and discarded. The cell suspension is applied to the column and the flow-through (unlabeled cells) is collected. This flow-through is the enriched T-cell fraction (PBLs). Wash the column with 3 mL of wash buffer and collect the flow-through in the same tube as the initial flow-through. Cap the tube and place on ice. This is the T-cell fraction, or PBLs. Remove the LS column from the magnetic field, wash the column with 5 mL of wash buffer, and collect the non-T-cell fraction (magnetically labeled cells) into another tube. Centrifuge both fractions at 400 g for 5 minutes to collect the cell pellets. Supernatants are aspirated from both samples, disrupt the pellet, and resuspend the cells in 1 mL of CM2 medium supplemented with 3000 IU/mL IL-2 to each pellet, and pipette up and down 5-10 times to break up the pellets. Add 1-2 mL of CM2 to each sample, and mix each sample well, and store in tissue culture incubator for next steps. Remove about a 50 uL aliquot from each sample, count cells, and record count and viability.

The T-cells (PBLs) are then cultured with Dunabeads™ Human T-Expander CD3/CD28. A stock vial of Dynabeads is vortexed for 30 seconds at medium speed. A required aliquot of beads is removed from the stock vial into a sterile 1.5 mL microtube. The beads are washed with bead wash solution by adding 1 mL of bead wash to the 1.5 mL microtube containing the beads. Mix gently. Place the tube onto the DynaMag™-2 magnet and let sit for 30 minutes while beads draw toward the magnet. Aspirate the wash solution off the beads and remove tube from the magnet. 1 mL of CM2 medium supplemented with 3000 IU/mL IL-2 is added to the beads. The entire contents of the microtube is transferred to a 15 or 50 mL conical tube. Bring the beads to a final concentration of about 500,000/mL using CM2 medium with IL-2.

The T-cells (PBLs) and beads are cultured together as follows. On day 0: In a G-Rex 24 well plate, in a total of 7 mL per well, add 500,000 T-cells, 500,000 CD3/CD28 Dynabeads, and CM2 supplemented with IL-2. The G-Rex plate is placed into a humidified 37° C., 5% CO₂ incubator until the next step in the process (on Day 4). Remaining cells are frozen in CS10 cryopreservation medium using a Mr. Frosty cell freezer. The non-T-cell fraction of cells are frozen in CS10 cryopreservation medium using a Mr. Frosty cell freezer. On day 4, medium is exchanged. Half of the medium (about 3.5 mL) is removed from each well of the G-rex plate. A sufficient volume (about 3.5 mL) of CM4 medium supplemented with 3000 IU/mL IL-2 warmed to 37° C. is added to replace the medium removed from each sample well. The G-rex plate is returned to the incubator.

On day 7, cells are prepared for expansion by REP. The G-rex plate is removed from the incubator and half of medium is removed from each well and discarded. The cells are resuspended in the remaining medium and transferred to a 15 mL conical tube. The wells are washed with 1 mL each of CM4 supplemented with 3000 IU/mL IL-2 warmed to 37° C. and the wash medium is transferred to the same 15 mL tube with the cells. A representative sample of cells is removed and counted using an automated cell counter. If there are less than $1 \times 10^6$ live cells, the Dynabead expansion process at Day 0 is repeated. The remainder of the cells are frozen for back-up expansion or for phenotyping and other characterization studies. If there are $1 \times 10^6$ live cells or more, the REP expansion is set up in replicate according to the protocol from Day 0. Alternatively, with enough cells, the expansion may be set up in a G-rex 10M culture flask using $10\text{-}15 \times 10^6$ PBLs per flask and a 1:1 ratio of Dynabeads: PBLs in a final volume of 100 mL/well of CM4 medium supplemented with 3000 IU/mL IL-2. The plate and/or flask is returned to the incubator. Excess PBLs may be aliquoted and slow-frozen in a Mr. Frosty cell freezer in a –80° C. freezer, and the transferred to liquid nitrogen storage after a minimum of 24 hours at –80° C. These PBLs may be used as back-up samples for expansion or for phenotyping or other characterization studies.

On Day 11, the medium is exchanged. Half of the medium is removed from either each well of the G-rex plate or the flask and replaced with the same amount of fresh CM4 medium supplemented with 3000 IU/mL IL-2 at 37° C.

On Day 14, the PBLs are harvested. If the G-rex plate is used, about half of the medium is removed from each well of the plate and discarded. The PBLs and beads are suspended in the remaining medium and transferred to a sterile 15 mL conical tube (Tube 1). The wells are washed with 1-2 mL of fresh AIM-V medium warmed to 37° C., and the wash is transferred to Tube 1. Tube 1 is capped and placed in the DynaMag™-15 Magnet for 1 minute to allow the beads to be drawn to the magnet. The cell suspension is transferred into a new 15 mL tube (Tube 2), and the beads are washed with 2 mL of fresh AIM-V at 37° C. Tube 1 is placed back in the magnet for an additional 1 minute, and the wash medium is then transferred to Tube 2. The wells may be combined if desired, after the final washing step. Remove a representative sample of cells and count, record count and viability. Tubes may be placed in the incubator while counting. Additional AIM-V medium may be added to the Tube 2 if cells appear very dense. If a flask is used, the volume in the flask should be reduced to about 10 mL. The contents of the flask is mixed and transferred to a 15 mL conical tube (Tube A). The flask is washed with 2 mL of the AIM-V medium as described above and the wash medium is also transferred to Tube A. Tube A is capped and placed in the DynaMag™-15 Magnet for 1 minute to allow the beads to be drawn to the magnet. The cell suspension is transferred into a new 15 mL tube (Tube B), and the beads are washed with 2 mL of fresh AIM-V at 37° C. Tube A is placed back in the magnet for an additional 1 minute, and the wash medium is then transferred to Tube B. The wells may be combined if desired, after the final washing step. Remove a representative sample of cells and count, record count and viability. Tubes may be placed in the incubator while counting. Additional AIM-V medium may be added to the Tube B if cells appear very dense. Cells may be used fresh or frozen in CS10 preservation medium at desired concentrations.

Example 10: A Phase 2, Multicenter Study of Autologous Tumor Infiltrating Lymphocytes in Patients with Solid Tumors Study Design

Overview

This example describes a prospective, open-label, multi-cohort, non-randomized, multicenter Phase 2 study evaluating ACT using TIL in combination with pembrolizumab or TIL as a single therapy, using TILs prepared as described in the present application as well as in this example.

Objectives

Primary:

To evaluate the efficacy of autologous TIL in combination with pembrolizumab in MM, HNSCC, or NSCLC patients or TIL as a single therapy in relapsed or refractory (r/r) NSCLC patients, who had previously progressed on or after treatment with CPIs, as determined by objective response rate (ORR), using the Response Evaluation Criteria in Solid Tumors (RECIST 1.1), as assessed by Investigator.

To characterize the safety profile of TIL in combination with pembrolizumab in MM, HNSCC, and NSCLC patients or TIL as a single therapy in r/r NSCLC patients as measured by the incidence of Grade ≥3 treatment-emergent adverse events (TEAEs).

Secondary:

To further evaluate the efficacy of autologous TIL in combination with pembrolizumab in MM, HNSCC, and NSCLC patients or TIL as a single therapy in r/r NSCLC patients using complete response (CR) rate, duration of response (DOR), disease control rate (DCR), progression-free survival (PFS) using RECIST 1.1, as assessed by Investigator, and overall survival (OS).

Cohorts:

Cohort 1A: TIL therapy in combination with pembrolizumab in patients with Stage IIIC or Stage IV unresectable or MM with ≤3 prior lines of systemic therapy excluding immunotherapy. If previously treated, patients must have had radiographically documented progression on or after most recent therapy.

Cohort 2A: TIL therapy in combination with pembrolizumab in patients with advanced, recurrent or metastatic HNSCC (e.g., Stages T1N1-N2B, T2-4N0-N2b) with ≤3 prior lines of systemic therapy, excluding immunotherapy. If previously treated, patients must have had radiographically documented progression on or after most recent therapy.

Cohort 3A: TIL therapy in combination with pembrolizumab in patients with locally advanced or metastatic (Stage III-IV) NSCLC with ≤3 prior lines of systemic therapy, excluding immunotherapy. If previously treated, patients must have had radiographically documented progression on or after most recent therapy.

Cohort 3B: TIL therapy as a single agent in patients Stage III or Stage IV NSCLC who have previously received systemic therapy with CPIs (e.g., anti-PD-1/anti-PD-L1) as part of ≤3 prior lines of systemic therapy. If previously treated, patients must have had radiographically documented progression on or after most recent therapy.

Patients in Cohorts 3A and 3B (NSCLC) with oncogene-driven tumors with available effective targeted therapy must have received at least one line of targeted therapy.

All patients received autologous cryopreserved TIL therapy (with or without pembrolizumab, depending on cohort assignment), preceded by a nonmyeloablative lymphodepletion (NMA-LD) preconditioning regimen consisting of cyclophosphamide and fludarabine. Following TIL infusion, up to 6 IV interleukin-2 (IL-2) doses maximum were administered.

The following general study periods took place in all 4 cohorts, unless specified otherwise.

Screening and Tumor Resection: Up to 4 weeks (28 days) from study entry; manufacturing of the TIL Product: approximately ≤22 days from tumor resection; and treatment period, as discussed below.

Treatment Period (Cohorts 1A, 2A, and 3A): up to 2 years, including NMA-LD (7 days), TIL infusion (1 day) followed by IL-2 administrations (1 to 4 days). Patients receive a single infusion of pembrolizumab after the completion of their tumor resection for TIL production and baseline scans but before the initiation of the NMA-LD regimen. The next dose of pembrolizumab will be no earlier than following the completion of IL-2 and continue Q3W±3 days thereafter for ≤2 years (24 months) or until disease progression or unacceptable toxicity, whichever occurs first. The end-of-treatment (EOT) visit occurred within 30 days after the last dose of pembrolizumab. The visit could be combined with end-of-assessment (EOA) visit if applicable (e.g., pembrolizumab discontinuation occurred at disease progression or at the start of new anticancer therapy).

Treatment Period (Cohort 3B): up to 12 days, including NMA-LD (7 days), TIL, infusion (1 day) followed by IL-2 administrations (1 to 4 days). The EOT visit occurred once a patient received the last dose of IL-2. The EOT visit was performed within 30 days after treatment discontinuation and it may be combined with any scheduled visit occurring within this interval during the assessment period.

Assessment Period: began after TIL infusion on Day 0 and ends upon disease progression, with the start of a new anticancer therapy, partial withdrawal of consent to study assessments, or 5 years (Month 60), whichever occurred first. An end-of assessment (EOA) visit occurred once a patient reached disease progression or started a new anti-cancer therapy.

The TIL autologous therapy with the TILs prepared as described herein was comprised of the following steps:

1. Tumor resection to provide the autologous tissue that serves as the source of the TIL cellular product;
2. TIL product produced at a central Good Manufacturing Practice (GMP) facility;
3. A 7-day NMA-LD preconditioning regimen;
4. Cohorts 1A, 2A, and 3A: Patients receive a single infusion of pembrolizumab after the completion of their tumor resection for TIL production and baseline scans but before the initiation of NMA-LD regimen. The next dose of pembrolizumab will be no earlier than following the completion of IL-2 and continue Q3W±3 days thereafter.
5. Infusion of the autologous TIL product (Day 0); and
6. IV IL-2 administrations for up to 6 doses maximum.

In Cohorts 1A, 2A, and 3A, the next dose of pembrolizumab was no earlier than following the completion of IL-2 and continue Q3W±3 days thereafter for ≤2 years (24 months), or until disease progression or unacceptable toxicity, whichever occurred first.

Figure 7:
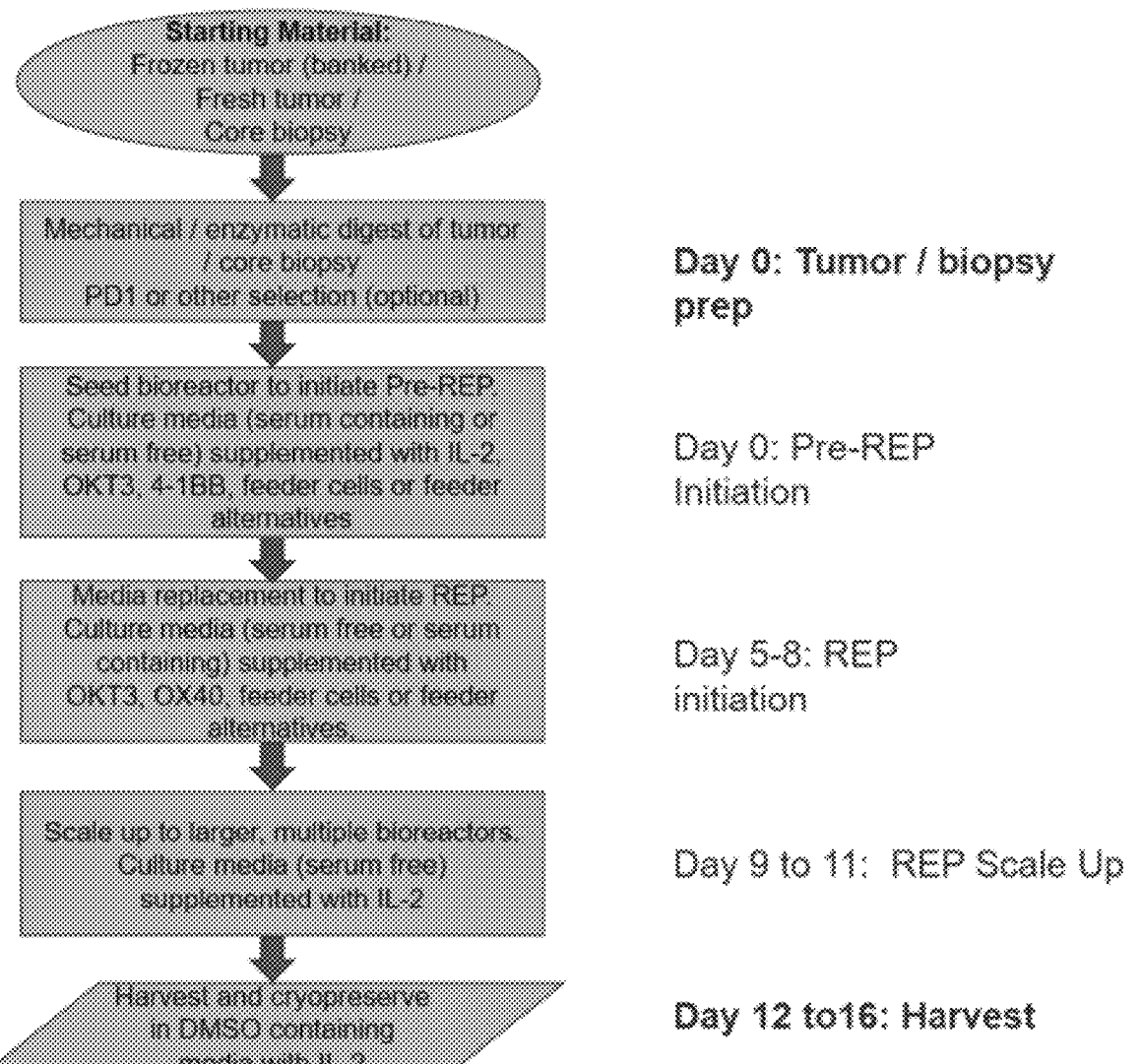
FIG. 7: Exemplary GEN 3 type process for NSCLC tumors.

Flowcharts for Cohorts 1A, 2A, and 3A can be found in FIG. 7. The Flowchart for Cohort 3B can be found in FIG. 8. Patients were assigned to the appropriate cohort by tumor indication.

TIL Therapy+Pembrolizumab (Cohorts 1A, 2A, and 3A)

Patients were screened and scheduled for surgery for tumor resection. Patients then had one or more tumor lesions resected, which were sent to a central manufacturing facility for TIL production.

Next, the NMA-LD regimen was imitated and consisted of 2 days of IV cyclophosphamide (60 mg/kg) with mesna (per site standard of care or USPI/SmPC) on Days −7 and Day −6 followed by 5 days of IV fludarabine (25 mg/m2: Day −5 through Day −1).

Patients in Cohorts 1A, 2A, and 3A received a single infusion of pembrolizumab after the completion of their tumor resection for TIL production and baseline scans and before the initiation of NMA-LD regimen. IL-2 administrations at a dose of 600,000 IU/kg IV begun as soon as 3 hours after, but no later than 24 hours after, completion of the TIL infusion on Day 0. Additional IL-2 administrations will be given approximately every 8 to 12 hours for up to 6 doses maximum. The second dose of pembrolizumab was no earlier than following the completion of IL-2. Patients should have recovered from all IL-2-related toxicities (Grade ≤2), prior to the second pembrolizumab administration. Pembrolizumab will continue Q3W±3 days thereafter for ≤2 years (24 months) or until disease progression or unacceptable toxicity, whichever occurred first.

TIL Therapy as a Single Agent (Cohort 3B)

Patients were screened and scheduled for surgery for tumor resection. Patients then had one or more tumor lesions resected, which were sent to a central manufacturing facility for TIL production.

Next, the NMA-LD regimen consisted of 2 days of IV cyclophosphamide (60 mg/kg) with mesna (per site standard of care or USPI/SmPC) on Day −7 and Day −6 followed by 5 days of IV fludarabine (25 mg/m2: Day −5 through Day −1).

Infusion of the tumor-derived autologous TIL product occurred no sooner than 24 hours after last dose of fludarabine. IL-2 administrations at a dose of 600,000 IU/kg IV may have begun as soon as 3 hours after, but no later than 24 hours after, completion of the TIL infusion.

Additional IL-2 administrations were given approximately every 8 to 12 hours for up to 6 doses maximum.

Production and Expansion of Tumor Infiltrating Lymphocytes

The TIL autologous cellular product was composed of viable cytotoxic T lymphocytes derived from a patient's tumor/lesion, which are manufactured ex vivo at a central GMP facility. An exemplary flow diagram depicting the TIL production process is provided in FIG. 9, for example.

The TIL manufacturing process begun at the clinical site after surgical excision of a primary or secondary metastatic tumor lesion(s) of ≥1.5 cm in diameter in each individual patient. Multiple tumor lesions from various anatomical locations can be excised to compile a total aggregate of tumor tissue; however, the aggregate should not exceed 4.0 cm in diameter, or 10 g in weight, due to the limited quantity of the biopreservation media present in the transport bottle.

Once the tumor lesion(s) was placed in the biopreservation transport bottle, it is shipped at 2° C. to 8° C. using an express courier to a central GMP manufacturing facility. Upon arrival, the tumor specimen(s) were dissected into fragments, which were then cultured in a pre-rapid expansion protocol (Pre-REP) with human recombinant IL-2 for −11 days.

These pre-REP cells were then further expanded using a rapid expansion protocol (REP) for 11 days in the presence of IL-2, OKT3 (a murine monoclonal antibody to human CD3, also known as [muromonab-CD3]) and irradiated allogenic peripheral blood mononuclear cells (PBMC) as feeder cells.

The expanded cells were then harvested, washed, formulated, cryopreserved, and shipped to the clinical site via an express courier. The dosage form of the TIL cellular product was a cryopreserved autologous "live-cell suspension" that was ready for infusion into the patient from whom the TIL were derived. Patients were to receive the full dose of product that was manufactured and released, which contained between $1\times10^9$ and $150\times10^9$ viable cells per the product specification. Clinical experience indicated that objective tumor responses were achieved across this dose range, which has also been shown to be safe (Radvanyi L. G., et al., Clin Cancer Res. 2012; 18(24):6758-70). The full dose of product was provided in up to four infusion bags.

Preparation of Patients to Receive the TIL Cellular Product

The NMA-LD preconditioning regimen used in this study (i.e., 2 days of cyclophosphamide plus mesna, followed by 5 days of fludarabine) was based on the method developed and tested by the National Cancer Institute (Rosenberg S. A., et al., Clin Cancer Res. 2011; 17(13):4550-7; Radvanyi L. G., et al., Clin Cancer Res. 2012; 18(24):6758-70; Dudley M. E., et al., J Clin Oncol. 2008; 26(32):5233-9; Pilon-Thomas S, et al., J Immunother. 2012; 35(8):615-20; Dudley M. E., et al., J Clin Oncol. 2005; 23(10):2346-57; and Dudley M. E., et al., Science. 2002; 298(5594):850-4). Following the 7-day preconditioning regimen, the patient was infused with the TIL cellular product.

The TIL infusion was followed by the administration of IV IL-2 (600,000 IU/kg) every 8 to 12 hours, with the first dose administered between 3 and 24 hours after the completion of the TIL infusion and continuing for up to 6 doses maximum. Per institutional standards, the doses of IL-2 can be calculated on the basis of actual weight.

Selection of Patient Populations

Cohort 1A:

Patients had a confirmed diagnosis of unresectable MM (Stage IIIC or Stage IV, histologically confirmed as per American Joint Committee on Cancer [AJCC] staging system). Ocular melanoma patients were excluded. Patients must not have received prior immuno-oncology targeted agents. If BRAF-mutation positive, patient could have received prior BRAF/MEK targeted therapy.

Cohort 2A:

Patients had advanced, recurrent and/or metastatic HNSCC and can be treatment naive; histologic diagnosis of the primary tumor is required via the pathology report. Patients must not have received prior immunotherapy regimens.

Cohort 3A:

Patients had a confirmed diagnosis of Stage III or Stage IV NSCLC (squamous, adenocarcinoma, large cell carcinoma). Patients with oncogene-driven tumors with available effective targeted therapy had received at least one line of targeted therapy.

Cohort 3B:

Patients had a confirmed diagnosis of Stage III or Stage IV NSCLC (squamous, adenocarcinoma, large cell carcinoma) and had previously received systemic therapy with CPIs (e.g., anti-PD-1/anti-PD-L1). Patients with oncogene-driven tumors with available effective targeted therapy had received at least one line of targeted therapy.

All patients had received up to 3 prior systemic anticancer therapies (see, inclusion criteria below), excluding immunotherapy for Cohorts 1A, 2A, and 3A. If previously treated, patients had radiographically confirmed progression on or after most recent therapy.

Inclusion Criteria

Patients must have met ALL of the following inclusion criteria for participation in the study:

1. All patients had a histologically or pathologically confirmed diagnosis of malignancy of their respective histologies:

Unresectable or metastatic melanoma (Cohort 1A)

Advanced, recurrent or metastatic squamous cell carcinoma of the head and neck (Cohort 2A)

Stage III or Stage IV NSCLC (squamous, nonsquamous, adenocarcinoma, large cell carcinoma) (Cohorts 3A and 3B).

2. Cohorts 1A, 2A, and 3A only: Patients were immunotherapy naïve. If previously treated, patients had progressed on or after most recent therapy. Cohorts 1A, 2A, and 3A may have received up to 3 prior systemic anticancer therapies, specifically:

In Cohort 1A: Patients with unresectable or metastatic melanoma (Stage IIIC or Stage IV); if BRAF mutation-positive, patients could have received a BRAF inhibitor.

In Cohort 2A: Patients with unresectable or metastatic HNSCC. Those who had received initial chemo-radio-therapy were allowed.

In Cohort 3A: Patients with Stage III or Stage IV NSCLC (squamous, nonsquamous, adenocarcinoma, or large cell carcinoma) and who were immunotherapy naïve and progressed after ≤3 lines of prior systemic therapy in the locally advanced or metastatic setting. Patients who received systemic therapy in the adjuvant or neoadjuvant setting, or as part of definitive chemoradiotherapy, were eligible and were considered to have had one line of therapy if the disease has progressed within 12 months of completion of prior systemic therapy. Patients with known oncogene drivers (e.g., EGFR, ALK, ROS) who had mutations that were sensitive to targeted therapies must had progressed after at least 1 line of targeted therapy.

3. Cohort 3B only: Patients with Stage III or Stage IV NSCLC (squamous, nonsquamous, adenocarcinoma, or large cell carcinoma) who had previously received systemic therapy with CPIs (e.g., anti-PD-1/anti-PD-L1) as part of ≤3 prior lines of systemic therapy.

Patients had radiographically confirmed progression on or after most recent therapy.

Patients who received systemic therapy in the adjuvant or neoadjuvant setting, or as part of definitive chemoradiotherapy, were eligible and were considered to have had 1 line of therapy if the disease had progressed within 12 months of completion of prior systemic therapy.

Patients with known oncogene drivers (e.g., EGFR, ALK, ROS) who had mutations that are sensitive to targeted therapies must have progressed after at least 1 line of targeted therapy.

4. Patients had at least 1 respectable lesion (or aggregate lesions) of a minimum 1.5 cm in diameter post-resection for TIL investigational product production. It was encouraged that tumor tissue be obtained from multiple and diverse metastatic lesions, as long as the surgical resection did not pose additional risks to the patient.

If the lesion considered for resection for TIL generation is within a previously irradiated field, the lesion must have demonstrated radiographic progression prior to resection.

Patients must have an adequate histopathology specimen for protocol-required testing.

5. Patients had remaining measurable disease as defined by the standard and well known RECIST 1.1 guidelines (see, for example, Eisenhauer, European Journal of Cancer 45:228-247 (2009), also available on the World Wide Web at project.eortc.org/recist/wp-content/uploads/sites/4/2015/03/RECISTGuidelines.pdf) following tumor resection for TIL manufacturing:

Lesions in previously irradiated areas were not be selected as target lesions unless there had been demonstrated progression of disease in those lesions;

Lesions that were partially resected for TIL generation that were still measurable per RECIST may be selected as nontarget lesions but could not serve as a target lesion for response assessment.

6. Patients were ≥18 years at the time of consent.

7. Patients had an Eastern Cooperative Oncology Group (ECOG) performance status of 0 or 1, and an estimated life expectancy of ≥3 months.

8. Patients of childbearing potential or those with partners of childbearing potential had to be willing to practice an approved method of highly effective birth control during treatment and continue for 12 months after receiving all protocol-related therapy (Note: Females of reproductive potential were to use effective contraception during treatment and for 12 months after their last dose of IL-2, or 4 months after their last dose of pembrolizumab whichever occurred later). Males could not donate sperm during the study or for 12 months after treatment discontinuation, whichever occurred later.

9. Patients had the following hematologic parameters:

Absolute neutrophil count (ANC) ≥1000/mm3;

Hemoglobin ≥9.0 g/dL;

Platelet count ≥100,000/mm3.

10. Patients had adequate organ function:

Serum alanine aminotransferase (ALT)/serum glutamic-pyruvic transaminase (SGPT) and aspartate amino-transferase (AST)/SGOT ≤3 times the upper limit of normal (ULN), patients with liver metastasis ≤5 times ULN.

An estimated creatinine clearance ≥40 mL/min using the Cockcroft Gault formula at Screening.

Total bilirubin ≤2 mg/dL.

Patients with Gilbert's Syndrome must have a total bilirubin ≤3 mg/dL.

11. Patients were seronegative for the human immunodeficiency virus (HIV1 and HIV2). Patients with positive serology for hepatitis B virus surface antigen (HBsAg), hepatitis B core antibody (anti HBc), or hepatitis C virus (anti-HCV) indicating acute or chronic infection were enrolled depending on the viral load based on polymerase chain reaction (PCR) and the local prevalence of certain viral exposures.

12. Patients had a washout period from prior anticancer therapy(ies) of a minimum duration, as detailed below prior to the first study treatment (i.e., start of NMA-LD or pembrolizumab):

Targeted therapy: prior targeted therapy with an epidermal growth factor receptor (EGFR), MEK, BRAF, ALK, ROS1 or other-targeted agents (e.g., erlotinib, afatinib, dacomitinib, osimertinib, crizotinib, ceritinib, lorlatinib) was allowed provided the washout is a minimum of 14 days prior to the start of treatment.

Chemotherapy: adjuvant, neoadjuvant or definitive chemotherapy/chemoradiation was allowed provided the washout is a minimum of 21 days prior to the start of treatment.

Immunotherapy for Cohort 3B only, prior checkpoint-targeted therapy with an anti-PD-1, other mAbs, or vaccines were allowed with a washout period of ≥21 days before the start of NMA-LD.

Palliative radiation therapy: prior external beam radiation was allowed provided all radiation-related toxicities were resolved to Grade 1 or baseline, excluding alopecia, skin pigmentation change, or other clinically insignificant events, e.g., small area radiation dermatitis or rectal or urinary urgency The tumor lesion(s) being assessed as target for response via RECIST 1.1 were outside of the radiation portal; however, if within the portal, they must have demonstrated progression (see Inclusion Criterion above).

Surgery/pre-planned procedure: previous surgical procedure(s) was permitted provided that wound healing had occurred, all complications had resolved, and at least 14 days have elapsed (for major operative procedures) prior to the tumor resection.

13. Patients had recovered from all prior anticancer treatment-related adverse events (TRAEs) to Grade ≤1 (per Common Terminology Criteria for Adverse Events [CTCAE]), except for alopecia or vitiligo, prior to cohort assignment.

14. Patients with stable Grade ≥2 toxicity from prior anticancer therapy were considered on a case by case basis after consultation with the Medical Monitor.

15. Cohorts 1A, 2A, and 3A patients with irreversible toxicity not reasonably expected to be exacerbated by treatment with pembrolizumab were included only after consultation with the Medical Monitor. For patients in Cohort 3B only, patients with documented Grade ≥2 or higher diarrhea or colitis as a result of a previous treatment with immune checkpoint inhibitor CPI(s) must have been asymptomatic for at least 6 months or had a normal by visual assessment colonoscopy post-treatment prior to tumor resection.

16. Patients must have provided written authorization for use and disclosure of protected health information.

Exclusion Criteria

Patients who meet ANY of the following criteria were excluded from the study:

1. Patients with melanoma of uveal/ocular origin

2. Patients who had received an organ allograft or prior cell transfer therapy that included a nonmyeloablative or myeloablative chemotherapy regimen within the past 20 years. (Note: This criterion was applicable for patients undergoing retreatment with TIL, with the exception that they had a prior NMA-LD regimen with their prior TIL treatment.)

3. Patients with symptomatic and/or untreated brain metastases.

Patients with definitively-treated brain metastases will be considered for enrollment after discussion with Medical Monitor; if, prior to the start of treatment the patient is clinically stable for ≥2 weeks, there are no new brain lesions via magnetic resonance imaging (MRI) post-treatment, and the patient does not require ongoing

337 corticosteroid treatment.

4. Patients who are on a systemic steroid therapy within 21 days of enrollment.

5. Patients who are pregnant or breastfeeding.

6. Patients who had an active medical illness(es), which in the opinion of the Investigator, posed increased risks for study participation; such as systemic infections (e.g., syphilis or any other infection requiring antibiotics), coagulation disorders, or other active major medical illnesses of the cardiovascular, respiratory, or immune systems.

7. Patients may not have active or prior documented autoimmune or inflammatory disorders (including pneumonitis, inflammatory bowel disease [e.g., colitis or Crohn's disease], diverticulitis [with the exception of diverticulosis], systemic lupus erythematosus, sarcoidosis syndrome, or Wegener syndrome [granulomatosis with polyangiitis, Graves' disease, rheumatoid arthritis, hypophysitis, uveitis, etc.]). The following were exceptions to this criterion:

Patients with vitiligo or alopecia.

Patients with hypothyroidism (e.g., following Hashimoto syndrome) stable on hormone replacement.

Any chronic skin condition that did not require systemic therapy.

Patients with celiac disease controlled by diet alone.

8. Patients who had received a live or attenuated vaccination within 28 days prior to the start of treatment.

9. Patients who had any form of primary immunodeficiency (such as severe combined immunodeficiency disease [SCID] and acquired immune deficiency syndrome [AIDS]).

10. Patients with a history of hypersensitivity to any component of the study drugs. TILs were not administered to patients with a known hypersensitivity to any component of TIL product formulation including, but not limited to any of the following:

NMA-LD (cyclophosphamide, mesna, and fludarabine)

Proleukin®, aldesleukin, IL-2

Antibiotics of the aminoglycoside group (i.e., streptomycin, gentamicin [excluding those who are skin-test negative for gentamicin hypersensitivity])

Any component of the TIL product formulation including dimethyl sulfoxide

[DMSO], HSA, IL-2, and dextran-40

Pembrolizumab

11. Patients who had a left ventricular ejection fraction (LVEF)<45% or who are New York Heart Association Class II or higher. A cardiac stress test demonstrating any irreversible wall movement abnormality in any patients ≥60 years of age or in patients who have a history of ischemic heart disease, chest pain, or clinically significant atrial and/or ventricular arrhythmias. Patients with an abnormal cardiac stress test could be enrolled if they had adequate ejection fraction and cardiology clearance with approval of the Sponsor's Medical Monitor.

12. Patients who had obstructive or restrictive pulmonary disease and have a documented FEV1 (forced expiratory volume in 1 second) of ≤60% of predicted normal. If a patient was not able to perform reliable spirometry due to abnormal upper airway anatomy (i.e., tracheostomy), a 6-minute walk test was used to assess pulmonary function. Patients who were unable to walk a distance of at least 80% predicted for age and sex or demonstrates evidence of hypoxia at any point during the test (SpO2<90%) are excluded.

13. Patients who had another primary malignancy within the previous 3 years (except for those which did not require treatment or had been curatively treated greater than 1 year ago, and in the judgment of the Investigator, did not pose a significant risk of recurrence including, but not limited to, non-melanoma skin cancer, DCIS, LCIS, prostate cancer Gleason score ≤6 or bladder cancer).

14. Participation in another clinical study with an investigational product within 21 days of the initiation of treatment.

Study Endpoints and Planned Analyses

The primary and secondary endpoints were analyzed separately by cohort.

Primary Endpoints:

The ORR was defined as the proportion of patients who achieved either a confirmed PR or CR as best response as assessed by Investigators per RECIST 1.1 among the efficacy analysis set.

Objective response was evaluated per each disease assessment and the ORR was expressed as a binomial proportion with the corresponding 2-sided 90% CI. The primary analysis for each cohort occurred when all treated patients per cohort have an opportunity to be followed for 12 months, unless progressed/expired or discontinued early from the assessment period.

The safety primary endpoint was measured by any Grade 3 or higher TEAE incidence rate within each cohort expressed as binomial proportions with the corresponding 2-sided 90% CI.

Secondary Endpoints:

Efficacy:

The secondary efficacy endpoints were defined as follows:

CR rate as based on responders who achieved confirmed CR as assessed by Investigators. DCR was derived as the sum of the number of patients who achieved confirmed PR/CR or sustained SD (at least 6 weeks) divided by the number of patients in the efficacy analysis set×100%. The CR rate and DCR was summarized using a point estimate and its 2-sided 90% CI.

DOR was defined among patients who achieved objective response. It was measured from the first-time response (PR/CR) criteria are met until the first date that recurrent or progressive disease was objectively documented, or receipt of subsequent anticancer therapy or the patient dies (whichever is first recorded). Patients not experiencing PD or have not died prior to the time of data cut or the final database lock will have their event times censored on the last date that an adequate assessment of tumor status is made.

PFS was defined as the time (in months) from the time of lymphodepletion to PD, or death due to any cause, whichever event is earlier. Patients not experiencing PD or not having expired at the time of the data cut or the final database lock had their event times censored on the last date that an adequate assessment of tumor status is made.

OS was defined as the time (in months) from the time of lymphodepletion to death due to any cause. Patients not having expired by the time of data cut or the final database lock had their event times censored on the last date of their known survival status.

DOR, PFS, and OS was subjected to right censoring. The Kaplan-Meier method will be used to summarize the time-to-event efficacy endpoints. The baseline data for the tumor assessment was the last scan before the lymphodepletion for all cohorts.

The above efficacy parameters will be estimated for applicable cohort for subsets defined by baseline disease characteristics; BRAF status (Cohort 1A only), HPV status (Cohort 2A only), squamous or non-squamous lung disease (Cohorts 3A and 3B only), and anti-PD-L1 status.

Example 11: An Exemplary Embodiment of the Gen 3 Expansion Platform at Day 0

Prepared tumor wash media. Media warmed prior to start. Added 5 mL of gentamicin (50 mg/mL) to the 500 mL bottle of HBSS. Added 5 mL of Tumor Wash Media to a 15 mL conical to be used for OKT3 dilution. Store at room temperature (RT)

Prepared feeder cell bags. Sterilely transferred feeder cells to feeder cell bags and stored at 37° C. until use or freeze. Counted feeder cells if at 37° C. Thawed and then counted feeder cells if frozen.

Optimal range for the feeder cell concentration is between $5\times10^4$ and $5\times10^6$ cells/mL. Prepared four conical tubes with 4.5 mL of AIM-V. Added 0.5 mL of cell fraction for each cell count.

If total viable feeder cell number was $\geq 1\times10^9$ cells, proceeded to the next step to adjust the feeder cell concentration. Calculated the volume of feeder cells to remove from the first feeder cell bag in order to add $1\times10^9$ cells to a second feeder cell bag.

Using the p1000 micropipette, transferred 900 µl of Tumor Wash Media to the OKT3 aliquot (100 µL). Using a syringe and sterile technique, drew up 0.6 mL of OKT3 and added into the second feeder cell bag. Adjusted media volume to a total volume of 2L. Transferred the second feeder cells bag to the incubator.

OKT3 formulation details: OKT3 may be aliquoted and frozen in original stock concentration from the vial (1 mg/mL) in 100 ul aliquots. ~10× aliquots per 1 mL vial. Stored at −80 C. Day 0: 15 ug/flask, i.e. 30 ng/mL in 500 mL-60 ul max ~1 aliquot.

Prepared tumor samples. Obtained 6-well plate and 100 mm petri dishes (4 total). Labeled the 6 well plate 'Excess Tumor Pieces'. Labeled one each of the four 100 mm petri dishes as 'Wash_01', 'Wash_02', 'Wash_03', 'Wash_04', and 'Holding'.

Added 5 mL of Tumor Wash Medium into all wells of the 6-well plate labelled Excess Tumor Pieces. Kept the Tumor Wash Medium available for further use in keeping the tumor hydrated during dissection.

Added 50 mL of Tumor Wash Medium to each 100 mm petri dish labelled Wash_01, Wash_02, Wash_03, and Holding. Using a marker, label each petri dish as Dissection 1 through Dissection 4. Incubated the tumor at ambient temperature in Wash_01 for ≥3 min. Incubated the tumor at ambient temperature in Wash_02 for ≥3 min. Incubated the tumor at ambient temperature in Wash_03 for ≥3 min. After washes were completed, moved tumor to the 'Holding' dish to ensure tissue stays hydrated.

Whittle tumor incubations were in progress, transferred 10 mL of tumor shipping medium into a tube labelled Tumor Shipping Medium. Drew 10 mL of the Tumor Shipping Medium into a syringe and inoculated one each anaerobic and aerobic sterility bottle with 5 mL of tumor shipping medium.

Placed ruler under the petri dish lid for the entirety of the dissection process. Measured and recorded length of the tumor and the number of fragments. Dissected the tumor into four intermediate pieces or group into four groups of equivalent volume and conserving the tumor structure of each intermediate piece. Keep tumor pieces hydrated.

Transferred any intermediate tumor pieces not being actively dissected to the Holding dish to keep the tissue hydrated.

Dissected the tumor into 27 mm$^3$ fragments (3×3×3 mm), using the ruler under the Dissection dish lid as a reference. Dissected intermediate fragment until 60 fragments were reached. Counted total number of final fragments and prepared G-Rex 100MCS flasks according to the number of final fragments generated (generally 60 fragments per flask).

Retained favorable tissue fragments in the conical tubes labeled as Fragments Tube 1 through Fragments Tube 4. Calculated the number of G-Rex 100MCS flasks to seed with feeder cell suspension according to the number of fragments tubes originated.

Removed feeder cells bag from the incubator and seed the G-Rex 100MCS. Label as D0 (Day 0).

Tumor Fragment Addition Culture in G-Rex100MCS

Under sterile conditions, unscrewed the cap of the G-Rex 100MCS labelled Tumor Fragments Culture (D0) 1 and the 50 mL conical tube labelled Fragments Tube. Swirled the opened Fragments Tube 1 and, at the same time, slightly lifted the cap of the G-Rex100MCS. Added the medium with the fragments to the G-Rex100MCS while being swirled. Recorded the number of fragments transferred into the G-Rex100MCS.

Once the fragments were located at the bottom of the GREX flask, drew 7 mL of media and created seven 1 mL aliquots-5 mL for extended characterization and 2 mL for sterility samples. Stored the 5 aliquots (final fragment culture supernatant) for extended characterization at −20° C. until needed.

Inoculated one anaerobic BacT/Alert bottle and one aerobic BacT/Alert bottle each with 1 mL of final fragment culture supernatant. Repeat for each flask sampled.

Example 12: An Exemplary Embodiment of E Gen 3 Expansion Platform at Day 7-8

Prepared feeder cell bags. Thawed feeder bags for 3-5 minutes in 37° C. water bath when frozen. Counted feeder cells if frozen.

Optimal range for the feeder cell concentration is between $5\times10^4$ and $5\times10^6$ cells/mL. Prepared four conical tubes with 4.5 mL of AIM-V. Added 0.5 mL of cell fraction for each cell count into a new cryovial tube. Mixed the samples well and proceeded with the cell count.

If total viable feeder cell number was $\geq 2\times10^9$ cells, proceeded to the next step to adjust the feeder cell concentration. Calculated the volume of feeder cells to remove from the first feeder cell bag in order to add $2\times10^9$ cells to the second feeder cell bag.

Using the p1000 micropipette, transfer 900 µl of HBSS to a 100 µL, OKT3 aliquot. Mix by pipetting up and down 3 times. Prepared two aliquots.

OKT3 formulation details: OKT3 may be aliquoted and frozen in original stock concentration from the vial (1 mg/mL) in 100 ul aliquots. ~10× aliquots per 1 mL vial. Stored at −80 C. Day 7/8: 30 ug/flask, i.e. 60 ng/mL in 500 mL-120 ul max ~2 aliquots.

Using a syringe and sterile technique, drew up 0.6 mL of OKT3 and added into the feeder cell bag, ensuring all added. Adjusted media volume to a total volume of 2L. Repeated with second OKT3 aliquot and added to the feeder cell bag. Transferred the second feeder cells bag to the incubator.

Prepare G-Rex100MCS Flask with Feeder Cell Suspension

Recorded the number of G-Rex 100MCS flasks to process according to the number of G-Rex flasks generated on Day 0. Removed G-Rex flask from incubator and removed second feeder cells bag from incubator.

Removal of Supernatant Prior to Feeder Cell Suspension Addition:

Connected one 10 mL syringe to the G-Rex100 flask and drew up 5 mL of media. Created five 1 mL aliquots-5 mL for extended characterization and stored the 5 aliquots (final fragment culture supernatant) for extended characterization at −20° C. until requested by sponsor. Labeled and repeated for each G-Rex100 flask.

5-20×1 mL samples for characterization, depending on number of flasks:

5 mL=1 flask
10 mL=2 flasks
15 mL=3 flasks
20 mL=4 flasks

Continued seeding feeder cells into the G-Rex100 MCS and repeated for each G-Rex100 MCS flask. Using sterile transfer methods, gravity transferred 500 mL of the second feeder cells bag by weight (assume 1 g=1 mL) into each G-Rex 100MCS flask and recorded amount. Labeled as Day 7 culture and repeated for each G-Rex100 flask. Transferred G-Rex 100MCS flasks to the incubator.

Example 13: An Exemplary Embodiment of the Gen 3 Expansion Platform at Day 10-11

Removed the first G-Rex 100MCS flask and using sterile conditions removed 7 mL of Pre-process Culture Supernatant using a 10 mL syringe. Created seven 1 mL aliquots-5 mL for extended characterization and 2 mL for sterility samples.

Mixed the flask carefully and using a new 10 mL syringe remove 10 mL supernatant and transfer to a 15 mL tube labelled as D10/11 Mycoplasma Supernatant.

Mixed the flask carefully and using a new syringe removed the volume below according to how many flasks were to be processed:

1 flask=40 mL
2 flask=20 mL/flask
3 flask=13.3 mL/flask
4 flask=10 mL/flask

A total of 40 mL should be pulled from all flasks and pooled in a 50 mL conical tube labeled 'Day 10/11 QC Sample' and stored in the incubator until needed. Performed a cell count and allocated the cells.

Stored the 5 aliquots (pre-process culture supernatant) for extended characterization at ≤−20° C. until needed. Inoculated one anaerobic BacT/Alert bottle and one aerobic BacT/Alert bottle each with 1 mL of pre-process culture supernatant.

Continued with cell suspension transferred to the G-Rex 500MCS and repeated for each G-Rex 100MCS. Using sterile conditions, transferred the contents of each G-Rex 100MCS into a G-Rex 500MCS, monitoring about 100 mL of fluid transfer at a time. Stopped transfer when the volume of the G-Rex 100MCS was reduced to 500 mL.

During transfer step, used 10 mL syringe and drew 10 mL of cell suspension into the syringe from the G-Rex 100MCS. Followed the instructions according to the number of flasks in culture. If only 1 flask: Removed 20 mL total using two syringes. If 2 flasks: removed 10 mL per flask. If 3 flasks: removed 7 mL per flask. If 4 flasks: removed 5 mL per flask. Transferred the cell suspension to one common 50 mL conical tube. Keep in the incubator until the cell count step and QC sample. Total number of cells needed for QC was ~20e6 cells: 4×0.5 mL cell counts (cell counts were undiluted first).

Cells needed for assays:
10e6 cells minimum for IFN-G assay
1e6 cells for mycoplasma
5e6 cells flow CD3+/CD45+

Transferred the G-Rex 500MCS flasks to the incubator.

Prepared QC Samples

Needed at least $15 \times 10^8$. Assays included: Cell count and viability; Mycoplasma ($1 \times 10^6$ cells/average viable concentration) Flow ($5 \times 10^6$ cells/average viable concentration) and IFN-g assay ($5 \times 10^6$ cells-$1 \times 10^6$ cells; $8$-$10 \times 10^6$ cells are required for the IFN-γ assay.

Calculated the volume of cells fraction for cryopreservation at $10 \times 10^6$ cells/mL and calculated the number of vials to prepare.

Example 14: An Exemplary Embodiment of Gen 3 Expansion Platform Day 16-17

Wash Buffer Preparation (1% HAS PLASMALYTE A)

Transferred HAS and PLasmalyte to 5L bag to make LOVO wash buffer. Using sterile conditions, transferred a total volume of 125 mL of 25% HSA to the 5L bag. Stored at room temperature.

Removed and transferred 10 mL or 40 mL of wash buffer in the 'IL-2 $6 \times 10^4$ IU/mL' tube (10 mL if IL-2 was prepared in advance or 40 mL if IL-2 was prepared fresh).

Calculated volume of reconstituted IL-2 to add to Plasmalyte+ 1% HSA: volume of reconstituted IL-2=(Final concentration of IL-2×Final volume)/specific activity of the IL-2 (based on standard assay). The Final Concentration of IL-2 was $6 \times 10^4$ IU/mL. The final volume was 40 mL.

Removed calculated initial volume of IL-2 needed of reconstituted IL-2 and transfer to the 'IL-2 $6 \times 10^4$ IU/mL' tube. Added 100 µL, of IL-2 $6 \times 10^6$ IU/mL from the aliquot prepared in advance to the tube labelled 'IL-2 $6 \times 10^4$ IU/mL' containing 10 mL of LOVO wash buffer.

Removed about 4500 mL of supernatant from the G-Rex 500MCS flasks. Swirled the remaining supernatant and transferred cells to the Cell Collection Pool bag. Repeated with all G-Rex 500MCS flasks.

Removed 60 mL of supernatant and add to supernatant tubes for quality control assays, including mycoplasma detection. Stored at +2-8° C.

Cell Collection

Counted cells. Prepare four 15 mL conicals with 4.5 mL of AIM-V. These may be prepared in advance. Optimal range=is between $5 \times 10^4$ and $5 \times 10^6$ cells/mL. (1:10 dilution was recommended). For 1:10 dilution, to 4500 µL, of AIM V prepared previously, add 500 µL, of CF. Recorded dilution factor.

Calculated the $TC$ (Total Cells) pre$-LOVO$ (live + dead) =

Average Total Cell Concentration ($TC$ conc pre $LOVO$) (live + dead) $X$ Volume of Source bag Calculated the $TVC$ (Total Cells) pre$-LOVO$ (live) = Average Total Cell Concentration ($TVC$ pre $LOVO$) (live) $X$ Volume of $LOVO$ Source bag When the total cell (TC) number was >5×10$^9$, remove 5×10$^8$ cells to be cryopreserved as MDA retention samples. 5×10$^8$÷avg TC concentration (step 14.44)=volume to remove.

When the total cell (TC) number was ≤5×10$^9$, remove 4×10$^6$ cells to be cryopreserved as MDA retention samples. 4×10$^6$÷avg TC concentration=volume to remove.

Used an appropriately sized syringe to remove the required volume from the LOVO Source Bag. Retained in incubator until cryopreservation steps.

When the total cell number was determined, the number of cells to remove should allow retention of 150×10$^9$ viable cells. Confirm TVC pre-LOVO 5×10$^8$ or 4×10$^6$ or not applicable. Calculated the volume of cells to remove.

Calculated the remaining Total Cells Remaining in Bag. Calculated the TC (Total Cells) pre-LOVO. [Avg. Total cell concentration X Remaining Volume=TC pre-LOVO Remaining]

According to the Total number of cells remaining, selected the corresponding process in the following table:

| Total cells: | Retentate (mL) |
| --- | --- |
| 0 < Total cells ≤ 31 × 10$^9$ | 115 |
| 31 × 10$^9$ < Total cells ≤ 71 × 10$^9$ | 165 |
| 71 × 10$^9$ < Total Cells ≤ 110 × 10$^9$ | 215 |
| 110 × 10$^9$ < Total Cells ≤ 115 × 10$^9$ | 265 |

Chose the volume of IL-2 to add corresponding to the used process. Volume calculated as: Retentate Volume×2× 300 IU/mL=IU of IL-2 required. IU of IL-2 required/6× 10$^4$IU/mL=Volume of IL-2 to add Post LOVO bag. Recorded all volumes added. Obtained samples in cryovial for further analyses.

Mixed the cell product well. Sealed all bags for further processing, included cryopreservation when applicable.

Performed Enodxoton, IFN-γ, sterility, and other assays as needed on cryovial samples obtained.

Example 15: Exemplary Gen 3 Process (Also Referred to as Gen 3.1)

Purpose

This example describes further studies regarding the "Comparability between the Gen 2 and Gen 3 processes for TIL expansion". The Gen 3 process was modified to include an activation step early in the process with the goal of increasing the final total viable cell (TVC) output to be comparable (or better) to that in Gen 2, while maintaining the phenotypic and functional profiles as previously seen.

Scope

Assessed TVC output through introduction of an activation step to the cultured tumor fragments on Day 0.

Demonstrated comparability in terms of functional and extended phenotypic characterization with the Gen 3 standard, as well as a control arm, across two independent patient tumors.

Analyzed media consumption and metabolite production to confirm processing parameters were maintained at physiologic conditions.

All runs for this example were performed at full-scale platform using commercial donor tumor tissue as the starting material.

Information

The Process Gen 3 embodiment was modified as a further embodiment and is referred to herein in this example as Gen 3.1.

Gen 3.1 TIL Manufacturing Concept has Four Operator Interventions:

1. Tumor Fragment Isolation and Activation: On Day 0 of the process the tumor was dissected and the final fragments generated awe-3×3 mm each (up to 240 fragments total) and cultured in 1-4 G-Rex100MCS flasks. Each flask contained up to 60 fragments, 500 mL of CM1 or DM1 media, and supplemented with 6,000 IU rhIL-2, 15 μg OKT3, and 2.5×10$^8$ irradiated allogeneic mononuclear cells. The culture was incubated at 37° C. for 6-8 days.

2. TIL Culture Reactivation: On Day 7-8 the culture was supplemented through slow addition of CM2 or DM1 media supplemented with 6,000 IU rhIL-2, 30 μg OKT3, and 5×10$^8$ irradiated allogeneic mononuclear cells in both cases. Care was taken to not disturb the existing cells at the bottom of the flask. The culture was incubated at 37° C. for 3-4 days.

3. Culture Scale Up: Occurs on day 10-11. During the culture scale-up, the entire contents of the G-Rex100MCS was transferred to a G-Rex500MCS flask containing 4L of CM4 or DM2 supplemented with 3,000 IU/mL of IL-2 in both cases. Flasks were incubated at 37° C. for 5-6 days until harvest.

4. Harvest/Wash/Formulate: On day 16-17 the flasks are volume reduced and pooled. Cells were concentrated and washed with PlasmaLyte A pH 7.4 containing 1% HSA. The washed cell suspension was formulated at a 1:1 ratio with CryoStor10 and supplemented with rhIL-2 to a final concentration of 3001 U/mL.

The DP was cryopreserved with a controlled rate freeze and stored in vapor phase liquid nitrogen. *Complete Standard TIL media 1, 2, or 4 (CM1, CM2, CM4) could be substituted for CTSTMOpTmizer™ T-Cell serum free expansion Medium, referred to as Defined Medium (DM1 or DM2), as noted above. For process overview, see for example, FIGS. 78 and 79.

Process Description

On day 0, the tumor was washed 3 times, then fragmented in 3×3×3 final fragments. Once the whole tumor was fragmented, then the final fragments were randomized equally and divided into three pools. One randomized fragment pool was introduced to each arm, adding the same number of fragments per the three experimental matrices.

Tumor L4063 expansion was performed with Standard Media and tumor L4064 expansion was performed with Defined Media (CTS OpTmizer) for the entire TIL expansion process. Components of the media are described herein.

CM1 Complete Media 1: RPMI+ Glutamine supplemented with 2 mM Glutamax, 10% Human AB Serum, Gentamicin (50 ug/mL), 2-Mercaptoethanol (55 uM). Final media formulation supplemented with 6000IU/mL IL-2

CM2 Complete Media 2: 50% CM1 medium+50% AIM-V medium. Final media formulation supplemented with 60001 U/mL IL-2

CM4 Complete Media 4: AIM-V supplemented with Glutamax (2 mM). Final media formulation supplemented with 3000IU/mL IL-2

CTS OpTmizer CTSTMOpTmizer™ T-Cell Expansion Basal Medium supplemented with CTS™ OpTmizer™ T-Cell Expansion Supplement (26 mL/L).

DM1: CTSTMOpTmizer™ T-Cell Expansion Basal Medium supplemented with CTS™ OpTmizer™ T-Cell Expansion Supplement (26 mL/L), and CTS™ Immune Cell SR (3%), with Glutamax (2 mM). Final formulation supplemented with 6,000 IU/mL of IL-2.

DM2: CTSTMOpTmizer™ T-Cell Expansion Basal Medium supplemented with CTS™ OpTmizer™ T-Cell Expansion Supplement (26 mL/L), and CTS™ Immune Cell SR (3%), with Glutamax (2 mM). Final formulation supplemented with 3,000 IU/mL of IL-2.

All types of media used, i.e., Complete (CM) and Defined (DM) media, were prepared in advance, held at 4° C. degree until the day before use, and warmed at 37° C. in an incubator for up to 24 hours in advance prior to process day.

TIL Culture Reactivation occurred on Day 7 for both tumors. Scale-up occurred on day 10 for L4063 and day 11 for L4064. Both cultures were harvested and cryopreserved on Day 16.

Expected Results

Gen 3.1 may reach a higher total viable cells number at harvest on day 16-17 compared to Gen 3.0.

Gen 3.1 may produce similar levels of IFNγ after restimulation, relative to Gen 3.0.

Gen 3.1 and Gen 3.0 may have a similar clonal diversity, measured by total unique CDR3 sequences present in the final TIL product.

Phenotypic characteristics in the Gen 3.1 process may be similar to Gen 3.0.

Results Achieved

Cells counted and % viability for Gen 3.0 and Gen 3.1 processes were determined. Expansion in all the conditions followed details described in this example.

Total Viable Cell Counts and Fold Expansion

For each tumor, the fragments were divided into three pools of equal numbers. Due to the small size of the tumors, the maximum number of fragments per flask was not achieved. For the three different processes, the total viable cells and cell viability were assessed for each condition. Cell counts were determined as TVC on day 7 for reactivation, TVC on day 10 (L4064) or day 11 (L4063) for scale-up, and TVC at harvest on day 16/17.

Cell counts for Day 7 and Day 10/11 were taken FIO. Fold expansion was calculated by dividing the harvest day 16/17 TVC by the day 7 reactivation day TVC. To compare the three arms, the TVC on harvest day was divided by the number of fragments added in the culture on Day 0 in order to calculate an average of viable cells per fragment.

Cell counts and viability assays were performed for L4063 and L4064. As indicated in FIG. 89, the Gen 3.1-Test process yielded more cells per fragment than the Gen 3.0 Process on both tumors.

FIG. 90: Total viable cell count and fold expansion

% Viability During the Process

On reactivation, scale up and harvest the percent viability was performed on all conditions. On day 16/17 harvest, the final TVC were compared against release criteria for % viability. All of the conditions assessed surpassed the 70% viability criterion and were comparable across processes and tumors as is shown in FIG. 82.

Immunophenotyping

Phenotypic characterization on TIL final product.

The final products were subjected to flow cytometry analysis to test purity, differentiation, and memory markers. Percent populations were consistent for TCRα/β, CD4+ and CD8+ cells for all conditions.

Extended phenotypic analysis of REP TIL was performed. TIL product showed a higher percentage of CD4+ cells for Gen 3.1 conditions compared to Gen 3.0 on both tumors, and higher percentage of CD28+ cells from CD8+ population for Gen 3.0 compared to Gen 3.1 conditions on both conditions.

TIL harvested from the Gen 3.0 and Gen 3.1 processes showed comparable phenotypic markers as CD27 and CD56 expression on CD4+ and CD8+ cells, and a comparable CD28 expression on CD4+ gated cells population. FIG. 83 shows the phenotypic markers of the final TIL product for Gen 3.0 and Gen 3.1 processes. FIG. 83: Phenotypic characterization of final TIL product for L4063 and L4064.

Memory Markers Comparison on TIL Final Product:

FIG. 84 shows the memory markers of TIL final product that were determined by multicolor flow cytometry. Frozen samples of TIL harvested on day 16 were stained for analysis. TIL memory status was comparable between Gen 3.0 and Gen 3.1 processes. FIG. 84: Memory marker analysis of TIL product for L4063 and L4064.

Activation and Exhaustion Markers Comparison on TIL Final Product:

FIGS. 85 and 86 show the activation and exhaustion of TIL final product that were determined by multicolor flow cytometry. Activation and exhaustion markers were comparable between the Gen 3.0 and Gen 3.1 processes gated on CD4+ (FIG. 85) and CD8+ (FIG. 86) cells. FIG. 85: Activation and exhaustion markers gated on CD4+ cells for L4063 and L4064. FIG. 86: Activation and exhaustion markers gated on CD8+ cells for L4063 and L4064.

Interferon Gamma Secretion Upon Restimulation:

Harvested TIL underwent an overnight restimulation with coated anti-CD3 plates for L4063 and L4064. Higher production of IFNγ from the Gen 3.1 process was observed in the two tumors analyzed compared to Gen 3.0 process. The IFNγ production on each condition is shown in FIG. 87. FIG. 87: IFN-γ production (pg/mL) for final product on processes Gen 3.0 and Gen 3.1.

Measurement of IL-2 Levels in Culture Media

To compare the levels of IL-2 consumption between all of the conditions and processes, cell supernatants were collected at initiation of reactivation on Day 7, at scale-up Day 10 (L4064)/11 (L4063), and at harvest Day 16/17, and frozen. The supernatants were subsequently thawed and then analyzed. The quantity of IL-2 in cell culture supernatant was measured by the manufacturer protocol. Data are shown in FIG. 88.

Overall Gen 3 and Gen 3.1 processes were comparable in terms of IL-2 consumption during the complete process assessed across same media conditions. FIG. 88: IL-2 concentration (pg/mL) analysis on spent media collected for L4063 and L4064.

Metabolite Analysis

Spent media supernatants was collected from L4063 and L4064 at reactivation initiation on day 7, scale-up on day 10 (L4064) or day 11 (L4063), and at harvest on days 16/17 for L4063 and L4064, for every condition. Supernatants were analyzed on a CEDEX Bio-analyzer for concentrations of glucose, lactate, glutamine, glutamax, and ammonia. FIG. 89 shows the concentration of glucose in spent media collected for Gen 3.0 and Gen 3.1 processes for L4063 and L4064 tumors.

Defined media has a higher glucose concentration of 4.5 g/L compared to complete media (2 g/L). Overall, the concentration and consumption of glucose were comparable for Gen 3.0 and Gen 3.1 processes within each media type. FIG. 89: Concentration of glucose (g/L) in spent media for L4063 and L4064.

An increase in lactate was observed for both tumors, L4063 and L4064, for all test conditions. The increase in lactate was comparable between the Gen 3.0 and Gen 3.1 conditions and between the two media used for reactivation expansion (complete media for L4063 and defined media for L4064).

FIG. 90 shows the concentration of lactate on spent media collected for Gen 3.0 and Gen 3.1 processes conditions for both tumors L4063 and L4064. FIG. 90: Concentration of lactate (g/L) in spent media for L4063 and L4064.

In the case of L4063, the standard basal media contained 2 mM L-glutamine and was supplemented with 2 mM glutamax to compensate for the natural degradation of L-glutamine in culture conditions to L-glutamate and ammonia.

For L4064 tumor, defined (serum free) media used did not contain L-glutamine on the basal media, and was supplemented only with glutamax to a final concentration of 2 mM. Glutamax is a dipeptide of L-alanine and L-glutamine, is more stable then L-glutamine in aqueous solutions and does not spontaneously degrade into glutamate and ammonia. Instead, the dipeptide is gradually dissociated into the individual amino acids, thereby maintaining a lower but sufficient concentration of L-glutamine to sustain robust cell growth. FIG. 91 and FIG. 92 shows the concentration of glutamine and glutamax respectively on spent media collected on Gen 3.0 and Gen 3.1 processes conditions for both tumors L4063 and L4064.

For L4063, the concentration of glutamine and glutamax slightly decreased on the scale-up day, but at harvest day showed an increase to similar or closer levels compared to reactivation day. For L4064, glutamine and glutamax concentration showed a slight degradation in a similar rate between different conditions, during the whole process. FIG. 91: Concentration of glutamine (mmol/L) in spent media for L4063 and L4064. FIG. 92: Concentration of glutamax (mmol/L) in spent media for L4063 and L4064.

FIG. 93 shows the concentration of ammonia on spent media collected for Gen 3.0 and Gen 3.1 processes for both tumors L4063 and L4064. As expected, ammonia concentrations were higher for L4063 (grown in standard media containing 2 mM glutamine+2 mM glutamax) than L4064 (grown in defined media containing 2 mM glutamax). Further, as expected, there was a gradual increase or accumulation of ammonia over the course of the culture. There were no differences in ammonia concentrations across the three different test conditions. FIG. 93: Concentration of Ammonia (mmol/L) in spent media for L4063 and L4064.

Telomere Repeats by Flow—FISH:

Flow-FISH technology was used to measure the average length of the telomere repeat on L4063 and L4064 under Gen 3 and Gen 3.1 processes. The determination of a relative telomere length (RTL) was calculated using Telomere PNA kit/FITC for flow cytometry analysis from DAKO. Telomere assay was performed.

Telomere length in samples of L4063 an L4064, were compared to a control cell line (1301 leukemia). The control cell line is a tetraploid cell line having long stable telomeres, that allows calculation of a relative telomere length. Gen 3 and Gen 3.1 processes assessed in both tumors showed comparable telomere length as shown in FIG. 94. FIG. 94: Summary of Relative Telomere Length (RTL) Compared to the Control (1301) Cell Line.

TCR Vβ repertoire Analysis

To determine the clonal diversity of the cell products generated in each process, TIL final products were assayed for clonal diversity analysis through sequencing of the CDR3 portion of the T-cell receptors.

Three parameters were compared between the three conditions:

Diversity index of Unique CDR3 (uCDR3)
% shared uCDR3
For the top 80% of uCDR3:

Compare the % shared uCDR3 copies
Compare the frequency of unique clonotypes

FIG. 95: TCR Vβ repertoire summary for L4063 and L4064. Describes the clonality of TIL for final TIL product on tumor L4063 and L4064 on Gen 3 and Gen 3.1 conditions as measured by the TCR Vβ repertoire.

FIG. 97: Comparison between Gen 3 and Gen3.1 Control and Gen 3.1 Test, percentage shared unique CDR3 sequences on L4063 on TIL harvested cell product for: 975 sequences are shared between Gen 3 and Gen 3.1 Test final product, equivalent to 88% of top 80% of unique CDR3 sequences from Gen 3 shared with Gen 3.1 Test final product.

FIG. 96: L4063 Frequency comparison of unique CDR3 sequences on TIL harvested final cell product between Gen 3.0 and Gen 3.1 processes.

FIG. 98: Comparison between Gen 3 and Gen3.1 Control and Gen 3.1 Test, percentage shared unique CDR3 sequences on L4064 on TIL harvested cell product for: 2163 sequences are shared between Gen 3 and Gen 3.1 Test final product, equivalent to 87% of top 80% of unique CDR3 sequences from Gen 3 shared with Gen 3.1 Test final product.

FIG. 99: L4064 Frequency comparison of unique CDR3 sequences on TIL harvested final cell product between Gen 3.0 and Gen 3.1 processes.

The number of unique CD3 sequences identified from $1 \times 10^6$ cells collected on Harvest day 16, for the different processes. Gen 3.1 Test condition showed a slightly higher clonal diversity compared to Gen 3.0 based on the number of unique peptide CDRs within the sample.

Shanon entropy diversity index is a more reliable and common metric for comparison, for Gen 3.1 conditions on both tumors showed slightly higher diversity than Gen 3 process, suggesting that TCR Vβ repertoire for Gen 3.1 Test condition is more polyclonal than the Gen 3.0 process.

Additionally, the TCR Vβ repertoire for Gen 3.1 Test condition showed more than 87% overlap with the corresponding repertoire for Gen 3.0 process on both tumor L4063 and L4064.

ADDITIONAL INFORMATION

The value of IL-2 concentration on spent media for Gen 3.1 Test L4064 on reactivation day was below to the expected value (similar to Gen 3.1 control and Gen 3.0 condition).

The low value could be due to a pipetting error, but because of the minimal sample taken it was not possible to repeat the assay.

Spent media from scale up day 10/11 on sample L4064 was not collected, and not included in the analysis of IL-2 concentration and metabolite analysis on supernatant.

CONCLUSIONS

Gen 3.1 test condition including feeders and OKT-3 on Day 0 showed a higher TVC of cell doses at Harvest day 16 compared to Gen 3.0 and Gen 3.1 control. TVC on the final product for Gen 3.1 test condition was around 2.5 times higher than Gen 3.0.

Gen 3.1 test condition with the addition of OKT-3 and feeders on day 0, for both tumors L4063 and L4064, reached a maximum capacity of the flask at harvest. Under these conditions, if a maximum of 4 flasks on day 0 is initiated, the final cell dose could be between 80-100E+09 TILs.

All the quality attributes such as phenotypic characterization including purity, exhaustion, activation and memory markers on final TIL product were maintained and comparable between Gen 3.1 Test and Gen 3.0 process. Telomere length on TIL final product and IL-2 consumption on spent media were comparable between Gen 3.0 and Gen 3.1 processes.

IFN gamma production on final TIL product was 3 times higher on Gen 3.1 with feeder and OKT-3 addition on day 0, compared to Gen 3.0 in the two tumors analyzed, suggesting Gen 3.1 process generated a potent TIL product.

No differences observed in glucose or lactate levels across test conditions. No differences observed on glutamine and ammonia between Gen 3.0 and Gen 3.1 processes across media conditions. The low levels of glutamine on the media are not limiting cell growth and suggest the addition of glutamax only in media is sufficient to give the nutrients needed to make cells proliferate.

The scale up day for L4063 and L4064 was on day 11 and day 10 respectively and did not show major differences in terms of cell number reached on the harvest day of the process and metabolite consumption was comparable in both cases during the whole process. This observation suggests of Gen 3.0 optimized process can have flexibility on processing days, thereby facilitating flexibility in the manufacturing schedule.

Gen 3.1 process with feeder and OKT-3 addition on day 0 showed a higher clonal diversity measured by CDR3 TCRab sequence analysis compared to Gen 3.0.

FIG. 100 describes an embodiment of the Gen 3 process (Gen 3 Optimized process). Standard media and CTS Optimizer serum free media can be used for Gen 3 Optimized process TIL expansion. In case of CTS Optimizer serum free media is recommended to increase the glutamax on the media to final concentration 4 mM.

Feasibility and Comparability:

Feasibility:

Feasibility was established for all study conditions in all experiments. Across all the experiments and conditions and between the donor tumor tissue, all the experiments were performed utilizing the same lots of critical raw material such as IL-2, Human Serum-AB, allogeneic feeder cells, OKT-3.

Comparability:

Comparability was determined by the ability of any arm of the study to meet release criteria of our clinical product according to LFP-002 Autologous Tumor infiltrating Lymphocytes (TIL) cryopreserved Day 22, as outlined in FIG. 101.

Example 16: Tumor Expansion Processes with Defined Medium

The processes disclosed in Examples 7 through 15 are performed with substituting the CM1 and CM2 media with a defined medium according to the present invention (e.g., CTS™ OpTmizer™ T-Cell Expansion SFM, ThermoFisher, including for example DM1 and DM2).

Example 17: A Phase 2, Multicenter Study of Autologous Tumor Infiltrating Lymphocytes in Patients with Solid Tumors Study Design

Overview

This example describes a prospective, open-label, multicohort, non-randomized, multicenter Phase 2 study evaluating ACT using TIL in combination with pembrolizumab or TIL as a single therapy, using TILs prepared as described in the present application as well as in this example.

Objectives

Primary:

To evaluate the efficacy of autologous TIL in combination with pembrolizumab in MM, HNSCC, or NSCLC patients or TIL as a single therapy in relapsed or refractory (r/r) NSCLC patients, who had previously progressed on or after treatment with CPIs, as determined by objective response rate (ORR), using the Response Evaluation Criteria in Solid Tumors (RECIST 1.1), as assessed by Investigator.

To characterize the safety profile of TIL in combination with pembrolizumab in MM, HNSCC, and NSCLC patients or TIL as a single therapy in r/r NSCLC patients as measured by the incidence of Grade ≥3 treatment-emergent adverse events (TEAEs).

Secondary:

To further evaluate the efficacy of autologous TIL in combination with pembrolizumab in MM, HNSCC, and NSCLC patients or TIL as a single therapy in r/r NSCLC patients using complete response (CR) rate, duration of response (DOR), disease control rate (DCR), progression-free survival (PFS) using RECIST 1.1, as assessed by Investigator, and overall survival (OS).

Cohorts:

Cohort 1A: TIL therapy in combination with pembrolizumab in patients with Stage IIIC or Stage IV unresectable or MM with ≤3 prior lines of systemic therapy excluding immunotherapy. If previously treated, patients must have had radiographically documented progression on or after most recent therapy.

Cohort 2A: TIL therapy in combination with pembrolizumab in patients with advanced, recurrent or metastatic HNSCC (e.g., Stages T1N1-N2B, T2-4N0-N2b) with ≤3 prior lines of systemic therapy, excluding immunotherapy. If previously treated, patients must have had radiographically documented progression on or after most recent therapy.

Cohort 3A: TIL therapy in combination with pembrolizumab in patients with locally advanced or metastatic (Stage III-IV) NSCLC with ≤3 prior lines of systemic therapy, excluding immunotherapy. If previously treated, patients must have had radiographically documented progression on or after most recent therapy.

Cohort 3B: TIL therapy as a single agent in patients Stage III or Stage IV NSCLC who have previously received systemic therapy with CPIs (e.g., anti-PD-1/anti-PD-L1) as part of ≤3 prior lines of systemic therapy. If previously treated, patients must have had radiographically documented progression on or after most recent therapy.

Patients in Cohorts 3A and 3B (NSCLC) with oncogene-driven tumors with available effective targeted therapy must have received at least one line of targeted therapy.

All patients received autologous cryopreserved TIL therapy (with or without pembrolizumab, depending on cohort assignment), preceded by a nonmyeloablative lymphodepletion (NMA-LD) preconditioning regimen consisting of cyclophosphamide and fludarabine. Following TIL infusion, up to 6 IV interleukin-2 (IL-2) doses maximum were administered.

The following general study periods took place in all 4 cohorts, unless specified otherwise.

Screening and Tumor Resection: Up to 4 weeks (28 days) from study entry; manufacturing of the TIL Product: approximately ≤22 days from tumor resection; and treatment period, as discussed below.

Treatment Period (Cohorts 1A, 2A, and 3A): up to 2 years, including NMA-LD (7 days), TIL infusion (1 day) followed by IL-2 administrations (1 to 4 days). Patients receive a single infusion of pembrolizumab after the completion of their tumor resection for TIL production and baseline scans but before the initiation of the NMA-LD regimen. The next dose of pembrolizumab will be no earlier than following the completion of IL-2 and continue Q3W±3 days thereafter for ≤2 years (24 months) or until disease progression or unacceptable toxicity, whichever occurs first. The end-of-treatment (EOT) visit occurred within 30 days after the last dose of pembrolizumab. The visit could be combined with end-of-assessment (EOA) visit if applicable (e.g., pembrolizumab discontinuation occurred at disease progression or at the start of new anticancer therapy).

Treatment Period (Cohort 3B): up to 12 days, including NMA-LD (7 days), TIL, infusion (1 day) followed by IL-2 administrations (1 to 4 days). The EOT visit occurred once a patient received the last dose of IL-2. The EOT visit was performed within 30 days after treatment discontinuation and it may be combined with any scheduled visit occurring within this interval during the assessment period.

Assessment Period: began after TIL infusion on Day 0 and ends upon disease progression, with the start of a new anticancer therapy, partial withdrawal of consent to study assessments, or 5 years (Month 60), whichever occurred first. An end-of assessment (EOA) visit occurred once a patient reached disease progression or started a new anti-cancer therapy.

The TIL autologous therapy with the TILs prepared as described herein was comprised of the following steps:

1. Tumor resection to provide the autologous tissue that serves as the source of the TIL cellular product;
2. TIL product produced at a central Good Manufacturing Practice (GMP) facility;
3. A 7-day NMA-LD preconditioning regimen;
4. Cohorts 1A, 2A, and 3A: Patients receive a single infusion of pembrolizumab after the completion of their tumor resection for TIL production and baseline scans but before the initiation of NMA-LD regimen. The next dose of pembrolizumab will be no earlier than following the completion of IL-2 and continue Q3W±3 days thereafter.
5. Infusion of the autologous TIL product (Day 0); and
6. IV IL-2 administrations for up to 6 doses maximum.

In Cohorts 1A, 2A, and 3A, the next dose of pembrolizumab was no earlier than following the completion of IL-2 and continue Q3W±3 days thereafter for ≤2 years (24 months), or until disease progression or unacceptable toxicity, whichever occurred first.

Flowcharts for Cohorts 1A, 2A, and 3A can be found in FIG. 7. The Flowchart for Cohort 3B can be found in FIG. 8. Patients were assigned to the appropriate cohort by tumor indication.

TIL Therapy+Pembrolizumab (Cohorts 1A, 2A, and 3A)

Patients were screened and scheduled for surgery for tumor resection. Patients then had one or more tumor lesions resected, which were sent to a central manufacturing facility for TIL production.

Next, the NMA-LD regimen was imitated and consisted of 2 days of IV cyclophosphamide (60 mg/kg) with mesna (per site standard of care or USPI/SmPC) on Days −7 and Day −6 followed by 5 days of IV fludarabine (25 mg/m2: Day −5 through Day −1).

Patients in Cohorts 1A, 2A, and 3A received a single infusion of pembrolizumab after the completion of their tumor resection for TIL production and baseline scans and before the initiation of NMA-LD regimen. IL-2 administrations at a dose of 600,000 IU/kg IV begun as soon as 3 hours after, but no later than 24 hours after, completion of the TIL infusion on Day 0. Additional IL-2 administrations will be given approximately every 8 to 12 hours for up to 6 doses maximum. The second dose of pembrolizumab was no earlier than following the completion of IL-2. Patients should have recovered from all IL-2-related toxicities (Grade ≤2), prior to the second pembrolizumab administration. Pembrolizumab will continue Q3W±3 days thereafter for ≤2 years (24 months) or until disease progression or unacceptable toxicity, whichever occurred first.

TIL Therapy as a Single Agent (Cohort 3B)

Patients were screened and scheduled for surgery for tumor resection. Patients then had one or more tumor lesions resected, which were sent to a central manufacturing facility for TIL production.

Next, the NMA-LD regimen consisted of 2 days of IV cyclophosphamide (60 mg/kg) with mesna (per site standard of care or USPI/SmPC) on Day −7 and Day −6 followed by 5 days of IV fludarabine (25 mg/m2: Day −5 through Day −1).

Infusion of the tumor-derived autologous TIL product occurred no sooner than 24 hours after last dose of fludarabine. IL-2 administrations at a dose of 600,000 IU/kg IV may have begun as soon as 3 hours after, but no later than 24 hours after, completion of the TIL infusion.

Additional IL-2 administrations were given approximately every 8 to 12 hours for up to 6 doses maximum.

Production and Expansion of Tumor Infiltrating Lymphocytes

The TIL autologous cellular product was composed of viable cytotoxic T lymphocytes derived from a patient's tumor/lesion, which are manufactured ex vivo at a central GMP facility. An exemplary flow diagram depicting the TIL production process is provided in FIG. 9, for example.

The TIL manufacturing process begun at the clinical site after surgical excision of a primary or secondary metastatic tumor lesion(s) of ≥1.5 cm in diameter in each individual patient. Multiple tumor lesions from various anatomical locations can be excised to compile a total aggregate of tumor tissue; however, the aggregate should not exceed 4.0 cm in diameter, or 10 g in weight, due to the limited quantity of the biopreservation media present in the transport bottle.

Once the tumor lesion(s) was placed in the biopreservation transport bottle, it is shipped at 2° C. to 8° C. using an express courier to a central GMP manufacturing facility. Upon arrival, the tumor specimen(s) were dissected into fragments, which were then cultured in a pre-rapid expansion protocol (Pre-REP) with human recombinant IL-2 for ~11 days.

These pre-REP cells were then further expanded using a rapid expansion protocol (REP) for 11 days in the presence of IL-2, OKT3 (a murine monoclonal antibody to human CD3, also known as [muromonab-CD3]) and irradiated allogenic peripheral blood mononuclear cells (PBMC) as feeder cells.

The expanded cells were then harvested, washed, formulated, cryopreserved, and shipped to the clinical site via an express courier. The dosage form of the TIL cellular product was a cryopreserved autologous "live-cell suspension" that was ready for infusion into the patient from whom the TIL were derived. Patients were to receive the full dose of product that was manufactured and released, which contained between $1 \times 10^9$ and $150 \times 10^9$ viable cells per the product specification. Clinical experience indicated that objective tumor responses were achieved across this dose range, which has also been shown to be safe (Radvanyi L. G., et al., Clin Cancer Res. 2012; 18(24):6758-70). The full dose of product was provided in up to four infusion bags. Preparation of Patients to Receive the TIL Cellular Product The NMA-LD preconditioning regimen used in this study (i.e., 2 days of cyclophosphamide plus mesna, followed by 5 days of fludarabine) was based on the method developed and tested by the National Cancer Institute (Rosenberg S. A., et al., Clin Cancer Res. 2011; 17(13):4550-7; Radvanyi L. G., et al., Clin Cancer Res. 2012; 18(24):6758-70; Dudley M. E., et al., J Clin Oncol. 2008; 26(32):5233-9; Pilon-Thomas S, et al., J Immunother. 2012; 35(8):615-20; Dudley M. E., et al., J Clin Oncol. 2005; 23(10):2346-57; and Dudley M. E., et al., Science. 2002; 298(5594):850-4). Following the 7-day preconditioning regimen, the patient was infused with the TIL cellular product.

The TIL infusion was followed by the administration of IV IL-2 (600,000 IU/kg) every 8 to 12 hours, with the first dose administered between 3 and 24 hours after the completion of the TIL infusion and continuing for up to 6 doses maximum. Per institutional standards, the doses of IL-2 can be calculated on the basis of actual weight.

Selection of Patient Populations

Cohort 1A:

Patients had a confirmed diagnosis of unresectable MM (Stage IIIC or Stage IV, histologically confirmed as per American Joint Committee on Cancer [AJCC] staging system). Ocular melanoma patients were excluded. Patients must not have received prior immuno-oncology targeted agents. If BRAF-mutation positive, patient could have received prior BRAF/MEK targeted therapy.

Cohort 2A:

Patients had advanced, recurrent and/or metastatic HNSCC and can be treatment naive; histologic diagnosis of the primary tumor is required via the pathology report. Patients must not have received prior immunotherapy regimens.

Cohort 3A:

Patients had a confirmed diagnosis of Stage III or Stage IV NSCLC (squamous, adenocarcinoma, large cell carcinoma). Patients with oncogene-driven tumors with available effective targeted therapy had received at least one line of targeted therapy.

Cohort 3B:

Patients had a confirmed diagnosis of Stage III or Stage IV NSCLC (squamous, adenocarcinoma, large cell carcinoma) and had previously received systemic therapy with CPIs (e.g., anti-PD-1/anti-PD-L1). Patients with oncogene-driven tumors with available effective targeted therapy had received at least one line of targeted therapy.

All patients had received up to 3 prior systemic anticancer therapies (see, inclusion criteria below), excluding immunotherapy for Cohorts 1A, 2A, and 3A. If previously treated, patients had radiographically confirmed progression on or after most recent therapy.

Inclusion Criteria

Patients must have met ALL of the following inclusion criteria for participation in the study:

1. All patients had a histologically or pathologically confirmed diagnosis of malignancy of their respective histologies:

Unresectable or metastatic melanoma (Cohort 1A)

Advanced, recurrent or metastatic squamous cell carcinoma of the head and neck (Cohort 2A)

Stage III or Stage IV NSCLC (squamous, nonsquamous, adenocarcinoma, large cell carcinoma) (Cohorts 3A and 3B).

2. Cohorts 1A, 2A, and 3A only: Patients were immunotherapy naïve. If previously treated, patients had progressed on or after most recent therapy. Cohorts 1A, 2A, and 3A may have received up to 3 prior systemic anticancer therapies, specifically:

In Cohort 1A: Patients with unresectable or metastatic melanoma (Stage IIIC or Stage IV); if BRAF mutation-positive, patients could have received a BRAF inhibitor.

In Cohort 2A: Patients with unresectable or metastatic HNSCC. Those who had received initial chemo-radiotherapy were allowed.

In Cohort 3A: Patients with Stage III or Stage IV NSCLC (squamous, nonsquamous, adenocarcinoma, or large cell carcinoma) and who were immunotherapy naïve and progressed after ≤3 lines of prior systemic therapy in the locally advanced or metastatic setting. Patients who received systemic therapy in the adjuvant or neoadjuvant setting, or as part of definitive chemoradiotherapy, were eligible and were considered to have had one line of therapy if the disease has progressed within 12 months of completion of prior systemic therapy. Patients with known oncogene drivers (e.g., EGFR, ALK, ROS) who had mutations that were sensitive to targeted therapies must had progressed after at least 1 line of targeted therapy.

3. Cohort 3B only: Patients with Stage III or Stage IV NSCLC (squamous, nonsquamous, adenocarcinoma, or large cell carcinoma) who had previously received systemic therapy with CPIs (e.g., anti-PD-1/anti-PD-L1) as part of ≤3 prior lines of systemic therapy.

Patients had radiographically confirmed progression on or after most recent therapy.

Patients who received systemic therapy in the adjuvant or neoadjuvant setting, or as part of definitive chemoradiotherapy, were eligible and were considered to have had 1 line of therapy if the disease had progressed within 12 months of completion of prior systemic therapy.

Patients with known oncogene drivers (e.g., EGFR, ALK, ROS) who had mutations that are sensitive to targeted therapies must have progressed after at least 1 line of targeted therapy.

4. Patients had at least 1 respectable lesion (or aggregate lesions) of a minimum 1.5 cm in diameter post-resection for TIL investigational product production. It was encouraged that tumor tissue be obtained from multiple and diverse metastatic lesions, as long as the surgical resection did not pose additional risks to the patient.

If the lesion considered for resection for TIL generation is within a previously irradiated field, the lesion must have demonstrated radiographic progression prior to resection.

Patients must have an adequate histopathology specimen for protocol-required testing.

5. Patients had remaining measurable disease as defined by the standard and well known RECIST 1.1 guidelines (see, for example, Eisenhauer, European Journal of Cancer 45:228-247 (2009), also available on the World Wide Web at project.eortc.org/recist/wp-content/uploads/sites/4/2015/03/ RECISTGuidelines.pdf) following tumor resection for TIL manufacturing:

Lesions in previously irradiated areas were not be selected as target lesions unless there had been demonstrated progression of disease in those lesions;

Lesions that were partially resected for TIL generation that were still measurable per RECIST may be selected as nontarget lesions but could not serve as a target lesion for response assessment.

6. Patients were ≥18 years at the time of consent.

7. Patients had an Eastern Cooperative Oncology Group (ECOG) performance status of 0 or 1, and an estimated life expectancy of ≥3 months.

8. Patients of childbearing potential or those with partners of childbearing potential had to be willing to practice an approved method of highly effective birth control during treatment and continue for 12 months after receiving all protocol-related therapy (Note: Females of reproductive potential were to use effective contraception during treatment and for 12 months after their last dose of IL-2, or 4 months after their last dose of pembrolizumab whichever occurred later). Males could not donate sperm during the study or for 12 months after treatment discontinuation, whichever occurred later.

9. Patients had the following hematologic parameters:

Absolute neutrophil count (ANC) ≥1000/mm3;

Hemoglobin ≥9.0 g/dL;

Platelet count ≥100,000/mm3.

10. Patients had adequate organ function:

Serum alanine aminotransferase (ALT)/serum glutamic-pyruvic transaminase (SGPT) and aspartate amino-transferase (AST)/SGOT ≤3 times the upper limit of normal (ULN), patients with liver metastasis ≤5 times ULN.

An estimated creatinine clearance ≥40 mL/min using the Cockcroft Gault formula at Screening.

Total bilirubin ≤2 mg/dL.

Patients with Gilbert's Syndrome must have a total bilirubin ≤3 mg/dL.

11. Patients were seronegative for the human immunodeficiency virus (HIV1 and HIV2). Patients with positive serology for hepatitis B virus surface antigen (HBsAg), hepatitis B core antibody (anti HBc), or hepatitis C virus (anti-HCV) indicating acute or chronic infection were enrolled depending on the viral load based on polymerase chain reaction (PCR) and the local prevalence of certain viral exposures.

12. Patients had a washout period from prior anticancer therapy(ies) of a minimum duration, as detailed below prior to the first study treatment (i.e., start of NMA-LD or pembrolizumab):

Targeted therapy: prior targeted therapy with an epidermal growth factor receptor (EGFR), MEK, BRAF, ALK, ROS1 or other-targeted agents (e.g., erlotinib, afatinib, dacomitinib, osimertinib, crizotinib, ceritinib, lorlatinib) was allowed provided the washout is a minimum of 14 days prior to the start of treatment.

Chemotherapy: adjuvant, neoadjuvant or definitive chemotherapy/chemoradiation was allowed provided the washout is a minimum of 21 days prior to the start of treatment.

Immunotherapy for Cohort 3B only, prior checkpoint-targeted therapy with an anti-PD-1, other mAbs, or vaccines were allowed with a washout period of ≥21 days before the start of NMA-LD.

Palliative radiation therapy: prior external beam radiation was allowed provided all radiation-related toxicities were resolved to Grade 1 or baseline, excluding alopecia, skin pigmentation change, or other clinically insignificant events, e.g., small area radiation dermatitis or rectal or urinary urgency The tumor lesion(s) being assessed as target for response via RECIST 1.1 were outside of the radiation portal; however, if within the portal, they must have demonstrated progression (see Inclusion Criterion above).

Surgery/pre-planned procedure: previous surgical procedure(s) was permitted provided that wound healing had occurred, all complications had resolved, and at least 14 days have elapsed (for major operative procedures) prior to the tumor resection.

13. Patients had recovered from all prior anticancer treatment-related adverse events (TRAEs) to Grade ≤1 (per Common Terminology Criteria for Adverse Events [CT-CAE]), except for alopecia or vitiligo, prior to cohort assignment.

14. Patients with stable Grade ≥2 toxicity from prior anticancer therapy were considered on a case by case basis after consultation with the Medical Monitor.

15. Cohorts 1A, 2A, and 3A patients with irreversible toxicity not reasonably expected to be exacerbated by treatment with pembrolizumab were included only after consultation with the Medical Monitor. For patients in Cohort 3B only, patients with documented Grade ≥2 or higher diarrhea or colitis as a result of a previous treatment with immune checkpoint inhibitor CPI(s) must have been asymptomatic for at least 6 months or had a normal by visual assessment colonoscopy post-treatment prior to tumor resection.

16. Patients must have provided written authorization for use and disclosure of protected health information.

Exclusion Criteria

Patients who meet ANY of the following criteria were excluded from the study:

1. Patients with melanoma of uveal/ocular origin

2. Patients who had received an organ allograft or prior cell transfer therapy that included a nonmyeloablative or myeloablative chemotherapy regimen within the past 20 years. (Note: This criterion was applicable for patients undergoing retreatment with TIL, with the exception that they had a prior NMA-LD regimen with their prior TIL treatment.)

3. Patients with symptomatic and/or untreated brain metastases.

Patients with definitively-treated brain metastases will be considered for enrollment after discussion with Medical Monitor; if, prior to the start of treatment the patient is clinically stable for ≥2 weeks, there are no new brain lesions via magnetic resonance imaging (MRI) post-treatment, and the patient does not require ongoing corticosteroid treatment.

4. Patients who are on a systemic steroid therapy within 21 days of enrollment.

5. Patients who are pregnant or breastfeeding.

6. Patients who had an active medical illness(es), which in the opinion of the Investigator, posed increased risks for study participation; such as systemic infections (e.g., syphilis or any other infection requiring antibiotics), coagulation disorders, or other active major medical illnesses of the cardiovascular, respiratory, or immune systems.

7. Patients may not have active or prior documented autoimmune or inflammatory disorders (including pneumonitis, inflammatory bowel disease [e.g., colitis or Crohn's disease], diverticulitis [with the exception of diverticulosis], systemic lupus erythematosus, sarcoidosis syndrome, or Wegener syndrome [granulomatosis with polyangiitis, Graves' disease, rheumatoid arthritis, hypophysitis, uveitis, etc.]). The following were exceptions to this criterion:

Patients with vitiligo or alopecia.

Patients with hypothyroidism (e.g., following Hashimoto syndrome) stable on hormone replacement.

Any chronic skin condition that did not require systemic therapy.

Patients with celiac disease controlled by diet alone.

8. Patients who had received a live or attenuated vaccination within 28 days prior to the start of treatment.

9. Patients who had any form of primary immunodeficiency (such as severe combined immunodeficiency disease [SCID] and acquired immune deficiency syndrome [AIDS]).

10. Patients with a history of hypersensitivity to any component of the study drugs. TILs were not administered to patients with a known hypersensitivity to any component of TIL product formulation including, but not limited to any of the following:

NMA-LD (cyclophosphamide, mesna, and fludarabine)

Proleukin®, aldesleukin, IL-2

Antibiotics of the aminoglycoside group (i.e., streptomycin, gentamicin [excluding those who are skin-test negative for gentamicin hypersensitivity])

Any component of the TIL product formulation including dimethyl sulfoxide

[DMSO], HSA, IL-2, and dextran-40

Pembrolizumab

11. Patients who had a left ventricular ejection fraction (LVEF)<45% or who are New York Heart Association Class II or higher. A cardiac stress test demonstrating any irreversible wall movement abnormality in any patients ≥60 years of age or in patients who have a history of ischemic heart disease, chest pain, or clinically significant atrial and/or ventricular arrhythmias.

Patients with an abnormal cardiac stress test could be enrolled if they had adequate ejection fraction and cardiology clearance with approval of the Sponsor's Medical Monitor.

12. Patients who had obstructive or restrictive pulmonary disease and have a documented FEV1 (forced expiratory volume in 1 second) of ≤60% of predicted normal. If a patient was not able to perform reliable spirometry due to abnormal upper airway anatomy (i.e., tracheostomy), a 6-minute walk test was used to assess pulmonary function. Patients who were unable to walk a distance of at least 80% predicted for age and sex or demonstrates evidence of hypoxia at any point during the test (SpO2<90%) are excluded.

13. Patients who had another primary malignancy within the previous 3 years (except for those which did not require treatment or had been curatively treated greater than 1 year ago, and in the judgment of the Investigator, did not pose a significant risk of recurrence including, but not limited to, non-melanoma skin cancer, DCIS, LCIS, prostate cancer Gleason score ≤6 or bladder cancer).

14. Participation in another clinical study with an investigational product within 21 days of the initiation of treatment.

Study Endpoints and Planned Analyses

The primary and secondary endpoints were analyzed separately by cohort.

Primary Endpoints:

The ORR was defined as the proportion of patients who achieved either a confirmed PR or CR as best response as assessed by Investigators per RECIST 1.1 among the efficacy analysis set.

Objective response was evaluated per each disease assessment and the ORR was expressed as a binomial proportion with the corresponding 2-sided 90% CI. The primary analysis for each cohort occurred when all treated patients per cohort have an opportunity to be followed for 12 months, unless progressed/expired or discontinued early from the assessment period.

The safety primary endpoint was measured by any Grade 3 or higher TEAE incidence rate within each cohort expressed as binomial proportions with the corresponding 2-sided 90% CI.

Secondary Endpoints:

Efficacy:

The secondary efficacy endpoints were defined as follows:

CR rate as based on responders who achieved confirmed CR as assessed by Investigators. DCR was derived as the sum of the number of patients who achieved confirmed PR/CR or sustained SD (at least 6 weeks) divided by the number of patients in the efficacy analysis set×100%. The CR rate and DCR was summarized using a point estimate and its 2-sided 90% CI.

DOR was defined among patients who achieved objective response. It was measured from the first-time response (PR/CR) criteria are met until the first date that recurrent or progressive disease was objectively documented, or receipt of subsequent anticancer therapy or the patient dies (whichever is first recorded). Patients not experiencing PD or have not died prior to the time of data cut or the final database lock will have their event times censored on the last date that an adequate assessment of tumor status is made.

PFS was defined as the time (in months) from the time of lymphodepletion to PD, or death due to any cause, whichever event is earlier. Patients not experiencing PD or not having expired at the time of the data cut or the final database lock had their event times censored on the last date that an adequate assessment of tumor status is made.

OS was defined as the time (in months) from the time of lymphodepletion to death due to any cause. Patients not having expired by the time of data cut or the final database lock had their event times censored on the last date of their known survival status.

DOR, PFS, and OS was subjected to right censoring. The Kaplan-Meier method will be used to summarize the time-to-event efficacy endpoints. The baseline data for the tumor assessment was the last scan before the lymphodepletion for all cohorts.

The above efficacy parameters will be estimated for applicable cohort for subsets defined by baseline disease characteristics; BRAF status (Cohort 1A only), HPV status (Cohort 2A only), squamous or non-squamous lung disease (Cohorts 3A and 3B only), and anti-PD-L1 status.

Example 18: A Phase 2, Multicenter Study of Autologous Tumor Infiltrating Lymphocytes in Patients with Solid Tumors The study in this example is a phase 2, multicenter, global open label study of autologous tumor infiltrating lymphocytes (TIL) in patients with select solid tumors (metastatic melanoma, head and neck squamous cell cancer, and non-small cell lung cancer (NSCLC)). The example uses the TIL product manufactured according to the Examples herein, including Examples 10-17, as well as described in throughout the present application, which is cryopreserved and has a 22-day manufacturing process. A single infusion of TIL produce was given after patients had completed the preparatory regimen of non-myeloablative lymphodepletion with cyclophosphamide (60 mg/kg×2 days) and fludarabine (25 mg²/m×5 days). There are 4 patient cohorts as described below:

Cohort 1A (combination cohort): Stage IIIC or IV unresectable or metastatic melanoma patients who are immunotherapy naïve with ≤3 prior lines of systemic therapy. These patients will be receiving TIL product in combination with pembrolizumab.

Cohort 2A (combination cohort): Advanced, recurrent or metastatic head and neck squamous cell carcinoma patients who are immunotherapy naïve with ≤3 prior lines of systemic therapy. These patients will be receiving TIL product in combination with pembrolizumab.

Cohort 3A (combination cohort): Locally advanced or metastatic (Stage III-IV) NSCLC patients who are immunotherapy naïve with ≤3 prior lines of systemic therapy. These patients will be receiving TIL product in combination with pembrolizumab.

Cohort 3B (single agent cohort): Stage III-IV NSCLC patients who have previously received systemic therapy with checkpoint inhibitors (anti-PD-1/anti-PD-L1) as part of ≤3 prior lines of systemic therapy. These patients will be receiving TIL product as single agent.

Two patients with NSCLC have been enrolled in Cohort 3B (TIL alone post immune checkpoint inhibitor) who had completed their first response assessment visit at day 42) are described below.

Patient A is a 63-year old female diagnosed with Stage IVA lung adenocarcinoma. She had received 3 prior lines of systemic therapy which included pembrolizumab, carboplatin/bevacizumab and vinorelbine. Her best response to prior pembrolizumab therapy was progressive disease; to carboplatin/bevacizumab was a partial response, and her vinorelbine response was non-evaluable (she discontinued prior to response assessment). She underwent left lower lobe lung resection for TIL generation and was infused with 3.75×10⁹ cells of TIL product. The patient had her first response assessment (Day 42) visit, at which computerized tomography (CT) scans showed a 4% reduction in the tumor load compared to baseline scans, which is a stable disease response per RECIST 1.1.

Patient B is a 70-year old female diagnosed with Stage IVB basaloid squamous cell carcinoma. She had received 3 prior lines of therapy which included carboplatin/abraxane, nivolumab and cisplatin/gemcitabine. Her best response to prior carbo/abraxane was not evaluable (therapy discontinued due to toxicity); to nivolumab was progressive disease and for cisplatin/gemcitabine was a partial response. She underwent splenic lesion resection for TIL generation and was infused with 39×10⁹ cells of TIL product. The patient had her first response assessment (Day 42) visit, at which CT scans showed a 44% reduction in the tumor load compared to baseline scans, which is a partial response per RECIST 1.1.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method of treating non-small cell lung carcinoma (NSCLC) in a patient with a population of tumor infiltrating lymphocytes (TILs) comprising the steps of:

(a) obtaining and/or receiving a first population of TILs that contains a mixture of tumor and TIL cells from a NSCLC tumor in the patient;

(b) contacting the sample with a first cell culture medium;

(c) performing an initial expansion of the first population of TILs in a first cell culture medium to obtain a second population of TILs, wherein the first cell culture medium comprises IL-2;

(d) performing a rapid expansion of the second population of TILs in a second cell culture medium to obtain a third population of TILs; wherein the second cell culture medium comprises IL-2, OKT-3 (anti-CD3 antibody), and optionally irradiated allogeneic peripheral blood mononuclear cells (PBMCs); and wherein the rapid expansion is performed over a period of 14 days or less;

(e) harvesting the third population of TILs; and (f) administering a therapeutically effective portion of the third population of TILs to the patient with the NSCLC;

wherein the NSCLC is refractory to treatment with an anti-PD-1 and/or an anti-PD-L1 antibody.

2. The method of claim 1, wherein the obtaining the first population of TILs comprises a multilesional sampling method.

3. The method of claim 1, wherein the NSCLC has been previously treated with an anti-PD-1 and/or anti-PD-L1 and/or anti-PD-L2 antibody, or wherein the NSCLC has not been previously treated with an anti-PD-1, and/or anti-PD-L1 antibody, optionally wherein the NSCLC has been treated with a chemotherapeutic agent.

4. The method of claim 1, wherein the NSCLC has not been previously treated with an anti-PD-1 and/or anti-PD-L1 antibody and has bulky disease at baseline, optionally wherein bulky disease is indicated where the maximal tumor diameter is greater than 7 cm measured in either the transverse or coronal plane or swollen lymph nodes with a short-axis diameter of 20 mm or greater.

5. The method of claim 1, wherein the NSCLC is refractory to at least two prior systemic treatment courses, not including neo-adjuvant or adjuvant therapies and/or wherein the NSCLC is refractory to an anti-PD-1 and/or an anti-PD-L1 antibody selected from the group consisting of nivolumab, pembrolizumab, JS001, TSR-042, pidilizumab, BGB-A317, SHR-1210, REGN2810, MDX-1106, PDR001, anti-PD-1 from clone: RMP1-14, durvalumab, atezolizumab, avelumab, and fragments, derivatives, variants, as well as biosimilars thereof, optionally wherein the NSCLC is refractory to pembrolizumab or a biosimilar thereof, nivolumab or a biosimilar thereof, ipilimumab or a biosimilar thereof and pembrolizumab or a biosimilar thereof, optionally wherein the NSCLC is refractory to ipilimumab or a biosimilar thereof and nivolumab or a biosimilar thereof.

6. The method of claim 1, wherein the NSCLC is refractory to durvalumab or a biosimilar thereof, atezolizumab or a biosimilar thereof, or avelumab or a biosimilar thereof.

7. The method of claim 1, wherein the initial expansion is performed over a period of 21 days or less or a period of 14 days or less.

8. The method of claim 1, wherein the IL-2 is present at an initial concentration of between 1000 IU/mL and 6000 IU/mL in the first cell culture medium, optionally wherein the IL-2 is present at an initial concentration of between 1000 IU/mL and 6000 IU/mL and the OKT-3 antibody is present at an initial concentration of about 30 ng/mL in the second cell culture medium.

9. The method of claim 1, wherein the initial expansion is performed using a gas permeable container and/or the rapid expansion is performed using a gas permeable container.

10. The method of claim 1, wherein the first cell culture medium further comprises a cytokine selected from the group consisting of IL-4, IL-7, IL-15, IL-21, and combinations thereof, and/or wherein the second cell culture medium further comprises a cytokine selected from the group consisting of IL-4, IL-7, IL-15, IL-21, and combinations thereof.

11. The method of claim 1, further comprising the step of treating the patient with a non-myeloablative lymphodepletion regimen prior to administering the third population of TILs to the patient, optionally wherein the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

12. The method of claim 1, further comprising the step of treating the patient with an IL-2 regimen starting on the day after administration of the third population of TILs to the patient, optionally wherein the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

\* \* \* \* \*